US011820751B2

(12) United States Patent
Rinsch et al.

(10) Patent No.: US 11,820,751 B2
(45) Date of Patent: Nov. 21, 2023

(54) UROLITHIN DERIVATIVES AND METHODS OF USE THEREOF

(71) Applicant: Vandria SA, Lausanne (CH)

(72) Inventors: Christopher L. Rinsch, Lausanne (CH); Penelope Andreux, Eclepens (CH); Jonathan Mark Sutton, Harlow (GB); Eileen Mary Seward, Harlow (GB); Jamie D. Knight, Harlow (GB); Ian Linney, London (GB); Peter C. Sennhenn, Munich (DE); Said Oumouch, Wittenheim (FR); Florent Beaufils, Bartenheim (FR); Thomas Christian Fessard, Küsnacht (CH)

(73) Assignee: Vandria SA, Lausanne (CH)

( * ) Notice: Subject to any disclaimer, the term of this patent is extended or adjusted under 35 U.S.C. 154(b) by 0 days.

(21) Appl. No.: 17/586,294

(22) Filed: Jan. 27, 2022

(65) Prior Publication Data
US 2022/0259173 A1    Aug. 18, 2022

Related U.S. Application Data

(60) Provisional application No. 63/142,333, filed on Jan. 27, 2021.

(51) Int. Cl.
| C07D 311/80 | (2006.01) |
| C07D 217/24 | (2006.01) |
| C07D 279/02 | (2006.01) |
| C07D 407/12 | (2006.01) |
| C07D 491/04 | (2006.01) |
| C07D 491/107 | (2006.01) |
| C07D 493/04 | (2006.01) |
| C07D 493/10 | (2006.01) |

(52) U.S. Cl.
CPC .......... *C07D 311/80* (2013.01); *C07D 217/24* (2013.01); *C07D 279/02* (2013.01); *C07D 407/12* (2013.01); *C07D 491/04* (2013.01); *C07D 491/107* (2013.01); *C07D 493/04* (2013.01); *C07D 493/10* (2013.01)

(58) Field of Classification Search
CPC .................................................. C07D 311/80
See application file for complete search history.

(56) References Cited

U.S. PATENT DOCUMENTS

| 8,933,217 | B2 | 1/2015 | Rinsch et al. |
| 9,394,269 | B2 | 7/2016 | Rinsch et al. |
| 9,573,922 | B2 | 2/2017 | Rinsch et al. |
| 9,872,850 | B2 | 1/2018 | Rinsch et al. |
| 9,962,366 | B2 | 5/2018 | Rinsch et al. |
| 9,980,980 | B2 | 5/2018 | Rinsch et al. |
| 9,994,542 | B2 | 6/2018 | Rinsch et al. |
| 10,028,932 | B2 | 7/2018 | Rinsch et al. |
| 10,113,171 | B2 | 10/2018 | Rosenblum et al. |
| 10,442,784 | B2 | 10/2019 | Andreux et al. |
| 10,485,782 | B2 | 11/2019 | Rinsch et al. |
| 10,532,992 | B2 | 1/2020 | Rinsch et al. |
| 10,676,747 | B2 | 6/2020 | Rosenblum et al. |
| 10,695,320 | B2 | 6/2020 | Andreux et al. |
| 10,792,276 | B2 | 10/2020 | Singh et al. |
| 10,857,126 | B2 | 12/2020 | Rinsch et al. |
| 10,906,883 | B2 | 2/2021 | Skranc et al. |
| 10,988,453 | B2 | 4/2021 | Andreux et al. |
| 11,020,373 | B2 | 6/2021 | Rinsch et al. |
| 11,166,937 | B2 | 11/2021 | Rinsch et al. |
| 11,166,972 | B2 | 11/2021 | Rinsch et al. |
| 11,180,468 | B2 | 11/2021 | Rinsch et al. |
| 11,234,960 | B2 | 2/2022 | Rinsch et al. |
| 2011/0065662 | A1 | 3/2011 | Rinsch et al. |
| 2012/0164243 | A1 | 6/2012 | Rinsch et al. |
| 2014/0018415 | A1 | 1/2014 | Rinsch et al. |
| 2015/0183758 | A1 | 7/2015 | Rinsch et al. |
| 2015/0196577 | A1 | 7/2015 | Rinsch et al. |
| 2016/0000753 | A1 | 1/2016 | Rinsch et al. |
| 2016/0213641 | A1 | 7/2016 | Rinsch et al. |
| 2016/0213643 | A1 | 7/2016 | Rinsch et al. |
| 2016/0326131 | A1 | 11/2016 | Rinsch et al. |
| 2016/0332982 | A1 | 11/2016 | Rinsch et al. |
| 2017/0143666 | A1 | 5/2017 | Rinsch et al. |
| 2017/0143667 | A1 | 5/2017 | Rinsch et al. |
| 2018/0015069 | A1 | 1/2018 | Rinsch et al. |
| 2018/0243261 | A1 | 8/2018 | Andreux et al. |
| 2018/0256471 | A1 | 9/2018 | Rinsch et al. |
| 2018/0256538 | A1 | 9/2018 | Rinsch et al. |
| 2018/0256539 | A1 | 9/2018 | Rinsch et al. |
| 2018/0303794 | A1 | 10/2018 | Rinsch et al. |
| 2019/0000867 | A1 | 1/2019 | Rinsch et al. |

(Continued)

FOREIGN PATENT DOCUMENTS

| CN | 101654401 A | 2/2010 |
| CN | 103772228 A | 5/2014 |

(Continued)

OTHER PUBLICATIONS

PubChem database entry for N-(6-Oxo-6H-dibenzo[b,d]pyran-3-yl)methanesulfonamide PubChem CID 248621, Create Date: Mar. 26, 2005.*
Gonzalez-Barrio "Metabolism of Oak Leaf Ellagitannins and Urolithin Production in Beef Cattle" J. Agric. Food Chem. 2012, 60, 3068-3077.*
Ghosal "The core structure of shilajit humus." Soil Biology & Biochemistry, 1991, 23(7), 673-80.*
Boutin et al., "S29434, a Quinone Reductase 2 Inhibitor: Main Biochemical and Cellular Characterization," Molecular Pharmacology, 95: 269-285 w/ Supplementary Material (2019).
Hennings et al., "Anion-Accelerated Palladium-Catalyzed Intramolecular Coupling of Phenols with Aryl Halides," The Journal of Organic Chemistry, 62(1): 2-3 (1997).

(Continued)

*Primary Examiner* — David K O'Dell
(74) *Attorney, Agent, or Firm* — Foley Hoag LLP; Dana M. Gordon; Lawrence P. Tardibono

(57) ABSTRACT

Disclosed are compounds, compositions, and methods useful for treating neuronal and mitochondrial diseases.

6 Claims, 70 Drawing Sheets

(56) References Cited

U.S. PATENT DOCUMENTS

| | | |
|---|---|---|
| 2019/0008883 A1 | 1/2019 | Andreux et al. |
| 2019/0010138 A1 | 1/2019 | Rinsch et al. |
| 2019/0062297 A1 | 2/2019 | Andreux et al. |
| 2019/0263772 A1 | 8/2019 | Skranc et al. |
| 2019/0328703 A1 | 10/2019 | Singh et al. |
| 2020/0140405 A1 | 5/2020 | Andreux et al. |
| 2020/0223813 A1 | 7/2020 | Rinsch et al. |
| 2020/0323818 A1 | 10/2020 | Andreux et al. |
| 2020/0397748 A1 | 12/2020 | Rinsch et al. |
| 2021/0059982 A1 | 3/2021 | Rinsch et al. |
| 2021/0085642 A1 | 3/2021 | Singh et al. |
| 2021/0198225 A1 | 7/2021 | Skranc et al. |
| 2021/0210190 A1 | 7/2021 | Rinsch et al. |
| 2021/0251869 A1 | 8/2021 | Rinsch et al. |
| 2021/0346342 A1 | 11/2021 | Rinsch et al. |
| 2021/0353591 A1 | 11/2021 | Rinsch et al. |
| 2022/0073488 A1 | 3/2022 | Andreux et al. |
| 2022/0259173 A1 | 8/2022 | Rinsch et al. |

FOREIGN PATENT DOCUMENTS

| | | | |
|---|---|---|---|
| CN | 105085463 A | 11/2015 | |
| CN | 106632214 A | 5/2017 | |
| CN | 109761902 A | 5/2019 | |
| CN | 110862368 A | 3/2020 | |
| EP | 1618101 A2 | 1/2006 | |
| EP | 2674422 A1 | 12/2013 | |
| FR | 2492378 A1 | 4/1982 | |
| JP | H02304080 A | 12/1990 | |
| JP | H05214334 A | 8/1993 | |
| JP | H06234753 A | 8/1994 | |
| JP | H07188215 A | 7/1995 | |
| JP | 2016 162983 A | 9/2016 | |
| WO | WO-92/21660 A1 | 12/1992 | |
| WO | WO-99/14217 A1 | 3/1999 | |
| WO | WO-99/62907 A1 | 12/1999 | |
| WO | WO-2002 065984 A2 | 8/2002 | |
| WO | WO-2004 073612 A2 | 9/2004 | |
| WO | WO-2005 105752 A1 | 11/2005 | |
| WO | WO-2009 059304 A2 | 5/2009 | |
| WO | WO-2010 133278 A1 | 11/2010 | |
| WO | WO-2011 093483 A1 | 8/2011 | |
| WO | WO-2012 092411 A2 | 7/2012 | |
| WO | WO-2013 004652 A1 | 1/2013 | |
| WO | WO-2013 041461 A1 | 3/2013 | |
| WO | WO-2015 065338 A1 | 5/2015 | |
| WO | WO-2015/100213 A2 | 7/2015 | |
| WO | WO-2015/154047 A1 | 10/2015 | |
| WO | WO-2018 119208 A1 | 6/2018 | |
| WO | WO-2018 161831 A1 | 9/2018 | |
| WO | WO-2019 222146 A1 | 11/2019 | |
| WO | WO-2020 124206 A1 | 6/2020 | |
| WO | WO-2020110089 A1 * | 6/2020 | ........... A61K 31/353 |
| WO | WO-2022/162471 A1 | 8/2022 | |

OTHER PUBLICATIONS

International Search Report and Written Opinion for International Application No. PCT/IB2022/000049 dated Apr. 13, 2022.

Kudo et al., "Scalable Synthesis of 8-Amino-3-hydroxy-6H-benzo[c]chromen-6-one: Key Intermediate for SEGRA via the Hurtley Reaction," Organic Process Research & Development, 19(1): 309-314 (2015).

Li et al., "Synthesis of substituted 5[H]phenanthridin-6-ones as potent poly(ADP-ribose)polymerase-1 (PARP1) inhibitors," Bioorganic & Medicinal Chemistry Letters, 11(13): 1687-1690 (2001).

Pandey et al., "Synthesis and biological activites of some new dibenzopyranones and dibenzopyrans: search for potential oestrogen receptor agonists and antagonists," Bioorganic & Medicinal Chemistry, 12(9): 2239-2249 (2004).

Plunkett et al., "Synthesis of 4-Alkylated Isocoumarins via Pd-Catalyzed cx-Arylation Reaction," Organic Letters, 22(19): 7662-7666 (2020).

Ryokawa et al., "Synthetic use of 1,1,2,2-tetraphenyldisilane for the preparation of biaryls through the intramolecular free radical ipso-substitution of N-(2-bromoaryl)arenesulfonamides," Tetrahedron, 57(28): 5915-5921 (2001).

Singh et al., "Enhancement of the gut barrier integrity by a microbial metabolite through the Nrf2 pathway." Nature Communications, 10(89): 18 pages (2019).

Tao et al., "Electrochemical C—O Bond Formation: Facile Access to Aromatic Lactones," Chemistry—A European Journal, 24(27): 6932-6935 (2018).

Wiesner et al., "Synthesis of Dimethylapoerysopine and an Approach to the Total Synthesis of the Unrearranged Erythrina Bases," Journal of the American Chemical Society, 77(3): 675-683 (1955).

Zhang et al., "Synthesis of Dibenzo[c,e]oxepin-5(7H)-ones from Benzyl Thioethers and Carboxylic Acids: Rhodium-Catalyzed Double CH Activation Controlled by Different Directing Groups," Angewandte Chemie International Edition, 54(18): 5478-5482 (2015).

* cited by examiner

FIG. 1

| Structure | Mitophagy (TOM20): Efficacy at 50 μM (%), ***** = ≥200, ****=100-199, ***=50-99, **=0-49, *=<0, -=Not Tested | Anti-inflammation (IL-6 MSD): Efficacy at 50 μM (%), ***=50-100, **=0-49, *=<0, -=Not Tested | ATP content (Cell-Titer Glo): Efficacy at 50 μM (%), ***=25-100, **=0-24, *=<0, -=Not Tested |
|---|---|---|---|
| [structure] | ** | *** | *** |
| [structure] | ** | *** | *** |
| [structure] | ***** | *** | *** |
| [structure] | *** | *** | * |
| [structure] | ***** | *** | ** |
| [structure] | ** | ** | ** |

| Structure | Solubility kin.: C (μM), *=≥100, =50-99, *=0-49, -=Not Tested | h Hepatocytes: CLint (μL/min/1Mio cells), *=≥200, =100-199, *=0-99, -=Not Tested | HLM: CLint (uL/min/mg protein), *=≥100, =50-99, *=0-49, -=Not Tested | MLM: CLint (uL/min/mg protein), *=≥100, =50-99, *=0-49, -=Not Tested |
|---|---|---|---|---|
| [structure] | *** | — | * | * |
| [structure] | *** | *** | * | * |
| [structure] | * | *** | * | * |
| [structure] | * | * | * | ** |
| [structure] | * | ** | ** | *** |
| [structure] | * | ** | * | *** |

| | | | | | | |
|---|---|---|---|---|---|---|
| ** | *** | | | * | ** | *** |
| * | ** | | *** | * | * | * |
| | | *** | | | | |
| * | * | | * | * | * | * |

| Structure | Respiration in myotubes - Max Efficacy, *** = ≥200, =100-199, *=50-99, **=0-49, *=<0, -=Not Tested | Respiration in myotubes - Conc. of max efficacy (µM), **=26-50, *=0-25 |
|---|---|---|
| [structure] | ****** | ** |
| [structure] | **** | ** |
| [structure] | ***** | ** |
| [structure] | **** | * |
| [structure] | **** | ** |
| [structure] | *** | ** |

| Structure | Mitophagy (TOM20): Efficacy at 50 μM (%), ***= ≥200, =100-199,*=50-99,**=0-49, *=<0, -=Not Tested | Anti-inflammation (IL-6 MSD): Efficacy at 50 μM (%), *=50-100,=0-49, *=<0, -=Not Tested | ATP content (Cell-Titer Glo): Efficacy at 50 μM (%), *=25-100,=0-24, *=<0, -=Not Tested | Mitophagy (TOM20): Max efficacy (%), ****= ≥250, *=100-249, =75-99, *=50-74, **=25-49,*=0-24, -=Not Tested | Mitophagy (TOM20): Max efficacy conc. (mM), *=26-50,=11-25, *0.1-10 -=Not Tested |
|---|---|---|---|---|---|
|  | | *** | ** | - | - |
|  | ** | ** | ** | - | - |
|  | **** | *** | *** | - | - |
|  | **** | ** | *** | - | - |
|  | ** | *** | ** | - | - |
|  | * | *** | ** | - | - |

| Structure | | | | | |
|---|---|---|---|---|---|
|  | ** | ** | ** | - | - |
|  | ** | *** | ** | - | - |
|  | *** | ** | ** | - | - |
|  | ** | *** | * | - | - |
|  | **** | *** | *** | - | - |
|  | ** | *** | ** | - | - |
|  | ** | ** | ** | - | - |

| Structure | | | | | |
|---|---|---|---|---|---|
|  | ** | ** | * | - | - |
|  | ** | ** | ** | - | - |
|  | ***** | ** | *** | - | - |
|  | ** | ** | ** | - | - |
|  | ** | *** | ** | - | - |
|  | ** | ** | ** | - | - |
|  | *** | *** | *** | - | - |
|  | ** | * | *** | - | - |

| Structure | | | | | |
|---|---|---|---|---|---|
|  | * | ** | *** | - | - |
|  | ** | ** | ** | - | - |
|  | ** | ** | *** | - | - |
|  | ** | ** | *** | - | - |
|  | ** | ** | ** | - | - |
|  | **** | ** | *** | - | - |
|  | ** | ** | ** | - | - |

| Structure | | | | | |
|---|---|---|---|---|---|
|  | ** | ** | ** | - | - |
|  | ** | ** | ** | - | - |
|  | ***** | * | *** | - | - |
|  | * | ** | ** | - | - |
|  | ** | ** | * | - | - |
|  | *** | *** | *** | - | - |
|  | *** | * | ** | - | - |
|  | *** | ** | *** | **** | ** |

FIG. 4 (cont'd)

| Structure | | | | | |
|---|---|---|---|---|---|
| | *** | ** | ** | *** | *** |
| | **** | *** | ** | ***** | *** |
| | * | *** | ** | **** | ** |
| | **** | ** | * | ***** | *** |
| | - | ** | ** | - | ** |
| | - | ** | ** | - | ** |
| | - | ** | ** | - | ** |

| Structure | | | | | |
|---|---|---|---|---|---|
|  | **** | * | ** | ***** | *** |
|  | *** | *** | *** | **** | *** |
|  | - | *** | *** | - | * |
|  | - | *** | *** | - | *** |
|  | ***** | *** | *** | ****** | *** |
|  | - | ** | *** | - | * |
|  | - | * | *** | - | ** |

| Structure | | | | | |
|---|---|---|---|---|---|
|  | ***** | *** | ** | ****** | *** |
|  | **** | *** | *** | ***** | *** |
|  | - | *** | ** | - | ** |
|  | *** | *** | ** | **** | *** |
|  | *** | *** | ** | ***** | ** |
|  | ** | *** | ** | ** | * |
|  | - | *** | ** | - | * |

| Structure | | | | | |
|---|---|---|---|---|---|
|  | * | ** | ** | * | ** |
|  | ** | ** | ** | * | * |
|  | ** | ** | * | * | * |
|  | ** | ** | ** | ** | *** |
|  | ** | *** | ** | ** | *** |
|  | * | * | * | ** | ** |

| Structure | | | | | |
|---|---|---|---|---|---|
|  | - | *** | *** | - | * |
|  | - | ** | ** | - | *** |
|  | - | * | ** | - | *** |
|  | - | *** | ** | - | * |
|  | * | *** | ** | * | ** |
|  | - | *** | *** | - | * |
|  | - | *** | *** | - | *** |

| Structure | | | | | |
|---|---|---|---|---|---|
|  | **** | *** | *** | ***** | *** |
|  | *** | *** | *** | ***** | ** |
|  | - | *** | ** | - | ** |
|  | *** | *** | *** | **** | *** |
|  | * | * | *** | *** | ** |
|  | - | ** | * | - | * |

| Structure | Solubility kin.: C (µM), *= ≥100, =50-99, *=0-49, -=Not Tested |
|---|---|
|  | * |
|  | * |
|  | * |
|  | *** |
|  | *** |
|  | *** |
|  | *** |

| | |
|---|---|
|  | * |
|  | * |
|  | * |
|  | *** |
|  | |
|  | *** |
|  | *** |
|  | *** |

FIG. 5 (cont'd)

| Structure | Activity |
|---|---|
| (structure) | * |
| (structure) | *** |
| (structure) | * |
| (structure) | *** |
| (structure) | * |
| (structure) | * |
| (structure) | * |
| (structure) | * |

FIG. 5 (cont'd)

| Structure | |
|---|---|
| (phenanthridinone with OH, F, OH, N-Me) | * |
| (hydroxy-dibenzo[b,d]pyran-6-one with alkyne-hydroxycyclobutyl) | * |
| (hydroxy-dibenzo[b,d]pyran-6-one with oxetanyloxy) | * |
| (hydroxy-dibenzo[b,d]pyran-6-one with hydroxymethyl-bicyclobutyl) | * |
| (hydroxy-dibenzo[b,d]pyran-6-one with tetrahydropyranyloxy) | * |
| (hydroxy-dibenzo[b,d]pyran-6-one with tetrahydrofuranyloxy) | * |
| (dihydroxy-dibenzo[b,d]pyran-6-one with F) | *** |

| | |
|---|---|
|  | * |
|  | * |
|  | * |
|  | *** |
|  | * |
|  | * |
|  | * |
|  | *** |

| | |
|---|---|
|  | *** |
|  | *** |
|  | *** |
|  | *** |
|  | *** |
|  | *** |
|  | *** |

| | |
|---|---|
|  | ** |
|  | *** |
|  | * |
|  | * |
|  | * |
|  | * |

| | |
|---|---|
|  | - |
|  | *** |
|  | *** |
|  | *** |
|  | * |
|  | *** |
|  | *** |

| | |
|---|---|
|  | *** |
|  | *** |
|  | - |
|  | *** |
|  | * |
|  | * |

| | |
|---|---|
|  | * |
|  | * |
|  | * |
|  | * |
|  | ** |
|  | ** |
|  | * |

FIG. 5 (cont'd)

| Structure | Activity |
|---|---|
| (cyclopropyl-N dibenzazepinone with two OH and two methyl groups) | *** |
| (spirocyclobutane dibenzofuran with two OH and two methyl groups) | * |
| (dimethyl pyran-fused biaryl with two OH and two methyl groups) | *** |
| (spirocyclobutane dibenzofuran with two OH and ethyl) | ** |
| (hydroxy phenanthridinone fused with cyclohexane) | * |

FIG. 6

| Structure | Respiration in myotubes - Max Efficacy (%), ***** = ≥200, **** = 100-199, ***=50-99, **=0-49, *=<0, - =Not Tested | Respiration in myotubes - Conc. of max efficacy (µM), **=26-50, *=0-25 |
|---|---|---|
| | **** | ** |
| | **** | ** |
| | ***** | ** |
| | ***** | ** |
| | **** | ** |
| | *** | ** |
| | ** | ** |

| Structure | | |
|---|---|---|
|  | **** | * |
|  | *** | ** |
|  | *** | ** |
|  | *** | ** |
|  | **** | ** |
|  | *** | ** |
|  | *** | ** |

| | | |
|---|---|---|
| | **** | ** |
| | ***** | * |
| | *** | ** |
| | **** | ** |
| | **** | ** |
| | **** | * |

| Structure | | |
|---|---|---|
|  | **** | * |
|  | *** | ** |
|  | *** | * |
|  | *** | ** |
|  | ** | ** |
|  | *** | ** |

| | | |
|---|---|---|
|  | *** | ** |
|  | ** | ** |
|  | *** | ** |
|  | *** | * |
|  | *** | * |
|  | **** | * |

| Structure | | |
|---|---|---|
|  | **** | * |
|  | ***** | ** |
|  | *** | ** |
|  | **** | * |
|  | ** | ** |
|  | ***** | * |
|  | *** | * |

| | | |
|---|---|---|
|  | **** | * |
|  | *** | ** |

| Structure | Brain Cmax (ng/g tissue), *=≥100, =51-100, *=0-50 | Muscle Cmax (ng/g tissue), *=≥100, =51-100, *=0-50 | Vss, volume of distribution at steady-state (l/kg), *=≥5, =2.6-5, *=0-2.5 | Lung Cmax (ng/g tissue), ***=≥500, =351-500, *=251-350, **=151-250, *=75-150 | Liver Cmax (ng/g tissue), ***=≥500, =351-500, *=251-350, **=151-250, *=75-150 |
|---|---|---|---|---|---|
|  | * | * | *** | - | - |
|  | * | *** | * | - | - |
|  | * | * | * | - | - |
|  | *** | *** | ** | - | - |
|  | * | ** | * | - | - |
|  | * | * | - | ** | ** |

FIG. 7 (cont'd)

| Structure | | | | | |
|---|---|---|---|---|---|
| (phenanthridinone with OH, OH, F) | * | * | * | - | - |
| (dihydrobenzazepinone with HO, OH) | * | ** | *** | - | - |
| (phenanthridinone with OH, OH, methyl) | * | * | * | - | - |
| (dibenzopyranone with HO, alkyne-CH₂OH) | * | - | - | - | - |
| (methyl dibenzopyran with HO, OH, F) | * | * | *** | - | - |
| (dihydrobenzazepinone with HO, OH, F) | * | * | - | *** | *** |

| Structure | | | | | |
|---|---|---|---|---|---|
|  | * | ** | - | ***** | *** |
|  | * | * | - | - | - |
|  | * | - | * | - | - |
|  | * | * | - | ** | * |
|  | * | * | - | ***** | ** |
|  | * | * | - | ***** | *** |
|  | * | ** | - | ** | *** |

FIG. 7 (cont'd)

| Structure | | | | | |
|---|---|---|---|---|---|
| (cyclopropyl-N phenanthridinone with 2 OH) | * | * | - | * | **** |
| (cyclopropyl-N phenanthridinone with 2 OH, 2 Me) | ** | * | - | ***** | **** |
| (cyclopropyl-N dibenzazepinone with 2 OH, Me) | * | * | - | **** | * |
| (spiro cyclobutane dibenzofuran with 2 OH, 2 Me) | * | * | - | ** | *** |
| (dimethyl dibenzopyran with 2 OH, 2 Me) | * | * | - | **** | * |

| Structure | Anti-ferroptotic activity. Maximal Percent efficacy (%), ***=80-100, =60-79, *=40-59, **=20-39, *=0-19 | Concentration at maximal Percent efficacy (μM), *=35-50, =20-34, *=0-19 |
|---|---|---|
| Urolithin A | *** | *** |
| Urolithin C | **** | ** |
|  | ***** | *** |
|  | *** | * |
|  | ***** | * |
|  | ** | *** |
|  | **** | *** |

| | | |
|---|---|---|
|  | *** | * |
|  | *** | * |
|  | *** | * |
|  | ** | *** |
|  | ***** | * |

| Structure | | |
|---|---|---|
|  | *** | * |
|  | ***** | * |
|  | ***** | ** |
|  | ***** | *** |
|  | **** | *** |
|  | * | *** |
|  | ** | *** |
|  | **** | *** |

| | | |
|---|---|---|
|  | **** | * |
|  | **** | * |
|  | ***** | * |
|  | ***** | * |

| Compound | Solubility (μM) Solubility kin.: C (μM), *= ≥100, =50-99, *=0-49 | Bioavailability (%), **= ≥50, *=25-49, *=10-24, *=0-9 |
|---|---|---|
|  | *** | * |
|  | * | * |
|  | *** | * |
|  | * | * |
|  | *** | *** |
|  | * | *** |
|  | *** | **** |

UROLITHIN DERIVATIVES AND METHODS OF USE THEREOF

RELATED APPLICATION

This application claims the benefit of priority to U.S. Provisional Patent Application No. 63/142,333, filed Jan. 27, 2021, the contents of which are hereby incorporated by reference.

BACKGROUND

Urolithins have potent effects on the improvement of a number of health conditions, and they have been shown to be highly biologically active in vitro and in vivo. Urolithins have been proposed as treatments of a variety of conditions including conditions related to inadequate mitochondrial activity, including obesity, memory decline, reduced metabolic rate, metabolic syndrome, diabetes mellitus, cardiovascular disease, hyperlipidemia, neurodegenerative diseases, cognitive disorder, mood disorder, stress, anxiety disorder, fatty liver disease (for example, NAFLD or NASH) and for improving liver function and weight management. In particular, urolithins have been shown to have beneficial effects in the enhancement of muscle function.

SUMMARY

One aspect of the invention provides compounds, compositions, and methods useful for treating neuronal and mitochondrial diseases.

Accordingly, provided herein is a compound having the structure of Formula (Ia):

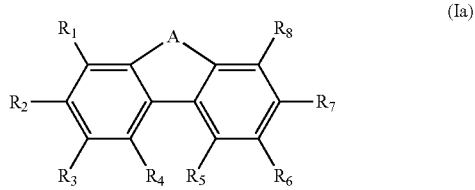

wherein
A is

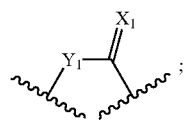

$X_1$ is selected from O and S;
$Y_1$ is O;
$R_1$, $R_4$, $R_5$ and $R_8$ are independently selected from H and halogen;
$R_3$ and $R_6$ are independently selected from H, CN, OH, $CF_3$, halogen, and alkyl;
one of $R_2$ and $R_7$ is H, OH, or OAc and the other of $R_2$ and $R_7$ is halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;

each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, C(O)-alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and
provided that if $X_1$ and $Y_1$ are each O, $R_2$ is OH, and $R_1$, $R_3$, $R_4$, $R_5$, $R_6$ and $R_8$ are each H, then $R_7$ is not OBn, if $X_1$ and $Y_1$ are each O, $R_7$ is OH, and $R_1$, $R_3$, $R_4$, $R_5$, $R_6$ and $R_8$ are each H, then $R_2$ is not $OCH_2C(O)NH_2$, or a pharmaceutically acceptable salt thereof.

Also provided herein is a compound of Formula (Ib):

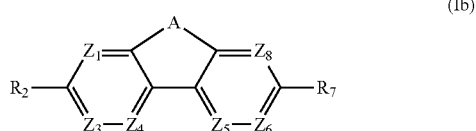

wherein
A is

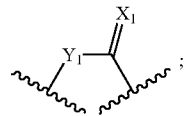

$X_1$ is selected from O and S;
$Y_1$ is O;
$Z_1$ is selected from N and C—$R_1$;
$Z_3$ is selected from N and C—$R_3$;
$Z_4$ is selected from N and C—$R_4$;
$Z_5$ is selected from N and C—$R_5$;
$Z_6$ is selected from N and C—$R_6$;
$Z_8$ is selected from N and C—$R_8$;
$R_1$, $R_4$, $R_5$, and $R_8$ are independently selected from is H, halogen, and aminoalkyl, and
$R_2$, $R_3$, $R_6$, and $R_7$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
or a pair of $R_1$ and $R_2$, $R_2$ and $R_3$, $R_6$ and $R_7$, or $R_7$ and $R_8$ together with the ring to which they are bonded form a biheteroaryl;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl- O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;

each occurrence of $R_{11}$ is selected from H and alkyl;

each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and provided that if $X_1$ and $Y_1$ are O, then at least one of $Z_1$, $Z_3$, $Z_4$, $Z_5$, $Z_6$, or $Z_8$ is N, or at least one of $R_1$, $R_3$, $R_4$, $R_5$, $R_6$, and $R_8$ is not H or OH, and $R_1$ and $R_8$ are not both halogen, and if $X_1$ and $Y_1$ are O, $R_2$ and $R_7$ are each OH, and $R_1$, $R_4$, $R_5$, $R_6$ and $R_8$ are each H, then $R_3$ is not Br, or a pharmaceutically acceptable salt thereof.

Also provided herein is a compound of Formula (Ic):

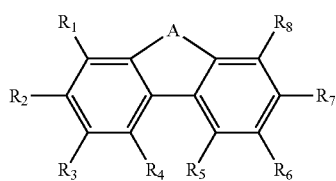

(Ic)

wherein
A is

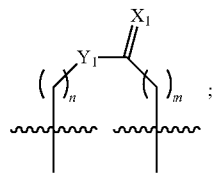

one of n and m is 0; and the other of n and m is 1;

$X_1$ and $Y_1$ are each O;

$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;

$R_4$ and $R_5$ are independently selected from H, halogen and alkyl;

each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;

$R_{11}$ is selected from H and alkyl; and $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl, or a pharmaceutically acceptable salt thereof.

Also provided herein is a compound of Formula (Id):

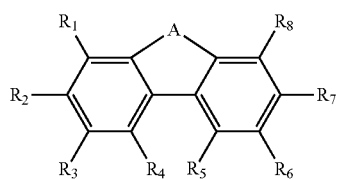

(Id)

wherein
A is

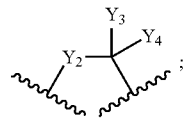

$Y_2$ is O;

$Y_3$ and $Y_4$ are independently selected from H, halogen and alkyl; or together with the carbon to which they are bonded combine to form a cycloalkyl or heterocycloalkyl;

$R_1$, $R_4$, $R_5$, and $R_8$ are independently selected from H and halogen;

$R_2$, $R_3$, $R_6$, and $R_7$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;

each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;

each occurrence of $R_{11}$ is selected from H and alkyl;

each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and provided that when $Y_2$ is O, $R_2$ and $R_7$ are each OH, $R_1$, $R_3$, $R_4$, $R_5$, $R_6$, and $R_8$ are each H, then $X_3$ and $X_4$ are not both halogen, or a pharmaceutically acceptable salt thereof.

Also provided herein is a compound of Formula (Ie):

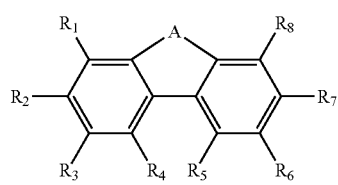

(Ie)

wherein
A is

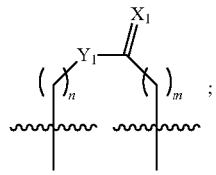

n and m are both 0; or one of n and m is 0, and the other of n and m is 1;
$X_1$ is O;
$Y_1$ is selected from NH, N—CH$_3$, N-t-Bu, N-cycloalkyl, and N-heterocycloalkyl;
$R_1$, $R_2$, $R_3$, $R_6$, $R_7$, and $R_8$ are independently selected from H, OH, OCH$_3$, OAc, NH$_2$, halogen, CN, CF$_3$, CO$_2$H, NO$_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, OR$_{10}$, NHR$_{10}$, NR$_{11}$C(O)R$_{12}$, C(O)NR$_{11}$R$_{12}$, and NR$_{11}$SO$_2$R$_{12}$;
$R_4$ and $R_5$ are independently selected from H, alkyl, and halogen;
each occurrence of $R_9$ is independently selected from OH, NH$_2$, O-alkyl, O-alkyl-O-alkyl, alkylamino, NHC(O)-alkyl, N(CH$_3$)C(O)-alkyl, NHSO$_2$-alkyl, N(CH$_3$)SO$_2$-alkyl, aryl, heteroaryl, cycloalkyl, and heterocycloalkyl;
$R_{10}$ is selected from C$_2$-C$_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, SO$_3$H, SO$_2$-alkyl, and SO$_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl;
provided that no more than two of $R_1$, $R_2$, $R_3$, $R_6$, $R_7$, and $R_8$ are OH or OCH$_3$,
if A is

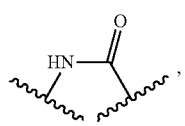 [SMILES: *NC(*)=O]

and $R_1$, $R_3$, $R_4$, $R_5$, $R_6$, and $R_8$ are each H, then $R_2$ and $R_7$ are not both OH, both OCH$_3$ or both OR$_{10}$, and
if A is

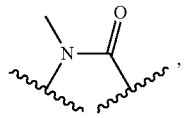 [SMILES: *C(=O)N(*)C]

and $R_1$, $R_3$, $R_4$, $R_5$, $R_6$, and $R_8$ are each H, then $R_2$ and $R_7$ are not both OR$_{10}$, or a pharmaceutically acceptable salt thereof.

Also provided herein is a compound of Formula (If):

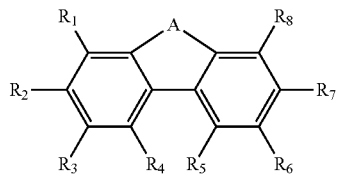

(If)

wherein
A is selected from

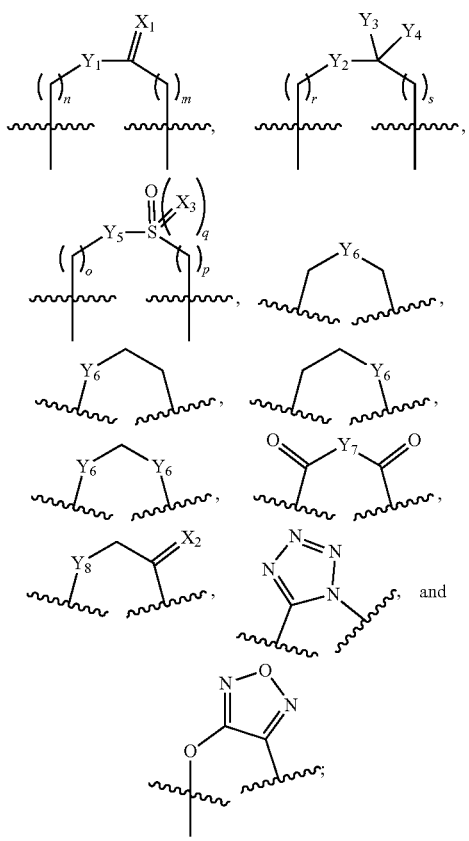

n and m are both 0; or one of n and m is 0 and the other of n and m is 1;
and p are both 0; or one of o and p is 0 and the other of o and p is 1;
q is 0 or 1;
r and s are both 0; or one of r and s is 0 and the other of r and s is 1;
$X_1$ and $X_2$ are each O;
$X_3$ is O or N(alkyl);
$Y_1$ is S;
$Y_2$ is selected from O, CH$_2$, NH, N-alkyl, S, S(O), and SO$_2$;
$Y_3$ and $Y_4$ are independently selected from H, halogen, OH, and alkyl, or together with the carbon to which they are bonded combine to form a cycloalkyl or cycloheteroalkyl;
$Y_5$ is selected from CH$_2$, NH, N-alkyl, N-aralkyl, N-cycloalkyl, and N-heterocycloalkyl;
Each occurrence of $Y_6$ is independently selected from O, S, S(O), SO$_2$, NH, N-alkyl, N-alkylaryl, and N-cycloalkyl;

$Y_7$ is selected from O, NH and N-alkyl;
$Y_8$ is selected from O and S;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
$R_4$ and $R_5$ are independently selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and provided that if $Y_2$ is $CH_2$, one of $Y_3$ or $Y_4$ is not H, or $Y_3$ or $Y_4$ together with the carbon to which they are bonded combine to form a cycloalkyl or heterocycloalkyl, and if $Y_2$ is O, then one of r and s is 0 and the other of r and s is 1, or a pharmaceutically acceptable salt thereof.

Also provided herein is a compound of Formula (Ig):

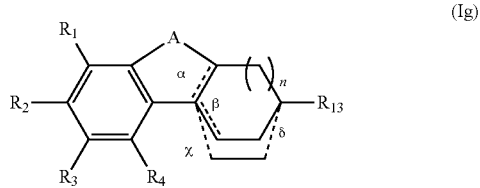

(Ig)

wherein
α and β, χ, and δ are each bonds which are present or absent, provided that when α is present, then β is absent and when β is present, then α is absent, and when either of α and β are present then χ and δ are each absent;
n is 0 or 1;
A is selected from

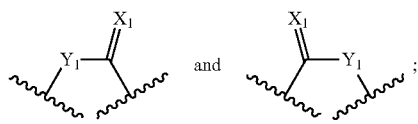

$X_1$ is O;
$Y_1$ is selected NH, N-alkyl, N-cycloalkyl, and O; $R_1$, $R_2$, and $R_3$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$, $R_4$ is selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl;
$R_{13}$ is selected from H, OH, $OCH_3$, OAc, $NH_2$, halogen, CN, $CF_3$, $CO_2H$, $NO_2$, and NHAc, or a pharmaceutically acceptable salt thereof.

Also provided herein is a compound of Formula (Ih):

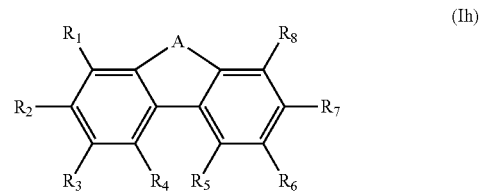

(Ih)

wherein
A is selected from

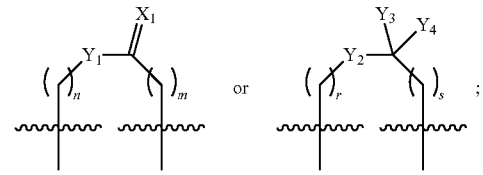

n and m are both 0; or one of n and m is 0 and the other of n and m is 1;
r and s are both 0; or one of r and s is 0 and the other of r and s is 1;
$X_1$ is O;
$Y_1$ is selected from O, NH, N-alkyl, and N-cycloalkyl;
$Y_2$ is O;
$Y_3$ and $Y_4$ are independently selected from H, halogen, and alkyl, or together with the carbon to which they are bonded combine to form a cycloalkyl or cycloheteroalkyl;
$R_1$, $R_4$, $R_5$ and $R_8$ are independently selected from H and halogen; $R_3$ and $R_6$ are independently selected from H, CN, OH, $CF_3$, halogen, and alkyl;
one of $R_2$ and $R_7$ is $NH_2$, $NHCH_3$, and $N(CH_3)_2$ and the other of $R_2$ and $R_7$ is H, halogen, $OCH_3$, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;

each occurrence of $R_{11}$ is selected from H and alkyl;

each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and provided that if A is

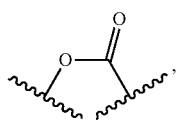 [SMILES: *OC(*)=O]

$R_1$, $R_3$, $R_4$, $R_5$, $R_6$, and $R_8$ are each H, and $R_7$ is $NH_2$, then $R_2$ is not OH.

Another aspect of the invention relates to a method of treating a neuronal disease or a mitochondrial disease, comprising administering to a subject in need thereof an effective amount of the compound of Formula (Ii):

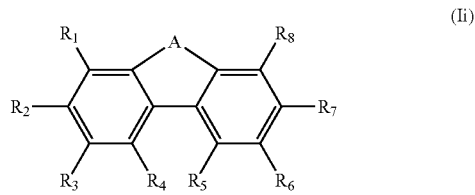

wherein
A is selected from

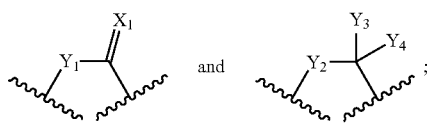

$X_1$ is O;
$Y_1$ is selected from O and NH;
$Y_2$ is O;
$Y_3$ and $Y_4$ are independently selected from H and halogen;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
$R_4$ and $R_5$ are independently selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
$R_{11}$ is selected from H and alkyl; and
$R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl,
or a pharmaceutically acceptable salt thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features, objects, and advantages of the invention will be apparent from the detailed description, and from the claims.

DETAILED DESCRIPTION

Definitions

Figure 1:
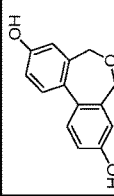
FIG. 1: A table summarizing anti-inflammatory assay (anti-inflammation (IL-6 MSD): Efficacy at 50 μM (%): Score at primary screening for the inhibition of IL-6 release in RAW macrophages. 0%=DMSO; 100%=no IL-6 detected); mitophagy assay (mitophagy (TOM20): Efficacy at 50 μM (%): Score at primary screening for the induction of mitophagy in C2C12 myoblasts. 0%=DMSO; 100%=Urolithin A); and cell efficacy assay (ATP content (Cell-Titer Glo): Efficacy at 50 μM (%): Score at primary screening for ATP content in C2C12 myoblasts. Marker of both cell division and cell death. 0%=DMSO; 100% no cells alive left) data for exemplary compounds of the invention.
Figure 1:
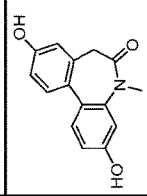
Figure 1:
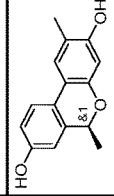
Figure 1:
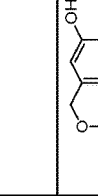
Figure 1:
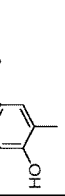
Figure 1:
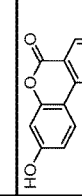
Figure 1:
Figure 1:
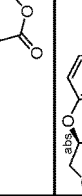
Figure 1:
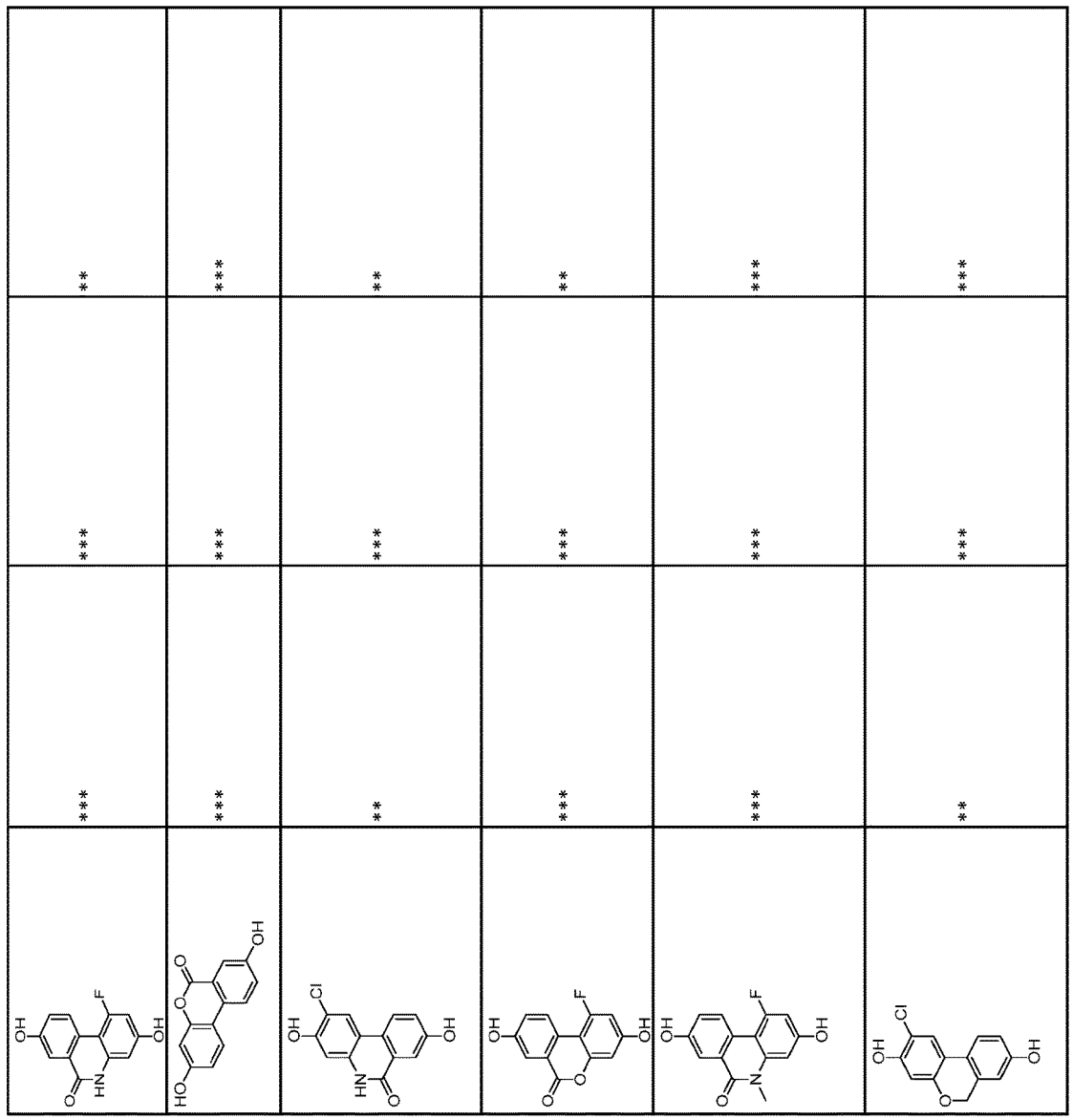
Figure 1:
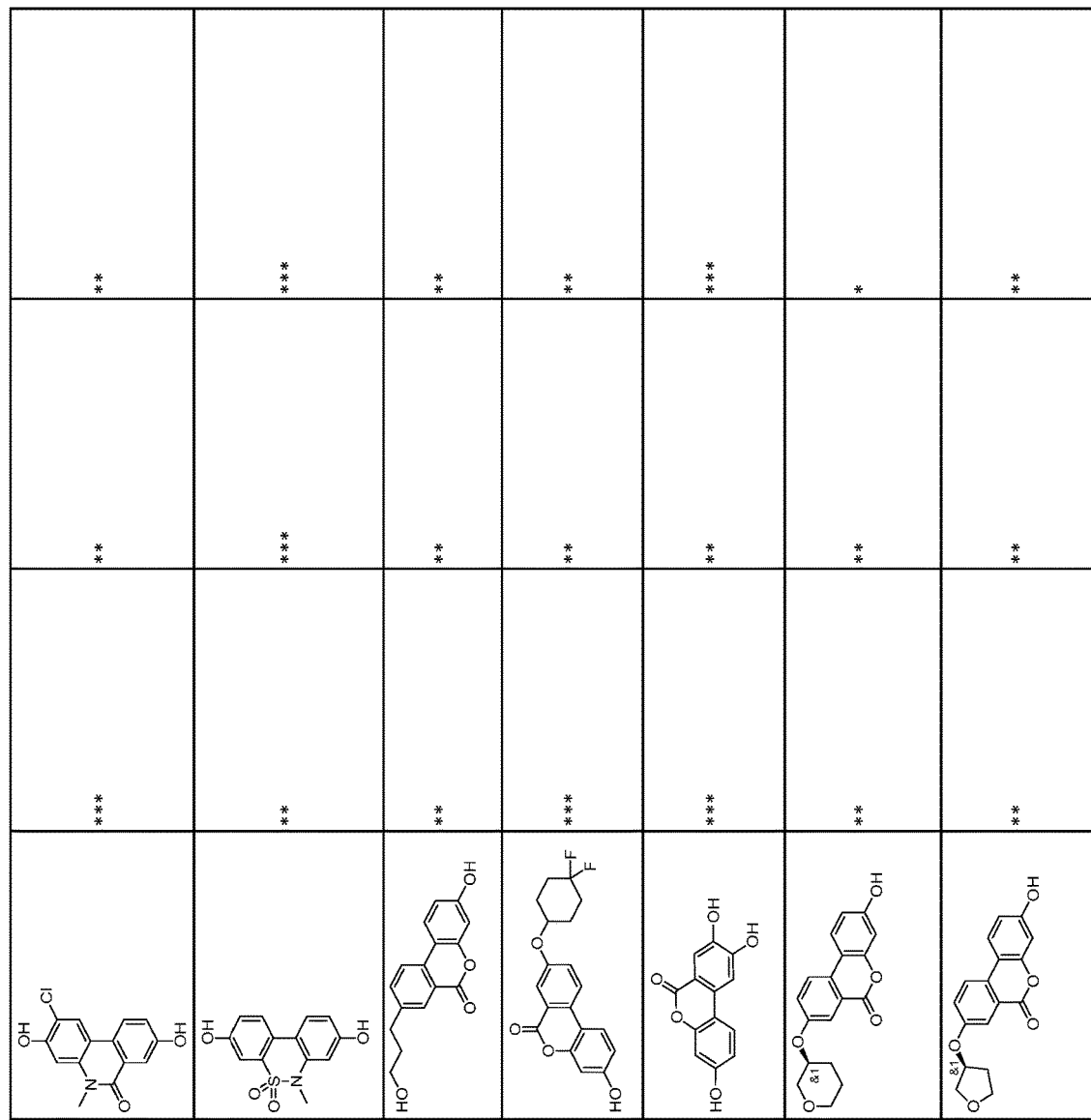
Figure 1:
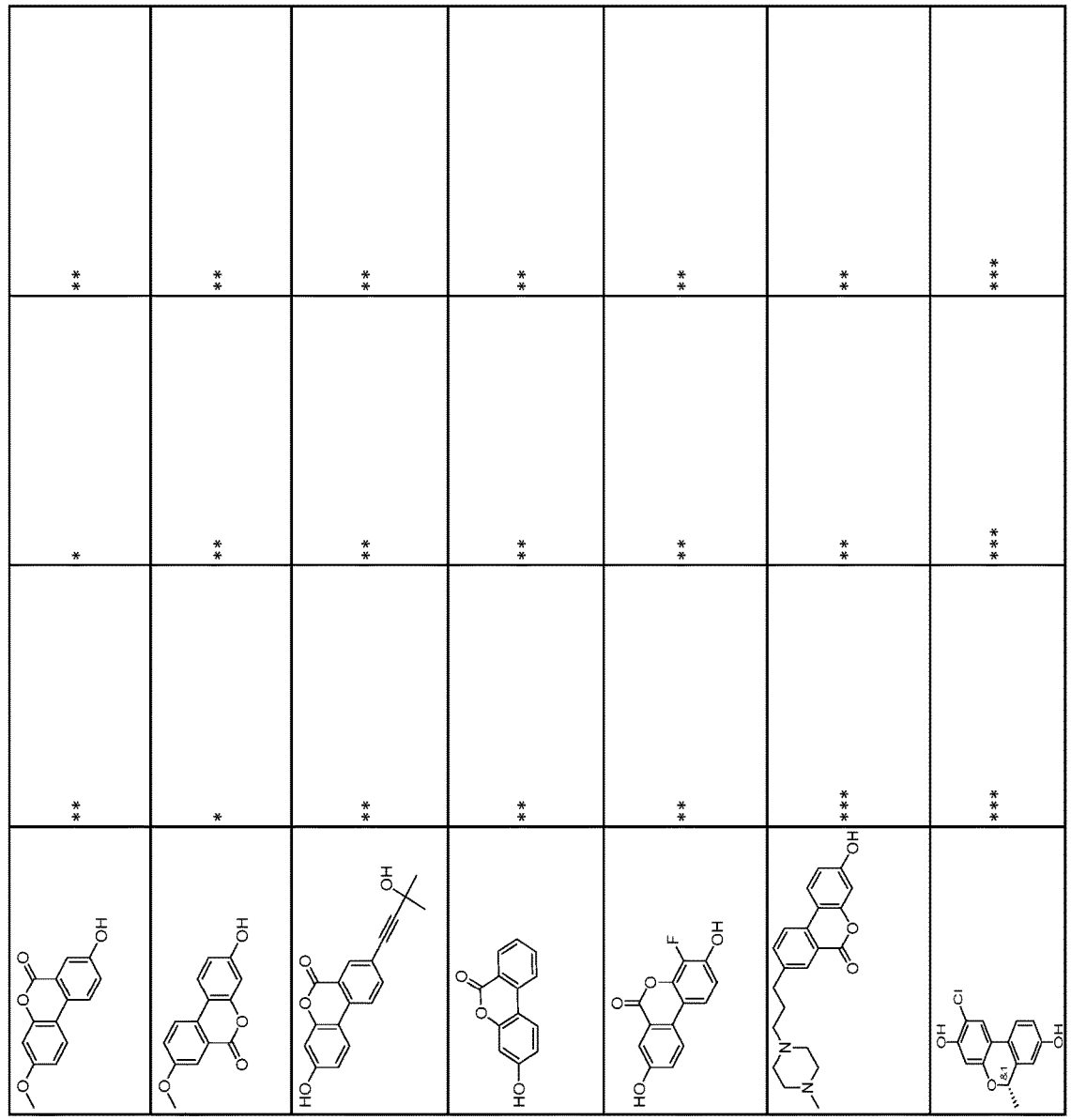
Figure 1:
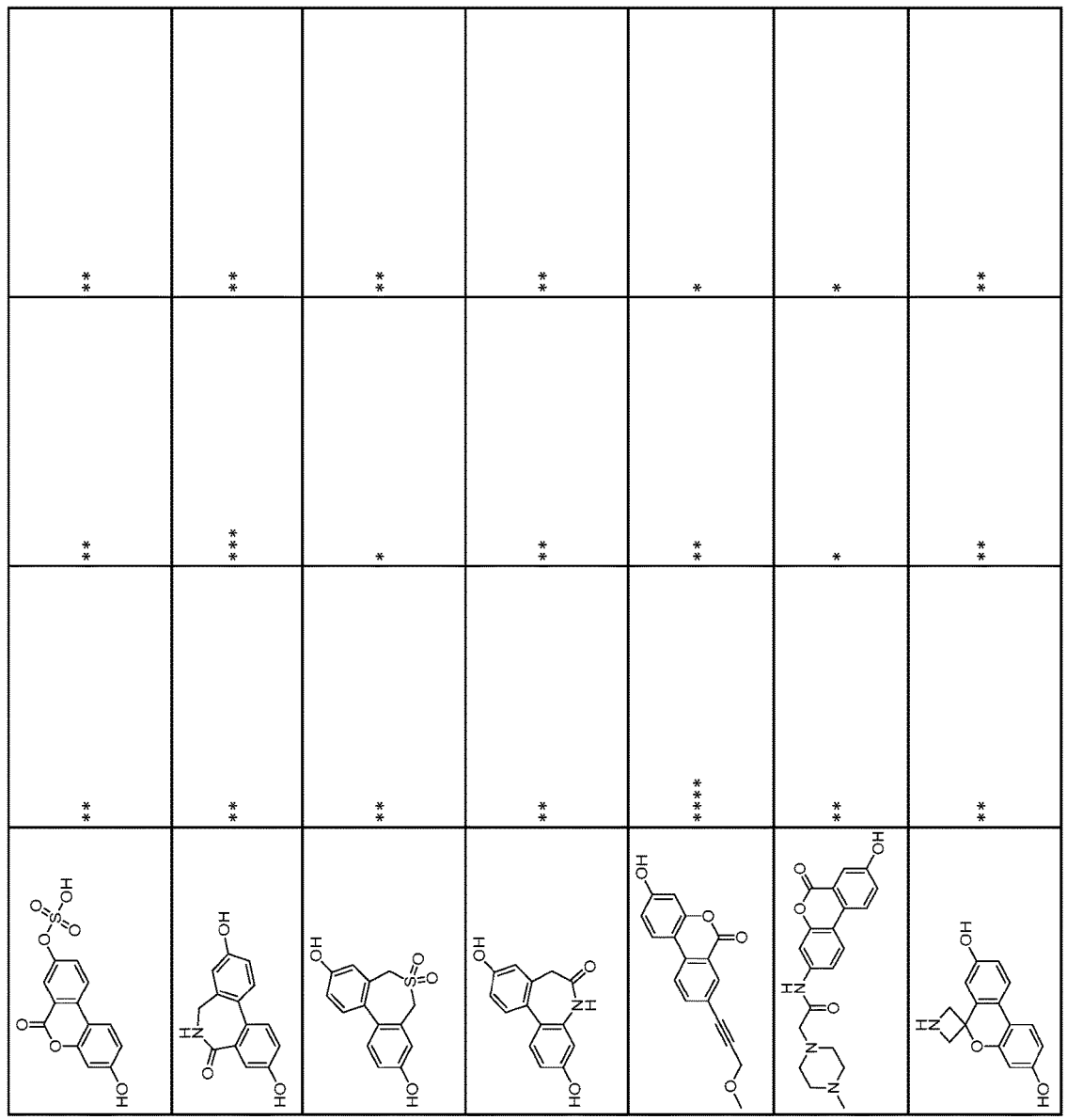
Figure 1:
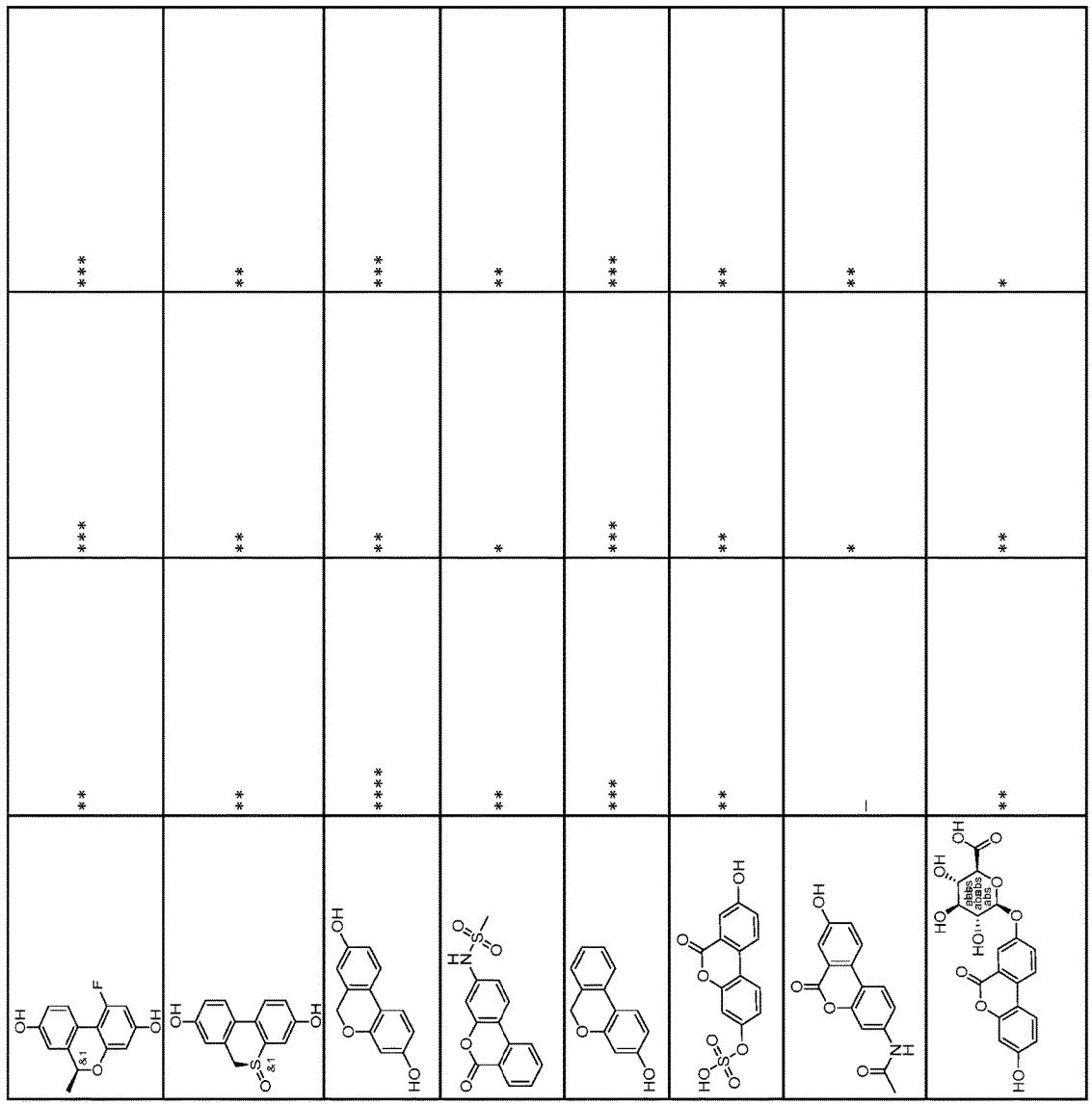
Figure 1:
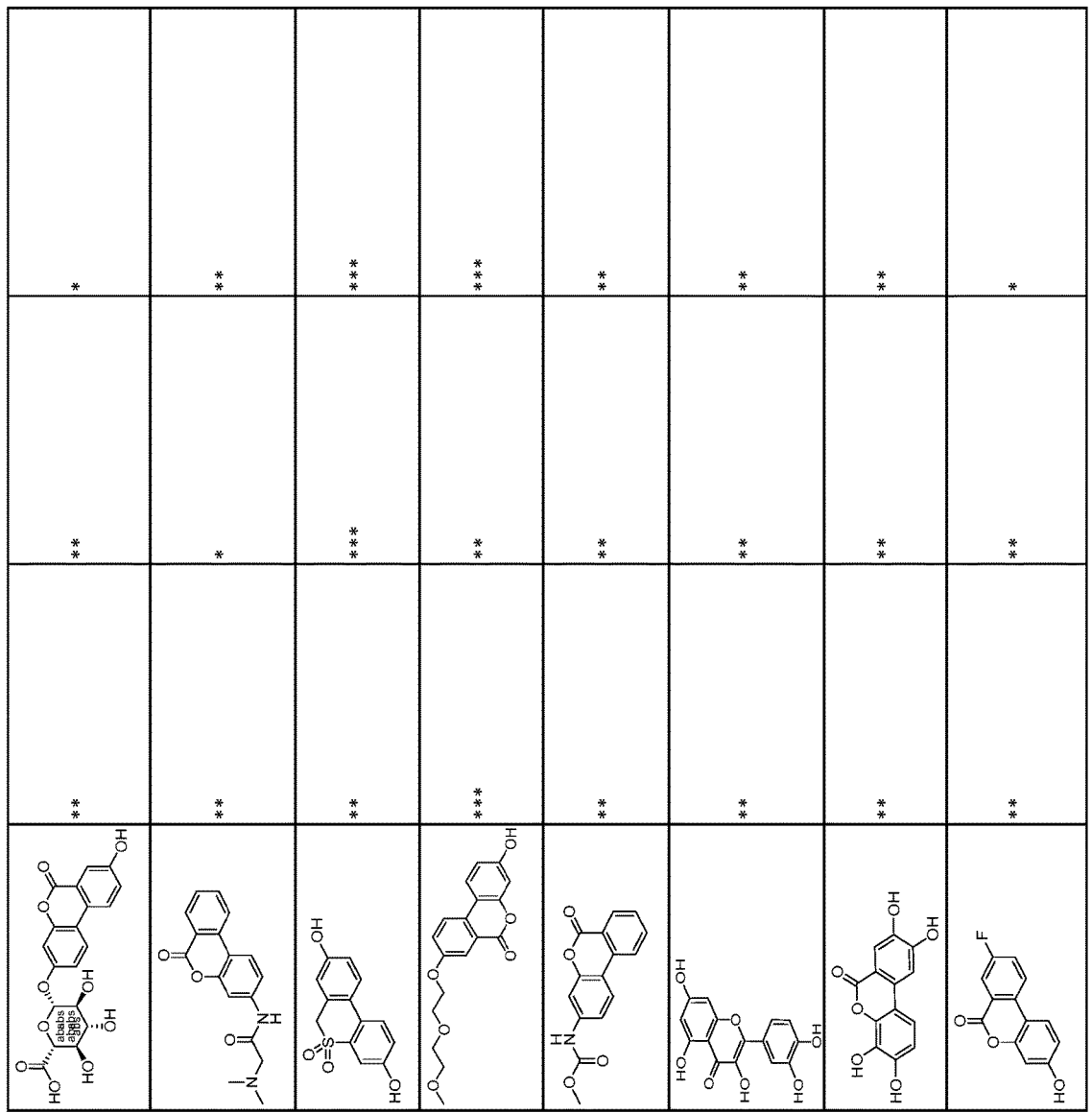
Figure 1:
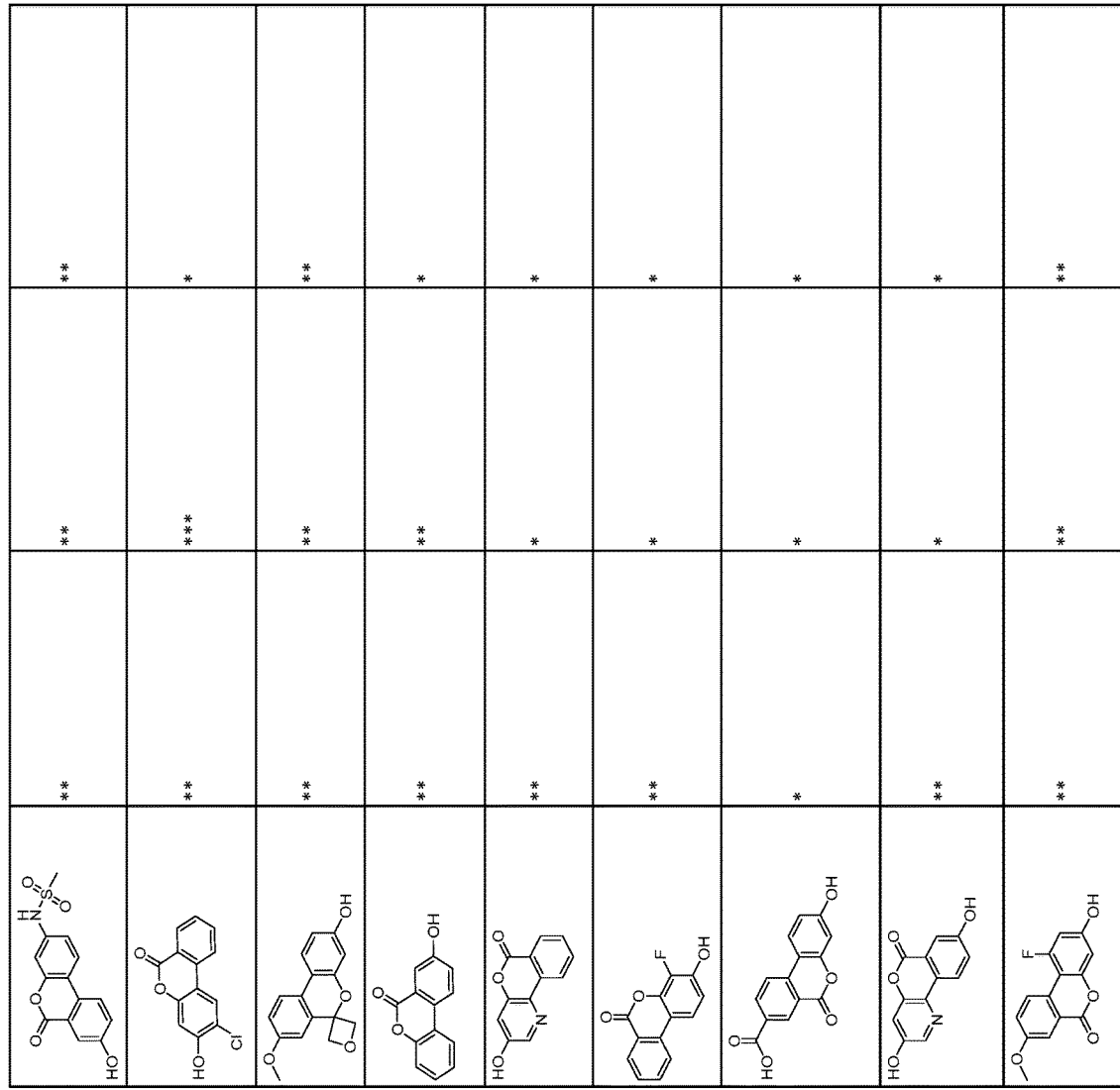
Figure 1:
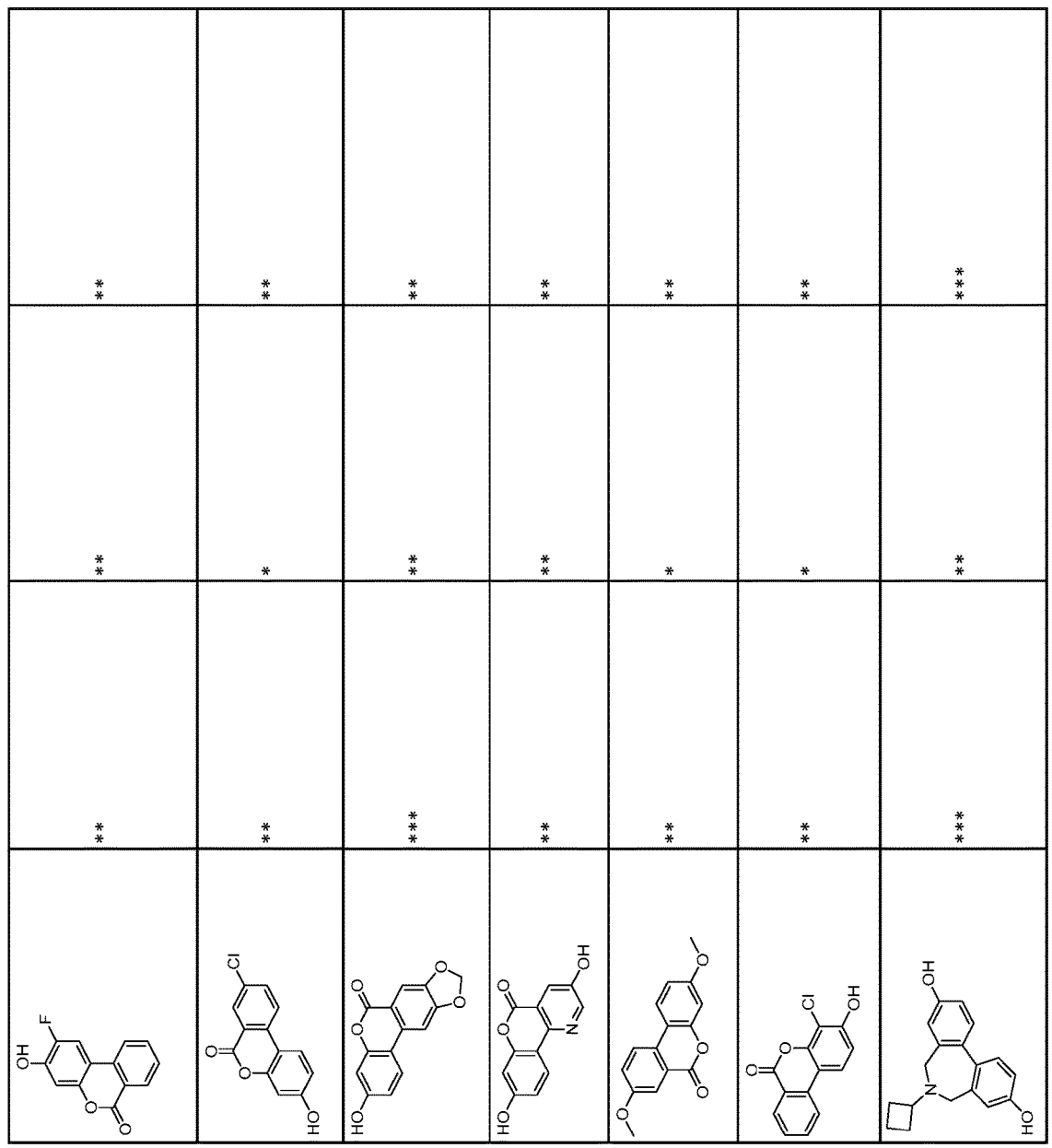
Figure 1:
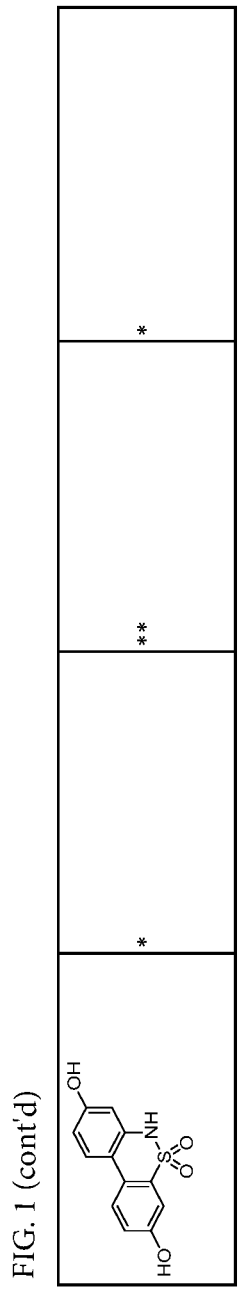
Figure 2:
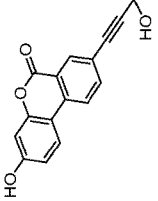
FIG. 2: A table summarizing solubility assay (Kinetic solubility: C (μM): Kinetic solubility measured in water); and pharmacokinetic assay (HLM: CLint (μL/min/mg protein): Intrinsic clearance measured in human liver microsomes. Indicative of Phase I metabolism; MLM: CLint (uL/min/mg protein): Intrinsic clearance measured in mouse liver microsomes. Indicative of Phase I metabolism; Hepatocytes: CLint (μL/min/1 Mil cells): Intrinsic clearance measured in humans intact hepatocytes. Indicative of Phase I and II metabolism) data for exemplary compounds of the invention.
Figure 2:
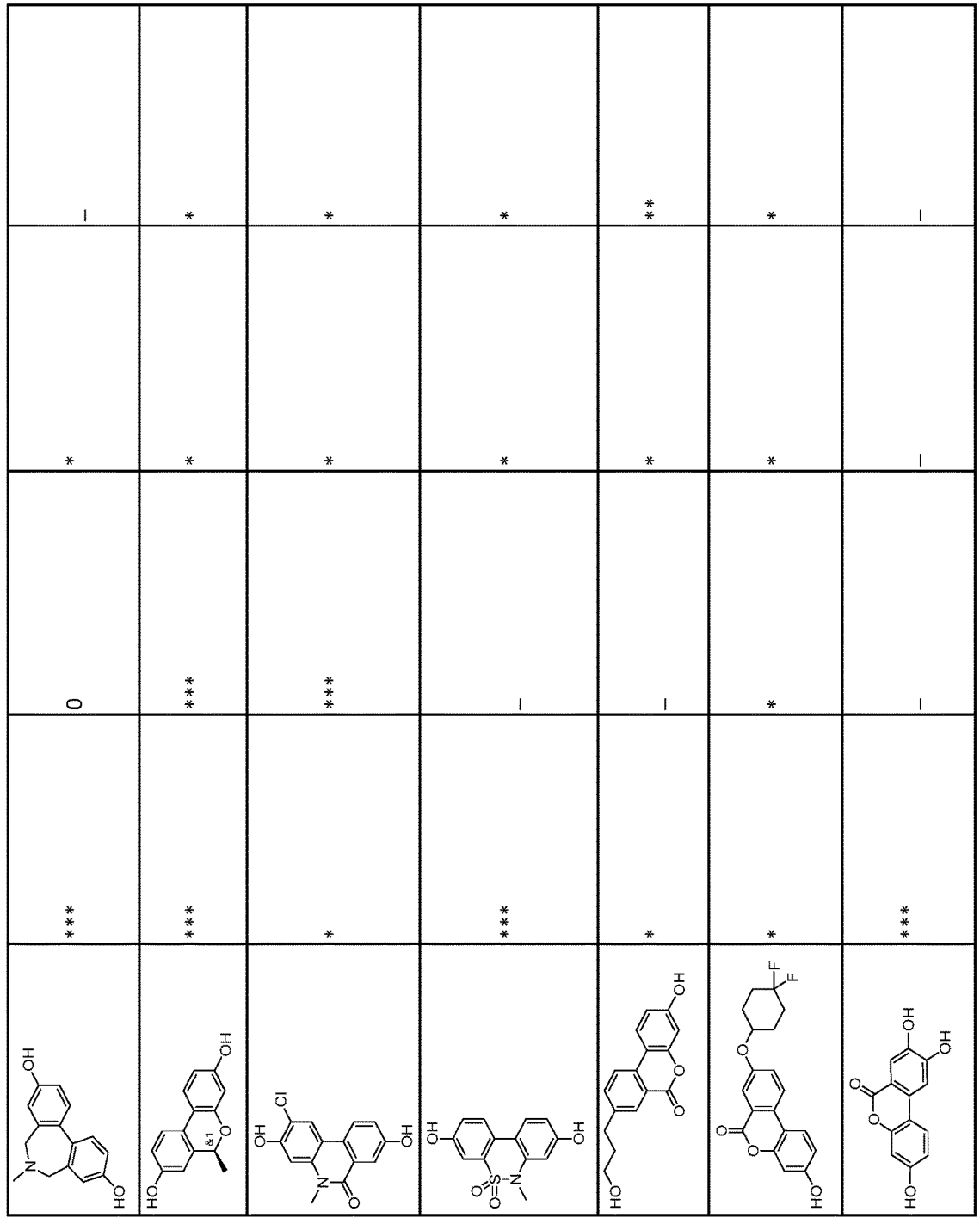
Figure 2:
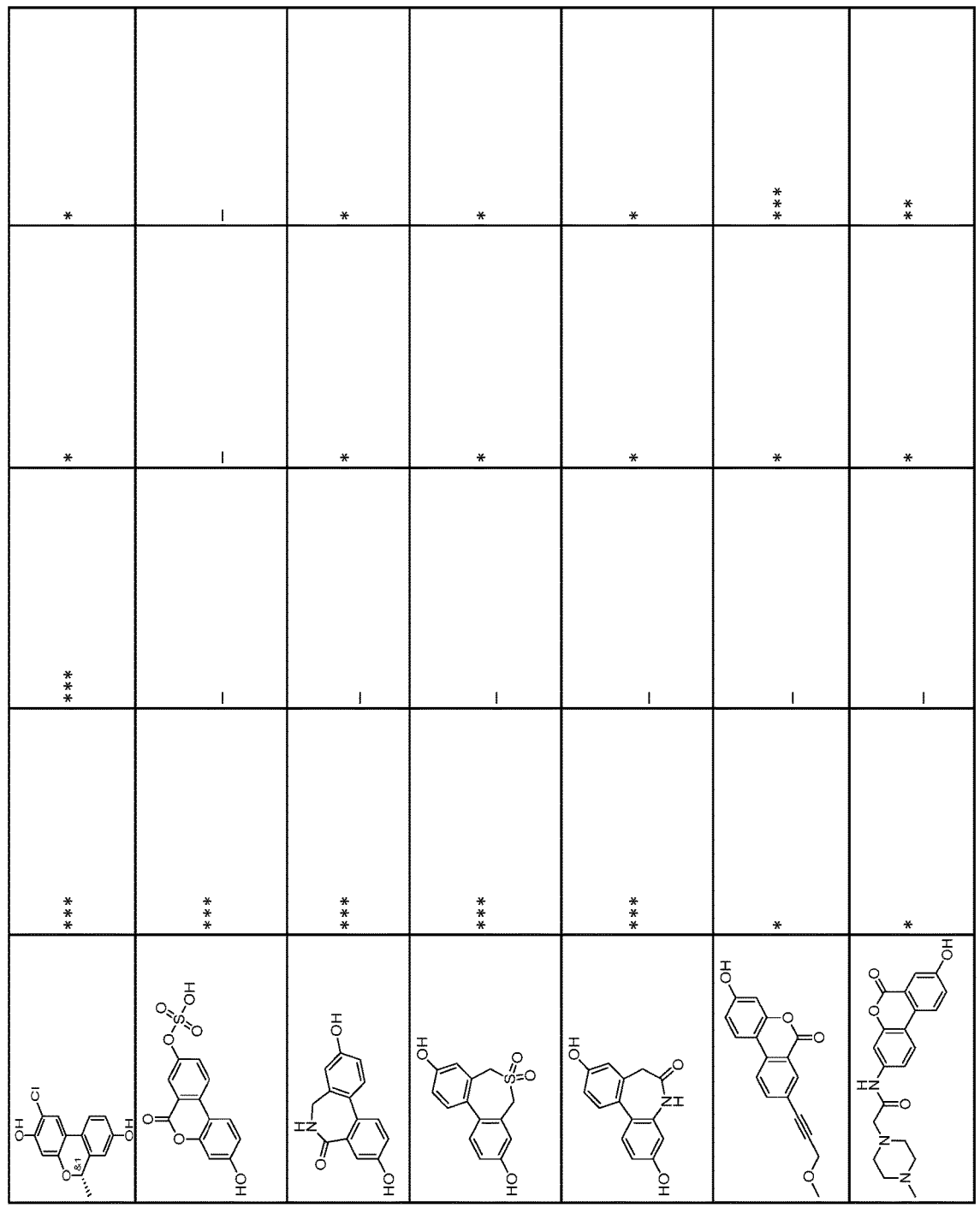
Figure 2:
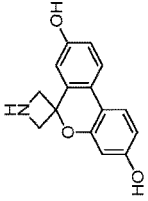
Figure 2:
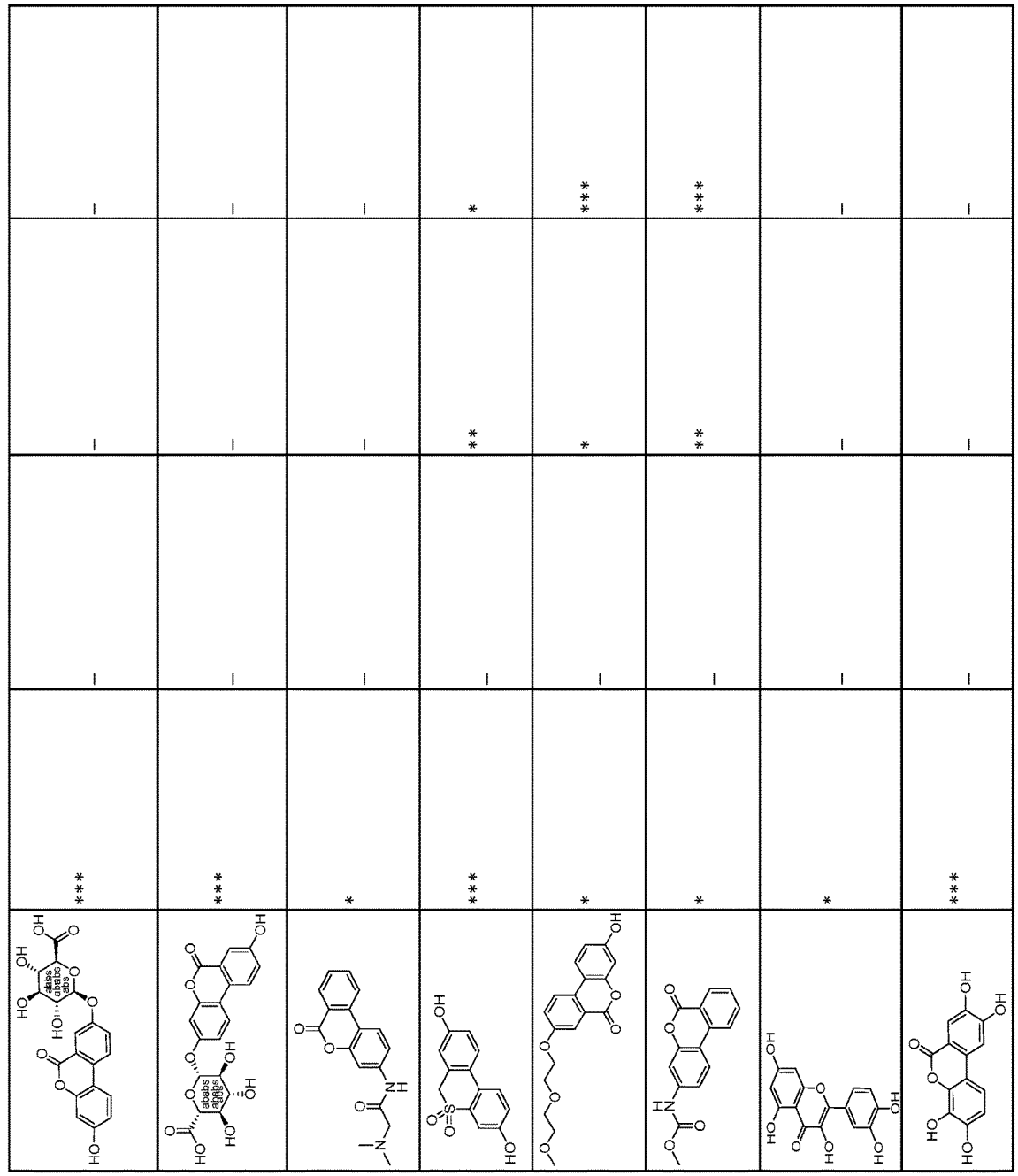
Figure 2:
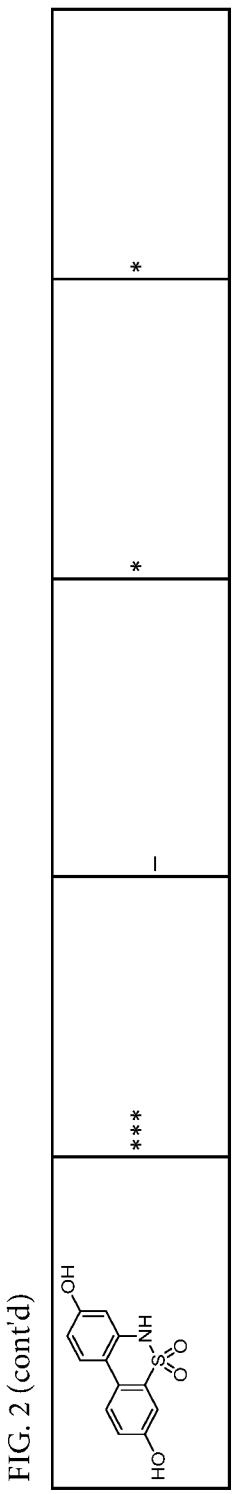
Figure 3:
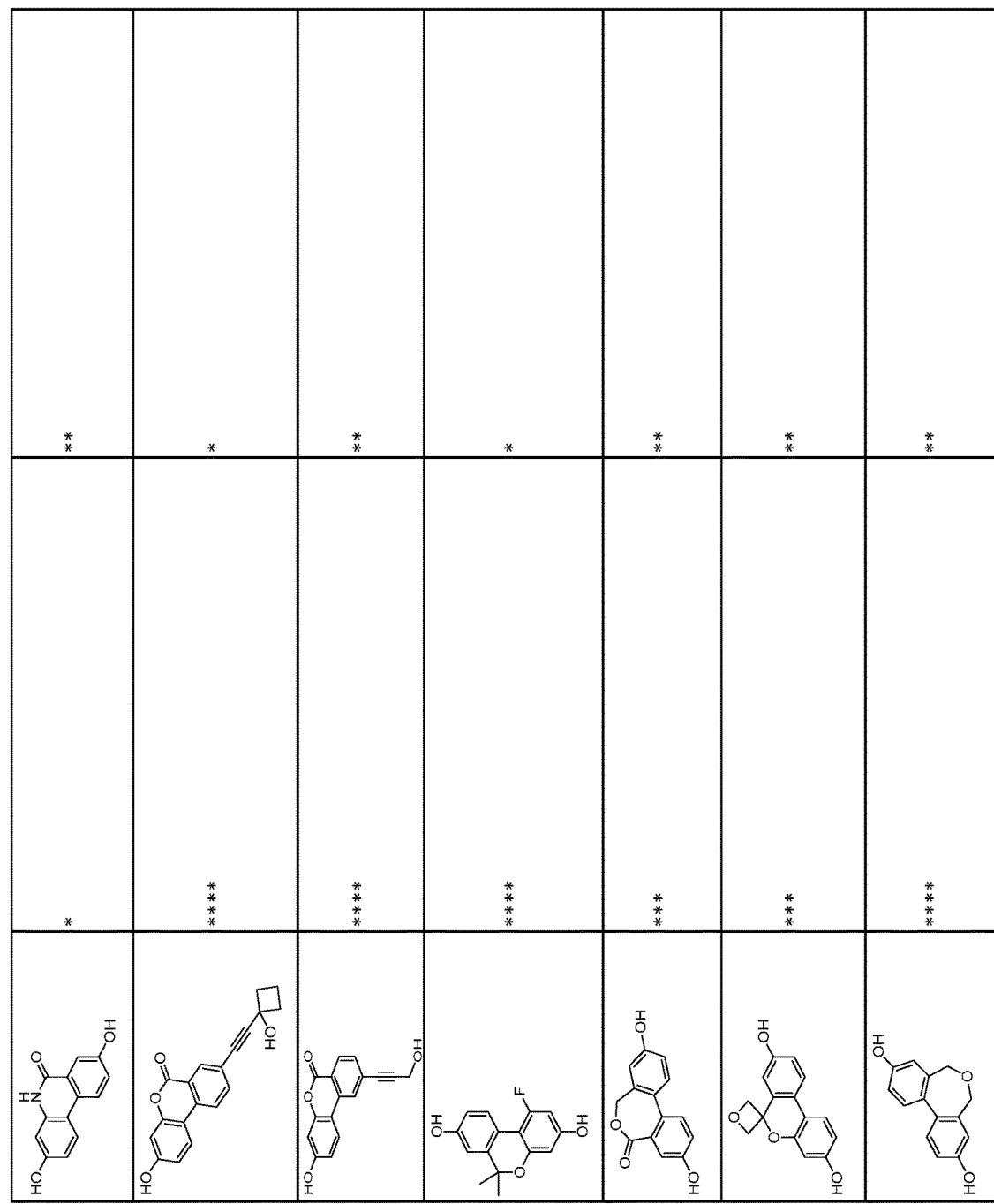
FIG. 3: A table summarizing respiratory assay (Respiration in myotubes: Max Efficacy (%): Score at secondary screening for basal respiration in C2C12 myotubes. 0%=DMSO; 100%=Urolithin A; Respiration in myotubes: Conc. of max efficacy (μM): Concentration at which maximal efficacy was observed in C2C12 myotubes; Respiration in myotubes: Signs of toxicity in C2C12 myotubes) data for exemplary compounds of the invention.
Figure 3:
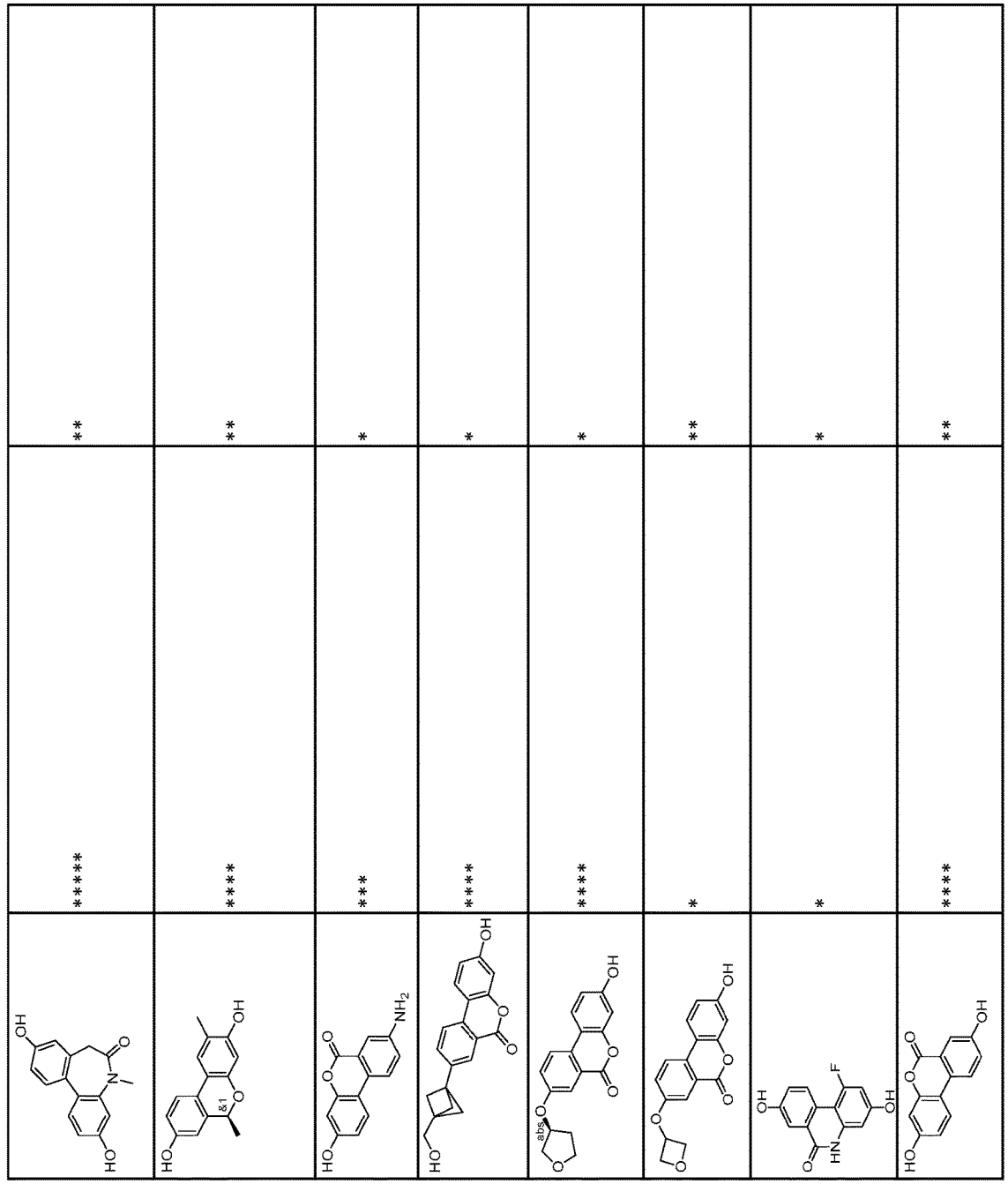
Figure 3:
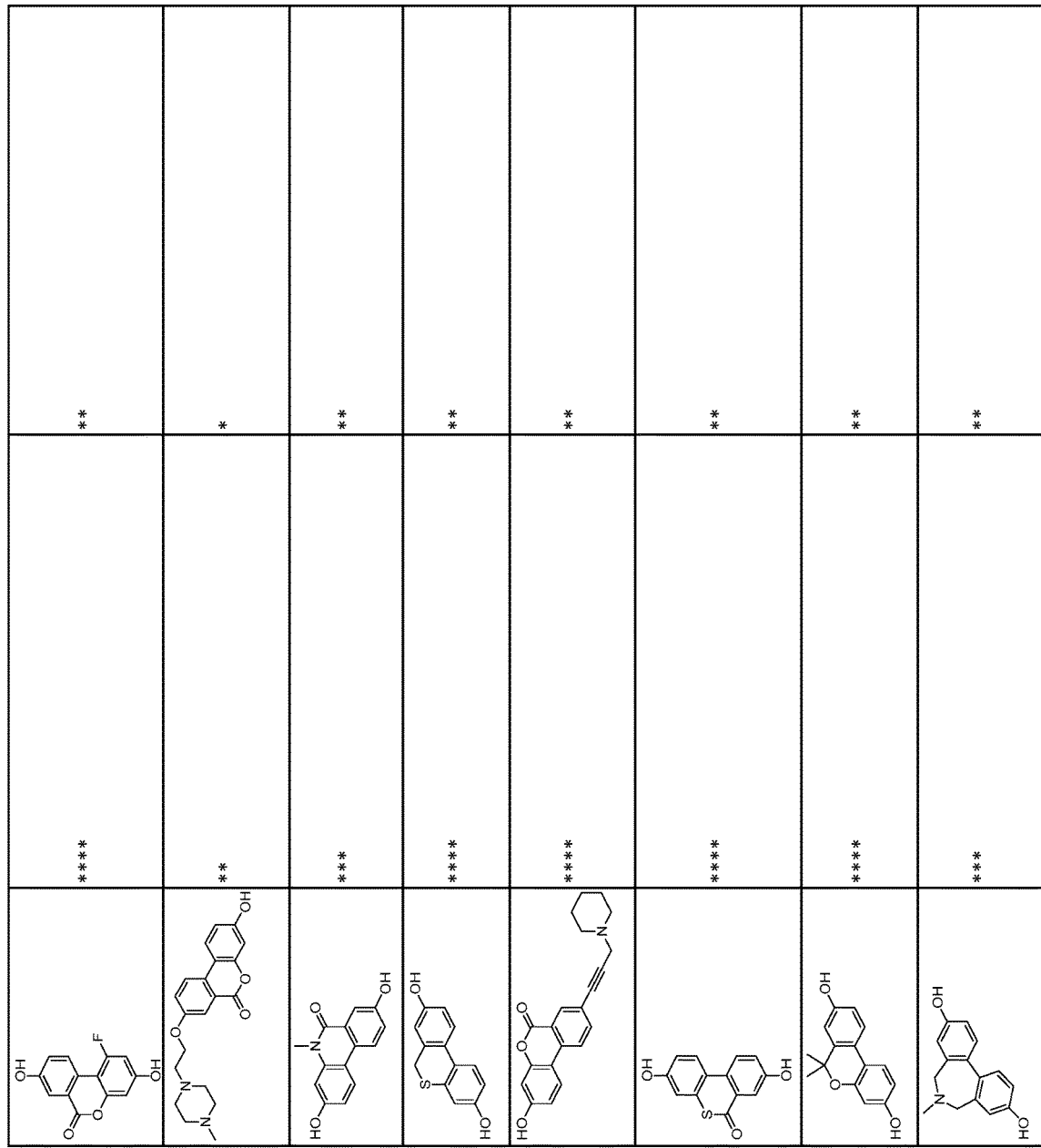
Figure 3:
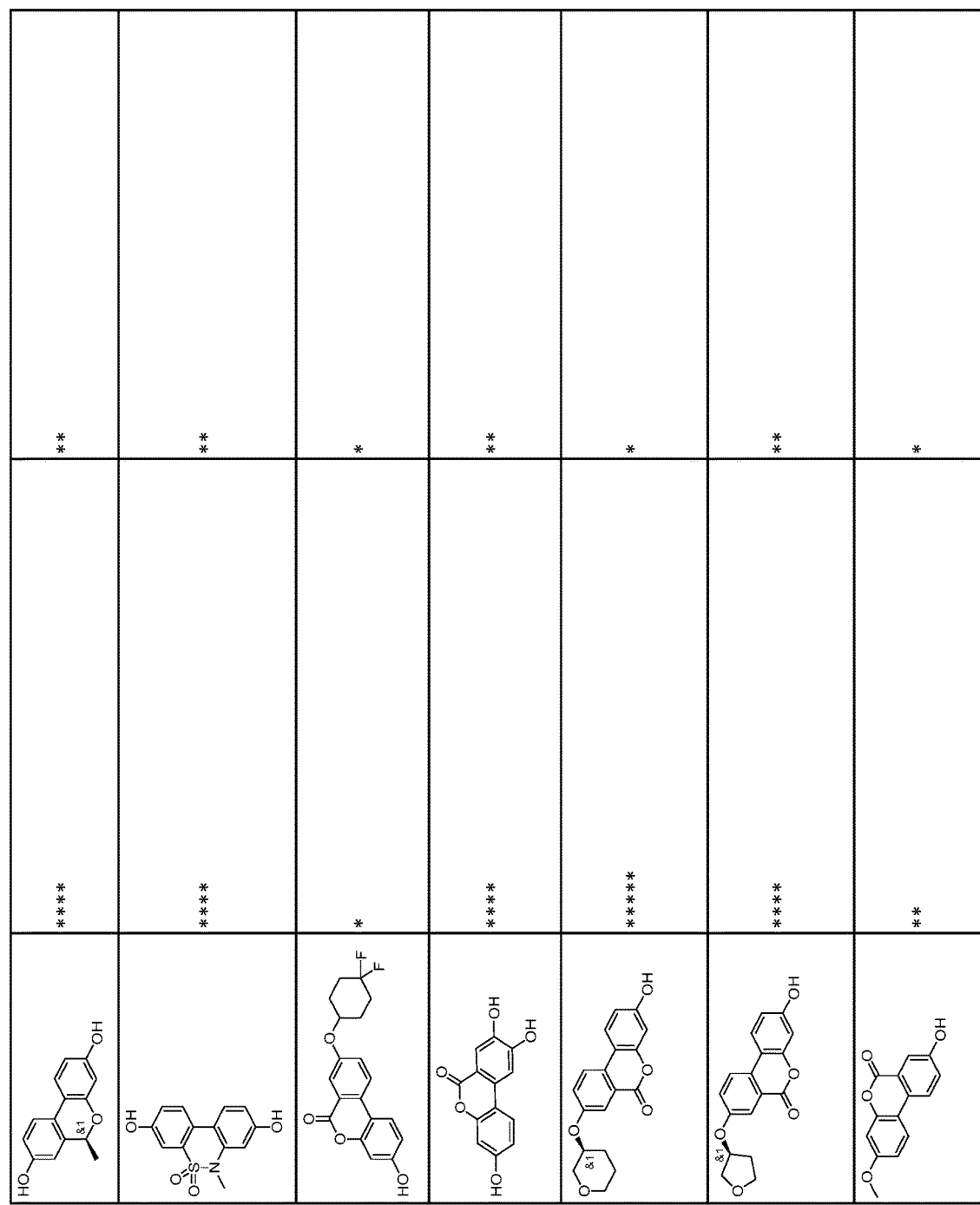
Figure 3:
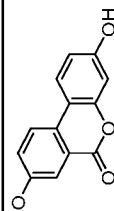
Figure 4:
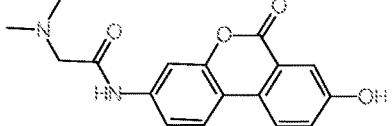
FIG. 4: A table summarizing additional anti-inflammatory assay (anti-inflammation (IL-6 MSD): Efficacy at 50 μM (%): Score at primary screening for the inhibition of IL-6 release in RAW macrophages. 0%=DMSO; 100%=no IL-6 detected); mitophagy assay (mitophagy (TOM20): Efficacy at 50 μM (%): Score at primary screening for the induction of mitophagy in C2C12 myoblasts. 0%=DMSO; 100%=Urolithin A), max efficacy %, and max efficacy concentration; cell efficacy assay (ATP content (Cell-Titer Glo): Efficacy at 50 μM (%): Score at primary screening for ATP content in C2C12 myoblasts. Marker of both cell division and cell death. 0%=DMSO; 100% no cells alive left) data for exemplary compounds of the invention.
Figure 4:
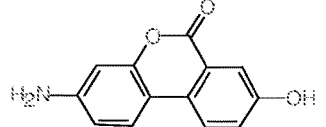
Figure 4:
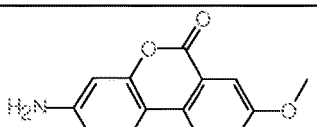
Figure 4:
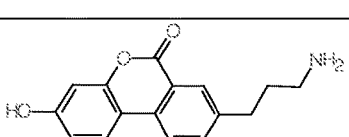
Figure 4:
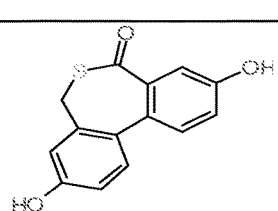
Figure 4:
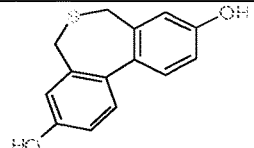
Figure 4:
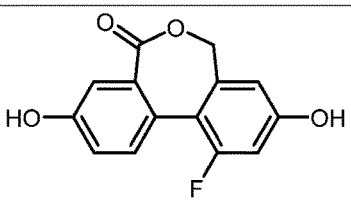
Figure 4:
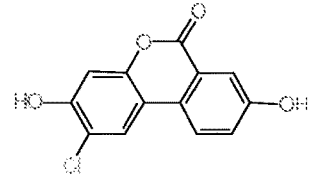
Figure 4:
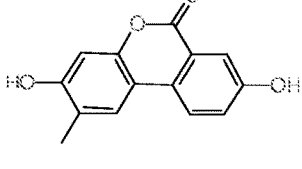
Figure 4:
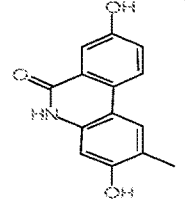
Figure 4:
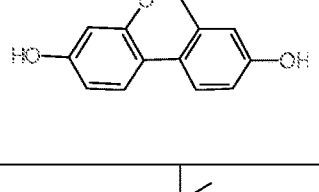
Figure 4:
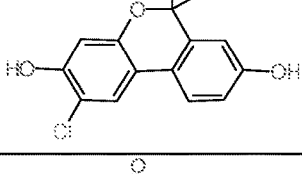
Figure 4:
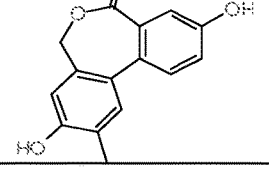
Figure 4:
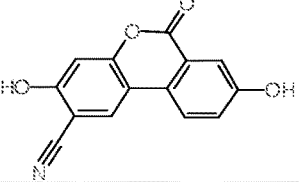
Figure 4:
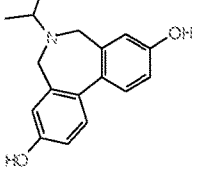
Figure 4:
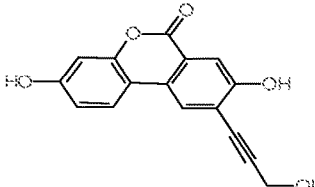
Figure 4:
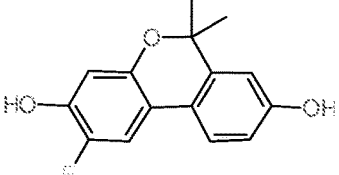
Figure 4:
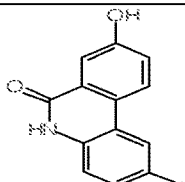
Figure 4:
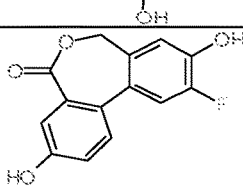
Figure 4:
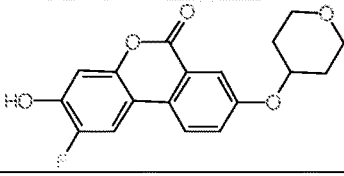
Figure 4:
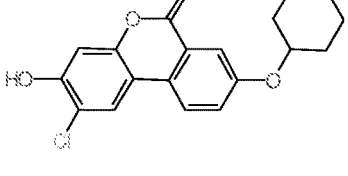
Figure 4:
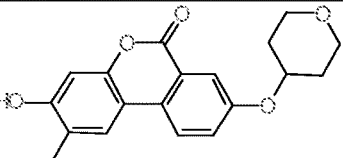
Figure 4:
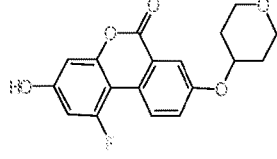
Figure 4:
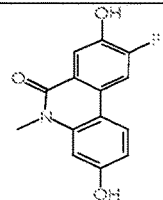
Figure 4:
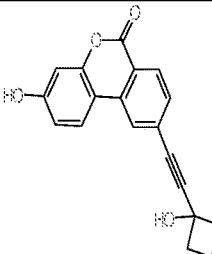
Figure 4:
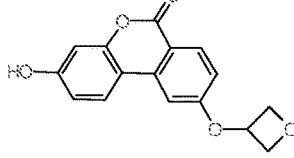
Figure 4:
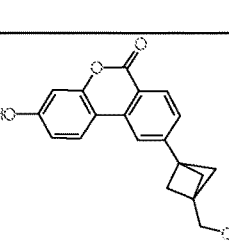
Figure 4:
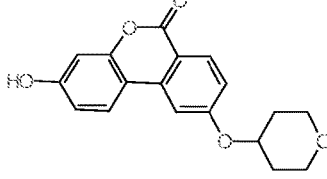
Figure 4:
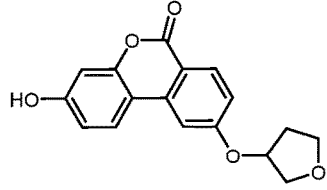
Figure 4:
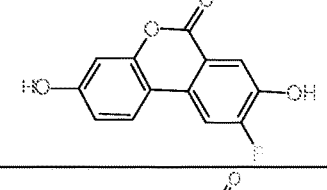
Figure 4:
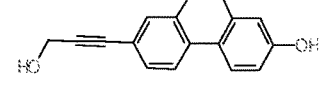
Figure 4:
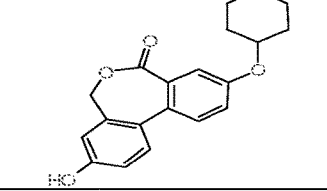
Figure 4:
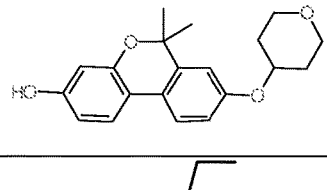
Figure 4:
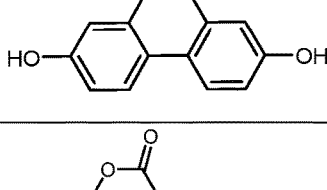
Figure 4:
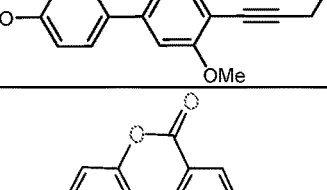
Figure 4:
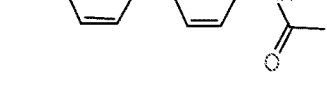
Figure 4:
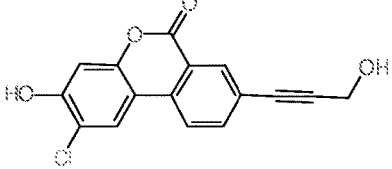
Figure 4:
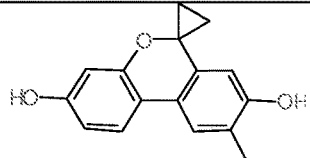
Figure 4:
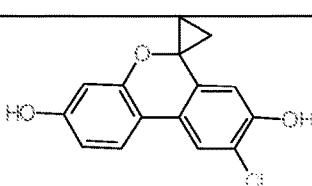
Figure 4:
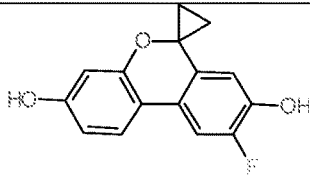
Figure 4:
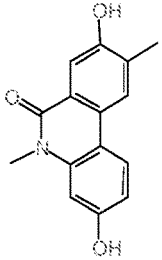
Figure 4:
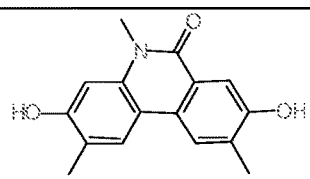
Figure 4:
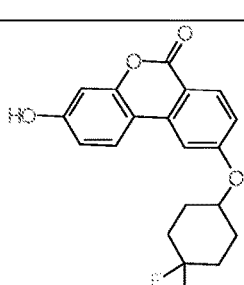
Figure 4:
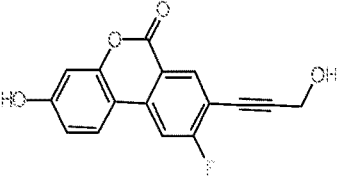
Figure 4:
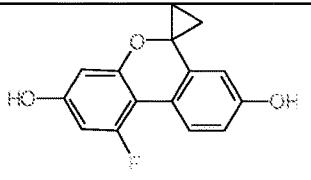
Figure 4:
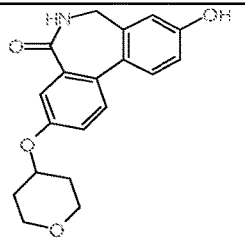
Figure 4:
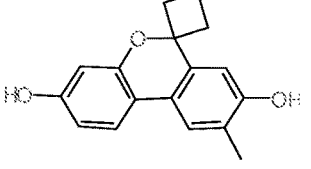
Figure 4:
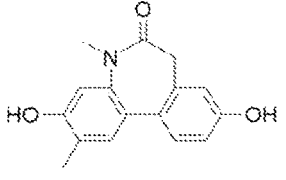
Figure 4:
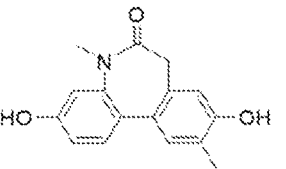
Figure 4:
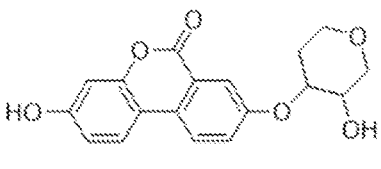
Figure 4:
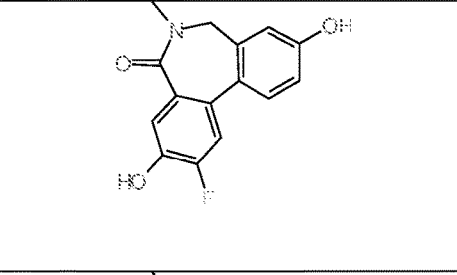
Figure 4:
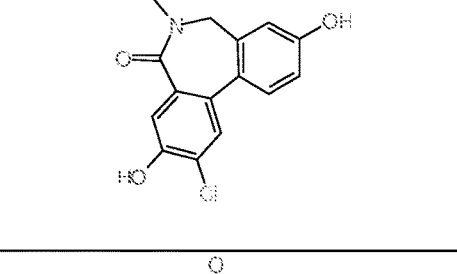
Figure 4:
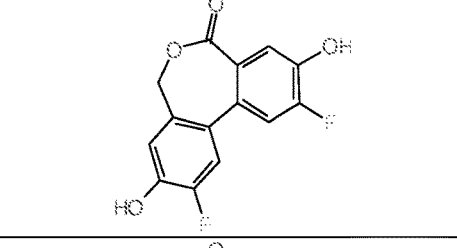
Figure 4:
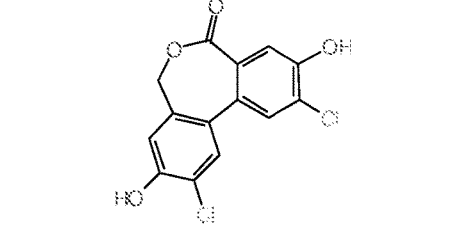
Figure 4:
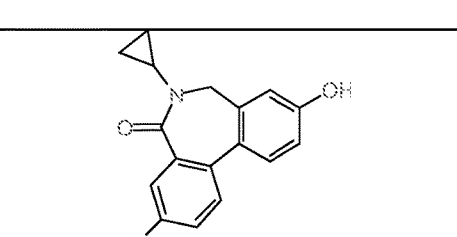
Figure 4:
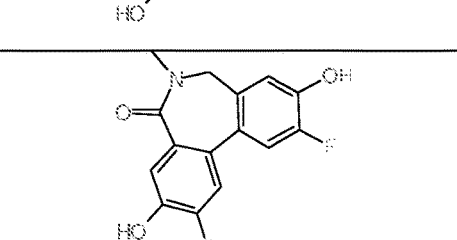
Figure 4:
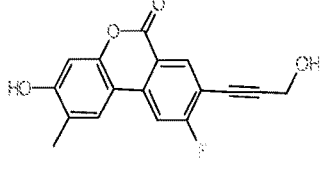
Figure 4:
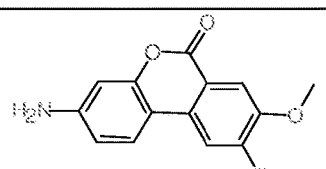
Figure 4:
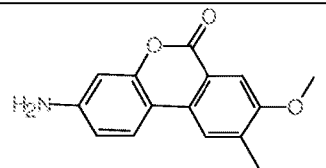
Figure 4:
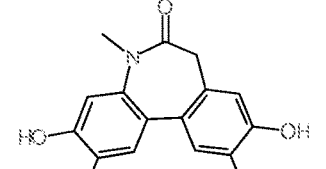
Figure 4:
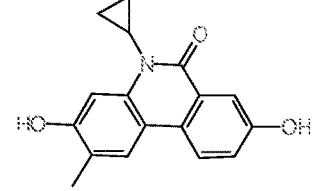
Figure 4:
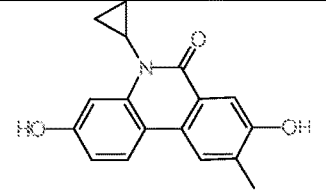
Figure 4:
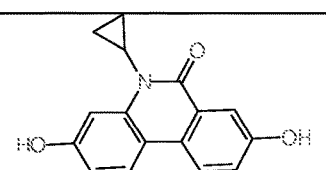
Figure 4:
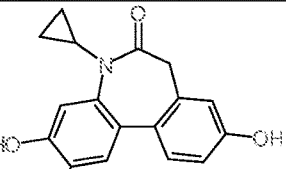
Figure 4:
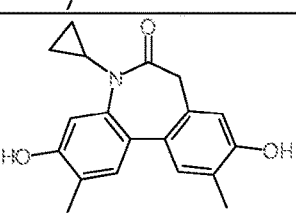
Figure 4:
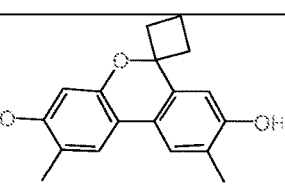
Figure 4:
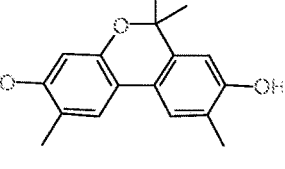
Figure 4:
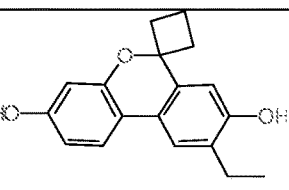
Figure 4:
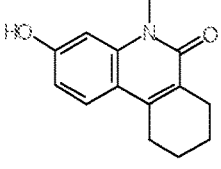
Figure 5:
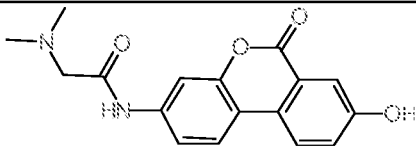
FIG. 5: A table summarizing additional solubility assay (Kinetic solubility: C (μM): Kinetic solubility measured in water) data.
Figure 5:
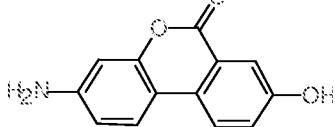
Figure 5:
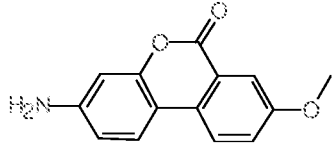
Figure 5:
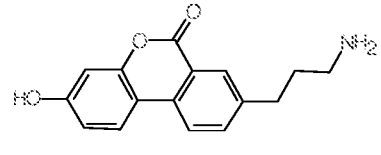
Figure 5:
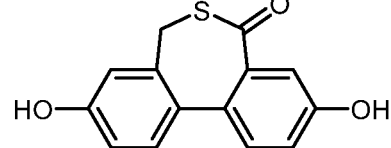
Figure 5:
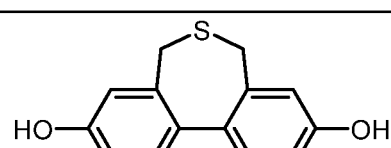
Figure 5:
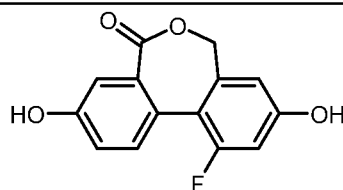
Figure 5:
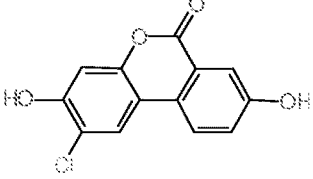
Figure 5:
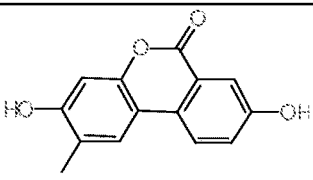
Figure 5:
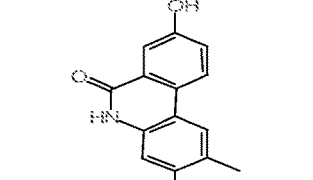
Figure 5:
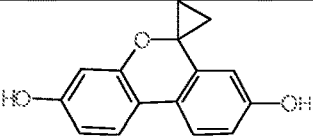
Figure 5:
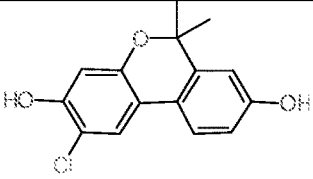
Figure 5:
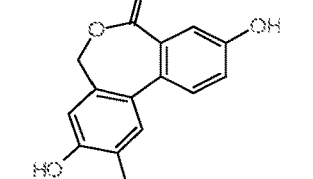
Figure 5:
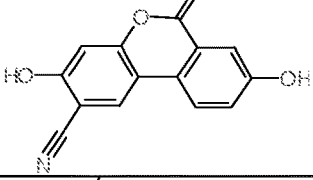
Figure 5:
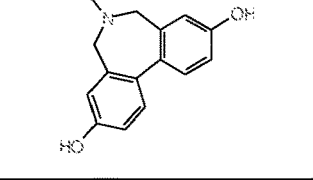
Figure 5:
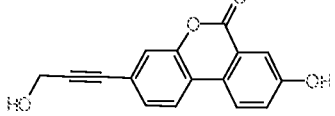
Figure 5:
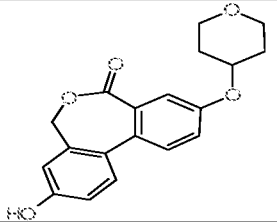
Figure 5:
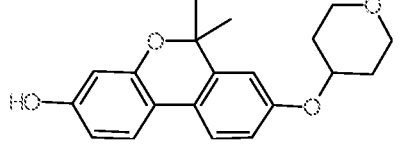
Figure 5:
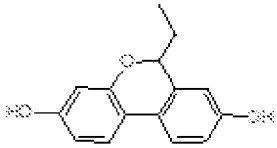
Figure 5:
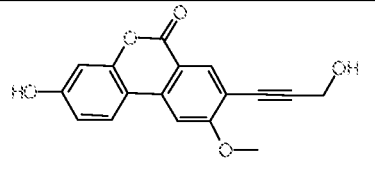
Figure 5:
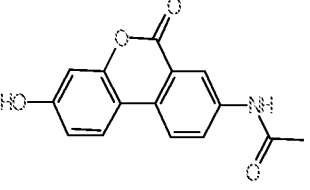
Figure 5:
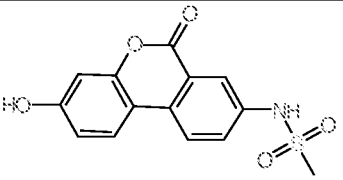
Figure 5:
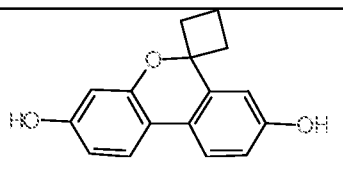
Figure 5:
Figure 5:
Figure 5:
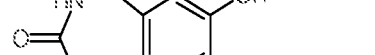
Figure 5:
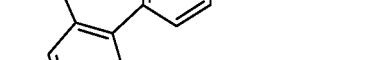
Figure 5:
Figure 5:
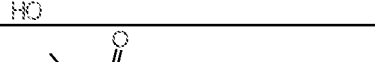
Figure 5:
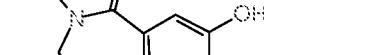
Figure 5:
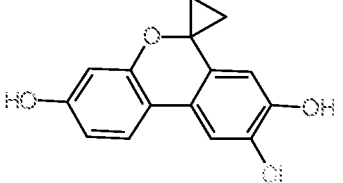
Figure 5:
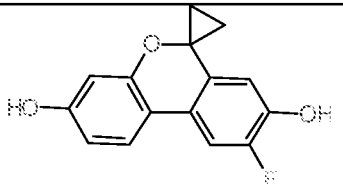
Figure 5:
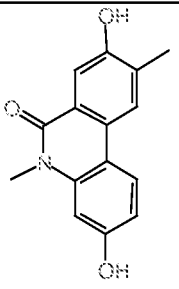
Figure 5:
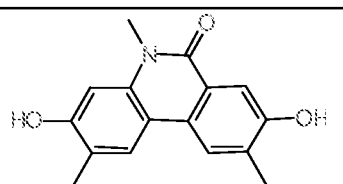
Figure 5:
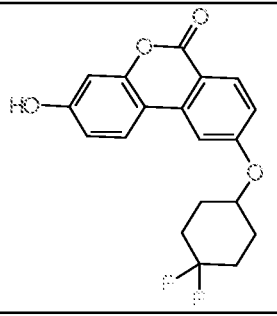
Figure 5:
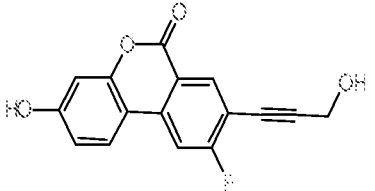
Figure 5:
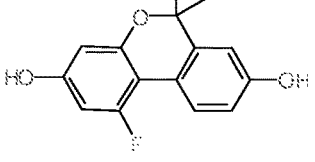
Figure 5:
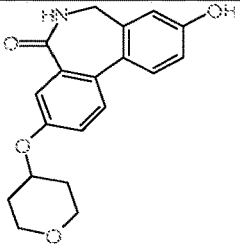
Figure 5:
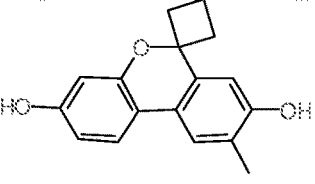
Figure 5:
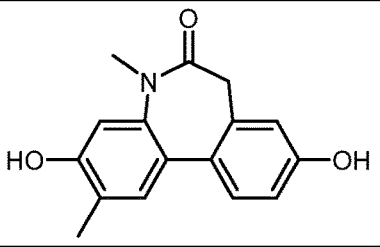
Figure 5:
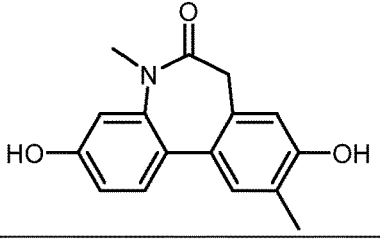
Figure 5:
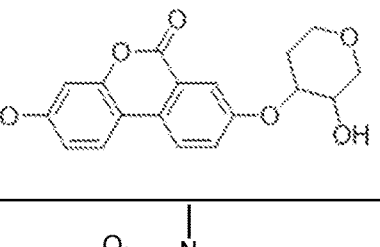
Figure 5:
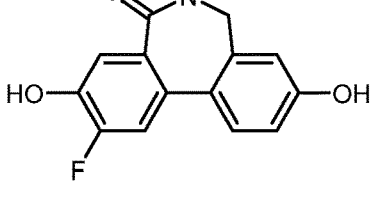
Figure 5:
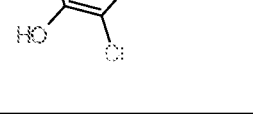
Figure 5:
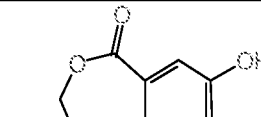
Figure 5:
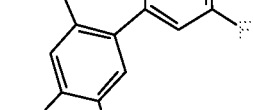
Figure 5:
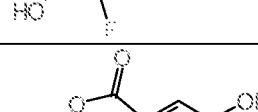
Figure 5:
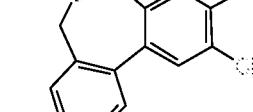
Figure 5:
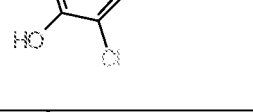
Figure 5:
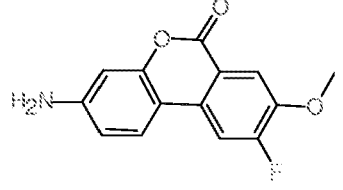
Figure 5:
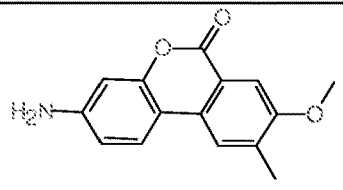
Figure 5:
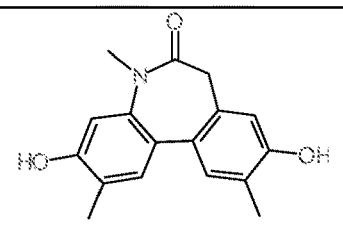
Figure 5:
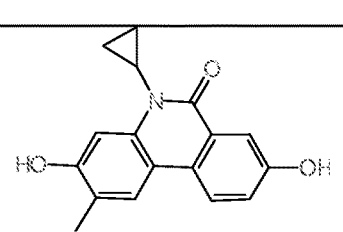
Figure 5:
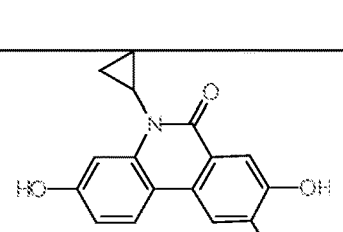
Figure 5:
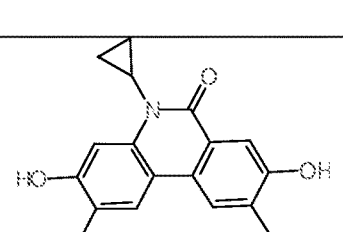
Figure 5:
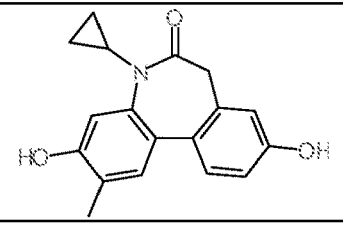
Figure 6:
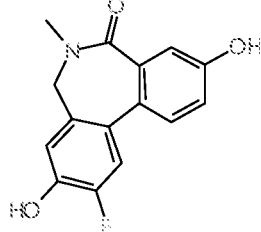
FIG. 6: A table summarizing additional respiratory assay (Respiration in myotubes: Max Efficacy (%): Score at secondary screening for basal respiration in C2C12 myotubes. 0%=DMSO; 100%=Urolithin A; Respiration in myotubes: Conc. of max efficacy (μM): Concentration at which maximal efficacy was observed in C2C12 myotubes; Respiration in myotubes: Signs of toxicity in C2C12 myotubes) data for exemplary compounds of the invention.
Figure 6:
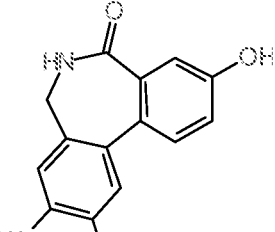
Figure 6:
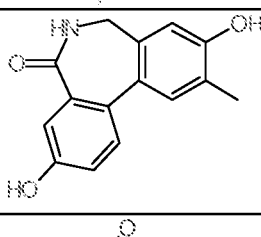
Figure 6:
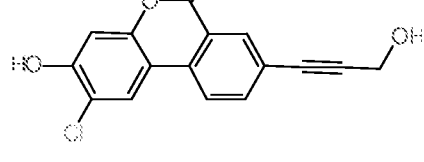
Figure 6:
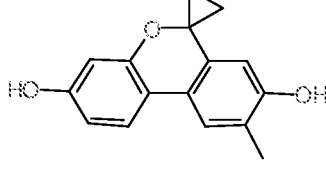
Figure 6:
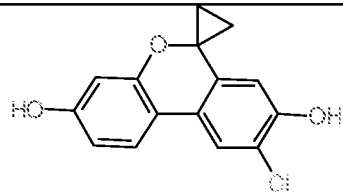
Figure 6:
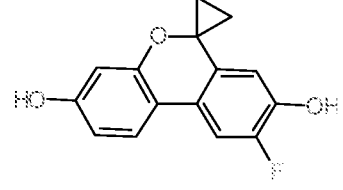
Figure 6:
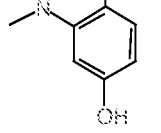
Figure 6:
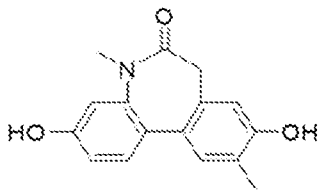
Figure 6:
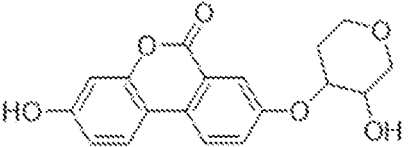
Figure 6:
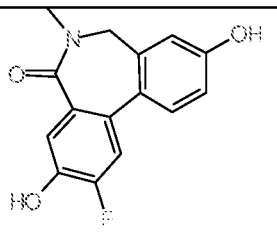
Figure 6:
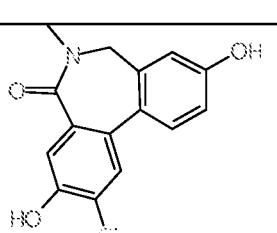
Figure 6:
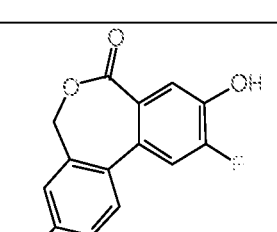
Figure 6:
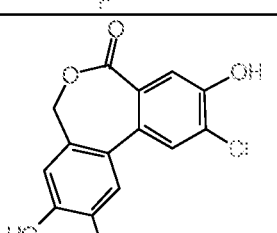
Figure 6:
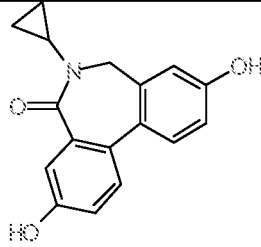
Figure 6:
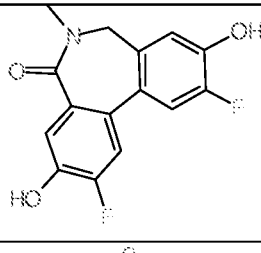
Figure 6:
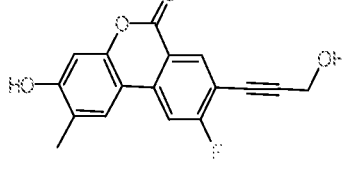
Figure 6:
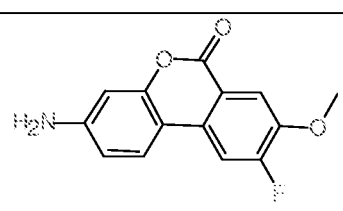
Figure 6:
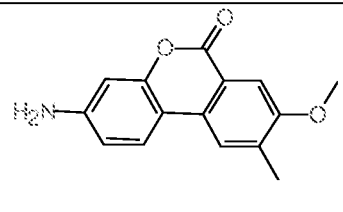
Figure 6:
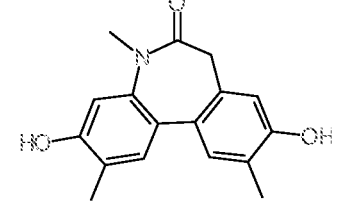
Figure 6:
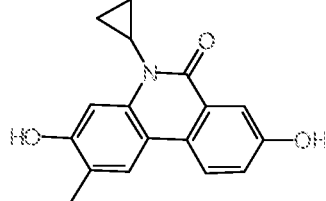
Figure 6:
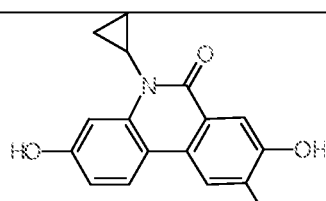
Figure 6:
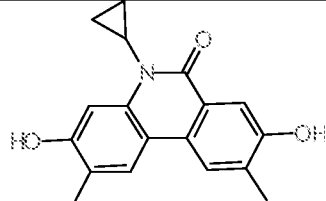
Figure 6:
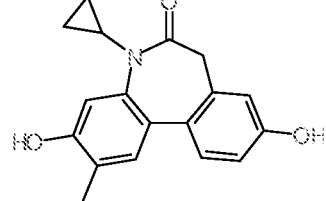
Figure 6:
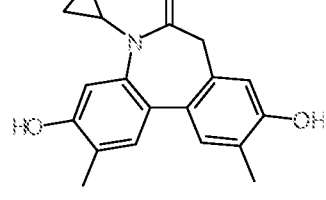
Figure 6:
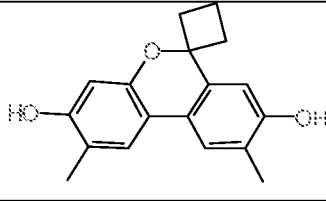
Figure 6:
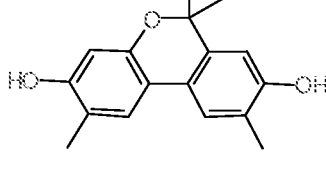
Figure 6:
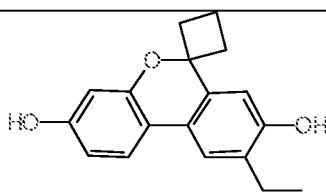
Figure 6:
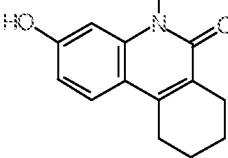
Figure 7:
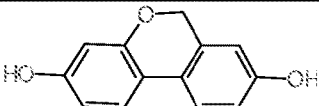
FIG. 7: A table summarizing muscle, brain tissue and lung penetration as measured by Cmax (ng/g tissue) in mice for exemplary compounds of the invention.
Figure 7:
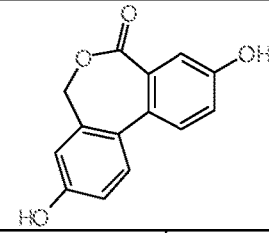
Figure 7:
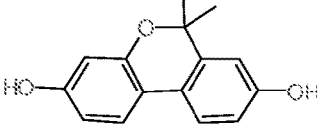
Figure 7:
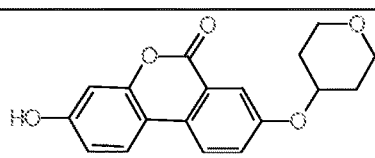
Figure 7:
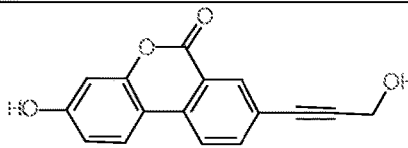
Figure 7:
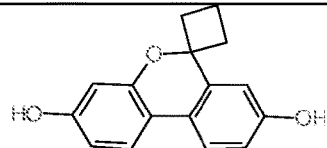
Figure 7:
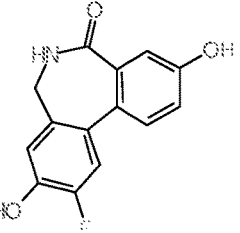
Figure 7:
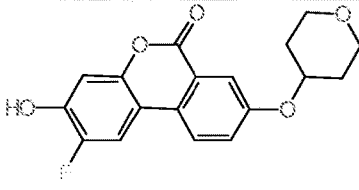
Figure 7:
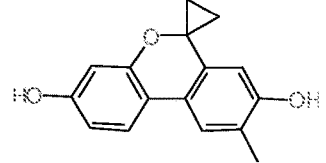
Figure 7:
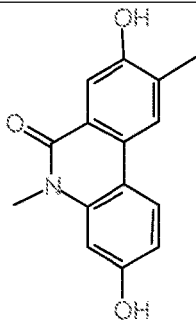
Figure 7:
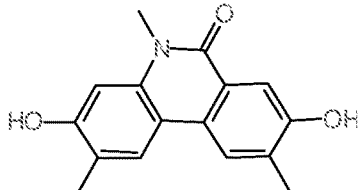
Figure 7:
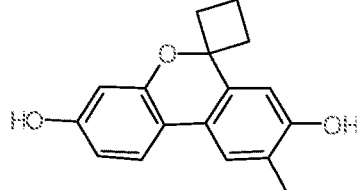
Figure 7:
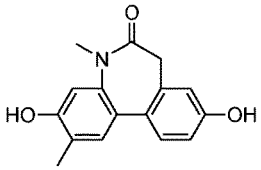
Figure 8:
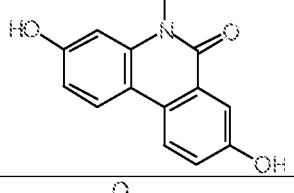
FIG. 8: A table summarizing the anti-ferroptotic activity of selected compounds: Anti-ferroptotic activity. Maximal Percent efficacy (%), Concentration at maximal Percent efficacy (μM) for exemplary compounds of the invention.
Figure 8:
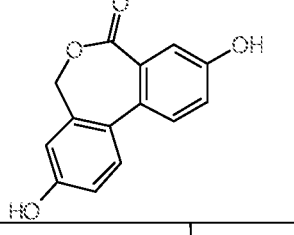
Figure 8:
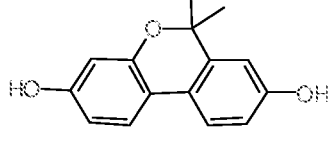
Figure 8:
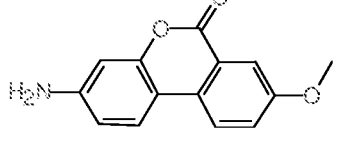
Figure 8:
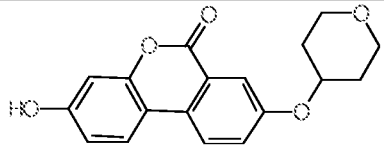
Figure 8:
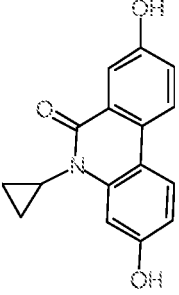
Figure 8:
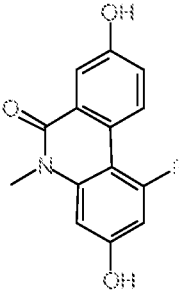
Figure 8:
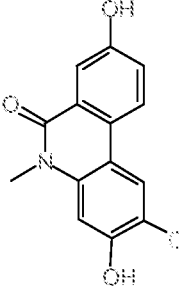
Figure 8:
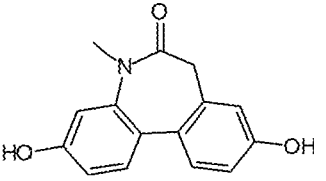
Figure 8:
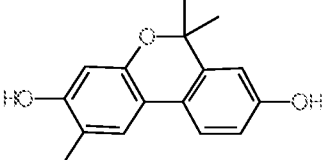
Figure 8:
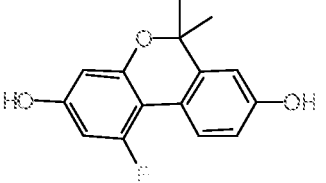
Figure 8:
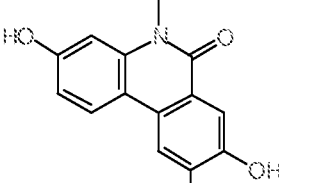
Figure 8:
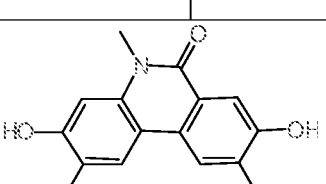
Figure 8:
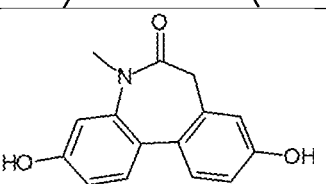
Figure 8:
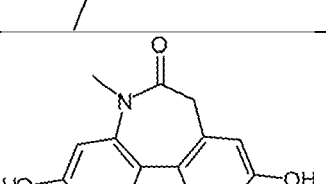
Figure 8:
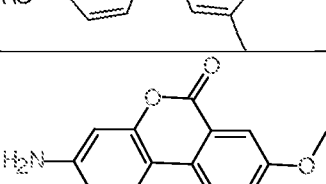
Figure 8:
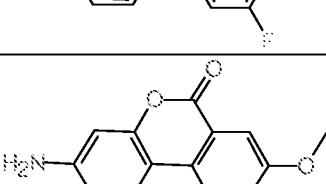
Figure 8:
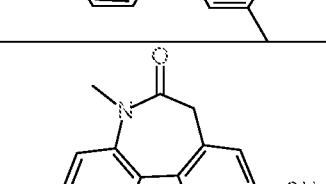
Figure 8:
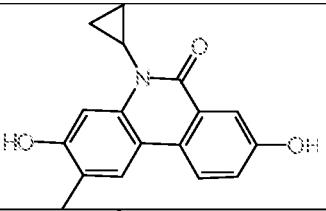
Figure 8:
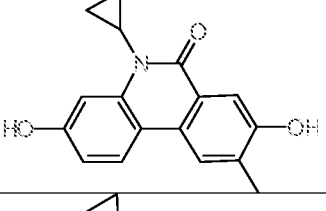
Figure 8:
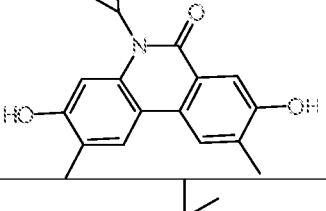
Figure 8:
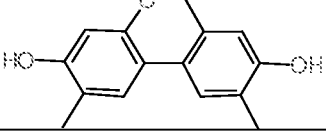

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

In order for the present invention to be more readily understood, certain terms and phrases are defined below and throughout the specification.

The articles "a" and "an" are used herein to refer to one or to more than one (i.e., to at least one) of the grammatical object of the article. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Certain compounds contained in compositions of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in "atropisomeric" forms or as "atropisomers." Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from a mixture of isomers. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Percent purity by mole fraction is the ratio of the moles of the enantiomer (or diastereomer) or over the moles of the enantiomer (or diastereomer) plus the moles of its optical isomer. When the stereochemistry of a disclosed compound is named or depicted by structure, the named or depicted stereoisomer is at least about 60%, about 70%, about 80%, about 90%, about 99% or about 99.9% by mole fraction pure relative to the other stereoisomers. When a single enantiomer is named or depicted by structure, the depicted or named enantiomer is at least about 60%, about 70%, about 80%, about 90%, about 99% or about 99.9% by mole fraction pure. When a single diastereomer is named or depicted by structure, the depicted or named diastereomer is at least about 60%, about 70%, about 80%, about 90%, about 99% or about 99.9% by mole fraction pure.

When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention.

The term "prodrug" as used herein encompasses compounds that, under physiological conditions, are converted into therapeutically active agents. A common method for making a prodrug is to include selected moieties that are hydrolyzed under physiological conditions to reveal the desired molecule. In other embodiments, the prodrug is converted by an enzymatic activity of the host animal.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material, involved in carrying or transporting the subject chemical from one organ or portion of the body, to another organ or portion of the body. Each carrier must be "acceptable" in the sense of being compatible with the other ingredients of the formulation, not injurious to the patient, and substantially non-pyrogenic. Some examples of materials which can serve as pharmaceutically acceptable carriers include: (1) sugars, such as lactose, glucose, and sucrose; (2) starches, such as corn starch and potato starch; (3) cellulose, and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. In certain embodiments, pharmaceutical compositions of the present invention are non-pyrogenic, i.e., do not induce significant temperature elevations when administered to a patient.

The term "pharmaceutically acceptable salts" refers to the relatively non-toxic, inorganic and organic acid addition salts of the compound(s). These salts can be prepared in situ during the final isolation and purification of the compound(s), or by separately reacting a purified compound(s) in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts, and the like. (See, for example, Berge et al. (1977) "Pharmaceutical Salts", *J. Pharm. Sci.* 66:1-19.)

In other cases, the compounds useful in the methods of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic inorganic and organic base addition salts of a compound(s). These salts can likewise be prepared in situ during the final isolation and purification of the compound(s), or by separately reacting the purified compound(s) in its free acid form with a suitable base, such as the hydroxide, carbonate, or bicarbonate of a pharmaceutically acceptable metal cation, with ammonia, or with a pharmaceutically acceptable organic primary, secondary, or tertiary amine. Representative alkali or alkaline earth salts include the lithium, sodium, potassium, calcium, magnesium, and aluminum salts, and the like. Representative organic amines useful for the formation of base addition salts include ethylamine, diethylamine, ethylenediamine, ethanolamine, diethanolamine, piperazine, and the like (see, for example, Berge et al., supra).

The term "pharmaceutically acceptable cocrystals" refers to solid coformers that do not form formal ionic interactions with the small molecule.

A "therapeutically effective amount" (or "effective amount") of a compound with respect to use in treatment, refers to an amount of the compound in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "patient" or "subject" refers to a mammal in need of a particular treatment. In certain embodiments, a patient is a primate, canine, feline, or equine. In certain embodiments, a patient is a human.

An aliphatic chain comprises the classes of alkyl, alkenyl and alkynyl defined below. A straight aliphatic chain is limited to unbranched carbon chain moieties. As used herein, the term "aliphatic group" refers to a straight chain, branched-chain, or cyclic aliphatic hydrocarbon group and includes saturated and unsaturated aliphatic groups, such as an alkyl group, an alkenyl group, or an alkynyl group.

"Alkyl" refers to a fully saturated cyclic or acyclic, branched or unbranched carbon chain moiety having the number of carbon atoms specified, or up to 30 carbon atoms if no specification is made. For example, alkyl of 1 to 8 carbon atoms refers to moieties such as methyl, ethyl, propyl, butyl, pentyl, hexyl, heptyl, and octyl, and those moieties which are positional isomers of these moieties. Alkyl of 10 to 30 carbon atoms includes decyl, undecyl, dodecyl, tridecyl, tetradecyl, pentadecyl, hexadecyl, heptadecyl, octadecyl, nonadecyl, eicosyl, heneicosyl, docosyl, tricosyl and tetracosyl. In certain embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. Alkyl groups may be substituted or unsubstituted.

As used herein, the term "heteroalkyl" refers to an alkyl moiety as hereinbefore defined which contain one or more oxygen, sulfur, nitrogen, phosphorus, or silicon atoms in place of carbon atoms.

As used herein, the term "haloalkyl" refers to an alkyl group as hereinbefore defined substituted with at least one halogen.

As used herein, the term "hydroxyalkyl" refers to an alkyl group as hereinbefore defined substituted with at least one hydroxyl.

As used herein, the term "alkylene" refers to an alkyl group having the specified number of carbons, for example from 2 to 12 carbon atoms, which contains two points of attachment to the rest of the compound on its longest carbon chain. Non-limiting examples of alkylene groups include methylene —($CH_2$)—, ethylene —($CH_2CH_2$)—, n-propylene —($CH_2CH_2CH_2$)—, isopropylene —($CH_2CH(CH_3)$)—, and the like. Alkylene groups can be cyclic or acyclic, branched or unbranched carbon chain moiety, and may be optionally substituted with one or more substituents.

"Cycloalkyl" means mono- or bicyclic or bridged or spirocyclic, or polycyclic saturated carbocyclic rings, each having from 3 to 12 carbon atoms. Preferred cycloalkyls have from 3-10 carbon atoms in their ring structure, and more preferably have 3-6 carbons in the ring structure. Cycloalkyl groups may be substituted or unsubstituted.

As used herein, the term "halocycloalkyl" refers to an cycloalkyl group as hereinbefore defined substituted with at least one halogen.

"Cycloheteroalkyl" or "heterocycloalkyl" refers to an cycloalkyl moiety as hereinbefore defined which contain one or more oxygen, sulfur, nitrogen, phosphorus, or silicon atoms in place of carbon atoms. Preferred cycloheteroalkyls have from 4-8 carbon atoms and heteroatoms in their ring structure, and more preferably have 4-6 carbons and heteroatoms in the ring structure. Cycloheteroalkyl or heterocycloalkyl groups may be substituted or unsubstituted.

Unless the number of carbons is otherwise specified, "lower alkyl," as used herein, means an alkyl group, as defined above, but having from one to ten carbons, more preferably from one to six carbon atoms in its backbone structure such as methyl, ethyl, n-propyl, isopropyl, n-butyl, isobutyl, sec-butyl, and tert-butyl. Likewise, "lower alkenyl" and "lower alkynyl" have similar chain lengths. Throughout the application, preferred alkyl groups are lower alkyls. In certain embodiments, a substituent designated herein as alkyl is a lower alkyl.

"Alkenyl" refers to any cyclic or acyclic, branched or unbranched unsaturated carbon chain moiety having the number of carbon atoms specified, or up to 26 carbon atoms if no limitation on the number of carbon atoms is specified; and having one or more double bonds in the moiety. Alkenyl of 6 to 26 carbon atoms is exemplified by hexenyl, heptenyl, octenyl, nonenyl, decenyl, undecenyl, dodenyl, tridecenyl, tetradecenyl, pentadecenyl, hexadecenyl, heptadecenyl, octadecenyl, nonadecenyl, eicosenyl, heneicosoenyl, docosenyl, tricosenyl, and tetracosenyl, in their various isomeric forms, where the unsaturated bond(s) can be located anywhere in the moiety and can have either the (Z) or the (E) configuration about the double bond(s).

"Alkynyl" refers to hydrocarbyl moieties of the scope of alkenyl, but having one or more triple bonds in the moiety.

The term "aryl" as used herein includes 3- to 12-membered substituted or unsubstituted single-ring aromatic groups in which each atom of the ring is carbon (i.e., carbocyclic aryl) or where one or more atoms are heteroatoms (i.e., heteroaryl). Preferably, aryl groups include 5- to 12-membered rings, more preferably 6- to 10-membered rings The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Carboycyclic aryl groups include benzene, naphthalene, phenanthrene, phenol, aniline, and the like. Heteroaryl groups include substituted or unsubstituted aromatic 3- to 12-membered ring structures, more preferably 5- to 12-membered rings, more preferably 5- to 10-membered rings, whose ring structures include one to four heteroatoms. Heteroaryl groups include, for example, pyrrole, furan, thiophene, imidazole, oxazole, thiazole, triazole, pyrazole, pyridine, pyrazine, pyridazine and pyrimidine, and the like. Aryl and heteroaryl can be monocyclic, bicyclic, or polycyclic.

The term "halo", "halide", or "halogen" as used herein means halogen and includes, for example, and without being limited thereto, fluoro, chloro, bromo, iodo and the like, in both radioactive and non-radioactive forms. In a preferred embodiment, halo is selected from the group consisting of fluoro, chloro and bromo.

The terms "heterocyclyl" or "heterocyclic group" refer to 3- to 12-membered ring structures, more preferably 5- to 12-membered rings, more preferably 5- to 10-membered rings, whose ring structures include one to four heteroatoms. Heterocycles can be monocyclic, bicyclic, spirocyclic, or polycyclic. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphate, phosphonate, phosphinate, carbonyl, carboxyl, silyl, sulfamoyl, sulfinyl, ether, alkylthio, sulfonyl, ketone, aldehyde, ester, a heterocyclyl, an aromatic or heteroaromatic moiety, —$CF_3$, —CN, and the like.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxy, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. In preferred embodiments, the substituents on substituted alkyls are selected from $C_1$-6 alkyl, $C_3$-6 cycloalkyl, halogen, carbonyl, cyano, or hydroxyl. In more preferred embodiments, the substituents on substituted alkyls are selected from fluoro, carbonyl, cyano, or hydroxyl. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

As used herein, the definition of each expression, e.g., alkyl, m, n, etc., when it occurs more than once in any structure, is intended to be independent of its definition elsewhere in the same structure.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

In some embodiments, a "small molecule" refers to an organic, inorganic, or organometallic compound typically having a molecular weight of less than about 1000. In some embodiments, a small molecule is an organic compound, with a size on the order of 1 nm. In some embodiments, small molecule drugs of the invention encompass oligopeptides and other biomolecules having a molecular weight of less than about 1000.

An "effective amount" is an amount sufficient to effect beneficial or desired results. For example, a therapeutic amount is one that achieves the desired therapeutic effect. This amount can be the same or different from a prophylactically effective amount, which is an amount necessary to prevent onset of disease or disease symptoms. An effective amount can be administered in one or more administrations, applications or dosages. A therapeutically effective amount of a composition depends on the composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the compositions described herein can include a single treatment or a series of treatments.

The terms "decrease," "reduce," "reduced", "reduction", "decrease," and "inhibit" are all used herein generally to mean a decrease by a statistically significant amount relative to a reference. However, for avoidance of doubt, "reduce," "reduction" or "decrease" or "inhibit" typically means a decrease by at least 10% as compared to a reference level and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the reference level, or any decrease between 10-99% as compared to the absence of a given treatment.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the term "modulate" includes up-regulation and down-regulation, e.g., enhancing or inhibiting a response.

A "radiopharmaceutical agent," as defined herein, refers to a pharmaceutical agent which contains at least one radiation-emitting radioisotope. Radiopharmaceutical agents are routinely used in nuclear medicine for the diagnosis and/or therapy of various diseases. The radiolabelled pharmaceutical agent, for example, a radiolabelled antibody, contains a radioisotope (RI) which serves as the radiation source. As contemplated herein, the term "radioisotope" includes metallic and non-metallic radioisotopes. The radioisotope is chosen based on the medical application of the radiolabeled pharmaceutical agents. When the radioisotope is a metallic radioisotope, a chelator is typically employed to bind the metallic radioisotope to the rest of the molecule. When the radioisotope is a non-metallic radioisotope, the non-metallic radioisotope is typically linked directly, or via a linker, to the rest of the molecule.

For purposes of this invention, the chemical elements are identified in accordance with the Periodic Table of the Elements, CAS version, *Handbook of Chemistry and Physics,* 67th Ed., 1986-87, inside cover.

Compounds of the Invention

In one embodiment, a compound f Formula (Ia):

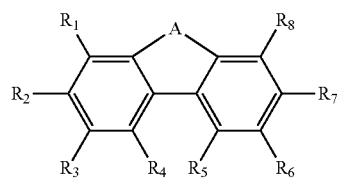

(Ia)

wherein
A is

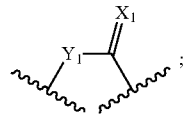

$X_1$ is selected from O and S;
$Y_1$ is O;
$R_1$, $R_4$, $R_5$ and $R_8$ are independently selected from H and halogen;
$R_3$ and $R_6$ are independently selected from H, CN, OH, $CF_3$, halogen, and alkyl;
one of $R_2$ and $R_7$ is H, OH, or OAc and the other of $R_2$ and $R_7$ is halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, C(O)-alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and
provided that if $X_1$ and $Y_1$ are each O, $R_2$ is OH, and $R_1$, $R_3$, $R_4$, $R_5$, $R_6$ and $R_8$ are each H, then $R_7$ is not OBn, if $X_1$ and $Y_1$ are each O, $R_7$ is OH, and $R_1$, $R_3$, $R_4$, $R_5$, $R_6$ and $R_8$ are each H, then $R_2$ is not $OCH_2C(O)NH_2$, or a pharmaceutically acceptable salt thereof.
In some embodiments, the compound wherein A is

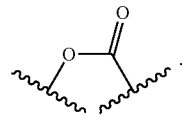 [SMILES: *OC(*)=O]

In some embodiments, $R_2$ is H. In other embodiments, $R_2$ is OH. In other embodiments, $R_2$ is OAc.

In some embodiments, the compound wherein $R_2$ is selected from haloalkyl, substituted cycloalkyl, alkynyl-$R_9$, $OR_{10}$, and $C(O)NR_{11}R_{12}$; $R_9$ is selected from OH, substituted cycloalkyl and heterocycloalkyl; $R_{10}$ is selected from alkyl, substituted cycloalkyl, heterocycloalkyl and alkyl-heterocycloalkyl; and $R_{11}$ is H and $R_{12}$ is alkyl-heterocycloalkyl.

In some embodiments, $R_7$ is H. In other embodiments, $R_7$ is OH. In other embodiments, $R_7$ is OAc.

In some embodiments, the compound wherein $R_7$ is selected from haloalkyl, substituted cycloalkyl, alkynyl-$R_9$, $OR_{10}$, and $C(O)NR_{11}R_{12}$; $R_9$ is selected from OH, substituted cycloalkyl and heterocycloalkyl; $R_{10}$ is selected from alkyl, substituted cycloalkyl, heterocycloalkyl and alkyl-heterocycloalkyl; and $R^{11}$ is H and $R_{12}$ is alkyl-heterocycloalkyl.

In some embodiments, each occurrence of substituted cycloalkyl is independently substituted with OH, halogen, or hydroxyalkyl.

In some embodiments, $R_1$, $R_3$, $R_4$, $R_5$, $R_6$, and $R_8$ are each H. In other embodiments, one of $R_1$, $R_3$, $R_4$, $R_5$, $R_6$, and $R_8$ is not H. In other embodiments, two of $R_1$, $R_3$, $R_4$, $R_5$, $R_6$, and $R_8$ are not H.

In some embodiments, one of $R_1$, $R_3$, $R_4$, $R_5$, $R_6$, and $R_8$ is alkyl or halogen. In other embodiments, two of $R_1$, $R_3$, $R_4$, $R_5$, $R_6$, and $R_8$ are independently alkyl or halogen.

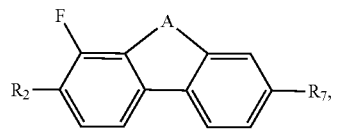
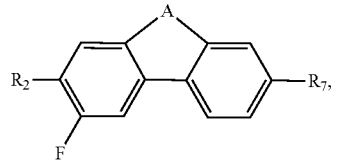
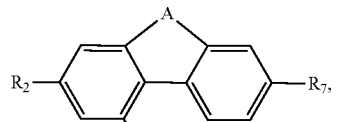
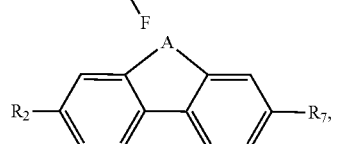
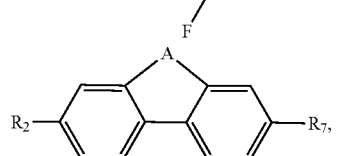
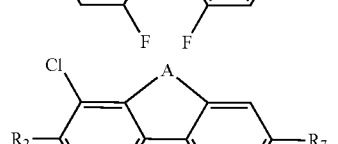
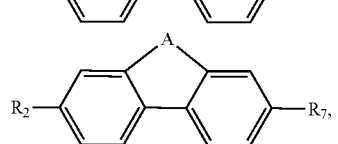
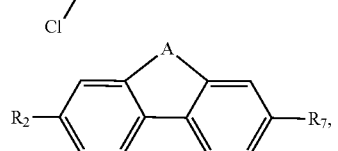
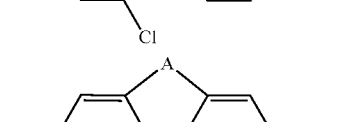
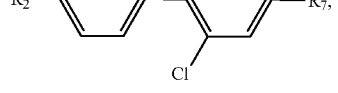

-continued

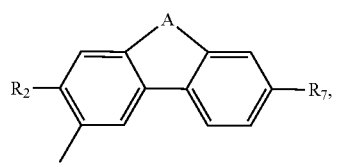
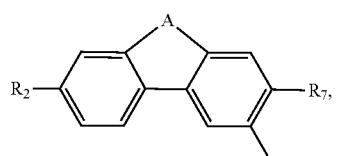
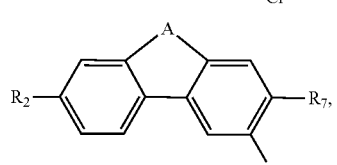
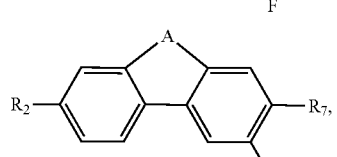
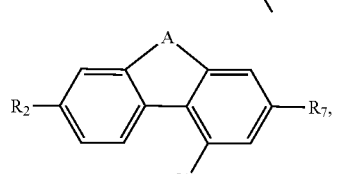
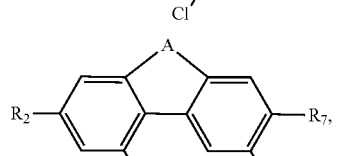
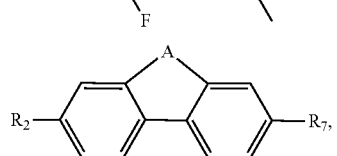
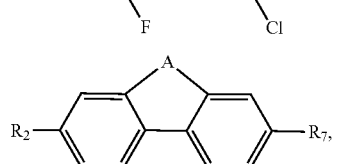
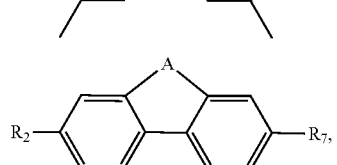
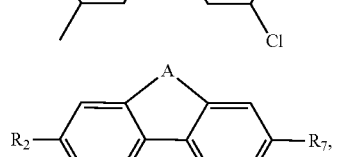
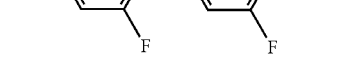

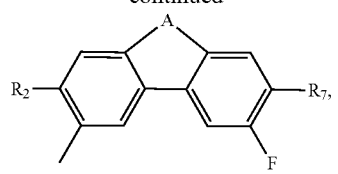
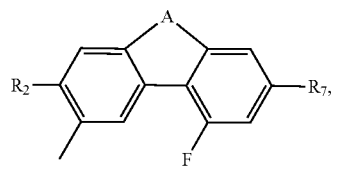
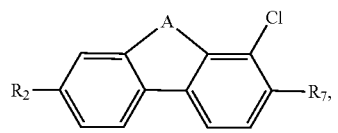
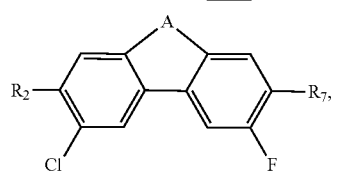
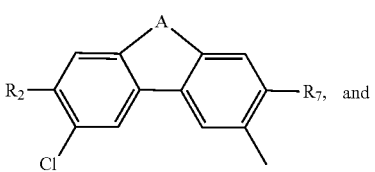 and
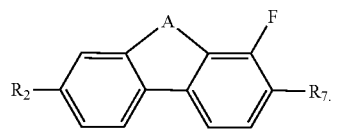
In some embodiments, the compound is selected from:
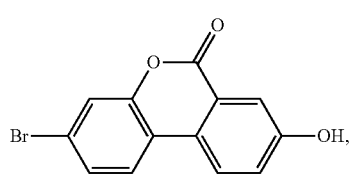
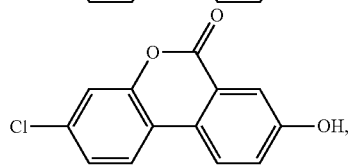
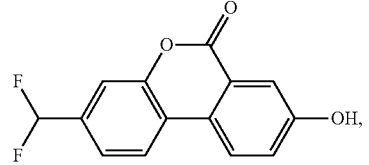
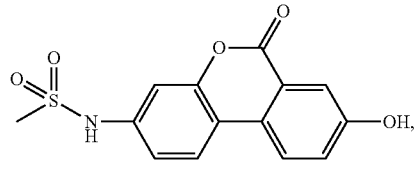
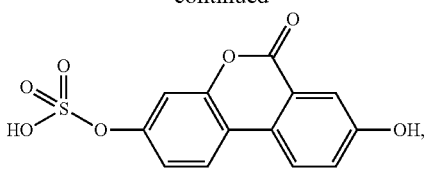
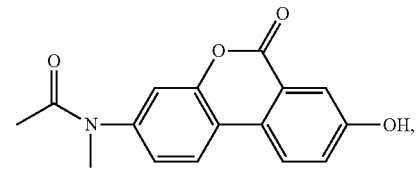
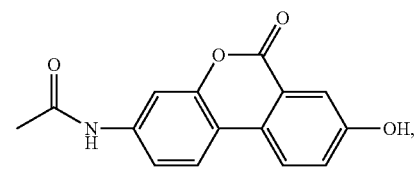
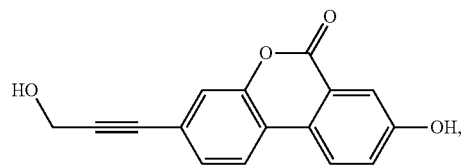
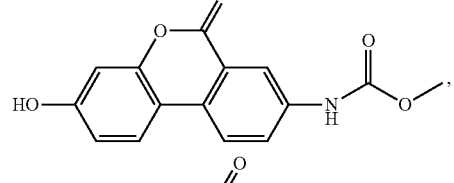
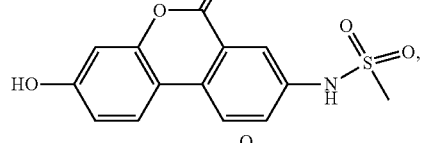
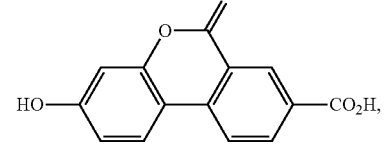
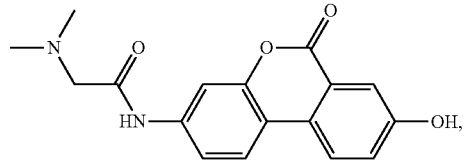
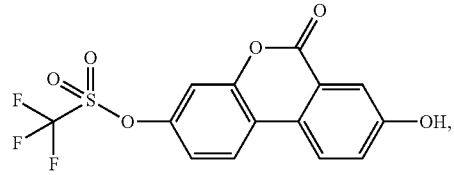
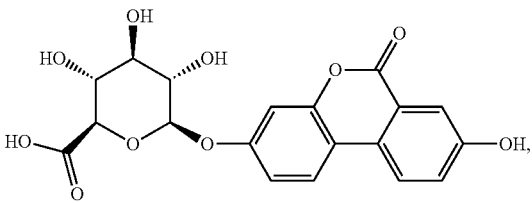

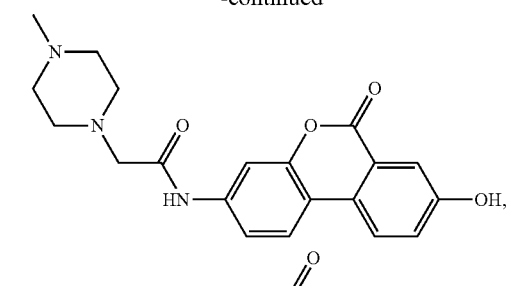
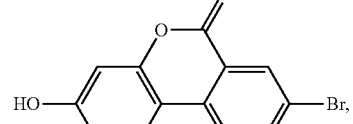
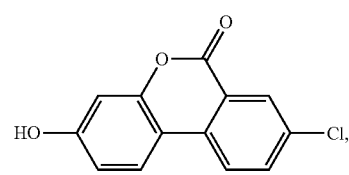
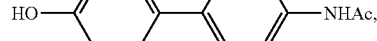
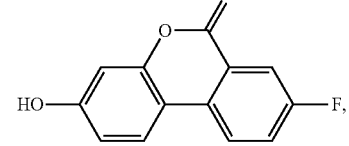
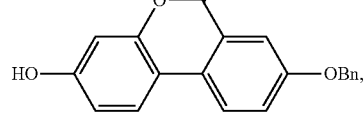
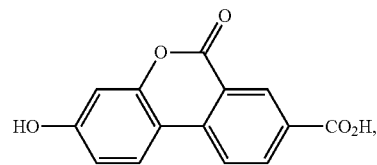
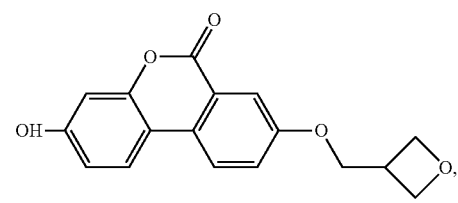
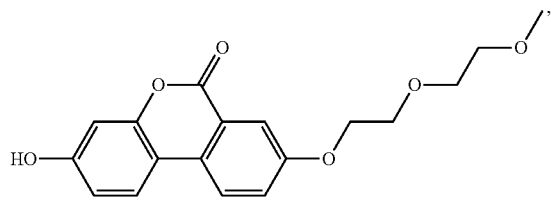
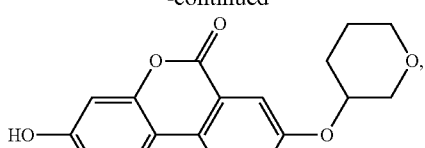
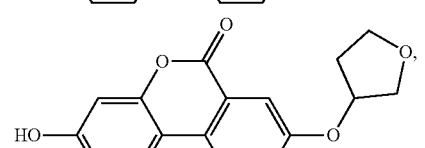
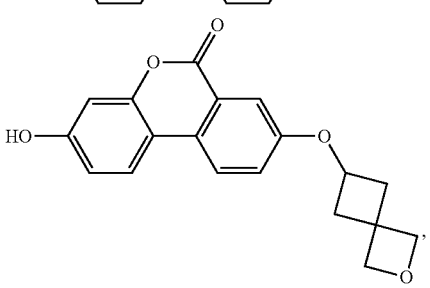
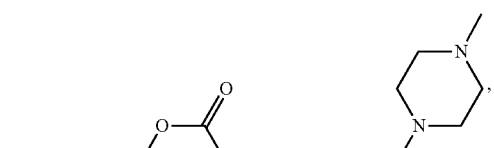
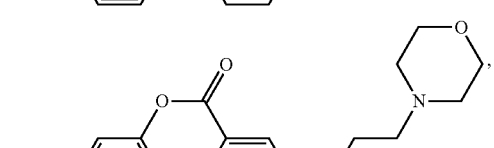
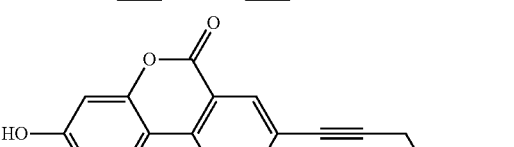
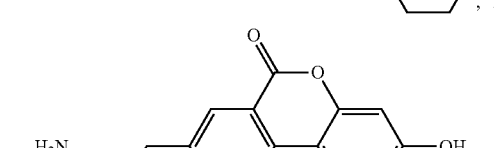
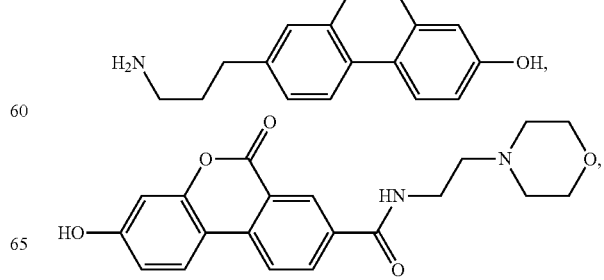

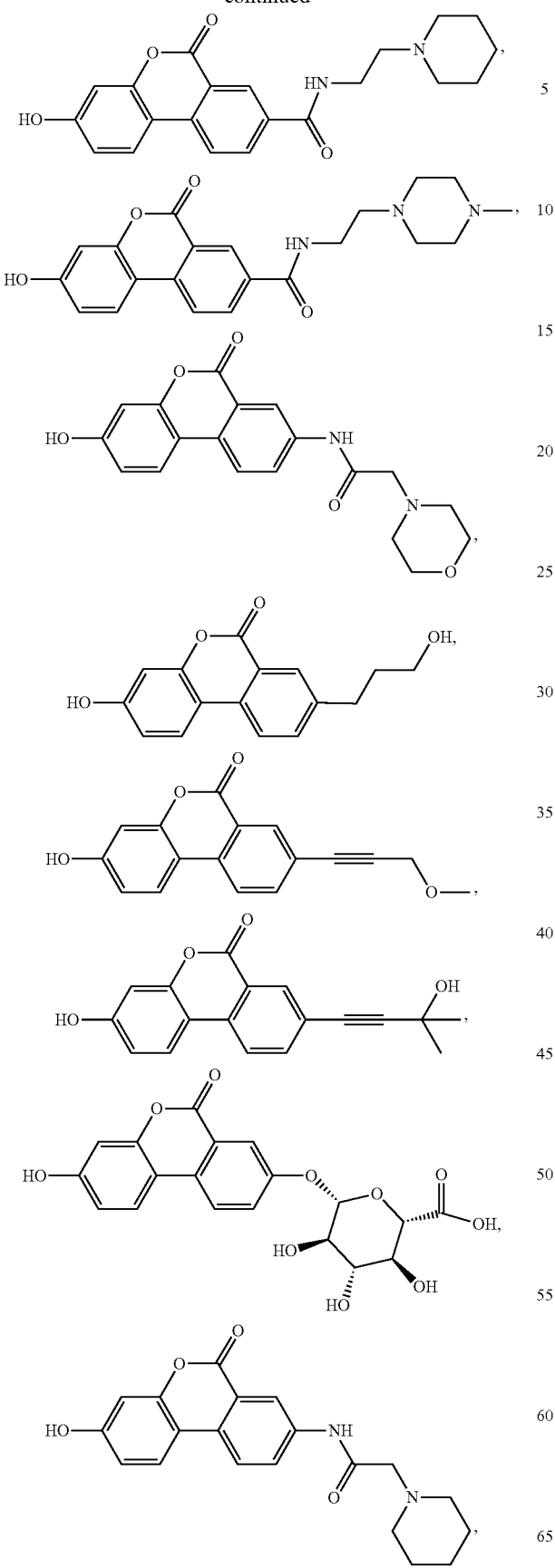
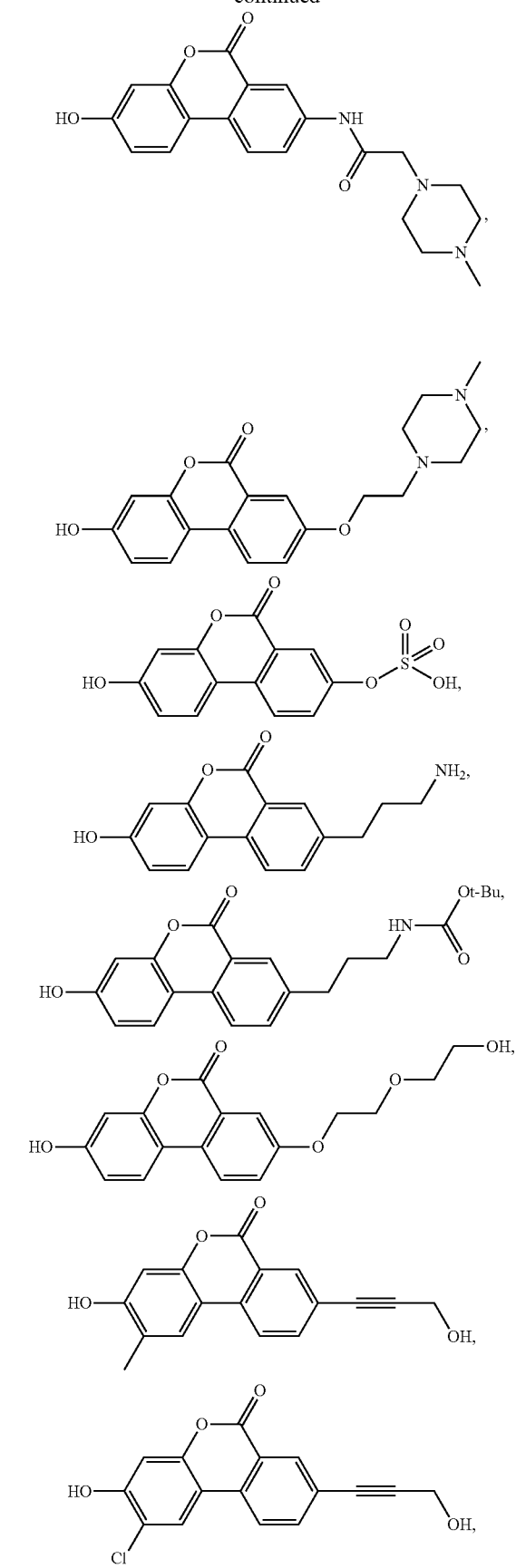

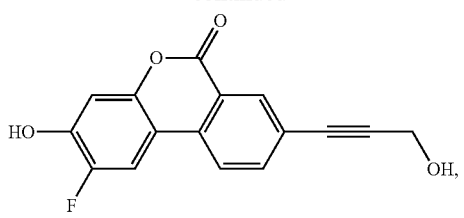
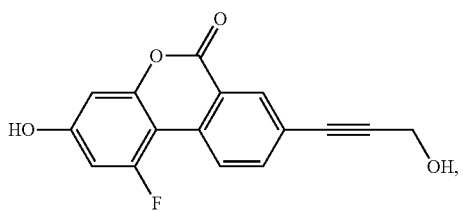
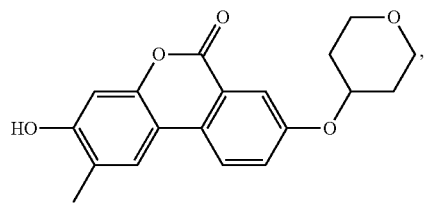
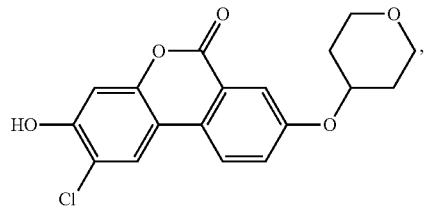
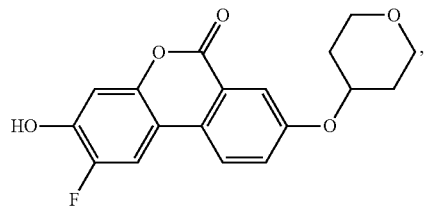
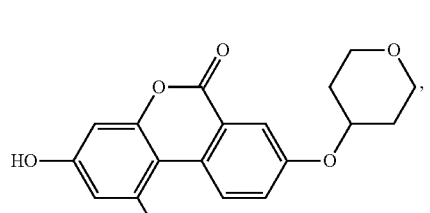
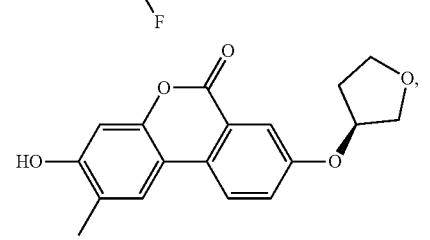
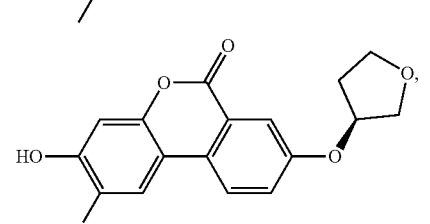
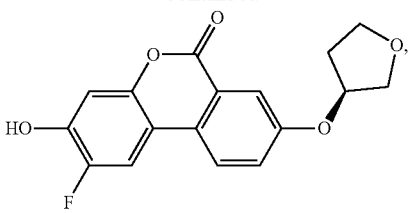
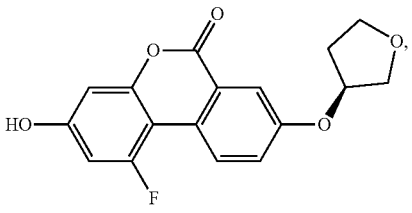
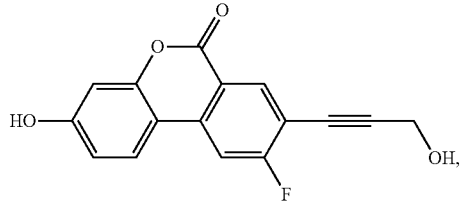
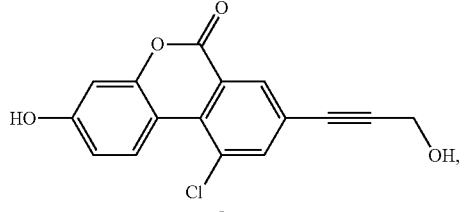
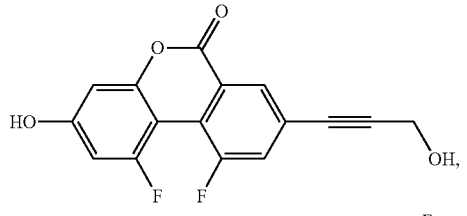
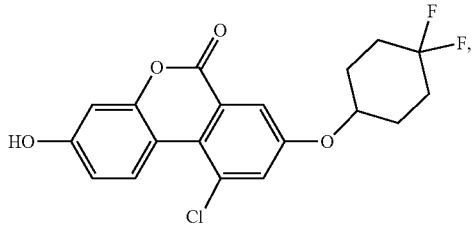
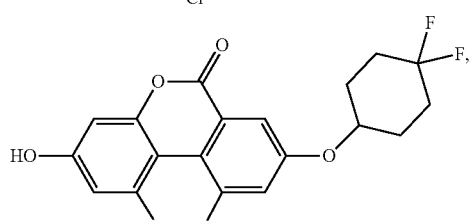
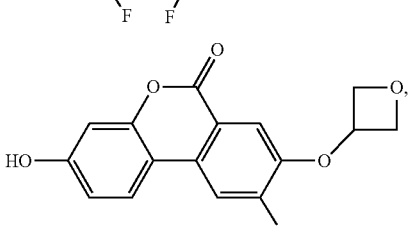

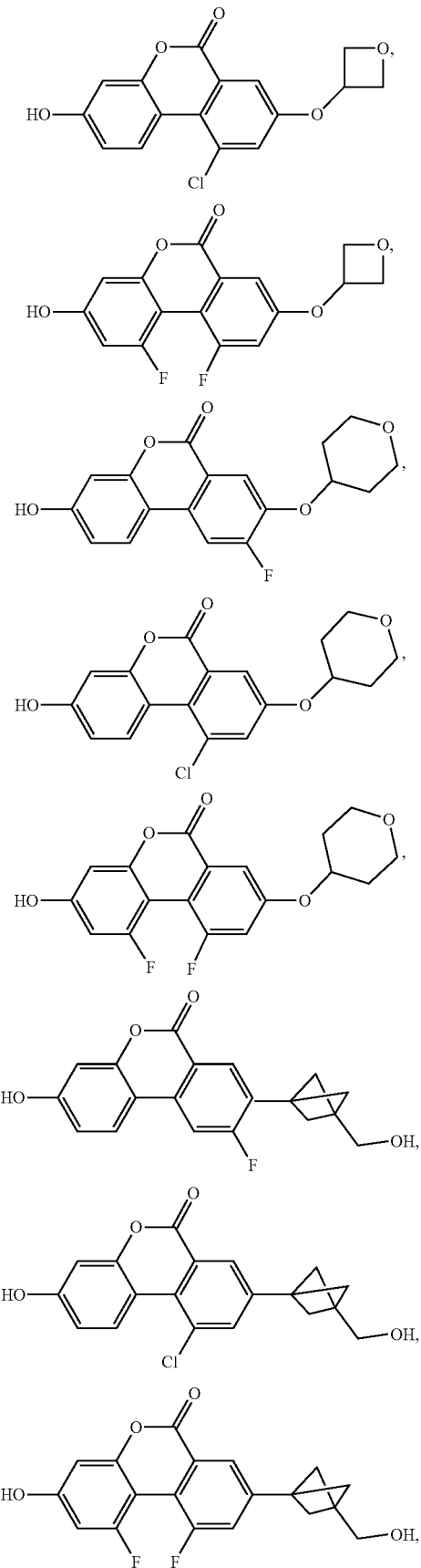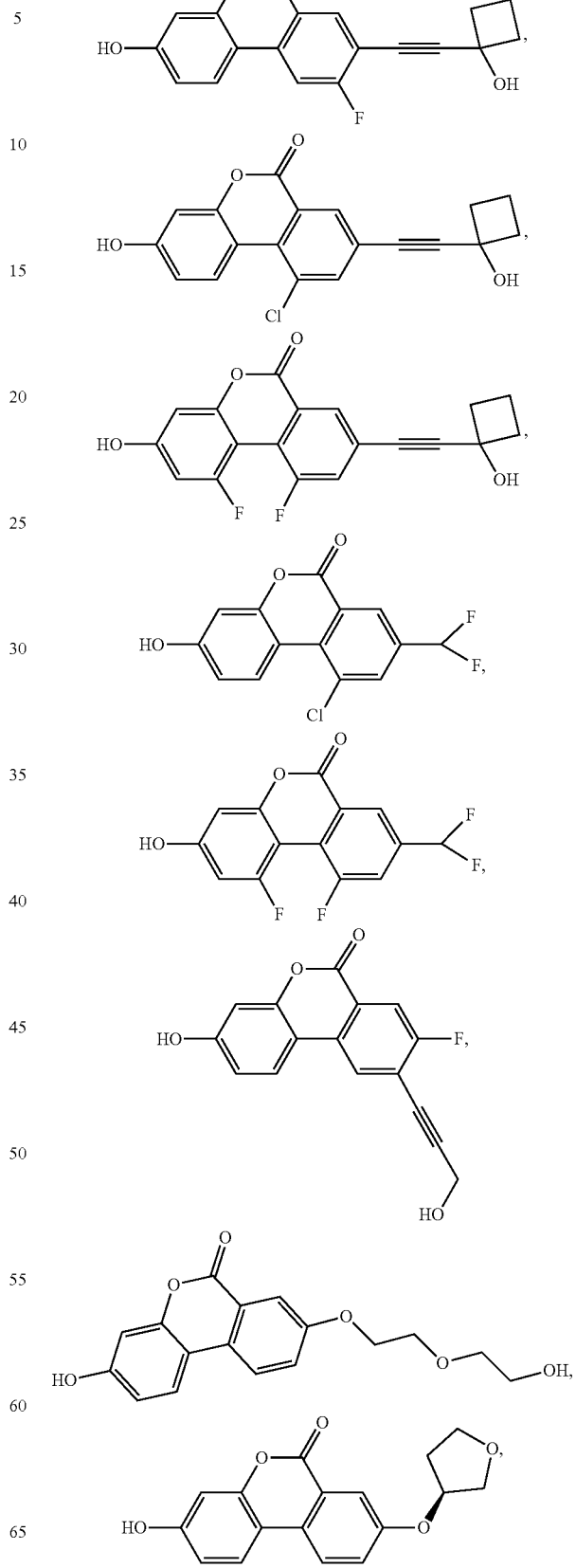

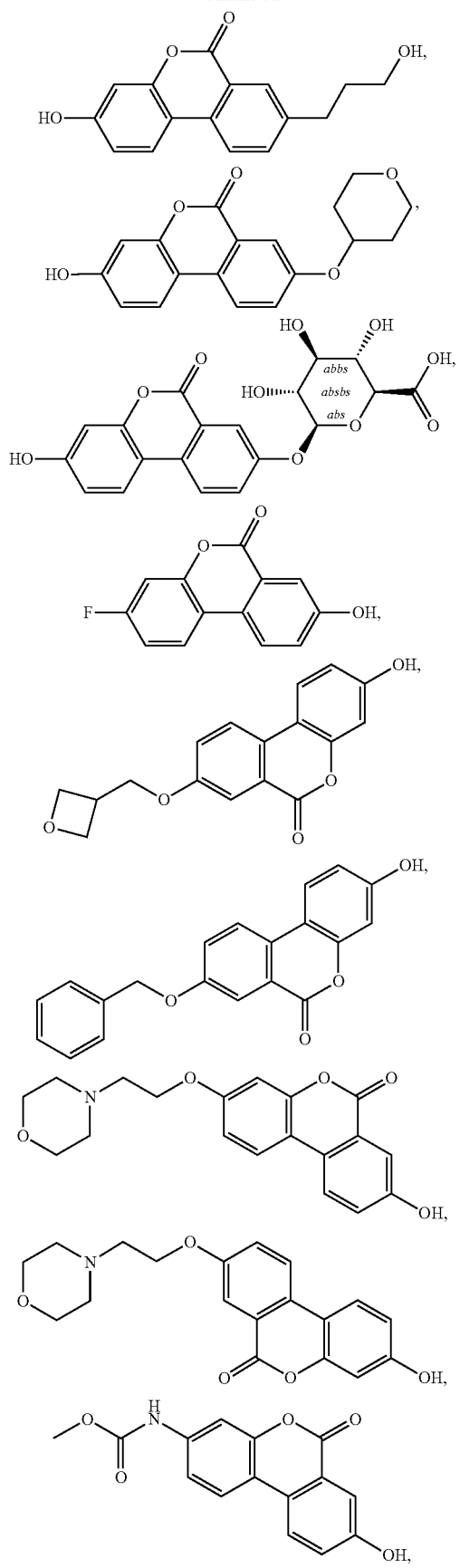
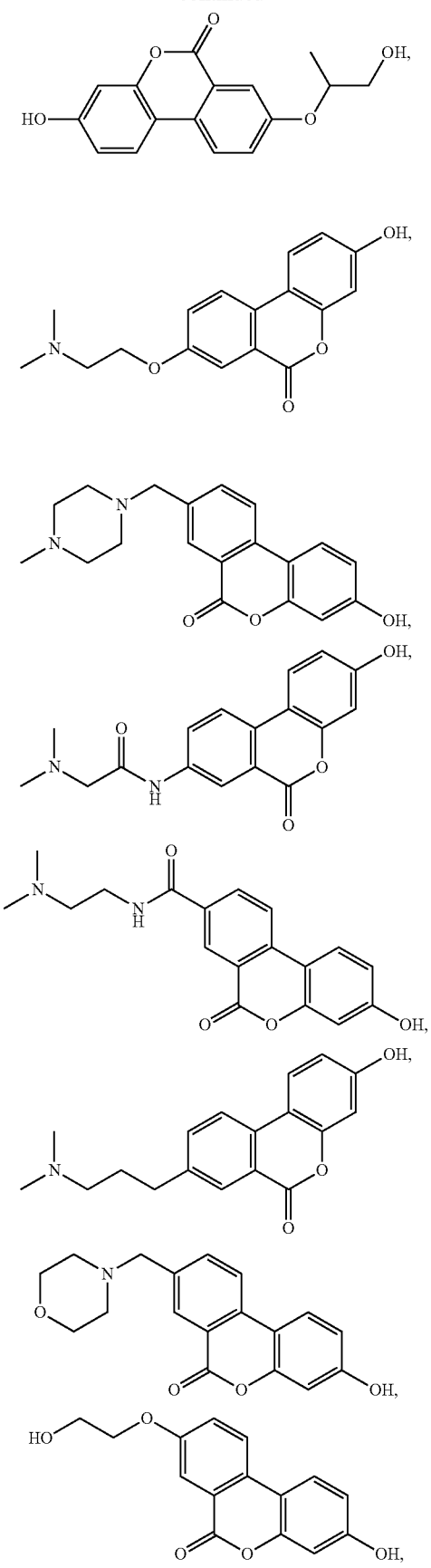

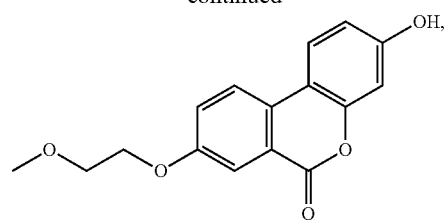
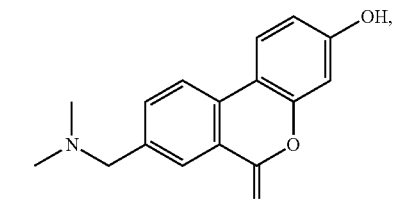
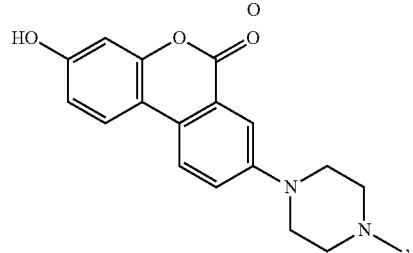
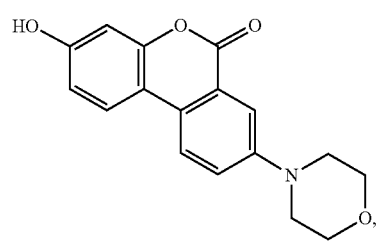
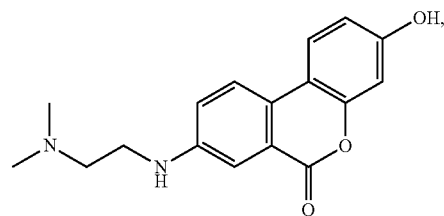
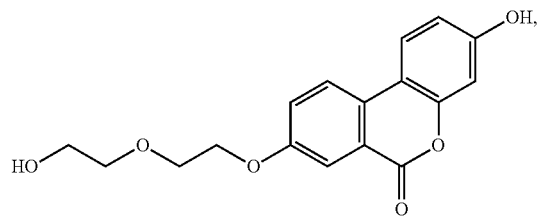
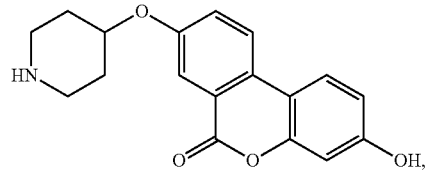
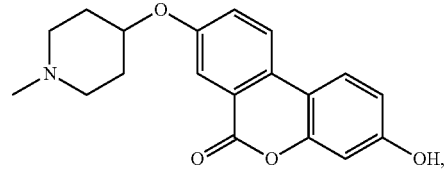
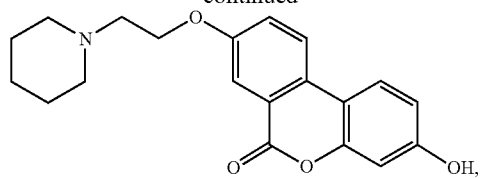
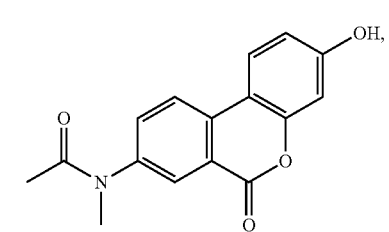
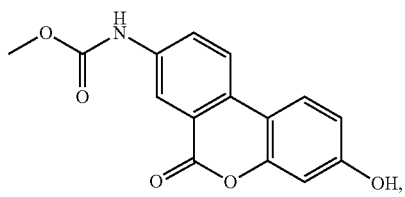
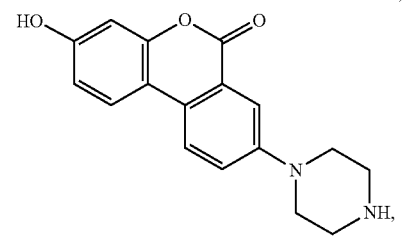
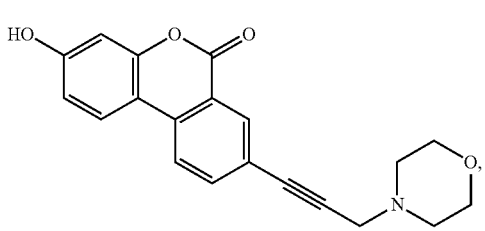
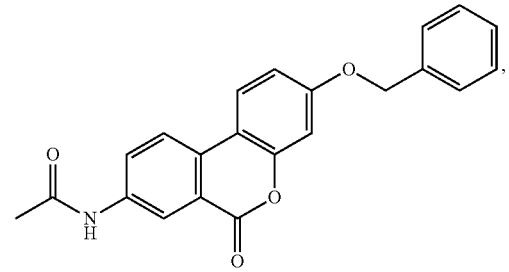
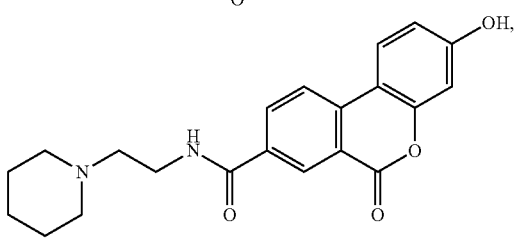

-continued
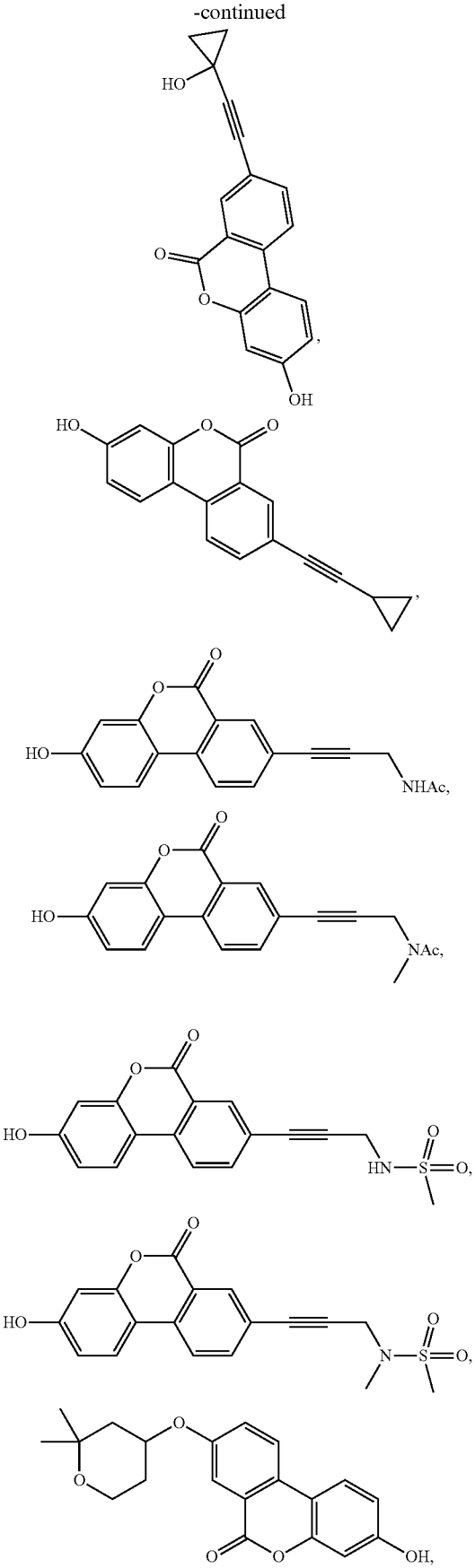
-continued
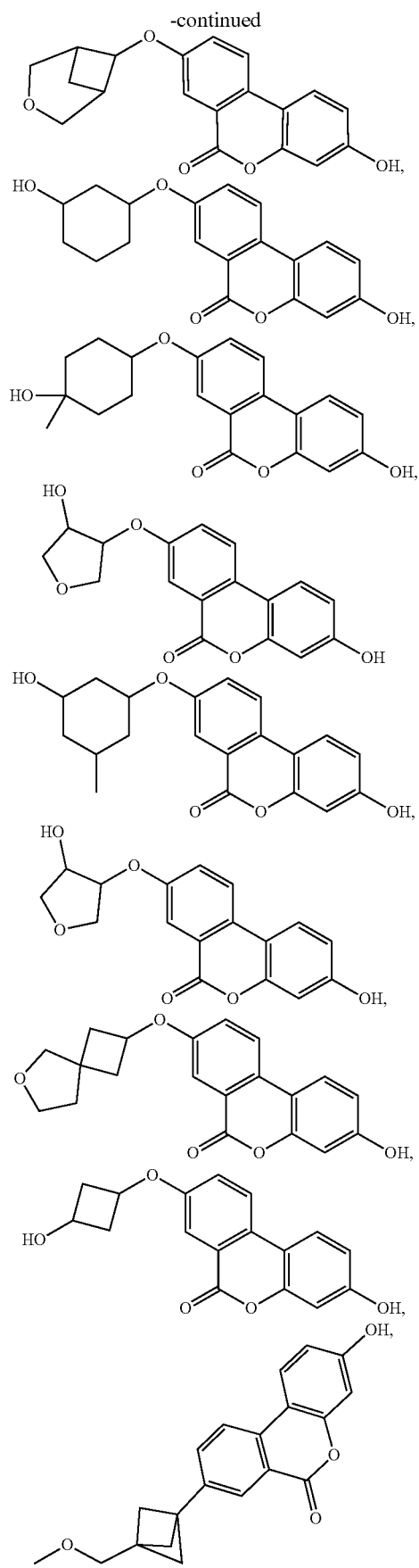

-continued
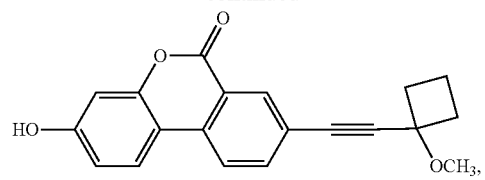
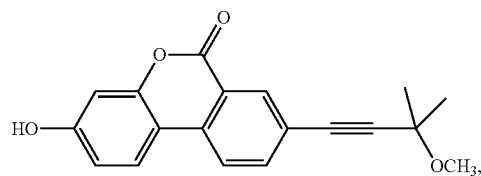
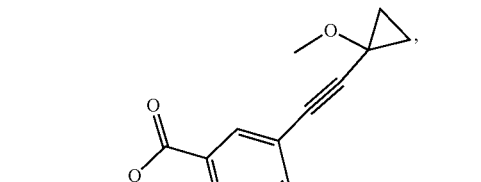
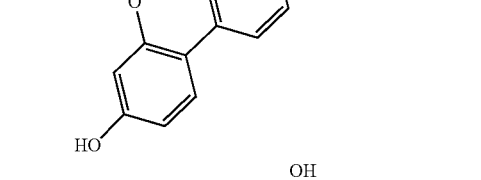
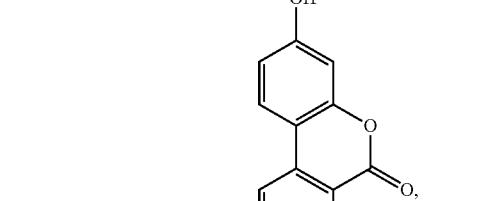

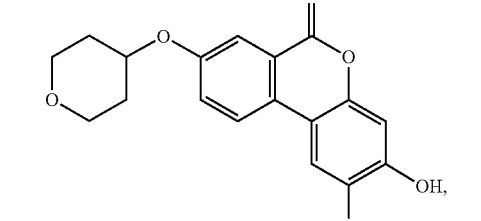
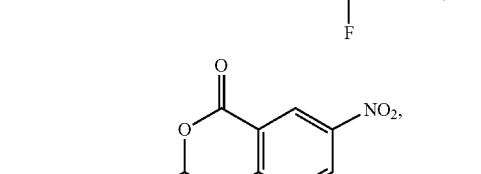
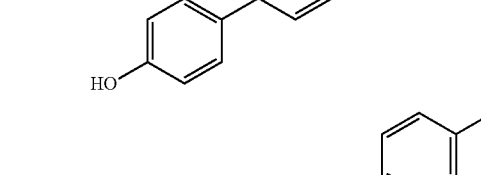

-continued
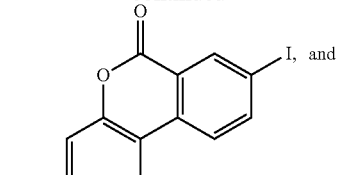
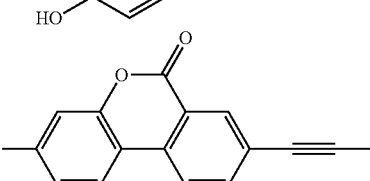
In some embodiments, the compound is selected from:
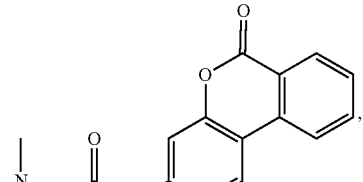
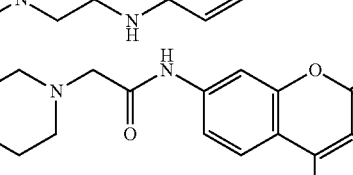
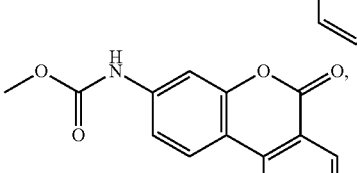
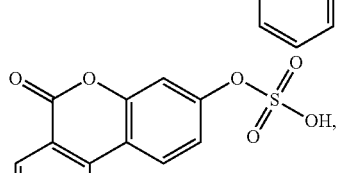
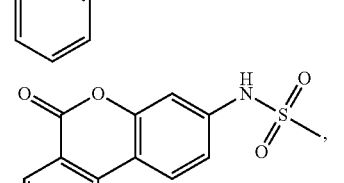
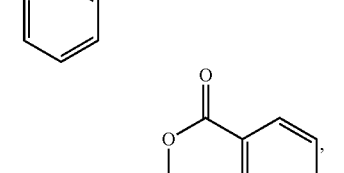
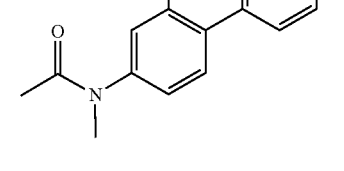

41
-continued
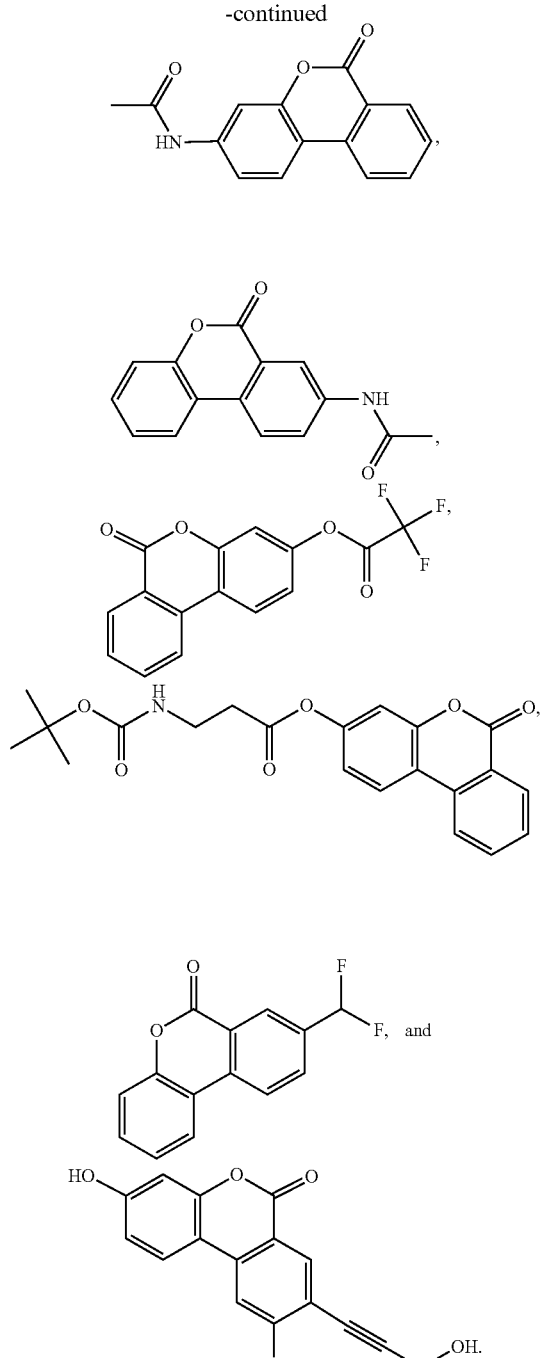
In some embodiments, the compound is selected from:
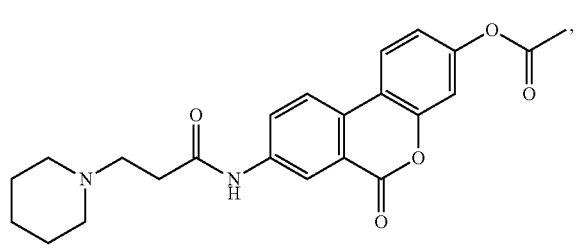
42
-continued
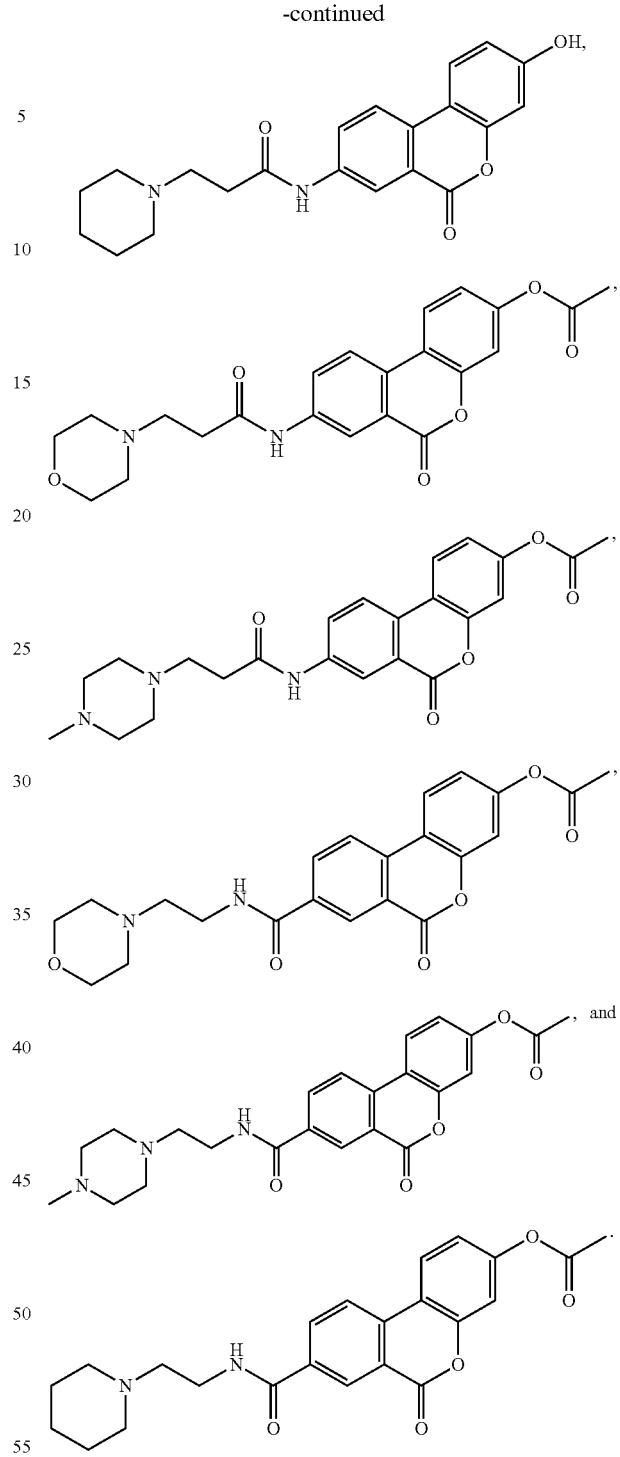
In some embodiments, the compound is selected from:
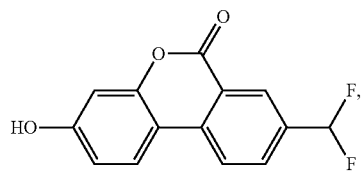

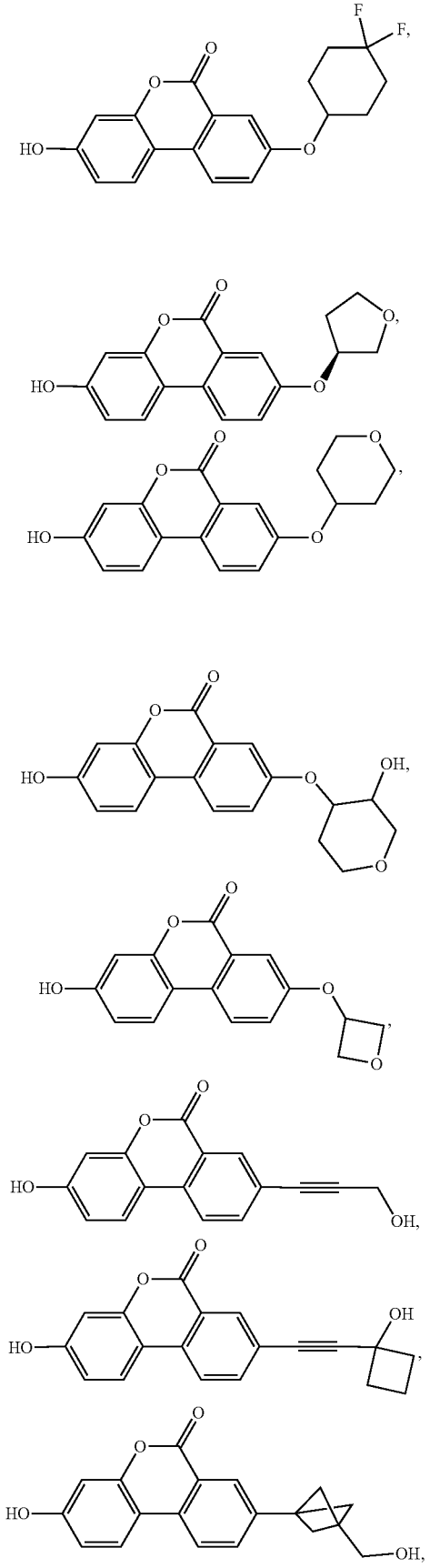
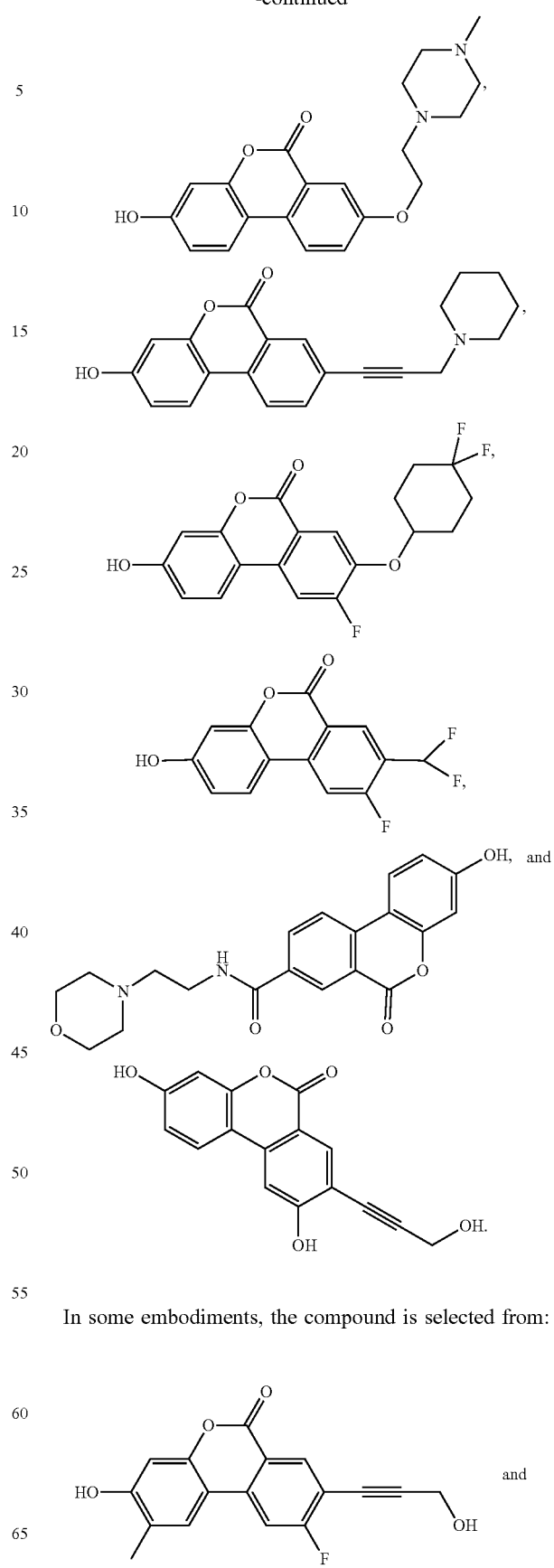
In some embodiments, the compound is selected from:
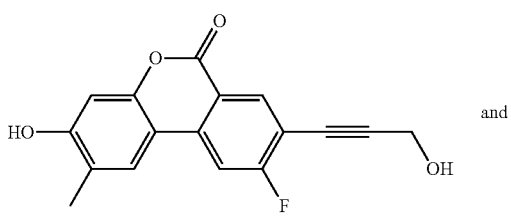

-continued

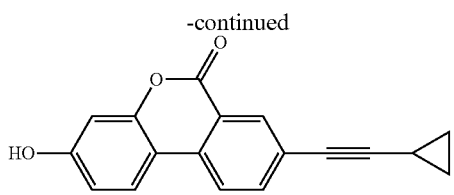

In one embodiment, a compound of compound of Formula (Ib):

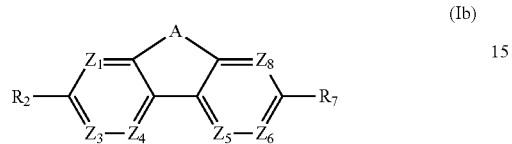

(Ib)

wherein
A is

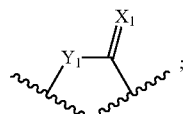

$X_1$ is selected from O and S;
$Y_1$ is O;
$Z_1$ is selected from N and C—$R_1$;
$Z_3$ is selected from N and C—$R_3$;
$Z_4$ is selected from N and C—$R_4$;
$Z_5$ is selected from N and C—$R_5$;
$Z_6$ is selected from N and C—$R_6$;
$Z_8$ is selected from N and C—$R_8$;
$R_1$, $R_4$, $R_5$, and $R_8$ are independently selected from is H, halogen, and aminoalkyl, and
$R_2$, $R_3$, $R_6$, and $R_7$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
or a pair of $R_1$ and $R_2$, $R_2$ and $R_3$, $R_6$ and $R_7$, or $R_7$ and $R_8$ together with the ring to which they are bonded form a biheteroaryl;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R^{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and
provided that if $X_1$ and $Y_1$ are O, then at least one of $Z_1$, $Z_3$, $Z_4$, $Z_5$, $Z_6$, or $Z_8$ is N, or at least one of $R_1$, $R_3$, $R_4$, $R_5$, $R_6$, and $R_8$ is not H or OH, and $R_1$ and $R_8$ are not both halogen, and if $X_1$ and $Y_1$ are O, $R_2$ and $R_7$ are each OH, and $R_1$, $R_4$, $R_5$, $R_6$ and $R_8$ are each H, then $R_3$ is not Br;
or a pharmaceutically acceptable salt thereof.

In some embodiments, the compound provided that at least one of $Z_1$, $Z_3$, $Z_4$, $Z_5$, $Z_6$, or $Z_8$ is N, or at least two of $R_1$, $R_3$, $R_4$, $R_5$, $R_7$, and $R_8$ are not H or OH.

In some embodiments, the wherein A is

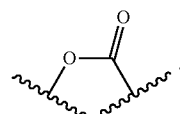

In some embodiments, the wherein both $R_2$ and $R_7$ are OH, or one of $R_2$ and $R_7$ is OH and the other of $R_2$ and $R_7$ is H, halogen, $NH_2$, or alkynyl-$R_9$.

In some embodiments, the wherein $R_9$ is OH.

In some embodiments, the wherein $Z_1$ is C—$R_1$; $Z_3$ is C—$R_3$; $Z_4$ is C—$R_4$; $Z_5$ is C—$R_5$; $Z_6$ is C—$R_6$; $Z_8$ is C—$R_8$; and one of $R_1$, $R_3$, $R_4$, $R_5$, $R_6$, and $R_8$ is alkyl or halogen.

In some embodiments, the wherein $Z_1$ is C—$R_1$; $Z_3$ is C—$R_3$; $Z_4$ is C—$R_4$; $Z_5$ is C—$R_5$; $Z_6$ is C—$R_6$; $Z_8$ is C—$R_8$; and two of $R_1$, $R_3$, $R_4$, $R_5$, $R_6$, and $R_8$ are alkyl or halogen.

In some embodiments, the compound is selected from:

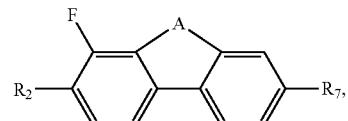

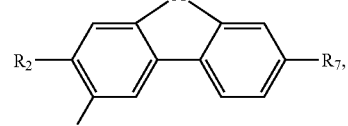

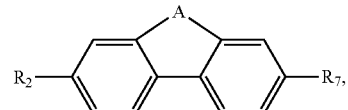

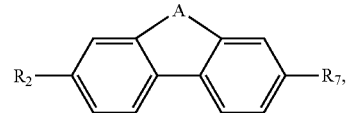

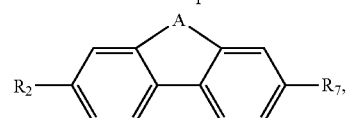

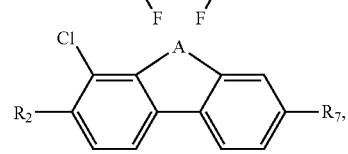

-continued
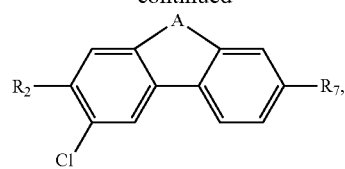
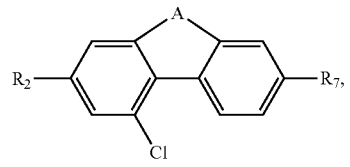
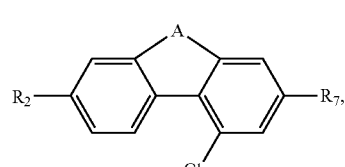
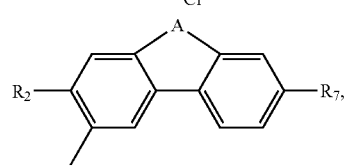
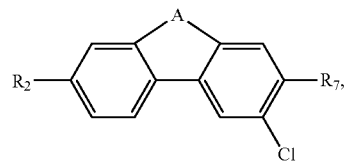
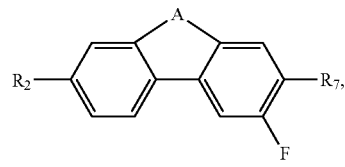
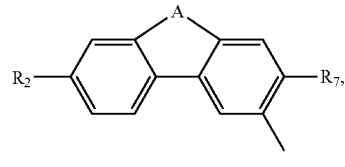
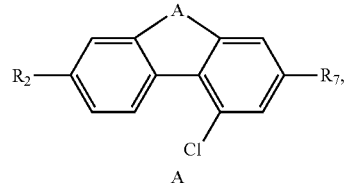
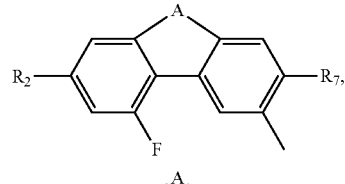
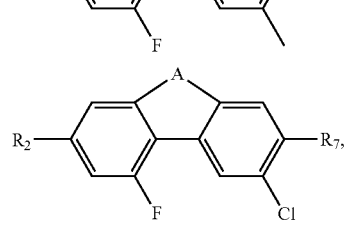
-continued
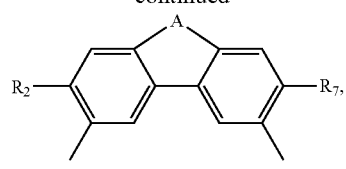
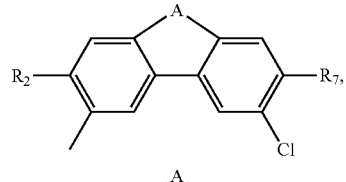
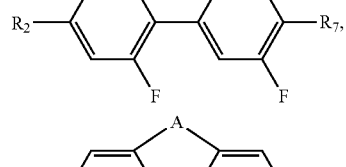
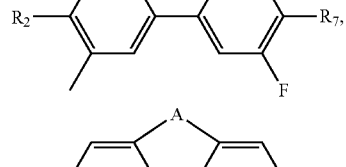
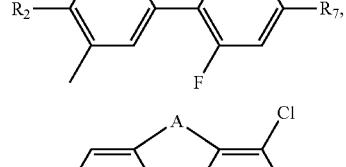
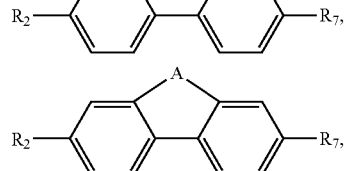
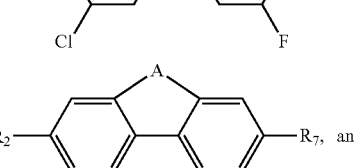
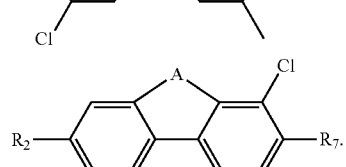
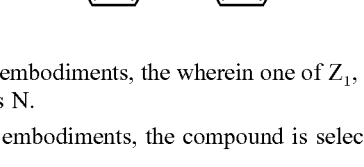
In some embodiments, the wherein one of $Z_1$, $Z_3$, $Z_4$, $Z_5$, $Z_6$, or $Z_8$ is N.
In some embodiments, the compound is selected from:
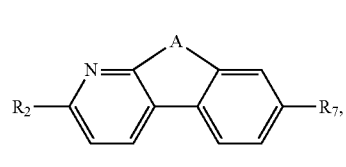

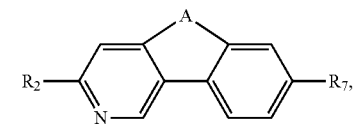

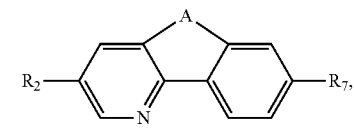

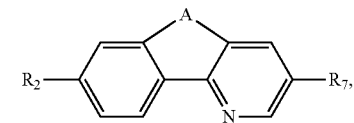

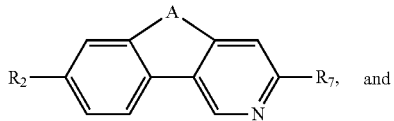 and

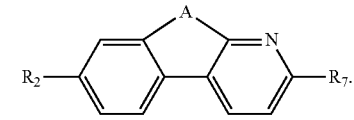

In some embodiments, wherein $R_1$ and $R_2$ together with the ring to which they are bonded form an unsubstituted or substituted biheteroaryl. In other embodiments, wherein $R_2$ and $R_3$ together with the ring to which they are bonded form an unsubstituted or substituted biheteroaryl. In other embodiments, wherein $R_6$ and $R_7$ together with the ring to which they are bonded form an unsubstituted or substituted biheteroaryl. In other embodiments, wherein $R_7$ and $R_8$ together with the ring to which they are bonded form an unsubstituted or substituted biheteroaryl.

In some embodiments, the compound is selected from:

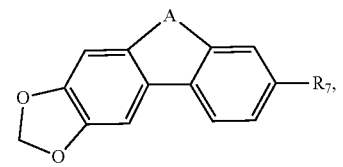

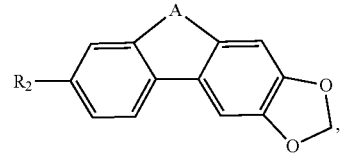

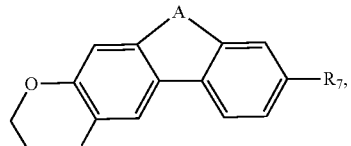

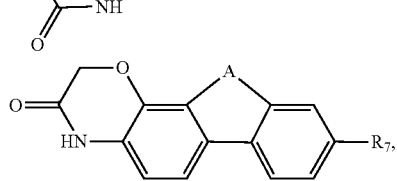

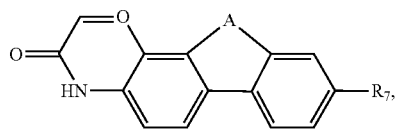

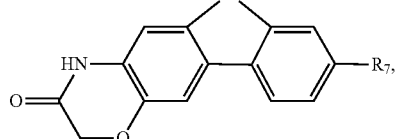

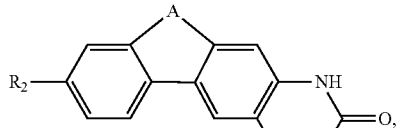

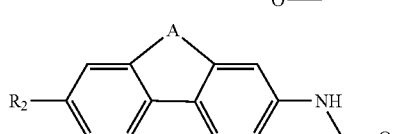

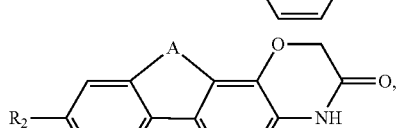

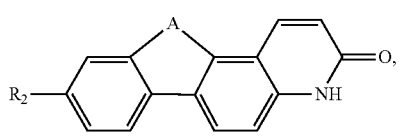

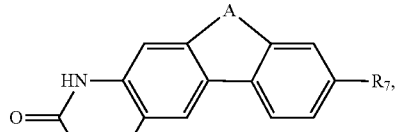

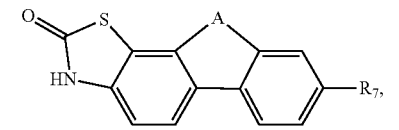

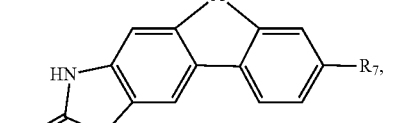

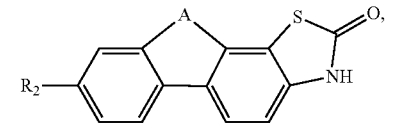

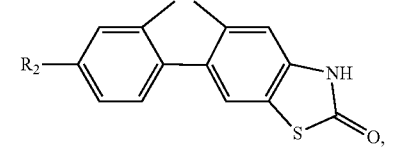

-continued
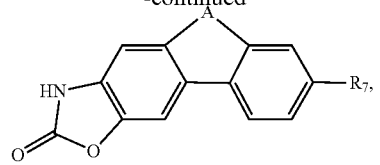
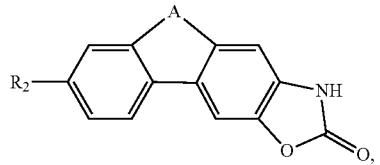
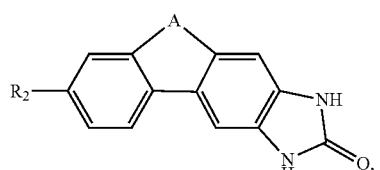
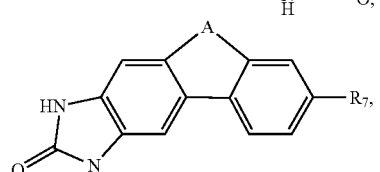
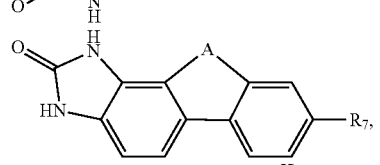
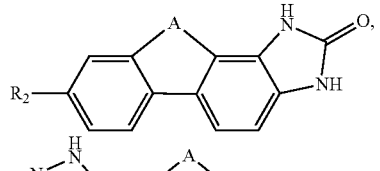
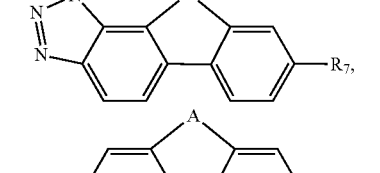
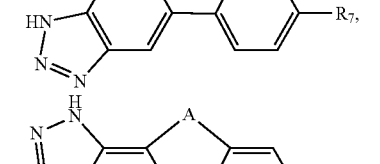
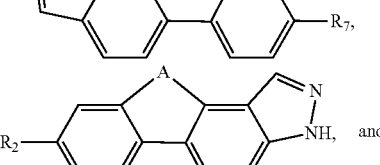  and
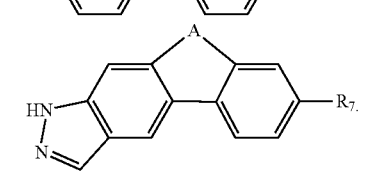
In some embodiments, wherein $R_2$ is H or OH; and $R_7$ is H or OH.
In some embodiments, the compound is selected from:
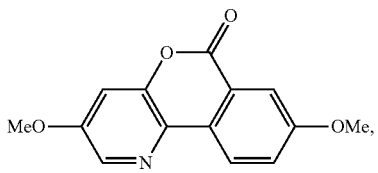
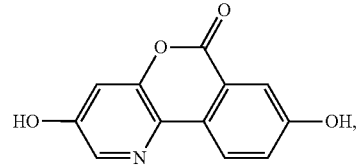
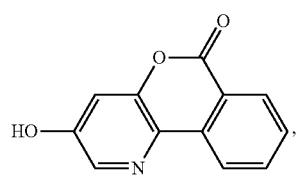
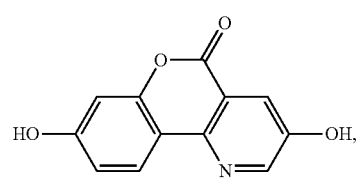
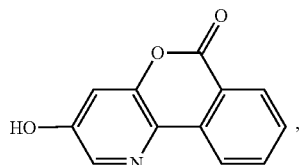
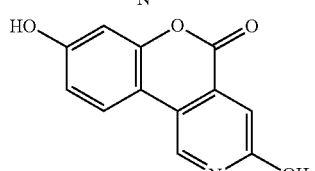
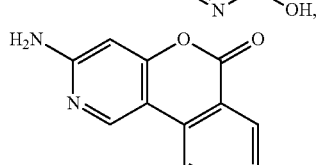
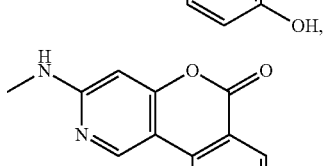
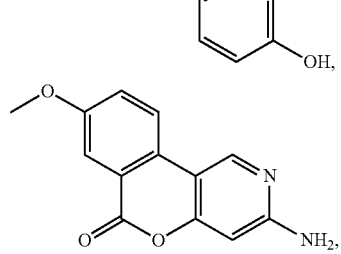

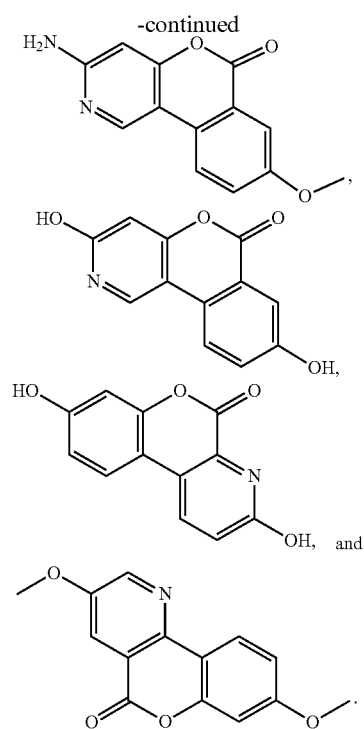
In some embodiments, the compound is selected from:
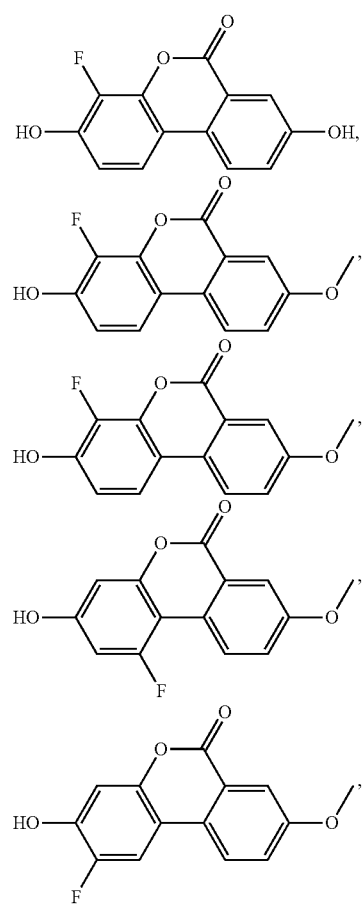
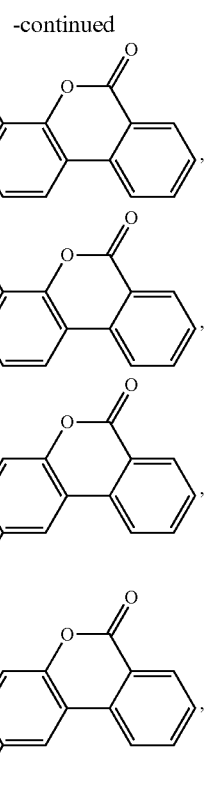
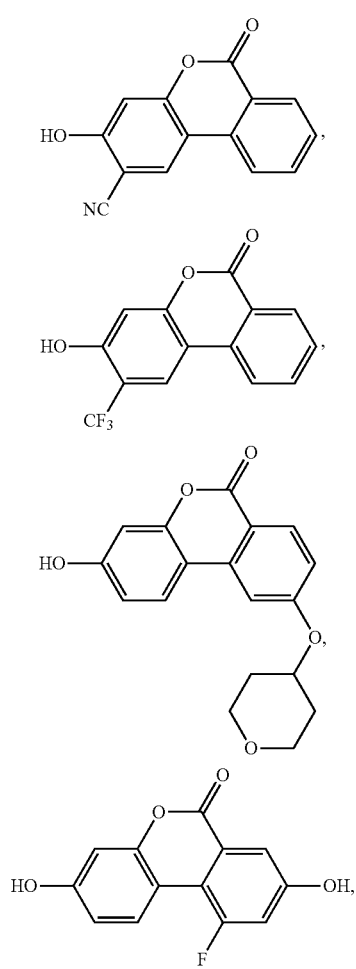

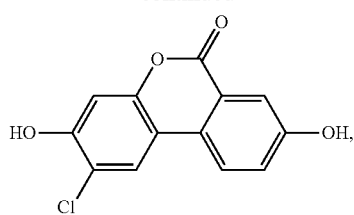
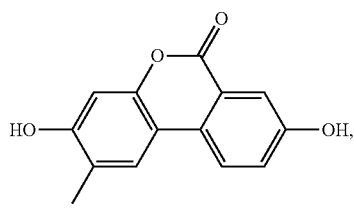
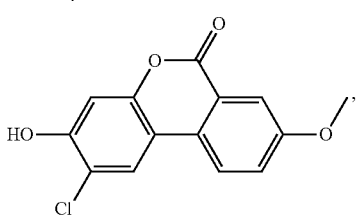
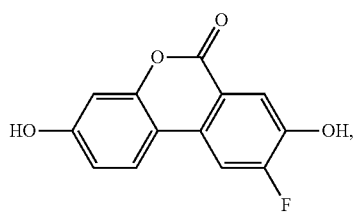
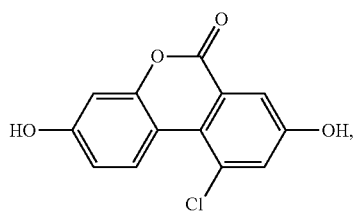
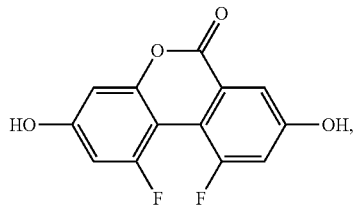
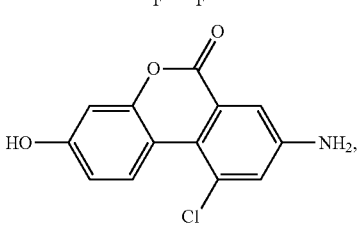
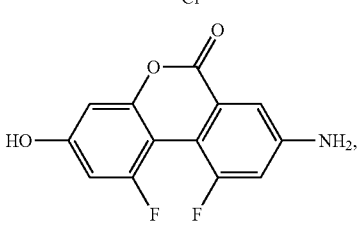
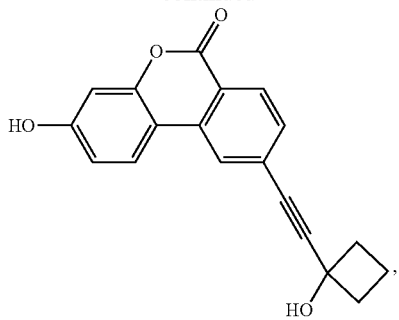
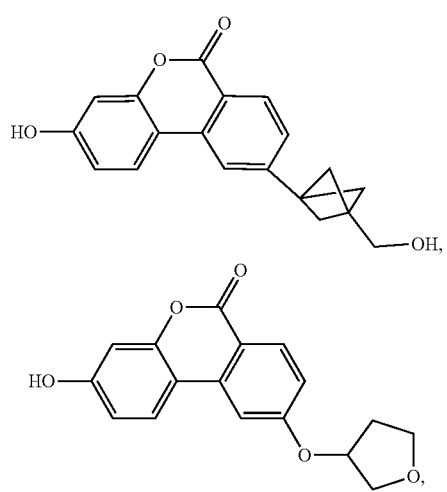
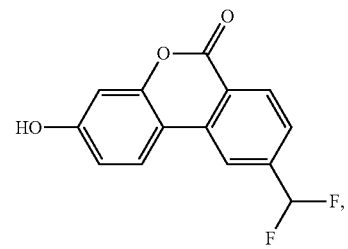
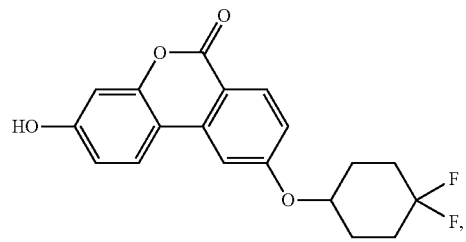
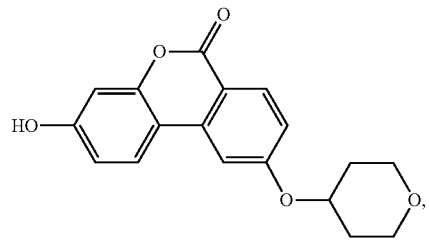

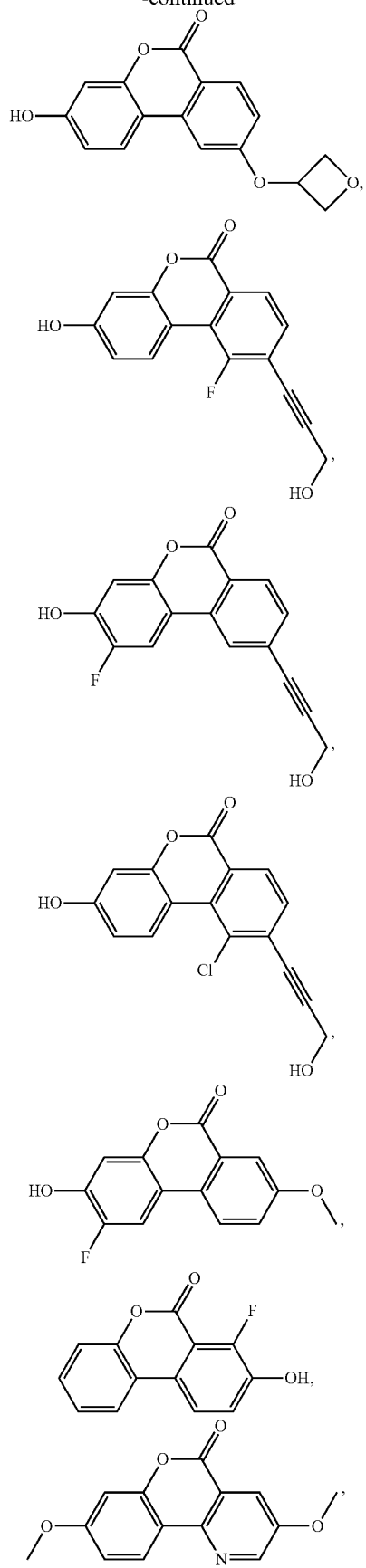
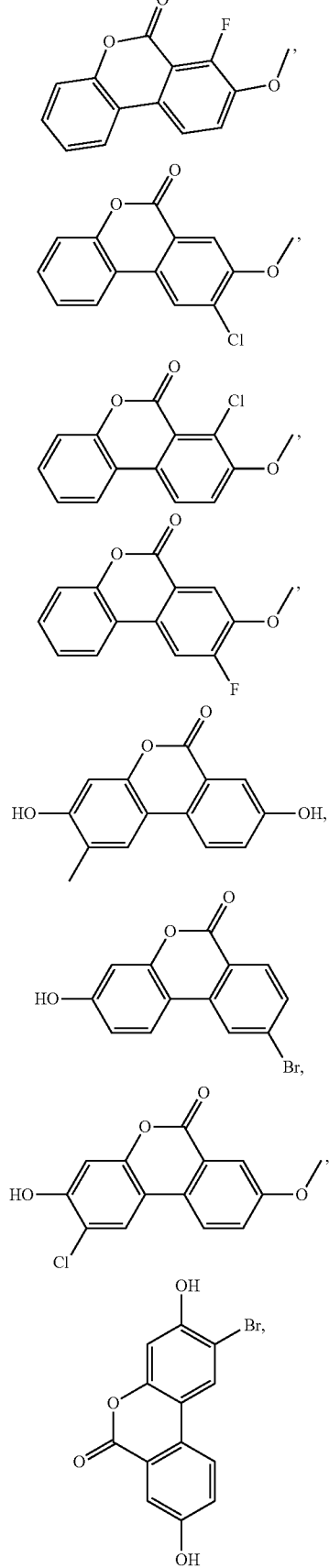

-continued
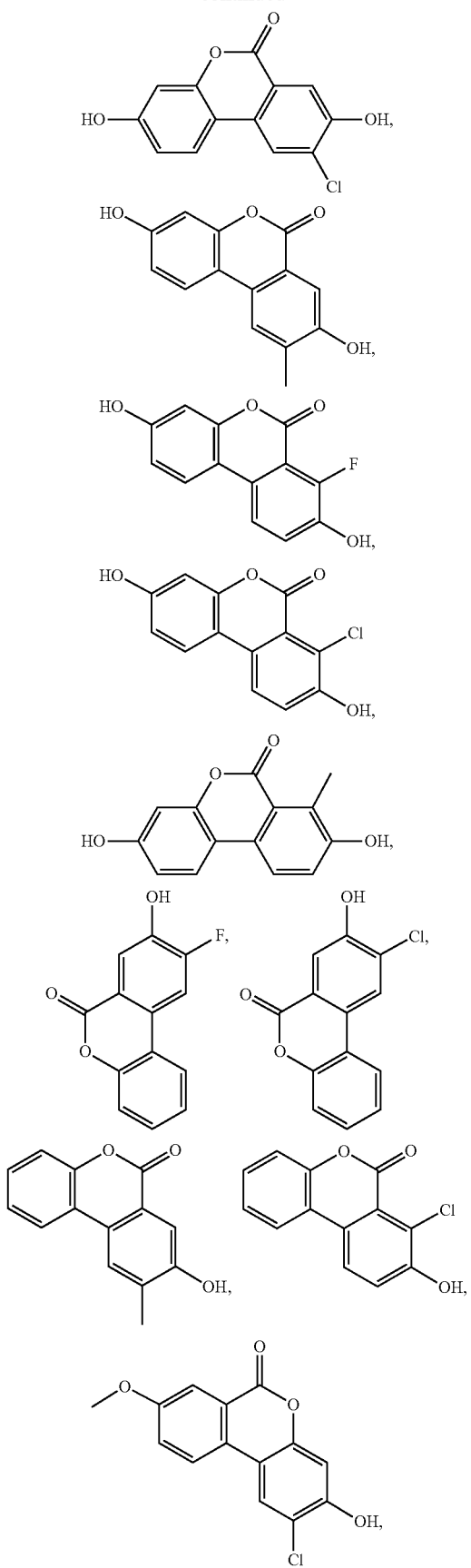
-continued
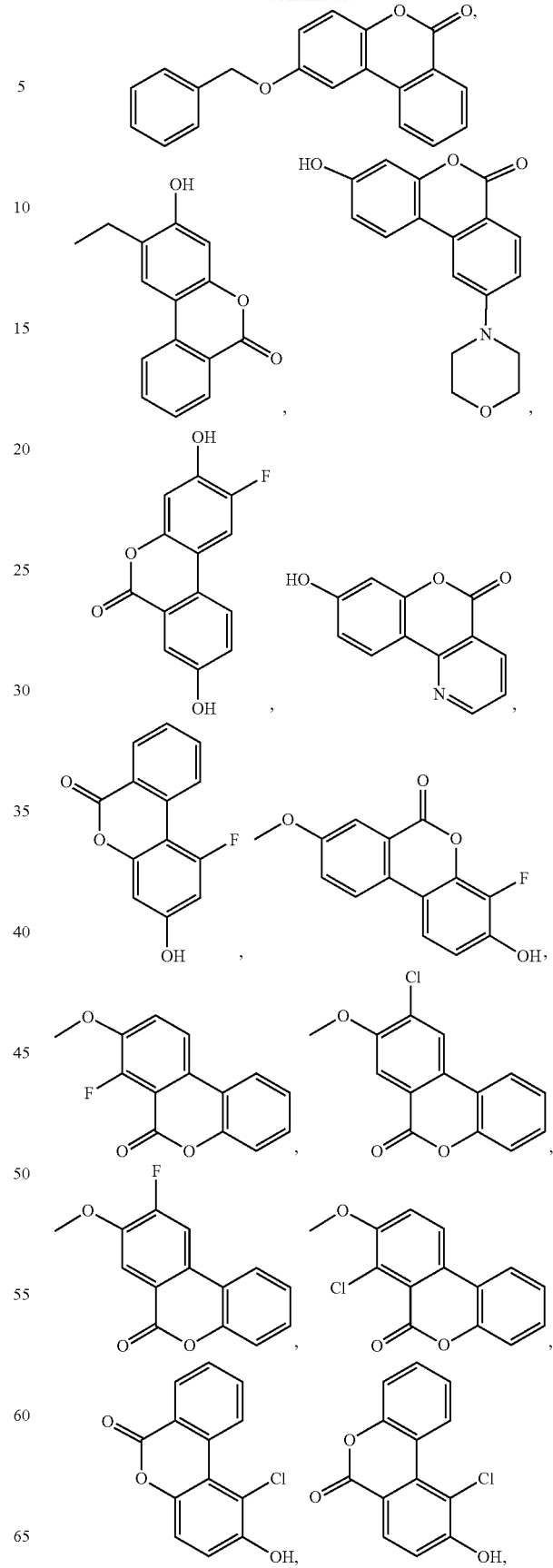

-continued
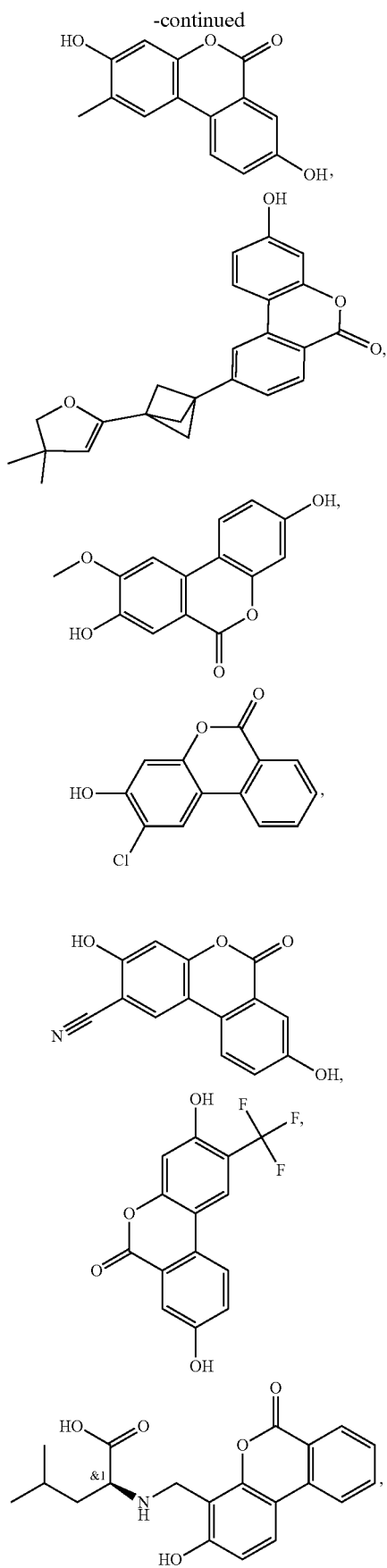
-continued
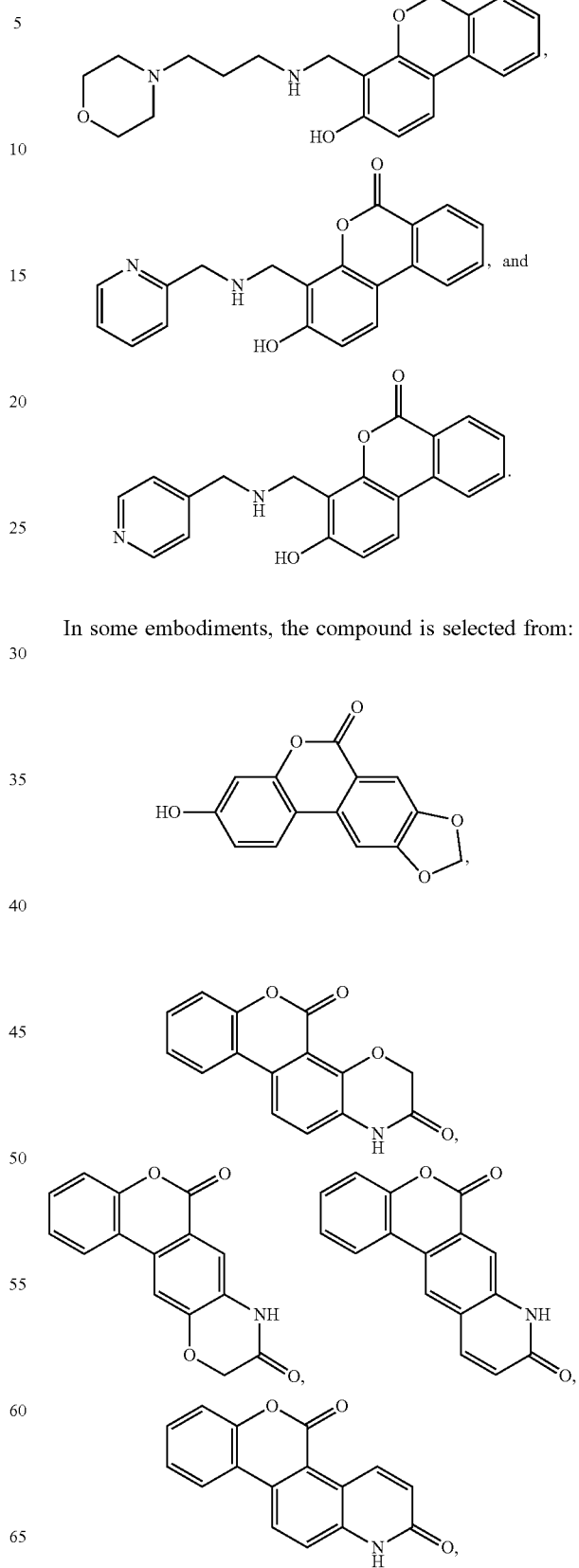
In some embodiments, the compound is selected from:

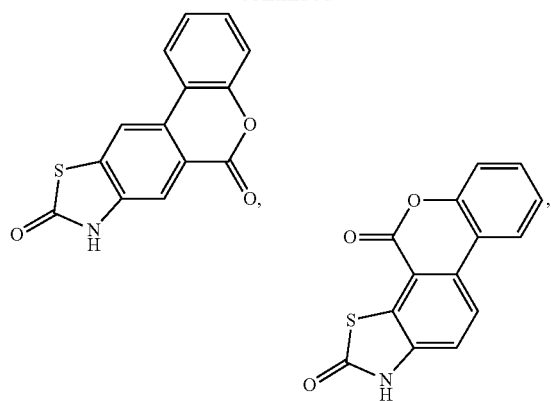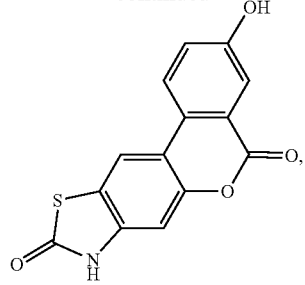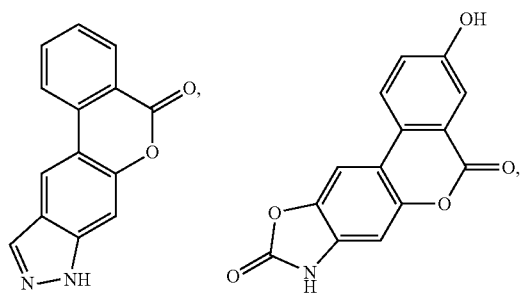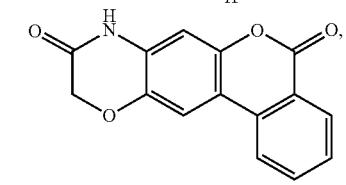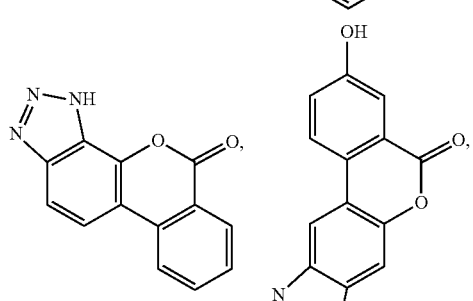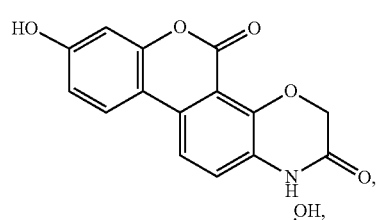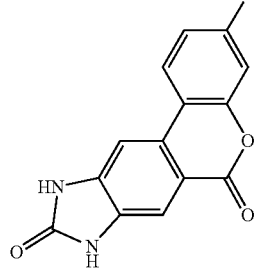

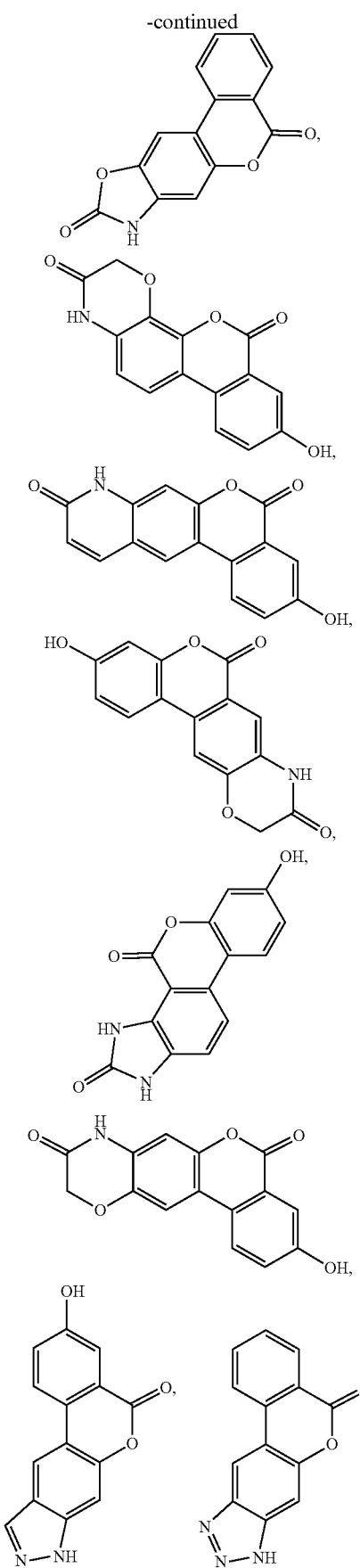
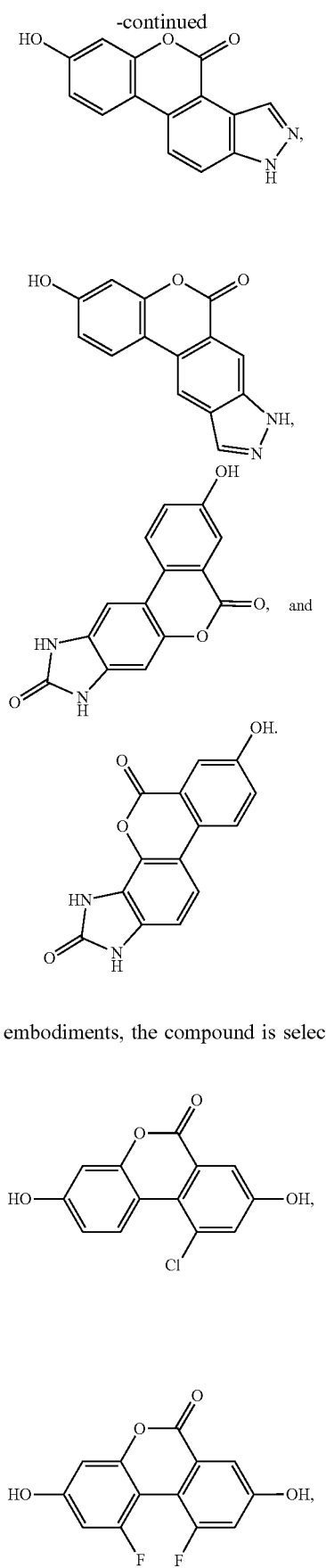
In some embodiments, the compound is selected from:

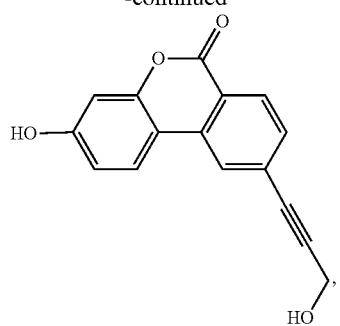
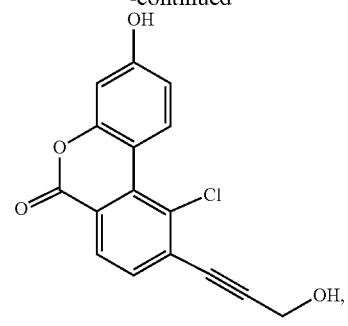
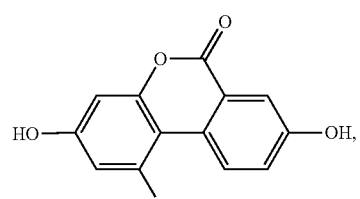
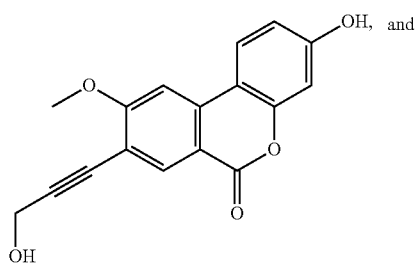
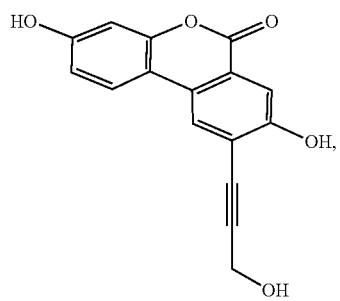
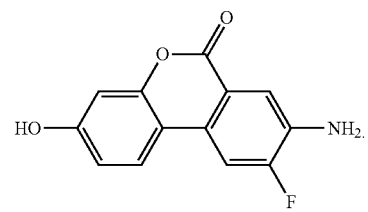
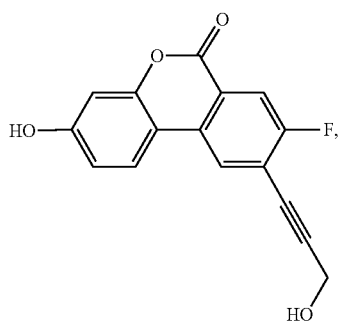
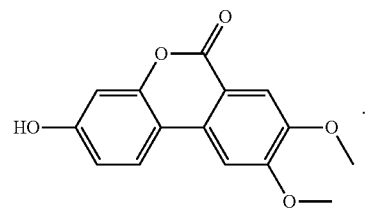 [SMILES: COc1cc2c(=O)oc3cc(O)ccc3c2cc1OC]
In some embodiments, the compound is
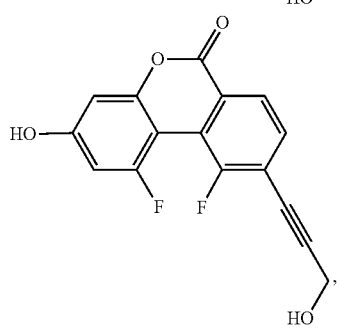
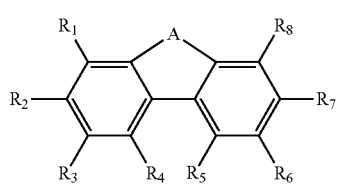
In one embodiment, a compound of Formula (Ic):
$$\text{(Ic)}$$

wherein
A is

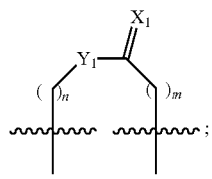

one of n and m is 0; and the other of n and m is 1;
$X_1$ and $Y_1$ are each O;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;
$R_4$ and $R_5$ are independently selected from H, halogen and alkyl;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl; and
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl,
or a pharmaceutically acceptable salt thereof.
In some embodiments, A is selected from

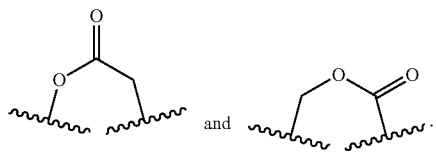 [SMILES: *CC(=O)O* ; *COC(*)=O]

In some embodiments, $R_2$ and $R_7$ are each OH. In other embodiments, wherein $R_2$ and $R_7$ are each O-alkyl. In other embodiments, wherein $R_2$ is OH; and $R_7$ is H or O-alkyl. In other embodiments, wherein $R_2$ is H or O-alkyl; and $R_7$ is OH.

In some embodiments, wherein $R_1$, $R_3$, $R_4$, $R_5$, $R_6$, and $R_8$ are each H. In other embodiments, wherein one of $R_1$, $R_3$, $R_4$, $R_5$, $R_6$, and $R_8$ is not H. In other embodiments, wherein two of $R_1$, $R_3$, $R_4$, $R_5$, $R_6$, and $R_8$ are not H. In other embodiments, wherein one of $R_1$, $R_3$, $R_4$, $R_5$, $R_6$, and $R_8$ is alkyl or halogen. In other embodiments, wherein two of $R_1$, $R_3$, $R_4$, $R_5$, $R_6$, and $R_8$ are alkyl or halogen.

In some embodiments, the compound is selected from:

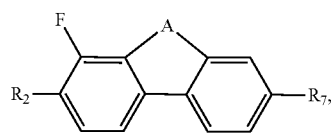

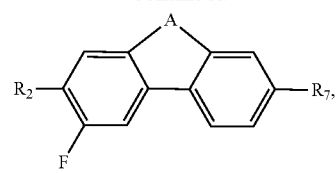

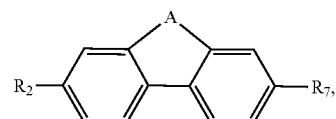

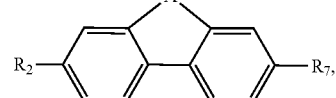

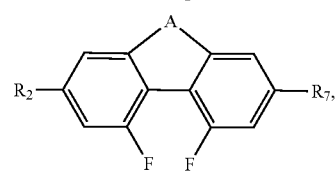

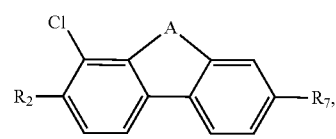

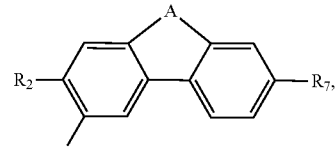

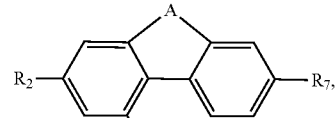

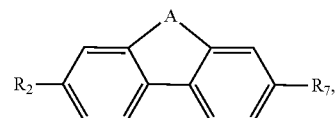

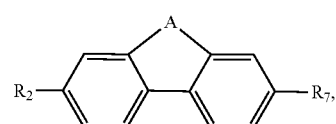

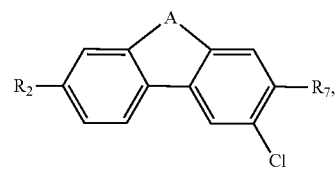

-continued
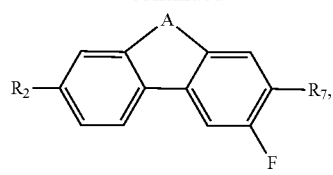
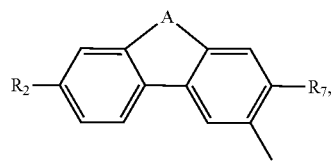
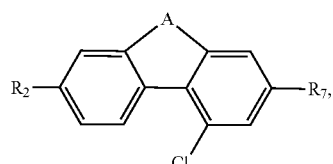
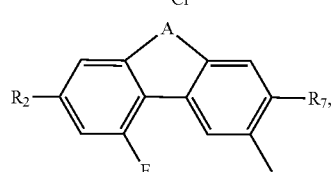
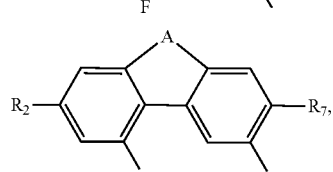
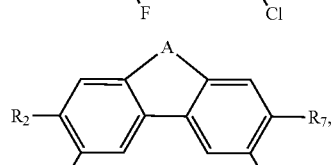
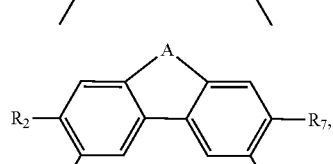

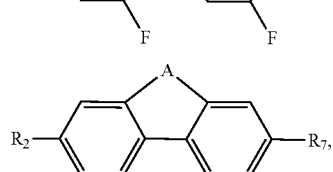
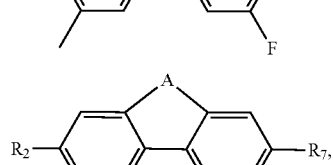
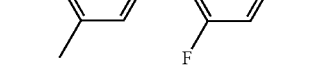
-continued
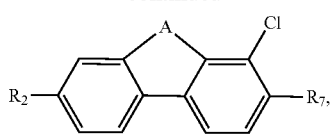
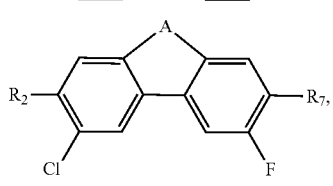
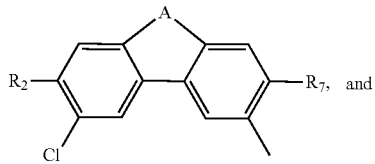 and
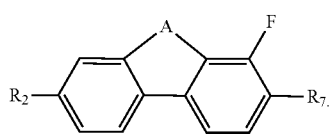
In some embodiments, the compound is selected from:
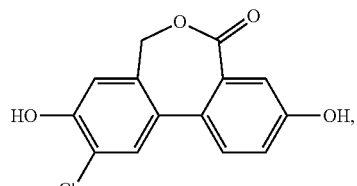
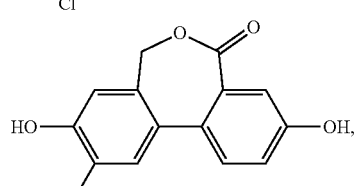
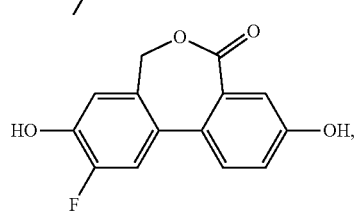
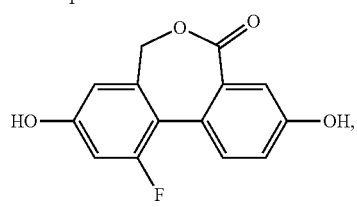
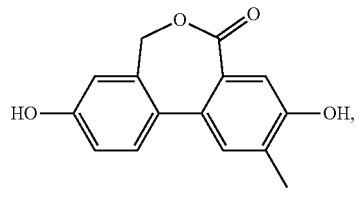

-continued

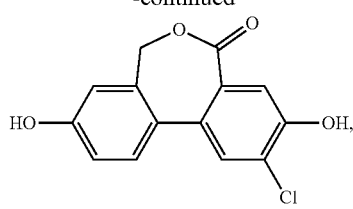
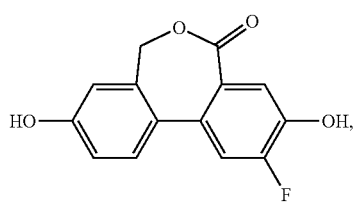
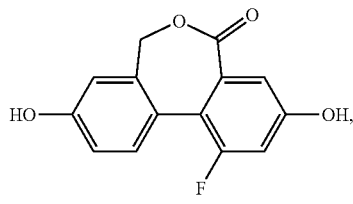
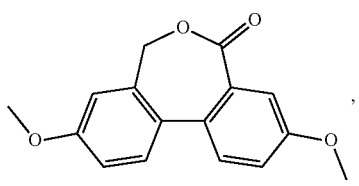
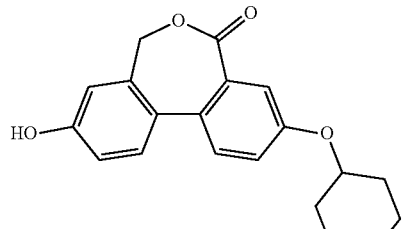
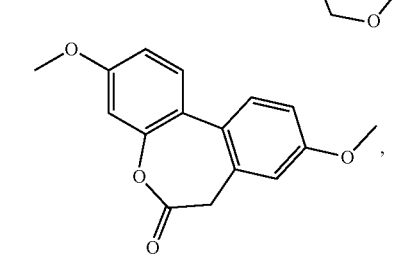
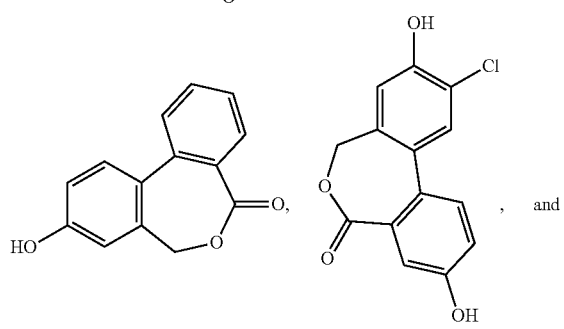 and 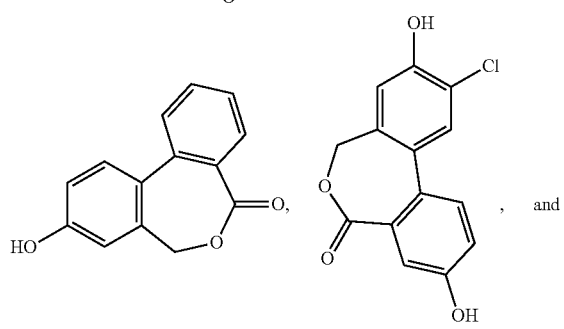

-continued

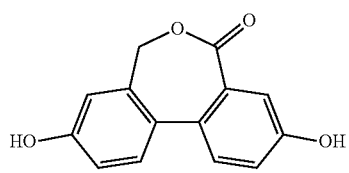

In some embodiments, the compound is selected from:

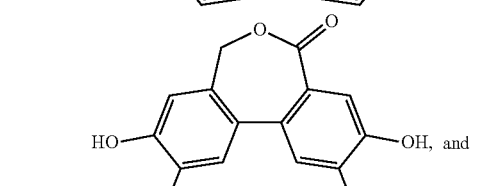
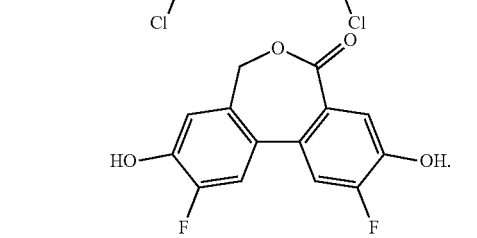, and
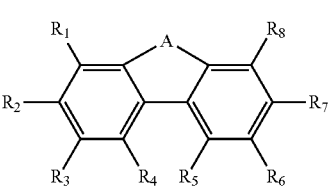

In one embodiment, a compound of Formula (Id):

(Id)

$$\begin{array}{c} R_1, R_8 \\ R_2, R_7 \\ R_3, R_4, R_5, R_6 \end{array}$$

wherein
A is

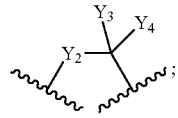;

$Y_2$ is O;
$Y_3$ and $Y_4$ are independently selected from H, halogen and alkyl; or together with the carbon to which they are bonded combine to form a cycloalkyl or heterocycloalkyl;
$R_1$, $R_4$, $R_5$, and $R_8$ are independently selected from H and halogen;

$R_2$, $R_3$, $R_6$, and $R_7$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;

each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;

each occurrence of $R_{11}$ is selected from H and alkyl;

each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and provided that when $Y_2$ is O, $R_2$ and $R_7$ are each OH, $R_1$, $R_3$, $R_4$, $R_5$, $R_6$, and $R_8$ are each H, then $X_3$ and $X_4$ are not both halogen, or a pharmaceutically acceptable salt thereof.

In some embodiments, A is selected from

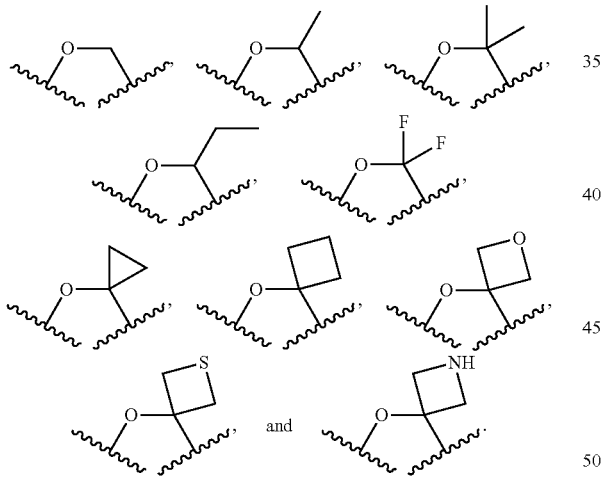

In some embodiments, $R_2$ and $R_7$ are each OH. In other embodiments, wherein one of $R_2$ and $R_7$ is OH and the other of $R_2$ and $R_7$ is O-alkyl. In other embodiments, wherein one of $R_1$, $R_3$, $R_4$, $R_5$, $R_6$, and $R_8$ is alkyl or halogen. In other embodiments, wherein two of $R_1$, $R_3$, $R_4$, $R_5$, $R_6$, and $R_8$ are alkyl or halogen In some embodiments, the compound is selected from:

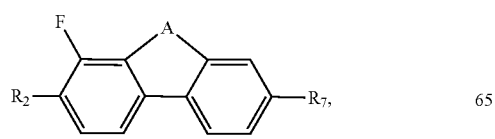

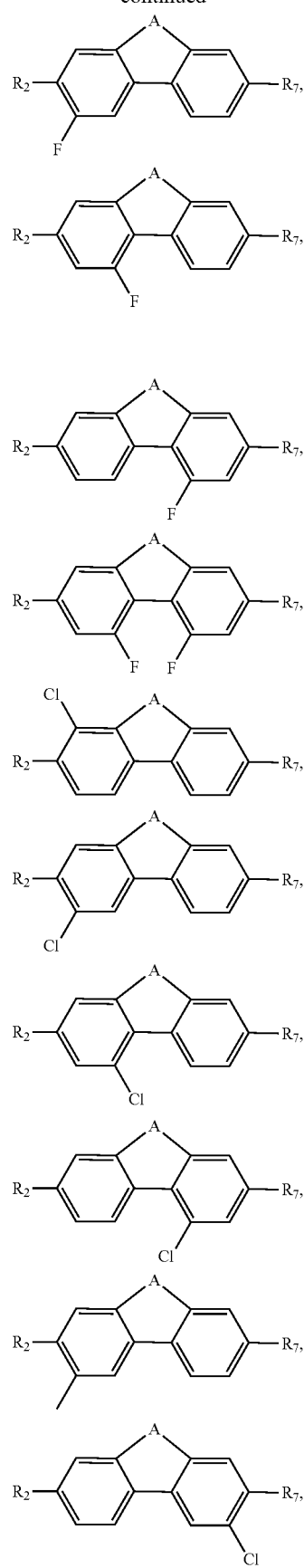

-continued
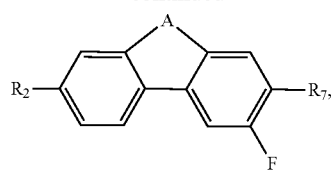
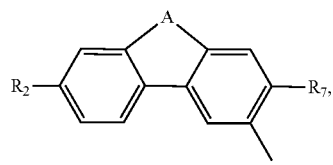
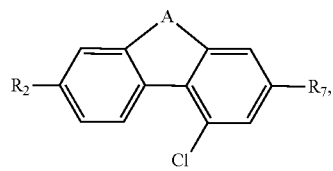
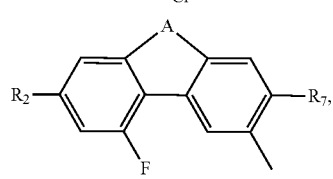

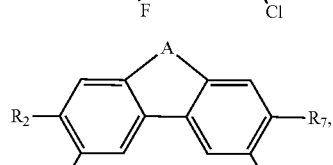
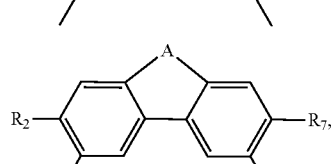
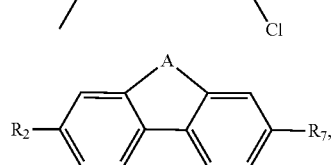
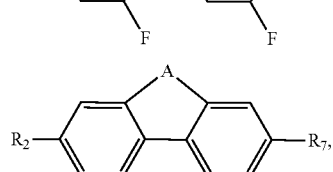
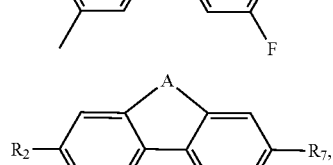
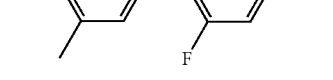
-continued
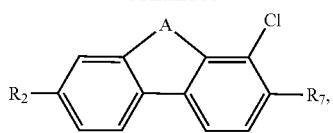
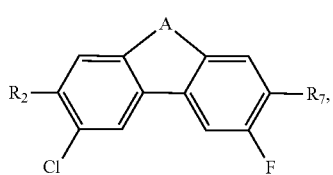
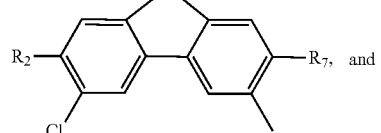, and
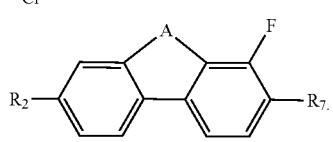
In some embodiments, the compound is selected from:
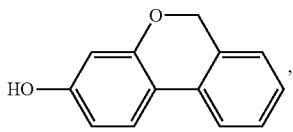,
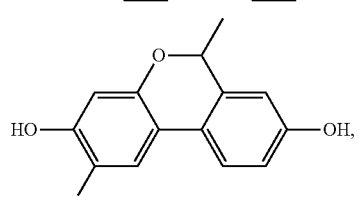,
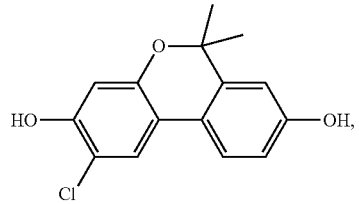,
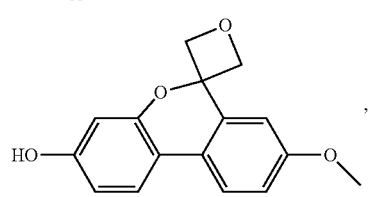,
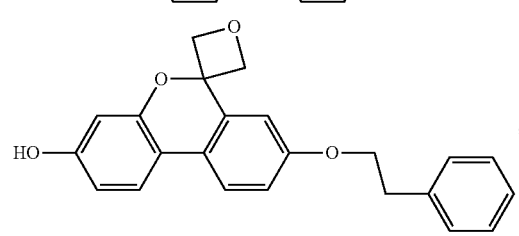, 79
-continued
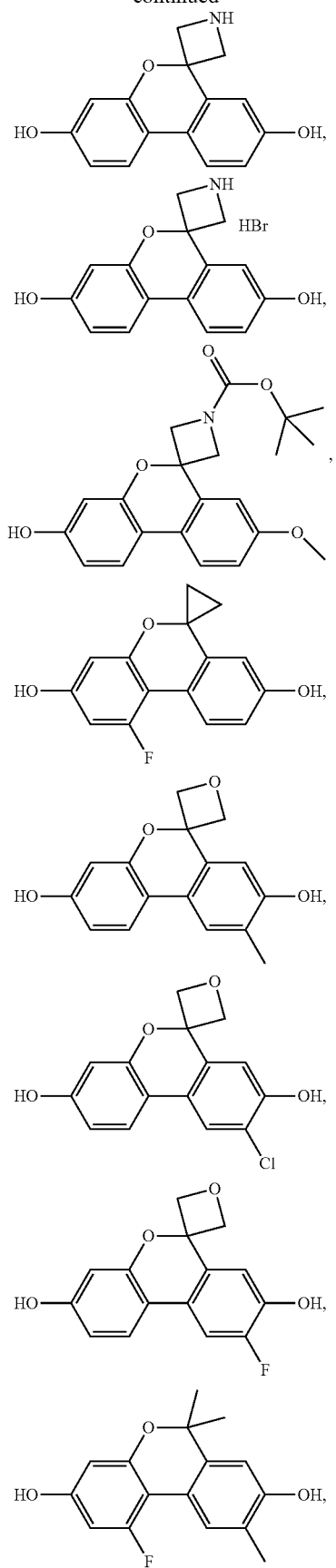
80
-continued
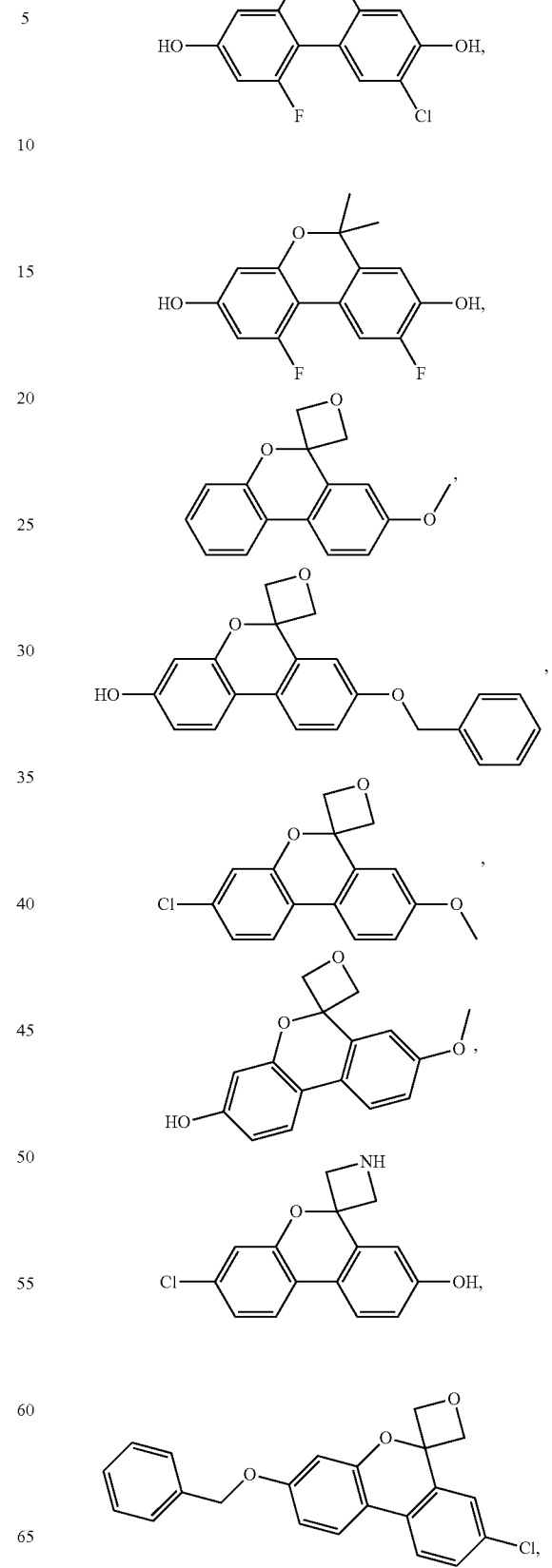

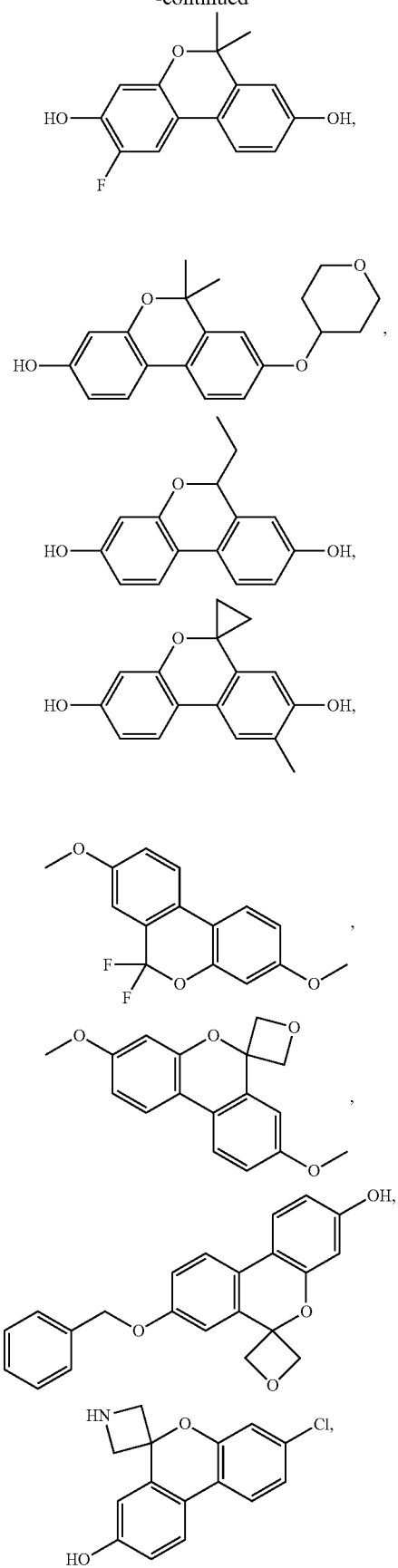
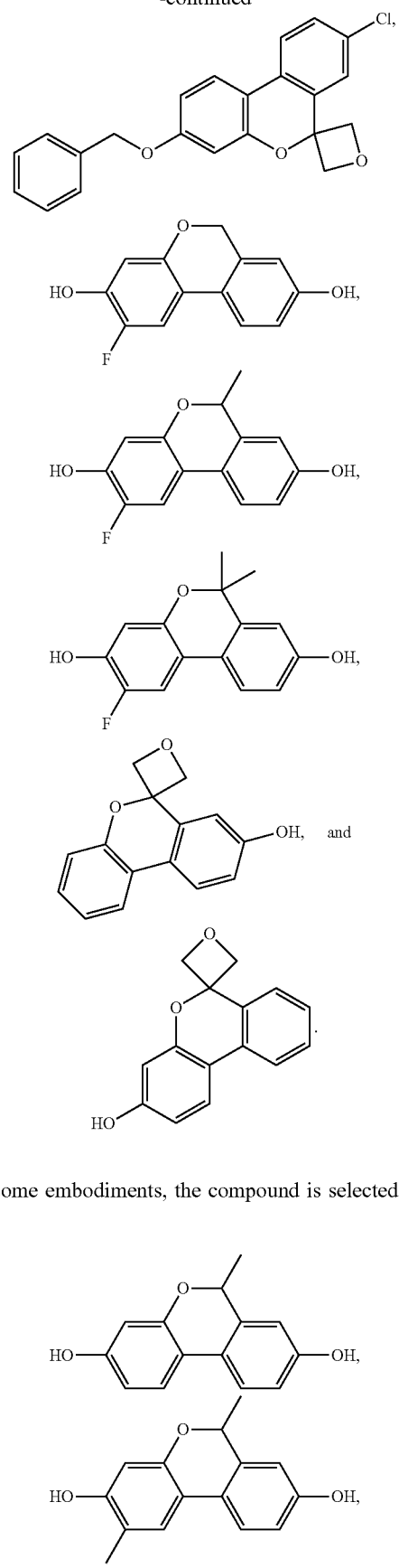
In some embodiments, the compound is selected from:

In some embodiments, the compound is selected from:

-continued

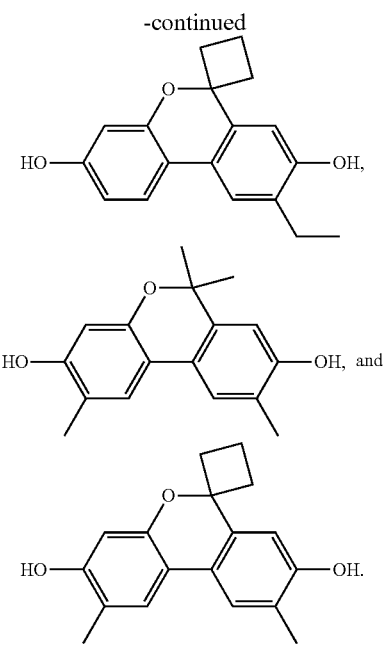

In one embodiment, a compound of Formula (Ie):

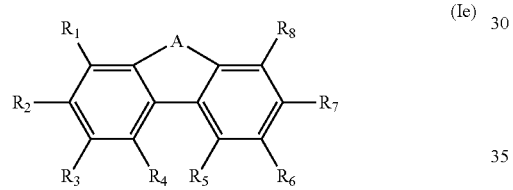

wherein
A is

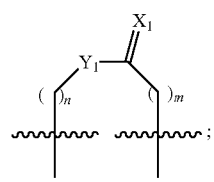

n and m are both 0; or one of n and m is 0, and the other of n and m is 1;
$X_1$ is O;
$Y_1$ is selected from NH, N—$CH_3$, N-t-Bu, N-cycloalkyl, and N-heterocycloalkyl;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;
$R_4$ and $R_5$ are independently selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl; and
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl;
provided that no more than two of $R_1$, $R_2$, $R_3$, $R_6$, $R_7$, and $R_8$ are OH or $OCH_3$,
if A is

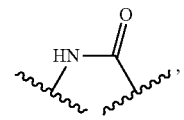

and $R_1$, $R_3$, $R_4$, $R_5$, $R_6$, and $R_8$ are each H, then $R_2$ and $R_7$ are not both OH, both $OCH_3$ or both $OR_{10}$, and
if A is

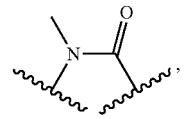

and $R_1$, $R_3$, $R_4$, $R_5$, $R_6$, and $R_8$ are each H, then $R_2$ and $R_7$ are not both $OR_{10}$,
or a pharmaceutically acceptable salt thereof.
In some embodiments, wherein n and m are both 0. In other embodiments, wherein one of n and m is 0, and the other of n and m is 1.
In some embodiments, wherein A is selected from

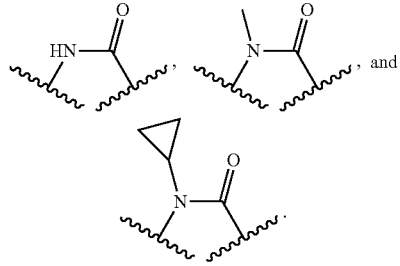

In other embodiments, wherein A is selected from

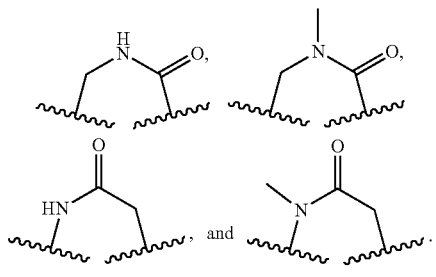

In some embodiments, wherein $R_2$ and $R_7$ are each OH.

In some embodiments, wherein one of $R_2$ and $R_7$ is OH and the other of $R_2$ and $R_7$ is OH is not OH. In other embodiments, wherein $R_2$ and $R_7$ are each O-alkyl. In other embodiments, wherein $R_2$ is OH and $R_7$ is O-alkyl; or $R_2$ is O-alkyl and $R_7$ is OH.

In some embodiments, wherein $R_1$, $R_3$, $R_4$, $R_5$, $R_6$, and $R_8$ are each H. In other embodiments, wherein one of $R_1$, $R_3$, $R_4$, $R_5$, $R_6$, and $R_8$ is not H. In other embodiments, a compound two of $R_1$, $R_3$, $R_4$, $R_5$, $R_6$, and $R_8$ are not H. In other embodiments, one of $R_1$, $R_3$, $R_4$, $R_5$, $R_6$, and $R_8$ is alkyl or halogen. In other embodiments, two of $R_1$, $R_3$, $R_4$, $R_5$, $R_6$, and $R_8$ are alkyl or halogen.

In some embodiments, the compound is selected from:

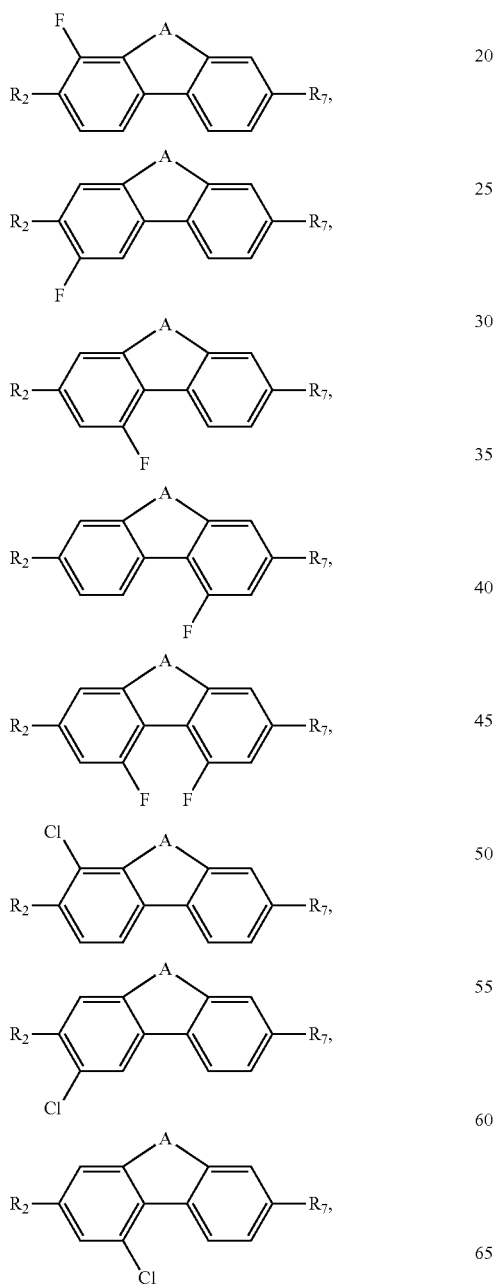

-continued

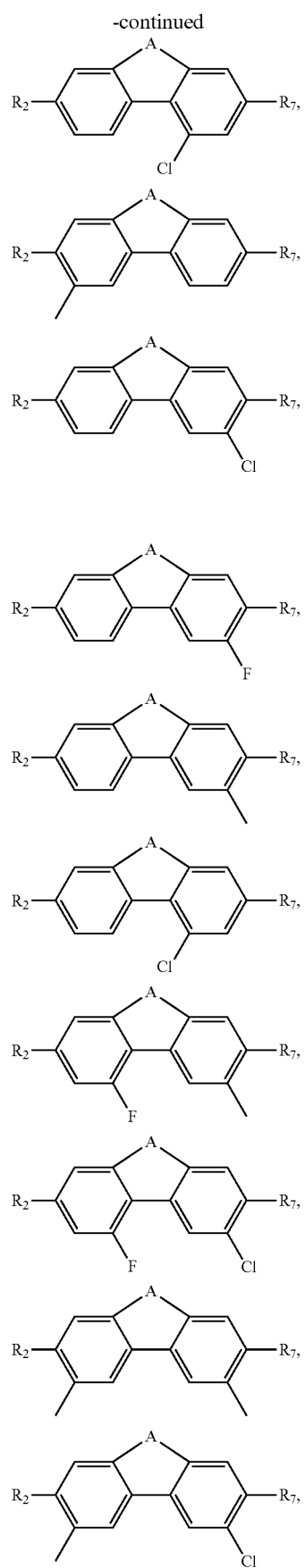

89
-continued
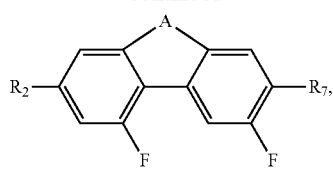
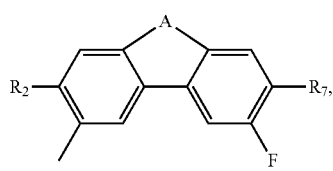
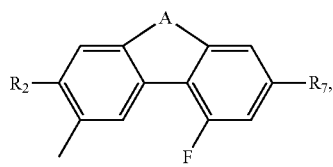
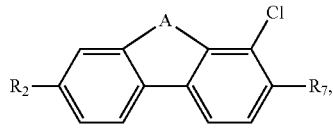
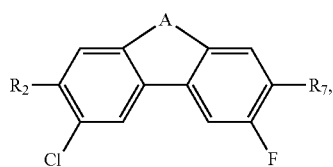
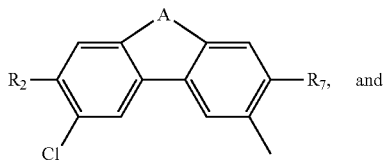 and
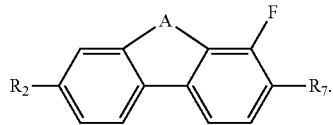
In some embodiments, the compound is selected from:
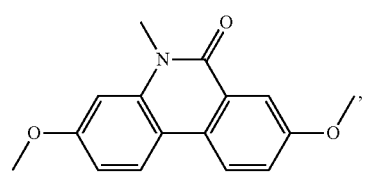
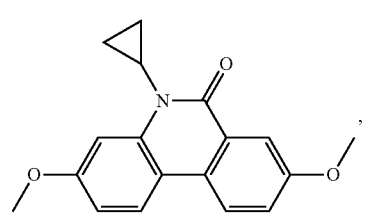
90
-continued
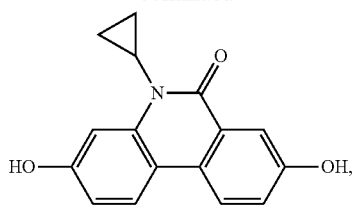
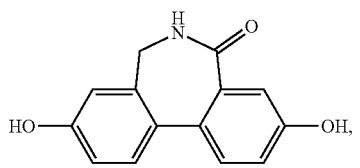
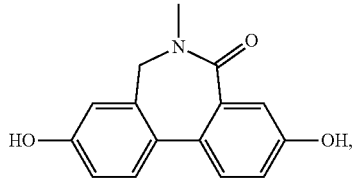
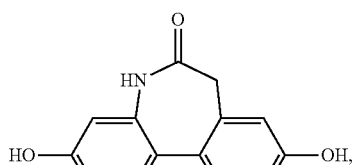
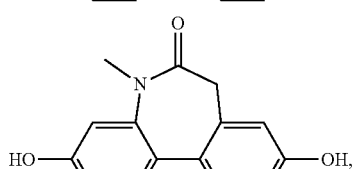
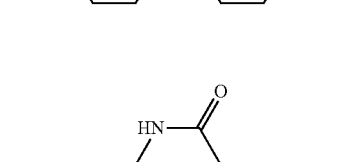
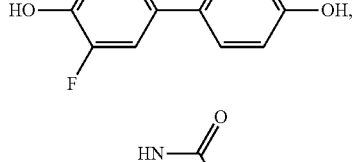
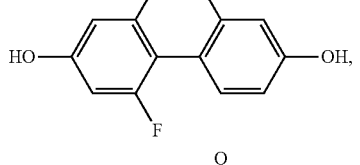
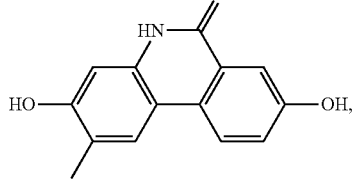

-continued
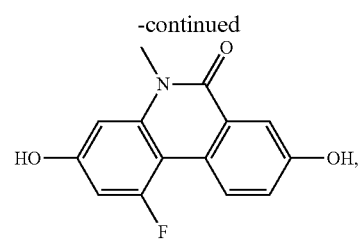
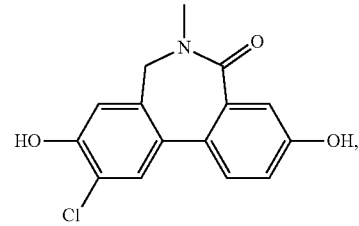
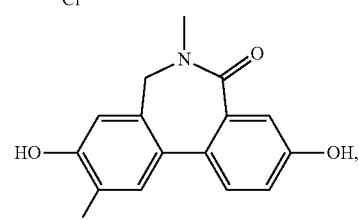
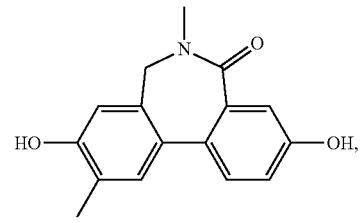
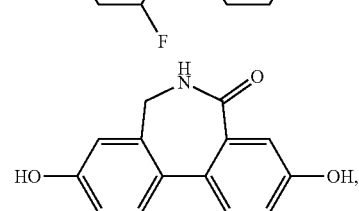
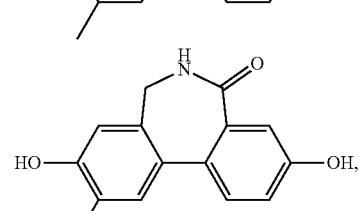
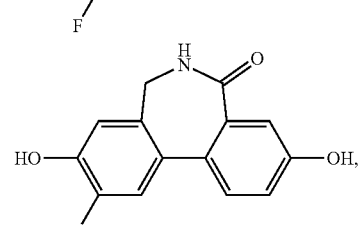
-continued
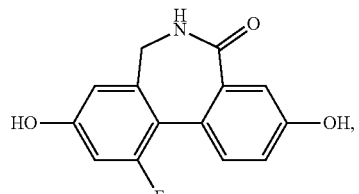
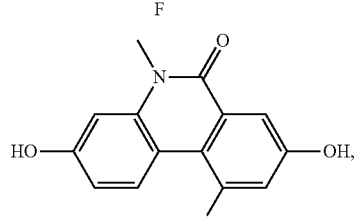
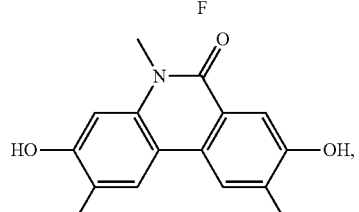
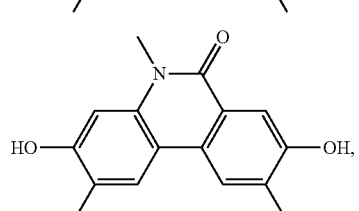
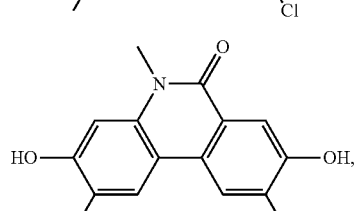
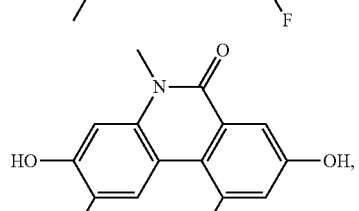
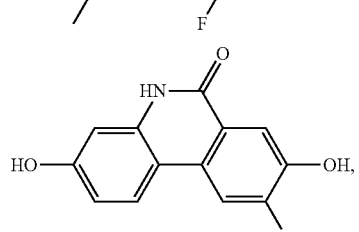
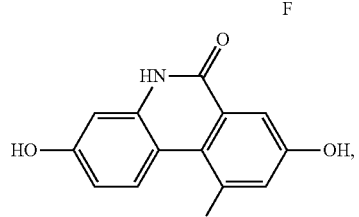

93
-continued
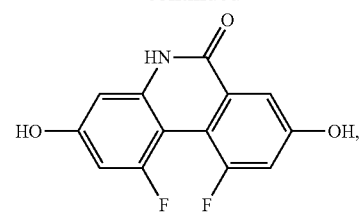
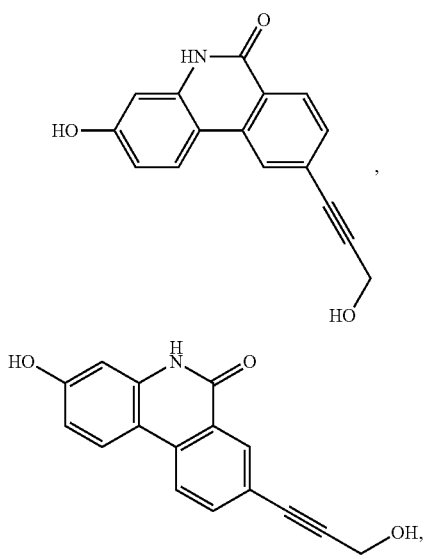
94
-continued
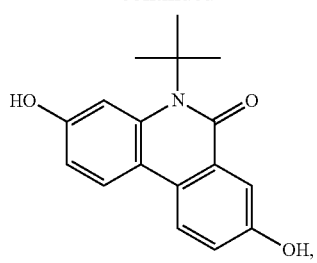
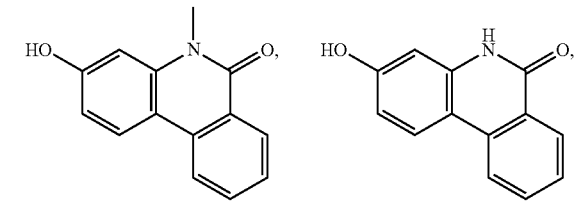
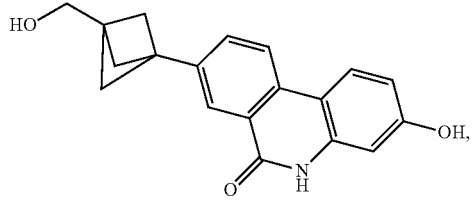
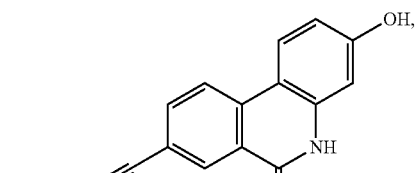
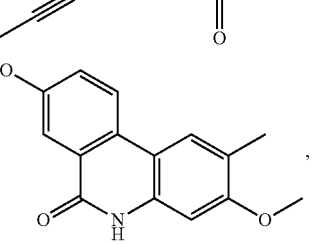
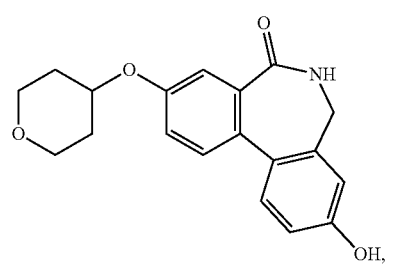
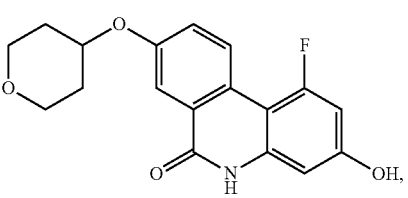

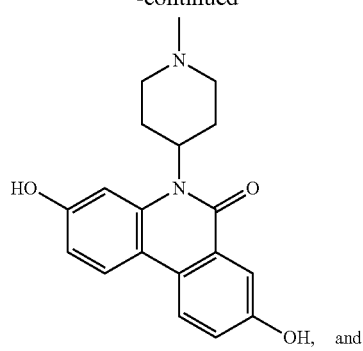
and
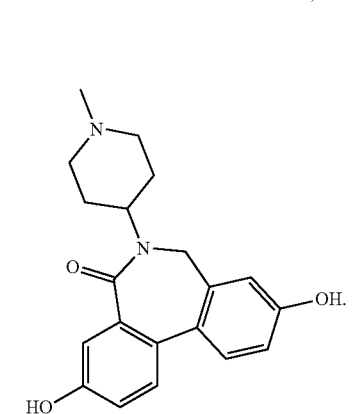
In some embodiments, the compound is selected from:
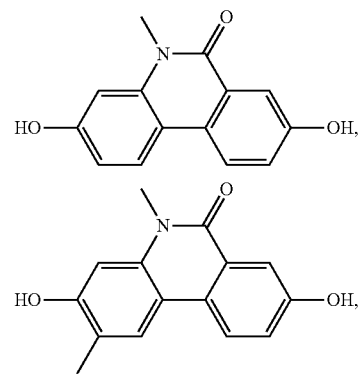
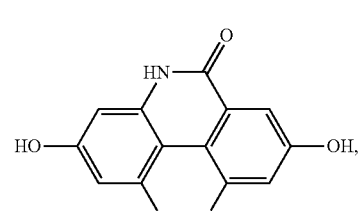
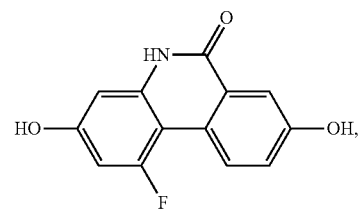
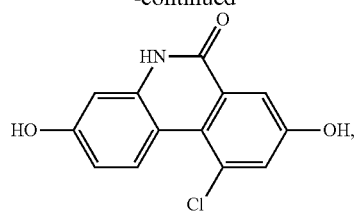
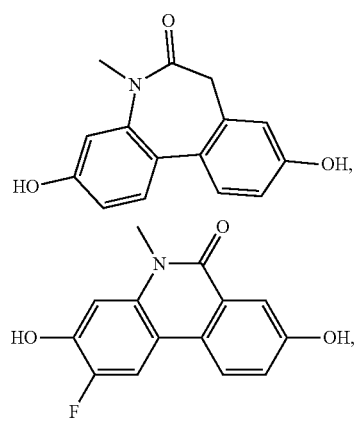
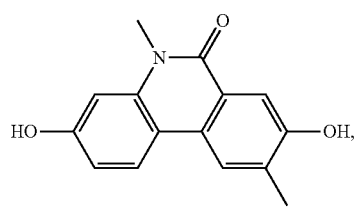
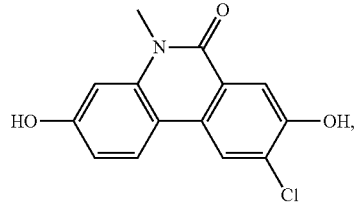
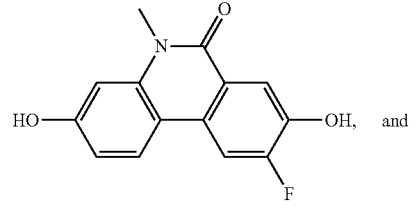
and
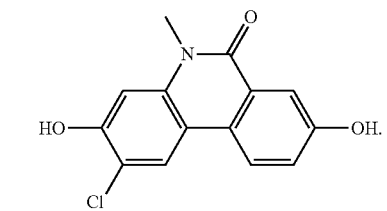

In one embodiment, the compound is selected from:
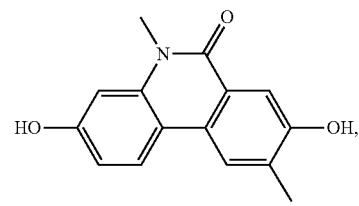
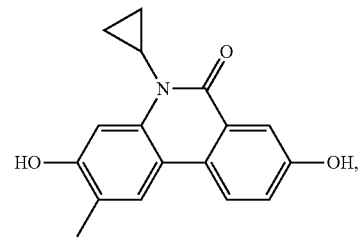
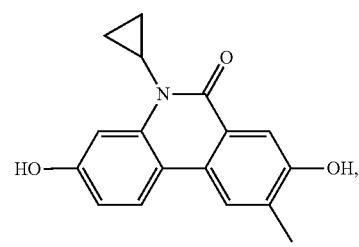
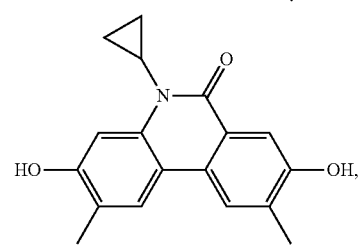
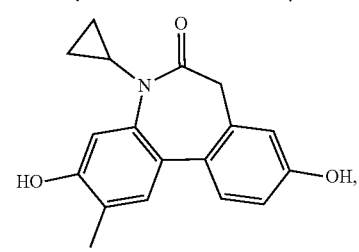
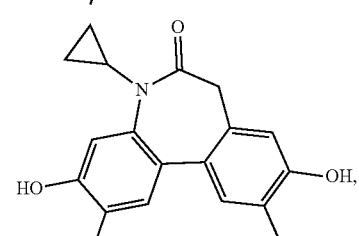
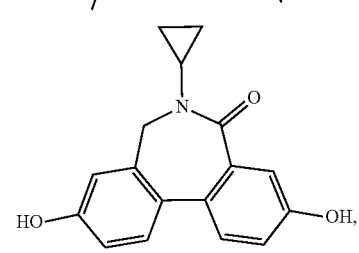
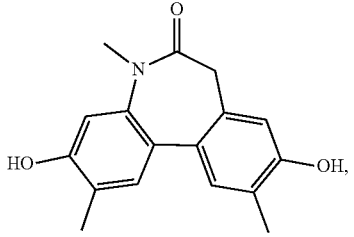
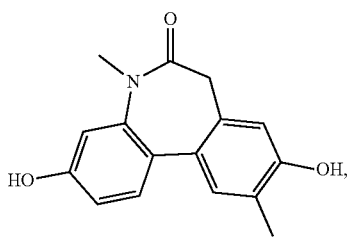
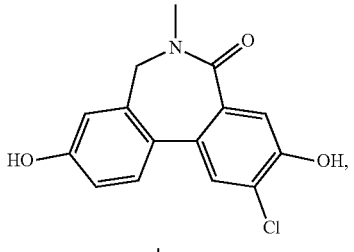
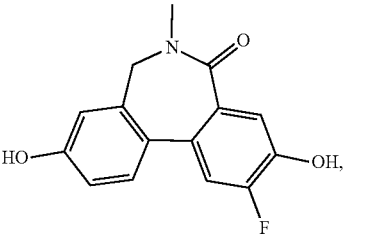
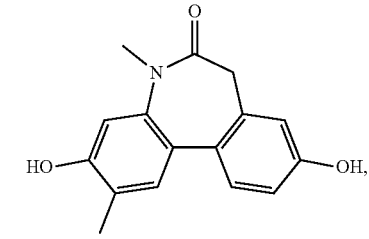
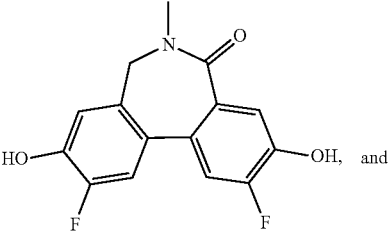 and
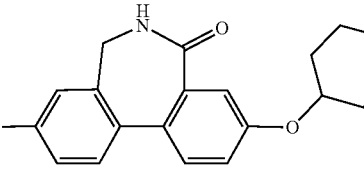

In one embodiment, a compound of Formula (If):

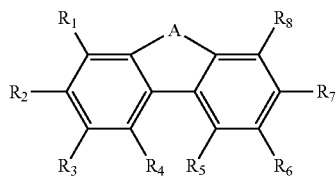
(If)

wherein
A is selected from

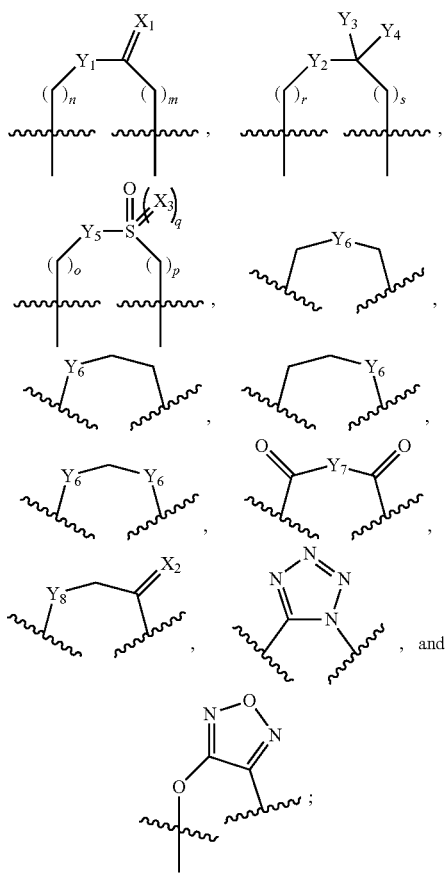

n and m are both 0; or one of n and m is 0 and the other of n and m is 1;
o and p are both 0; or one of o and p is 0 and the other of o and p is 1;
q is 0 or 1;
r and s are both 0; or one of r and s is 0 and the other of r and s is 1;
$X_1$ and $X_2$ are each O;
$X_3$ is 0 or N(alkyl);
$Y_1$ is S;
$Y_2$ is selected from O, $CH_2$, NH, N-alkyl, S, S(O), and $SO_2$;
$Y_3$ and $Y_4$ are independently selected from H, halogen, OH, and alkyl, or together with the carbon to which they are bonded combine to form a cycloalkyl or cycloheteroalkyl;
$Y_5$ is selected from $CH_2$, NH, N-alkyl, N-aralkyl, N-cycloalkyl, and N-heterocycloalkyl;

Each occurrence of $Y_6$ is independently selected from O, S, S(O), $SO_2$, NH, N-alkyl, N-alkylaryl, and N-cycloalkyl;
$Y_7$ is selected from O, NH and N-alkyl;
$Y_8$ is selected from O and S;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
$R_4$ and $R_5$ are independently selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and
provided that if $Y_2$ is $CH_2$, one of $Y_3$ or $Y_4$ is not H, or $Y_3$ or $Y_4$ together with the carbon to which they are bonded combine to form a cycloalkyl or heterocycloalkyl, and
if $Y_2$ is O, then one of r and s is 0 and the other of r and s is 1,
or a pharmaceutically acceptable salt thereof.
In some embodiments, A is

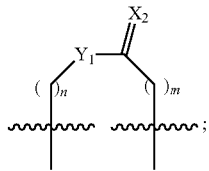

and n and m are both 0. In other embodiments, A is

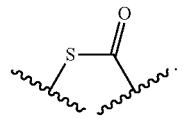

In some embodiments, A is

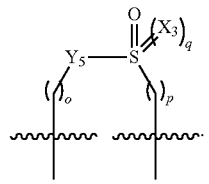

In other embodiments, A is selected from
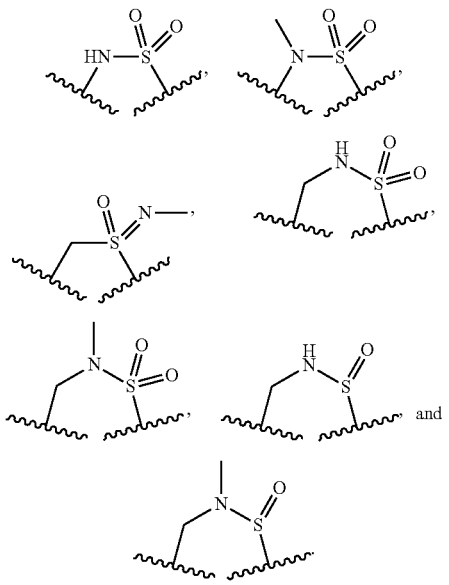
In some embodiments, A is
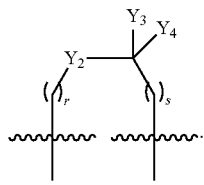
In other embodiments, A is selected from
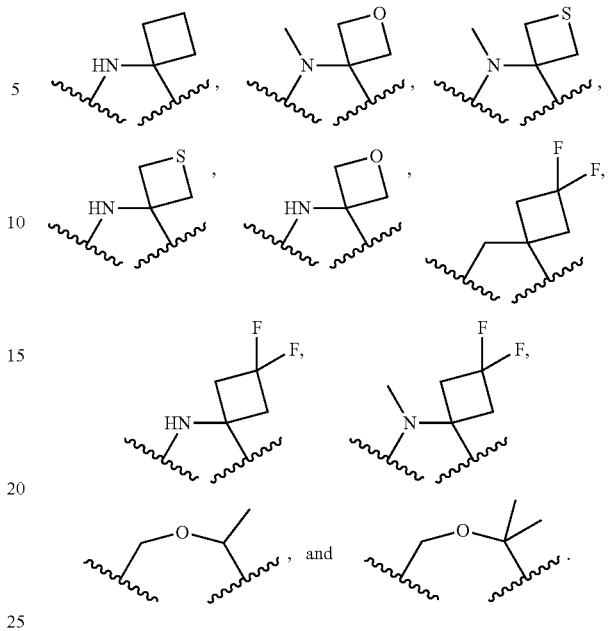
In some embodiments, A is selected from
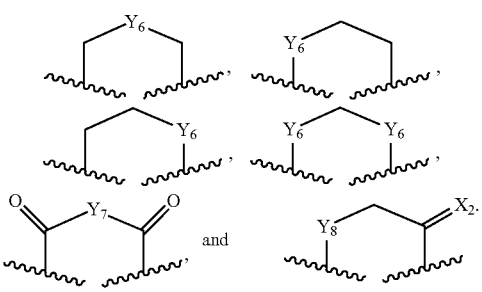
In other embodiments, A is selected from
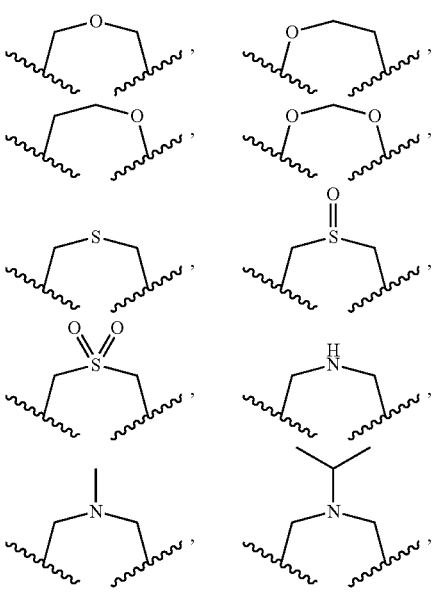

-continued

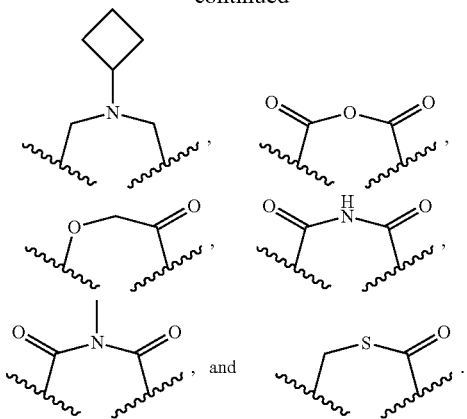

In some embodiments, $R_2$ and $R_7$ are each OH. In other embodiments, one of $R_2$ and $R_7$ is OH and the other of $R_2$ and $R_7$ is OH is not OH. In other embodiments, $R_2$ and $R_7$ are each O-alkyl. In other embodiments, $R_2$ is OH and $R_7$ is O-alkyl; or $R_2$ is O-alkyl and $R_7$ is OH.

In some embodiments, $R_1$, $R_3$, $R_4$, $R_5$, $R_6$, and $R_8$ are each H. In other embodiments, one of $R_1$, $R_3$, $R_4$, $R_5$, $R_6$, and $R_8$ is not H. In other embodiments, two of $R_1$, $R_3$, $R_4$, $R_5$, $R_6$, and $R_8$ are not H. In other embodiments, one of $R_1$, $R_3$, $R_4$, $R_5$, $R_6$, and $R_8$ is alkyl or halogen. In other embodiments, two of $R_1$, $R_3$, $R_4$, $R_5$, $R_6$, and $R_8$ are alkyl or halogen.

In some embodiments, the compound is selected from:

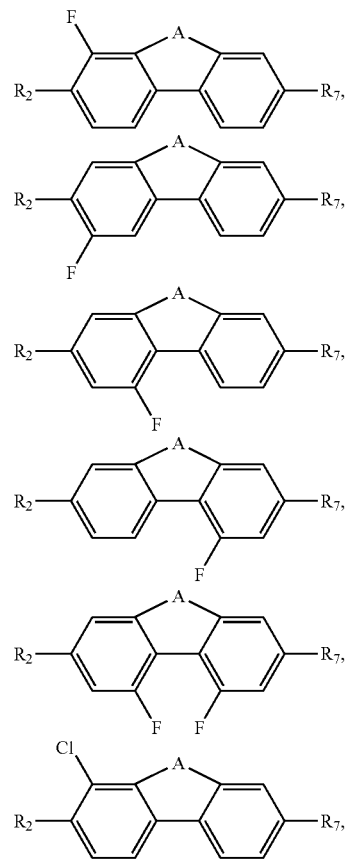

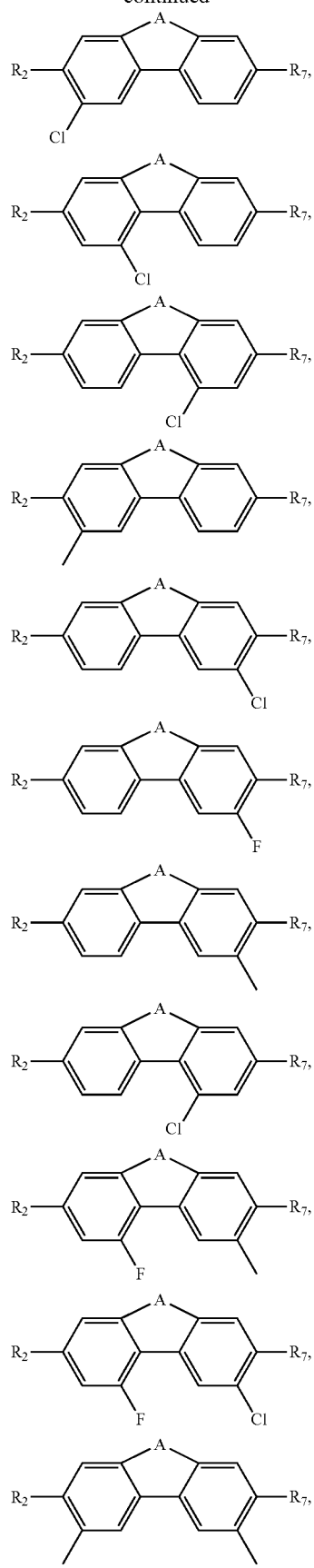

-continued
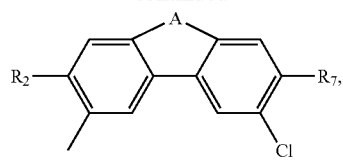
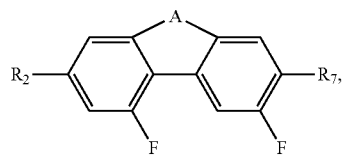
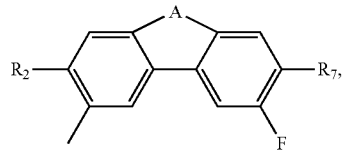
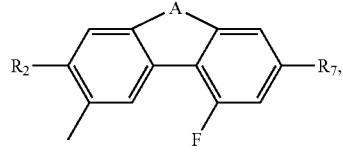
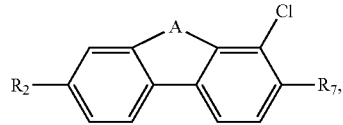
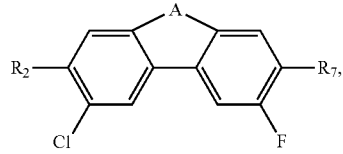
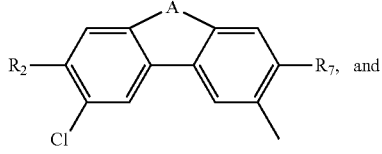 and
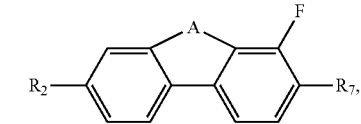
In some embodiments, the compound is selected from:
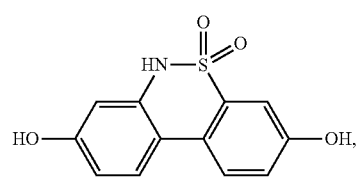
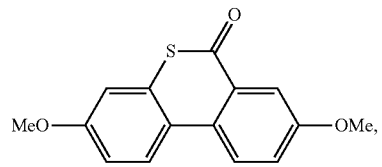
-continued
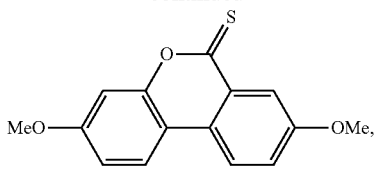
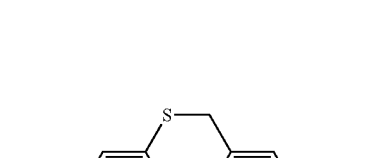
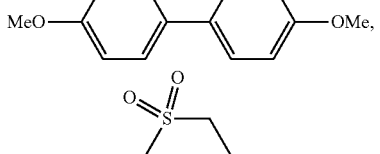
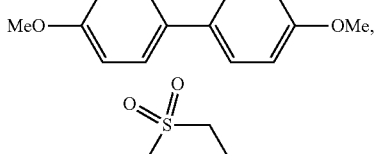
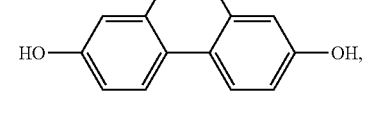
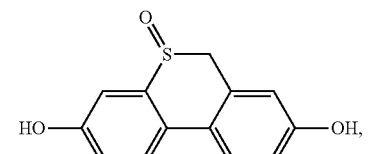
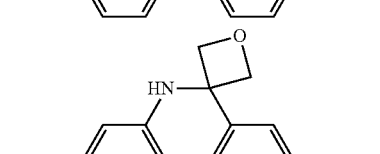
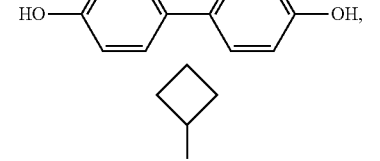
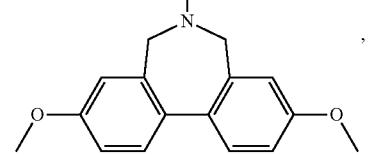
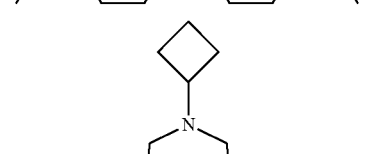
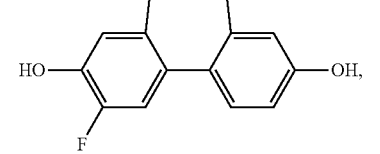

107
-continued
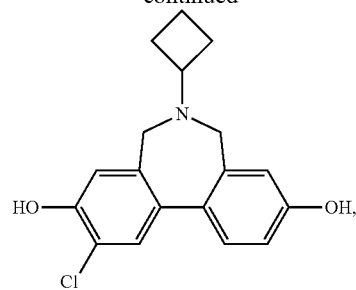
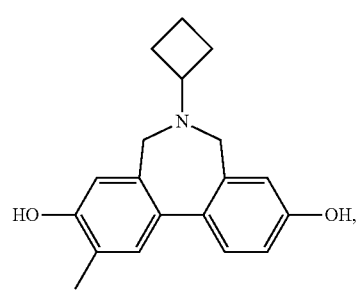
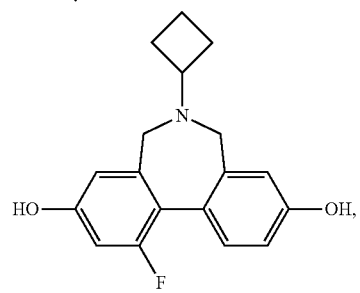
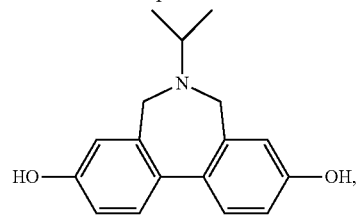
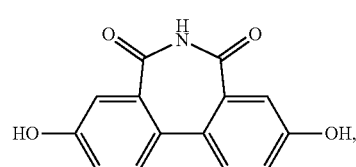
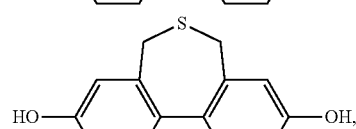
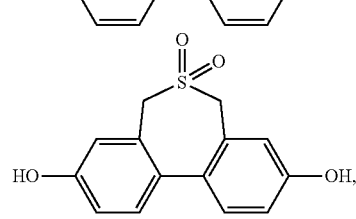
108
-continued
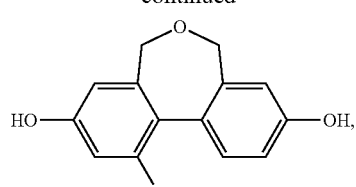
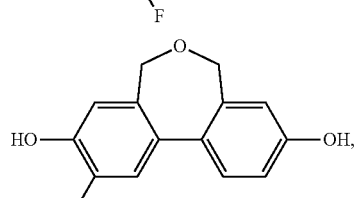
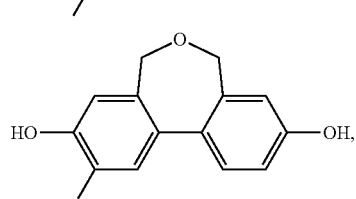
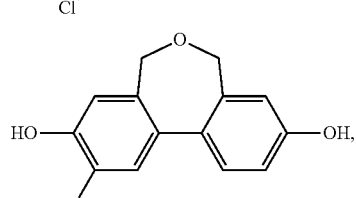
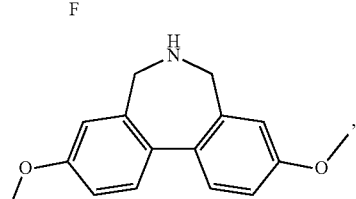
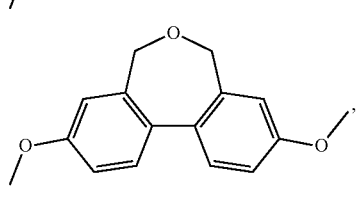
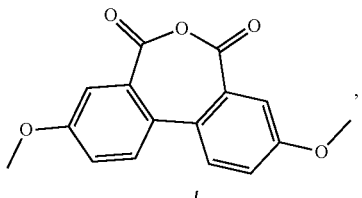
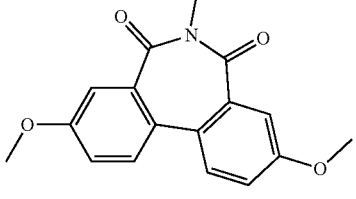
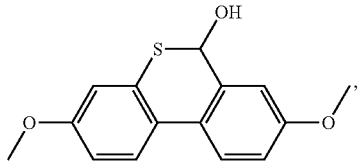

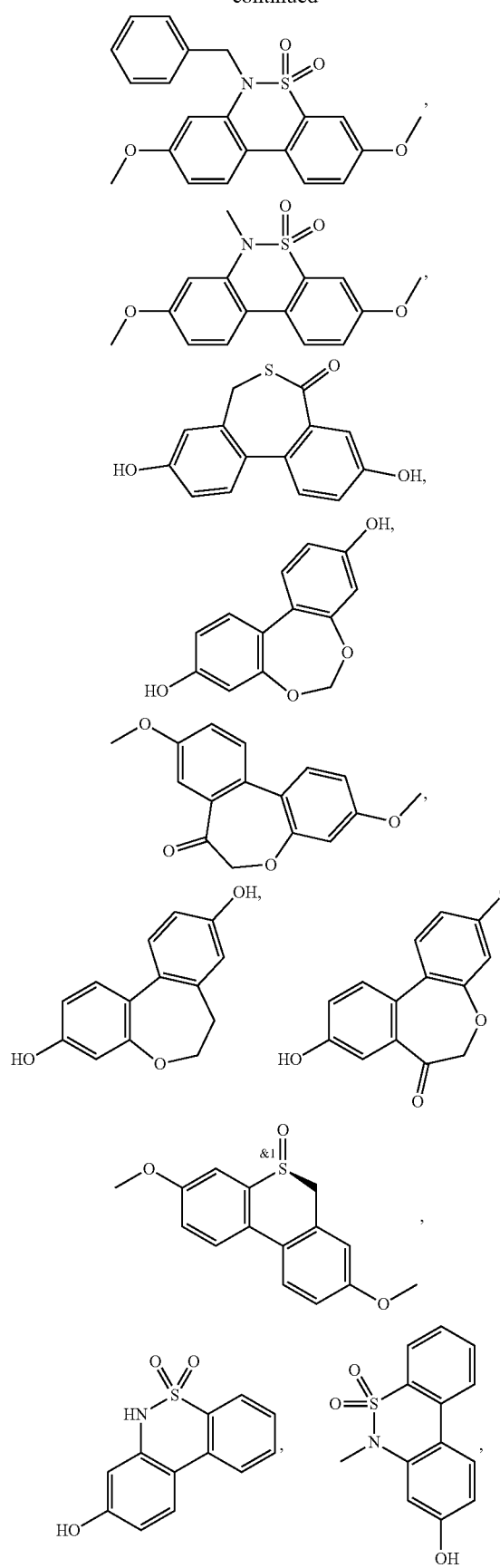
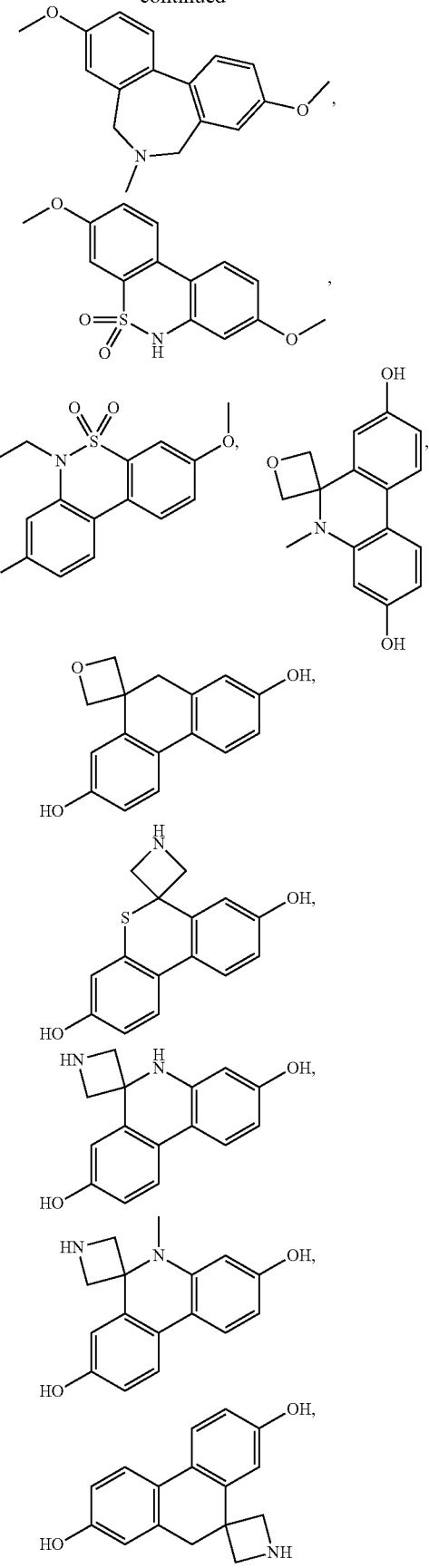

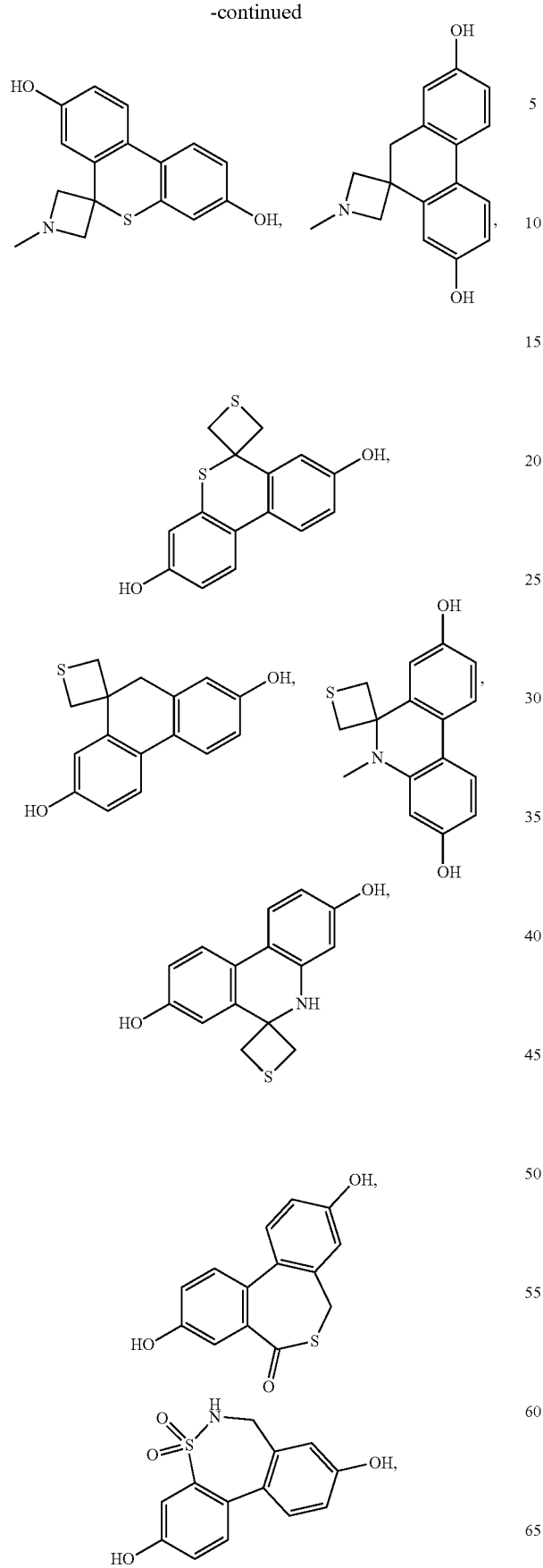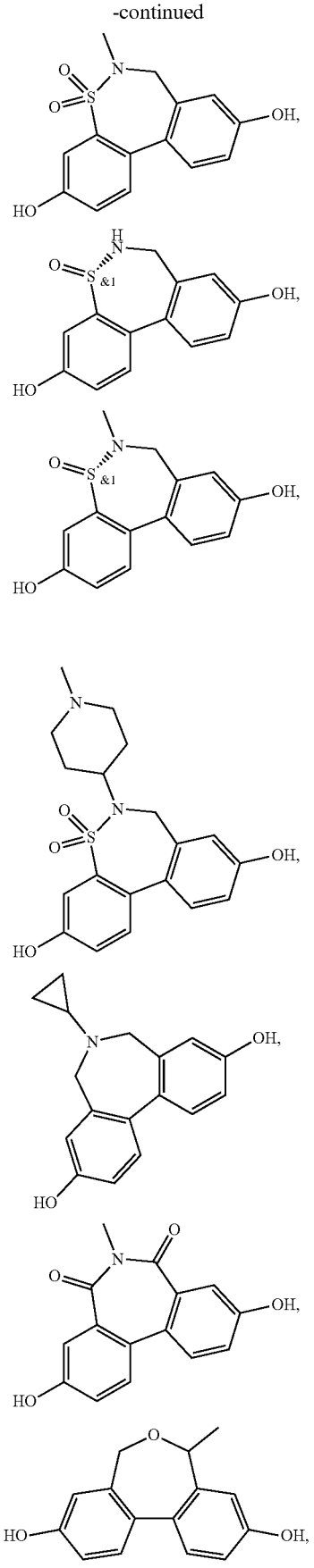

-continued
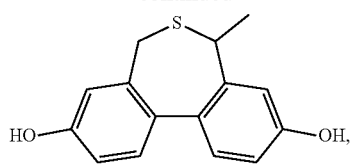
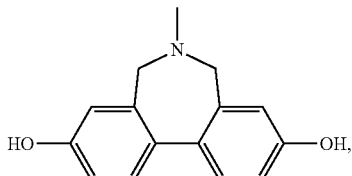
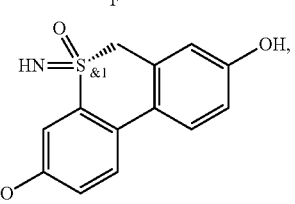
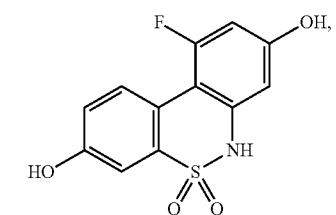
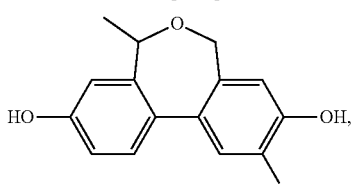
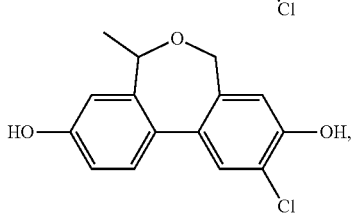
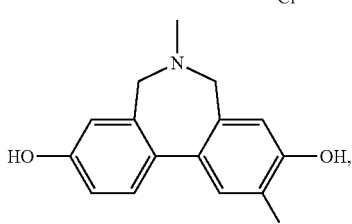
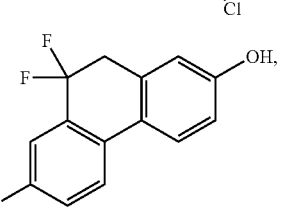
-continued
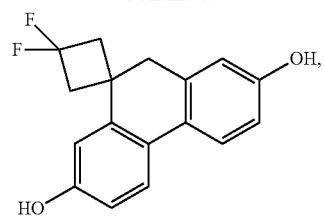
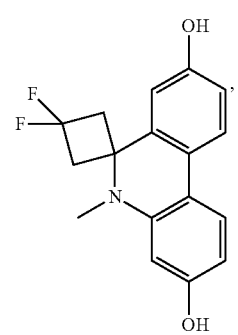
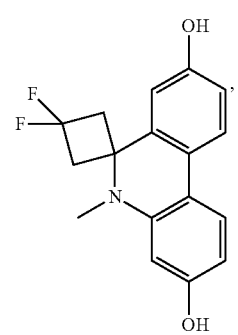
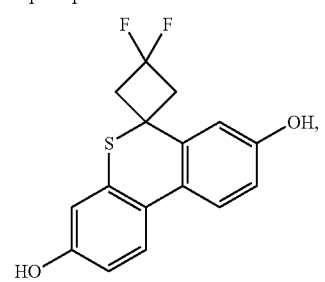
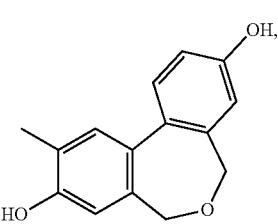
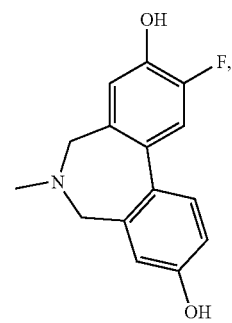
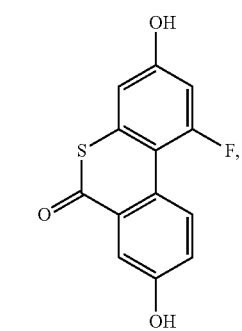

115
-continued

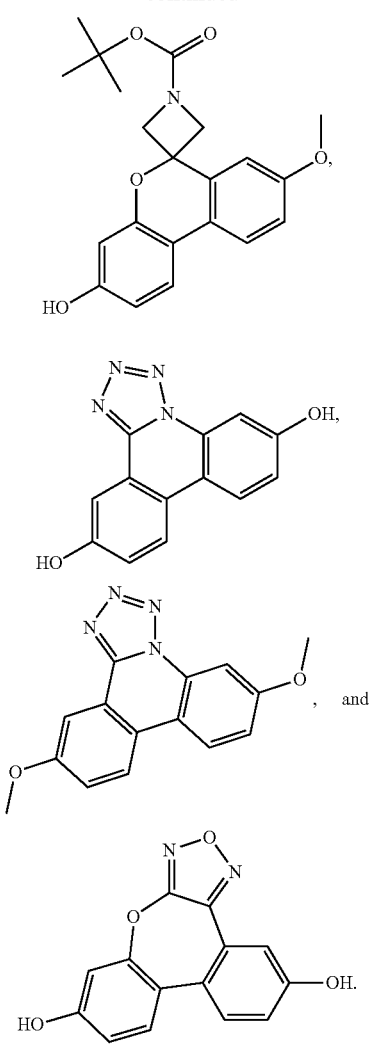

In some embodiments, the compound is selected from:

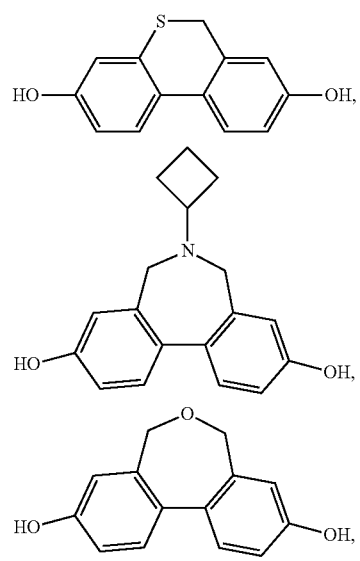

116
-continued

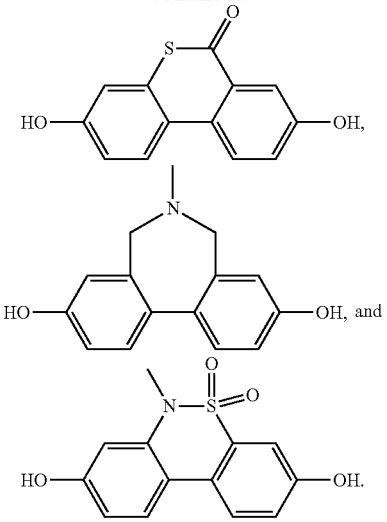

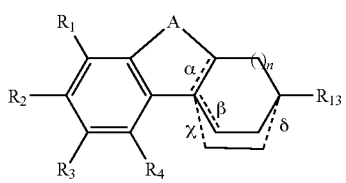

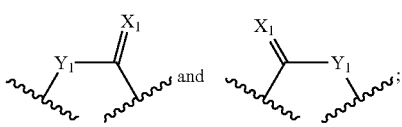

In one embodiment, a compound of Formula (Ig):

$$\text{(Ig)}$$

[Structure showing R₁, R₂, R₃, R₄ substituents on a bicyclic system with A bridge, and α, β, χ, δ bonds, with R₁₃ substituent and (O)ₙ group]

wherein

α and β, χ, and δ are each bonds which are present or absent, provided that when α is present, then β is absent and when β is present, then α is absent, and when either of α and β are present, then χ and δ are each absent;

n is 0 or 1;

A is selected from

[Two structures with X₁, Y₁ groups]

$X_1$ is O;

$Y_1$ is selected NH, N-alkyl, N-cycloalkyl, and O;

$R_1$, $R_2$, and $R_3$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$, $R_4$ is selected from H, alkyl, and halogen;

each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;

$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, SO$_3$H, SO$_2$-alkyl, and SO$_2$-haloalkyl;

each occurrence of R$_{11}$ is selected from H and alkyl;

each occurrence of R$_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and R$_{13}$ is selected from H, OH, OCH$_3$, OAc, NH$_2$, halogen, CN, CF$_3$, CO$_2$H, NO$_2$, and NHAc, or a pharmaceutically acceptable salt thereof.

In some embodiments, wherein A is

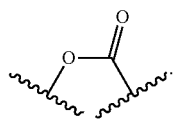 [SMILES: *OC(*)=O]

In other embodiments, A is

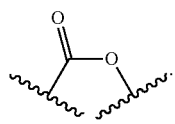 [SMILES: *OC(*)=O]

In some embodiments, wherein A is

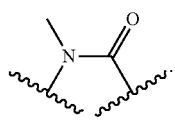 [SMILES: *C(=O)N(*)C]

In other embodiments, A is

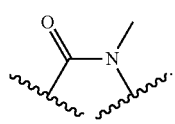 [SMILES: *C(=O)N(*)C]

In some embodiments, X$_1$ and Y$_1$ are each O

In some embodiments, X$_1$ is O and Y$_1$ is N(CH$_3$).

In some embodiments, α is present. In other embodiments, β is present. In other embodiments, α and β are each absent.

In some embodiments, wherein n is 0. In other embodiments, wherein n is 1.

In some embodiments, R$_{13}$ is OH.

In some embodiments, R$_1$, R$_2$, R$_3$, and R$_4$ are each H. In other embodiments, R$_2$ is OH. In other embodiments, one of R$_1$, R$_3$, and R$_4$ is not H. In other embodiments, one of R$_1$, R$_3$, and R$_4$ is alkyl or halogen.

In some embodiments, the compound is selected from:

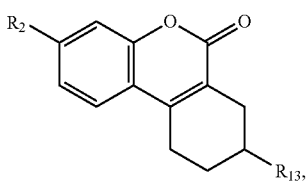

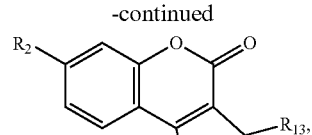

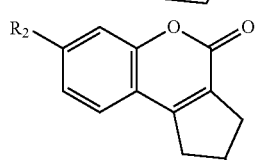

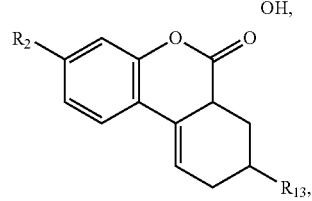

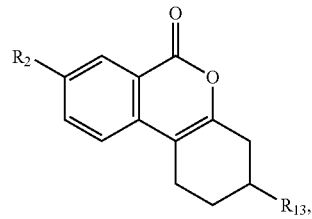

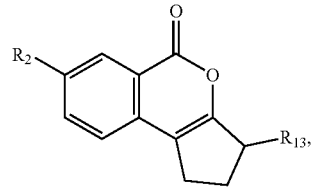

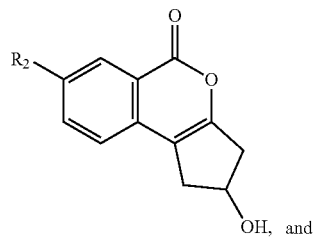

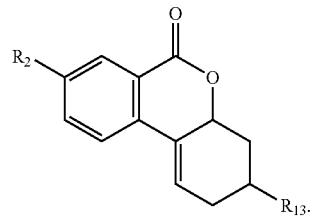

In some embodiments, the compound is selected from:

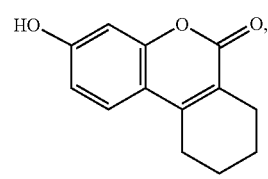

-continued

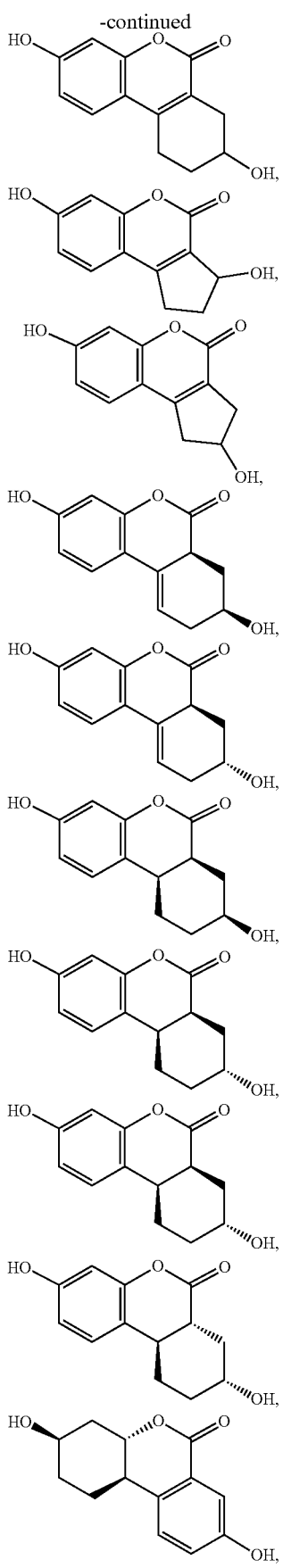

-continued

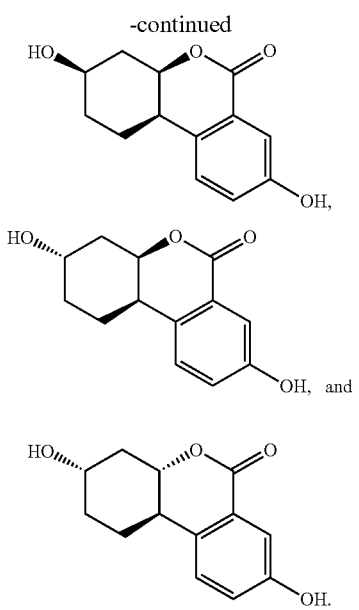

In some embodiments, the compound is selected from:

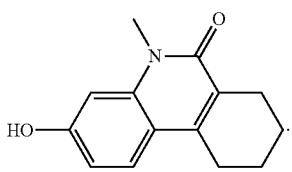 [SMILES: Cn1c(=O)c2c(c3ccc(O)cc31)CCCC2]

In some embodiments, n is 1.

In some embodiments, n a and β are each absent and χ and δ are each present.

In some embodiments, n A is

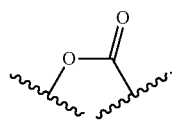 [SMILES: *OC(*)=O]

In other embodiments, wherein A is

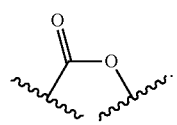 [SMILES: *OC(*)=O]

In some embodiments, $R_{13}$ is OH.

In some embodiments, $R_1$, $R_2$, $R_3$, and $R_4$ are each H. In other embodiments, $R_2$ is OH. In other embodiments, one of $R_1$, $R_3$, and $R_4$ is not H. In other embodiments, $R_1$, $R_3$, and $R_4$ is alkyl or halogen.

In some embodiments, the compound is selected from:

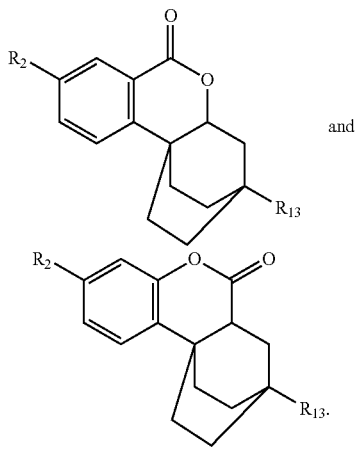

and

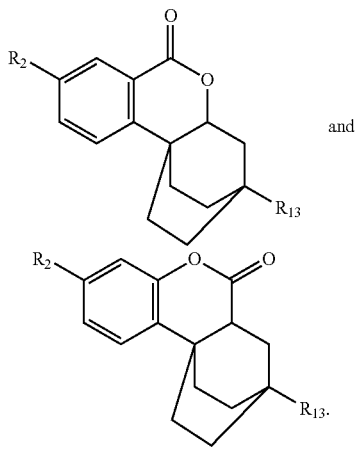

In other embodiments, the compound is selected from:

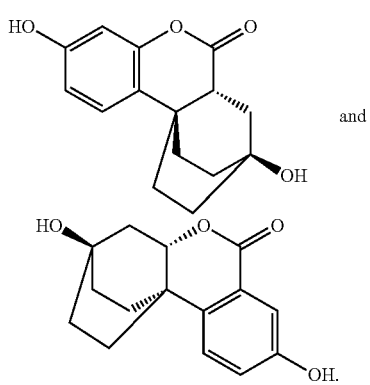

In some embodiments, a compound of Formula (Ih):

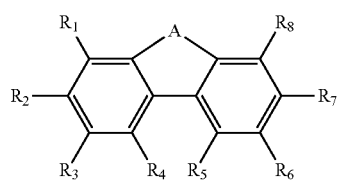

(Ih)

wherein
A is selected from

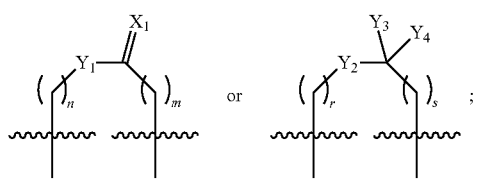

n and m are both 0; or one of n and m is 0 and the other of n and m is 1;
r and s are both 0; or one of r and s is 0 and the other of r and s is 1;

$X_1$ is O;
$Y_1$ is selected from O, NH, N-alkyl, and N-cycloalkyl;
$Y_2$ is O;
$Y_3$ and $Y_4$ are independently selected from H, halogen, and alkyl, or together with the carbon to which they are bonded combine to form a cycloalkyl or cycloheteroalkyl;
$R_1$, $R_4$, $R_5$ and $R_8$ are independently selected from H and halogen;
$R_3$ and $R_6$ are independently selected from H, CN, OH, $CF_3$, halogen, and alkyl;
one of $R_2$ and $R_7$ is $NH_2$, $NHCH_3$, and $N(CH_3)_2$ and the other of $R_2$ and $R_7$ is H, halogen, $OCH_3$, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
each occurrence of $R_{11}$ is selected from H and alkyl;
each occurrence of $R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl; and
provided that if A is

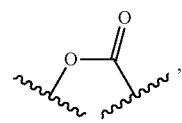

$R_1$, $R_3$, $R_4$, $R_5$, $R_6$, and $R_8$ are each H, and $R_7$ is $NH_2$, then $R_2$ is not OH.
In some embodiments, $Y_1$ is selected from O, NH, and N-alkyl.
In some embodiments, A is

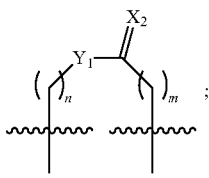

and n and m are both 0. In other embodiments, A is

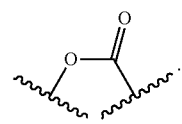

In other embodiments, A is

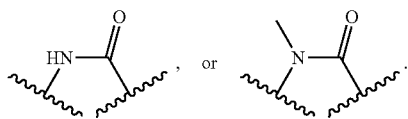

In some embodiments, A is

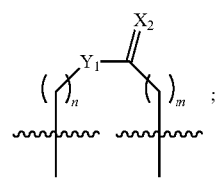

and one of n or m is 0 and the other of n or m is 1. In other embodiments, A is

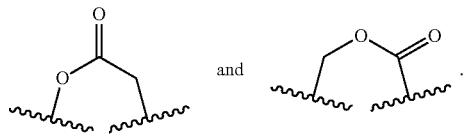 [SMILES: *CC(=O)O* ; *COC(*)=O]

In other embodiments, A is selected from

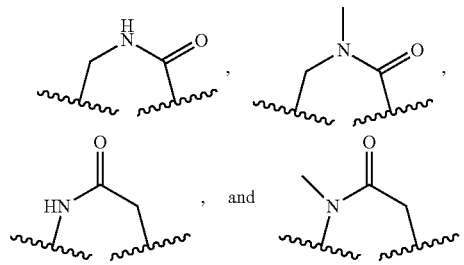

In some embodiments, A is

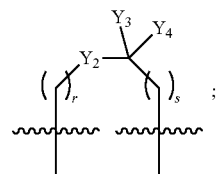

and r and s are both 0. In other embodiments, A is selected from

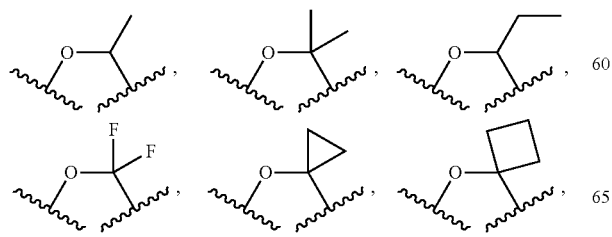

-continued

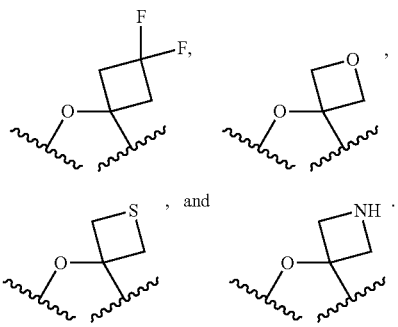

In other embodiments, A is selected from

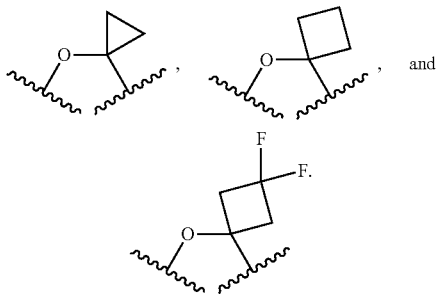

In some embodiments, wherein $R_2$ is selected from $NH_2$, $NHCH_3$, and $N(CH_3)_2$.

In some embodiments, $R_7$ is selected from H, OH, halogen, O-alkyl, and haloalkyl.

In some embodiments, $R_7$ is selected from alkynyl-$R_9$ and $OR_{10}$; $R_9$ is OH; and $R_{10}$ is alkyl-heterocycloalkyl.

In some embodiments, wherein $R_1$, $R_3$, $R_4$, $R_5$, $R_6$, and $R_8$ are each H. In other embodiments, one of $R_1$, $R_3$, $R_4$, $R_5$, $R_6$, and $R_8$ is not H. In other embodiments, two of $R_1$, $R_3$, $R_4$, $R_5$, $R_6$, and $R_8$ are not H. In other embodiments, one of $R_1$, $R_3$, $R_4$, $R_5$, $R_6$, and $R_8$ is alkyl or halogen. In other embodiments, two of $R_1$, $R_3$, $R_4$, $R_5$, $R_6$, and $R_8$ are independently alkyl or halogen.

In some embodiments, the compound is selected from:

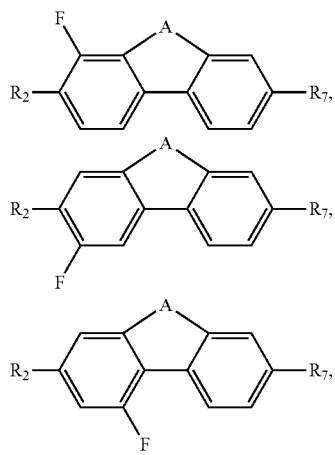

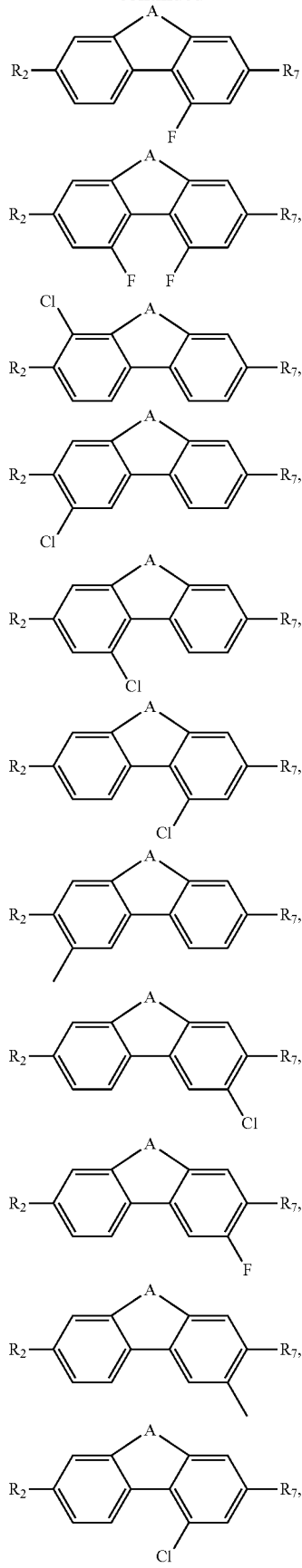
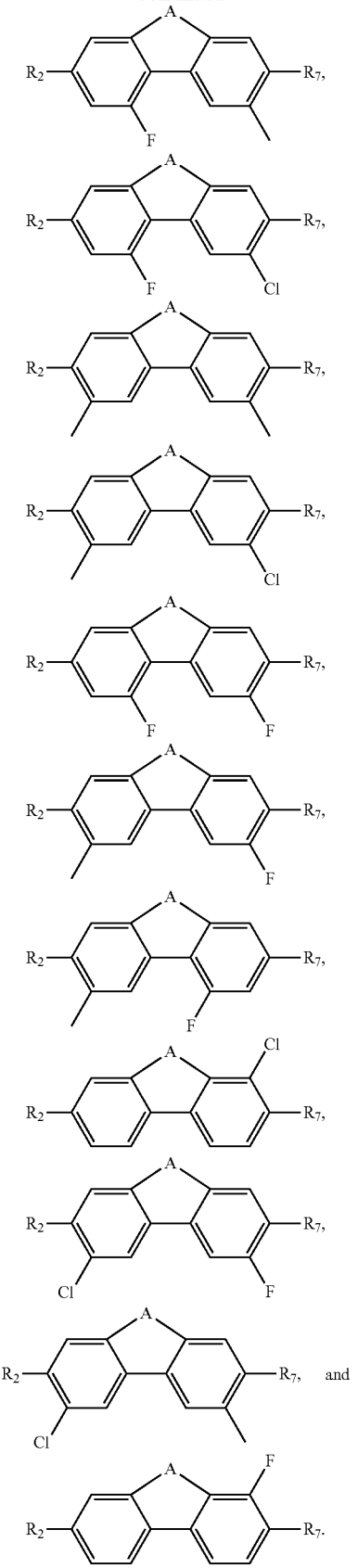

In some embodiments, the compound is selected from:
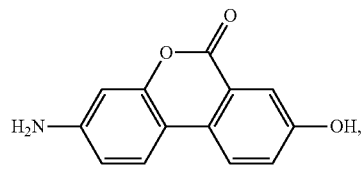
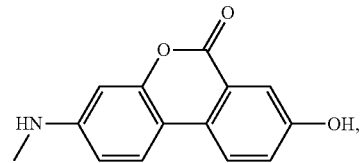
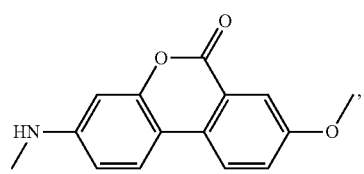
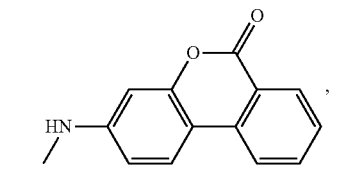
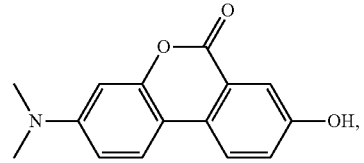
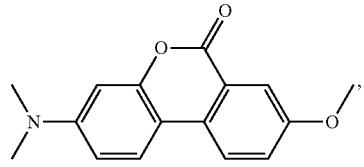
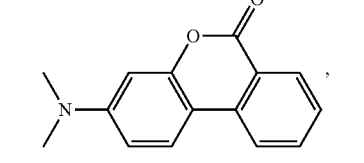
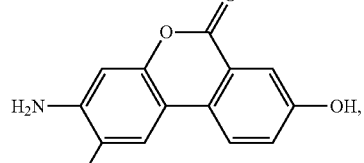
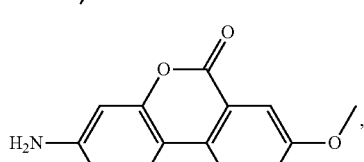
-continued
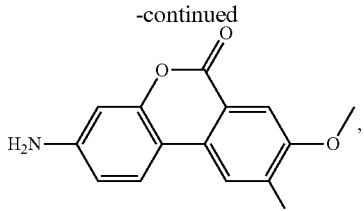
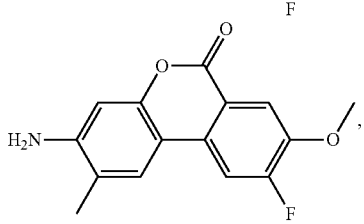
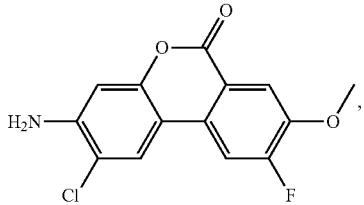
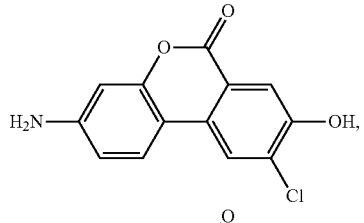
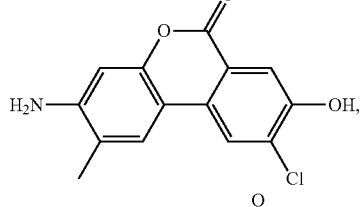
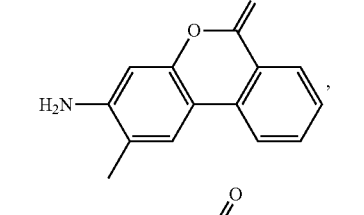
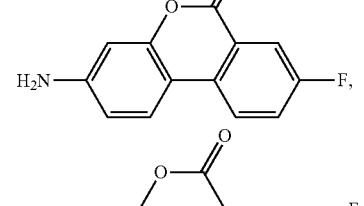
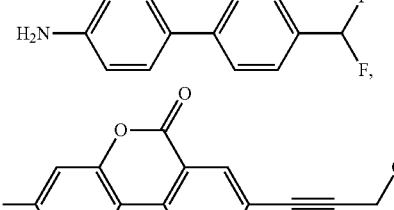

-continued
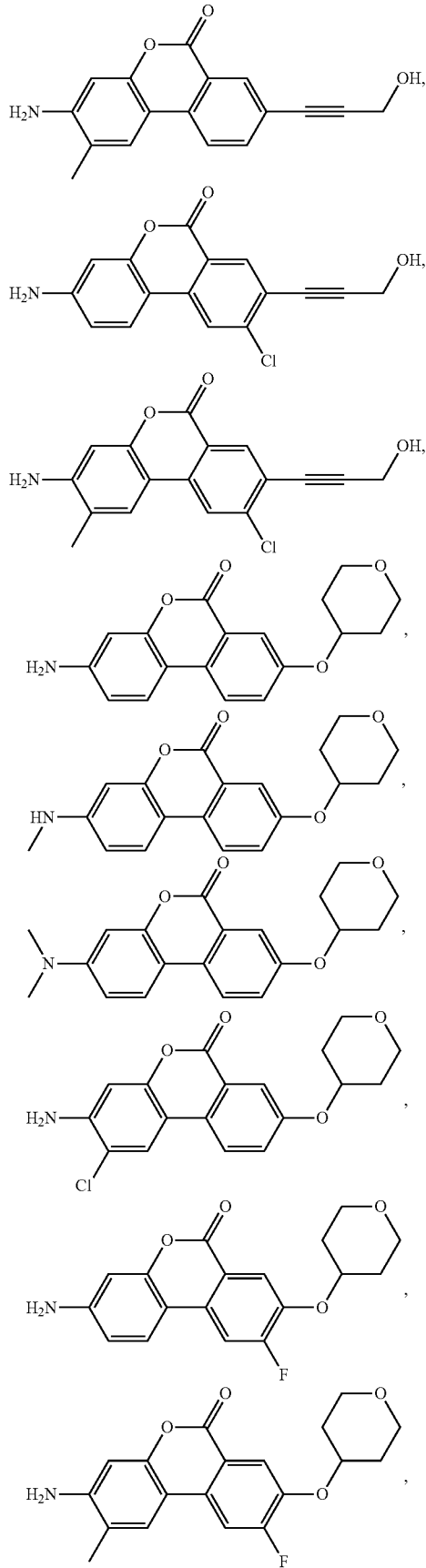
-continued
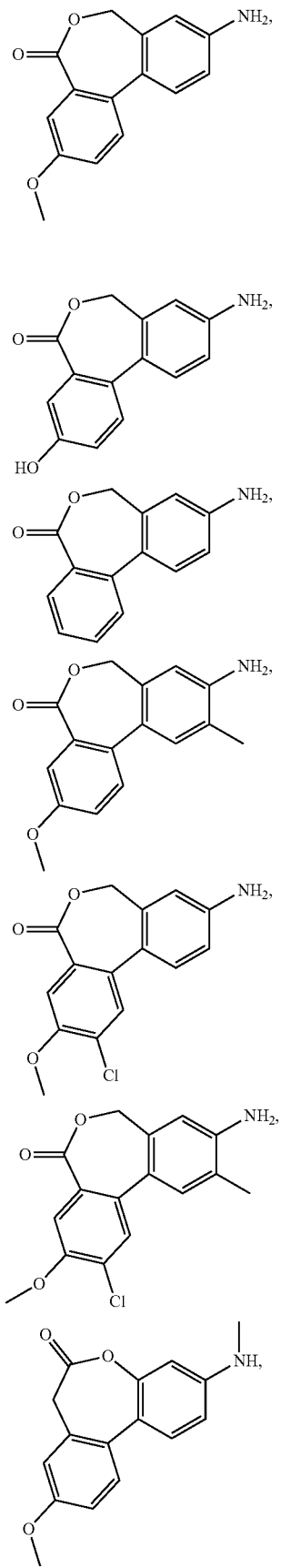

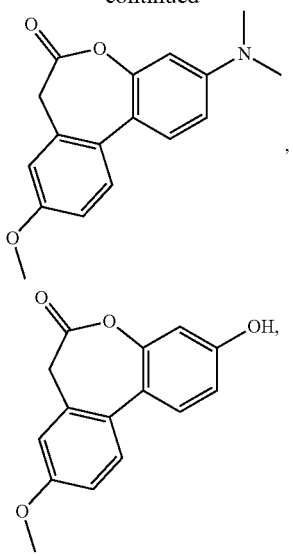
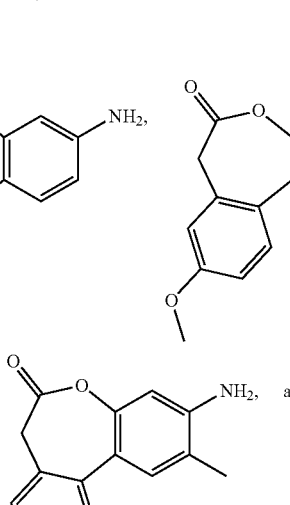
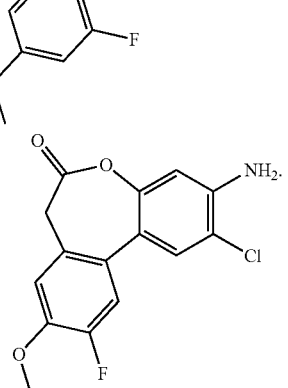
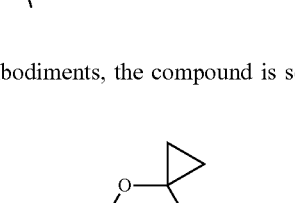
In some embodiments, the compound is selected from:
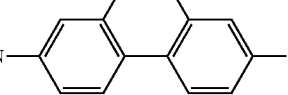
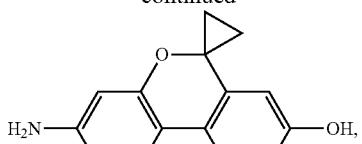
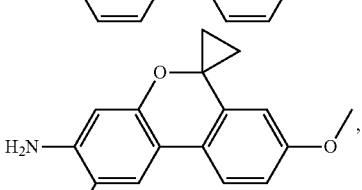
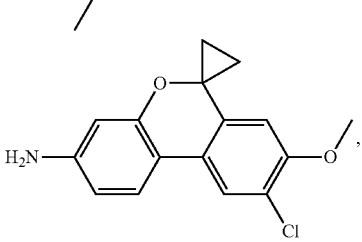
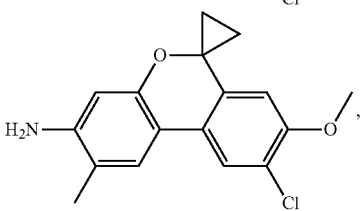
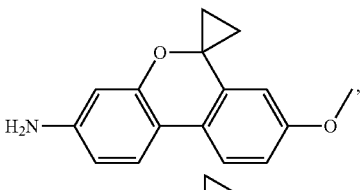
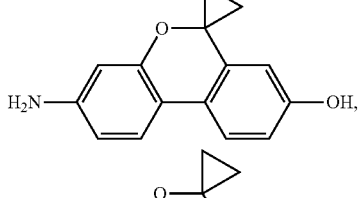
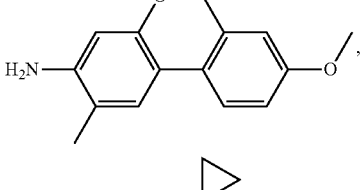
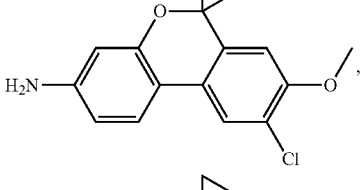
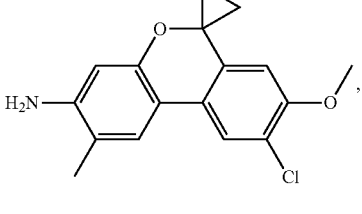

-continued
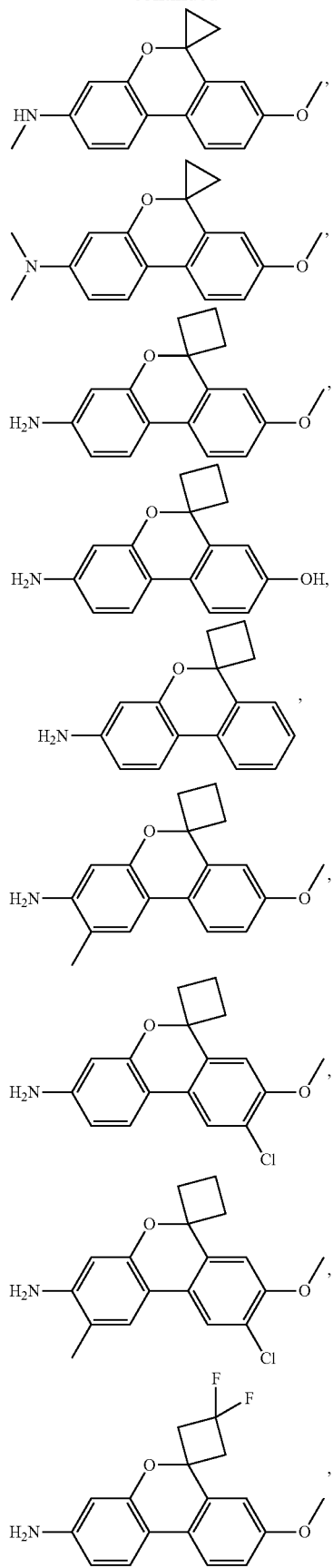
-continued
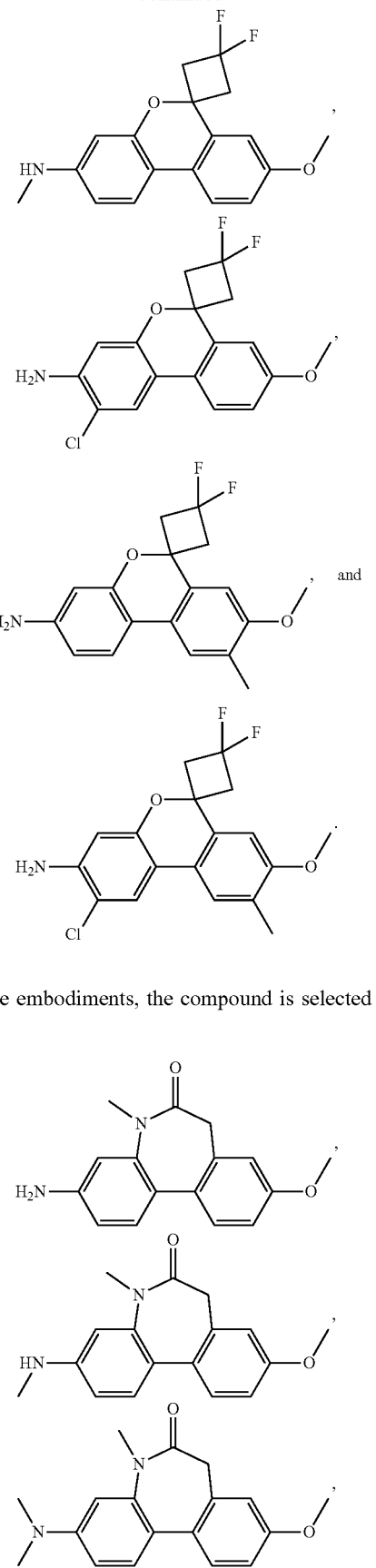
In some embodiments, the compound is selected from:
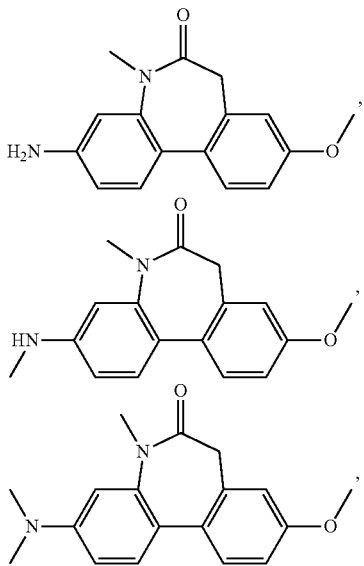

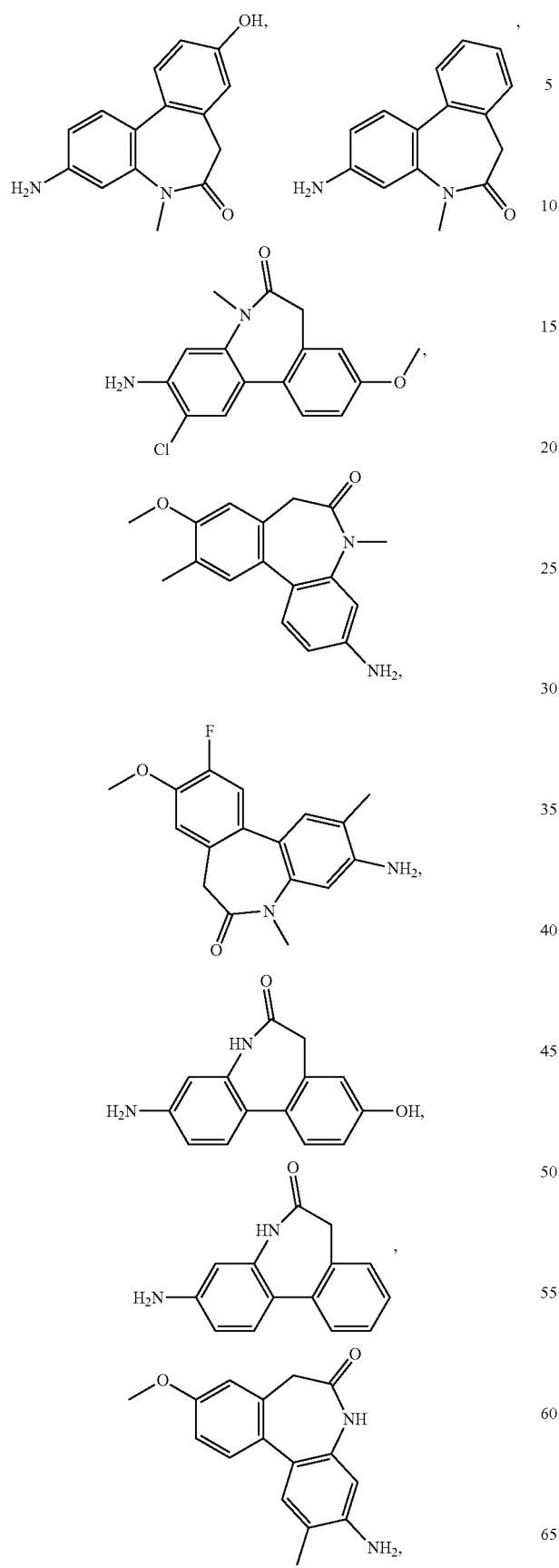
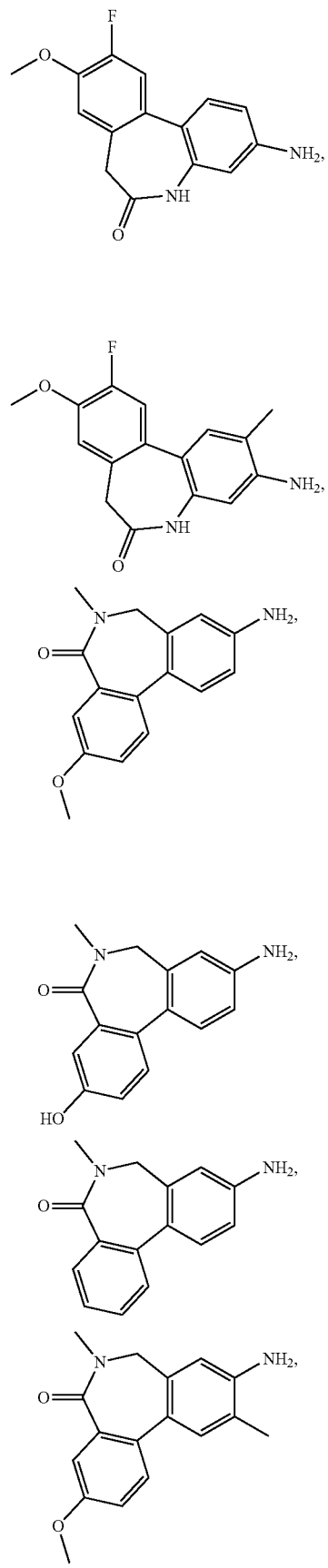

-continued
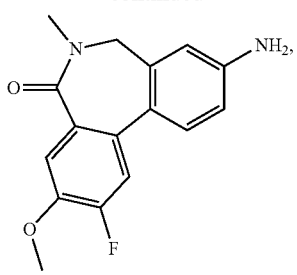
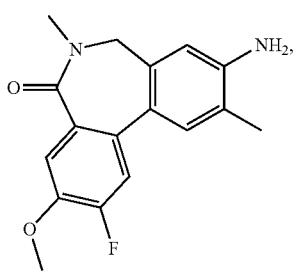
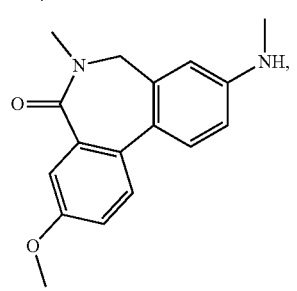
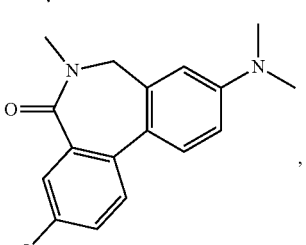
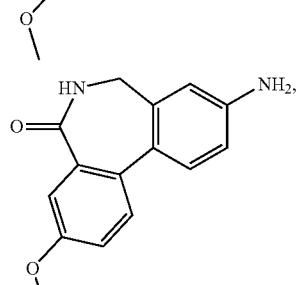
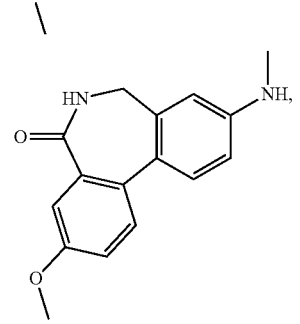
-continued
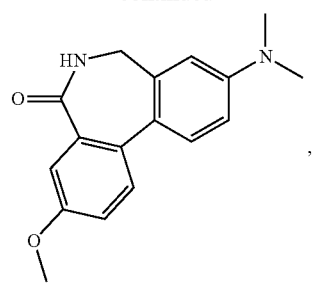
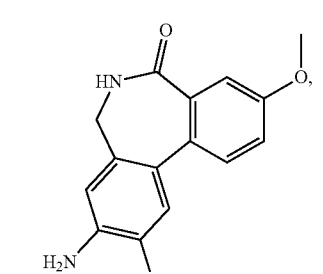
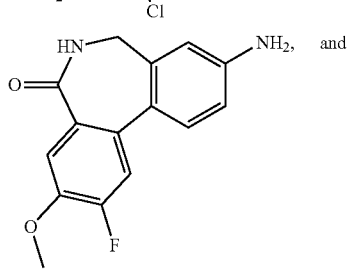
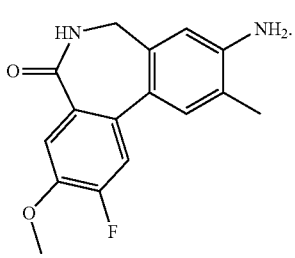 [SMILES: COc1cc2c(cc1F)-c1cc(C)c(N)cc1CNC2=O]
In some embodiments, the compound is selected from:
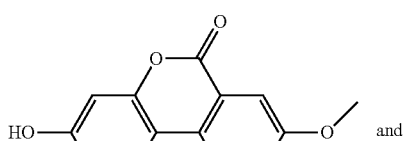 and
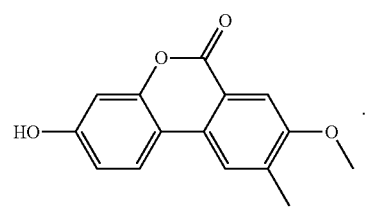

In some embodiments, the compound is selected from:
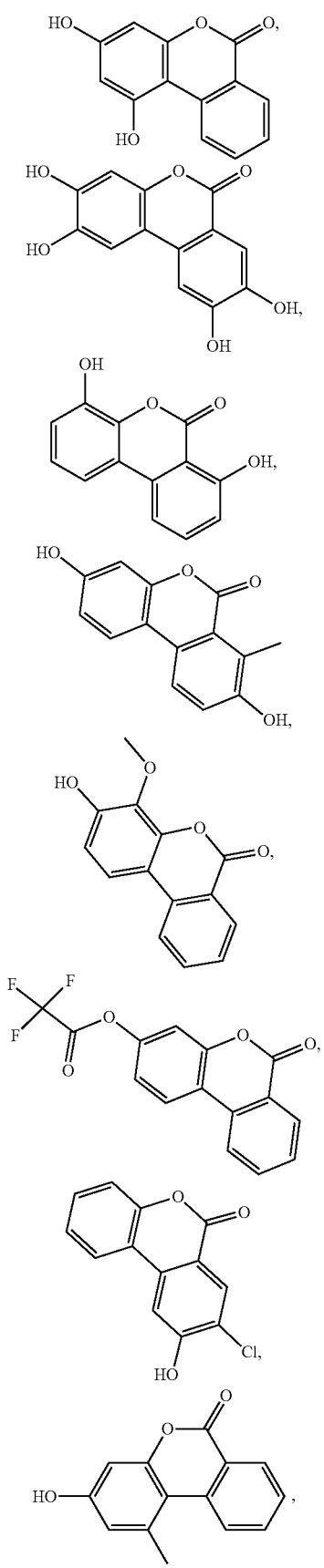
-continued
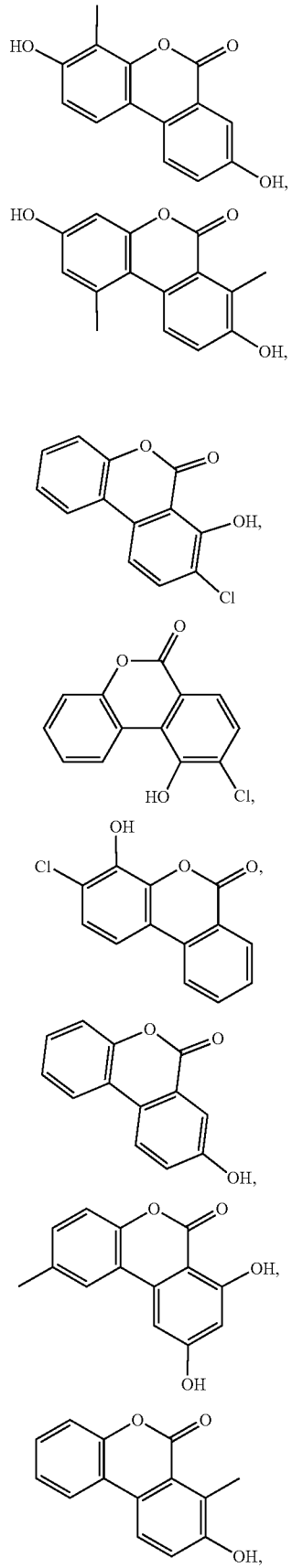

141
-continued
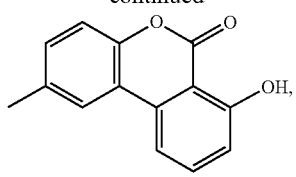
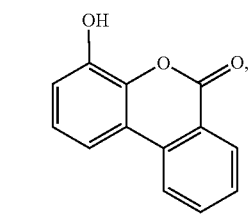
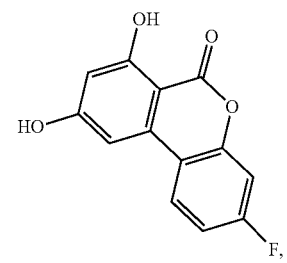
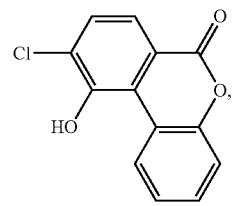
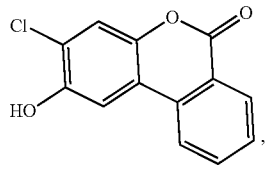
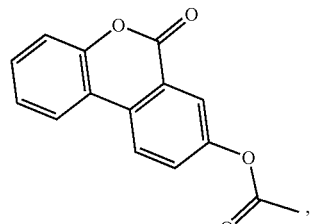
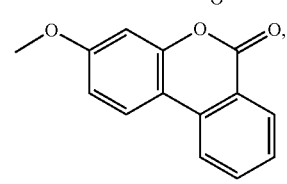
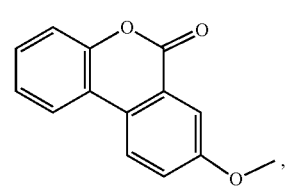
142
-continued
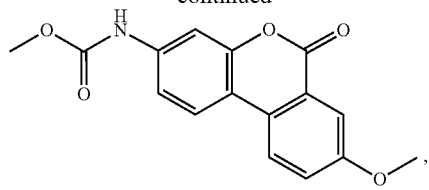
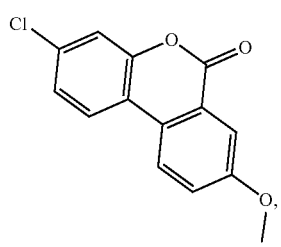
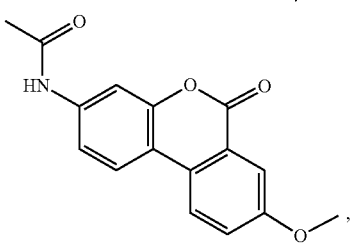
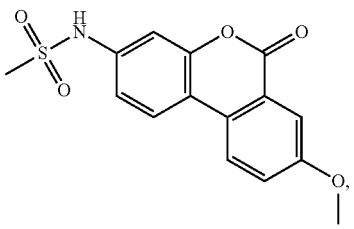
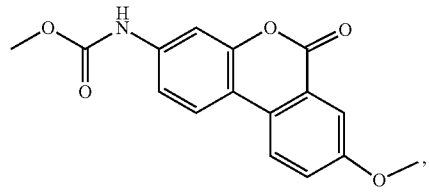
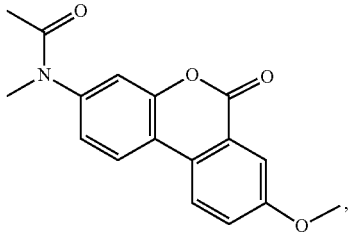
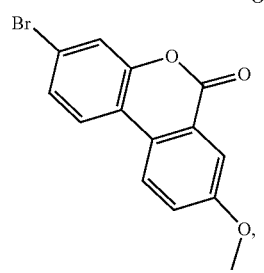

-continued

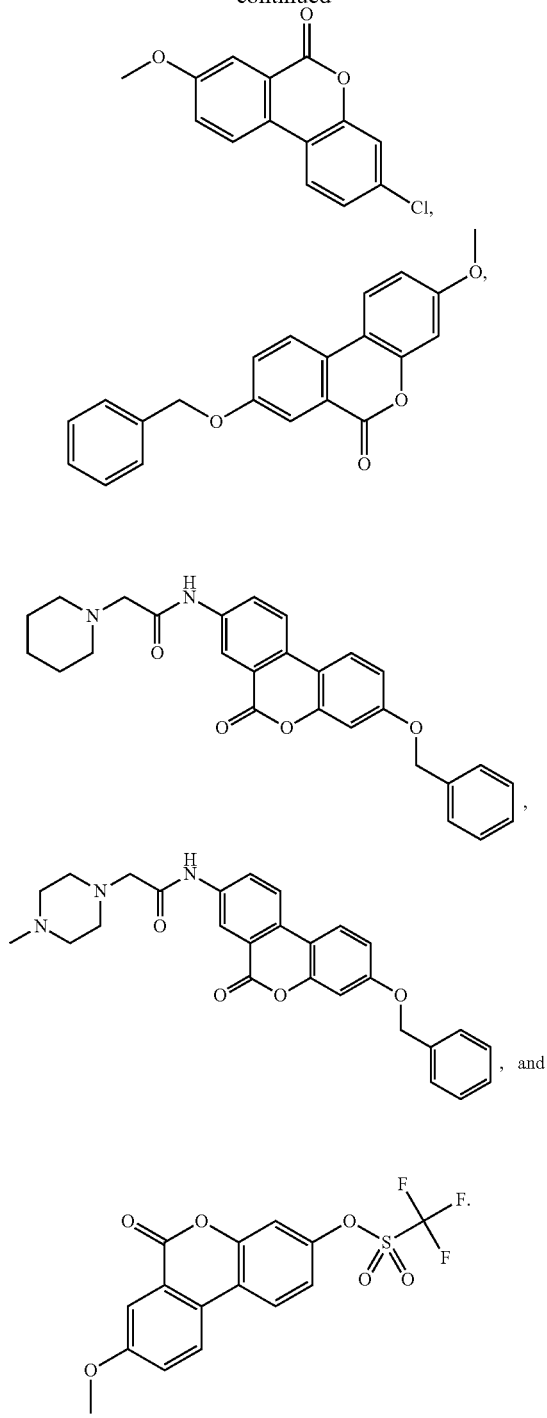

or a pharmaceutically acceptable salt thereof.

In some embodiments, $R_2$ and $R_7$ are each OH. In other embodiments, $R_2$ is OH and $R_7$ is not OH. In other embodiments, $R_2$ is OH and $R_7$ is not $OCH_3$. In other embodiments, $R_2$ is OH and $R_7$ is not H.

In some embodiments, $R_2$ is OH and $R_7$ is $OCH_3$. In other embodiments, $R_2$ is OH and $R_7$ is H. In other embodiments, $R_2$ is OH and $R_7$ is alkynyl-$R_9$. In other embodiments, $R_2$ is OH and $R_7$ is $OR_{10}$. In other embodiments, $R_2$ is OH and $R_7$ is $OR_{10}$.

In some embodiments, $R_2$ is OH and $R_7$ is

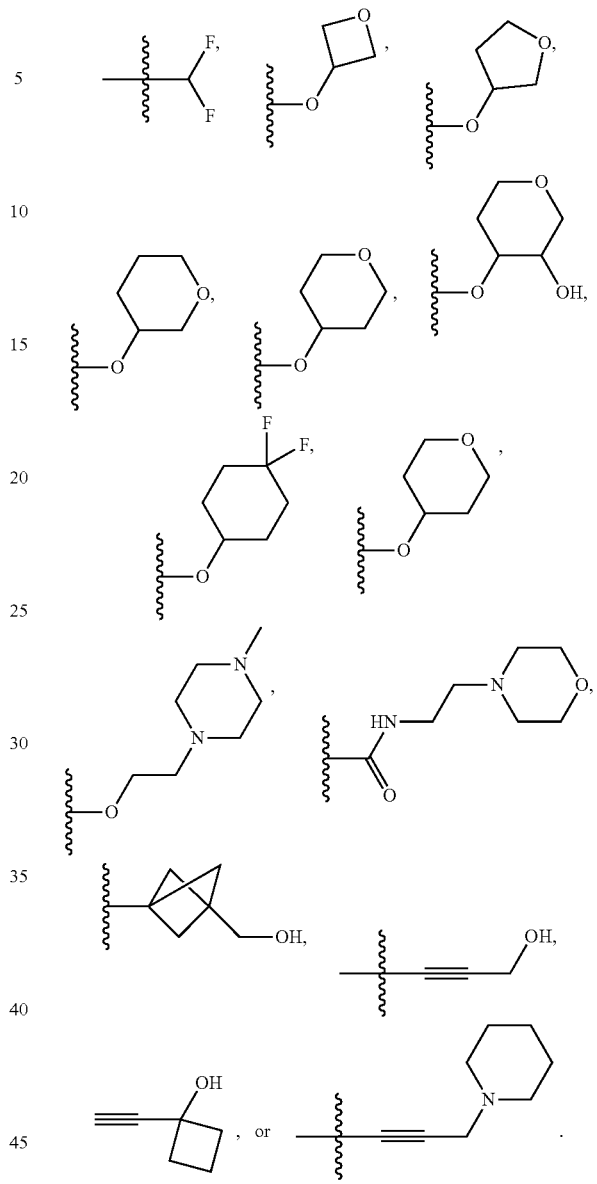

In some embodiments, the compounds are atropisomers. Additionally, unless otherwise stated, structures depicted herein are also meant to include compounds that differ only in the presence of one or more isotopically enriched atoms. For example, compounds produced by the replacement of a hydrogen with deuterium or tritium, or of a carbon with a $^{13}$C- or $^{14}$C-enriched carbon are within the scope of this invention. Such compounds are useful, for example, as analytical tools, as probes in biological assays, or as therapeutic agents in accordance with the present invention. For example, in the case of variable $R^1$, the $(C_1$-$C_4)$alkyl or the —O—$(C_1$-$C_4)$alkyl can be suitably deuterated (e.g., —$CD_3$, —$OCD_3$).

Any compound of the invention can also be radiolabeled for the preparation of a radiopharmaceutical agent.

Methods of Treatment

One aspect of the invention relates to a method of treating a neuronal or a mitochondrial disease in a subject in need thereof comprising administering to the subject an effective amount of a compound of Formula (Ii):

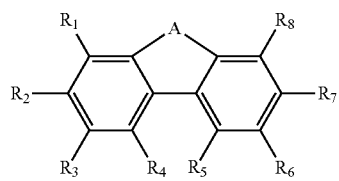

(Ii)

wherein
A is selected from

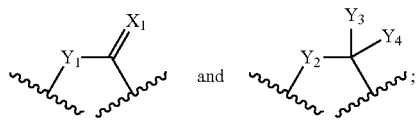

$X_1$ is O;
$Y_1$ is selected from O and NH;
$Y_2$ is O;
$Y_3$ and $Y_4$ are independently selected from H and halogen;
$R_1$, $R_2$, $R_3$, $R_6$, $R_7$, and $R_8$ are independently selected from H, OH, $OCH_3$, OAc, $NH_2$, halogen, CN, $CF_3$, $CO_2H$, $NO_2$, NHAc, alkyl, haloalkyl, alkenyl, alkynyl, cycloalkyl, heterocycloalkyl, alkylamino, alkyl-$R_9$, alkenyl-$R_9$, alkynyl-$R_9$, $OR_{10}$, $NHR_{10}$, $NR_{11}C(O)R_{12}$, $C(O)NR_{11}R_{12}$, and $NR_{11}SO_2R_{12}$,
$R_4$ and $R_5$ are independently selected from H, alkyl, and halogen;
each occurrence of $R_9$ is independently selected from OH, $NH_2$, O-alkyl, O-alkyl-O-alkyl, alkylamino, NHC(O)-alkyl, $N(CH_3)C(O)$-alkyl, $NHSO_2$-alkyl, $N(CH_3)SO_2$-alkyl, aryl, heteroaryl, cycloalkyl, and heterocycloalkyl;
$R_{10}$ is selected from $C_2$-$C_{12}$ alkyl, hydroxyalkyl, aminoalkyl, alkyl-O-alkyl, alkyl-O-alkyl-OH, alkyl-O-alkyl-O-alkyl, alkenyl, alkynyl, aralkyl, heteraralkyl, alkyl-cycloalkyl, alkyl-heterocycloalkyl, aryl, heteroaryl, cycloalkyl, heterocycloalkyl, $SO_3H$, $SO_2$-alkyl, and $SO_2$-haloalkyl;
$R_{11}$ is selected from H and alkyl; and
$R_{12}$ is selected from alkyl, alkenyl, alkynyl, cycloalkyl, heterocycloalkyl, O-alkyl, aminoalkyl, aralkyl, heteraralkyl, alkyl-cycloalkyl, and alkyl-heterocycloalkyl,
or a pharmaceutically acceptable salt thereof.

In some embodiments of the above method, the compound is selected from:

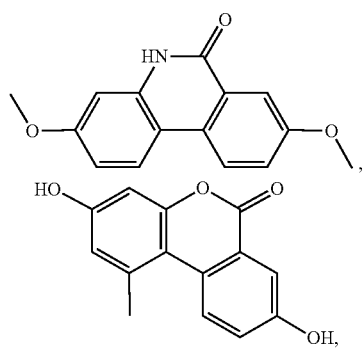

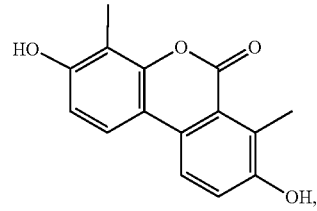

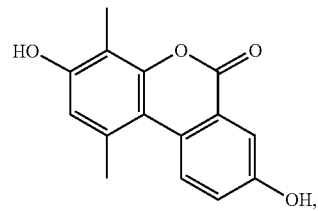

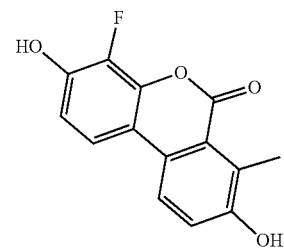

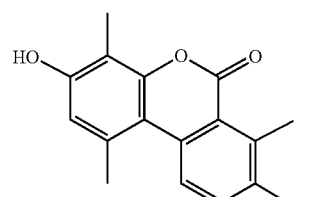

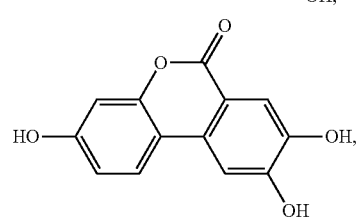

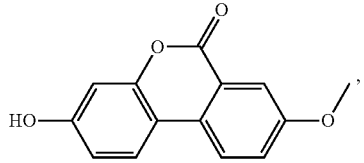

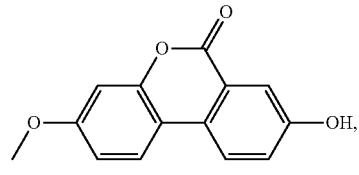

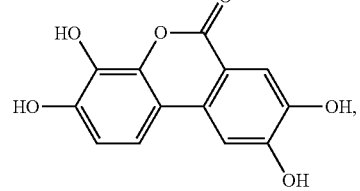

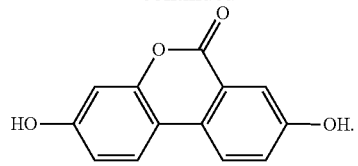

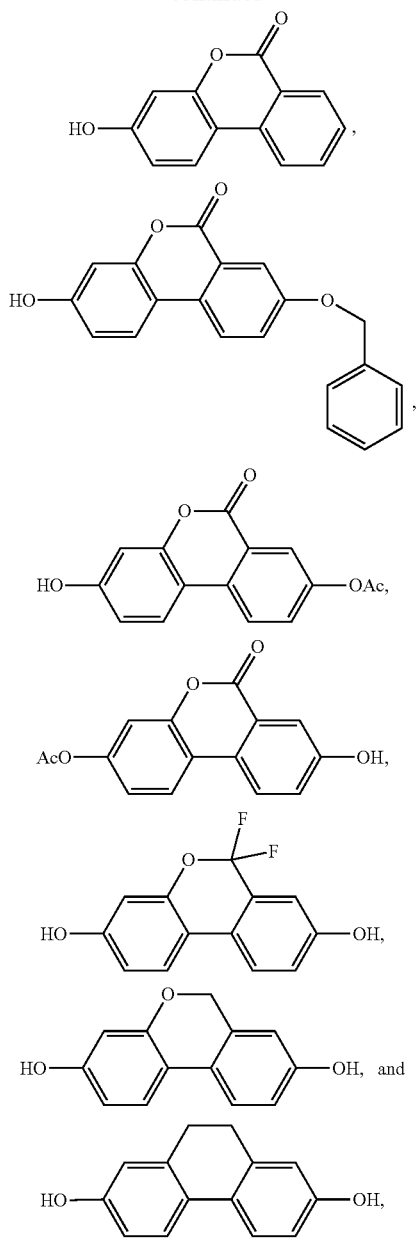

In other embodiments of the above method, the compound is selected from:

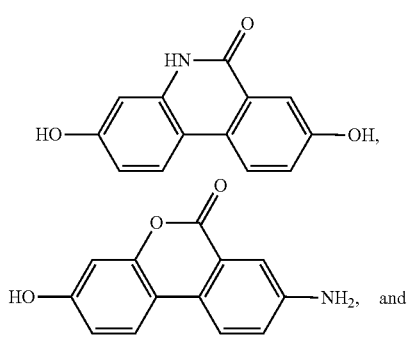

In one embodiment of the above method, wherein a neuronal disease is treated.

In another embodiment of the above method, wherein a mitochondrial disease is treated.

Another aspect of the invention relates to methods of treating a mitochondrial disease in a subject in need thereof comprising administering to the subject an effective amount of the compound of the compound of any one of Formulas (Ia)-(Ii). In one embodiment, the mitochondrial disease affects the muscle of the subject, e.g. mitochondrial myopathies. In another embodiment, the mitochondrial disease affects the eye of the subject, e.g. external progressive ophthalmoplegia. In other embodiments, the mitochondrial disease is Alper's disease, Barth syndrome, beta-oxidation defects, carnitine deficiency, carnitine-acyl-carnitine deficiency, chronic progressive external ophthalmoplegia syndrome, or co-enzyme Q10 deficiency.

In one aspect, the invention relates to methods of treating a muscle or a neuromuscular disease in a subject in need thereof comprising administering to the subject an effective amount of the compound of any one of Formulas (Ia)-(Ii). In one embodiment, the muscle or neuromuscular disease is sarcopenia. In another embodiment, the muscle or neuromuscular disease is a muscular dystrophy. In another embodiment, the muscle or neuromuscular disease is a myopathy. In another embodiment, the muscle or neuromuscular disease is Duchenne muscular dystrophy. In another embodiment, the muscle or neuromuscular disease is inclusion body myositis (IBM) or sporadic inclusion body myositis (sIBM). In another embodiment, the muscle or neuromuscular disease is selected from mitochondrial myopathies. In other embodiments, the muscle or neuromuscular disease is muscle aging and weakness, frailty, sarcopenia, mitochondrial myopathies, or muscle rhabdomyolysis.

In one aspect, the invention relates to methods of treating a neuronal or neurodegenerative disease in a subject in need thereof comprising administering to the subject an effective amount of the compound of any one of Formulas (Ia)-(Ii). In some embodiments, the neuronal or neurodegenerative disease is Alzheimer's disease, Parkinson's disease, Huntington's disease, amyotrophic lateral sclerosis (also known as ALS and as Lou Gehrig's disease), as well as AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado-Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome.

In one aspect, the invention relates to methods of inhibiting ferroptosis in a subject in need thereof comprising administering to the subject an effective amount of the compound of any one of Formulas (Ia)-(Ii).

In one aspect, the invention relates to methods of treating ischemia-reperfusion injury. In another aspect, the invention relates to methods of treating an inflammatory disease mediated by ferroptosis. In one aspect, the invention relates to methods of treating a neuronal or neurodegenerative disease mediated by ferroptosis.

Pharmaceutical Compositions, Routes of Administration, and Dosing

In certain embodiments, the invention is directed to a pharmaceutical composition, comprising a compound of the invention and a pharmaceutically acceptable carrier. In certain embodiments, the invention is directed to a pharmaceutical composition, comprising the compound of any one of Formulas (Ia)-(Ii) and a pharmaceutically acceptable carrier. In certain embodiments, the pharmaceutical composition comprises a plurality of compounds of the invention and a pharmaceutically acceptable carrier.

In certain embodiments, a pharmaceutical composition of the invention further comprises at least one additional pharmaceutically active agent other than a compound of the invention. The at least one additional pharmaceutically active agent can be an agent useful in the treatment of ischemia-reperfusion injury.

Pharmaceutical compositions of the invention can be prepared by combining one or more compounds of the invention with a pharmaceutically acceptable carrier and, optionally, one or more additional pharmaceutically active agents.

As stated above, an "effective amount" refers to any amount that is sufficient to achieve a desired biological effect. Combined with the teachings provided herein, by choosing among the various active compounds and weighing factors such as potency, relative bioavailability, patient body weight, severity of adverse side-effects and mode of administration, an effective prophylactic or therapeutic treatment regimen can be planned which does not cause substantial unwanted toxicity and yet is effective to treat the particular subject. The effective amount for any particular application can vary depending on such factors as the disease or condition being treated, the particular compound of the invention being administered, the size of the subject, or the severity of the disease or condition. One of ordinary skill in the art can empirically determine the effective amount of a particular compound of the invention and/or other therapeutic agent without necessitating undue experimentation. A maximum dose may be used, that is, the highest safe dose according to some medical judgment. Multiple doses per day may be contemplated to achieve appropriate systemic levels of compounds. Appropriate systemic levels can be determined by, for example, measurement of the patient's peak or sustained plasma level of the drug. "Dose" and "dosage" are used interchangeably herein.

The formulations of the invention can be administered in pharmaceutically acceptable solutions, which may routinely contain pharmaceutically acceptable concentrations of salt, buffering agents, preservatives, compatible carriers, adjuvants, and optionally other therapeutic ingredients.

Pharmaceutical compositions of the invention contain an effective amount of a compound as described herein and optionally therapeutic agents included in a pharmaceutically acceptable carrier. The term "pharmaceutically acceptable carrier" means one or more compatible solid or liquid filler, diluents or encapsulating substances which are suitable for administration to a human or other vertebrate animal. The term "carrier" denotes an organic or inorganic ingredient, natural or synthetic, with which the active ingredient is combined to facilitate the application. The components of the pharmaceutical compositions also are capable of being commingled with the compounds of the present invention, and with each other, in a manner such that there is no interaction which would substantially impair the desired pharmaceutical efficiency.

It will be understood by one of ordinary skill in the relevant arts that other suitable modifications and adaptations to the compositions and methods described herein are readily apparent from the description of the invention contained herein in view of information known to the ordinarily skilled artisan, and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

The invention is further described in the following examples, which do not limit the scope of the invention described in the claims.

Example 1: Synthesis of Representative Compounds of the Invention

All reactions were performed with oven-dried glassware and under an inert atmosphere (nitrogen) unless otherwise stated. All solvents were used as purchased unless otherwise stated. Commercial reagents were used as purchased without further purification. Organic solutions were concentrated under reduced pressure on a Büchi rotary evaporator.

Thin-layer chromatography was carried out using Merck Kieselgel 60 F254 (230-400 mesh) fluorescent treated silica and were visualized under UV light (254 and 366 nm) and/or by staining with aqueous potassium permanganate solution. 1H NMR spectra were recorded in deuterated solvents on Bruker spectrometer at 400 MHz or Nanalysis NMReady-60PRO spectrometer at 60 MHz, with residual protic solvent as the internal standard. 13C NMR spectra were recorded in deuterated solvents on Bruker spectrometer at 100 MHz, with the central peak of the deuterated solvent as the internal standard. Chemical shifts ($\delta$) are given in parts per million (ppm) and coupling constants (J) are given in Hertz (Hz) rounded to the nearest 0.1 Hz. The 1H NMR spectra are reported as $\delta$/ppm downfield from tetramethylsilane (multiplicity, number of protons, coupling constant J/Hz). The $^{13}$C NMR spectra are reported as $\delta$/ppm. TLC-MS data was obtained on Advion Expression CMS coupled with Plate Express TLC-plate Reader. Medium pressure liquid chromatography (MPLC) was performed on a Biotage Isolera Four with built-in UV-detector and fraction collector with Interchim silica gel columns.

1. Synthesis of 6-Membered Urolithin a Analogues

A) Ester "A" Group Analogues Via the Hurtley Reaction General Procedure 1A (GP1a)

General procedure for cyclisation using NaOH and CuSO$_4$ (GP1a) using the synthesis of 3-hydroxy-8-methoxy-6H-benzo[c]chromen-6-one (1) as a generic example.

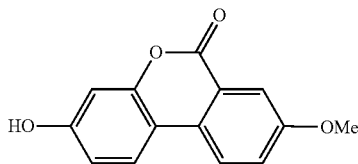

1

A mixture of 2-bromo-5-methoxybenzoic acid (0.500 g, 2.16 mmol, 1.0 eq), resorcinol (0.477 g, 4.33 mmol, 2.0 eq) and sodium hydroxide (0.2 g, 4.98 mmol, 2.4 eq) in water (10 ml) was heated under reflux for 30 minutes. After the addition of copper sulphate (5% aqueous solution, 2.5 ml), the mixture was refluxed again o/n, a precipitate was formed which was filtered off and washed with 1 M HCl, then dried under vacuum to afford 3-hydroxy-8-methoxy-6H-benzo[c]chromen-6-one (300 mg, 1.24 mmol 57%). $^1$H NMR (400 MHz, DMSO) δ 8.27 (d, J=8.9 Hz, 1H), 8.14 (d, J=8.8 Hz, 1H), 7.67 (d, J=2.8 Hz, 1H), 7.56 (dd, J=8.8, 2.9 Hz, 1H), 6.88 (dd, J=8.7, 2.4 Hz, 1H), 6.80 (d, J=2.4 Hz, 1H), 3.95 (s, 3H).

General Procedure 1B (GP1b)

General procedure for cyclisation using $Na_2CO_3$ and CuI (GP1b) using the synthesis of 3-hydroxy-6-oxo-6H-benzo[c]chromen-8-carboxylic acid (2) as a generic example.

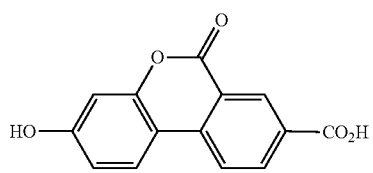

2

Resorcinol (8.9 g, 81.6 mmol, 2.0 eq) was dissolved in water and sodium carbonate (8.60 g, 81.6 mmol, 2.0 eq) was added and the mixture heated to 50° C. until everything had dissolved. Then, the acid (10.00 g, 40.8 mmol, 1.0 eq) was added and stirring at 50° C. was continued for Afterwards, CuI (0.77 g, 4.08 mmol) was added in one portion and the reaction was stirred o.n. A precipitate was formed which was filtered and washed with 1 M HCl twice to get 3-hydroxy-6-oxo-6H-benzo[c]chromene-8-carboxylic acid (4.45 g, 17.4 mmol, 43%) as a beige solid. $^1$H NMR (400 MHz, DMSO) δ 13.31 (s, 1H), 10.52 (s, 1H), 8.65 (s, 1H), 8.35 (d, J=5.9 Hz, 1H), 8.29 (s, 1H), 8.18 (d, J=8.7 Hz, 1H), 6.85 (dd, J=8.7, 2.3 Hz, 1H), 6.75 (d, J=2.2 Hz, 1H).

Synthesis of 8-bromo-3-hydroxy-6H-benzo[c]chromen-6-one (3)

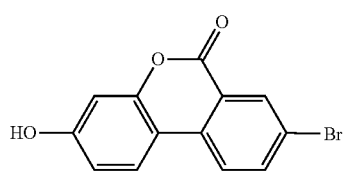

3

The compound was prepared according to GP1a starting from resorcinol (3.93 g, 35.7 mmol) and 2,5-dibromobenzoic acid (5.00 g, 17.9 mmol) to afford of 8-bromo-3-hydroxy-6H-benzo[c]chromen-6-one (2.14 g, 42%) as a brownish solid, $^1$H NMR (400 MHz, DMSO) δ 10.44 (s, 1H), 8.21 (d, J=2.2 Hz, 1H), 8.18 (d, J=8.8 Hz, 1H), 8.12 (d, J=8.8 Hz, 1H), 8.01 (dd, J=8.7, 2.2 Hz, 1H), 6.84 (dd, J=8.7, 2.4 Hz, 1H), 6.74 (d, J=2.4 Hz, 1H).

Synthesis of N-(3-hydroxy-6-oxo-6H-benzo[c]chromen-8-yl)acetamide (4)

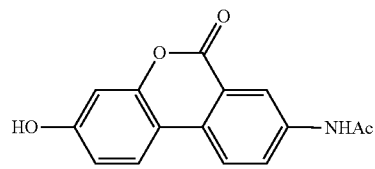

4

The compound was prepared according to GP1b starting from resorcinol (1.40, 12.8 mmol) and 5-acetamido-2-bromobenzoic acid (1.00 g, 3.87 mmol) to afford N-(3-hydroxy-6-oxo-6H-benzo[c]chromen-8-yl)acetamide (620 mg, 29%) as a beige solid. $^1$H NMR (400 MHz, DMSO) δ 10.32 (s, 1H), 10.27 (s, 1H), 8.50 (d, J=2.2 Hz, 1H), 8.20 (d, J=8.8 Hz, 1H), 8.07 (d, J=8.7 Hz, 1H), 7.99 (dd, J=8.8, 2.3 Hz, 1H), 6.83 (dd, J=8.7, 2.4 Hz, 1H), 6.74 (d, J=2.3 Hz, 1H), 2.10 (s, 3H).

Deprotection of 4 Afforded 8-amino-3-hydroxy-6H-benzo[c]chromen-6-one (5)

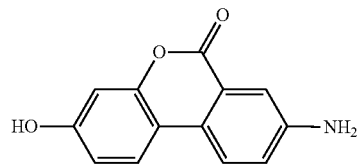

5

Synthesis of 8-fluoro-3-hydroxy-6H-benzo[c]chromen-6-one (6)

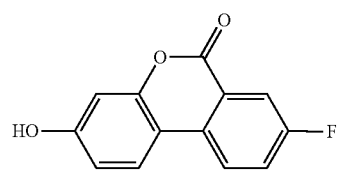

6

The compound was prepared according to GP1a starting from resorcinol (2.01 g, 18.3 mmol) and 2-bromo-5-fluorobenzoic acid (2.00 g, 9.13 mmol) to afford of 8-fluoro-3-hydroxy-6H-benzo[c]chromen-6-one (1.00 g, 48%) as a brownish solid. $^1$H NMR (400 MHz, DMSO) δ 10.54 (s, 1H), 8.31 (d, J=2.2 Hz, 1H), 8.28 (d, J=8.8 Hz, 1H), 8.32 (d, J=8.8 Hz, 1H), 8.21 (dd, J=8.7, 2.2 Hz, 1H), 7.04 (dd, J=8.7, 2.4 Hz, 1H), 6.94 (d, J=2.4 Hz, 1H).

Synthesis of 3-hydroxy-6H-benzo[c]chromen-6-one (Urolithin B, UB)

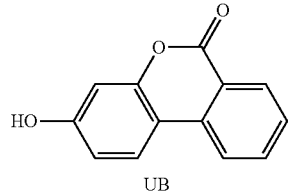
UB

The compound was prepared according to GP1a starting from resorcinol (5.48 g, 49.7 mmol) and 2-bromobenzoic acid (5.00 g, 24.9 mmol) to afford of 3-hydroxy-6H-benzo[c]chromen-6-one (3.00 g, 57%) as a pale rose solid. $^1$H NMR (400 MHz, DMSO) δ 10.39 (s, 1H), 8.26 (d, J=8.1 Hz, 1H), 8.22-8.13 (m, 2H), 7.89 (ddd, J=8.4, 7.2, 1.5 Hz, 1H), 7.64-7.51 (m, 1H), 6.85 (dd, J=8.7, 2.3 Hz, 1H), 6.76 (d, J=2.3 Hz, 1H).

Synthesis of 4-fluoro-3-hydroxy-8-methoxy-6H-benzo[c]chromen-6-one (7)

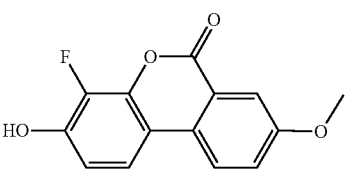

The compound was prepared according to GP1a starting from 2-fluorobenzene-1,3-diol (554 mg, 4.33 mmol) and 2-bromo-5-methoxybenzoic acid (500 mg, 2.16 mmol) to afford of 4-fluoro-3-hydroxy-8-methoxy-6H-benzo[c]chromen-6-one (190 mg, 34%) as a brownish solid. $^1$H NMR (400 MHz, DMSO) δ 10.61 (s, 1H), 8.20 (s, 1H), 7.88 (s, 1H), 7.57 (d, J=42.1 Hz, 2H), 6.96 (s, 1H), 3.90 (s, 3H).

Synthesis of 1-fluoro-3-hydroxy-8-methoxy-6H-benzo[c]chromen-6-one (8)

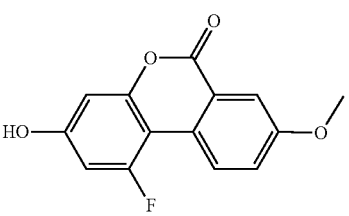

The compound was prepared according to GP1a starting from 5-fluorobenzene-1,3-diol (554 mg, 4.33 mmol) and 2-bromo-5-methoxybenzoic acid (500 mg, 2.16 mmol) to afford 1-fluoro-3-hydroxy-8-methoxy-6H-benzo[c]chromen-6-one (170 mg, 30%) as a brownish solid. $^1$H NMR (400 MHz, DMSO) δ 10.90 (s, 1H), 8.21 (s, 1H), 7.59 (d, J=59.1 Hz, 2H), 7.01-6.42 (m, 2H), 3.89 (s, 3H).

Synthesis of 2-fluoro-3-hydroxy-8-methoxy-6H-benzo[c]chromen-6-one (9)

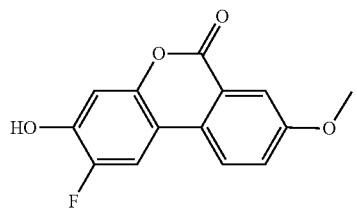

The compound was prepared according to GP1a starting from 4-fluorobenzene-1,3-dio (388 mg, 3.03 mmol) and 2-bromo-5-methoxybenzoic acid (350 mg, 1.51 mmol) to afford 2-fluoro-3-hydroxy-8-methoxy-6H-benzo[c]chromen-6-one (88 mg, 22%) as a light brownish solid. $^1$H NMR (400 MHz, DMSO) δ 10.72 (s. 11-1). 8.27-8.20 (m, 1H), 8.13 (d, J=12.0 Hz, 1H), 7.60 (d, J=2.8 Hz, 1H), 7.49 (dd, J=8.8, 2.7 Hz, 6.92 (d, J=7.6 Hz, 1H), 3.89 (s, 3H).

Synthesis of 3-hydroxy-6H-[1,3]dioxolo[4',5':4,5]benzo[1,2-c]chromen-6-one (10)

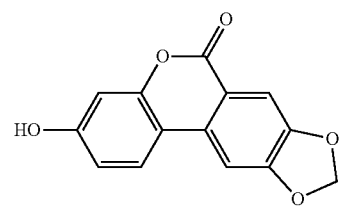

The compound was prepared according to GP1a starting from resorcinol (449 mg, 4.08 mmol) 6-bromobenzo[d][1,3]dioxole-5-carboxylic acid (500 mg, 2.04 mmol) to afford of 3-hydroxy-6H-[1,3]dioxolo[4',5':4,5]benzo[1,2-c]chromen-6-one (280 mg, 53%) as a purple solid. $^1$H NMR (400 MHz, DMSO) δ 8.07 (d, J=8.8 Hz, 1H), 7.81 (s, 1H), 7.50 (s, 1H), 6.80 (dd, J=8.7, 2.4 Hz, 1H), 6.72 (d, J=2.3 Hz, 1H), 6.22 (s, 2H).

Synthesis of 4-fluoro-3-hydroxy-6H-benzo[c]chromen-6-one (11)

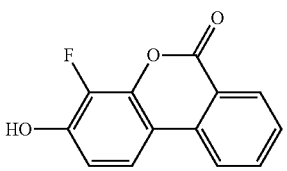

The compound was prepared according to GP1a starting from 2-fluorobenzene-1,3-diol (637 mg, 4.97 mmol) and 2-bromobenzoic acid (550 mg, 2.74 mmol) to afford 4-fluoro-3-hydroxy-6H-benzo[c]chromen-6-one (170 mg, 27%) as a brownish solid. $^1$H NMR (400 MHz, DMSO) δ 10.79 (s, 1H), 8.29 (d, J=8.1 Hz, 1H), 8.22 (dd, J=7.9, 1.4

Hz, 1H), 7.97 (dd, J=8.8, 1.9 Hz, 1H), 7.92 (t, J=7.0 Hz, 1H), 7.62 (t, J=7.6 Hz, 1H), 7.00 (t, J=8.4 Hz, 1H).
MS (ESI+): m/z=231.

General Procedure 2 (GP2)

General procedure for deprotection with BBr$_3$ in DCM (GP2) using the synthesis of 4-fluoro-3,8-dihydroxy-6H-benzo[c]chromen-6-one (12) as a generic example.

Synthesis of 4-fluoro-3,8-dihydroxy-6H-benzo[c]chromen-6-one (12)

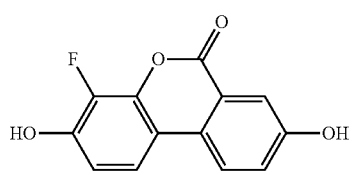

12

BBr$_3$ (1.5 ml, 1.5 mmol, 1 M in THF) was added to a solution of 4-fluoro-3-hydroxy-8-methoxy-6H-benzo[c]chromen-6-one (130 mg, 0.500 mmol), in DCM (2 ml) at 0° C. and the mixture was allowed to warm to rt o.n. TLC showed complete conversion of the starting material. MeOH was added slowly at 0° C. and the solvent was evaporated under vacuum. The crude was purified by MPLC (SiO$_2$, EtOAc/Cyclohexane 0% to 50%) to afford 4-fluoro-3,8-dihydroxy-6H-benzo[c]chromen-6-one (40 mg, 0.16 mmol, 33%). R$_f$=0.50 (EtOAc/hexane 50/50). $^1$H NMR (400 MHz, DMSO) δ 10.54 (s, 1H), 10.32 (s, 1H), 8.14 (d, J=8.8 Hz, 1H), 7.83 (dd, J=9.0, 2.0 Hz, 1H), 7.54 (d, J=2.7 Hz, 1H), 7.35 (dd, J=8.8, 2.7 Hz, 1H), 6.98-6.93 (m, 1H).

Synthesis of 1-fluoro-3,8-dihydroxy-6H-benzo[c]chromen-6-one (13)

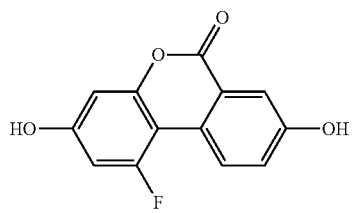

13

The compound was prepared according to GP2 starting from 1-fluoro-3-hydroxy-8-methoxy-6H-benzo[c]chromen-6-one (1 h) (100 mg, 0.380 mmol) and BBr$_3$ (1.54 ml, 1.54 mmol, 1 M in THF). The crude was purified by MPLC (SiO$_2$, EtOAc/Cyclohexane 0% to 50%) to afford 1-fluoro-3,8-dihydroxy-6H-benzo[c]chromen-6-one (40 mg, 0.16 mmol, 42%) as brownish solid. R$_f$=0.50 (EtOAc/hexane 50/50). $^1$H NMR (400 MHz, DMSO) δ 10.59 (s, 1H), 10.34 (s, 1H), 8.30-8.07 (m, 1H), 7.59 (dd, J=2.8, 1.0 Hz, 1H), 7.41-7.28 (m, 1H), 6.72-6.56 (m, 2H).

Synthesis of 8-hydroxy-3-methoxy-6H-benzo[c]chromen-6-one

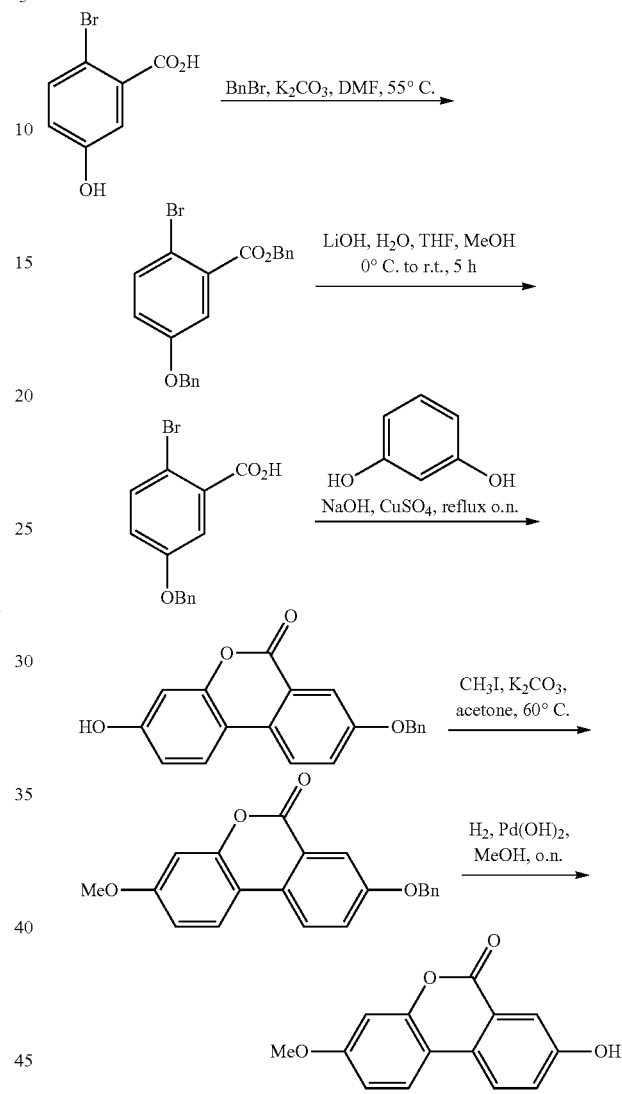

Step 1: Synthesis of benzyl 5-(benzyloxy)-2-bromobenzoate

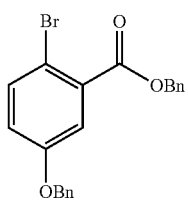 [SMILES: O=C(OCc1ccccc1)c1cc(OCc2ccccc2)ccc1Br]

Benzyl bromide (1.44 ml, 12.1 mmol, 2.1 eq.) was added to a suspension of 2-bromo-5-hydroxybenzoic acid (1.25 g, 5.76 mmol, 1.0 eq.) and potassium carbonate (1.99 g, 11.5 mmol, 2.0 eq.) in DMF (40 ml) and the mixture was heated at 55° C. o.n. The mixture was extracted with EtOAc/NH4Cl saturated solution then washed with water. The combined organic phases were dried over sodium sulfate and concentrated under vacuum. The crude was purified by MPLC (SiO$_2$, EtOAC/cyclohexane 0% to 20%) to afford benzyl 5-(benzyloxy)-2-bromobenzoate (1.20 g, 52%) as colorless oil. R$_f$=0.60 (EtOAc/hexane 50/50). $^1$H NMR (400 MHz, CDCl$_3$) δ 7.55 (d, J=8.8 Hz, 1H), 7.52-7.34 (m, 11H), 6.97 (dd, J=8.8, 3.1 Hz, 1H), 5.39 (s, 2H), 5.08 (s, 2H).

Step 2: Synthesis of 5-(benzyloxy)-2-bromobenzoic acid

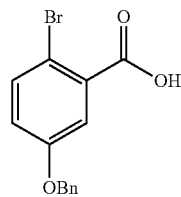 [SMILES: O=C(O)c1cc(OCc2ccccc2)ccc1Br]

A solution of aq. LiOH (790 mg, 19.3 mmol) was added at 0° C. to a solution of benzyl 5-(benzyloxy)-2-bromobenzoate (1.28 g, 3.22 mmol) in THF (10 ml) and MeOH (5 ml) and the mixture was allowed to warm to rt over 4 h. Water was added and the aqueous phase was extracted with Et$_2$O twice. The aqueous phase was acidified to pH 1 with 1 M HCl and extracted twice with EtOAc. The organic phase was dried over sodium sulfate and evaporated under vacuum to afford 5-(benzyloxy)-2-bromobenzoic acid (700 mg, 71%) as a white solid. R$_f$=0.3 (EtOAc, KMnO$_4$). $^1$H NMR (400 MHz, CDCl$_3$) δ 7.31 (d, J=3.2 Hz, 1H), 7.27 (d, J=8.8 Hz, 1H), 7.15-7.00 (m, 5H), 6.70 (dd, J=8.8, 3.1 Hz, 1H), 4.78 (s, 2H).

Step 3: Synthesis of 8-(benzyloxy)-3-hydroxy-6H-benzo[c]chromen-6-one (14)

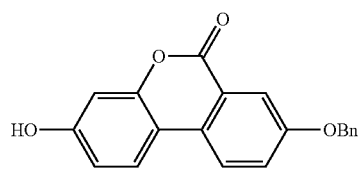

14 was prepared according to GP1a starting from resorcinol (538 mg, 4.88 mmol) and 5-(benzyloxy)-2-bromobenzoic acid (750 mg, 2.44 mmol) to afford 8-(benzyloxy)-3-hydroxy-6H-benzo[c]chromen-6-one (338 mg, 43%) as a light brownish solid. $^1$H NMR (400 MHz, DMSO) δ 10.22 (s, 1H), 8.21 (d, J=9.0 Hz, 1H), 8.08 (d, J=8.8 Hz, 1H) 7.70 (d, J=2.8 Hz, 1H), 7.56 (dd, J=8.8, 2.8 Hz, 1H), 7.52-7.28 (m, 5H), 6.82 (dd, J=8.7, 2.4 Hz, 1H), 6.74 (d, J=2.4 Hz, 1H), 5.26 (s, 2H).

Step 4: Synthesis of 8-(benzyloxy)-3-methoxy-6H-benzo[c]chromen-6-one (15)

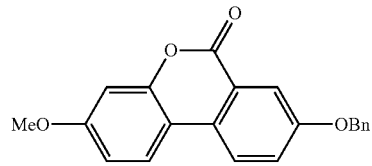

Methyliodide (178 mg, 1.26 mmol) was added to a suspension of 8-(benzyloxy)-3-hydroxy-6H-benzo[c]chromen-6-one (200 mg, 0.620 mmol) and potassium carbonate (178 mg, 1.26 mml) acetone (5 ml) and the mixture heated at 60° C. for 2 h. TLC showed complete conversion of the starting material. The mixture was filtered off and the filtered solid was triturated MeOH and filtered to afford 8-(benzyloxy)-3-methoxy-6H-benzo[c]chromen-6-one (130 mg, 62%) as a beige solid. R$_f$=0.6 (EtOAc/Hexane 40%). $^1$H NMR (400 MHz, DMSO) δ 8.28 (d, J=8.9 Hz, 1H), 8.19 (d, J=8.6 Hz, 1H), 7.71 (d, J=2.8 Hz, 1H), 7.59 (dd, J=8.8, 2.8 Hz, 1H), 7.53-7.30 (m, 5H), 6.98 (d, J=9.4 Hz, 2H), 5.27 (s, 2H), 3.85 (s, 3H).

Step 5: Synthesis of 8-hydroxy-3-methoxy-6H-benzo[c]chromen-6-one (16)

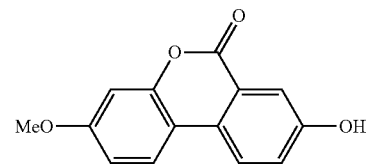

A suspension of 8-(benzyloxy)-3-methoxy-6H-benzo[c]chromen-6-one (130 mg, 0.390 mmol) and Pd(OH)$_2$/C (27 mg, 0.039 mmol) in Methanol (5 ml) was hydrogenated under atmospheric pressure overnight. The mixture was filtered over a pad of celite and washed with methanol. The solvent was evaporated under vacuum to afford 8-hydroxy-3-methoxy-6H-benzo[c]chromen-6-one (30 mg, 32%) as a grey solid. $^1$H NMR (400 MHz, DMSO) δ 8.16 (d, J=8.8 Hz, 1H), 8.13 (d, J=8.6 Hz, 1H), 7.53 (d, J=2.7 Hz, 1H), 7.34 (dd, J=8.7, 2.7 Hz, 1H), 7.00-6.93 (m, 2H), 3.84 (s, 3H).

Synthesis of 3,8-dimethoxy-6H-benzo[c]chromen-6-one (17)

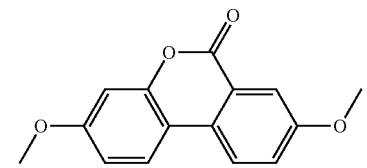

Methyl iodide (1.18 ml, 18.9 mmol) was added to a mixture of Urolthin A (1.80 g, 7.88 mmol) and potassium carbonate (3.80 g, 27.6 mmol) in acetone (50 ml) and refluxed overnight. The yellow suspension was cooled to r.t. and filtered. Acetone was evaporated under vacuum and the crude was triturated in diethyl ether and filtered to afford 3,8-dimethoxy-6H-benzo[c]chromen-6-one (2.00 g, 98%) as a white solid. $^1$H NMR (400 MHz, CDCl$_3$) δ 7.93 (d, J=8.9 Hz, 1H), 7.87 (d, J=8.8 Hz, 1H), 7.77 (d, J=2.8 Hz, 1H), 7.37 (dd, J=8.8, 2.8 Hz, 1H), 6.91 (dd, J=8.8, 2.6 Hz, 1H), 6.87 (d, J=2.5 Hz, 1H), 3.93 (s, 3H), 3.88 (s, 3H).

B) Amide "A" Group Analogues

Synthesis of 3,8-dihydroxyphenanthridin-6(5H)-one (18)

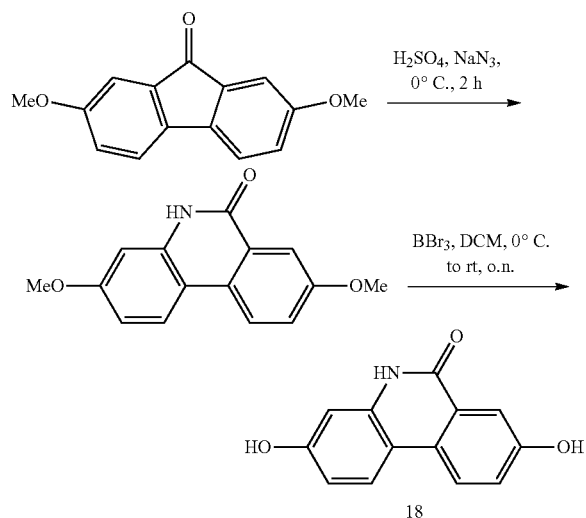

Step 1: Synthesis of 3,8-dimethoxyphenanthridin-6(5H)-one

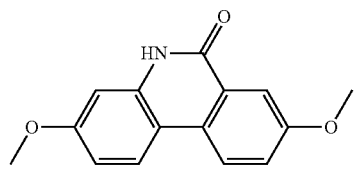

To cold sulfuric acid (10 ml) was added at 0° C. 2,7-dimethoxy-9H-fluoren-9-one (1.10 g, 4.57 mmol), and then carefully sodium azide (387 mg, 5.95 mmol). The reaction mixture was stirred at 0° C. for 3 h. EtOAc (10 ml) was added and the mixture was poured into ice water and stirred for 1 h. The brownish precipitate was filtered and the aqueous phase was extracted with EtOAc 3 times. The organic phase was dried over sodium sulfate and evaporated under vacuum. The crude was purified by MPLC (SiO$_2$, EtOAc/cyclohexane from 0% to 80%) to afford 3,8-dimethoxyphenanthridin-6(5H)-one (150 mg, 13%) as a brown solid. R$_f$=0.4 (EtOAc/hexane 50%). $^1$H NMR (400 MHz, DMSO) δ 11.60 (s, 1H), 8.32 (d, J=8.9 Hz, 1H), 8.20 (d, J=8.7 Hz, 1H), 7.70 (d, J=2.8 Hz, 1H), 7.40 (dd, J=8.9, 2.9 Hz, 1H), 6.91-6.81 (m, 2H), 3.89 (s, 3H), 3.81 (s, 3H).

Step 2: Synthesis of 3,8-dihydroxyphenanthridin-6(5H)-one

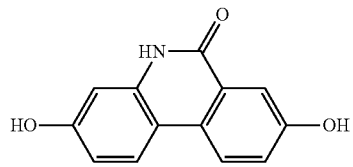 [SMILES: O=c1[nH]c2cc(O)ccc2c2ccc(O)cc12]

18 was prepared according to GP2 from 3,8-dimethoxyphenanthridin-6(5H)-one (90 mg, 0.35 mmol) and BBr$_3$ (1 M in THF, 2.10 ml, 2.10 mmol) to afford after purification by MPLC (SiO$_2$, MeOH/DCM 0% to 10%) 3,8-dihydroxyphenanthridin-6(5H)-one (70 mg, 87%) as a brownish solid. R$_f$=0.2 (MeOH in DCM 10%). $^1$H NMR (400 MHz, DMSO) δ 11.91-11.20 (m, 1H), 10.34-9.57 (m, 2H), 8.08 (d, J=49.2 Hz, 2H), 7.82-7.48 (m, 1H), 7.23 (s, 1H), 6.70 (d, J=27.5 Hz, 2H).

Synthesis of 3,8-dihydroxy-5-methylphenanthridin-6(5H)-one (20)

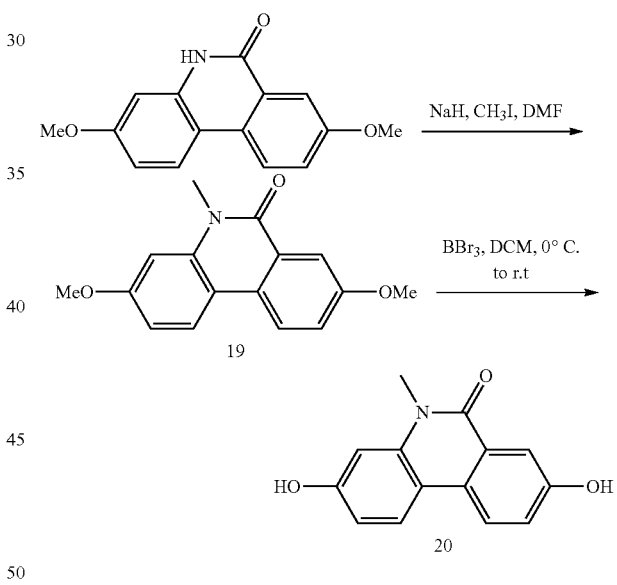

Step 1: Synthesis of 3,8-dimethoxy-5-methylphenanthridin-6(5H)-one (19)

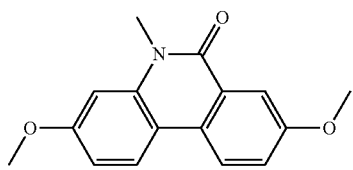

NaH (60% mineral oil dispersion, 59 mg, 1.5 mmol) was added to a solution of 3,8-dimethoxyphenanthridin-6(5H)- one (250 mg, 0.98 mmol) in DMF (10 ml) at 0° C. and the mixture was stirred for 30 min at 0° C. Then, MeI (0.122 ml, 1.96 mmol) was added and stirring continued at rt for 2 h. The reaction mixture was poured into a sat. aq. Solution of NH₄Cl and extracted with EtOAc 3 times. The combined organic phases were dried over sodium sulfate and concentrated under vacuum. The crude product was purified by MPLC (SiO₂, EtOAc/cyclohexane 0% to 40%) to afford 3,8-dimethoxy-5-methylphenanthridin-6(5H)-one (176 mg, 67%). $R_f$=0.3 eluent (EtOAc/hexane 50%). ¹H NMR (400 MHz, CDCl₃) δ 8.10 (dd, J=9.2, 8.0 Hz, 2H), 7.93 (d, J=2.8 Hz, 1H), 7.32 (dd, J=8.9, 2.9 Hz, 1H), 6.93-6.86 (m, 2H), 3.95 (s, 3H), 3.93 (s, 3H), 3.80 (s, 3H).

Step 2: Synthesis of
3,8-dihydroxy-5-methylphenanthridin-6(5H)-one
(20)

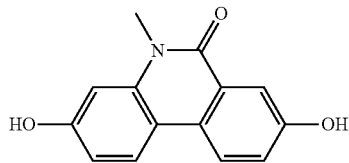

UA-0034

20 was prepared according to GP2 starting from 3,8-dimethoxy-5-methylphenanthridin-6(5H)-one (150 mg, 0.550 mmol) to afford after purification by MPLC (SiO₂, MeOH/DCM 0% to 10%) 3,8-dihydroxy-5-methylphenanthridin-6(5H)-one (120 mg, 89%) as a beige solid. $R_f$=0.8 (MeOH/DCM 10/90). ¹H NMR (400 MHz, DMSO) δ 9.92 (s, 2H), 8.18 (d, J=8.9 Hz, 1H), 8.13 (d, J=8.8 Hz, 1H), 7.64 (d, J=2.7 Hz, 1H), 7.22 (dd, J=8.8, 2.7 Hz, 1H), 6.85 (d, J=2.3 Hz, 1H), 6.77 (dd, J=8.7, 2.3 Hz, 1H), 3.63 (s, 3H).

Synthesis of
5-cyclopropyl-3,8-dihydroxyphenanthridin-6(5H)-one
(21)

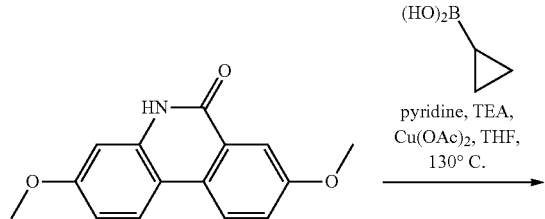

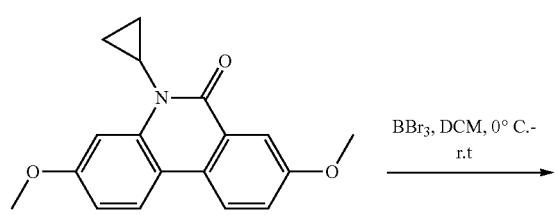

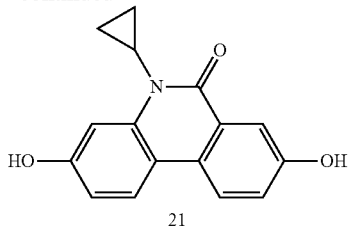

21

Step 1: Synthesis of
5-cyclopropyl-3,8-dimethoxyphenanthridin-6(5H)-one

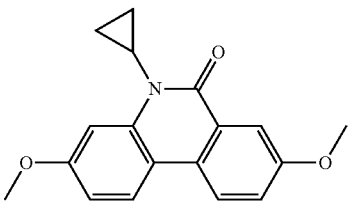

A microwave vial was charged with 3,8-dimethoxyphenanthridin-6(5H)-one (120 mg, 0.470 mmol, 1.0 eq.), cyclopropylboronic acid (121 mg, 1.41 mmol, 3.0 eq.), pyridine (355 mg, 4.23 mmol, 9.0 eq.), triethylamine (285 mg, 2.82 mmol, 6.0 eq.) and THF (2.0 mL) and the resulting mixture was degassed with a N₂ balloon for 10 min at r.t. Then, Cu(OAc)₂ (171 mg, 0.940 mmol, 2.0 eq.) was added in one portion and the vial was closed and put into a preheated 130° C. oil-bath for 2 h. Upon complete consumption of the starting material the reaction was allowed to cool to r.t., and subsequently quenched with water, extracted with EtOAc, dried over Na₂SO₄, and concentrated under vacuum. The crude product was purified by MPLC (SiO₂, 25 g, EtOAc in Hex 0-50%) to afford 5-cyclopropyl-3,8-dimethoxyphenanthridin-6(5H)-one (50 mg, 36%) as a brown solid.

¹H NMR (400 MHz, CDCl₃) δ 8.02 (dd, J=8.9, 2.1 Hz, 2H), 7.87 (d, J=2.8 Hz, 1H), 7.39 (d, J=2.5 Hz, 1H), 7.29 (dd, J=8.9, 2.8 Hz, 1H), 6.87 (dd, J=8.8, 2.5 Hz, 1H), 3.93 (d, J=3.2 Hz, 6H), 3.05-2.99 (m, 1H), 1.45-1.36 (m, 2H), 0.97-0.90 (m, 2H).

Step 2: Synthesis of
5-cyclopropyl-3,8-dihydroxyphenanthridin-6(5H)-one

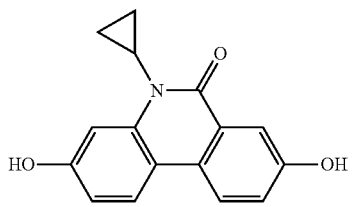

5-cyclopropyl-3,8-dimethoxyphenanthridin-6(5H)-one (20 mg, 0.070 mmol, 1.0 eq.) was dissolved in DCM (1 mL) and cooled down to 0° C. in an ice-bath and stirring was continued for 5 min. Then, BBr₃ (0.20 ml, 1 M in DCM, 0.020 mmol, 3.0 eq.) was added dropwise to the reaction mixture. Upon complete addition the mixture was left in the ice bath and was allowed to warm to r.t. over the course of 2 h. When no more starting material could be observed (TLC), the reaction mixture was dropwise added into 0° C. cold methanol (10 mL) and stirred for an additional 10 min. Then, the mixture was concentrated and loaded on silica to be purified by MPLC (SiO₂, 12 g, MeOH in DCM 0-5%) to afford 5-cyclopropyl-3,8-dihydroxyphenanthridin-6(5H)-one (13 mg, 0.050 mmol, 71%) as white solid. MS (ESI+): m/z=268. ¹H NMR (400 MHz, DMSO) δ 9.86 (d, J=9.3 Hz, 2H), 8.12 (d, J=8.9 Hz, 1H), 8.06 (d, J=8.8 Hz, 1H), 7.57 (d, J=2.7 Hz, 1H), 7.27 (d, J=2.3 Hz, 1H), 7.18 (dd, J=8.7, 2.8 Hz, 1H), 6.73 (dd, J=8.7, 2.3 Hz, 1H), 2.94 (dt, J=7.0, 3.1 Hz, 1H), 1.35-1.18 (m, 2H), 0.74 (p, J=5.4, 5.0 Hz, 2H).

C) Sulfonamide "A" Group Analogues

Synthesis of 3,8-dihydroxy-6H-dibenzo[c,e][1,2]thiazine 5,5-dioxide (22)

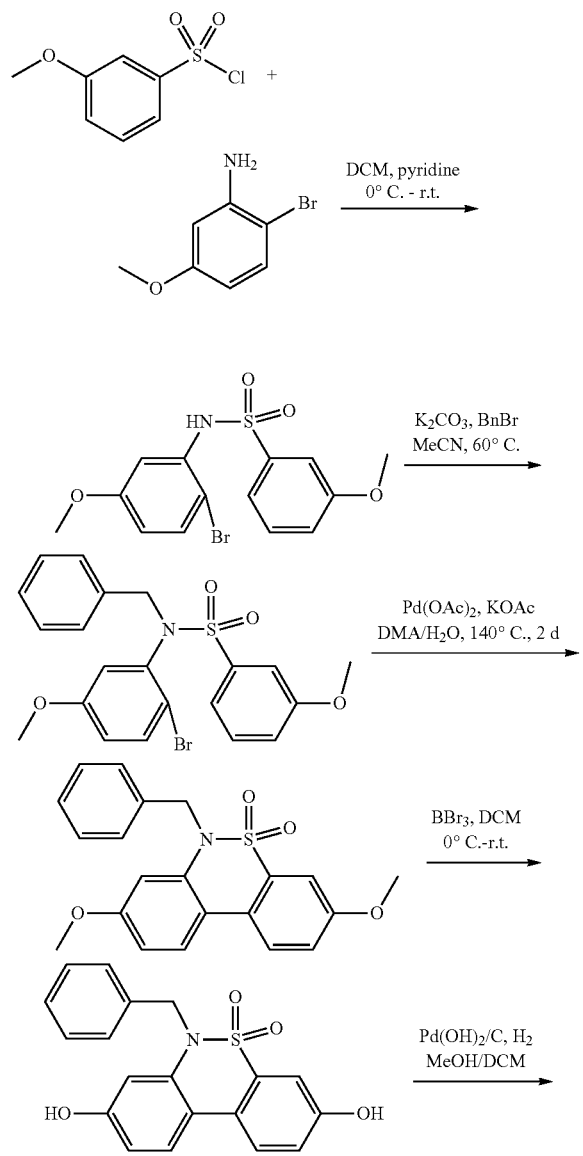

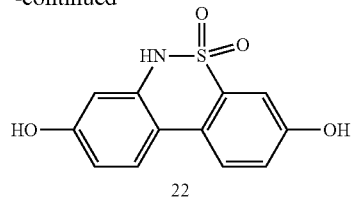

22

Step 1: Synthesis of N-(2-bromo-5-methoxyphenyl)-3-methoxybenzenesulfonamide

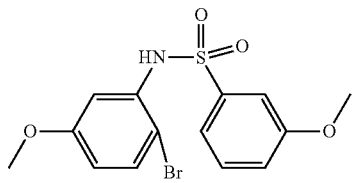

3-methoxybenzenesulfonyl chloride (2.00 g, 9.68 mmol, 1.3 eq.) was slowly added to a solution of 2-bromo-5-methoxyaniline (1.79 g, 8.81 mmol, 1.0 eq.) and pyridine (2.79 g, 35.2 mmol, 4.0 eq.) in DCM (20 mL) at 0° C. Upon warming up to r.t. no more starting material could be observed by TLC, and the reaction mixture was concentrated under vacuum. The reaction mixture was diluted with EtOAc and washed with 1N aqueous HCl. The organic phase was dried over Na₂SO₄ and concentrated in vacuum to afford N-(2-bromo-5-methoxyphenyl)-3-methoxybenzenesulfonamide (3.28 g, 99%) as a brown oil. ¹H NMR (400 MHz, CDCl₃) δ 7.41-7.21 (m, 4H), 7.07 (ddd, J=7.7, 2.5, 1.5 Hz, 1H), 6.94 (s, 1H), 6.55 (dd, J=8.9, 3.0 Hz, 1H), 3.78 (s, 3H), 3.77 (s, 3H).

Step 2: Synthesis of N-benzyl-N-(2-bromo-5-methoxyphenyl)-3-methoxybenzenesulfonamide

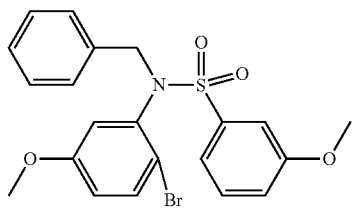

N-(2-bromo-5-methoxyphenyl)-3-methoxybenzenesulfonamide (5.90 g, 18.9 mmol, 1.0 eq.) was dissolved in MeCN (53 mL) and K₂CO₃ (6.57 g, 47.6 mmol, 3.0 eq.) was added in one portion. At r.t. benzyl bromide (2.98 g, 17.4 mmol, 1.1 eq.) was added dropwise and upon complete addition the reaction mixture was heated to 60° C. in an oil bath for 3 h. After complete consumption of the starting material (as indicated by TLC) the reaction mixture was allowed to cool down to r.t. and filtered. The filtrate was concentrated under vacuum and loaded on silica to be purified by MPLC (SiO₂, 240 g, EtOAc in Hex 0-10%) to afford N-benzyl-N-(2-bromo-5-methoxyphenyl)-3-methoxybenzenesulfonamide (6.83 g, 93%) as a light brown solid. ¹H NMR (400 MHz, CDCl₃) δ 7.42-7.34 (m, 3H), 7.28-7.18 (m, 6H), 7.15-7.10 (m, 1H), 6.69 (dd, J=8.9, 3.0 Hz, 1H), 6.48 (d, J=3.0 Hz, 1H), 4.89 (d, J=14.4 Hz, 1H), 4.66 (d, J=14.3 Hz, 1H), 3.79 (s, 3H), 3.59 (s, 3H).

Step 3: Synthesis of 6-benzyl-3,8-dimethoxy-6H-dibenzo[c,e][1,2]thiazine 5,5-dioxide

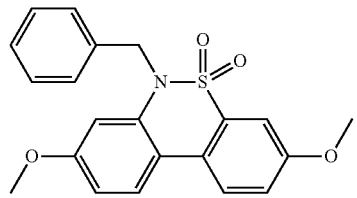 [SMILES: COc1ccc2c(c1)N(Cc1ccccc1)S(=O)(=O)c1cc(OC)ccc1-2]

N-benzyl-N-(2-bromo-5-methoxyphenyl)-3-methoxy-benzenesulfonamide (2.00 g, 4.33 mmol, 1.0 eq.) was dissolved in a mixture of DMA (20 mL) and water (5 mL) and thereupon were added Pd(OAc)₂ (291 mg, 1.30 mmol, 0.3 eq.) and KOAc (1.69 g, 17.3 mmol, 4.0 eq.). Upon complete dissolution of the reagents, the flask was put into a 140° C. oil bath and stirring was continued over a period of 48 h. Afterwards the reaction mixture was concentrated to complete dryness using a rotary evaporator at 90° C. The reaction mixture was loaded on silica and purified by MPLC (SiO₂, 80 g, EtOAc in Hex 0-15%) to afford 6-benzyl-3,8-dimethoxy-6H-dibenzo[c,e][1,2]thiazine 5,5-dioxide (560 mg, 34%) as a white solid. ¹H NMR (400 MHz, DMSO) δ 8.00 (t, J=8.5 Hz, 2H), 7.39 (d, J=2.7 Hz, 1H), 7.34 (dd, J=8.8, 2.7 Hz, 1H), 7.25-7.09 (m, 5H), 6.95 (d, J=2.5 Hz, 1H), 6.91 (dd, J=8.8, 2.5 Hz, 1H), 5.16 (s, 2H), 3.91 (s, 3H), 3.75 (s, 3H).

Step 4: Synthesis of 6-benzyl-3,8-dihydroxy-6H-dibenzo[c,e][1,2]thiazine 5,5-dioxide

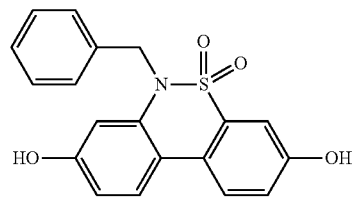 [SMILES: O=S1(=O)c2cc(O)ccc2-c2ccc(O)cc2N1Cc1ccccc1]

6-benzyl-3,8-dimethoxy-6H-dibenzo[c,e][1,2]thiazine 5,5-dioxide (180 mg, 0.470 mmol, 1.0 eq.) was dissolved in DCM (2 mL) and cooled down to 0° C. in an ice-bath and stirring was continued for 5 min. Then, BBr₃ (1.89 ml, 1 M in DCM, 1.88 mmol, 4.0 eq.) was added dropwise to the reaction mixture. Upon complete addition the mixture was left in the ice bath and was allowed to warm to r.t. over the course of 2 h. When no more starting material could be observed (TLC), the reaction mixture was dropwise added into 0° C. cold methanol (20 mL) and stirred for an additional 10 min. Then, the mixture was concentrated, loaded on silica, and purified by MPLC (SiO₂, 20 g, MeOH in DCM 0-3%) to afford 6-benzyl-3,8-dihydroxy-6H-dibenzo[c,e][1,2]thiazine 5,5-dioxide (100 mg, 60%) as a light yellow solid. ¹H NMR (400 MHz, DMSO) δ 10.33 (s, 1H), 9.94 (s, 1H), 7.90-7.80 (m, 2H), 7.39-7.09 (m, 7H), 6.83-6.62 (m, 2H), 5.04 (s, 2H).

Step 5: Synthesis of 3,8-dihydroxy-6H-dibenzo[c,e][1,2]thiazine 5,5-dioxide

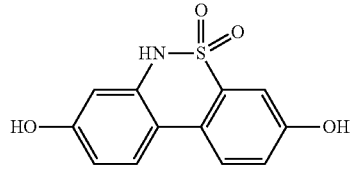 [SMILES: O=S1(=O)Nc2cc(O)ccc2-c2ccc(O)cc21]

6-benzyl-3,8-dihydroxy-6H-dibenzo[c,e][1,2]thiazine 5,5-dioxide (100 mg, 0.370 mmol, 1.0 eq.) was dissolved in MeOH (10 mL) and Pd(OH)₂/C (26 mg) was added in one portion. Then, the reaction mixture was evacuated and backfilled with N₂ three times before putting it under hydrogen atmosphere (balloon). The reaction mixture was stirred for 4 h and upon complete consumption of starting material (as indicated by TLC) filtered over silica and concentrated under vacuum. The crude product was loaded on silica, and purified by MPLC (SiO₂, 12 g, EtOAc in Hex 0-50%) to give 3,8-dihydroxy-6H-dibenzo[c,e][1,2]thiazine 5,5-dioxide (65 mg, 67%) as a white solid. ¹H NMR (400 MHz, DMSO) δ 10.24 (s, 1H), 9.87 (s, 1H), 7.88 (d, J=8.8 Hz, 1H), 7.83 (d, J=8.5 Hz, 1H), 7.17 (d, J=2.6 Hz, 1H), 7.11 (dd, J=8.7, 2.6 Hz, 1H), 6.64 (dd, J=8.7, 2.5 Hz, 1H), 6.55 (d, J=2.5 Hz, 1H).

D) Ether "A" Group Analogues

Synthesis of 6H-benzo[c]chromene-3,8-diol (23)

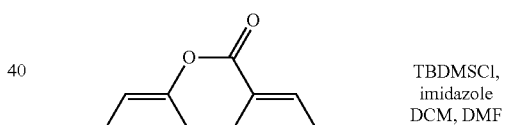

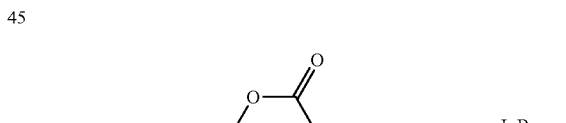

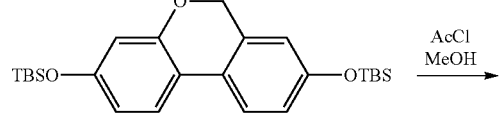

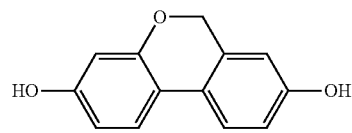

23

Step 1: Synthesis of 3,8-bis((tert-butyldimethylsilyl)oxy)-6H-benzo[c]chromen-6-one

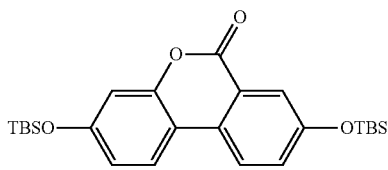 [SMILES: CC(C)(C)[Si](C)(C)Oc1ccc2c(c1)oc(=O)c1cc(O[Si](C)(C)C(C)(C)C)ccc12]

Urolithin A (12 g 53 mmol) was added to a solution of imidazole (9.0 g, 0.13 mol) in DCM (100 ml). stirred for 1 h. No reaction took place, therefore DMF (20 ml) was added and stirring continued overnight. DCM was removed in vacuum. Water was added and the mixture was extracted with $Et_2O$ (3*), the organic layers were washed successively with water twice and brine, dried with $Na_2SO_4$, filtered over silica and concentrated. The crude product was purified by MPLC ($SiO_2$, EtOAc/Cyclohexane 0 to 20%) to afford 3,8-bis((tert-butyldimethylsilyl)oxy)-6H-benzo[c]chromen-6-one (20 g, 96%) as a white solid. $^1$H NMR (400 MHz, $CDCl_3$) δ 7.89 (d, J=8.8 Hz, 1H), 7.85-7.80 (m, 1H), 7.76 (d, J=2.6 Hz, 1H), 7.29 (dd, J=8.7, 2.7 Hz, 1H), 6.86-6.80 (m, 2H), 1.02 (s, 9H), 0.98 (s, 9H), 0.26 (s, 6H), 0.24 (s, 6H).

Step 2: Synthesis of ((6H-benzo[c]chromene-3,8-diyl)bis(oxy))bis(tert-butyldimethylsilane

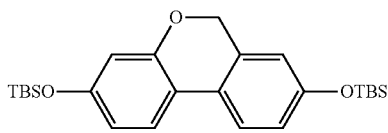

$InBr_3$ (142 mg, 0.400 mmol) was added to a solution of 3,8-bis((tert-butyldimethylsilyl)oxy)-6H-benzo[c]chromen-6-one (1.8 g, 4.0 mmol) in toluene (20 ml) and the reaction mixture was heated at 70° C. for 1 hour. The reaction mixture was cooled down to room temperature and filtered. The solvent was evaporated under vacuum and the crude was purified by MPLC ($SiO_2$, cyclohexane/dichloromethane from 0% to 10%) to afford ((6H-benzo[c]chromene-3,8-diyl)bis(oxy))bis(tert-butyldimethylsilane), 81 mg, 88%) as a white solid. $^1$H NMR (400 MHz, $CDCl_3$) δ 7.48 (t, J=8.5 Hz, 2H), 6.81 (dd, J=8.4, 2.5 Hz, 1H), 6.60 (d, J=2.4 Hz, 1H), 6.53 (dd, J=8.4, 2.5 Hz, 1H), 6.47 (d, J=2.4 Hz, 1H), 5.02 (s, 2H), 1.00 (s, 9H), 0.98 (s, 9H), 0.22 (s, 6H), 0.20 (s, 6H).

Step 3: Synthesis of 6H-benzo[c]chromene-3,8-diol

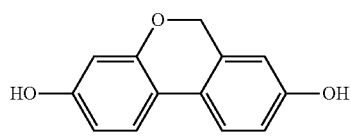 [SMILES: Oc1ccc2c(c1)COc1cc(O)ccc1-2]

Acetyl chloride (0.105 ml, 1.40 mmol) was added to a solution of ((6H-benzo[c]chromene-3,8-diyl)bis(oxy))bis(tert-butyldimethylsilane) (421 mg, 0.950 mmol) in methanol (10 ml) at room temperature and stirred overnight. The reaction mixture was concentrated under vacuum and purified by MPLC ($SiO_2$, EtOAc in Hex 0-100%) to afford 6H-benzo[c]chromene-3,8-diol (203 mg, 0.950 mmol, 99%) as a white solid. $^1$H NMR (400 MHz, DMSO) δ 9.50 (s, 1H), 9.48 (s, 1H), 7.49 (dd, J=12.5, 8.4 Hz, 2H), 6.74 (dd, J=8.4, 2.6 Hz, 1H), 6.60 (d, J=2.5 Hz, 1H), 6.45 (dd, J=8.4, 2.4 Hz, 1H), 6.32 (d, J=2.4 Hz, 1H), 4.96 (s, 2H).

Synthesis of 6-methyl-6H-benzo[c]chromene-3,8-diol (24)

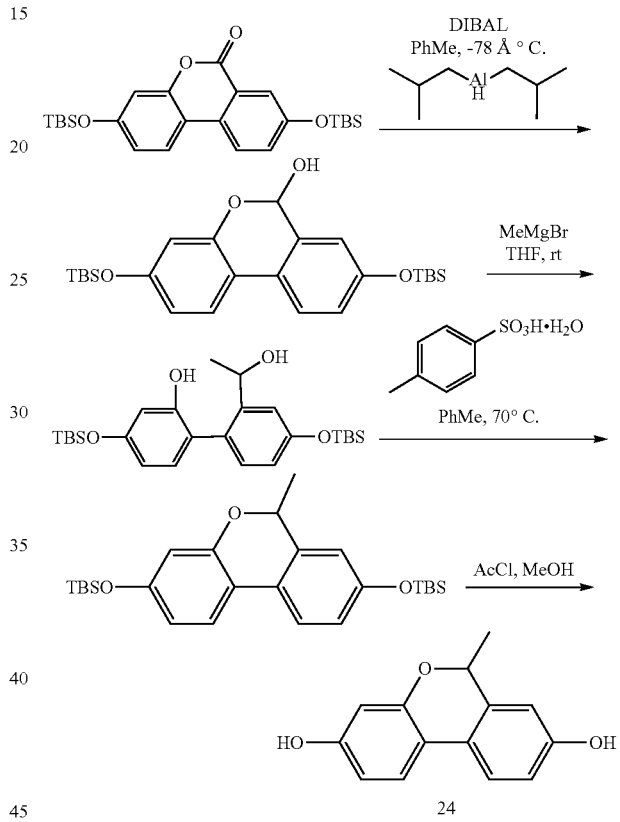

Step 1: Synthesis of 3,8-bis((tert-butyldimethylsilyl)oxy)-6H-benzo[c]chromen-6-ol

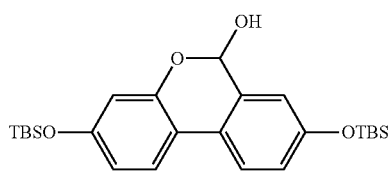 [SMILES: CC(C)(C)[Si](C)(C)Oc1ccc2c(c1)OC(O)c1cc(O[Si](C)(C)C(C)(C)C)ccc1-2]

DIBAL-H (2.10 ml, 2.10 mmol) was added slowly along the side of the flask to a solution of 3,8-bis((tert-butyldimethylsilyl)oxy)-6H-benzo[c]chromen-6-one (912 mg, 2.00 mmol) in toluene (20 ml) under nitrogen at −78° C. The reaction was monitored by TLC eluent (Cyclohexane/DCM 1:1). The reaction was complete within 1 hour stirring. After a Fieser work-up the product was used in the step without further purification. ¹H NMR (400 MHz, CDCl₃) δ 7.60 (dd, J=8.9, 6.9 Hz, 2H), 6.93 (dd, J=8.5, 2.5 Hz, 1H), 6.83 (d, J=2.6 Hz, 1H), 6.62-6.58 (m, 2H), 6.26 (s, 1H), 1.00 (s, 9H), 0.98 (s, 9H), 0.25-0.18 (m, 12H).

Step 2: Synthesis of 4,4'-bis((tert-butyldimethylsilyl)oxy)-2'-(1-hydroxyethyl)-[1,1'-biphenyl]-2-ol

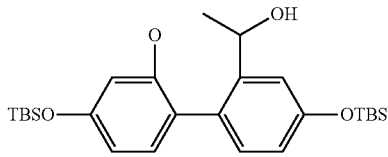 [SMILES: CC(O)c1cc(O[Si](C)(C)C(C)(C)C)ccc1-c1ccc(O[Si](C)(C)C(C)(C)C)cc1O]

To a solution of 3,8-bis((tert-butyldimethylsilyl)oxy)-6H-benzo[c]chromen-6-ol (456 mg, 1.00 mmol, 1.0 eq.) in anhydrous THF (10 mL) was slowly added at 0° C. MeMgr (3 M in Et₂O, 1.0 mL, 3.0 mmol, 3.0 eq.) under a nitrogen atmosphere. The reaction was complete within 1 hour. The reaction mixture was diluted with ether, filtered over a pad of silica, with ether washings, and concentrated to afford the title product as a thick colourless oily 60:40 mixture of rota/diastereomers (474 mg, quant.), which was used in the next step without further purification. ¹H NMR (400 MHz, CDCl₃) δ 7.15 (d, J=2.6 Hz, 0.4H), 7.12 (d, J=2.6 Hz, 0.6H), 7.07 (s, 0.4H), 7.04 (s, 0.6H), 6.96 (d, J=8.1 Hz, 0.4H), 6.90 (d, J=8.5 Hz, 0.6H), 6.86-6.78 (m, 1H), 6.52-6.43 (m, 2H), 4.79 (q, J=6.4 Hz, 0.4H), 4.73 (q, J=6.5 Hz, 0.6H), 1.36 (d, J=6.4 Hz, 1.2H), 1.30 (d, J=6.4 Hz, 1.8H), 1.01 (s, 7.2H), 1.00 (s, 10.8H), 0.25 (s, 4.8H), 0.24 (s, 7.2H).

Step 3: ((6-methyl-6H-benzo[c]chromene-3,8-diyl)bis(oxy))bis(tert-butyldimethylsilane

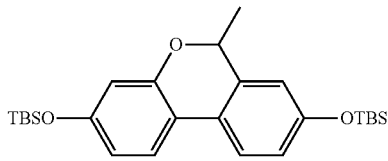 [SMILES: CC1Oc2cc(O[Si](C)(C)C(C)(C)C)ccc2-c2ccc(O[Si](C)(C)C(C)(C)C)cc21]

A solution of 4-methylbenzenesulfonic acid hydrate (19 mg, 0.19 mmol) and 4,4'-bis((tert-butyldimethylsilyl)oxy)-2'-(1-hydroxyethyl)-[1,1'-biphenyl]-2-ol (474 mg, 1.00 mmol) in toluene (10 ml) was heated at 80° C. overnight. TLC (Cyclohexane/dichloromethane 9:1) showed no more starting material. The reaction mixture was concentrated under vacuum and purified by column (SiO₂, CyH/DCM) to afford ((6-methyl-6H-benzo[c]chromene-3,8-diyl)bis(oxy)) bis(tert-butyldimethylsilane) (411 mg, 90%) as a white solid. ¹H NMR (400 MHz, CDCl₃) δ 7.48 (dd, J=8.5, 4.1 Hz, 2H), 6.80 (dd, J=8.4, 2.5 Hz, 1H), 6.61 (dd, J=2.4, 0.8 Hz, 1H), 6.52 (dd, J=8.4, 2.4 Hz, 1H), 6.47 (d, J=2.4 Hz, 1H), 5.17 (q, J=6.5 Hz, 1H), 1.00 (s, 9H), 0.98 (s, 9H) 0.92-0.84 (m, 3H), 0.21 (s, 6H), 0.20 (s, 6H).

Step 4: 6-methyl-6H-benzo[c]chromene-3,8-diol

Acetylchloride (0.100 ml, 1.40 mmol) was added to a solution of ((6H-benzo[c]chromene-3,8-diyl)bis(oxy))bis (tert-butyldimethylsilane) (411 mg, 0.900 mmol) in methanol (10 ml) at room temperature and stirred overnight. The reaction mixture was concentrated under vacuum and purified by MPLC (SiO₂, EtOAc in Hex 0-100%) to afford the 6-methyl-6H-benzo[c]chromene-3,8-diol (202 mg, 98%) as a white solid. ¹H NMR (400 MHz, DMSO) δ 9.47 (s, 1H), 9.45 (s, 1H), 7.49 (t, J=8.7 Hz, 2H), 6.73 (dd, J=8.4, 2.5 Hz, 1H), 6.60 (d, J=2.4 Hz, 1H), 6.43 (dd, J=8.4, 2.4 Hz, 1H), 6.30 (d, J=2.4 Hz, 1H), 5.14 (q, J=6.5 Hz, 1H), 1.44 (d, J=6.5 Hz, 3H).

Synthesis of 6,6-dimethyl-6H-benzo[c]chromene-3,8-diol (25)

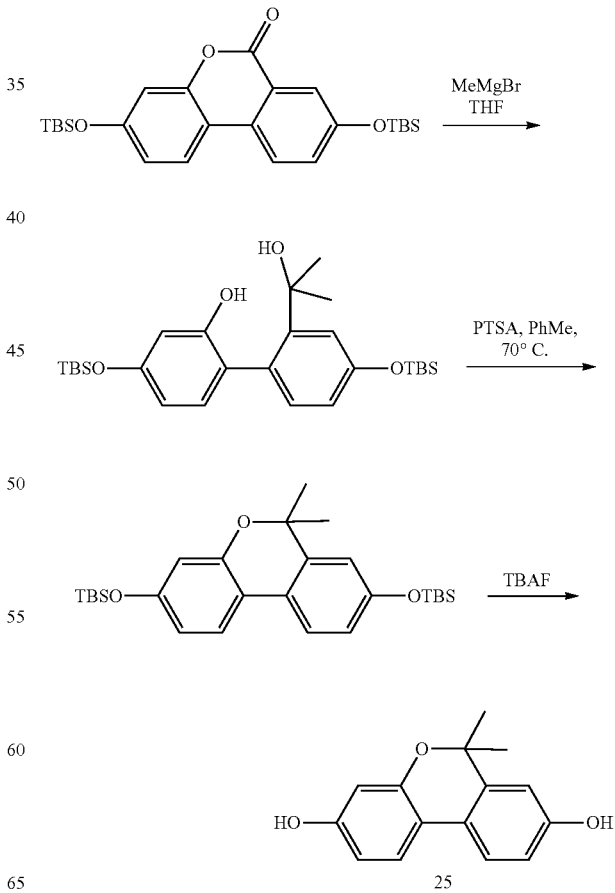

Step 1: Synthesis of 4,4'-bis((tert-butyldimethylsilyl)oxy)-T-(2-hydroxypropan-2-yl)-[1,1'-biphenyl]-2-ol

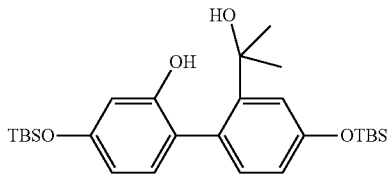 [SMILES: CC(C)(O)c1cc(O[Si](C)(C)C(C)(C)C)ccc1-c1ccc(O[Si](C)(C)C(C)(C)C)cc1O]

To a solution of 3,8-bis((tert-butyldimethylsilyl)oxy)-6H-benzo[c]chromen-6-one (456 mg, 1.00 mmol, 1.0 eq.) in anhydrous THF (10 mL) was slowly added at 0° C. MeMgBr (3 M in Et₂O, 1.00 mL, 3.00 mmol, 3.0 eq.) under a nitrogen atmosphere. The reaction was complete within 1 hour. The reaction mixture was diluted with ether, filtered over a pad of silica, with ether washings, and concentrated to afford the synthesis of 4,4'-bis((tert-butyldimethylsilyl)oxy)-T-(2-hydroxypropan-2-yl)-[1,1'-biphenyl]-2-ol as a thick colourless oil (489 mg, quant.), which was used in the next step without further purification. $^1$H NMR (400 MHz, CDCl$_3$) δ 7.13 (d, J=2.5 Hz, 1H), 6.96 (d, J=1.0 Hz, 1H), 6.94 (d, J=1.1 Hz, 1H), 6.76 (dd, J=8.2, 2.6 Hz, 1H), 6.49 (d, J=2.4 Hz, 1H), 6.45 (dd, J=8.2, 2.4 Hz, 1H), 1.52 (s, 3H), 1.40 (s, 3H), 1.01 (s, 9H), 1.00 (s, 9H), 0.25 (s, 6H), 0.23 (s, 6H).

Step 2: Synthesis of ((6,6-dimethyl-6H-benzo[c]chromene-3,8-diyl)bis(oxy))bis(tert-butyldimethylsilane)

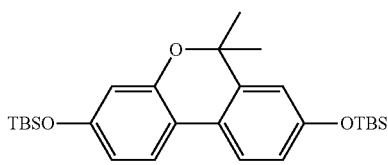 [SMILES: CC1(C)Oc2cc(O[Si](C)(C)C(C)(C)C)ccc2-c2ccc(O[Si](C)(C)C(C)(C)C)cc21]

A solution of 4-methylbenzenesulfonic acid hydrate (19 mg, 0.19 mmol) and 4,4'-bis((tert-butyldimethylsilyl)oxy)-T-(1-hydroxyethyl)-[1,1'-biphenyl]-2-ol (489 mg, 1.00 mmol) in toluene (10 ml) was heated at 80° C. overnight. TLC (Cyclohexane/dichloromethane 9:1) showed no more starting material. The reaction mixture was concentrated under vacuum and purified by MPLC (SiO₂, CyH/DCM) to afford ((6-methyl-6H-benzo[c]chromene-3,8-diyl)bis(oxy))bis(tert-butyldimethylsilane) (446 mg, 95%) as a white solid. $^1$H NMR (400 MHz, CDCl$_3$) δ 7.49 (dd, J=8.5, 3.4 Hz, 2H), 6.79 (dd, J=8.4, 2.4 Hz, 1H), 6.69 (d, J=2.4 Hz, 1H), 6.50 (dd, J=8.4, 2.4 Hz, 1H), 6.45 (d, J=2.4 Hz, 1H), 1.58 (s, 6H), 1.00 (s, 9H), 0.99 (s, 9H), 0.22 (s, 6H), 0.21 (s, 6H).

Step 3: Synthesis 6,6-dimethyl-6H-benzo[c]chromene-3,8-diol

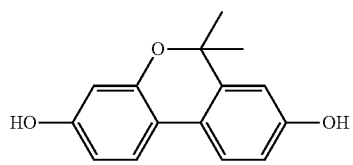 [SMILES: CC1(C)Oc2cc(O)ccc2-c2ccc(O)cc21]

Acetyl chloride (0.100 ml, 1.40 mmol) was added to a solution of 4,4'-bis((tert-butyldimethylsilyl)oxy)-T-(2-hydroxypropan-2-yl)-[1,1'-biphenyl]-2-ol (446 mg, 0.900 mmol) in methanol (10 ml) at room temperature and the solution was stirred overnight. The reaction mixture was concentrated under vacuum and the residue purified by MPLC (SiO₂, EtOAc in Hex 0-100%) to afford the 6,6-dimethyl-6H-benzo[c]chromene-3,8-diol (228 mg, 98%) as a white solid. MS (ESI+): m/z=243. $^1$H NMR (400 MHz, DMSO) δ 9.44 (s, 1H), 9.42 (s, 1H), 7.49 (dd, J=8.5, 4.2 Hz, 2H), 6.72 (dd, J=8.4, 2.5 Hz, 1H), 6.67 (d, J=2.4 Hz, 1H), 6.40 (dd, J=8.4, 2.4 Hz, 1H), 6.26 (d, J=2.4 Hz, 1H), 1.49 (s, 6H).

E) Ester "A" Group Analogues with Pyridine Ring

Synthesis of 3,8-dihydroxy-6H-isochromeno[4,3-b]pyridin-6-one (27)

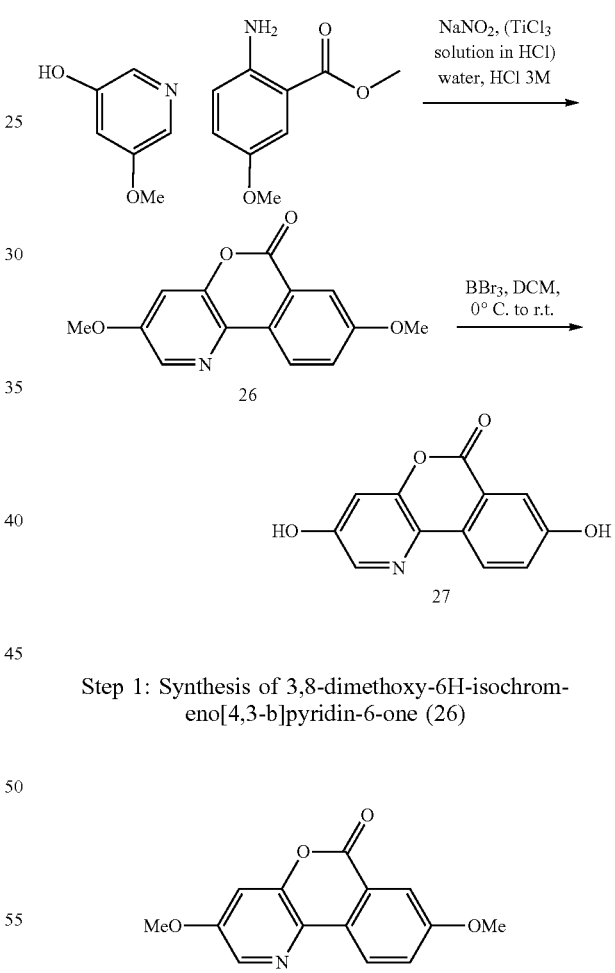

Step 1: Synthesis of 3,8-dimethoxy-6H-isochromeno[4,3-b]pyridin-6-one (26)

Sodium nitrite (130 mg, 1.88 mmol) was added to a solution of methyl 2-amino-5-methoxybenzoate (341 mg, 1.88 mmol) in water (1 ml) and HCl (3N, 1 ml) at 0° C. The reaction mixture was stirred 15 min at 0° C., and this solution was added dropwise to a solution of 5-methoxypyridin-3-ol (1.18 g, 9.42 mmol) in water (1 ml) and HCl (3N, 1 ml) and TiCl₃ (0.25 ml, 1.88 mmol) at 0° C., and stirring continued o.n. at rt. A saturated solution of Na₂CO₃ was added. After extraction with EtOAc 3 times the combined organic phases were dried over sodium sulfate and concentrated under vacuum. The crude product was purified by MPLC (SiO$_2$, EtOAc/cyclohexane 0% to 30%) to afford 3,8-dimethoxy-6H-isochromeno[4,3-b]pyridin-6-one (85 mg, 18%) as a white solid. R$_f$=0.25 (EtOAc/hexane 20%). $^1$H NMR (400 MHz, CDCl$_3$) δ 8.47 (d, J=8.8 Hz, 1H), 8.33 (d, J=2.6 Hz, 1H), 7.74 (d, J=2.7 Hz, 1H), 7.45 (dd, J=8.8, 2.7 Hz, 1H), 7.14 (d, J=2.6 Hz, 1H), 3.95 (s, 3H), 3.93 (s, 3H).

Step 2: Synthesis of 3,8-dihydroxy-6H-isochromeno [4,3-b]pyridin-6-one (27)

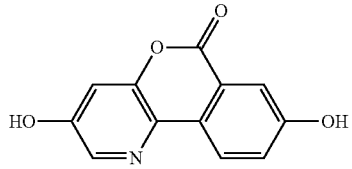 [SMILES: O=c1oc2cc(O)cnc2c2ccc(O)cc12]

27 was prepared according to GP2 starting from 3,8-dimethoxy-6H-isochromeno[4,3-b]pyridin-6-one 26 (120 mg, 0.460 mmol) to afford after purification by MPLC (SiO$_2$, EtOAc/cyclohexane 5% to 90%) 3,8-dihydroxy-6H-isochromeno[4,3-b]pyridin-6-one (20 mg, 19%) as a white solid. R$_f$=0.1 (EtOAc/hexane 80%). $^1$H NMR (400 MHz, DMSO) δ 10.60 (s, 1H), 10.39 (s, 1H), 8.30 (d, J=8.7 Hz, 1H), 8.19 (d, J=2.4 Hz, 1H), 7.50 (d, J=2.6 Hz, 1H), 7.38 (dd, J=8.7, 2.6 Hz, 1H), 7.15 (d, J=2.4 Hz, 1H).

Synthesis of 3,8-dihydroxy-5H-chromeno[4,3-b] pyridin-5-one (28)

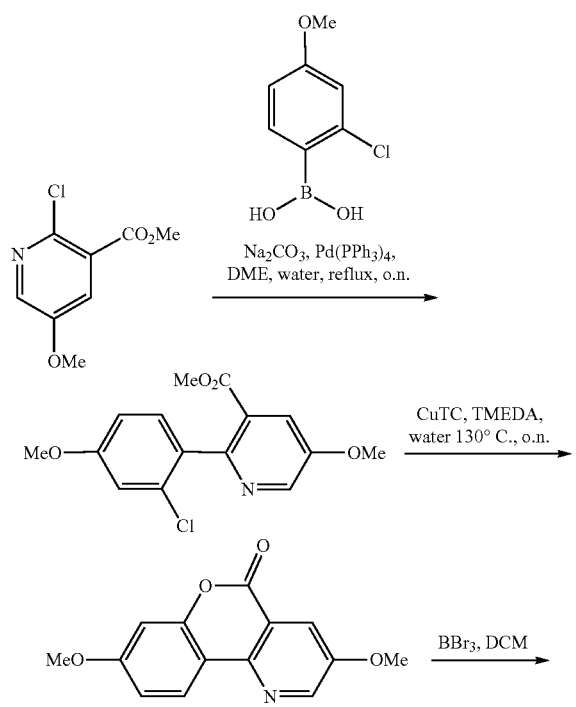

Step 1: Synthesis of methyl 2-(2-chloro-4-methoxyphenyl)-5-methoxynicotinate

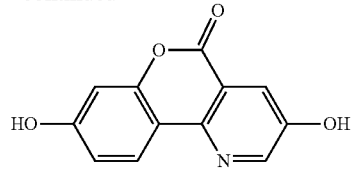

Water (1 ml) was added to a mixture of (2-hydroxy-4-methoxyphenyl)boronic acid (144 mg, 0.774 mmol), methyl 2-chloro-5-methoxynicotinate (120 mg, 0.595 mmol), cesium carbonate (170 mg, 1.61 mmol) and palladium tetrakis(triphenylphosphine)palladium (35 mg, 0.029 mmol) in DME (5 ml) and the mixture was refluxed for 3 h. TLC showed complete conversion of the starting material. A saturated solution of NH$_4$Cl was added and the aqueous phase was extracted with EtOAc 3 times. The combined organic phases were dried over sodium sulfate and concentrated under vacuum. The crude product was purified by MPLC (SiO$_2$, EtOAc/hexane 0% to 60%) to afford methyl 2-(2-chloro-4-methoxyphenyl)-5-methoxynicotinate (160 mg, 87%) as a colorless oil. R$_f$=0.3 (EtOAc/hexane 50%). $^1$H NMR (400 MHz, CDCl$_3$) δ 8.49 (d, J=3.0 Hz, 1H), 7.77 (d, J=3.0 Hz, 1H), 7.33 (d, J=8.5 Hz, 1H), 6.96 (d, J=2.5 Hz, 1H), 6.90 (dd, J=8.5, 2.5 Hz, 1H), 3.95 (s, 3H), 3.84 (s, 3H), 3.74 (s, 3H).

Step 2: Synthesis of 3,8-dimethoxy-5H-chromeno [4,3-b]pyridin-5-one

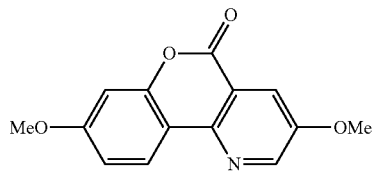 [SMILES: COc1ccc2c(c1)oc(=O)c1cc(OC)cnc12]

In a microwave vessel, to a mixture of methyl 2-(2-chloro-4-methoxyphenyl)-5-methoxynicotinate (900 mg, 2.92 mmol, 1.0 eq.), Copper(I) thiophene-2-carboxylate (278 mg, 1.46 mmol, 0.5 eq.), Cs$_2$CO$_3$ (476 mg, 1.46 mmol, 0.5 eq.) in deionized water (10 mL) was added TMEDA (339 mg, 2.92 mmol, 1.0 eq.) via micro-syringe. The mixture was allowed to stir at room temperature for 15 min and then refluxed at 130° C. overnight. The reaction mixture was cooled down to r.t. and extracted with EtOAc and with a saturated solution of NH$_4$Cl. The organic phases were dried over sodium sulfate and concentrated under vacuum. The crude product was purified by MPLC (SiO$_2$, EtOAc/cyclohexane 0% to 30%) to afford 3,8-dimethoxy-5H-chromeno[4,3-b]pyridin-5-one (120 mg, 16%) as a white solid. $R_f$=0.4 (EtOAc/hexane 80%). $^1$H NMR (400 MHz, CDCl$_3$) δ 8.69 (d, J=3.1 Hz, 1H), 8.37 (d, J=8.8 Hz, 1H), 7.93 (d, J=3.1 Hz, 1H), 6.96 (dd, J=8.8, 2.5 Hz, 1H), 6.87 (d, J=2.4 Hz, 1H), 3.96 (s, 3H), 3.89 (s, 3H).

Step 3: Synthesis of 3,8-dihydroxy-5H-chromeno[4,3-b]pyridin-5-one

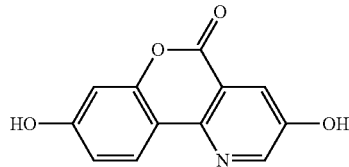

28 was prepared according to GP2 starting from 3,8-dimethoxy-5H-chromeno[4,3-b]pyridin-5-one (120 mg, 0.460 mmol) to afford after purification by MPLC (SiO$_2$, MeOH/DCM 0% to 10%) 3,8-dihydroxy-5H-chromeno[4,3-b]pyridin-5-one (26 mg, 56%) as a white solid. $R_f$=0.1 (EtOAc/hexane 80%). $^1$H NMR (400 MHz, DMSO) δ 10.55 (s, 1H), 10.50 (s, 1H), 8.62 (d, J=2.9 Hz, 1H), 8.19 (dd, J=8.6, 1.5 Hz, 1H), 7.74 (d, J=2.9 Hz, 1H), 6.86 (dd, J=8.7, 2.3 Hz, 1H), 6.76 (d, J=2.3 Hz, 1H).

F) Ester "A" Ring Analogues with Ether Substitution Prepared by Mitsunobu Reaction The Mitsunobu targets were achieved starting from two common intermediates (CI1 and CI2) which are described below.

Synthesis of CI1

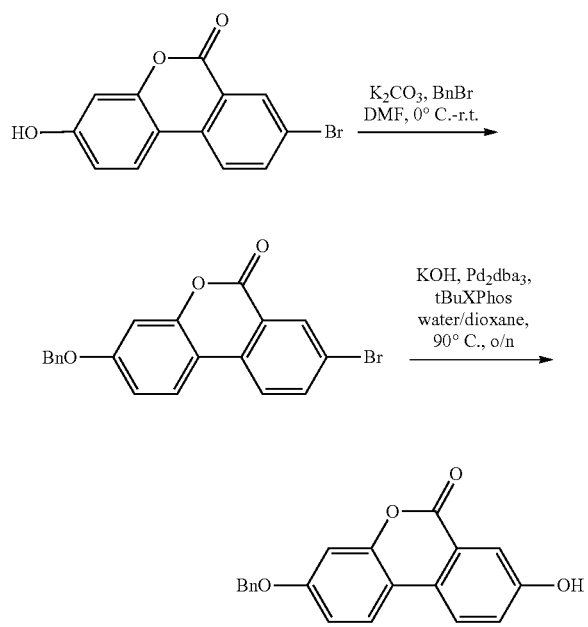

Step 1: Synthesis of 3-(benzyloxy)-8-bromo-6H-benzo[c]chromen-6-one

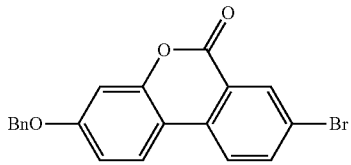

To a suspension of 3 (synthesis vide supra) (500 mg, 1.72 mmol, 1.0 eq.) in DMF (5 mL) was added in one portion K$_2$CO$_3$ (522 mg, 3.78 mmol, 2.2 eq.). Following the suspension was cooled to 0° C. in an ice-bath and stirred for 5 min. Benzyl bromide (323 mg, 1.89 mmol, 1.2 eq.) was added dropwise over a period of 1 min and upon complete addition the reaction mixture was stirred at 0° C. for 10 min before being allowed to warm up to room temperature overnight. After the complete consumption of starting material (as indicated by TLC) the reaction mixture was quenched with half-saturated aqueous sodium bicarbonate solution. The precipitate was filtered over a Buchner funnel, washed with hexanes and dried to obtain 3-(benzyloxy)-8-bromo-6H-benzo[c]chromen-6-one (400 mg, 61%) as a light brown solid. $^1$H NMR (400 MHz, CDCl$_3$) δ 10.27 (s, 1H), 8.18 (d, J=8.8 Hz, 1H), 8.14 (d, J=8.9 Hz, 1H), 7.53 (d, J=2.7 Hz, 1H), 7.51-7.47 (m, 2H), 7.44-7.39 (m, 2H), 7.37-7.32 (m, 1H), 7.07 (d, J=2.5 Hz, 1H), 7.04 (dd, J=8.7, 2.5 Hz, 1H), 5.21 (s, 2H).

Step 2: Synthesis of 3-(benzyloxy)-8-hydroxy-6H-benzo[c]chromen-6-one CI1

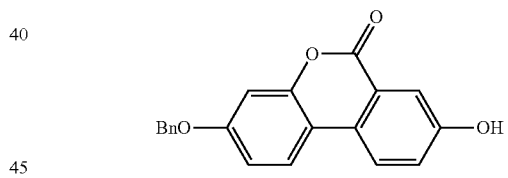

3-(benzyloxy)-8-bromo-6H-benzo[c]chromen-6-one (700 mg, 1.84 mmol, 1.0 eq.) was suspended in 1,4-dioxane (7 mL) in a 20 mL Biotage MW vial. To this suspension was added Pd$_2$dba$_3$ (43 mg, 0.18 mmol, 0.1 eq.) followed by tBuXPhos (175 mg, 0.370 mmol, 0.2 eq.). Subsequently the MW vial was sealed and degassed with nitrogen for 10 min. Then, a solution of KOH (412 mg, 7.34 mmol, 4.4 eq.) in H$_2$O (3 mL) was added slowly to the reaction mixture, which was then stirred in a pre-heated oil bath at 90° C. for 3 h. Upon complete consumption of starting material (as indicated by TLC) the reaction mixture was cooled to 0° C. and the pH was adjusted to 1 with 6 M aqueous HCl. The mixture was extracted with ethyl acetate (3×10 mL) and the combined organic phases were dried over anhydrous Na$_2$SO$_4$ and concentrated under vacuum. The crude material was purified by MPLC (SiO$_2$, 40 g, EtOAc in Hexanes 0-30%) to afford 3-(benzyloxy)-8-hydroxy-6H-benzo[c]chromen-6-one (390 mg, 67%) as a light yellow solid. $^1$H NMR (400 MHz, DMSO) δ 10.27 (s, 1H), 8.18 (d, J=8.8 Hz, 1H), 8.14 (d, J=8.9 Hz, 1H), 7.53 (d, J=2.7 Hz, 1H), 7.51-7.47 (m, 2H), 7.44-7.39 (m, 2H), 7.37-7.32 (m, 2H), 7.07 (d, J=2.5 Hz, 1H), 7.04 (dd, J=8.7, 2.5 Hz, 1H), 5.21 (s, 2H).

Synthesis of Cl2

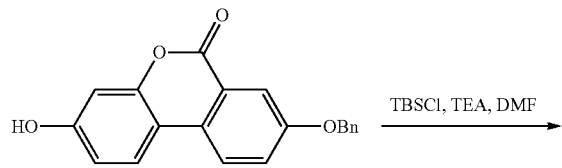

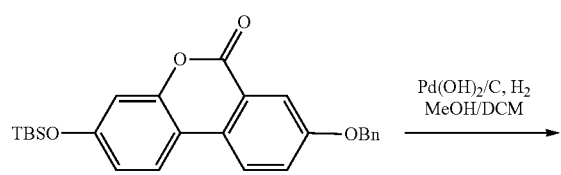

Step 1: Synthesis of 8-(benzyloxy)-3-((tert-butyldimethylsilyl)oxy)-6H-benzo[c]chromen-6-one 8-(benzyloxy)-3-hydroxy-6H-benzo[c]chromen-6-one (1.46 g, 4.59 mmol) was dissolved in dry THF 12 ml. Triethylamine (1.92 ml, 13.8 mmol) was added dropwise at room temperature and stirred for 15 minutes then tert-butylchlorodimethylsilane (832 mg, 5.51 mmol) was added and stirring continued for 3 hours at room temperature. TLC showed no more starting material. The reaction mixture was extracted with EtOAc and HCl (1 M) twice. The organic phases were washed successively with water and brine then dried over sodium sulfate to afford 8-(benzyloxy)-3-((tert-butyldimethylsilyl)oxy)-6H-benzo[c]chromen-6-one (1.83 g, 92%) as a brownish solid. $^1$H NMR (400 MHz, CDCl$_3$) δ 7.94 (d, J=8.9 Hz, 1H), 7.88 (d, J=2.8 Hz, 1H), 7.86-7.81 (m, 1H), 7.50-7.34 (m, 6H), 6.86-6.80 (m, 2H), 5.18 (s, 2H), 1.00 (s, 9H), 0.25 (s, 6H).

Step 2: Synthesis of 3-((tert-butyldimethylsilyl)oxy)-8-hydroxy-6H-benzo[c]chromen-6-one C$_2$

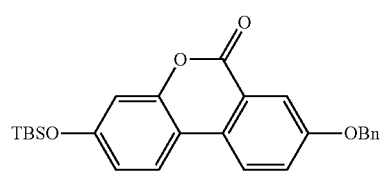 [SMILES: CC(C)(C)[Si](C)(C)Oc1ccc2c(c1)oc(=O)c1cc(OCc3ccccc3)ccc12]

8-(benzyloxy)-3-((tert-butyldimethylsilyl)oxy)-6H-benzo[c]chromen-6-one (1.83 g, 4.23 mmol, 1.0 eq) was dissolved in Methanol (20 ml) and dichloromethane (10 ml), Pd(OH)$_2$/C (368 mg, 0.5 mmol, 0.12 eq) was added and the reaction mixture was hydrogenated under atmospheric pressure o.n. The mixture was filtered over a pad of celite and the solvent evaporated under vacuum to afford 3-((tert-butyldimethylsilyl)oxy)-8-hydroxy-6H-benzo[c]chromen-6-one (1.3 g, 3.8 mmol, 90%) as a beige solid. $^1$H NMR (400 MHz, CDCl$_3$) δ 7.95 (d, J=8.8 Hz, 1H), 7.91 (d, J=2.7 Hz, 1H), 7.89-7.83 (m, 1H), 7.39 (dd, J=8.7, 2.8 Hz, 1H), 6.92-6.83 (m, 2H), 6.21 (s, 1H), 1.03 (s, 9H), 0.28 (s, 6H).

Synthesis of 3-hydroxy-8-(oxetan-3-ylmethoxy)-6H-benzo[c]chromen-6-one (29)

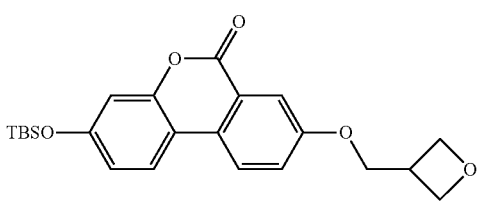 [SMILES: CC(C)(C)[Si](C)(C)Oc1ccc2c(c1)oc(=O)c1cc(OCC3COC3)ccc12]

Step 1: Synthesis of 3-((tert-butyldimethylsilyl)oxy)-8-(oxetan-3-ylmethoxy)-6H-benzo[c]chromen-6-one In a sealed tube, DIAD (0.187 ml, 0.960 mmol) was added to a solution of a solution of 3-((tert-butyldimethylsilyl)oxy)-8-hydroxy-6H-benzo[c]chromen-6-one (150 mg, 0.430 mmol) and oxetan-3-ylmethanol (58 mg, 0.65 mmol) in THF (2 ml) at 0° C. and stirring continued overnight at room temperature. TLC indicated complete conversion of the starting material. The reaction mixture was loaded on silica gel and purified by MPLC (SiO$_2$, EtOAc/cyclohexane 0% to 30%) to afford 280 mg of a mixture of 3-((tert-butyldimethylsilyl)oxy)-8-(oxetan-3-ylmethoxy)-6H-benzo[c]chromen-6-one and reduced DIAD. R$_f$=0.3 (EtOAc/hexane 20/80). After purification there was a significant amount of reduced DIAD present in the NMR therefore it is not further described since it was used crude in the next step.

Step 2: Synthesis of 3-hydroxy-8-(oxetan-3-yl-methoxy)-6H-benzo[c]chromen-6-one

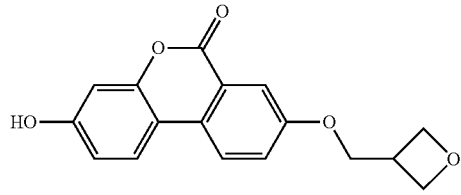 [SMILES: O=c1oc2cc(O)ccc2c2ccc(OCC3COC3)cc12]

KHF$_2$ (108 mg, 1.38 mmol) was added in one portion at r.t. to a solution of 3-((tert-butyldimethylsilyl)oxy)-8-(oxetan-3-ylmethoxy)-6H-benzo[c]chromen-6-one (285 mg, 0.690 mmol) (crude mixture of PPh$_3$O and reduced DIAD) in MeOH (5 ml) and was stirred for 4 h. The formed white precipitate was filtered and dried under vacuum to afford 3-hydroxy-8-(oxetan-3-ylmethoxy)-6H-benzo[c]chromen-6-one (65 mg, 32%) as a white solid. $^1$H NMR (400 MHz, DMSO) δ 10.27 (s, 1H), 8.26-8.06 (m, 2H), 7.64-7.52 (m, 1H), 7.52-7.27 (m, 1H), 7.08-6.96 (m, 1H), 6.85-6.71 (m, 1H), 4.73 (ddd, J=7.6, 6.0, 1.4 Hz, 2H), 4.46 (dt, J=11.9, 6.1 Hz, 2H), 4.33 (dd, J=18.2, 6.7 Hz, 2H), 3.43 (tt, J=6.8, 6.8 Hz, 1H).

Synthesis of 3-hydroxy-8-(2-(4-methylpiperazin-1-yl)ethoxy)-6H-benzo[c]chromen-6-one (30)

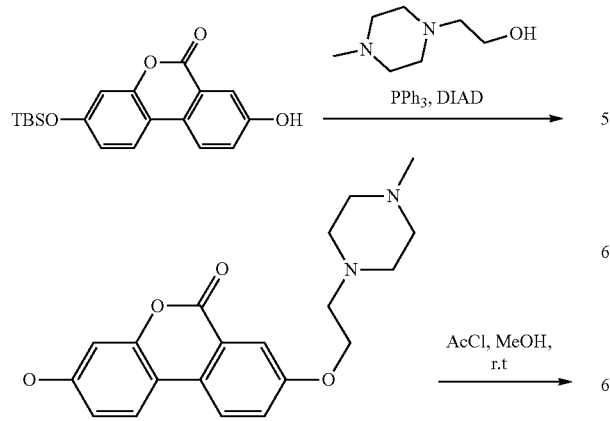

Step 1: Synthesis of 3-((tert-butyldimethylsilyl)oxy)-8-(2-(4-methylpiperazin-1-yl)ethoxy)-6H-benzo[c]chromen-6-one

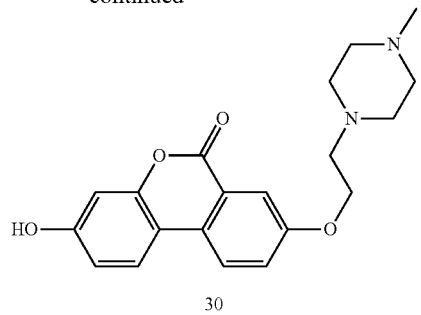

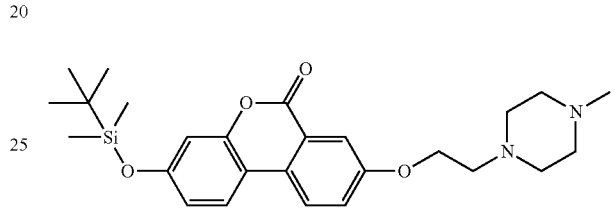

3-((tert-butyldimethylsilyl)oxy)-8-(2-(4-methylpiperazin-1-yl)ethoxy)-6H-benzo[c]chromen-6-one was prepared from 3-((tert-butyldimethylsilyl)oxy)-8-hydroxy-6H-benzo[c]chromen-6-one (80 mg, 0.23 mmol) and 2-(4-Methyl-piperazin-1-yl)-ethanol (34 mg, 0.23 mmol) (according to the synthesis of 29) to afford after MPLC purification (SiO$_2$, MeOH/DCM 0% to 20%) 3-((tert-butyldimethylsilyl)oxy)-8-(2-(4-methylpiperazin-1-yl)ethoxy)-6H-benzo[c]chromen-6-one (60 mg, 55%) as yellowish oil. The NMR still showed significant amounts of reduced DIAD, but the impure/crude material was carried forward to the next step. R$_f$=0.4 (20% MeOH/DCM).

Step 2: Synthesis of 3-hydroxy-8-(2-(4-methylpiperazin-1-yl)ethoxy)-6H-benzo[c]chromen-6-one

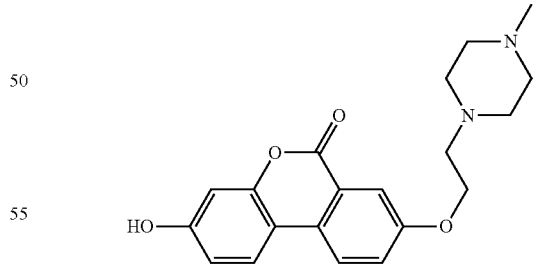

Acetyl chloride (0.046 ml, 0.64 mmol, 5.0 eq) was added to a solution of 3-((tert-butyldimethylsilyl)oxy)-8-(2-(4-methylpiperazin-1-yl)ethoxy)-6H-benzo[c]chromen-6-one (60 mg, 0.13 mmol, 1.0 eq) in MeOH (2 ml) at r.t. and the reaction mixture was stirred overnight. Methanol was evaporated under vacuum, the crude product was diluted with EtOAc and washed with a saturated solution of sodium carbonate. The aqueous layer was extracted with EtOAc, and the combined organic phases were dried over sodium sulfate. The crude product was purified by MPLC (SiO₂, MeOH/DCM 0% to 30%) to afford 3-hydroxy-8-(2-(4-methylpiperazin-1-yl)ethoxy)-6H-benzo[c]chromen-6-one (17 mg, 0.048 mmol, 37%). ¹H NMR (400 MHz, DMSO) δ 10.23 (br, 1H), 8.25-8.06 (m, 2H), 7.53 (d, J=2.7 Hz, 1H), 7.50 (dd, J=8.8, 2.9 Hz, 1H), 7.02-6.94 (m, 1H), 6.86-6.71 (m, 1H), 4.18 (dt, J=18.4, 5.7 Hz, 3H), 2.76-2.65 (m, 6H), 2.34-2.32 (m, 3H), 2.14 (s, 3H).

Synthesis of (S)-3-hydroxy-8-((tetrahydrofuran-3-yl)oxy)-6H-benzo[c]chromen-6-one (31)

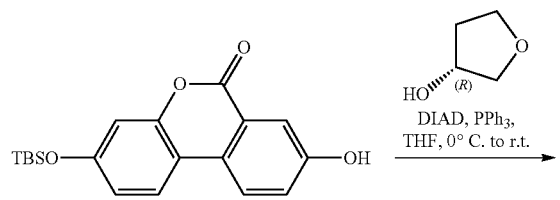

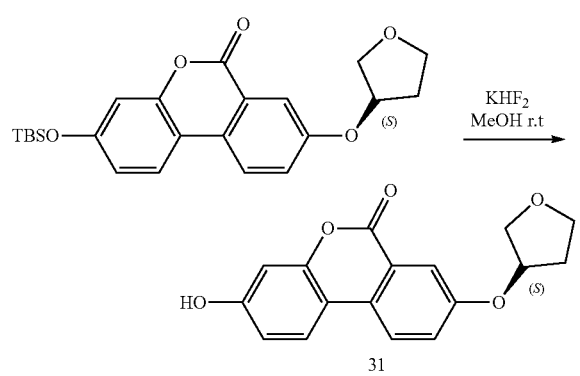

Step 1: Synthesis of (S)-3-((tert-butyldimethylsilyl)oxy)-8-((tetrahydrofuran-3-yl)oxy)-6H-benzo[c]chromen-6-one

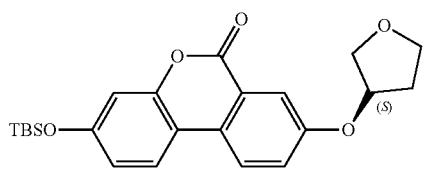

(S)-3-((tert-butyldimethylsilyl)oxy)-8-((tetrahydrofuran-3-yl)oxy)-6H-benzo[c]chromen-6-one was prepared (according to synthesis of 29) starting from C2 (80 mg, 0.23 mmol) and (R)-tetrahydrofuran-3-ol (31 mg, 0.35 mmol) to afford (S)-3-((tert-butyldimethylsilyl)oxy)-8-((tetrahydrofuran-3-yl)oxy)-6H-benzo[c]chromen-6-one (45 mg, 47%) as yellowish oil. R_f=0.6 (EtOAc/hexane 1/1). ¹H NMR (400 MHz, CDCl₃) δ 8.00-7.80 (m, 2H), 7.74 (dd, J=23.0, 2.7 Hz, 1H), 7.33 (ddd, J=26.5, 8.8, 2.7 Hz, 1H), 6.90-6.80 (m, 2H), 5.09-4.95 (m, 1H), 4.13-3.88 (m, 4H), 2.43-2.07 (m, 2H), 1.02 (s, J=3.8 Hz, 9H), 0.27 (s, 3H), 0.25 (s, 3H).

Step 2: Synthesis of (S)-3-hydroxy-8-((tetrahydrofuran-3-yl)oxy)-6H-benzo[c]chromen-6-one

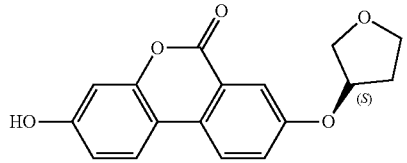

31 was prepared according to synthesis of 29 starting from (S)-3-((tert-butyldimethylsilyl)oxy)-8-((tetrahydrofuran-3-yl)oxy)-6H-benzo[c]chromen-6-one (40 mg, 0.097 mmol) and KHF₂ (27 mg, 0.34 mmol) to give (S)-3-hydroxy-8-((tetrahydrofuran-3-yl)oxy)-6H-benzo[c]chromen-6-one (22 mg, 76%) as a white solid. ¹H NMR (400 MHz, CDCl₃) δ 7.92-7.76 (m, 2H), 7.69 (s, 1H), 7.29 (ddd, J=11.3, 8.8, 2.8 Hz, 1H), 6.88-6.70 (m, 2H), 5.41-5.35 (m, 1H), 4.01-3.82 (m, 4H), 2.36-2.04 (m, 2H).

Synthesis of 3-hydroxy-8-(2-(2-methoxyethoxy)ethoxy)-6H-benzo[c]chromen-6-one (32)

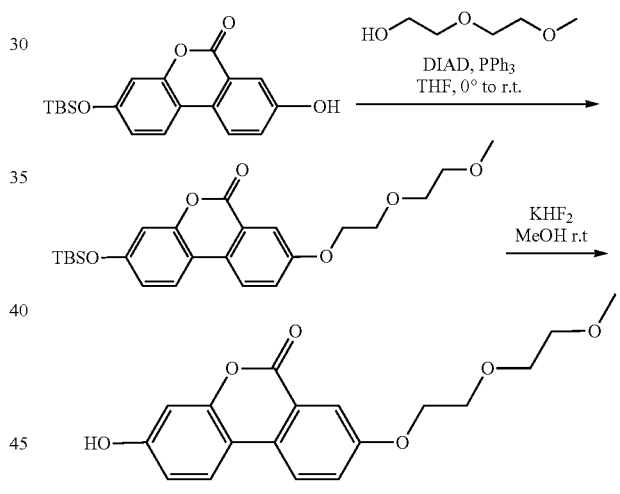

Step 1: Synthesis of 3-((tert-butyldimethylsilyl)oxy)-8-(2-(2-methoxyethoxy)ethoxy)-6H-benzo[c]chromen-6-one

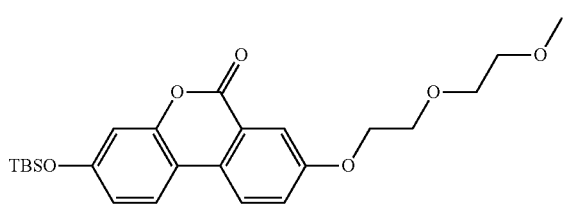 [SMILES: COCCOCCOc1ccc2c(c1)c(=O)oc1cc(O[Si](C)(C)C(C)(C)C)ccc12]

3-((tert-butyldimethylsilyl)oxy)-8-(2-(2-methoxyethoxy)ethoxy)-6H-benzo[c]chromen-6-one was prepared (according to synthesis of 29) starting from $C_2$ (100 mg, 0.29 mmol) and 2-(2-methoxyethoxy)ethan-1-ol (42 mg, 0.35 mmol) to afford 3-((tert-butyldimethylsilyl)oxy)-8-(2-(2-methoxyethoxy)ethoxy)-6H-benzo[c]chromen-6-one (125 mg, 47%), which is contaminated with reduced DIAD as yellowish oil. $R_f$=0.5 (EtOAc/hexane 1/1). $^1$H NMR (400 MHz, CDCl$_3$) δ 7.91-7.66 (m, 3H), 7.32-7.24 (m, 1H), 6.88-6.74 (m, 2H), 4.22-4.11 (m, 2H), 3.87-3.81 (m, 2H), 3.74-3.63 (m, 2H), 3.59-3.49 (m, 2H), 3.33 (s, 3H), 0.95-0.93 (m, 9H), 0.20 (s, 3H).

Step 2: Synthesis of 3-hydroxy-8-(2-(2-methoxyethoxy)ethoxy)-6H-benzo[c]chromen-6-one

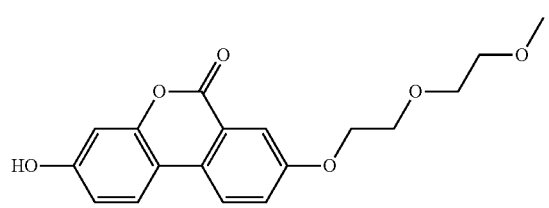 [SMILES: COCCOCCOc1ccc2c(c1)c(=O)oc1cc(O)ccc12]

32 was prepared according to synthesis of 29 starting from (100 mg, 0.220 mmol) and KHF$_2$ (70 mg, 0.90 mmol) to afford after purification by MPLC (SiO$_2$, EtAOc/hexane from 0% to 30%) 3-hydroxy-8-(2-(2-methoxyethoxy)ethoxy)-6H-benzo[c]chromen-6-one (24 mg, 32%) as a white solid as mixture of two compounds. $^1$H NMR (400 MHz, CDCl$_3$) δ 7.75-7.56 (m, 2H), 7.34 (dd, J=42.4, 2.8 Hz, 1H), 7.21-6.48 (m, 3H), 4.05 (dt, J=14.8, 4.4 Hz, 2H), 3.92-3.85 (m, 2H), 3.80 (dt, J=6.1, 2.5 Hz, 2H), 3.70 (ddd, J=4.4, 3.5, 1.5 Hz, 2H), 3.46 (d, J=1.4 Hz, 3H).

Synthesis of 3-hydroxy-8-((tetrahydro-2H-pyran-4-yl)oxy)-6H-benzo[c]chromen-6-one (33)

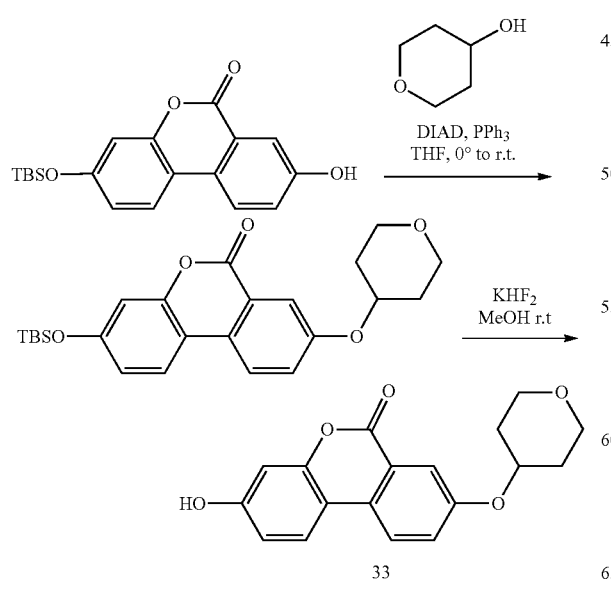

Step 1: Synthesis of 3-((tert-butyldimethylsilyl)oxy)-8-((tetrahydro-2H-pyran-4-yl)oxy)-6H-benzo[c]chromen-6-one

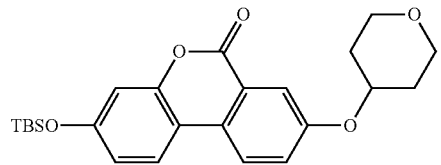 [SMILES: CC(C)(C)[Si](C)(C)Oc1ccc2c(c1)oc(=O)c1cc(OC3CCOCC3)ccc12]

Compound was prepared according to synthesis of 29 starting from $C_2$ (100 mg, 0.29 mmol) and tetrahydro-2H-pyran-4-ol (36 mg, 0.35 mmol) to afford 3-((tert-butyldimethylsilyl)oxy)-8-((tetrahydro-2H-pyran-4-yl)oxy)-6H-benzo[c]chromen-6-one (64 mg, 51%) as yellowish oil. $R_f$=0.67 (EtOAc/hexane 4/6). $^1$H NMR (400 MHz, CDCl$_3$) δ 7.98-7.81 (m, 2H), 7.77 (dd, J=7.3, 2.7 Hz, 1H), 7.42-7.27 (m, 1H), 6.96-6.80 (m, 2H), 4.61 (dtt, J=44.2, 7.8, 3.9 Hz, 1H), 4.01 (ddd, J=10.4, 5.9, 3.9 Hz, 2H), 3.62 (ddt, J=11.9, 7.8, 3.7 Hz, 2H), 2.06 (d, J=12.6 Hz, 2H), 1.83 (dtd, J=12.5, 8.2, 3.9 Hz, 2H), 1.01 (d, J=3.7 Hz, 9H), 0.32-0.20 (m, 6H).

Step 2: Synthesis of 3-hydroxy-8-((tetrahydro-2H-pyran-4-yl)oxy)-6H-benzo[c]chromen-6-one

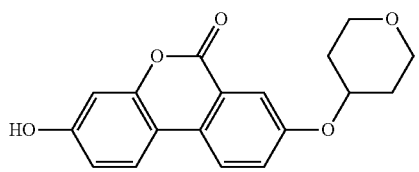 [SMILES: O=c1oc2cc(O)ccc2c2ccc(OC3CCOCC3)cc12]

33 was prepared starting from 3-((tert-butyldimethylsilyl)oxy)-8-((tetrahydro-2H-pyran-4-yl)oxy)-6H-benzo[c]chromen-6-one (60 mg, 0.14 mmol) and KHF$_2$ (38 mg, 0.49 mmol) to afford 3-hydroxy-8-((tetrahydro-2H-pyran-4-yl)oxy)-6H-benzo[c]chromen-6-one (29 mg, 66%) as a white solid. MS (ESI+): m/z=313. $^1$H NMR (400 MHz, DMSO) δ 10.30-10.11 (m, 1H), 8.23-7.98 (m, 2H), 7.66-7.28 (m, 2H), 7.09-6.68 (m, 2H), 4.74 (dtt, J=25.7, 8.6, 4.0 Hz, 1H), 3.86 (dt, J=10.3, 4.2 Hz, 2H), 3.52 (tdd, J=11.6, 8.9, 2.7 Hz, 2H), 2.01 (dd, J=13.2, 3.5 Hz, 2H), 1.62 (dtt, J=14.1, 9.1, 4.6 Hz, 2H).

Synthesis of 3-hydroxy-8-((tetrahydro-2H-pyran-3-yl)oxy)-6H-benzo[c]chromen-6-one (34)

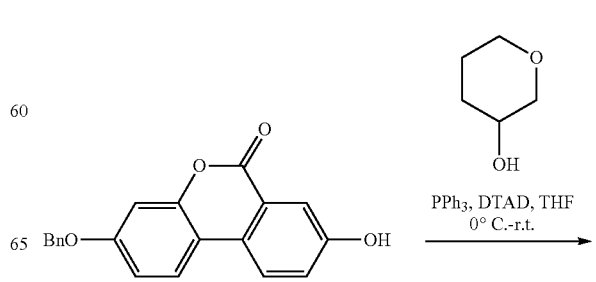

-continued

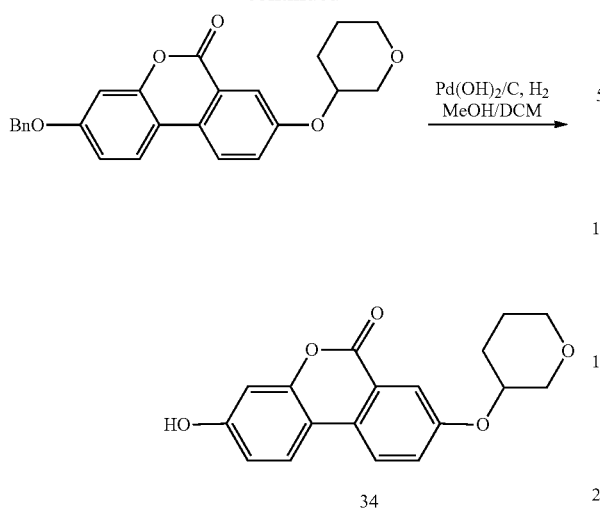

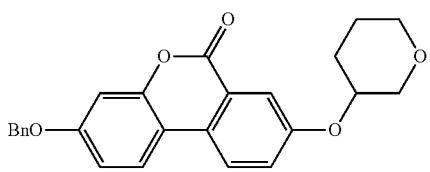 [SMILES: O=c1oc2cc(OCc3ccccc3)ccc2c2ccc(OC3CCCOC3)cc12]

34

Step 1: Synthesis of 3-(benzyloxy)-8-((tetrahydro-2H-pyran-3-yl)oxy)-6H-benzo[c]chromen-6-one 3-(benzyloxy)-8-hydroxy-6H-benzo[c]chromen-6-one (64 mg, 0.20 mmol, 1.0 eq.) was dissolved in THF (0.7 mL) in a 10 mL Biotage MW vial. Subsequently PPh₃ (79 mg, 0.30 mmol, 1.5 eq.) and Tetrahydro-2H-pyran-3-ol (31 mg, 0.30 mmol, 1.5 eq.) were added and the reaction mixture was cooled to 0° C. in an ice-bath in which it was stirred for 5 min. Then a solution of Di-tert-butyl-diazene-1,2-dicarboxylate (69 mg, 0.30 mmol, 1.5 eq.) (DTAD) in THF (0.1 mL) was added dropwise to the reaction mixture. Upon complete addition the reaction mixture turned dark yellow and stirring was continued overnight at r.t. After overnight stirring starting material was still present, therefore PPh₃ (79 mg, 0.30 mmol, 1.5 eq.), Tetrahydro-2H-pyran-3-ol (31 mg, 0.30 mmol, 1.5 eq.) and a solution of Di-tert-butyl-diazene-1,2-dicarboxylate (DTAD) in THF (0.1 mL) were added to reaction mixture to bring the reaction to completion. After an additional 2 h of stirring at room temperature the reaction mixture was concentrated under vacuum and loaded on silica to be purified by MPLC (SiO₂, 12 g, EtOAc in Hex 0-35%) to afford 3-(benzyloxy)-8-((tetrahydro-2H-pyran-3-yl)oxy)-6H-benzo[c]chromen-6-one (50 mg, 62%) as a light yellow solid. ¹H NMR (400 MHz, CDCl₃) δ 7.92 (d, J=8.9 Hz, 1H), 7.86 (d, J=8.9 Hz, 1H), 7.77 (d, J=2.8 Hz, 1H), 7.46-7.31 (m, 5H), 6.97 (dd, J=8.8, 2.6 Hz, 1H), 6.92 (d, J=2.5 Hz, 1H), 5.12 (s, 2H), 4.47 (tt, J=6.8, 3.5 Hz, 1H), 3.95 (ddd, J=11.6, 3.2, 1.2 Hz, 1H), 3.75 (ddd, J=10.6, 6.2, 3.9 Hz, 1H), 3.70-3.60 (m, 2H), 2.12 (tt, J=11.8, 6.0 Hz, 1H), 1.89 (dddt, J=31.0, 17.3, 8.0, 3.9 Hz, 3H), 1.70-1.59 (m, 1H).

Step 2: Synthesis of 3-hydroxy-8-((tetrahydro-2H-pyran-3-yl)oxy)-6H-benzo[c]chromen-6-one 3-(benzyloxy)-8-((tetrahydro-2H-pyran-3-yl)oxy)-6H-benzo[c]chromen-6-one (50 mg, 0.12 mmol, 1.0 eq.) was dissolved in MeOH/DCM (5 mL, 10/1) and Pd(OH)₂/C (20 mg) was added in one portion. Then the reaction mixture was evacuated and backfilled with N₂ three times before putting it under hydrogen atmosphere (balloon). The reaction mixture was stirred for 2 h and upon complete consumption of starting material (as indicated by TLC) filtered over silica and concentrated under vacuum to afford the crude product which was loaded on silica and purified by MPLC (SiO₂, 12 g, EtOAc in Hex 0-50%) to obtain 3-hydroxy-8-((tetrahydro-2H-pyran-3-yl)oxy)-6H-benzo[c]chromen-6-one (33 mg, 0.11 mmol, 89%) as a white solid. ¹H NMR (400 MHz, DMSO) δ 10.21 (s, 1H), 8.20 (d, J=9.0 Hz, 1H), 8.09 (d, J=8.8 Hz, 1H), 7.61 (d, J=2.8 Hz, 1H), 7.53 (dd, J=8.9, 2.8 Hz, 1H), 6.82 (dd, J=8.7, 2.4 Hz, 1H), 6.74 (d, J=2.4 Hz, 1H), 4.57 (dt, J=6.2, 3.2 Hz, 1H), 3.84 (dd, J=11.6, 2.1 Hz, 1H), 3.64 (ddd, J=10.8, 6.5, 3.7 Hz, 1H), 3.56 (dd, J=11.7, 5.6 Hz, 2H), 2.05 (dd, J=8.9, 4.9 Hz, 1H), 1.87-1.68 (m, 2H), 1.63-1.48 (m, 1H).

Synthesis of 3-hydroxy-8-((tetrahydrofuran-3-yl)oxy)-6H-benzo[c]chromen-6-one (35)

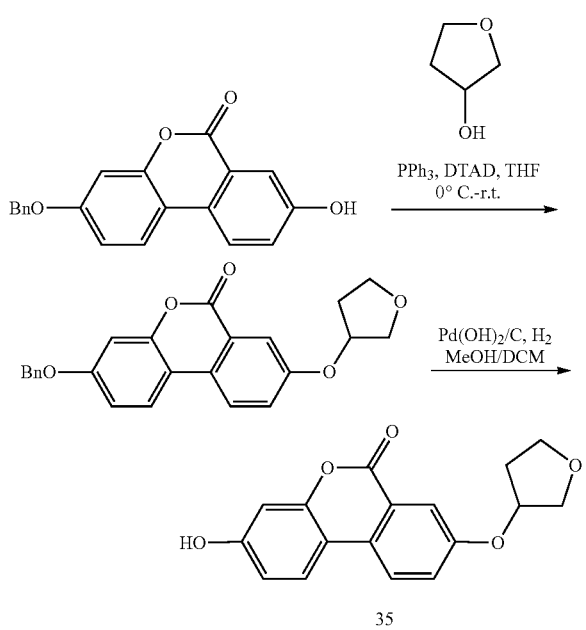

35

Step 1: Synthesis of 3-(benzyloxy)-8-((tetrahydrofuran-3-yl)oxy)-6H-benzo[c]chromen-6-one

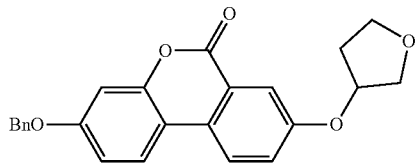 [SMILES: O=c1oc2cc(OCc3ccccc3)ccc2c2ccc(OC3CCOC3)cc12]

3-(benzyloxy)-8-hydroxy-6H-benzo[c]chromen-6-one (100 mg, 0.31 mmol, 1.0 eq.) was dissolved in THF (1.1 mL). Subsequently PPh$_3$ (124 mg, 0.470 mmol, 1.5 eq.) and Tetrahydrofuran-3-ol (42 mg, 0.47 mmol, 1.5 eq.) were added and the reaction mixture was cooled to 0° C. in an ice-bath in which it was stirred for 5 min. Then a solution of Di-tert-butyl-diazene-1,2-dicarboxylate (109 mg, 0.470 mmol, 1.5 eq.) (DTAD) in THF (0.2 mL) was added dropwise to the reaction mixture. Upon complete addition the reaction mixture turned dark yellow and stirring was continued overnight at r.t. After overnight stirring starting material was still present, therefore PPh$_3$ (124 mg, 0.470 mmol, 1.5 eq.), Tetrahydrofuran-3-ol (42 mg, 0.47 mmol, 1.5 eq.) and a solution of Di-tert-butyl-diazene-1,2-dicarboxylate (109 mg, 0.470 mmol, 1.5 eq.) (DTAD) in THF (0.2 mL) were added to reaction mixture to bring the reaction to completion. After an additional 2 h of stirring at room temperature the reaction mixture was concentrated under vacuum and loaded on silica to be purified by MPLC (SiO$_2$, 12 g, EtOAc in Hex 0-35%) to afford 3-(benzyloxy)-8-((tetrahydrofuran-3-yl)oxy)-6H-benzo[c]chromen-6-one (100 mg, 82%) as a light yellow solid. The NMR after purification still showed a significant amount of reduced DTAD but the reaction was taken to the next step crude, therefore the NMR is not reported here.

Step 2: Synthesis of 3-hydroxy-8-((tetrahydrofuran-3-yl)oxy)-6H-benzo[c]chromen-6-one

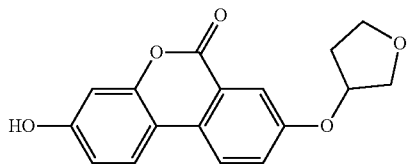 [SMILES: O=c1oc2cc(O)ccc2c2ccc(OC3CCOC3)cc12]

3-(benzyloxy)-8-((tetrahydrofuran-3-yl)oxy)-6H-benzo[c]chromen-6-one (100 mg, 0.260 mmol, 1.0 eq.) was dissolved in MeOH/DCM (7 mL, 10/1) and Pd(OH)$_2$/C (60 mg) was added in one portion. Then the reaction mixture was evacuated and backfilled with N$_2$ three times before putting it under hydrogen atmosphere with the use of a balloon. The reaction mixture was stirred for 2 h and upon complete consumption of starting material (as indicated by TLC) filtered over silica and concentrated under reduced pressure to give the crude product which was loaded on silica and purified by flash column chromatography (SiO$_2$, 12 g, EtOAc in Hex 0-50%) to give 3-hydroxy-8-((tetrahydrofuran-3-yl)oxy)-6H-benzo[c]chromen-6-one (65 mg, 72%) as a white solid. $^1$H NMR (400 MHz, DMSO) δ 10.21 (s, 1H), 8.22 (d, J=8.8 Hz, 1H), 8.09 (d, J=8.8 Hz, 1H), 7.57 (d, J=2.7 Hz, 1H), 7.49 (dd, J=8.9, 2.8 Hz, 1H), 6.83 (dd, J=8.7, 2.4 Hz, 1H), 6.75 (d, J=2.4 Hz, 1H), 5.25-5.19 (m, 1H), 3.92 (dd, J=10.2, 4.4 Hz, 1H), 3.88-3.83 (m, 2H), 3.78 (td, J=8.4, 4.6 Hz, 1H), 2.36-2.20 (m, 1H), 2.02 (dd, J=14.2, 7.5 Hz, 1H).

Synthesis of 3-hydroxy-8-(oxetan-3-yloxy)-6H-benzo[c]chromen-6-one (36)

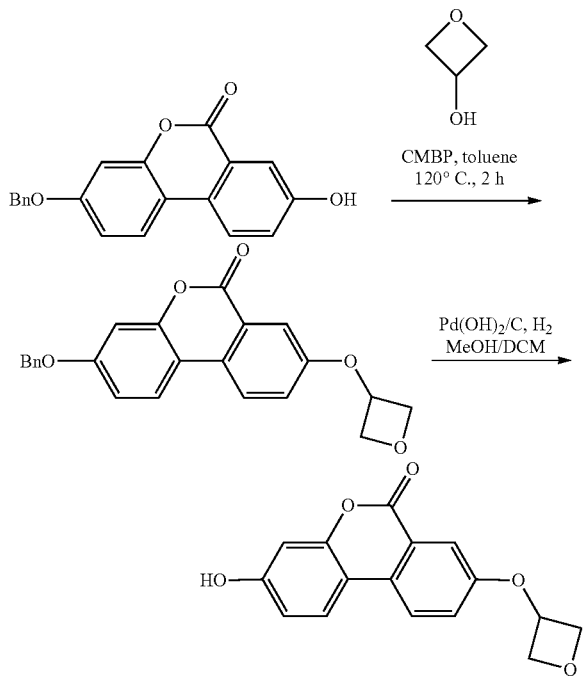

36

Step 1: Synthesis of 3-(benzyloxy)-8-(oxetan-3-yloxy)-6H-benzo[c]chromen-6-one

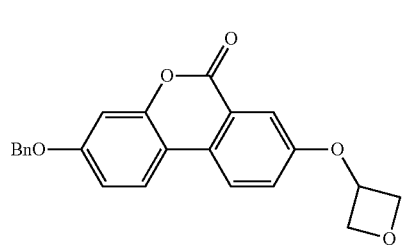 [SMILES: O=c1oc2cc(OCc3ccccc3)ccc2c2ccc(OC3COC3)cc12]

Cyanomehtylenetributylphosphorane (150 mg, 0.630 mmol, 2.5 eq.) was added at r.t. to a solution of 3-(benzyloxy)-8-hydroxy-6H-benzo[c]chromen-6-one (80 mg, 0.25 mmol, 1.0 eq.) and oxetan-3ol (56 mg, 0.75 mmol, 3.0 eq.) in toluene (1.3 mL) in one portion and the reaction mixture was heated to 120° C. for 2 h in a sealed vial. After the full conversion of starting material, the reaction mixture was allowed to cool down to r.t., concentrated and loaded on silica to be purified by MPLC (SiO$_2$, 12 g, EtOAc in Hex 0-30%) to afford 3-(benzyloxy)-8-(oxetan-3-yloxy)-6H-benzo[c]chromen-6-one (74 mg, 79%) as a light yellow foam. $^1$H NMR (400 MHz, CDCl$^3$) δ 7.96 (d, J=8.8 Hz, 1H), 7.88 (d, J=8.9 Hz, 1H), 7.48-7.34 (m, 7H), 6.99 (dd, J=8.8, 2.6 Hz, 1H), 6.94 (d, J=2.5 Hz, 1H), 5.39-5.29 (m, 1H), 5.14 (s, 2H), 5.07 (ddd, J=7.1, 6.0, 0.9 Hz, 2H), 4.79 (ddd, J=7.4, 5.0, 1.0 Hz, 2H).

Step 2: Synthesis of 3-hydroxy-8-(oxetan-3-yloxy)-6H-benzo[c]chromen-6-one

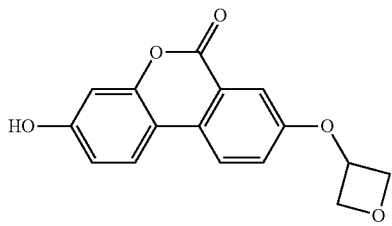 [SMILES: O=c1oc2cc(O)ccc2c2ccc(OC3COC3)cc12]

3-(benzyloxy)-8-(oxetan-3-yloxy)-6H-benzo[c]chromen-6-one (70 mg, 0.19 mmol, 1.0 eq.) was dissolved in MeOH/DCM (5 mL, 10/1) and Pd(OH)$_2$/C (15 mg) was added in one portion. Then the reaction mixture was evacuated and backfilled with N$_2$ three times before putting it under hydrogen atmosphere with the use of a balloon. The reaction mixture was stirred for 4 h and upon complete consumption of starting material (as indicated by TLC) filtered over silica and concentrated under reduced pressure to give the crude product which was loaded on silica and purified by flash column chromatography (SiO$_2$, 12 g, EtOAc in Hex 0-50%) to afford 3-hydroxy-8-(oxetan-3-yloxy)-6H-benzo[c]chromen-6-one (25 mg, 0.09 mmol, 47%) as a white solid. $^1$H NMR (400 MHz, DMSO) δ 10.24 (s, 1H), 8.24 (d, J=8.9 Hz, 1H), 8.10 (d, J=8.8 Hz, 1H), 7.45 (dd, J=8.8, 2.8 Hz, 1H), 7.35 (d, J=2.8 Hz, 1H), 6.83 (dd, J=8.7, 2.4 Hz, 1H), 6.75 (d, J=2.4 Hz, 1H), 5.47 (q, J=5.4, 4.8 Hz, 1H), 4.98 (t, J=7.0 Hz, 2H), 4.59 (dd, J=7.7, 5.1 Hz, 2H).

Synthesis of 8-((2-oxaspiro[3.3]heptan-6-yl)oxy)-3-hydroxy-6H-benzo[c]chromen-6-one (37)

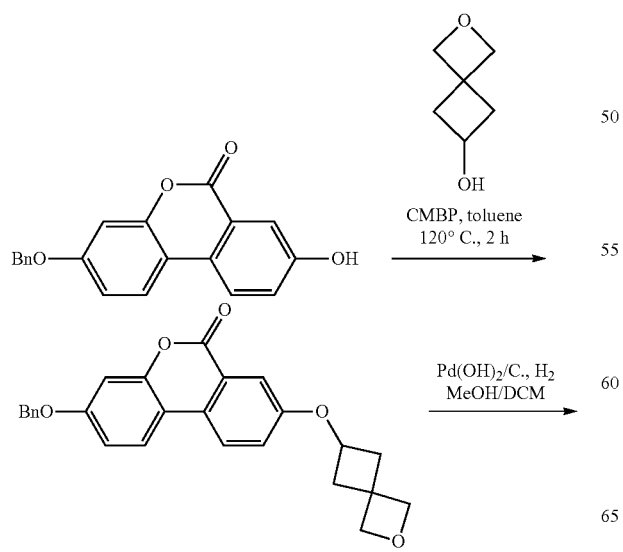

Step 1: Synthesis of 8-((2-oxaspiro[3.3]heptan-6-yl)oxy)-3-(benzyloxy)-6H-benzo[c]chromen-6-one

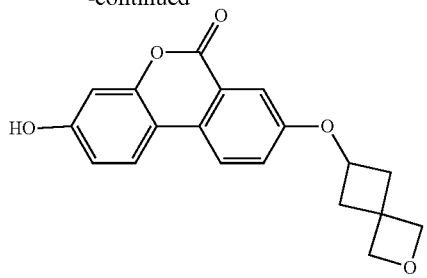

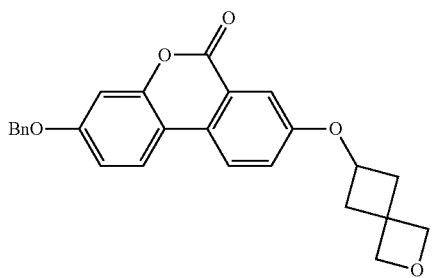 [SMILES: O=c1oc2cc(OCc3ccccc3)ccc2c2ccc(OC3CC4(COC4)C3)cc12]

37

Cyanomehtylenetributylphosphorane (95 mg, 0.39 mmol, 2.5 eq.) was added at r.t. to a solution of 3-(benzyloxy)-8-hydroxy-6H-benzo[c]chromen-6-one (50 mg, 0.16 mmol, 1.0 eq.) and 2-oxaspiro[3.3]heptan-6-ol (39 mg, 0.35 mmol, 2.2 eq.) in toluene (3.0 mL) in one portion and the reaction mixture was heated to 120° C. for 2 h in a sealed vial. After the full conversion of starting material, the reaction mixture was allowed to cool down to r.t., concentrated and loaded on silica to be purified by flash column chromatography (SiO$_2$, 12 g, EtOAc in Hex 0-30%) to afford 8-((2-oxaspiro[3.3]heptan-6-yl)oxy)-3-(benzyloxy)-6H-benzo[c]chromen-6-one (40 mg, 0.10 mmol, 61%) as a light yellow solid. $^1$H NMR (400 MHz, DMSO) δ 8.26 (d, J=8.9 Hz, 1H), 8.20 (d, J=8.9 Hz, 1H), 7.54-7.32 (m, 7H), 7.09 (d, J=2.5 Hz, 1H), 7.06 (dd, J=8.7, 2.6 Hz, 1H), 5.22 (s, 2H), 4.77 (p, J=6.8 Hz, 1H), 4.66 (s, 2H), 4.55 (s, 2H), 2.88-2.78 (m, 2H), 2.33-2.24 (m, 2H).

Step 2: Synthesis of 8-((2-oxaspiro[3.3]heptan-6-yl)oxy)-3-hydroxy-6H-benzo[c]chromen-6-one

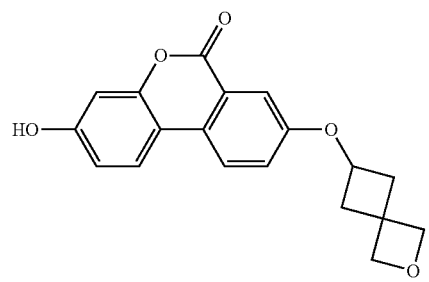 [SMILES: O=c1oc2cc(O)ccc2c2ccc(OC3CC4(COC4)C3)cc12]

8-((2-oxaspiro[3.3]heptan-6-yl)oxy)-3-(benzyloxy)-6H-benzo[c]chromen-6-one (40 mg, 0.10 mmol, 1.0 eq.) was dissolved in MeOH/DCM (5 mL, 10/1) and Pd(OH)$_2$/C (14 mg) was added in one portion. Then the reaction mixture was evacuated and backfilled with N$_2$ three times before putting it under hydrogen atmosphere with the use of a balloon. The reaction mixture was stirred for 4 h and upon complete consumption of starting material (as indicated by TLC) filtered over silica and concentrated under vacuum to afford the crude product which was loaded on silica and purified by flash column chromatography (SiO$_2$, 12 g, EtOAc in Hex 0-50%) to give 8-((2-oxaspiro[3.3]heptan-6-yl)oxy)-3-hydroxy-6H-benzo[c]chromen-6-one (26 mg, 0.08 mmol, 83%) as a white solid. MS (ESI+): m/z=325. $^1$H NMR (400 MHz, DMSO) δ 10.23 (s, 1H), 8.19 (d, J=8.9 Hz, 1H), 8.08 (d, J=8.8 Hz, 1H), 7.46 (d, J=2.8 Hz, 1H), 7.41 (dd, J=8.8, 2.8 Hz, 1H), 6.82 (dd, J=8.7, 2.4 Hz, 1H), 6.74 (d, J=2.4 Hz, 1H), 4.76 (q, J=6.8 Hz, 1H), 4.66 (s, 2H), 4.55 (s, 2H), 2.87-2.76 (m, 2H), 2.32-2.18 (m, 2H).

In a similar fashion, the 9-substituted analogue 38 was prepared according to the scheme below:

Synthesis of 3-hydroxy-9-((tetrahydro-2H-pyran-4-yl)oxy)-6H-benzo[c]chromen-6-one (38)

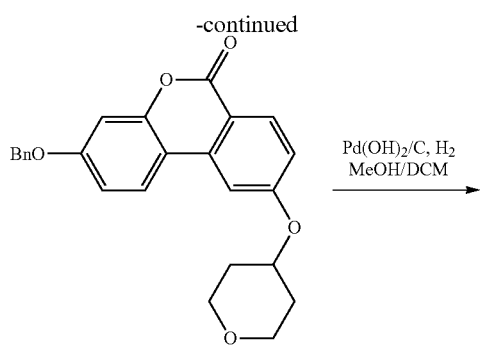

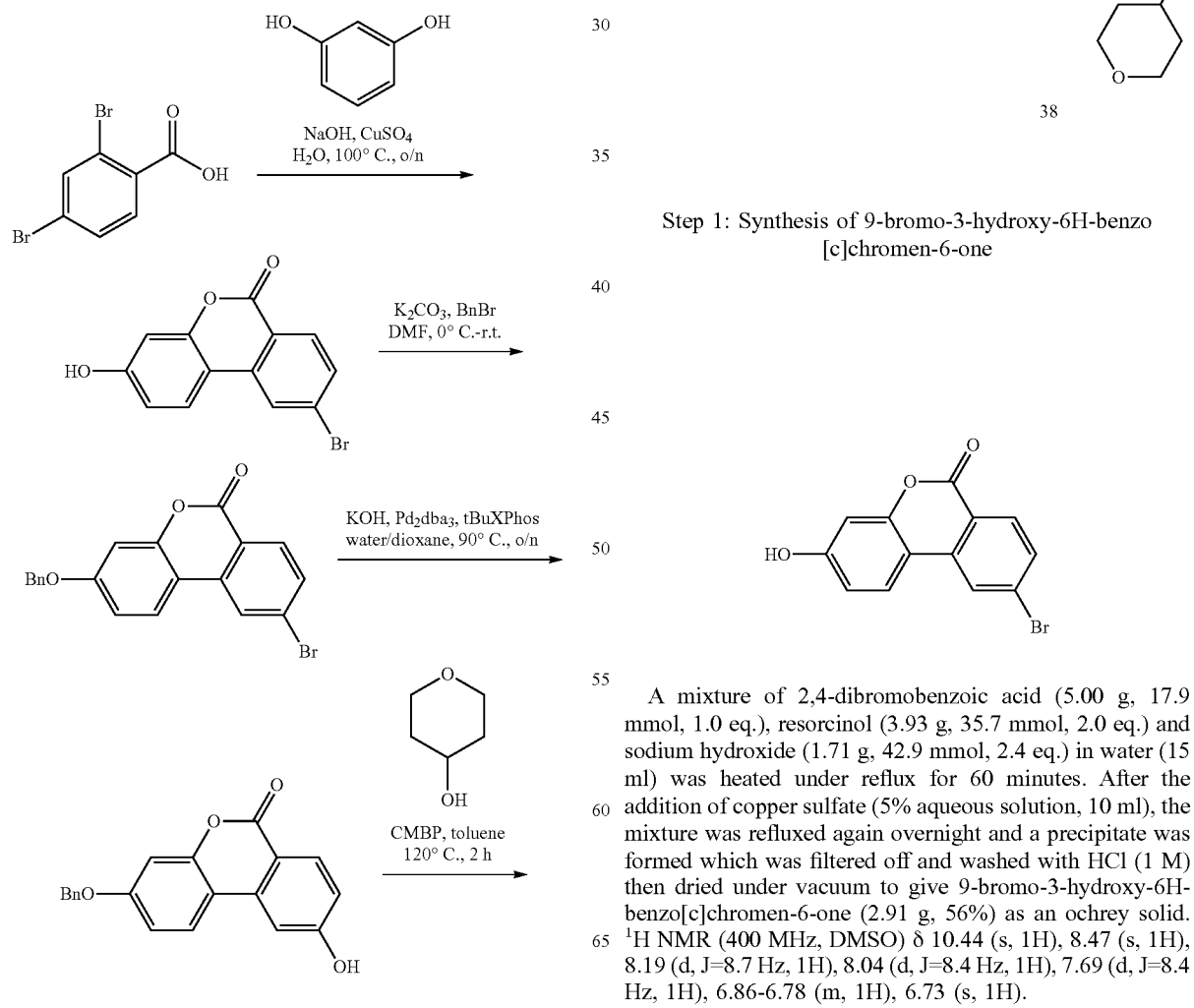

38

Step 1: Synthesis of 9-bromo-3-hydroxy-6H-benzo[c]chromen-6-one

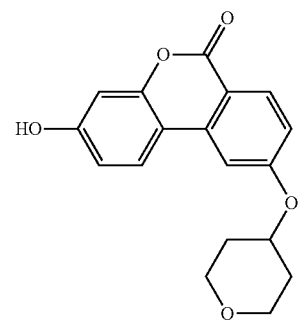

A mixture of 2,4-dibromobenzoic acid (5.00 g, 17.9 mmol, 1.0 eq.), resorcinol (3.93 g, 35.7 mmol, 2.0 eq.) and sodium hydroxide (1.71 g, 42.9 mmol, 2.4 eq.) in water (15 ml) was heated under reflux for 60 minutes. After the addition of copper sulfate (5% aqueous solution, 10 ml), the mixture was refluxed again overnight and a precipitate was formed which was filtered off and washed with HCl (1 M) then dried under vacuum to give 9-bromo-3-hydroxy-6H-benzo[c]chromen-6-one (2.91 g, 56%) as an ochrey solid. $^1$H NMR (400 MHz, DMSO) δ 10.44 (s, 1H), 8.47 (s, 1H), 8.19 (d, J=8.7 Hz, 1H), 8.04 (d, J=8.4 Hz, 1H), 7.69 (d, J=8.4 Hz, 1H), 6.86-6.78 (m, 1H), 6.73 (s, 1H).

Step 2: Synthesis of 3-(benzyloxy)-9-bromo-6H-benzo[c]chromen-6-one

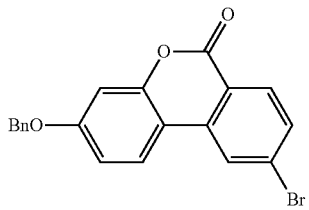 [SMILES: O=c1oc2cc(OCc3ccccc3)ccc2c2cc(Br)ccc12]

To a suspension of 9-bromo-3-hydroxy-6H-benzo[c]chromen-6-one (2.00 mg, 6.87 mmol, 1.0 eq.) in DMF (35 mL) was added in one portion $K_2CO_3$ (2.09 g, 15.1 mmol, 2.2 eq.). The suspension was cooled to 0° C. and stirred for 5 min. Benzyl bromide (1.41 g, 8.24 mmol, 1.2 eq.) was added dropwise over a period of 5 min and upon complete addition the reaction mixture was stirred at 0° C. for 10 min before being allowed to warm up to room temperature over 2 h. After the complete consumption of starting material (as indicated by TLC) the reaction mixture was quenched with half-saturated aqueous sodium bicarbonate solution. The precipitate was filtered over a Buchner funnel, washed with hexanes and dried to afford 3-(benzyloxy)-9-bromo-6H-benzo[c]chromen-6-one (1.49 g, 61%) as a light brown solid. $^1$H NMR (400 MHz, $CDCl_3$) δ 8.20 (d, J=8.7 Hz, 1H), 7.78 (d, J=8.9 Hz, 1H), 7.41-7.28 (m, 6H), 6.91-6.88 (m, 2H), 6.85 (d, J=2.5 Hz, 1H), 5.07 (s, 2H).

Step 3: Synthesis of 3-(benzyloxy)-9-hydroxy-6H-benzo[c]chromen-6-one

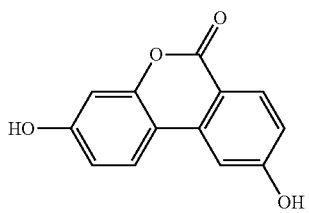 [SMILES: O=c1oc2cc(O)ccc2c2cc(O)ccc12]

3-(benzyloxy)-9-bromo-6H-benzo[c]chromen-6-one (800 mg, 2.10 mmol, 1.0 eq) was suspended in 1,4-dioxane (7 mL) in a 20 mL Biotage MW vial. To this suspension was added $Pd_2dba_3$ (49 mg, 0.21 mmol, 0.1 eq.) followed by tBuXPhos (200 mg, 0.42 mmol, 0.2 eq.). Subsequently the MW vial was sealed and degassed with nitrogen for 10 min. Then, a solution of KOH (471 mg, 8.39 mmol, 4.4 eq.) in $H_2O$ (3 mL) was added slowly to the reaction mixture, and put in a pre-heated oil bath at 90° C. for 3 h. Upon complete consumption of starting material (as indicated by TLC) the reaction mixture was cooled to 0° C. and the pH adjusted to 1 with 6 M aqueous HCl. The mixture was extracted with ethyl acetate (3×10 mL) and the combined organic phases were dried over anhydrous $Na_2SO_4$ and concentrated under vacuum. The crude material was purified by MPLC ($SiO_2$, 40 g, EtOAc in Hexanes 0-30%) to afford 3-(benzyloxy)-9-hydroxy-6H-benzo[c]chromen-6-one (225 mg, 37%) as a light yellow solid. $^1$H NMR (400 MHz, $CDCl_3$) δ 8.20 (d, J=8.7 Hz, 1H), 7.78 (d, J=8.9 Hz, 1H), 7.41-7.28 (m, 6H), 6.91-6.88 (m, 2H), 6.85 (d, J=2.5 Hz, 1H), 5.07 (s, 2H).

Step 4: Synthesis of 3-(benzyloxy)-9-((tetrahydro-2H-pyran-4-yl)oxy)-6H-benzo[c]chromen-6-one

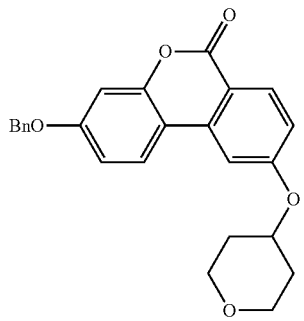 [SMILES: O=c1oc2cc(OCc3ccccc3)ccc2c2cc(OC3CCOCC3)ccc12]

Cyanomehtylenetributylphosphorane (227 mg, 0.940 mmol, 2.5 eq.) was added at r.t. to a solution of 3-(benzyloxy)-9-hydroxy-6H-benzo[c]chromen-6-one (120 mg, 0.380 mmol, 1.0 eq.) and tetrahydro-2H-pyran-4-ol (77 mg, 0.71 mmol, 2.0 eq.) in toluene (3.8 mL) in one portion and the reaction mixture was heated to 120° C. for 2 h in a sealed vial. After the full conversion of starting material, the reaction mixture was allowed to cool down to r.t., concentrated and loaded on silica to be purified by MPLC ($SiO_2$, 12 g, EtOAc in Hex 0-30%) to afford 3-(benzyloxy)-9-((tetrahydro-2H-pyran-4-yl)oxy)-6H-benzo[c]chromen-6-one (135 mg, 89%) as a light yellow foam. $^1$H NMR (400 MHz, $CDCl_3$) δ 8.28 (d, J=8.8 Hz, 1H), 7.86 (d, J=8.9 Hz, 1H), 7.51-7.32 (m, 6H), 7.03 (dd, J=8.9, 2.4 Hz, 1H), 6.97 (dd, J=8.8, 2.6 Hz, 1H), 6.91 (d, J=2.5 Hz, 1H), 5.13 (s, 2H), 4.73 (tt, J=7.7, 3.8 Hz, 1H), 4.02 (ddd, J=11.8, 6.3, 3.8 Hz, 2H), 3.65 (ddd, J=11.5, 8.1, 3.3 Hz, 2H), 2.17-2.05 (m, 2H), 1.94-1.82 (m, 2H).

Step 5: Synthesis of 3-hydroxy-9-((tetrahydro-2H-pyran-4-yl)oxy)-6H-benzo[c]chromen-6-one

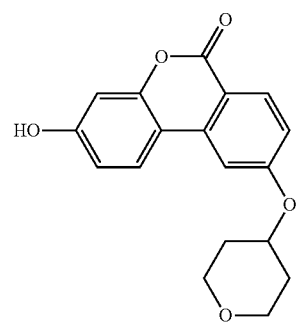 [SMILES: O=c1oc2cc(O)ccc2c2cc(OC3CCOCC3)ccc12]

3-(benzyloxy)-9-((tetrahydro-2H-pyran-4-yl)oxy)-6H-benzo[c]chromen-6-one (135 mg, 0.340 mmol, 1.0 eq.) was dissolved in MeOH/DCM (10 mL, 10/1) and $Pd(OH)_2/C$ (70 mg) was added in one portion. Then the reaction mixture was evacuated and backfilled with $N_2$ three times before putting it under hydrogen atmosphere (balloon). The reaction mixture was stirred for 4 h and upon complete consumption of starting material (as indicated by TLC) filtered over silica and concentrated under vacuum to afford the crude product which was loaded on silica and purified by MPLC ($SiO_2$, 12 g, EtOAc in Hex 0-50%) to afford 3-hydroxy-9-((tetrahydro-2H-pyran-4-yl)oxy)-6H-benzo[c]chromen-6-one (40 mg, 34%) as a white solid. ¹H NMR (400 MHz, DMSO) δ 10.33 (s, 1H), 8.25 (d, J=8.9 Hz, 1H), 8.11 (d, J=8.9 Hz, 1H), 7.72 (d, J=2.4 Hz, 1H), 7.17 (dd, J=8.9, 2.4 Hz, 1H), 6.83 (dd, J=8.7, 2.4 Hz, 1H), 6.73 (d, J=2.4 Hz, 1H), 4.97 (tt, J=8.6, 4.1 Hz, 1H), 3.90 (dt, J=11.7, 4.3 Hz, 2H), 3.56 (ddd, J=11.8, 9.6, 2.7 Hz, 2H), 2.07 (dd, J=11.3, 7.7 Hz, 2H), 1.66 (ddt, J=13.7, 9.1, 4.6 Hz, 2H).

G) Ester "A" Ring Analogues with Alkynyl Substitution Prepared by Sonogashira Reaction Synthesis of 3-hydroxy-8-(3-hydroxyprop-1-yn-1-yl)-6H-benzo[c]chromen-6-one (39)

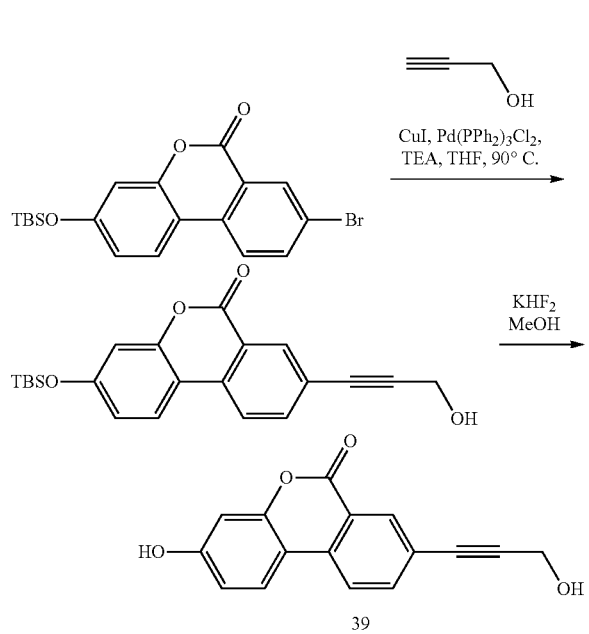

Step 1: Synthesis of 3-((tert-butyldimethylsilyl)oxy)-8-(3-hydroxyprop-1-yn-1-yl)-6H-benzo[c]chromen-6-one

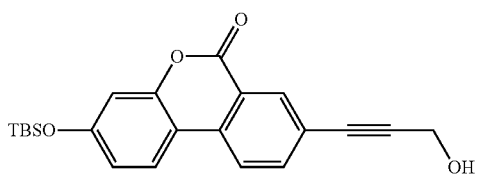

To a solution of S8-bromo-3-((tert-butyldimethylsilyl)oxy)-6H-benzo[c]chromen-6-one (1.45 g, 3.58 mmol, 1.0 eq.) in THF (50 mL) in a 250 mL flask was subsequently added propargyl alcohol (501 mg, 8.94 mmol, 2.5 eq.), Pd(PPh₃)₂Cl₂ (251 mg, 0.360 mmol, 0.1 eq.) and CuI (68 mg, 0.36 mmol, 0.1 eq.) and the reaction was degassed at r.t. with N₂ for 10 min. Triethylamine (724 mg, 7.15 mmol, 2.0 eq.) was added in one portion and the reaction mixture was put into a pre-heated oil-bath at 90° C. Upon full conversion of the starting material (as indicated by TLC) the reaction mixture was allowed to cool to r.t. and quenched with water and extracted with EtOAc (2×100 mL). The combined organic layers were dried over anhydrous Na₂SO₄ and concentrated under vacuum. The crude product was purified by MPLC (SiO₂, 80 g, EtOAc in Hex 0-40%) to afford 3-((tert-butyldimethylsilyl)oxy)-8-(3-hydroxyprop-1-yn-1-yl)-6H-benzo[c]chromen-6-one (490 mg, 36%) as a brownish solid. ¹H NMR (400 MHz, CDCl₃) δ 8.41 (d, J=1.8 Hz, 1H), 7.94 (d, J=8.4 Hz, 1H), 7.88 (d, J=8.5 Hz, 1H), 7.79 (dd, J=8.3, 1.8 Hz, 1H), 6.94-6.80 (m, 2H), 4.54 (d, J=6.1 Hz, 2H), 1.00 (s, 9H), 0.26 (s, 6H).

Step 2: Synthesis of 3-hydroxy-8-(3-hydroxyprop-1-yn-1-yl)-6H-benzo[c]chromen-6-one

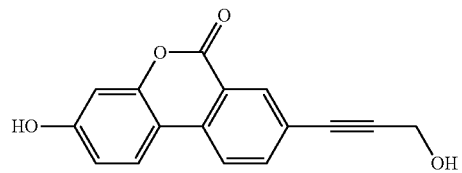

3-((tert-butyldimethylsilyl)oxy)-8-(3-hydroxyprop-1-yn-1-yl)-6H-benzo[c]chromen-6-one (160 mg, 0.420 mmol, 1.0 eq.) was dissolved in MeOH (2 mL) and cooled to r.t. in an ice-bath and the resulting yellow solution was stirred for 10 min. Then KHF₂ (66 mg, 0.82 mmol, 2.0 eq.) was added in on portion and the reaction was stirred at room temperature overnight. Upon complete consumption of the starting material (as indicated by TLC), the reaction mixture was filtered over a glass frit (Por.4) and the filter residue was washed with MeOH and dried under vacuum to afford 3-hydroxy-8-(3-methoxyprop-1-yn-1-yl)-6H-benzo[c]chromen-6-one (112 mg, 0.420 mmol, 99%) as a pale brown solid. ¹H NMR (400 MHz, DMSO) δ 10.45 (s, 1H), 8.26 (d, J=8.4 Hz, 1H), 8.15 (d, J=8.8 Hz, 1H), 8.12 (d, J=1.8 Hz, 1H), 7.87 (dd, J=8.4, 1.9 Hz, 1H), 6.85 (dd, J=8.7, 2.4 Hz, 1H), 6.75 (d, J=2.4 Hz, 1H), 5.41 (s, 1H), 4.35 (s, 2H).

Additionally, the hydrogenation of the above compound was carried out as described below:

Step 3: Synthesis of 3-hydroxy-8-(3-hydroxypropyl)-6H-benzo[c]chromen-6-one (40)

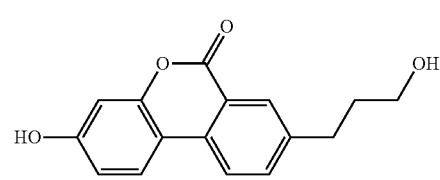

3-hydroxy-8-(3-methoxyprop-1-yn-1-yl)-6H-benzo[c]chromen-6-one (86 mg, 0.32 mmol, 1.0 eq.) and Pd(OH)₂/C (9 mg, 0.07 mmol. 0.2 eq.) in MeOH (5 ml) was hydrogenated under atmospheric pressure overnight. The reaction mixture was filtered over a pad of celite and the solvent was evaporated concentrate under vacuum to afford 3-hydroxy-8-(3-hydroxypropyl)-6H-benzo[c]chromen-6-one (70 mg, 80%) as a white solid. MS (ESI+): m/z=271. ¹H NMR (400 MHz, DMSO) δ 8.13 (d, J=8.3 Hz, 1H), 8.04 (dd, J=8.8, 2.2 Hz, 1H), 7.97 (d, J=1.9 Hz, 1H), 7.70 (dd, J=8.3, 2.0 Hz, 1H), 6.76 (dd, J=8.7, 2.4 Hz, 1H), 6.64 (d, J=2.5 Hz, 1H), 4.52 (s, 1H), 3.43 (t, J=6.4 Hz, 2H), 2.81-2.71 (m, 2H), 1.86-1.73 (m, 2H).

Synthesis of 3-hydroxy-8-(3-methoxyprop-1-yn-1-yl)-6H-benzo[c]chromen-6-one (41)

Step 2: Synthesis of 3-hydroxy-8-(3-methoxyprop-1-yn-1-yl)-6H-benzo[c]chromen-6-one

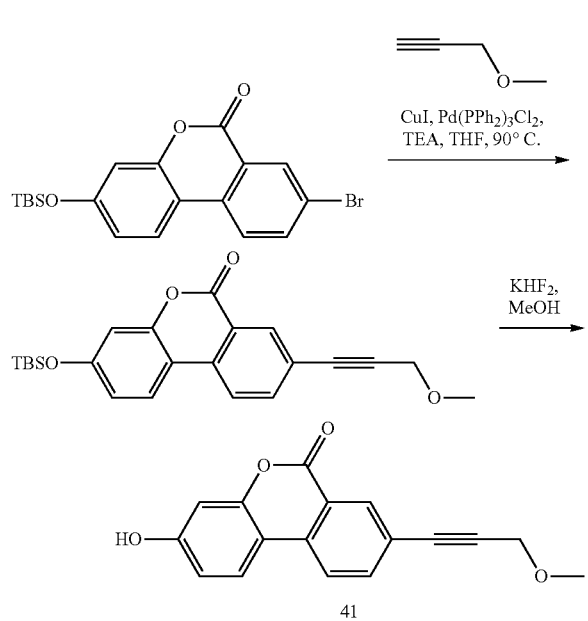

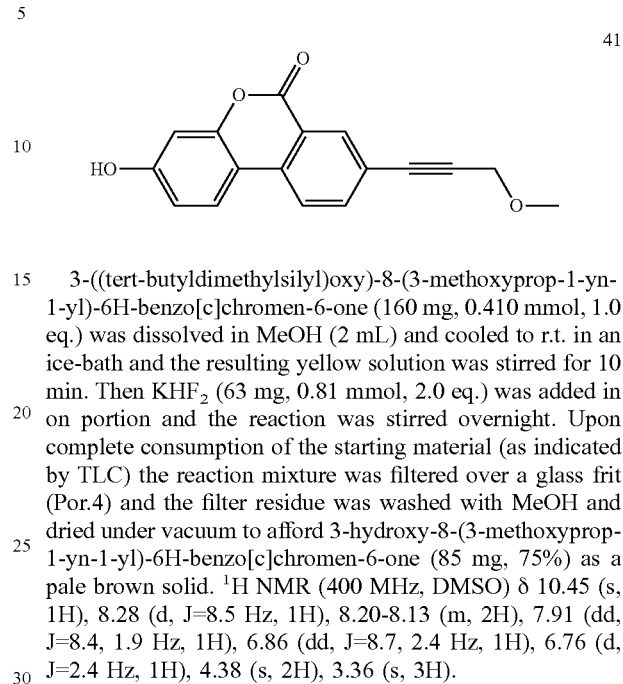

3-((tert-butyldimethylsilyl)oxy)-8-(3-methoxyprop-1-yn-1-yl)-6H-benzo[c]chromen-6-one (160 mg, 0.410 mmol, 1.0 eq.) was dissolved in MeOH (2 mL) and cooled to r.t. in an ice-bath and the resulting yellow solution was stirred for 10 min. Then KHF$_2$ (63 mg, 0.81 mmol, 2.0 eq.) was added in on portion and the reaction was stirred overnight. Upon complete consumption of the starting material (as indicated by TLC) the reaction mixture was filtered over a glass frit (Por.4) and the filter residue was washed with MeOH and dried under vacuum to afford 3-hydroxy-8-(3-methoxyprop-1-yn-1-yl)-6H-benzo[c]chromen-6-one (85 mg, 75%) as a pale brown solid. $^1$H NMR (400 MHz, DMSO) δ 10.45 (s, 1H), 8.28 (d, J=8.5 Hz, 1H), 8.20-8.13 (m, 2H), 7.91 (dd, J=8.4, 1.9 Hz, 1H), 6.86 (dd, J=8.7, 2.4 Hz, 1H), 6.76 (d, J=2.4 Hz, 1H), 4.38 (s, 2H), 3.36 (s, 3H).

Step 1: Synthesis of 3-((tert-butyldimethylsilyl)oxy)-8-(3-methoxyprop-1-yn-1-yl)-6H-benzo[c]chromen-6-one Synthesis of 3-hydroxy-8-(3-hydroxy-3-methylbut-1-yn-1-yl)-6H-benzo[c]chromen-6-one (42)

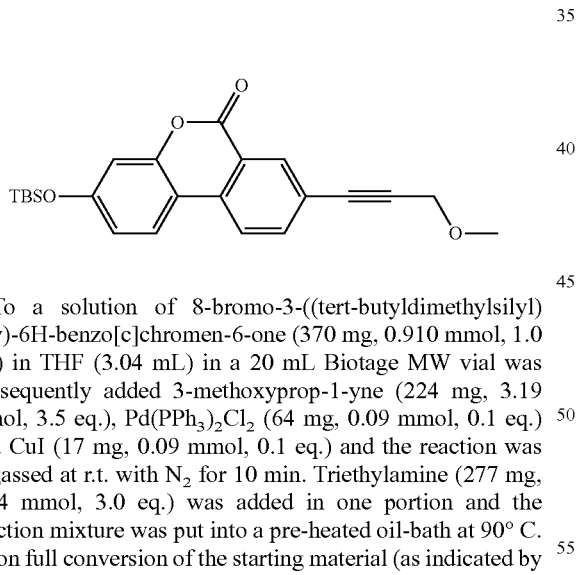

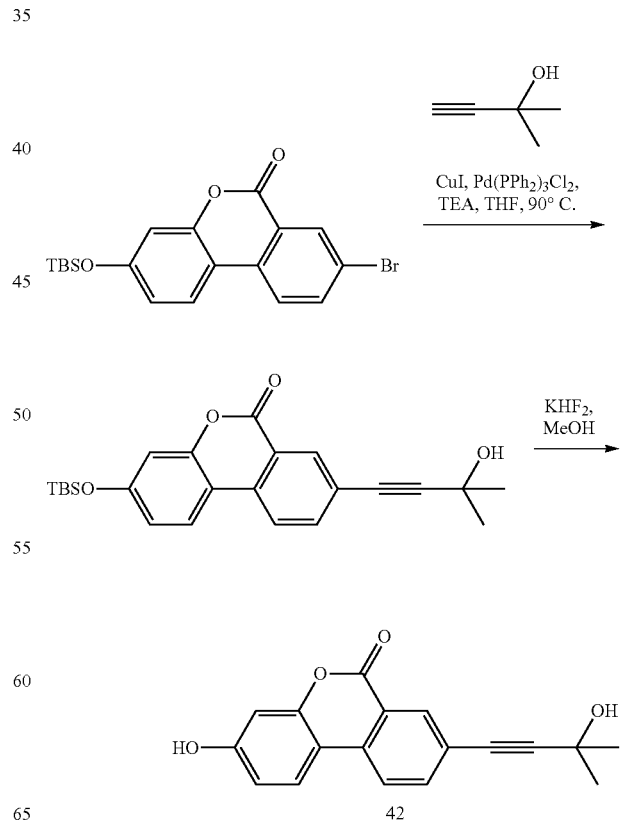

To a solution of 8-bromo-3-((tert-butyldimethylsilyl)oxy)-6H-benzo[c]chromen-6-one (370 mg, 0.910 mmol, 1.0 eq.) in THF (3.04 mL) in a 20 mL Biotage MW vial was subsequently added 3-methoxyprop-1-yne (224 mg, 3.19 mmol, 3.5 eq.), Pd(PPh$_3$)$_2$Cl$_2$ (64 mg, 0.09 mmol, 0.1 eq.) and CuI (17 mg, 0.09 mmol, 0.1 eq.) and the reaction was degassed at r.t. with N$_2$ for 10 min. Triethylamine (277 mg, 2.74 mmol, 3.0 eq.) was added in one portion and the reaction mixture was put into a pre-heated oil-bath at 90° C. Upon full conversion of the starting material (as indicated by TLC) the reaction mixture was allowed to cool to r.t. and quenched with water and extracted with EtOAc (2×25 mL). The combined organic layers were dried over anhydrous Na$_2$SO$_4$ and concentrated under vacuum. The crude product was purified by MPLC (SiO$_2$, 40 g, EtOAc in Hex 0-40%) to afford 3-((tert-butyldimethylsilyl)oxy)-8-(3-methoxyprop-1-yn-1-yl)-6H-benzo[c]chromen-6-one (160 mg 44%) as a brownish solid. $^1$H NMR (400 MHz, CDCl$_3$) δ 8.42 (d, J=1.8 Hz, 1H), 7.94 (d, J=8.4 Hz, 1H), 7.87 (d, J=8.4 Hz, 1H), 7.80 (dd, J=8.4, 1.8 Hz, 1H), 6.86-6.81 (m, 2H), 4.35 (s, 2H), 3.48 (s, 3H), 1.00 (s, 9H), 0.26 (s, 6H).

Step 1: Synthesis of 3-((tert-butyldimethylsilyl)oxy)-8-(3-hydroxy-3-methylbut-1-yn-1-yl)-6H-benzo[c]chromen-6-one

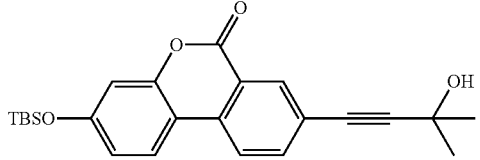 [SMILES: CC(C)(O)C#Cc1ccc2c(c1)c(=O)oc1cc(O[Si](C)(C)C(C)(C)C)ccc12]

To a solution of 8-bromo-3-((tert-butyldimethylsilyl)oxy)-6H-benzo[c]chromen-6-one (370 mg, 0.910 mmol, 1.0 eq.) in THF (3.0 mL) in a 20 mL Biotage MW vial was subsequently added 2-methylbut-3-yn-2-ol (269 mg, 3.19 mmol, 3.5 eq.), Pd(PPh$_3$)$_2$Cl$_2$ (64 mg, 0.090 mmol, 0.1 eq.) and CuI (17 mg, 0.090 mmol, 0.1 eq.) and the reaction was degassed at r.t. with N$_2$ for 10 min. Triethylamine (277 mg, 2.74 mmol, 3.0 eq.) was added in one portion and the reaction mixture was put into a pre-heated oil-bath at 90° C. Upon full conversion of the starting material (as indicated by TLC) the reaction mixture was allowed to cool to r.t. and quenched with water and extracted with EtOAc (2×25 mL). The combined organic layers were dried over anhydrous Na$_2$SO$_4$ and concentrated under vacuum. The crude product was purified by MPLC (SiO$_2$, 40 g, EtOAc in Hex 0-40%) to afford 3-((tert-butyldimethylsilyl)oxy)-8-(3-hydroxy-3-methylbut-1-yn-1-yl)-6H-benzo[c]chromen-6-one (233 mg, 0.570 mmol, 63%) as a yellowish solid. $^1$H NMR (400 MHz, CDCl$_3$) δ 8.41 (d, J=1.8 Hz, 1H), 7.94 (d, J=8.4 Hz, 1H), 7.88 (d, J=8.3 Hz, 1H), 7.78 (dd, J=8.4, 1.9 Hz, 1H), 6.88-6.82 (m, 2H), 1.65 (s, 6H), 1.00 (s, 9H), 0.26 (s, 6H).

Step 2: Synthesis of 3-hydroxy-8-(3-hydroxy-3-methylbut-1-yn-1-yl)-6H-benzo[c]chromen-6-one

42

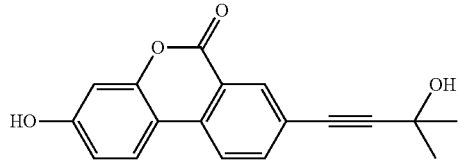

3-((tert-butyldimethylsilyl)oxy)-8-(3-hydroxy-3-methylbut-1-yn-1-yl)-6H-benzo[c]chromen-6-one (233 mg, 0.570 mmol, 1.0 eq.) was dissolved in MeOH (3 mL) and cooled to r.t. in an ice-bath and the resulting yellow solution was stirred for 10 min. Then KHF$_2$ (89 mg, 1.1 mmol, 2.0 eq.) was added in portion and the reaction was stirred overnight. Upon complete consumption of the starting material (as indicated by TLC) the reaction mixture was filtered over a glass frit (Por.4) and the filter residue was washed with MeOH and dried under vacuum to afford 3-hydroxy-8-(3-hydroxy-3-methylbut-1-yn-1-yl)-6H-benzo[c]chromen-6-one (120 mg, 0.410 mmol, 72%) as a pale brown solid. $^1$H NMR (400 MHz, DMSO) δ 10.44 (s, 1H), 8.25 (d, J=8.5 Hz, 1H), 8.16 (d, J=8.9 Hz, 1H), 8.10 (d, J=1.8 Hz, 1H), 7.83 (dd, J=8.4, 1.9 Hz, 1H), 6.86 (dd, J=8.8, 2.4 Hz, 1H), 6.76 (d, J=2.4 Hz, 1H), 5.54 (s, 1H), 3.32 (s, 6H).

Synthesis of 3-hydroxy-8-((1-hydroxycyclobutyl)ethynyl)-6H-benzo[c]chromen-6-one (43)

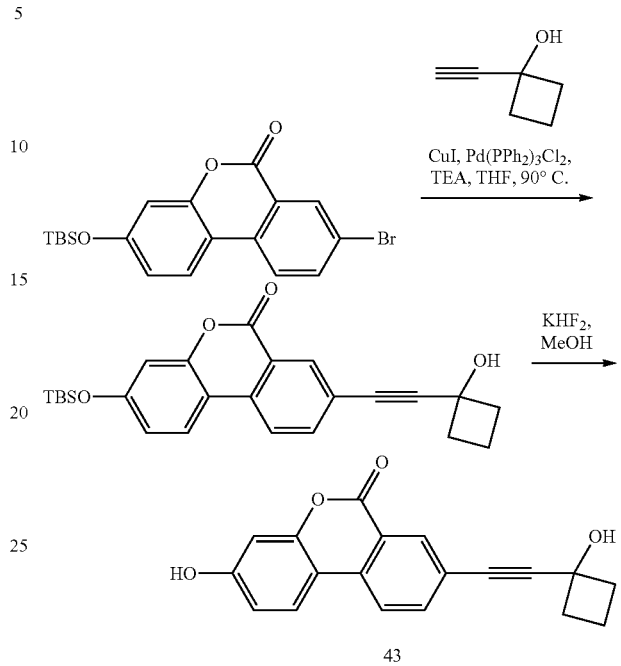

43

Step 1: Synthesis of 3-((tert-butyldimethylsilyl)oxy)-8-((1-hydroxycyclobutyl)ethynyl)-6H-benzo[c]chromen-6-one

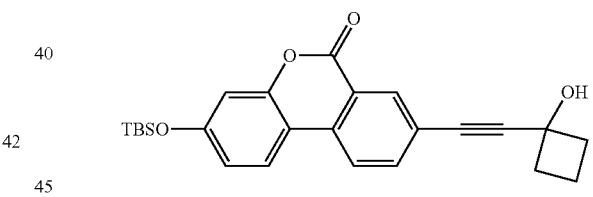

To a solution of 8-bromo-3-((tert-butyldimethylsilyl)oxy)-6H-benzo[c]chromen-6-one (250 mg, 0.620 mmol, 1.0 eq.) in THF (2.06 mL) in a 20 mL Biotage MW vial was subsequently added 1-ethynylcyclobutan-1-ol (208 mg, 2.16 mmol, 3.5 eq.), Pd(PPh$_3$)$_2$Cl$_2$ (43 mg, 0.060 mmol, 0.1 eq.) and CuI (12 mg, 0.060 mmol, 0.1 eq.) and the reaction was degassed at r.t. with N$_2$ for 10 min. Triethylamine (187 mg, 1.85 mmol, 3.00 eq.) was added in one portion and the reaction mixture was put into a pre-heated oil-bath at 90° C. Upon full conversion of the starting material (as indicated by TLC) the reaction mixture was allowed to cool to r.t., quenched with water and extracted with EtOAc (2×20 mL). The combined organic layers were dried over anhydrous Na$_2$SO$_4$ and concentrated under vacuum. The crude product was purified by MPLC (SiO$_2$, 40 g, EtOAc in Hex 0-40%) to afford 3-((tert-butyldimethylsilyl)oxy)-8-((1-hydroxycyclobutyl)ethynyl)-6H-benzo[c]chromen-6-one (195 mg, 75%) as a yellowish solid. $^1$H NMR (400 MHz, CDCl$_3$) δ 8.38 (d, J=1.8 Hz, 1H), 7.90 (d, J=8.4 Hz, 1H), 7.85 (d, J=8.6 Hz, 1H), 7.76 (dd, J=8.4, 1.9 Hz, 1H), 6.86-6.78 (m, 2H), 2.61-2.52 (m, 2H), 2.36 (td, J=9.3, 2.8 Hz, 2H), 2.06-1.79 (m, 2H), 1.00 (s, 9H), 0.25 (s, 6H).

Step 2: Synthesis of 3-hydroxy-8-((1-hydroxycyclobutyl)ethynyl)-6H-benzo[c]chromen-6-one

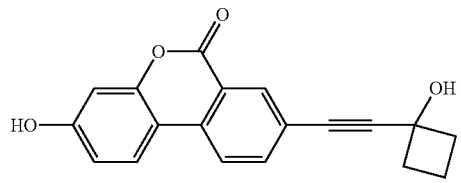

43

3-((tert-butyldimethylsilyl)oxy)-8-((1-hydroxycyclobutyl)ethynyl)-6H-benzo[c]chromen-6-one (195 mg, 0.460 mmol, 1.0 eq.) was dissolved in MeOH (2 mL) and cooled to r.t. in an ice-bath and the resulting yellow solution was stirred for 10 min. Then KHF$_2$ (72 mg, 0.93 mmol, 2.0 eq.) was added in on portion and the reaction was stirred overnight. Upon complete consumption of the starting material (as indicated by TLC) the reaction mixture was filtered over a glass frit (Por.4) and the filter residue was washed with MeOH and dried under vacuum to afford 3-hydroxy-8-((1-hydroxycyclobutyl)ethynyl)-6H-benzo[c]chromen-6-one (100 mg, 70%) as a white solid. $^1$H NMR (400 MHz, DMSO) δ 10.44 (s, 1H), 8.26 (d, J=8.4 Hz, 1H), 8.17 (d, J=8.9 Hz, 1H), 8.13 (d, J=1.8 Hz, 1H), 7.87 (dd, J=8.4, 1.9 Hz, 1H), 6.86 (dd, J=8.7, 2.4 Hz, 1H), 6.76 (d, J=2.4 Hz, 1H), 5.95 (s, 1H), 2.41 (ddd, J=9.2, 7.6, 4.4 Hz, 2H), 2.25 (td, J=9.3, 2.7 Hz, 2H), 1.84-1.76 (m, 2H).

Synthesis of 3-hydroxy-9-(3-hydroxyprop-1-yn-1-yl)-6H-benzo[c]chromen-6-one (44)

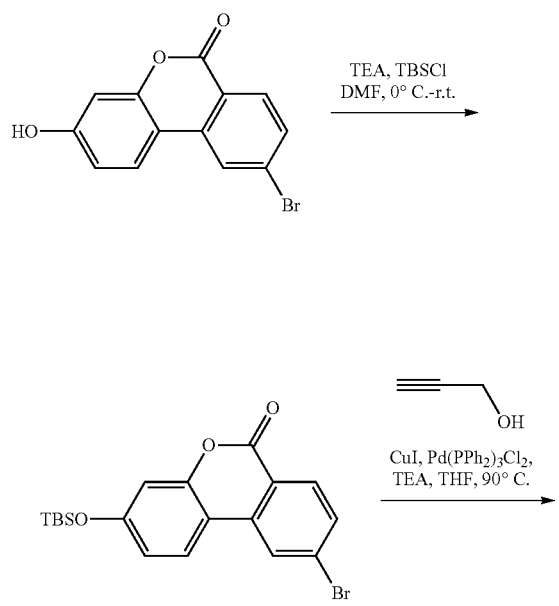

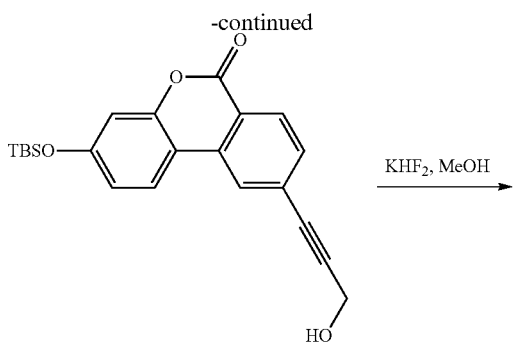

Step 1: Synthesis of 9-bromo-3-((tert-butyldimethylsilyl)oxy)-6H-benzo[c]chromen-6-one

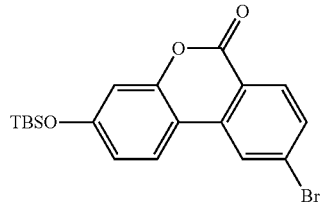 [SMILES: CC(C)(C)[Si](C)(C)Oc1ccc2c(c1)oc(=O)c1ccc(Br)cc12]

9-bromo-3-hydroxy-6H-benzo[c]chromen-6-one (610 mg, 2.10 mmol, 1.0 eq.) was suspended in DMF (10 mL) and triethylamine (636 mg, 6.29 mmol, 3.0 eq.) was added in one portion. The reaction mixture was cooled to 0° C. in an ice-bath and stirred at this temperature for 10 min. Subsequently, TBSCl (411 mg, 2.72 mmol, 1.3 eq.) was added in one portion and the reaction mixture was allowed to warm to r.t. and stirred for an additional 2 h. Upon full conversion of the starting material (as indicated by TLC) the reaction mixture was quenched with half-saturated aqueous sodium bicarbonate solution, extracted with ethyl acetate and the combined organic phases dried over anhydrous Na$_2$SO$_4$. The crude product was purified by MPLC (SiO$_2$, 80 g, EtOAc in Hex 0-15%) to afford 9-bromo-3-((tert-butyldimethylsilyl)oxy)-6H-benzo[c]chromen-6-one (566 mg, 67%) as a light brown solid. $^1$H NMR (400 MHz, CDCl$_3$) δ 8.10 (d, J=8.4 Hz, 1H), 8.04 (d, J=1.8 Hz, 1H), 7.75 (d, J=8.5 Hz, 1H), 7.52 (dd, J=8.5, 1.8 Hz, 1H), 6.84-6.67 (m, 2H), 0.90 (s, 9H), 0.17 (s, 6H).

Step 2: Synthesis of 3-((tert-butyldimethylsilyl)oxy)-9-(3-hydroxyprop-1-yn-1-yl)-6H-benzo[c]chromen-6-one

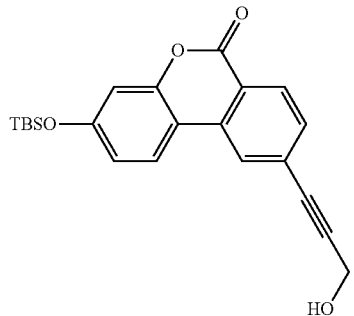 [SMILES: CC(C)(C)[Si](C)(C)Oc1ccc2c(c1)oc(=O)c1ccc(C#CCO)cc12]

To a solution of 9-bromo-3-((tert-butyldimethylsilyl)oxy)-6H-benzo[c]chromen-6-one (250 mg, 0.620 mmol, 1.0 eq.) in THF (2.0 mL) in a 20 mL Biotage MW vial was subsequently added propargyl alcohol (208 mg, 2.16 mmol, 3.5 eq.), Pd(PPh$_3$)$_2$Cl$_2$ (43 mg, 0.060 mmol, 0.1 eq.) and CuI (12 mg, 0.060 mmol, 0.1 eq.) and the reaction was sparged at r.t. with N$_2$ for 10 min. Triethylamine (187 mg, 1.85 mmol, 3.0 eq.) was added in one portion and the reaction mixture was put into a pre-heated oil-bath at 90° C. Upon full conversion of the starting material (as indicated by TLC) the reaction mixture was allowed to cool to r.t., quenched with water and extracted with EtOAc (2×20 mL). The combined organic layers were dried over anhydrous Na$_2$SO$_4$ and concentrated under vacuum. The crude product was purified by MPLC (SiO$_2$, 40 g, EtOAc in Hex 0-40%) to afford 3-((tert-butyldimethylsilyl)oxy)-9-(3-hydroxyprop-1-yn-1-yl)-6H-benzo[c]chromen-6-one (176 mg, 75%) as a yellowish solid. $^1$H NMR (500 MHz, DMSO) δ 11.36 (s, 1H), 8.28 (s, 1H), 8.19 (dd, J=8.8, 1.6 Hz, 1H), 8.13 (d, J=8.2 Hz, 1H), 7.51 (d, J=8.2 Hz, 1H), 6.80 (dd, J=8.8, 2.4 Hz, 1H), 6.71 (d, J=2.4 Hz, 1H), 5.63 (d, J=124.9 Hz, 1H), 4.39 (s, 2H), 0.90 (s, 9H), 0.17 (s, 6H).

Step 2: Synthesis of 3-hydroxy-9-(3-hydroxyprop-1-yn-1-yl)-6H-benzo[c]chromen-6-one

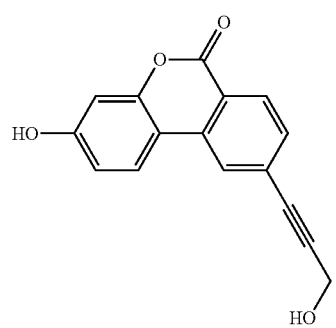

3-((tert-butyldimethylsilyl)oxy)-9-(3-hydroxyprop-1-yn-1-yl)-6H-benzo[c]chromen-6-one (176 mg, 0.460 mmol, 1.0 eq.) was dissolved in MeOH (2 mL) and the resulting yellow solution was stirred for 10 min. Then KHF$_2$ (72 mg, 0.93 mmol, 2.0 eq.) was added in on portion and the reaction was stirred overnight. Upon complete consumption of the starting material (as indicated by TLC) the reaction mixture was filtered over a glass frit (Por.4) and the filter residue was washed with MeOH and dried under vacuum to yield 3-hydroxy-8-((1-hydroxycyclobutyl)ethynyl)-6H-benzo[c]chromen-6-one (90 mg, 0.34 mmol, 73%) as a white solid. MS (ESI+): m/z=267. $^1$H NMR (500 MHz, DMSO) δ 11.36 (s, 1H), 8.28 (s, 1H), 8.19 (dd, J=8.8, 1.6 Hz, 1H), 8.13 (d, J=8.2 Hz, 1H), 7.51 (d, J=8.2 Hz, 1H), 6.80 (dd, J=8.8, 2.4 Hz, 1H), 6.71 (d, J=2.4 Hz, 1H), 5.63 (d, J=124.9 Hz, 1H), 4.39 (s, 2H).

Synthesis of 3-((tert-butyldimethylsilyl)oxy)-8-(3-(4-methylpiperazin-1-yl)prop-1-yn-1-yl)-6H-benzo[c]chromen-6-one

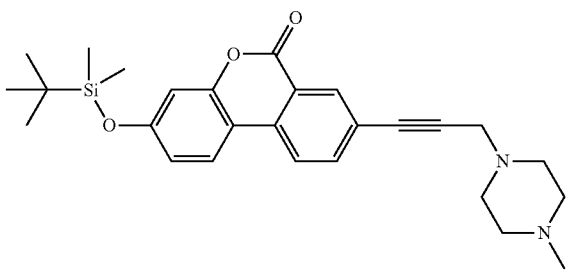 [SMILES: CN1CCN(CC#Cc2ccc3c(c2)c(=O)oc2cc(O[Si](C)(C)C(C)(C)C)ccc23)CC1]

Mesyl Chloride (0.037 ml, 0.47 mmol) was added to a solution of 3-((tert-butyldimethylsilyl)oxy)-8-(3-hydroxyprop-1-yn-1-yl)-6H-benzo[c]chromen-6-one (140 mg, 0.360 mmol) and NEt$_3$ (0.150 ml, 1.10 mmol) in THF (5 ml) at 0° C. and the reaction mixture was stirred at rt for 1 h. TLC showed complete conversion of the starting material. N-methylpiperazine (111 mg, 1.10 mmol) was added and the mixture was heated at 60° C. overnight. A saturated solution of Ammonium chloride was added and the aqueous layer was extracted with EtOAc 3 times. The combined organic layers were dried over sodium sulfate and concentrated under vacuum. The crude product was purified by MPLC (SiO$_2$, MeOH/DCM 0% to 20%) to afford 3-((tert-butyldimethylsilyl)oxy)-8-(3-(4-methylpiperazin-1-yl)prop-1-yn-1-yl)-6H-benzo[c]chromen-6-one, which was used without further purification in the next step.

Synthesis of 3-((tert-butyldimethylsilyl)oxy)-8-(3-(4-methylpiperazin-1-yl)propyl)-6H-benzo[c]chromen-6-one

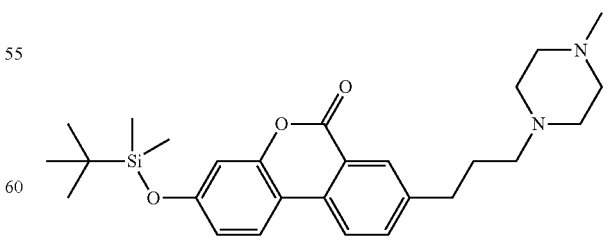

A suspension 3-((tert-butyldimethylsilyl)oxy)-8-(3-(4-methylpiperazin-1-yl)prop-1-yn-1-yl)-6H-benzo[c]chromen-6-one 10 (67 mg, 0.14 mmol) and Pd(OH)$_2$/C (20 mg, 0.030 mmol) in MeOH (5 ml) was hydrogenated under atmospheric pressure overnight. The reaction mixture was filtered over a pad of celite and the solvent was evaporated concentrate under vacuum to afford 3-((tert-butyldimethylsilyl)oxy)-8-(3-(4-methylpiperazin-1-yl)propyl)-6H-benzo[c]chromen-6-one (64 mg, 95%) as yellowish oil, which was used without further purification in the next step.

Synthesis of 3-hydroxy-8-(3-(4-methylpiperazin-1-yl)propyl)-6H-benzo[c]chromen-6-one (45)

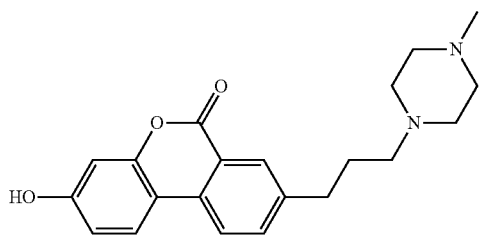

45

45 was prepared starting from 3-((tert-butyldimethylsilyl)oxy)-8-(3-(4-methylpiperazin-1-yl)propyl)-6H-benzo[c]chromen-6-one (65 mg, 0.14 mmol) and KHF$_2$ (22 mg, 0.28 mmol) to afford after purification by MPLC (SiO$_2$, MeOH/DCM 5% to 30%) 3-hydroxy-8-(3-(4-methylpiperazin-1-yl)propyl)-6H-benzo[c]chromen-6-one (36 mg, 73%) as a yellowish solid. R$_f$=0.4 (MeOH/DCM 30/70). $^1$H NMR (400 MHz, CDCl$_3$) δ 8.04 (s, 1H), 7.73 (d, J=8.5 Hz, 1H), 7.66 (d, J=8.8 Hz, 1H), 7.51 (d, J=6.5 Hz, 1H), 6.61 (d, J=9.1 Hz, 1H), 6.53 (s, 1H), 2.86-2.48 (m, 12H), 2.39 (s, 3H), 1.99 (s, 2H).

Synthesis of 3-((tert-butyldimethylsilyl)oxy)-8-(3-morpholinoprop-1-yn-1-yl)-6H-benzo[c]chromen-6-one

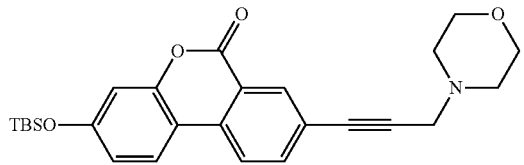

45

Mesyl Chloride (0.04 ml, 0.51 mmol) was added to a solution of 3-((tert-butyldimethylsilyl)oxy)-8-(3-hydroxyprop-1-yn-1-yl)-6H-benzo[c]chromen-6-one (150 mg, 0.39 mmol) and NEt$_3$ (0.160 ml, 1.18 mmol) in THF (5 ml) at 0° C. and the reaction mixture was stirred at rt for 1 h. TLC showed complete conversion of the starting material. Morpholine (0.100 ml, 1.18 mmol) was added and the mixture was heated at 60° C. overnight. A saturated solution of Ammonium chloride was added and the reaction mixture was extracted with EtOAc 3 times. The combined organic layers were dried over sodium sulfate and concentrated under vacuum. The crude product was purified by MPLC (SiO$_2$, MeOH/DCM 0% to 20%) to afford 3-((tert-butyldimethylsilyl)oxy)-8-(3-morpholinoprop-1-yn-1-yl)-6H-benzo[c]chromen-6-one (101 mg, 57%), which was used without further purification in the next step.

Synthesis of 3-((tert-butyldimethylsilyl)oxy)-8-(3-morpholinopropyl)-6H-benzo[c]chromen-6-one

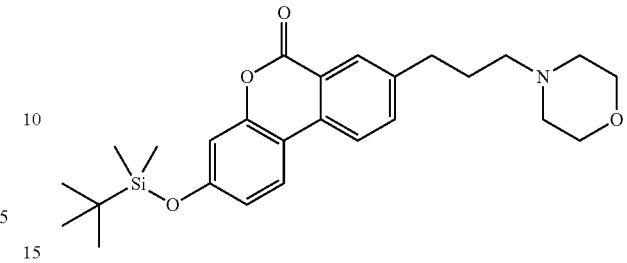

3-(3-((tert-butyldimethyl silyl)oxy)-6-oxo-6H-benzo[c]chromen-8-yl)prop-2-yn-1-yl methanesulfonate OTBS-morpholine (100 mg, 0.220 mmol) and Pd(OH)$_2$/C (31 mg, 0.22 mmol) in MeOH (5 ml) was hydrogenated under atmospheric pressure overnight. The reaction mixture was filtered over a pad of celite and the solvent was concentrated under vacuum to afford 3-((tert-butyldimethylsilyl)oxy)-8-(3-morpholinopropyl)-6H-benzo[c]chromen-6-one (70 mg, 69%) as a yellowish oil. $^1$H NMR (400 MHz, CDCl$_3$) δ 8.16 (d, J=1.9 Hz, 1H), 7.91 (d, J=8.3 Hz, 1H), 7.87 (d, J=9.4 Hz, 1H), 7.61 (dd, J=8.2, 2.0 Hz, 1H), 6.82 (h, J=2.4 Hz, 2H), 3.71 (t, J=4.7 Hz, 4H), 2.76 (d, J=7.8 Hz, 2H), 2.43 (t, J=4.6 Hz, 4H), 2.36 (dd, J=8.4, 6.4 Hz, 2H), 1.87 (h, J=7.4, 6.8 Hz, 2H), 0.99 (s, 9H), 0.24 (s, 6H).

Synthesis of 3-hydroxy-8-(3-morpholinopropyl)-6H-benzo[c]chromen-6-one (46)

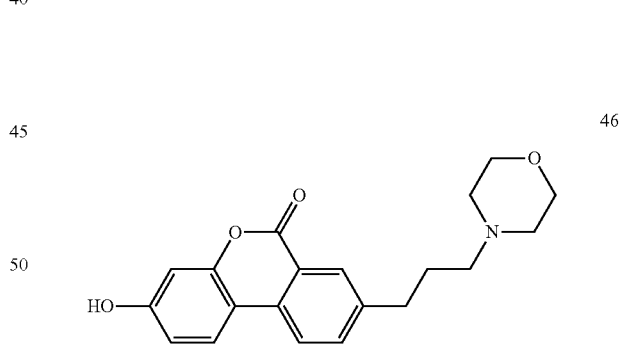

46

46 was prepared starting from 3-((tert-butyldimethylsilyl)oxy)-8-(3-morpholinopropyl)-6H-benzo[c]chromen-6-one (70 mg, 0.15 mmol) and KHF$_2$ (24 mg, 0.31 mmol) to afford after purification by MPLC (SiO$_2$, MeOH/DCM 5% to 30%) 3-hydroxy-8-(3-morpholinopropyl)-6H-benzo[c]chromen-6-one (70 mg, 69%) as a yellowish solid. R$_f$=0.4 (MeOH/DCM 30/70). $^1$H NMR (400 MHz, DMSO) δ 10.31 (s, 1H), 8.18 (d, J=8.3 Hz, 1H), 8.13 (d, J=8.9 Hz, 1H), 8.01 (d, J=1.9 Hz, 1H), 7.75 (dd, J=8.3, 2.0 Hz, 1H), 6.83 (dd, J=8.7, 2.4 Hz, 1H), 6.74 (d, J=2.4 Hz, 1H), 3.57 (t, J=4.7 Hz, 4H), 2.74 (t, J=7.6 Hz, 2H), 2.35-2.31 (m, 4H), 2.28 (t, J=7.2 Hz, 2H), 1.78 (p, J=7.4 Hz, 2H).

Synthesis of 3-((tert-butyldimethylsilyl)oxy)-8-(3-(piperidin-1-yl)prop-1-yn-1-yl)-6H-benzo[c]chromen-6-one

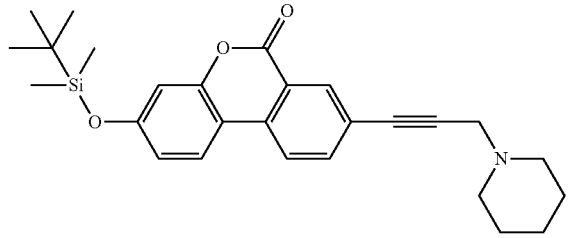 [SMILES: CC(C)(C)[Si](C)(C)Oc1ccc2c(c1)oc(=O)c1cc(C#CCN3CCCCC3)ccc12]

Mesyl Chloride (0.0980 ml, 1.26 mmol) was added to a solution of 3-((tert-butyldimethylsilyl)oxy)-8-(3-hydroxyprop-1-yn-1-yl)-6H-benzo[c]chromen-6-one (240 mg, 0.630 mmol) and NEt$_3$ (0.260 ml, 1.89 mmol) in THF (10 ml) at 0° C. and the reaction mixture was stirred at rt for 1 h. TLC showed complete conversion of the starting material. Piperidine (0.081 ml, 0.82 mmol) was added and the mixture was heated at 60° C. overnight. A saturated solution of Ammonium chloride was added and the reaction mixture was extracted with EtOAc 3 times. The combined organic layers were dried over sodium sulfate and concentrated under vacuum. The crude product was purified by MPLC (SiO$_2$, MeOH/DCM 0% to 20%) to afford 3-((tert-butyldimethylsilyl)oxy)-8-(3-(piperidin-1-yl)prop-1-yn-1-yl)-6H-benzo[c]chromen-6-one (66 mg, 23%). $^1$H NMR (400 MHz, CDCl$_3$) δ 8.41 (d, J=1.8 Hz, 1H), 7.93 (d, J=8.4 Hz, 1H), 7.88 (d, J=8.3 Hz, 1H), 7.79 (dd, J=8.3, 1.8 Hz, 1H), 6.85 (d, J=8.2 Hz, 2H), 3.53 (s, 2H), 2.61 (s, 4H), 1.70-1.45 (m, 6H), 1.00 (s, 9H), 0.26 (s, 6H).

Synthesis of 3-hydroxy-8-(3-(piperidin-1-yl)prop-1-yn-1-yl)-6H-benzo[c]chromen-6-one (47)

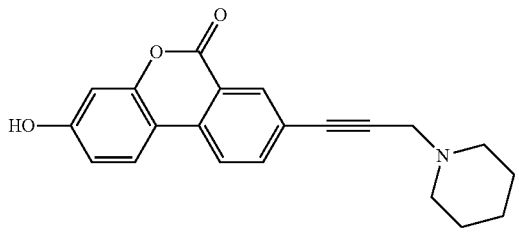

47 was prepared starting from 3-((tert-butyldimethylsilyl)oxy)-8-(3-(piperidin-1-yl)prop-1-yn-1-yl)-6H-benzo[c]chromen-6-one (60 mg, 0.13 mmol) and KHF$_2$ (21 mg, 0.27 mmol) to afford after purification by MPLC (SiO$_2$, EtOAc/cyclohexane 0% to 80%) to afford 3-hydroxy-8-(3-(piperidin-1-yl)prop-1-yn-1-yl)-6H-benzo[c]chromen-6-one (37 mg, 83%) as a yellowish solid. R$_f$=0.4 (EtOAc/hexane 40%). $^1$H NMR (400 MHz, CDCl$_3$) δ 7.70-7.62 (m, 2H), 7.59 (d, J=1.7 Hz, 1H), 7.54 (dd, J=8.4, 1.8 Hz, 1H), 6.82 (dd, J=8.7, 2.4 Hz, 1H), 6.55 (d, J=2.4 Hz, 1H), 3.36 (s, 2H), 2.77 (s, 4H), 1.80 (q, J=5.7 Hz, 4H), 1.58 (b, 2H).

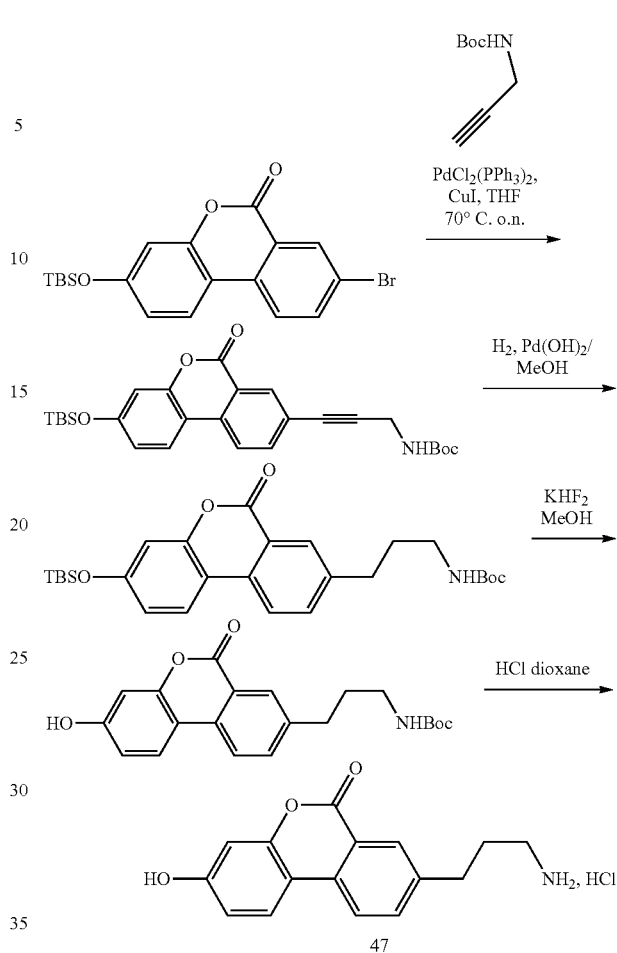

Synthesis of tert-butyl (3-(3-((tert-butyldimethylsilyl)oxy)-6-oxo-6H-benzo[c]chromen-8-yl)prop-2-yn-1-yl)carbamate To a well degassed solution of Pd(PPh$_3$)$_2$Cl$_2$ (41.8 mg, 0.059 mmol, 0.1 eq) and CuI (11.3 mg, 0.059 mmol, 0.1 eq) in THF (10 ml) and 8-bromo-3-((dimethyl(tert-butyl)silyl)oxy)-6H-benzo[c]chromen-6-one (250 mg, 0.590 mmol) and Prop-2-ynyl-carbamic acid tert-butyl ester (277 mg, 1.79 mmol, 3.0 eq) was added NEt$_3$ (0.330 ml, 2.38 mmol, 4.0 eq) and the mixture was heated at 70° C. overnight. The reaction mixture was diluted with a saturated solution of NH$_4$Cl, and extracted with EtOAc. The organic layers was dried over sodium sulfate and concentrated under vacuum. The crude product was purified by MPLC (SiO$_2$, EtOAc/hexane 0% to 20%) to afford tert-butyl (3-(3-((tert-butyldimethylsilyl)oxy)-6-oxo-6H-benzo[c]chromen-8-yl)prop-2-yn-1-yl)carbamate (190 mg, 0.39 mmol, 66%) as a yellowish foam. R$_f$=0.4 (EtOAc/hexane 20%). $^1$H NMR (400 MHz, CDCl$_3$) δ 8.39 (d, J=1.7 Hz, 1H), 7.93 (d, J=8.4 Hz, 1H), 7.87 (dd, J=8.5, 0.8 Hz, 1H), 7.77 (dd, J=8.3, 1.8 Hz, 1H), 6.89-6.81 (m, 2H), 4.79 (s, 1H), 4.19 (d, J=5.6 Hz, 2H), 1.48 (s, 9H), 1.00 (s, 9H), 0.26 (s, 6H).

Synthesis of tert-butyl (3-(3-((tert-butyldimethylsilyl)oxy)-6-oxo-6H-benzo[c]chromen-8-yl)propyl)carbamate A suspension of tert-butyl (3-(3-((tert-butyldimethylsilyl)oxy)-6-oxo-6H-benzo[c]chromen-8-yl)prop-2-yn-1-yl)carbamate (190 mg, 0.390 mmol) and Pd(OH)$_2$/C 20% (56 mg, 0.79 mmol) was hydrogenated under atmospheric pressure in methanol, and stirred overnight. The reaction mixture was filtered over a pad of celite, and the solvent was evaporated under vacuum. The crude product was purified by MPLC (SiO$_2$, EtOAc/cyclohexane 0% to 20%) to afford tert-butyl (3-(3-((tert-butyldimethylsilyl)oxy)-6-oxo-6H-benzo[c]chromen-8-yl)propyl)carbamate (175 mg, 91%) as a yellowish oil. R$_f$=0.4 (EtOAc/hexane 20%). $^1$H NMR (400 MHz, CDCl$_3$) δ 8.17 (d, J=1.9 Hz, 1H), 7.93 (d, J=8.3 Hz, 1H), 7.88 (d, J=9.3 Hz, 1H), 7.62 (dd, J=8.2, 2.0 Hz, 1H), 6.84 (dq, J=4.5, 2.4 Hz, 2H), 4.57 (s, 1H), 3.18 (d, J=7.0 Hz, 2H), 2.89-2.71 (m, 2H), 1.88 (p, J=7.3 Hz, 2H), 1.45 (s, 9H), 1.00 (s, 9H), 0.26 (s, 6H).

Synthesis of tert-butyl (3-(3-hydroxy-6-oxo-6H-benzo[c]chromen-8-yl)propyl)carbamate (48)

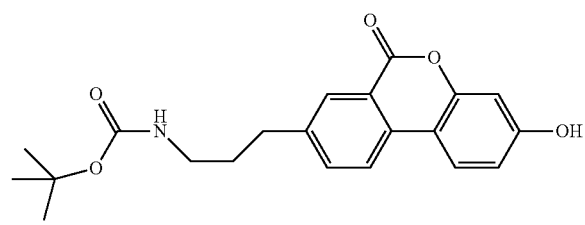

48 was prepared starting from tert-butyl (3-(3-((tert-butyldimethylsilyl)oxy)-6-oxo-6H-benzo[c]chromen-8-yl)propyl)carbamate (170 mg, 0.350 mmol) and KHF$_2$ (55 mg, 0.70 mmol) to afford after purification by MPLC (SiO$_2$, EtOAc/cyclohexane 0% to 20%) tert-butyl (3-(3-hydroxy-6-oxo-6H-benzo[c]chromen-8-yl)propyl)carbamate (108 mg, 0.290 mmol, 83%) as a white solid. R$_f$=0.4 (EtOAc/hexane 20/100). $^1$H NMR (400 MHz, DMSO) δ 10.27 (s, 1H), 8.15 (dd, J=21.4, 8.5 Hz, 2H), 8.00 (d, J=1.9 Hz, 1H), 7.73 (dd, J=8.3, 2.0 Hz, 1H), 6.87 (t, J=5.4 Hz, 1H), 6.82 (dd, J=8.7, 2.4 Hz, 1H), 6.73 (d, J=2.3 Hz, 1H), 2.94 (q, J=6.6 Hz, 2H), 2.70 (t, J=7.6 Hz, 2H), 1.72 (p, J=7.3 Hz, 2H), 1.36 (s, 9H).

Synthesis of 8-(3-aminopropyl)-3-hydroxy-6H-benzo[c]chromen-6-one hydrochloride (49)

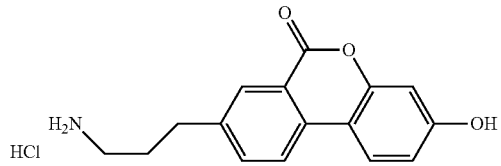

HCl (4 M in Dioxane, 1.35 ml, 5.4 mmol) was added to a solution of tert-butyl (3-(3-hydroxy-6-oxo-6H-benzo[c]chromen-8-yl)propyl)carbamate (100 mg, 0.270 mmol) in dioxane (0.5 ml) at r.t. and the reaction mixture was stirred at r.t. overnight, and a precipitate was formed. The solvent was concentrated under vacuum and the crude product was triturated in Et$_2$O, filtered, and dried to afford (3-aminopropyl)-3-hydroxy-6H-benzo[c]chromen-6-one hydrochloride (70 mg, 86%) as a white solid. MS (ESI+): m/z=270. $^1$H NMR (400 MHz, DMSO) δ 10.36 (s, 1H), 8.22 (d, J=8.3 Hz, 1H), 8.14 (d, J=8.8 Hz, 1H), 8.05 (d, J=1.9 Hz, 1H), 7.83 (s, 3H), 7.76 (dd, J=8.3, 2.0 Hz, 1H), 6.85 (dd, J=8.7, 2.4 Hz, 1H), 6.76 (dd, J=2.4, 1.2 Hz, 1H), 2.81 (q, J=7.7, 6.4 Hz, 4H), 1.98-1.85 (m, 2H).

H) Spirocycle (Oxetane & Azetidine) "A" Ring Analogies

Synthesis of spiro[benzo[c]chromene-6,3'-oxetane]-3,8-diol (50)

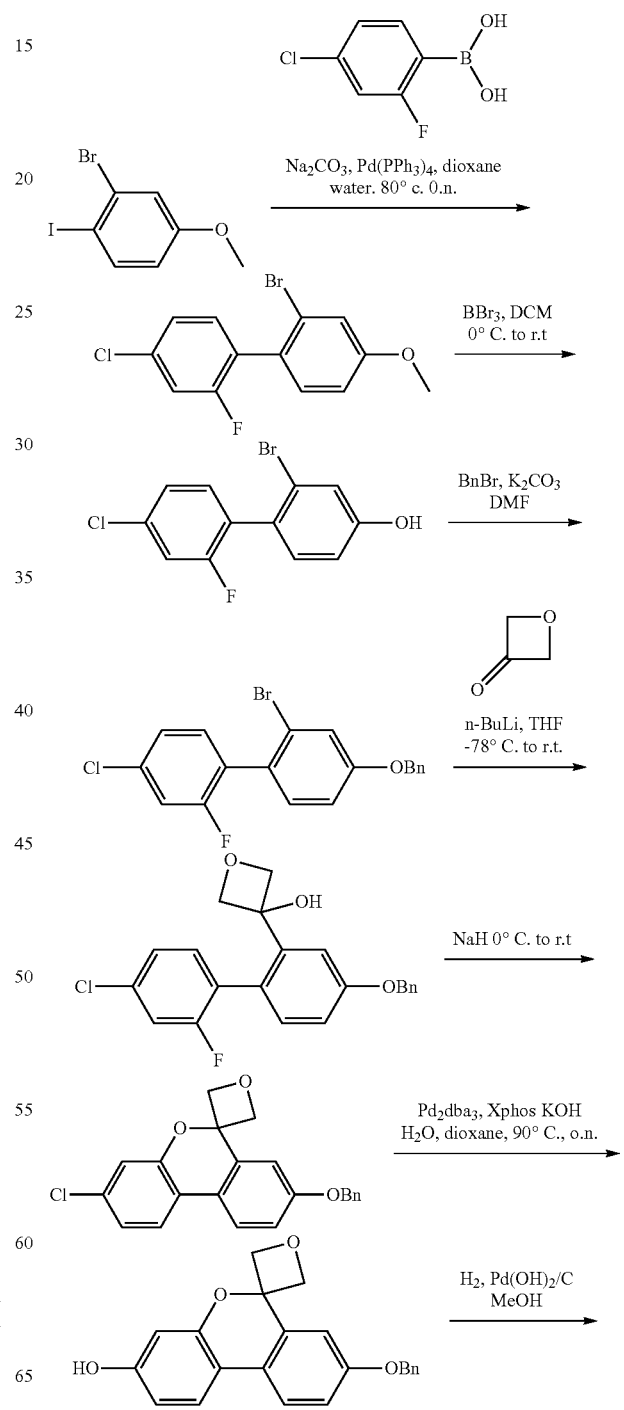

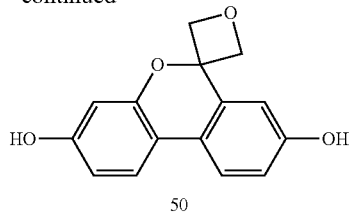

Step 1: Synthesis of 7-bromo-4'-chloro-2'-fluoro-4-methoxy-1,1'-biphenyl

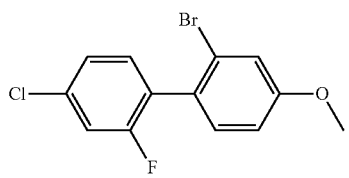 [SMILES: COc1ccc(-c2ccc(Cl)cc2F)c(Br)c1]

2-bromo-1-iodo-4-methoxybenzene (4.00 g, 12.8 mmol) and (4-chloro-2-fluorophenyl) boronic acid (1.01 g, 23.0 mmol) were dissolved in Dioxane (80 ml). Tetrakis(triphenylphosphine)palladium(0) (738 mg, 0.640 mmol) was added followed by a solution of $Na_2CO_3$ (2.70 g, 25.6 mmol) and the reaction mixture was heated at 80° C. overnight. The reaction mixture was diluted with a saturated solution of sodium carbonate, and extracted with EtOAc twice. The combined organic layers were dried over sodium sulfate, and concentrated in vacuum. The crude product was purified by MPLC ($SiO_2$, 0 to 8% DCM/cyclohexane) to afford 2-bromo-4'-chloro-2'-fluoro-4-methoxy-1,1'-biphenyl (1.80 g, 45%) as a colorless oil. $R_f$=0.2 (DCM/cyclohexane 3%). $^1$H NMR (400 MHz, $CDCl_3$) δ 7.24-7.14 (m, 5H), 6.92 (dd, J=8.5, 2.6 Hz, 1H), 3.84 (s, 3H).

Step 2: Synthesis of 2-bromo-4'-chloro-T-fluoro-[1,1'-biphenyl]-4-ol

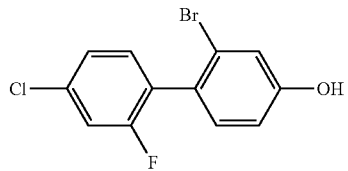 [SMILES: Oc1ccc(-c2ccc(Cl)cc2F)c(Br)c1]

$BBr_3$ (1 M in DCM, 6.97 ml, 6.97 mmol) was added at 0° C. to a solution of 2-bromo-4'-chloro-2'-fluoro-4-methoxy-1,1'-biphenyl (1.10 g, 3.48 mmol) in DCM (5 ml) and the reaction mixture was allowed to warm to r.t. overnight. Methanol (10 ml) was added at 0° C. and the solvent was evaporated under vacuum. The crude product was diluted with a saturated solution of sodium bicarbonate and extracted with EtOAc. The combined organic layers were dried over sodium sulfate and concentrate under vacuum to afford 2-bromo-4'-chloro-2'-fluoro-[1,1'-biphenyl]-4-ol (1.10 g), which was used in the next step without further purification. $^1$H NMR (400 MHz, $CDCl_3$) δ 7.23-7.01 (m, 5H), 6.79 (dd, J=8.4, 2.6 Hz, 1H).

Step 3: Synthesis of 4-(benzyloxy)-2-bromo-4'-chloro-2'-fluoro-1,1'-biphenyl

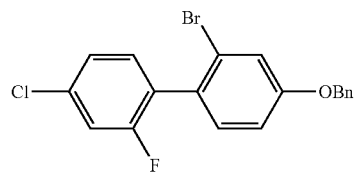 [SMILES: Fc1cc(Cl)ccc1-c1ccc(OCc2ccccc2)cc1Br]

Benzyl bromide (0.470 ml, 3.98 mmol) was added to a solution of 2-bromo-4'-chloro-2'-fluoro-[1,1'-biphenyl]-4-ol (1.00 g, 3.31 mmol) and potassium carbonate (0.916 g, 6.63 mmol) in ACN (10 ml) and the mixture was heated at 60° C. overnight. The crude was cooled to room temperature and extracted with Ethyl acetate from bicarbonate saturated solution. The combined organic layers were dried over sodium sulfate and concentrated under vacuum. The crude product was purified by MPLC (25 g silica cartridge, EtOAc/cyclohexane 0% to 10%) to afford 4-(benzyloxy)-2-bromo-4'-chloro-2'-fluoro-1,1'-biphenyl (1.10 g, 85%) as colorless oil. $^1$H NMR (400 MHz, $CDCl_3$) δ 7.48-7.35 (m, 5H), 7.32 (d, J=2.6 Hz, 1H), 7.23-7.15 (m, 4H), 6.99 (dd, J=8.5, 2.6 Hz, 1H), 5.09 (s, 2H).

Step 4: Synthesis of 3-(4-(benzyloxy)-4'-chloro-2'-fluoro-[1,1'-biphenyl]-2-yl)oxetan-3-ol

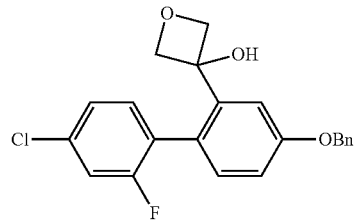 [SMILES: OC1(c2cc(OCc3ccccc3)ccc2-c2ccc(Cl)cc2F)COC1]

nBuLi (1.6 M in hexane, 2.58 ml, 4.13 mmol) was added dropwise at −78° c. to a solution of 4-(benzyloxy)-2-bromo-4'-chloro-T-fluoro-1,1'-biphenyl (900 mg, 2.29 mmol) in dry THF (8 ml). The red pale solution was stirred at −78° C. for 45 min then a solution of oxetan-3-one (662 mg, 9.19 mmol) was added dropwise and the reaction was allowed to warm to room temperature over 5 h. The reaction mixture was quenched with $NH_4Cl$ saturated solution and extracted with Ethyl acetate. The organic layers were dried overs sodium sulfate. The crude product was purified by MPLC (25 g silica cartridge, EtOAc/cyclohexane 0% to 50%) to afford 3-(4-(benzyloxy)-4'-chloro-2'-fluoro-[1,1'-biphenyl]-2-yl)oxetan-3-ol (383 mg, 85%) as colorless oil. $R_f$=0.3 (EtOAc/hexane 50/50). $^1$H NMR (400 MHz, $CDCl_3$) δ 7.55-7.28 (m, 6H), 7.19-7.14 (m, 3H), 7.00 (dd, J=8.5, 2.6 Hz, 1H), 6.85 (d, J=2.6 Hz, 1H), 5.11 (s, 2H), 4.82 (s, 2H), 4.36 (s, 2H), 2.77 (s, 1H).

Step 5: Synthesis of 8-(benzyloxy)-3-chlorospiro[benzo[c]chromene-6,3'-oxetane]

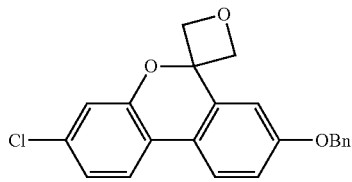 [SMILES: Clc1ccc2c(c1)OC1(COC1)c1cc(OCc3ccccc3)ccc1-2]

NaH (70.5 mg, 1.76 mmol, 60% dispersion in mineral oil) was added at 0° c. to a solution of 3-(4-(benzyloxy)-4'-chloro-2'-fluoro-[1,1'-biphenyl]-2-yl)oxetan-3-ol (377 mg, 0.980 mmol) in DMF 4 ml and the reaction was allowed to warm to room temperature overnight. The crude was extracted with ½ saturated solution of bicarbonate and ethyl acetate. The organic phase was dried over sodium sulfate and evaporated under vacuum. The crude product was purified by MPLC (25 g silica cartridge, EtOAc/cyclohexane 0% to 5%) to afford 8-(benzyloxy)-3-chlorospiro[benzo[c]chromene-6,3'-oxetane] (290 mg, 81%) as a yellow solid. $R_f$=0.3 (EtOAc/hexane 10%). $^1$H NMR (400 MHz, CDCl$_3$) δ 7.63 (d, J=8.7 Hz, 1H), 7.54 (d, J=8.3 Hz, 1H), 7.49-7.35 (m, 5H), 7.32 (d, J=2.5 Hz, 1H), 7.08 (d, J=2.1 Hz, 1H), 7.04 (dd, J=8.7, 2.6 Hz, 1H), 7.01 (dd, J=8.3, 2.1 Hz, 1H), 5.17 (s, 2H), 5.08-5.01 (m, 2H), 4.90-4.78 (m, 2H).

Step 6: Synthesis of 8-(benzyloxy)spiro[benzo[c]chromene-6,3'-oxetan]-3-ol

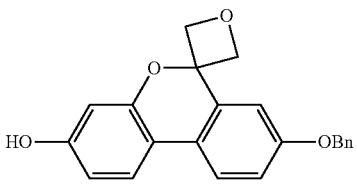 [SMILES: Oc1ccc2c(c1)OC1(COC1)c1cc(OCc3ccccc3)ccc1-2]

t-BuXPhos (9 mg, 0.020 mmol) was added to a suspension of Pd$_2$dba$_3$ (2.3 mg, 0.099 mmol) in Dioxane (1 ml), degassed and stirred for 5 minutes. 8-(benzyloxy)-3-chlorospiro[benzo[c]chromene-6,3'-oxetane] (45 mg, 0.12 mmol) was added followed by a solution of KOH (15 mg, 0.27 mmol) in water (0.3 ml) at rt and the mixture was heated at 90° C. overnight. Water was added and the mixture was extracted with EtOAc 3 times and the combined organic layers was dried over sodium sulfate, filtered and evaporated under vacuum. The crude product was purified by MPLC (25 g silica cartridge, EtOAc/cyclohexane 0% to 30%) to afford 8-(benzyloxy)spiro[benzo[c]chromene-6,3'-oxetan]-3-ol (30 mg, 0.87 mmol, 70%) as a white solid. $R_f$=0.3 (EtOAc/hexane 20%). MS (ESI+): m/z=347. $^1$H NMR (400 MHz, DMSO) δ 9.72 (s, 1H), 7.69 (d, J=8.7 Hz, 1H), 7.60 (d, J=8.3 Hz, 1H), 7.53-7.36 (m, 6H), 7.09 (dd, J=8.6, 2.6 Hz, 1H), 6.56-6.43 (m, 2H), 5.21 (s, 2H), 4.86-4.80 (m, 4H).

Step 7: Synthesis spiro[benzo[c]chromene-6,3'-oxetane]-3,8-diol

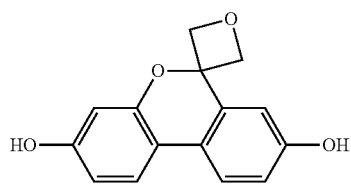

A suspension of 8-(benzyloxy)spiro[benzo[c]chromene-6,3'-oxetan]-3-ol (40 mg, 0.12 mmol) and Pd(OH)$_2$/C (16 mg, 0.23 mmol) in methanol (4 ml) was hydrogenated under atmospheric pressure o.n. The reaction mixture was filtered over a pad of celite the solvent was evaporated and the product further purified by filtration over a pad of silica using DCM/methanol 10% to afford spiro[benzo[c]chromene-6,3'-oxetane]-3,8-diol (23 mg, 0.09 mmol, 78%) as a light yellow solid. MS (ESI+): m/z=257. $^1$H NMR (400 MHz, DMSO) δ 9.66 (d, J=19.6 Hz, 2H), 7.57 (d, J=8.5 Hz, 1H), 7.54 (d, J=8.4 Hz, 1H), 7.09 (d, J=2.4 Hz, 1H), 6.84 (dd, J=8.4, 2.4 Hz, 1H), 6.51-6.44 (m, 2H), 4.83 (d, J=7.3 Hz, 2H), 4.74 (d, J=7.2 Hz, 2H).

Synthesis of spiro[azetidine-3,6'-benzo[c]chromene]-3',8'-diol (51)

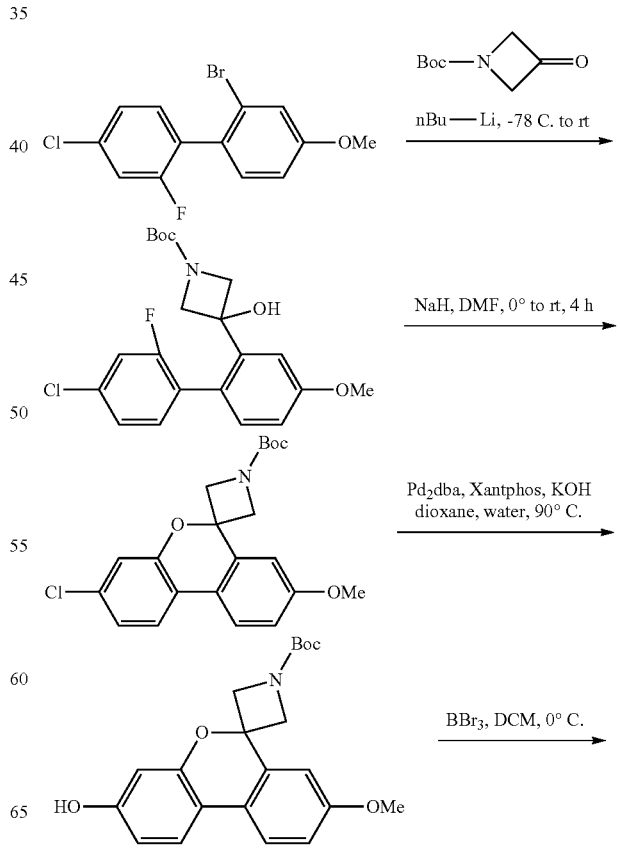

-continued

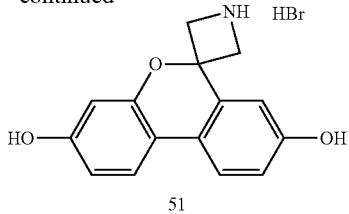

51

Step 1: Synthesis of tert-butyl 3-(4'-chloro-2'-fluoro-4-methoxy-[1,1'-biphenyl]-2-yl)-3-hydroxyazetidine-1-carboxylate

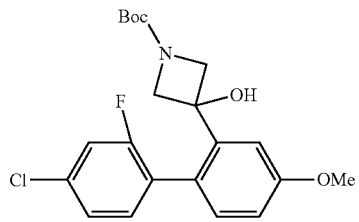 [SMILES: COc1ccc(-c2ccc(Cl)cc2F)c(C2(O)CN(C(=O)OC(C)(C)C)C2)c1]

nBuLi (1.6 M in hexane, 2.69 ml, 4.31 mmol) was added dropwise at −78° c. to a solution of 4-(benzyloxy)-2-bromo-4'-chloro-T-fluoro-1,1'-biphenyl (900 mg, 2.29 mmol) in dry THF (8 ml). The red pale solution was stirred at −78° C. for 45 min then a solution of tert-butyl 3-oxoazetidine-1-carboxylate (1.84 g, 10.8 mmol) in dry THF (5 ml) was added dropwise and the reaction was allowed to warm to room temperature over 5 hours. The reaction mixture was quenched with NH$_4$Cl saturated solution and extracted with Ethyl acetate. The organic phases were dried overs sodium sulfate. The crude product was purified by MPLC (80 g silica cartridge, EtOAc/cyclohexane 0% to 50%) to afford tert-butyl 3-(4'-chloro-2'-fluoro-4-methoxy-[1,1'-biphenyl]-2-yl)-3-hydroxyazetidine-1-carboxylate (400 mg, 36%) as a mixture of two compounds as a colorless oil. R$_f$=0.3 (EtOAc/hexane 50/50). $^1$H NMR (400 MHz, CDCl$_3$) δ 7.32 (t, J=8.2 Hz, 1H), 7.21-7.12 (m, 3H), 6.93 (dd, J=8.5, 2.7 Hz, 1H), 6.86 (d, J=2.6 Hz, 1H), 4.18-3.97 (m, 1H), 3.95-3.87 (m, 1H), 3.86 (s, 3H), 3.73 (s, 2H), 2.70 (d, J=14.5 Hz, 1H), 1.39 (s, 9H).

Step 2: Synthesis of tert-butyl 3'-chloro-8'-methoxyspiro[azetidine-3,6'-benzo[c]chromene]-1-carboxylate

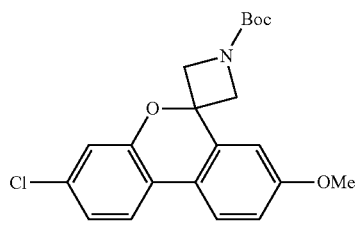 [SMILES: COc1ccc2c(c1)C1(CN(C(=O)OC(C)(C)C)C1)Oc1cc(Cl)ccc1-2]

NaH (12 mg, 0.30 mmol) was added at 0° C. to a solution of tert-butyl 3-(4'-chloro-T-fluoro-4-methoxy-[1,1'-biphenyl]-2-yl)-3-hydroxyazetidine-1-carboxylate (67 mg, 0.16 mmol) in DMF 3 ml and the reaction mixture was stirred for 3 h. NH4Cl saturated solution was added and the aqueous phase was extracted twice with Ethyl acetate. The combined organic phases were dried over sodium sulfate, filtered and concentrated under vacuum. The crude was purified by MPLC (EtOAc/cyclohexane 0% to 8%) to give tert-butyl 3'-chloro-8'-methoxyspiro[azetidine-3,6'-benzo[c]chromene]-1-carboxylate (30 mg, 47%) as a yellowish solid. $^1$H NMR (400 MHz, CDCl$_3$) δ 7.63 (d, J=8.5 Hz, 1H), 7.55 (d, J=8.3 Hz, 1H), 7.09-6.93 (m, 4H), 4.31 (d, J=9.5 Hz, 2H), 4.19 (s, 2H), 3.88 (s, 3H), 1.47 (s, 9H).

Step 3: Synthesis of tert-butyl 3'-hydroxy-8'-methoxyspiro[azetidine-3,6'-benzo[c]chromene]-1-carboxylate

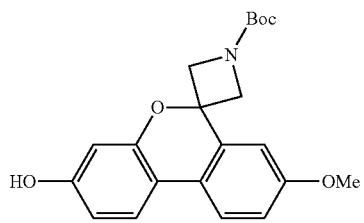 [SMILES: COc1ccc2c(c1)C1(CN(C(=O)OC(C)(C)C)C1)Oc1cc(O)ccc1-2]

3'-chloro-8'-methoxyspiro[azetidine-3,6'-benzo[c]chromene]-1-carboxylate (155 mg, 0.400 mmol, 1.0 eq.) was dissolved in 1,4-dioxane (1.5 mL) and Pd$_2$dba$_3$ (9 mg, 0.04 mmol, 0.1 eq.) as well as tBuXPhos (38 mg, 0.080 mmol, 0.2 eq.) were added to the solution. Following the mixture was degassed using a N$_2$ balloon for 10 min. Subsequently a solution of KOH (67 mg, 1.2 mmol, 3.0 eq.) in water (0.3 mL) was added in on portion before putting the reaction mixture in a pre-heated oil-bath at 90° C. Stirring was continued overnight and then the reaction was allowed to cool to r.t., quenched with water, the aq. phase extracted with ethyl acetate (3×10 mL) and the combined organic layers dried over Na$_2$SO$_4$ and concentrated under reduced pressure. The crude material was purified by flash column chromatography (SiO$_2$, 20 g, EtOAc in Hex 0-30%) to yield tert-butyl 3'-hydroxy-8'-methoxyspiro [azetidine-3,6'-benzo [c]chromene]-1-carboxylate (120 mg, 0.330 mmol, 81%) as a light yellow solid. R$_f$=0.3 (EtOAc/hexane 20%) as yellowish solid. $^1$H NMR (400 MHz, DMSO) δ 9.70 (s, 1H), 7.68 (d, J=8.6 Hz, 1H), 7.61 (d, J=8.5 Hz, 1H), 7.05 (d, J=2.6 Hz, 1H), 7.00 (dd, J=8.6, 2.6 Hz, 1H), 6.51 (dd, J=8.5, 2.4 Hz, 1H), 6.45 (d, J=2.4 Hz, 1H), 4.19 (d, J=9.6 Hz, 2H), 4.10 (d, J=9.7 Hz, 2H), 3.83 (s, 3H), 1.41 (s, 9H).

Step 4: Synthesis of spiro[azetidine-3,6'-benzo[c]chromene]-3',8'-diol hydrobromide

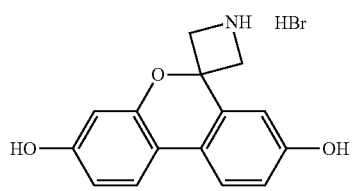

51

BBr₃ (0.54 ml, 0.54 mmol, 2.0 eq) was added to a solution of tert-butyl 3'-hydroxy-8'-methoxyspiro[azetidine-3,6'-benzo[c]chromene]-1-carboxylate (100 mg, 0.270 mmol, 1.0 eq.) in DCM (5 mL) at 0° C. and the mixture was allowed to warm to room temperature overnight. Methanol was added to the mixture at 0° C. was concentrated under vacuum and loaded on silica then purified by FC eluent MeOH/DCM 0% to 8% to give spiro[azetidine-3,6'-benzo[c]chromene]-3',8'-diol hydrobromide (40 mg, 44%) as a white solid. MS (ESI+): m/z=256. ¹H NMR (400 MHz, DMSO) δ 9.76 (d, J=22.3 Hz, 2H), 9.42 (s, 1H), 8.91 (s, 1H), 7.59 (t, J=8.7 Hz, 2H), 7.06 (d, J=2.4 Hz, 1H), 6.95-6.83 (m, 1H), 6.54 (dd, J=8.4, 2.4 Hz, 1H), 6.49 (d, J=2.3 Hz, 1H), 4.38 (dt, J=12.6, 6.8 Hz, 2H), 4.24 (ddd, J=12.2, 7.4, 4.0 Hz, 2H).

I) Ester "A" Ring Analogues with Peptide Substitution

Synthesis of 3-acetoxy-6-oxo-6H-benzo[c]chromene-8-carboxylic acid as the Common Intermediate

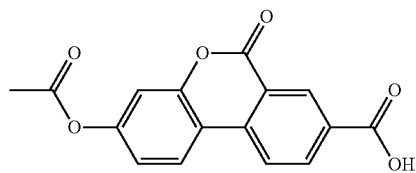 [SMILES: CC(=O)Oc1ccc2c(c1)oc(=O)c1cc(C(=O)O)ccc12]

Acetylchloride (0.36 ml, 5.2 mmol) was added at 0° C. to a suspension of 3-hydroxy-6-oxo-6H-benzo[c]chromene-8-carboxylic acid (2 (600 mg, 2.34 mmol) in THF (8 ml) and the reaction mixture was allowed to warm to room temperature overnight. The reaction mixture is still a suspension (nothing solubilises). HCl 1 M was added to the suspension and stirred 30 minutes at room temperature. The white suspension was filtered off and the solid was washed with cooled water and dried under vacuum to give (17) as a white solid (400 mg, 57%). ¹H NMR (400 MHz, CDCl₃) δ 8.72 (d, J=1.8 Hz, 1H), 8.53 (d, J=8.5 Hz, 1H), 8.47 (d, J=8.8 Hz, 1H), 8.39 (dd, J=8.4, 1.9 Hz, 1H), 7.34 (d, J=2.2 Hz, 1H), 7.26 (dd, J=8.7, 2.3 Hz, 1H), 2.33 (s, 3H).

General Procedure Peptide Coupling Using FDPP and Deprotection Using Potassium Carbonate Synthesis of 8-((2-morpholinoethyl)carbamoyl)-6-oxo-6H-benzo[c]chromen-3-yl acetate (52)

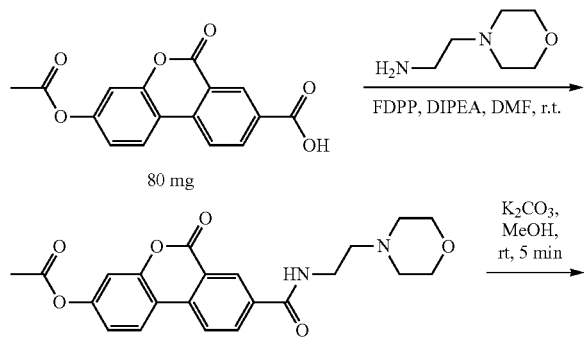

Step 1: Synthesis of 8-((2-morpholinoethyl)carbamoyl)-6-oxo-6H-benzo[c]chromen-3-yl acetate

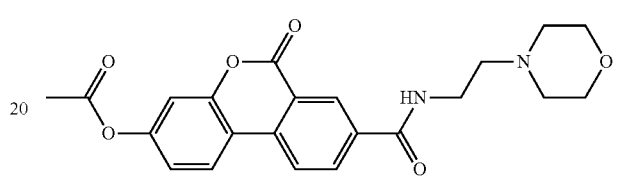

DIPEA (0.15 ml, 0.86 mmol) was added to a solution of 3-acetoxy-6-oxo-6H-benzo[c]chromene-8-carboxylic acid (80 mg, 0.21 mmol) in DMF (2 ml) followed by Pentafluorophenyldiphenylphosphinate (91 mg, 0.24 mmol) and the mixture was stirred 15 min then add 2-morpholinoethan-1-amine (28 mg, 0.21 mmol) dropwise and stirring continued for 1 h. The reaction mixture was extracted with EtOAc and bicarbonate ½ saturated solution 3 times. The combined organic phases were dried over sodium sulfate and concentrated under vacuum. The crude was purified by MPLC (SiO₂, MeOH/DCM from 0% to 10%) to afford 8-((2-morpholinoethyl)carbamoyl)-6-oxo-6H-benzo[c]chromen-3-yl acetate (45 mg, 51%) R_f=0.3 (10% MeOH/DCM). ¹H NMR (400 MHz, CDCl₃) δ 8.69 (d, J=1.9 Hz, 1H), 8.39 (dd, J=8.4, 2.0 Hz, 1H), 8.17 (d, J=8.4 Hz, 1H), 8.10 (d, J=8.7 Hz, 1H), 7.20 (d, J=2.2 Hz, 1H), 7.17 (dd, J=8.6, 2.3 Hz, 1H), 7.00 (s, 1H), 3.78 (t, J=4.6 Hz, 4H), 3.63 (q, J=5.6 Hz, 2H), 2.68 (d, J=4.6 Hz, 2H), 2.57 (s, 4H), 2.36 (s, 3H).

Step 2: Synthesis of 3-hydroxy-N-(2-morpholinoethyl)-6-oxo-6H-benzo[c]chromene-8-carboxamide

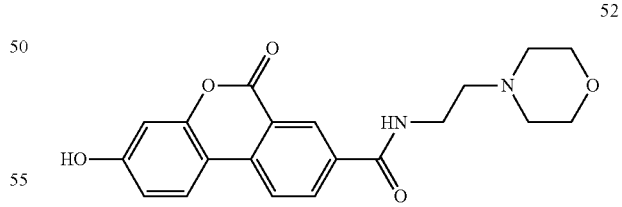

Potassium carbonate (36 mg, 0.26 mmol) was added at rt to solution of 8-((2-morpholinoethyl)carbamoyl)-6-oxo-6H-benzo[c]chromen-3-yl acetate (36 mg, 0.088 mmol) in MeOH and the reaction mixture was stirred at room temperature 10 min. The mixture was loaded on silica gel and purified by MPLC (SiO₂, MeOH/dichloromethane 0% to 10%) to afford 3-hydroxy-N-(2-morpholinoethyl)-6-oxo-6H-benzo[c]chromene-8-carboxamide UA0350 (23 mg, 71%). R_f=0.2 (10% MeOH/DCM). ¹H NMR (400 MHz, DMSO) δ 10.48 (s, 1H), 8.76 (t, J=5.6 Hz, 1H), 8.68 (d,

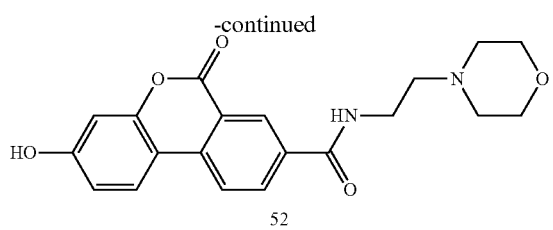

J=1.9 Hz, 1H), 8.36 (d, J=8.6 Hz, 1H), 8.29 (dd, J=8.5, 1.9 Hz, 1H), 8.24-8.19 (m, 1H), 6.90-6.84 (m, 1H), 6.78 (d, J=2.4 Hz, 1H), 3.58 (t, J=4.6 Hz, 4H), 3.43 (q, J=6.5 Hz, 2H), 2.43 (s, 4H) (2 missing protons are overshadowed by solvent).

Synthesis of 3-hydroxy-6-oxo-N-(2-(piperidin-1-yl)ethyl)-6H-benzo[c]chromene-8-carboxamide (53)

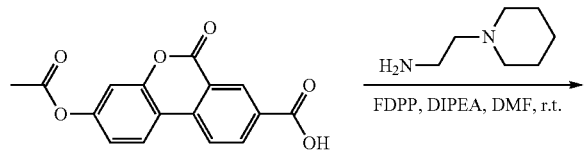

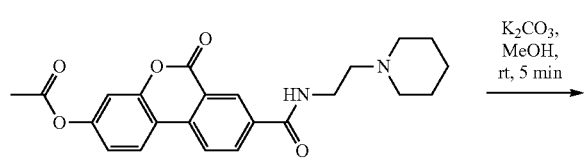

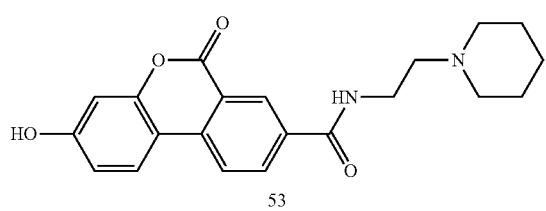

Step 1: Synthesis of 6-oxo-8-((2-(piperidin-1-yl)ethyl)carbamoyl)-6H-benzo[c]chromen-3-yl acetate

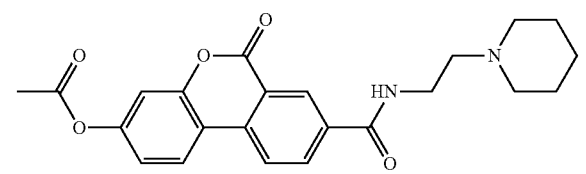 [SMILES: CC(=O)Oc1ccc2c(c1)oc(=O)c1cc(C(=O)NCCN3CCCCC3)ccc12]

Compound was prepared according to general procedure starting from 3-acetoxy-6-oxo-6H-benzo[c]chromene-8-carboxylic acid (120 mg, 0.320 mmol), Pentafluorophenyldiphenylphosphinate (136 mg, 0.35 mmol), 2-(piperidin-1-yl)ethan-1-amine (41 mg, 0.32 mmol) and DIPEA (0.224 ml, 1.29 mmol) to afford after purification by MPLC (SiO$_2$, MeOH/DCM 0% to 10%) 6-oxo-8-((2-(piperidwiin-1-yl)ethyl)carbamoyl)-6H-benzo[c]chromen-3-yl acetate 19 (65 mg, 49%) as a white solid. R$_f$=0.3 (MeOH/DCM 10%). $^1$H NMR (400 MHz, CDCl$_3$) δ 8.74 (d, J=1.9 Hz, 1H), 8.40 (dd, J=8.4, 1.9 Hz, 1H), 8.16 (d, J=8.5 Hz, 1H), 8.09 (d, J=8.7 Hz, 1H), 7.54-7.36 (m, 1H), 7.22-7.13 (m, 2H), 3.63 (q, J=5.5 Hz, 2H), 2.68 (t, J=5.8 Hz, 2H), 2.56 (s, 4H), 2.36 (s, 3H), 1.75-1.60 (m, 4H), 1.51 (s, 2H).

Step 2: Synthesis of 3-hydroxy-6-oxo-N-(2-(piperidin-1-yl)ethyl)-6H-benzo[c]chromene-8-carboxamide

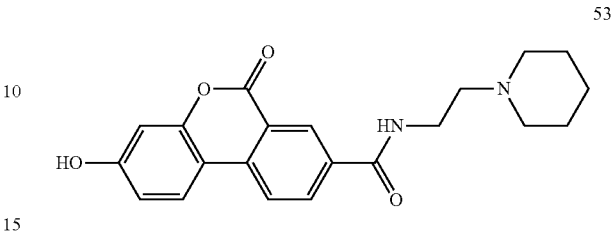

3-hydroxy-6-oxo-N-(2-(piperidin-1-yl)ethyl)-6H-benzo[c]chromene-8-carboxamide was prepared according to GP5 starting from 6-oxo-8-((2-(piperidin-1-yl)ethyl)carbamoyl)-6H-benzo[c]chromen-3-yl acetate 19 (49 mg, 0.12 mmol) and potassium carbonate (50 mg, 0.36 mmol) to afford after purification by MPLC (SiO$_2$, MeOH/DCM 5% to 35%) 3-hydroxy-6-oxo-N-(2-(piperidin-1-yl)ethyl)-6H-benzo[c]chromene-8-carboxamide 53 (15 mg, 34%) as a white solid. R$_f$=0.3 (MeOH/DCM 20%). $^1$H NMR (400 MHz, DMSO) δ 10.52 (s, 1H), 8.83 (s, 1H), 8.68 (d, J=1.9 Hz, 1H), 8.36 (d, J=8.6 Hz, 1H), 8.29 (dd, J=8.5, 1.9 Hz, 1H), 8.22 (d, J=8.8 Hz, 1H), 6.87 (dd, J=8.7, 2.4 Hz, 1H), 6.78 (d, J=2.4 Hz, 1H), 3.47 (d, J=21.5 Hz, 5H), 1.65-1.19 (m, 9H).

Synthesis of—hydroxy-N-(2-(4-methylpiperazin-1-yl)ethyl)-6-oxo-6H-benzo[c]chromene-8-carboxamide (54)

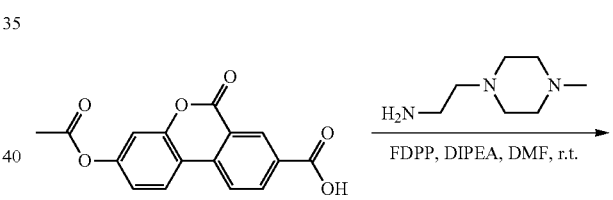

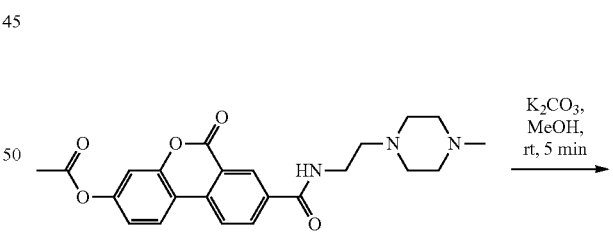

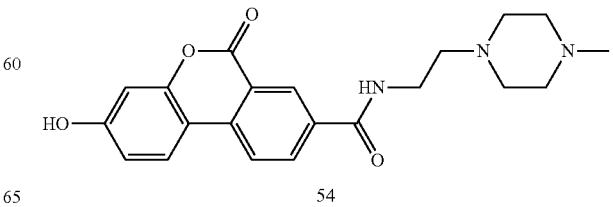

Step 1: Synthesis of 8-((2-(4-methylpiperazin-1-yl)ethyl)carbamoyl)-6-oxo-6H-benzo[c]chromen-3-yl acetate

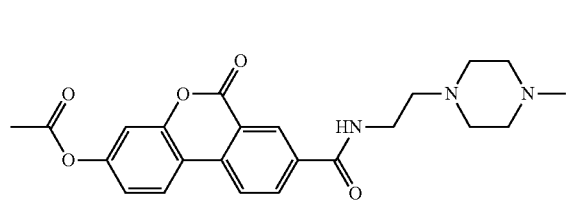 [SMILES: CC(=O)Oc1ccc2c(c1)oc(=O)c1cc(C(=O)NCCN3CCN(C)CC3)ccc12]

Compound was prepared according to GP4 starting from 3-acetoxy-6-oxo-6H-benzo[c]chromene-8-carboxylic acid (120 mg, 0.260 mmol) Pentafluorophenyldiphenylphosphinate (113 mg, 0.290 mmol) and DIPEA (0.187 ml, 1.070 mmol) to afford after purification by MPLC (SiO$_2$, MeOH/DCM 0% to 10%) 8-((2-(4-methylpiperazin-1-yl)ethyl)carbamoyl)-6-oxo-6H-benzo[c]chromen-3-yl acetate 20 (73 mg, 59%) as a white solid. R$_f$=0.3 eluent (MeOH/DCM 10%). $^1$NMR (400 MHz, CDCl$_3$) δ 8.68 (d, J=1.9 Hz, 1H), 8.39 (dd, J=8.4, 2.0 Hz, 1H), 8.16 (d, J=8.5 Hz, 1H), 8.09 (d, J=8.7 Hz, 1H), 7.19 (d, J=2.2 Hz, 1H), 7.16 (dd, J=8.6, 2.3 Hz, 1H), 7.11 (s, 1H), 3.62 (q, J=5.6 Hz, 2H), 2.73-2.58 (m, 10H), 2.37 (d, J=5.2 Hz, 6H).

Step 2: Synthesis of—hydroxy-N-(2-(4-methylpiperazin-1-yl)ethyl)-6-oxo-6H-benzo[c]chromene-8-carboxamide

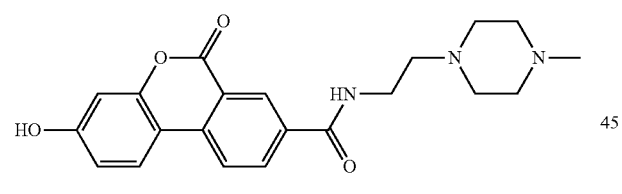

54

3-hydroxy-N-(2-(4-methylpiperazin-1-yl)ethyl)-6-oxo-6H-benzo[c]chromene-8-carboxamide was prepared according to GP5 starting from 8-((2-(4-methylpiperazin-1-yl)ethyl)carbamoyl)-6-oxo-6H-benzo[c]chromen-3-yl acetate 20 (60 mg, 0.14 mmol) and potassium carbonate (39 mg, 0.28 mmol) to afford after purification by MPLC (RP-C18, MeOH/water 0% to 95%) 3-hydroxy-N-(2-(4-methylpiperazin-1-yl)ethyl)-6-oxo-6H-benzo[c]chromene-8-carboxamide (27 mg, 51%). R$_f$=0.1 eluent (MeOH/DCM 30%). $^1$H NMR (400 MHz, DMSO) δ 8.75 (t, J=5.6 Hz, 1H), 8.68 (d, J=1.8 Hz, 1H), 8.36 (d, J=8.6 Hz, 1H), 8.29 (dd, J=8.5, 1.9 Hz, 1H), 8.22 (d, J=8.9 Hz, 1H), 8.18 (s, 1H), 6.88 (dd, J=8.7, 2.4 Hz, 1H), 6.78 (d, J=2.4 Hz, 1H), 3.47-3.40 (m, 2H), 2.48-2.30 (m, 10H), 2.20 (s, 3H).

J) Ester "A" Group Analogs with Inverse Amide Substitution

The syntheses of inverse amides was based on a common intermediate that is described below.

Synthesis of N-(3-(benzyloxy)-6-oxo-6H-benzo[c]chromen-8-yl)-2-chloroacetamide

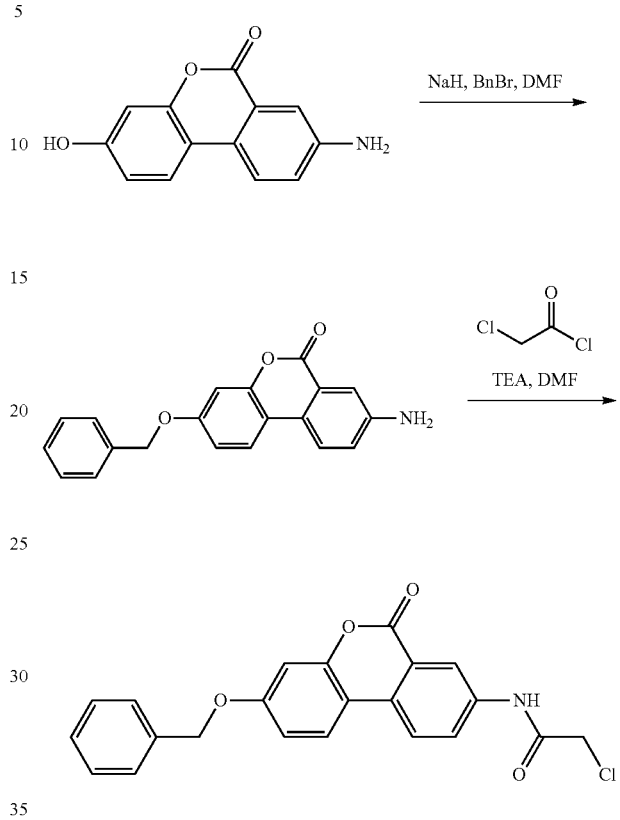

Step 1: Synthesis of 8-amino-3-(benzyloxy)-6H-benzo[c]chromen-6-one

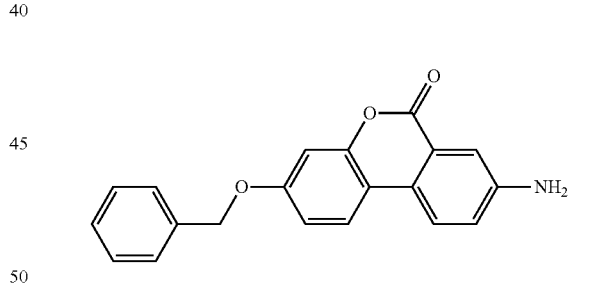

8-amino-3-hydroxy-6H-benzo[c]chromen-6-one 15 (864 mg, 3.80 mmol) was dissolved in DMF (13 ml) then cooled to 0° C. Subsequently NaH (152 mg, 3.80 mmol) was added in one portion. Upon stirring for 15 min benzyl chloride (0.44 ml, 3.80 mmol) was added dropwise and the reaction mixture was allowed to warm to r.t. and stirring overnight was continued. Following the reaction was quenched with half-saturated NaHCO$_3$ solution and extracted with ethyl acetate (3×25 ml). The combined organic layers were dried over Na$_2$SO$_4$ and concentrated under reduced pressure. The crude product was purified by MPLC (SiO$_2$, ethyl acetate/Hex 0-50%) to afford 8-amino-3-(benzyloxy)-6H-benzo[c]chromen-6-one (738 mg, 61%) as an ocher colored solid. $^1$H NMR (400 MHz, DMSO) δ 8.02 (dd, J=17.2, 8.7 Hz, 2H), 7.51-7.34 (m, 6H), 7.14 (dd, J=8.7, 2.6 Hz, 1H), 7.06-6.95 (m, 2H), 5.79 (s, 2H), 5.19 (s, 2H).

Step 2: Synthesis of N-(3-(benzyloxy)-6-oxo-6H-benzo[c]chromen-8-yl)-2-chloroacetamide

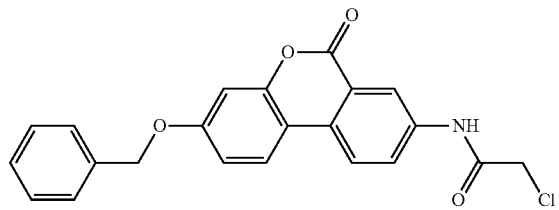 [SMILES: O=C(CCl)Nc1ccc2c(c1)c(=O)oc1cc(OCc3ccccc3)ccc12]

8-amino-3-(benzyloxy)-6H-benzo[c]chromen-6-one (738 mg, 2.33 mmol) was added to a solution of DMF (16 ml) containing TEA (0.324 ml, 2.56 mmol). The mixture was stirred for 10 min at room temperature. Chloroacetylchloride (0.205 ml, 2.33 mmol) was added to the above mixture, maintaining the temperature between 0 and 5° C. The obtained solution was then stirred at room temperature for 4-6 h. The completion of reaction was monitored with TLC. The solution was then added onto crushed ice and the separated precipitates were filtered and dried under vacuum. The product was recrystallized from methanol to afford N-(3-(benzyloxy)-6-oxo-6H-benzo[c]chromen-8-yl)-2-chloroacetamide (833 mg, 91%) as a lightly yellowish solid. $^1$H NMR (400 MHz, DMSO) δ 10.72 (s, 1H), 8.52 (d, J=2.4 Hz, 1H), 8.31 (d, J=8.8 Hz, 1H), 8.19 (d, J=8.8 Hz, 1H), 8.03 (dd, J=8.8, 2.4 Hz, 1H), 7.48-7.35 (m, 5H), 7.10-7.06 (m, 2H), 5.22 (s, 2H), 4.32 (s, 2H).

Synthesis of N-(3-(hydroxy)-6-oxo-6H-benzo[c]chromen-8-yl)-2-morpholinoacetamide (55)

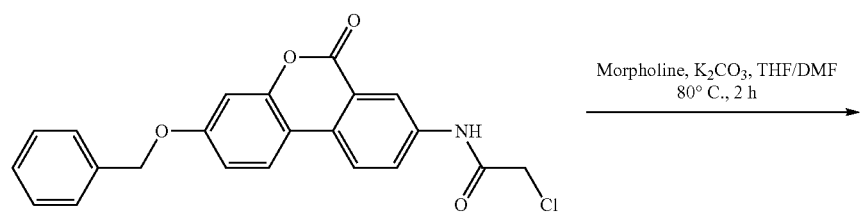

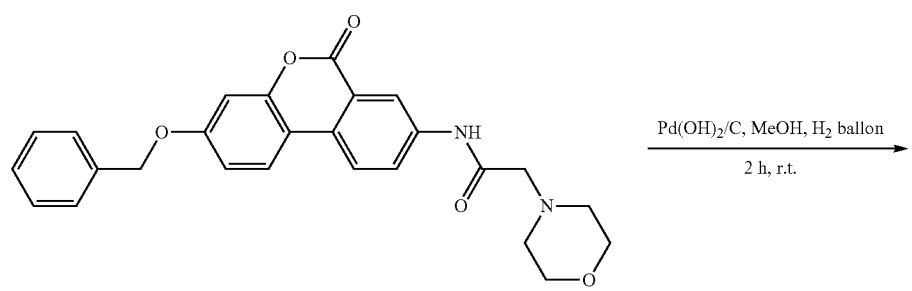

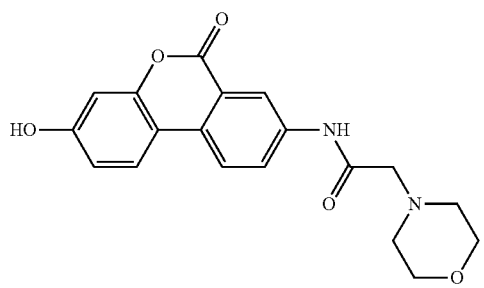

55

Step 1: Synthesis of N-(3-(benzyloxy)-6-oxo-6H-benzo[c]chromen-8-yl)-2-morpholinoacetamide Step 2: Synthesis of N-(3-hydroxy-6-oxo-6H-benzo[c]chromen-8-yl)-2-morpholinoacetamide

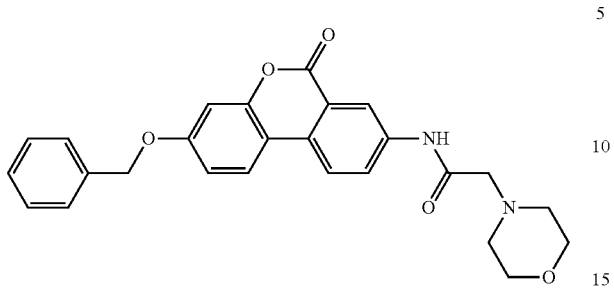

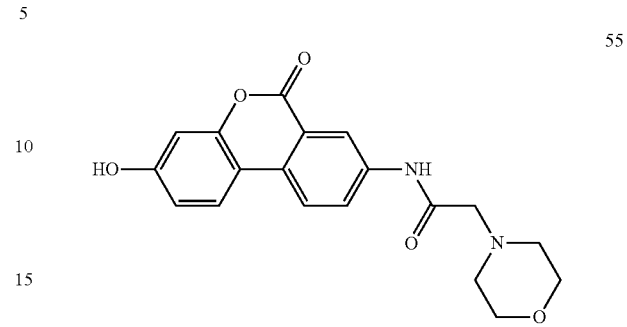

N-(3-(benzyloxy)-6-oxo-6H-benzo[c]chromen-8-yl)-2-chloro acetamide (60 mg, 0.15 mmol) was suspended in THF (5 ml) and the potassium carbonate (42 mg, 0.30 mmol) was added in one portion. The minimum amount of DMF (2-3 ml) were added dropwise in order to solubilize the suspension. Then morpholine (0.014 ml, 0.17 mmol) was added via syringe and the reaction was heated to 80° C. for 2 h. Upon complete consumption of the starting material (as indicated by TLC) the reaction was allowed to cool down to r.t. and then the mixture was concentrated under reduced pressure. The crude product was purified by MPLC (SiO$_2$, MeOH in DCM 0-10%) to afford N-(3-(benzyloxy)-6-oxo-6H-benzo[c]chromen-8-yl)-2-morpholinoacetamide (46 mg, 0.10 mmol, 68%) as a white solid. $^1$H NMR (400 MHz, DMSO) δ 10.17 (s, 1H), 8.60 (d, J=2.3 Hz, 1H), 8.29 (d, J=8.9 Hz, 1H), 8.21 (d, J=8.7 Hz, 1H), 8.13 (dd, J=8.8, 2.4 Hz, 1H), 7.50-7.35 (m, 5H), 7.11-7.06 (m, 2H), 5.23 (s, 2H), 3.66 (t, J=4.7 Hz, 4H), 3.19 (s, 2H), 2.55-2.52 (m, 4H).

A solution of N-(3-(benzyloxy)-6-oxo-6H-benzo[c]chromen-8-yl)-2-morpholinoacetamide (40 mg, 0.090 mmol) and Pd(OH)$_2$/C (7 mg, 0.009 mmol) in MeOH (2 ml) and DCM (2 ml) was stirred under hydrogen at atmospheric pressure overnight. The reaction mixture was filtered over a pad of celite and the solvent was evaporated under vacuum to give N-(3-hydroxy-6-oxo-6H-benzo[c]chromen-8-yl)-2-morpholinoacetamide (25 mg. 78%) as an off-white solid. $^1$H NMR (400 MHz, DMSO) δ 10.26 (s. 1H). 10.14 (s. 1H). 8.57 (d, J=2.3 Hz, 1H), 8.23 (d, J=9.0 Hz, 11H), 8.10 (d, J=8.8 Hz. 2H). 6.83 (dd, J=8.7, 2.5 Hz, 1H), 6.75 (d, J=2.4 Hz, 1H), 3.65 (t, J=4.8 Hz, 4H), 3.18 (s, 2H). (clean, but 4 aliphatic protons are overshadowed by solvent)

Synthesis of N-(3-(hydroxy)-6-oxo-6H-benzo[c]chromen-8-yl)-2-(piperidin-1-yl)acetamide (56)

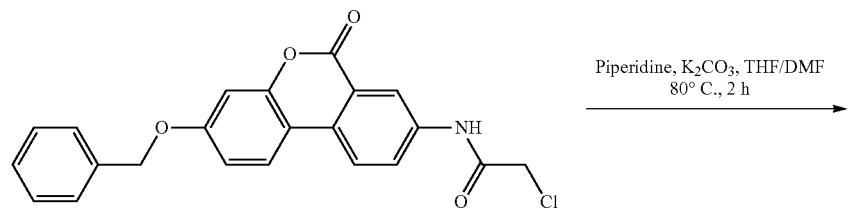

Piperidine, K$_2$CO$_3$, THF/DMF
80° C., 2 h

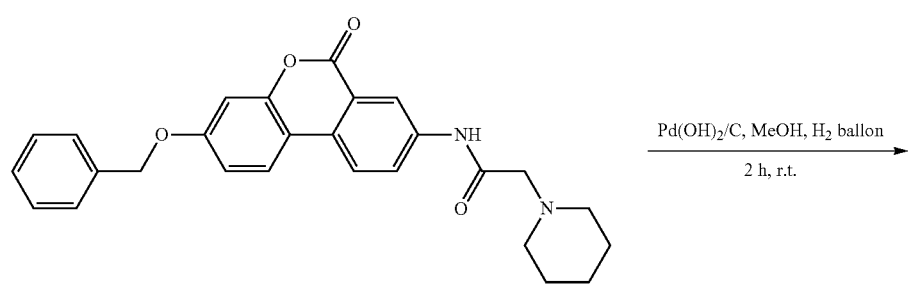

Pd(OH)$_2$/C, MeOH, H$_2$ ballon 2 h, r.t.

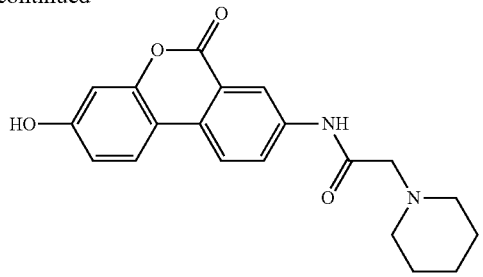

56

Step 1: Synthesis of N-(3-(benzyloxy)-6-oxo-6H-benzo[c]chromen-8-yl)-2-(piperidin-1-yl)acetamide Step 2: Synthesis N-(3-hydroxy-6-oxo-6H-benzo[c]chromen-8-yl)-2-(piperidin-1-yl)acetamide

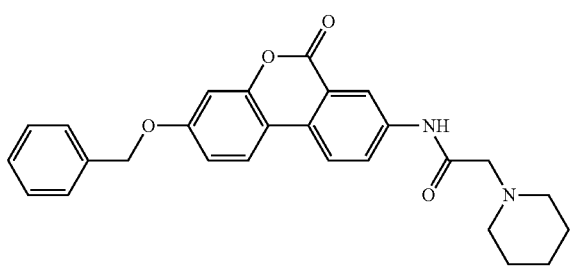 [SMILES: O=C(CN1CCCCC1)Nc1ccc2c(c1)c(=O)oc1cc(OCc3ccccc3)ccc12]

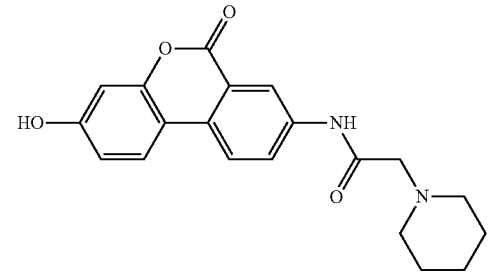

56

N-(3-(benzyloxy)-6-oxo-6H-benzo[c]chromen-8-yl)-2-chloroacetamide (200 mg, 0.510 mmol) was suspended in THF (5 ml) and the potassium carbonate (140 mg, 1.02 mmol) was added in one portion. The minimum amount of DMF (5-6 ml) were added in order to solubilize the suspension. Then piperidine (0.055 ml, 0.56 mmol) was added dropwise via syringe and the reaction was heated to 80° C. for 2 h. Upon complete consumption of the starting material (as indicated by TLC) the reaction was allowed to cool down to r.t. and then the mixture was concentrated under reduced pressure. The crude product was purified by flash column chromatography (MeOH in DCM 0-10%) to obtain N-(3-(benzyloxy)-6-oxo-6H-benzo[c]chromen-8-yl)-2-(piperidin-1-yl)acetamide (154 mg, 0.51 mmol, 69%) as a white solid. $^1$H NMR (400 MHz, DMSO) δ 10.10 (s, 1H), 8.61 (d, J=2.3 Hz, 1H), 8.28 (d, J=8.9 Hz, 1H), 8.20 (d, J=8.8 Hz, 1H), 8.12 (dd, J=8.8, 2.4 Hz, 1H), 7.53-7.37 (m, 5H), 7.13-7.05 (m, 2H), 5.23 (s, 2H), 3.13 (s, 2H), 2.47 (d, J=5.0 Hz, 4H), 1.58 (p, J=5.6 Hz, 4H), 1.41 (q, J=6.0 Hz, 2H).

A solution of N-(3-(benzyloxy)-6-oxo-6H-benzo[c]chromen-8-yl)-2-(piperidin-1-yl)acetamide (154 mg, 0.350 mmol) and Pd(OH)$_2$/C (34 mg, 0.035 mmol) in MeOH (3 ml) and DCM (3 ml) was stirred under hydrogen at atmospheric pressure overnight. The reaction mixture was filtered over a pad of celite and the solvent was evaporated under vacuum to give N-(3-hydroxy-6-oxo-6H-benzo[c]chromen-8-yl)-2-(piperidin-1-yl)acetamide (95 mg, 77%) as a dark yellow solid. $^1$H NMR (400 MHz. DMSO) δ 10.07 (s. 1H). 8.58 (d, J=2.3 Hz. 1H), 8.21 (d, J=8.9 Hz, 1H), 8.09 (dd, J=8.8, 2.8 Hz, 21), 6.83 (dd, J=8.7, 2.4 Hz, 11). 6.74 (d, J=2.4 Hz, 11H), 3.12 (s, 21), 2.47 (d, J=5.6 Hz, 4H), 1.59 (q. J=5.6 Hz. 4H). 1.41 (q. J=6.2 Hz. 2H).

MS (ESI+): m/z=353

Synthesis of N-(3-(hydroxy)-6-oxo-6H-benzo[c]chromen-8-yl)-2-(4-methylpiperazin-1-yl)acetamide (57)

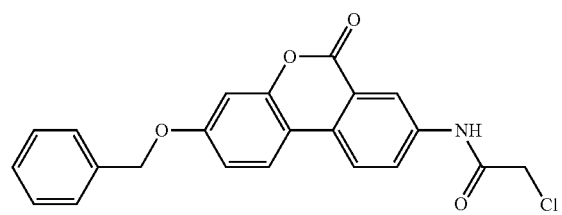

N—Me-Piperazine, K$_2$CO$_3$, THF/DMF
$\xrightarrow{80° C., 2 h}$

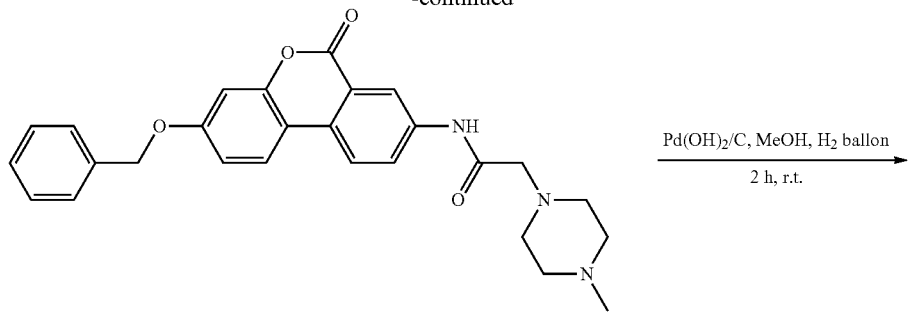

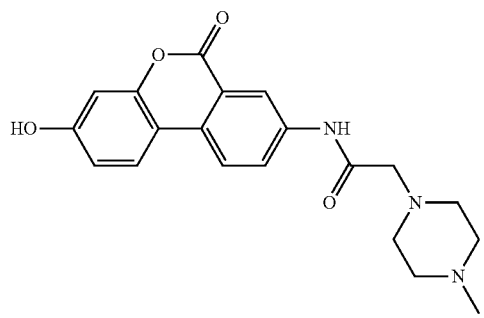

57

Step 1: Synthesis of N-(3-(benzyloxy)-6-oxo-6H-benzo[c]chromen-8-yl)-2-(piperidin-1-yl)acetamide

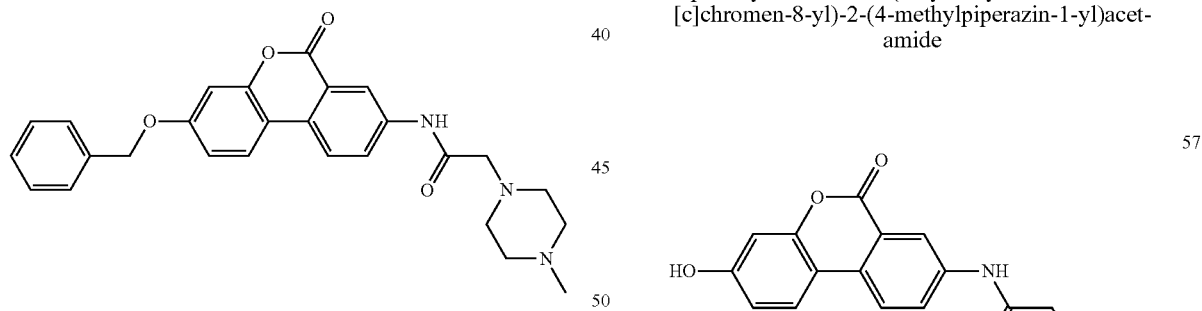

N-(3-(benzyloxy)-6-oxo-6H-benzo[c]chromen-8-yl)-2-chloroacetamide (200 mg, 0.510 mmol) was suspended in THF (5 ml) and the potassium carbonate (140 mg, 1.02 mmol) was added in one portion. The minimum amount of DMF (5-6 ml) were added in order to solubilize the suspension. Then 1-methylpiperazine (0.062 ml, 0.56 mmol) was added dropwise via syringe and the reaction was heated to 80° C. for 2 h. Upon complete consumption of the starting material (as indicated by TLC) the reaction was allowed to cool down to r.t. and then the mixture was concentrated under reduced pressure. The crude product was purified by flash column chromatography (MeOH in DCM 0-20%) to obtain N-(3-(benzyloxy)-6-oxo-6H-benzo[c]chromen-8-yl)-2-(piperidin-1-yl)acetamide (148 mg, 64%) as a white solid. $^1$H NMR (400 MHz, DMSO) δ 10.21 (s, 1H), 8.59 (d, J=2.3 Hz, 1H), 8.29 (d, J=8.9 Hz, 1H), 8.20 (d, J=8.8 Hz, 1H), 8.11 (dd, J=8.8, 2.3 Hz, 1H), 7.55-7.30 (m, 5H), 7.14-7.03 (m, 2H), 5.23 (s, 2H), 3.17 (s, 2H), 2.68-2.66 (m, 8H), 2.39 (s, 3H).

Step 2: Synthesis of N-(3-hydroxy-6-oxo-6H-benzo[c]chromen-8-yl)-2-(4-methylpiperazin-1-yl)acetamide A solution of N-(3-(benzyloxy)-6-oxo-6H-benzo[c]chromen-8-yl)-2-(piperidin-1-yl)acetamide (148 mg. 0.320 mmol) Pd(OH)$_2$/C (40 mg, 0.032 mmol) in MeOH (3 ml) and DCM (3 ml) was stirred under hydrogen at atmospheric pressure overnight. The reaction mixture was filtered over a pad of celite and the solvent was evaporated under vacuum to give N-(3-hydroxy-6-oxo-6H-benzo[c]chromen-8-yl)-2-(4-methylpiperazin-1-yl)acetamide (69 ng, 58%) as a pale yellow solid.

MS (ESI+): m/z=368.

K) Thionoester "A" Group Analogues

Synthesis of 3,8-dimethoxy-6H-benzo[c]chromene-6-thione (58)

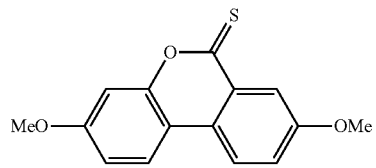

58

A mixture of 3,8-dimethoxy-6H-benzo[c]chromen-6-one (previously described above) (140 mg, 0.154 mmol) and lawesson's reagent (552 mg, 1.34 mmol) were refluxed in toluene o.n. The reaction was monitored by TLC which showed that reaction is not complete so lawesson's reagent (884 mg, 2.19 mmol) were added and reflux continued overnight. The reaction mixture was filtered off and the solvent was evaporated under vacuum. The crude was purified by MPLC (SiO$_2$, EtOAc/cyclohexane 0% to 25%) to afford 3,8-dimethoxy-6H-benzo[c]chromene-6-thione (110 mg, 74%,) as a yellow solid. R$_f$=0.4 (EtOAc/hexane 20%) yellow solid. $^1$H NMR (400 MHz, CDCl3) δ 8.21 (d, J=2.8 Hz, 1H), 7.92 (dd, J=8.9, 6.7 Hz, 2H), 7.39 (dd, J=8.9, 2.8 Hz, 1H), 7.03 (d, J=2.6 Hz, 1H), 6.99-6.95 (dd, J=1H), 3.96 (s, 3H), 3.88 (s, 3H).

Synthesis of 3,8-dihydroxy-6H-benzo[c]thiochromen-6-one (59)

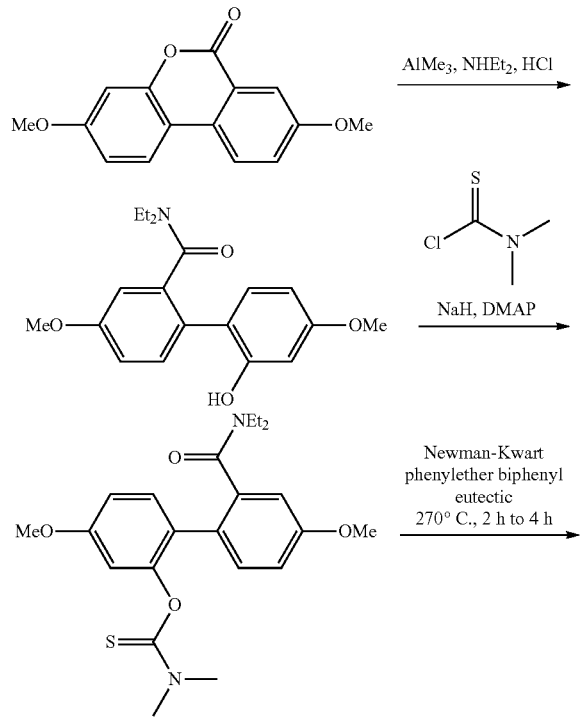

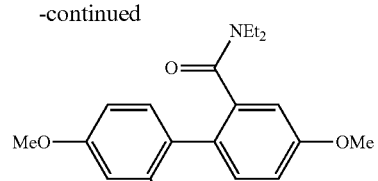

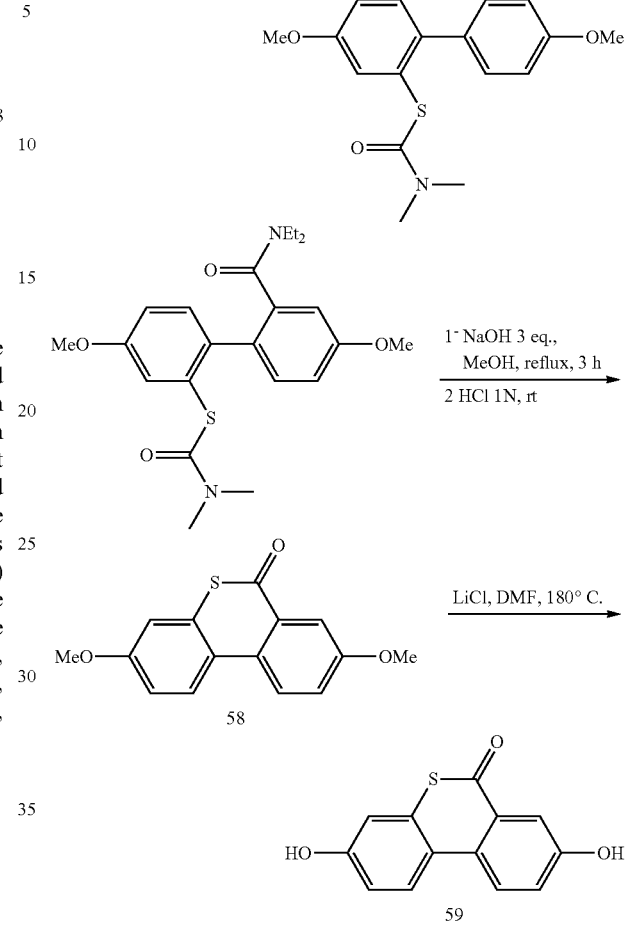

58 was prepared in 4 steps from 17 according to a described procedure in Org. Lett., Vol. 7, No. 3, 2005, 41.1-414. The product was obtained as a white solid. The analytical data fully matched to the one that was previously, reported in the literature.

Step 5: Synthesis of 3,8-dihydroxy-6H-benzo[c]thiochromen-6-one

In a sealed tube, a mixture of Lithium Chloride (65 mg, 1.5 mmol) and 3,8-dimethoxy-6H-benzo[c]thiochromen-6-one (70 mg, 0.26 mmol) in DMF (1 ml) was heated at 130° C. for 2 days. The solvent was evaporated under vacuum and the crude was loaded on silica gel and was purified by MPLC (SiO$_2$, Methanol/Dichloromethane 0% to 10%) to afford 3,8-dihydroxy-6H-benzo[c]thiochromen-6-one (28 mg, 45%). as a yellow solid. $^1$H NMR (400 MHz, DMSO) δ 10.19 (s, 2H), 8.32 (dd, J=15.6, 9.1 Hz, 2H), 7.53 (d, J=2.8 Hz, 1H), 7.31 (dd, J=8.9, 2.9 Hz, 1H), 6.92 (dd, J=8.9, 2.6 Hz, 1H), 6.87 (d, J=2.5 Hz, 1H).

Synthesis of
3,8-dihydroxy-6H-benzo[c]thiochromene
5,5-dioxide (62)

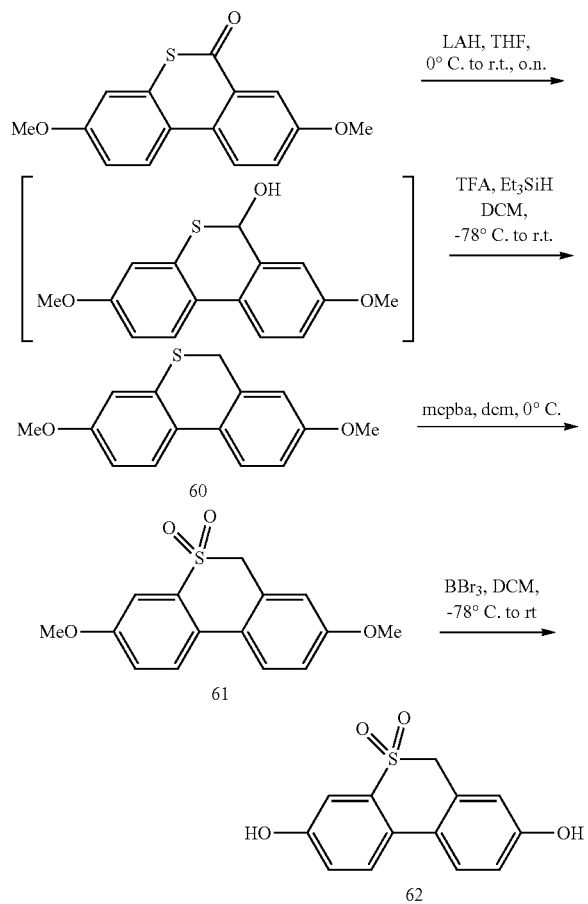

Step 1: Synthesis of
3,8-dimethoxy-6H-benzo[c]thiochromene (60)

LAH (35 mg, 0.91 mmol) was added to solution of 3,8-dimethoxy-6H-benzo[c]thiochromen-6-one (250 mg, 0.910 mmol) in DCM (10 ml) at 0° C. and the mixture was stirred overnight at room temperature. workup: add 10 ml Et$_2$O followed by 0.05 ml of MeOH, NaOH 1N 0.025 ml then water 3 drops and stirring continued for 15 min. Na$_2$SO$_4$ was added and the reaction mixture was filtered off and concentrated under vacuum. The crude was dissolved in DCM (5 ml) and cooled down to −78° C., TFA (0.354 ml, 4.59 mmol) was added dropwise and stirred 60 min at −78° C., then EtSi$_3$H (0.290 ml, 1.84 mmol) was added and the reaction was allowed to warm to room temperature overnight. The reaction mixture was washed with Na$_2$CO$_3$ saturated solution and the organic layer was dried over sodium sulfate and concentrated under vacuum to afford 230 mg of crude material, which was triturated in Et$_2$O to afford 3,8-dimethoxy-6H-benzo[c]thiochromene (160 mg, 67%) as a white solid. $^1$H NMR (400 MHz, CDCl$_3$) δ 7.64 (d, J=8.7 Hz, 1H), 7.54 (d, J=8.6 Hz, 1H), 6.94 (d, J=2.7 Hz, 1H), 6.89 (dd, J=8.6, 2.7 Hz, 1H), 6.81 (dd, J=8.7, 2.7 Hz, 1H), 6.77 (d, J=2.7 Hz, 1H), 3.84 (s, 3H), 3.82 (s, 3H), 3.81 (s, 2H).

Step 2: Synthesis of
3,8-dimethoxy-6H-benzo[c]thiochromene
5,5-dioxide (61)

m-CPBA (150 mg, 0.62 mmol) was added to a solution of 3,8-dimethoxy-6H-benzo[c]thiochromene (80 mg, 0.31 mmol) in dichloromethane (4 ml) at 0° C. and the mixture was allowed to warm to room temperature over 2 h. 1 M Na$_2$S$_2$O$_3$ solution was added to the reaction mixture. The aqueous phase was extracted with EtOAc and the organic phase was washed with bicarbonate saturated solution twice. The organic phase was dried over sodium sulfate. The organic phase was concentrated under vacuum and filtered over a pad of celite using EtOAc then concentrated to afford 3,8-dimethoxy-6H-benzo[c]thiochromene 5,5-dioxide (66 mg, 73%) as a yellowish solid. $^1$H NMR (400 MHz, CDCl$_3$) δ 7.71 (dd, J=8.7, 4.4 Hz, 2H), 7.52 (d, J=2.8 Hz, 1H), 7.20 (dd, J=8.8, 2.7 Hz, 1H), 7.01 (dd, J=8.7, 2.7 Hz, 1H), 6.83 (d, J=2.7 Hz, 1H), 4.36 (s, 2H), 3.91 (s, 3H), 3.86 (s, 3H).

Step 3: Synthesis of
3,8-dihydroxy-6H-benzo[c]thiochromene
5,5-dioxide (62)

BBr$_3$ (0.76 ml, 0.76 mmol) was added to a solution of 3,8-dimethoxy-6H-benzo[c]thiochromene 5,5-dioxide (55 mg, 0.19 mmol) in DCM 2 ml at −70° C. and the mixture was allowed to warm to room temperature overnight. TLC showed 2 spots. Methanol was added to the mixture at 0° C. was concentrated under vacuum and loaded on silica then purified by MPLC (SiO$_2$, MeOH/DCM 0% to 8%) to afford 3,8-dihydroxy-6H-benzo[c]thiochromene 5,5-dioxide (23 mg, 46%) as a yellowish solid. $^1$H NMR (400 MHz, DMSO) δ 10.29 (s, 1H), 9.87 (s, 1H), 7.79 (d, J=8.8 Hz, 1H), 7.71 (d, J=8.6 Hz, 1H), 7.24 (d, J=2.6 Hz, 1H), 7.11 (dd, J=8.6, 2.7 Hz, 1H), 6.86 (dd, J=8.5, 2.6 Hz, 1H), 6.82 (d, J=2.6 Hz, 1H), 4.65 (s, 2H).

Synthesis of
3,8-dihydroxy-6H-benzo[c]thiochromene 5-oxide
(64)

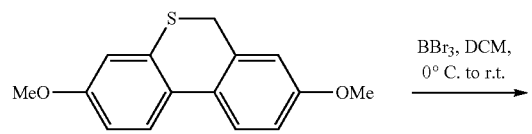

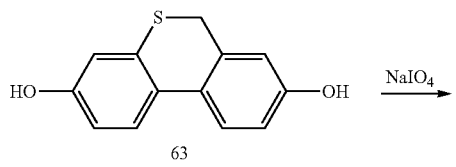

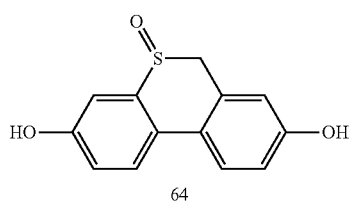

Step 1: Synthesis of
6H-benzo[c]thiochromene-3,8-diol (63)

BBr$_3$ (0.81 ml, 0.81 mmol) was added at 0° C. to a solution of 3,8-dimethoxy-6H-benzo[c]thiochromene (70 mg, 0.27 mmol) in DCM 4 ml and allowed to warm to room temperature overnight. The reaction mixture was poured into methanol at 0° C. and stirred for 10 minutes then the solvent was evaporated under vacuum. The crude was filtered over a pad of silica to afford 6H-benzo[c]thiochromene-3,8-diol (40 mg, 64%) as a grey solid. R$_f$=0.75 (EtOAc/hexane 50/50). $^1$H NMR (400 MHz, DMSO) δ 9.56 (s, 1H), 9.50 (s, 1H), 7.56 (d, J=8.6 Hz, 1H), 7.44 (d, J=8.5 Hz, 1H), 6.75-6.64 (m, 4H), 5.76 (s, 1H), 3.78 (s, 2H).

Step 2: Synthesis of
3,8-dihydroxy-6H-benzo[c]thiochromene 5-oxide
(64)

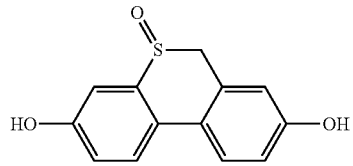 [SMILES: O=S1Cc2cc(O)ccc2-c2ccc(O)cc21]

A solution of NaIO4 (26 mg 0.12 mmol) in water 0.3 ml was added to a solution of 6H-benzo[c]thiochromene-3,8-diol (28 mg, 0.12 mmol) in MeOH 1.5 ml at r.t and the mixture stirred o.n. A precipitate was formed. TLC showed still starting material. Hence, 0.2 eq of NaIO4 dissolved in water 0.2 ml was added and stirring continued; reaction not complete but stopped. DCM was added to dissolve the precipitate and the crude was loaded on silica and purified by MPLC (SiO$_2$, MeOH/DCM 0% to 8%) to afford 3,8-dihydroxy-6H-benzo[c]thiochromene 5-oxide (16 mg, 53%) as a grey solid. R$_f$=0.3 (MeOH/DCM 5%). $^1$H NMR (400 MHz, DMSO) δ 10.05 (s, 1H), 9.72 (s, 1H), 7.64 (dd, J=32.7, 8.5 Hz, 2H), 7.11 (d, J=2.6 Hz, 1H), 7.00 (dd, J=8.5, 2.6 Hz, 1H), 6.83 (d, J=6.7 Hz, 2H), 4.21 (dd, J=90.8, 14.2 Hz, 2H).

1) Ester "A" Group with Bicyclopentane Substitution

Synthesis of 3-hydroxy-8-(3-(hydroxymethyl)bicyclo[1.1.1]pentan-1-yl)-6H-benzo[c]chromen-6-one
(65

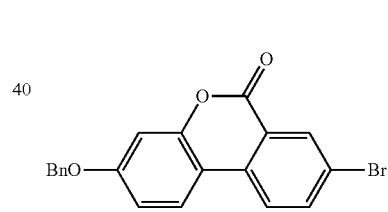

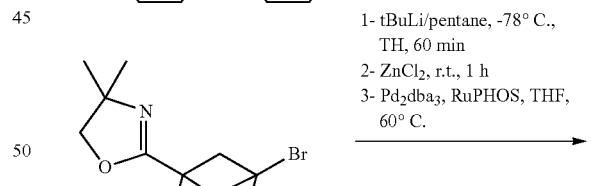

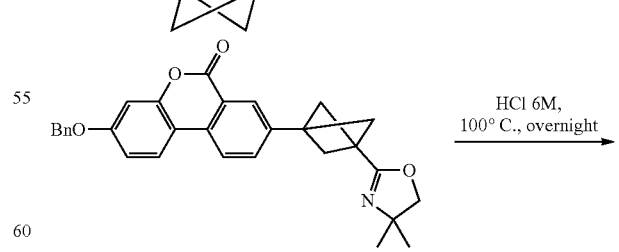

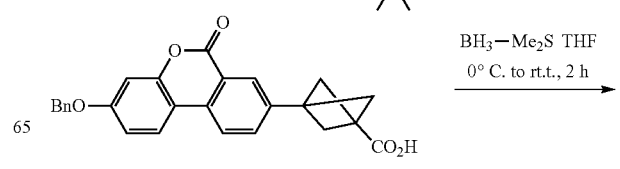

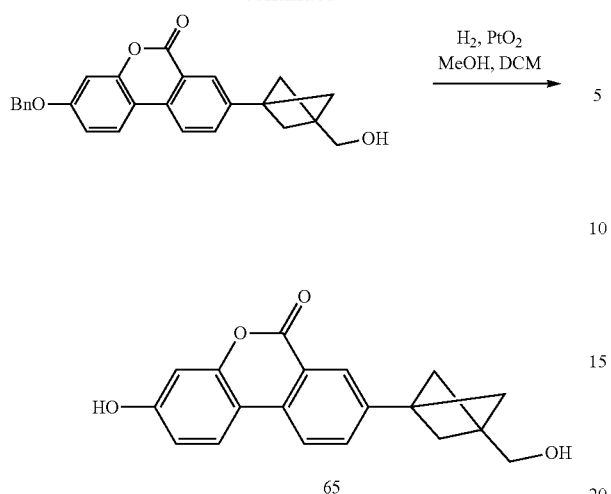

Step 1: Synthesis of 3-(benzyloxy)-8-(3-(4,4-dimethyl-4,5-dihydrooxazol-2-yl)bicyclo[1.1.1]pentan-1-yl)-6H-benzo[c]chromen-6-one To a cooled −78° C. solution of 2-(3-bromobicyclo[1.1.1]pentan-1-yl)-4,4-dimethyl-4,5-dihydrooxazole (192 mg, 0.788 mmol) in anhydrous 2.7 ml was added carefully dropwise tert-butyllithium (1.7 M in pentane, 0.95 ml, 1.63 mmol). The reaction mixture was stirred at −78° C. for 60 min. A solution of ZnCl2 [0.5 M in THF] (1.78 ml, 0.89 mmol) was added dropwise. The reaction mixture was allowed to reach room temperature for 60 min. The resulting zincate solution was slowly added dropwise to a mixture of 3-(benzyloxy)-8-bromo-6H-benzo[c]chromen-6-one (200 mg, 0.525 mmol), RuPhos (49 mg, 0.105 mmol) and Tris(dibezylideneacetone)dipalladium (48 mg, 0.052 mmol) under $N_2$ atmosphere at room temperature. The reaction vessel was sealed and heated at 60° C. for 12 hrs. The reaction mixture was concentrated under reduced pressure and the resulting residue was absorbed on $SiO_2$. Purification of the residue by MPLC ($SiO_2$, EtOAc/cyclohexane 0% to 20%) to give 3-(benzyloxy)-8-(3-(4,4-dimethyl-4,5-dihydrooxazol-2-yl)bicyclo[1.1.1]pentan-1-yl)-6H-benzo[c]chromen-6-one (90 mg, 0.19 mmol, 37%). $^1$H NMR (500 MHz, CDCl$_3$) δ 8.18 (d, J=1.9 Hz, 1H), 7.94 (t, J=8.4 Hz, 2H), 7.64 (dd, J=8.2, 1.9 Hz, 1H), 7.45-7.35 (m, 5H), 6.99 (dd, J=8.8, 2.6 Hz, 1H), 6.93 (d, J=2.6 Hz, 1H), 5.14 (s, 2H), 3.97 (s, 2H), 2.40 (s, 6H), 1.31 (s, 6H).

Step 2: Synthesis of 3-(3-(benzyloxy)-6-oxo-6H-benzo[c]chromen-8-yl)bicyclo[1.1.1]pentane-1-carboxylic acid

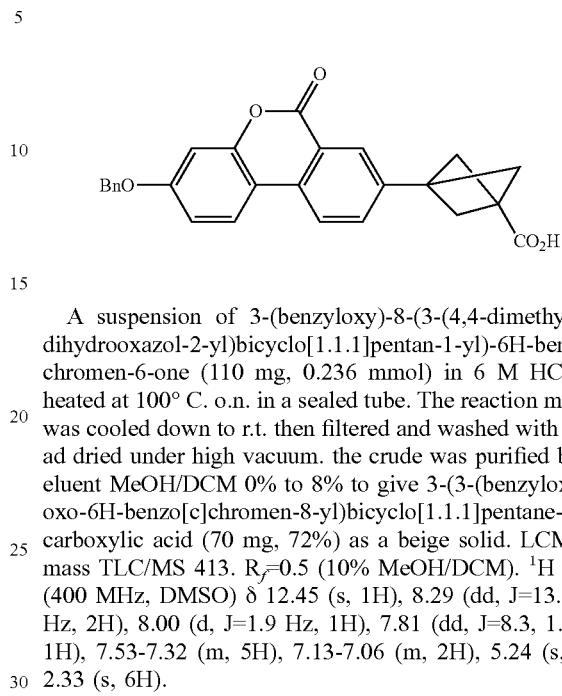

A suspension of 3-(benzyloxy)-8-(3-(4,4-dimethyl-4,5-dihydrooxazol-2-yl)bicyclo[1.1.1]pentan-1-yl)-6H-benzo[c]chromen-6-one (110 mg, 0.236 mmol) in 6 M HCl was heated at 100° C. o.n. in a sealed tube. The reaction mixture was cooled down to r.t. then filtered and washed with water ad dried under high vacuum. the crude was purified by FC eluent MeOH/DCM 0% to 8% to give 3-(3-(benzyloxy)-6-oxo-6H-benzo[c]chromen-8-yl)bicyclo[1.1.1]pentane-1-carboxylic acid (70 mg, 72%) as a beige solid. LCMS no mass TLC/MS 413. R$_f$=0.5 (10% MeOH/DCM). $^1$H NMR (400 MHz, DMSO) δ 12.45 (s, 1H), 8.29 (dd, J=13.3, 8.6 Hz, 2H), 8.00 (d, J=1.9 Hz, 1H), 7.81 (dd, J=8.3, 1.9 Hz, 1H), 7.53-7.32 (m, 5H), 7.13-7.06 (m, 2H), 5.24 (s, 2H), 2.33 (s, 6H).

Step 3: Synthesis of 3-(benzyloxy)-8-(3-(hydroxymethyl)bicyclo[1.1.1]pentan-1-yl)-6H-benzo[c]chromen-6-one Borane dimethyl sulfide complex (0.22 ml, 0.44 mmol, 2 M in THF, 3.0 eq) was added to a solution of (3-(3-(benzyloxy)-6-oxo-6H-benzo[c]chromen-8-yl)bicyclo[1.1.1]pentane-1-carboxylic acid (60 mg, 0.15 mmol, 1.0 eq) at 0° C. in THF 2 ml and stirring continued for 2 h from 0° C. to rt. MeOH was added and the crude was loaded on silica and purified by FC eluent MeOH/DCM 0% to 5% to give 3-(benzyloxy)-8-(3-(hydroxymethyl)bicyclo[1.1.1]pentan-1-yl)-6H-benzo[c]chromen-6-one (47 mg, 0.12 mmol, 81%) as a beige solid. R$_f$=0.6 (MeOH/DCM 5%). $^1$H NMR (400 MHz, CDCl$_3$) δ 8.19 (d, J=1.9 Hz, 1H), 7.94 (dd, J=8.6, 3.3 Hz, 2H), 7.65 (dd, J=8.3, 1.9 Hz, 1H), 7.42 (dtdd, J=14.5, 8.7, 6.9, 1.8 Hz, 5H), 6.99 (dd, J=8.8, 2.6 Hz, 1H), 6.94 (d, J=2.5 Hz, 1H), 5.30 (s, 1H), 5.14 (s, 2H), 3.74 (s, 2H), 2.07 (s, 6H).

Step 4: Synthesis of 3-hydroxy-8-(3-(hydroxymethyl)bicyclo[1.1.1]pentan-1-yl)-6H-benzo[c]chromen-6-one

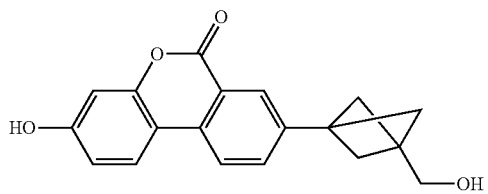 [SMILES: O=c1oc2cc(O)ccc2c2ccc(C34CC(CO)(C3)C4)cc12]

3-(benzyloxy)-8-(3-(hydroxymethyl)bicyclo[1.1.1]pentan-1-yl)-6H-benzo[c]chromen-6-one (45 mg, 0.11 mmol) was dissolved in MeOH 3 ml and DCM 1 ml. $PtO_2$ (6.4 mg, 0.023 mmol) was added and the mixture was hydrogenated under atmospheric pressure for 5 h. The reaction mixture was filtered over a pad of celite and concentrated under vacuum. The crude was purified by FC MeOH/DCM 0% to 10% to give 3-hydroxy-8-(3-(hydroxymethyl)bicyclo[1.1.1]pentan-1-yl)-6H-benzo[c]chromen-6-one (1.5 mg, 0.069 mmol, 62%) as a white solid. $R_f$=0.3 (EtOAc/hexane 50%); $R_f$=0.5 (MeOH/DCM 10%). $^1$H NMR (400 MHz, DMSO) δ 10.31 (s, 1H), 8.21 (d, J=8.3 Hz, 1H), 8.14 (d, J=8.8 Hz, 1H), 7.94 (d, J=1.9 Hz, 1H), 7.74 (dd, J=8.2, 1.9 Hz, 1H), 6.84 (dd, J=8.7, 2.4 Hz, 1H), 6.75 (d, J=2.4 Hz, 1H), 4.58 (t, J=5.5 Hz, 1H), 3.48 (d, J=5.6 Hz, 2H), 1.96 (s, 6H).

2. Synthesis of 7-Membered Urolithin a Analogues

A) Lactones and Ethers "A" Group Analogues

Synthesis of 3,9-dihydroxydibenzo[c,e]oxepin-5(7H)-one (66)

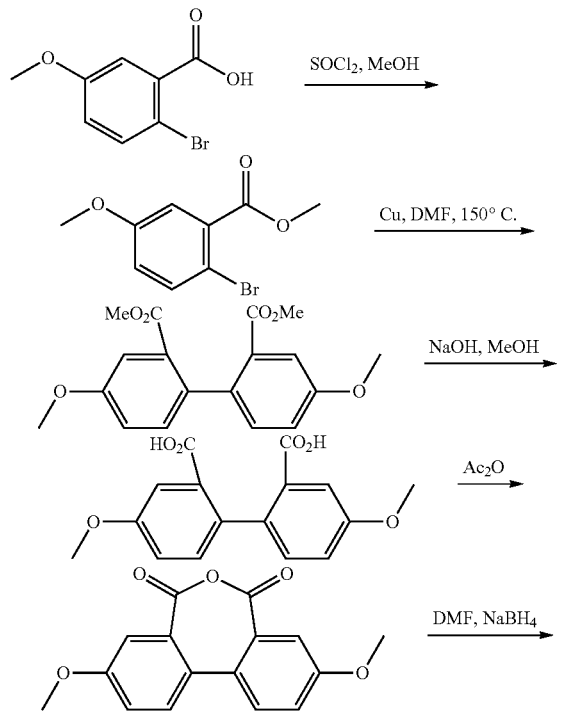

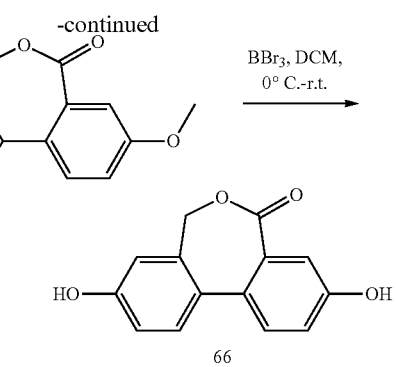

Step 1: Synthesis of 2-bromo-5-methoxybenzoate

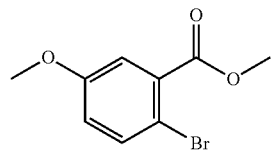

2-bromo-5-methoxybenzoic acid (11.6 g, 50.0 mmol, 1.00 eq.) was dissolved in MeOH (250 mL) and the resulting solution was cooled down to 0° C. in an ice-bath. Stirring at 0° C. was continued for 10 min and then $SOCl_2$ (17.8 g, 150 mmol, 3.00 eq.) was added dropwise via a dropping funnel. The reaction was allowed to warm up to r.t. and as soon as no more starting material could be observed (overnight stirring) all the volatiles were evaporated and the crude residue taken up in diethyl ether and filtered through silica. The filtrate was concentrated under vacuo to afford pure methyl 2-bromo-5-methoxybenzoate (12.3 g, 49.9 mmol, 99%) as a colorless oil that solidified upon storage. NMR matched precedent literature.

Step 2: Synthesis of dimethyl 4,4'-dimethoxy-[1,1'-biphenyl]-2,2'-dicarboxylate

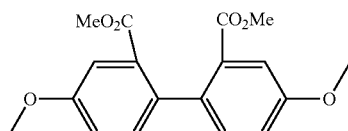

2-bromo-5-methoxybenzoate (12.3 g, 50 mmol, 1.00 eq.) was dissolved in DMF (60 mL) and copper powder (12.7 g, 200 mmol, 4.00 eq.) was added to the solution in one portion. Subsequently the reaction mixture was heated to 150° C. overnight. After overnight stirring the reaction was allowed to cool to r.t. and diluted with a copious amount of water and extracted with diethyl ether (3×100 mL). The combined organic layers were washed with water and brine, dried over $Na_2SO_4$, filtered through silica and concentrated in vacuo. The crude product was purified by flash column chromatography ($SiO_2$, 330 g, EtOAc in Hex 0-30%) to give dimethyl 4,4'-dimethoxy-[1,1*-biphenyl]-2,2'-dicarboxylate (7.5 g, 23 mmol, 91%) as a colorless oil. $^1$H NMR (400

MHz, CDCl$_3$) δ 7.49 (d, J=2.7 Hz, 2H), 7.11 (d, J=8.3 Hz, 2H), 7.06 (dd, J=8.4, 2.7 Hz, 2H), 3.88 (s, 6H), 3.63 (s, 6H).

Step 3: Synthesis of 4,4'-dimethoxy-[1,1'-biphenyl]-2,2'-dicarboxylic acid

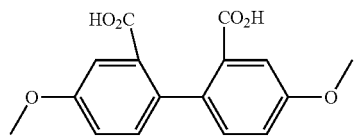

dimethyl 4,4'-dimethoxy-[1,1'-biphenyl]-2,2'-dicarboxylate (7.5 g, 23 mmol, 1.0 eq.) was dissolved in MeOH (90 mL) and a 2 M aq. solution of NaOH (57 mL, 110 mmol, 5.0 eq.) was added dropwise via an addition funnel. The reaction was refluxed over the weekend before being allowed to cool to r.t. upon which the reaction mixture was concentrated under vacuo. The remaining organic layer was slightly diluted with water and washed with DCM to remove all organic impurities. The layers were separated and the aqueous layer was transferred into a conical flask and with stirring acidified to pH1 with 2 M KHSO$_4$. Stirring was continued for 30 min and the formed precipitate was filtered, washed with water and dried under high vacuum to obtain 4,4'-dimethoxy-[1,1'-biphenyl]-2,2'-dicarboxylic acid (6.64 g, 22.0 mmol, 97%) as a free-flowing white solid. $^1$H NMR (400 MHz, DMSO) δ 12.43 (s, 2H), 7.33 (d, J=2.6 Hz, 2H), 7.14-7.01 (m, 4H), 3.82 (s, 6H).

Step 4: Synthesis of 3,9-dimethoxydibenzo[c,e]oxepine-5,7-dione

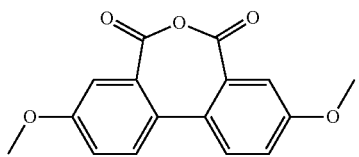

4,4'-dimethoxy-[1,1'-biphenyl]-2,2'-dicarboxylic acid (2.60 g, 10.1 mmol, 1.0 eq.) was suspended in Ac$_2$O (50 mL) and the suspension was stirred overnight. The reaction was monitored by LCMS and after overnight stirring the starting material completely disappeared. Then the reaction mixture was filtered and washed with diethyl ether to facilitate drying. The filter cake was dried under high vacuum to yield 3,9-dimethoxydibenzo[c,e]oxepine-5,7-dione (2.87 g, 10.1 mmol, 99%). The NMR matched with the one reported in the literature.

Step 5: Synthesis of 3,9-dimethoxydibenzo[c,e]oxepin-5(7H)-one

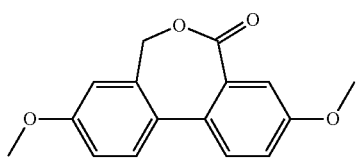

3,9-dimethoxydibenzo[c,e]oxepine-5,7-dione (150 mg, 0.530 mmol, 1.0 eq.) was suspended in DMF (5 mL) and cooled to 0° C. before sodium borohydride (20 mg, 0.53 mmol, 1.0 eq.) was added slowly. After two hours the reaction mixture was poured into aq. HCl (6 M, 5 mL) which was then subsequently diluted with water (10 mL) and stirred overnight. The product was precipitated overnight and was filtered before being taken up in DCM (25 mL) and washed with water (3×10 mL). The organic layer was dried over anhydrous Na$_2$SO$_4$, filtered, concentrated in vacuo, filtered through basic alumina with DCM and dried to afford 3,9-dimethoxydibenzo[c,e]oxepin-5(7H)-one (85 mg, 0.31 mmol, 60%) as a white solid. $^1$H NMR (400 MHz, CDCl$_3$) δ 7.52 (d, J=8.6 Hz, 1H), 7.50-7.44 (m, 2H), 7.19 (dd, J=8.7, 2.8 Hz, 1H), 7.05 (dd, J=8.6, 2.7 Hz, 1H), 6.97 (d, J=2.7 Hz, 1H), 4.98 (d, J=28.5 Hz, 2H), 3.90 (s, 3H), 3.87 (s, 3H).

Step 5: Synthesis of 3,9-dihydroxydibenzo[c,e]oxepin-5(7H)-one

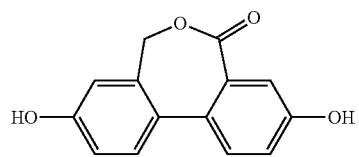

66

3,9-dimethoxydibenzo[c,e]oxepin-5(7H)-one (75 mg, 0.28 mmol, 1.0 eq.) was dissolved in DCM (6 mL) and cooled down to 0° C. in an ice-bath and stirring was continued for 5 min. Then BBr$_3$ (0.83 ml, 1 M in DCM, 0.83 mmol, 3.00 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO$_2$, 12 g, MeOH in DCM 0-5%) 3,9-dihydroxydibenzo[c,e]oxepin-5(7H)-one (19 mg, 0.8 mmol, 28%) as white solid. $^1$H NMR (400 MHz, MeOD) δ 7.49 (dd, J=8.5, 7.3 Hz, 2H), 7.28 (d, J=2.7 Hz, 1H), 7.14 (dd, J=8.6, 2.7 Hz, 1H), 6.97 (dd, J=8.4, 2.6 Hz, 1H), 6.93 (d, J=2.6 Hz, 1H), 4.96 (d, J=19.5 Hz, 2H).

Synthesis of 5,7-dihydrodibenzo[c,e]oxepine-3,9-diol (67)

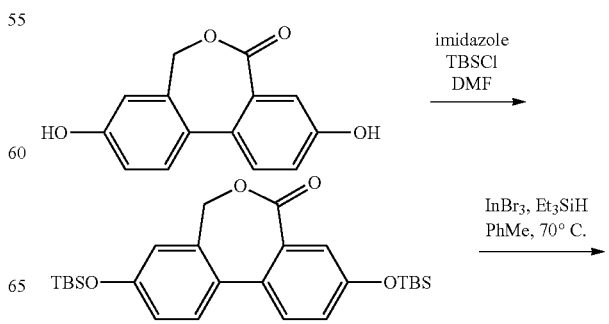

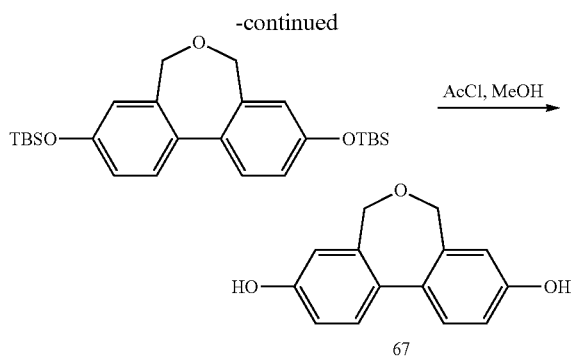

Step 1: Synthesis of 3,9-bis((tert-butyldimethylsilyl)oxy)dibenzo[c,e]oxepin-5(7H)-one

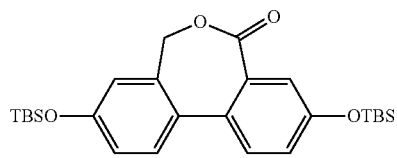 [SMILES: CC(C)(C)[Si](C)(C)Oc1ccc2c(c1)COC(=O)c1cc(O[Si](C)(C)C(C)(C)C)ccc1-2]

TBSCl (174 mg, 1.15 mmol, 2.2 eq.) was dissolved in DCM (9 mL) and the resulting solution was cooled to 0° C. in an ice-bath and stirred for 5 min. Then imidazole (89 mg, 1.3 mmol, 2.5 eq.) was slowly added in portions and upon complete addition stirring was continued for 15 min. Subsequently 3,9-dihydroxydibenzo[c,e]oxepin-5(7H)-one (127 mg, 0.520 mmol, 1.0 eq.) was added to the reaction mixture which became heterogenous upon addition of the substrate. Therefore DMF (1 mL) was added in order to homogenize the mixture. Stirring at r.t. was continued overnight before the DCM was removed at the rotary evaporator and the remaining DMF solution was quenched with copious amounts of water and extracted with diethyl ether (3×10 mL). The combined organic layers were washed with water and brine, dried over anhydrous $Na_2SO_4$, filtered and concentrated to give the crude product which was further purified by MPLC ($SiO_2$, 40 g, EtOAc in Hex 0-20%) to afford 3,9-bis((tert-butyldimethylsilyl)oxy)dibenzo[c,e]oxepin-5(7H)-one (199 mg, 0.42 mmol 82%) as a white solid. $^1$H NMR (400 MHz, $CDCl_3$) δ 7.47-7.38 (m, 3H), 7.10 (dd, J=8.6, 2.6 Hz, 1H), 6.97 (dd, J=8.4, 2.6 Hz, 1H), 6.90 (d, J=2.6 Hz, 1H), 4.88 (d, J=2H), 1.01 (d, J=1.9 Hz, 18H), 0.25 (d, J=8.8 Hz, 12H).

Step 2: Synthesis of 3,9-bis((tert-butyldimethylsilyl)oxy)-5,7-dihydrodibenzo[c,e]oxepine

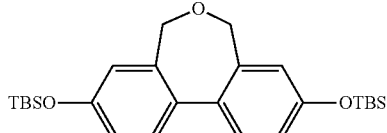

3,9-bis((tert-butyldimethylsilyl)oxy)dibenzo[c,e]oxepin-5(7H)-one (200 mg, 0.430 mmol, 1.0 eq.) was dissolved in toluene (5 mL) and $Et_3SiH$ (0.27 ml, 1.7 mmol, 4.0 eq.) was added in one portion. The reaction mixture was heated to 70° C. in a pre-heated oil-bath. Upon stirring for 5 min at 70° C. $InBr_3$ (15 mg, 0.04 mmol, 0.10 eq.) was added in one portion. A quick color change to orange as well as the evolution of gas could be observed and stirring was continued for 1 h and the TLC did not show any more starting material. The reaction mixture was cooled down, filtered and the precipitate washed with DCM. The filtrate was loaded on silica and the crude was purified by flash column chromatography ($SiO_2$, 25 g, DCM in Hex 0-10%) to yield 3,9-bis((tert-butyldimethylsilyl)oxy)-5,7-dihydrodibenzo[c,e]oxepine (194 mg, 0.430 mmol, 99%) as a white solid. $^1$H NMR (400 MHz, $CDCl^3$) δ 7.36 (d, J=8.3 Hz, 2H), 6.94 (dd, J=8.3, 2.5 Hz, 2H), 6.90 (d, J=2.5 Hz, 2H), 4.31 (s, 4H), 1.01 (s, 18H), 0.24 (s, 12H).

Step 3: Synthesis of 5,7-dihydrodibenzo[c,e]oxepine-3,9-diol

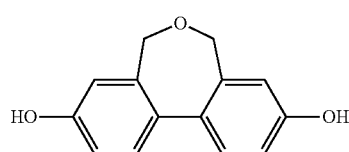

3,9-bis((tert-butyldimethylsilyl)oxy)-5,7-dihydrodibenzo[c,e]oxepine (194 mg, 0.430 mmol, 1.0 eq.) was dissolved in MeOH (12 mL) and the reaction mixture was cooled to 0° C. and AcCl (167 mg, 2.12 mmol, 5.0 eq.) were added dropwise via syringe. Upon complete addition, the reaction mixture was allowed to r.t. and stirring was continued over the weekend. The reaction was quenched with water and extracted into diethyl ether (3×15 mL) and the combined organic layers were washed with $NaHCO_3$ and brine, dried over $Na_2SO_4$ and filtered through silica with diethyl ether washings and then concentrated to give pure 5,7-dihydrodibenzo[c,e]oxepine-3,9-diol (71 mg, 0.31 mmol, 73%) as a white solid. $^1$H NMR (400 MHz, DMSO) δ 9.55 (s, 2H), 7.30 (d, J=8.2 Hz, 2H), 6.87 (dd, J=8.2, 2.6 Hz, 2H), 6.84 (d, J=2.5 Hz, 2H), 4.13 (s, 4H).

B) Amine "A" Group Analogues

Synthesis of 6-methyl-6,7-dihydro-5H-dibenzo[c,e]azepine-3,9-diol (68)

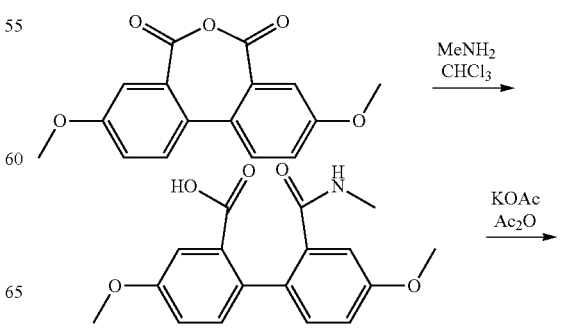

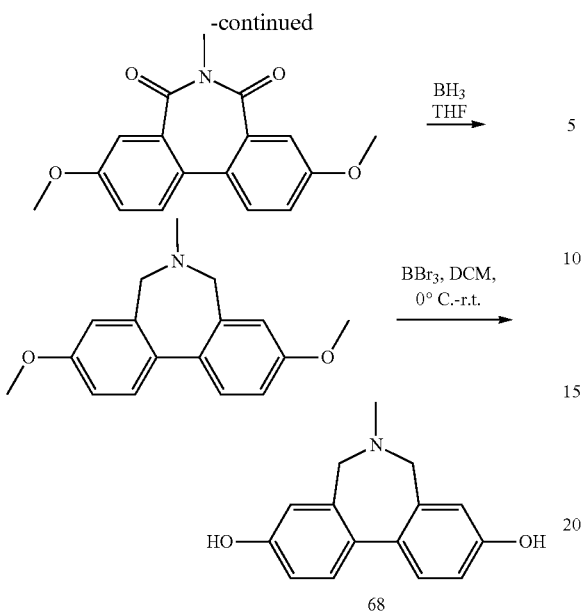

Step 1: Synthesis of 4,4'-dimethoxy-T-(methylcarbamoyl)-[1,1'-biphenyl]-2-carboxylic acid 3,9-dimethoxydibenzo[c,e]oxepine-5,7-dione (569 mg, 2.00 mmol, 1.0 eq.) was dissolved in CHCl₃ (20 mL) and to the resulting solution a 2 M solution of MeNH₂ (1.20 mL, 2.40 mmol, 1.2 eq.) was added in one portion. Upon addition of the MeNH₂ a precipitate formed and the complete disappearance of starting material could be observed via LCMS. The precipitate was filtered over a glass frit (Por.4) and the filter residue was dried under vacuo to afford pure 4,4'-dimethoxy-2'-(methylcarbamoyl)-[1,1'-biphenyl]-2-carboxylic acid (631 mg, 2.00 mmol, 99%) as a light brown solid. LCMS showed clean product which was carried on further to the next step.

Step 2: Synthesis of 3,9-dimethoxy-6-methyl-5H-dibenzo[c,e]azepine-5,7(6H)-dione 4,4'-dimethoxy-2'-(methylcarbamoyl)-[1,1'-biphenyl]-2-carboxylic acid (631 mg, 2.00 mmol, 1.00 eq.) were suspended in Ac₂O (20 mL) and KOAc (393 mg, 4.00 mmol, 2.00 eq.) were added in one portion. The reaction was stirred overnight and LCMS showed the complete conversion of starting material, therefore the suspension was filtered and the filter residue was dried under high vacuum to afford 3,9-dimethoxy-6-methyl-5H-dibenzo[c,e]azepine-5,7(6H)-dione (595 mg, 2.00 mmol, 99%). ¹H NMR (400 MHz, CDCl₃) δ 7.51 (d, J=8.7 Hz, 2H), 7.38 (d, J=2.8 Hz, 2H), 7.16 (dd, J=8.7, 2.8 Hz, 2H), 3.90 (s, 6H), 3.54 (s, 3H).

Step 3: Synthesis of 3,9-dimethoxy-6-methyl-6,7-dihydro-5H-dibenzo[c,e]azepine 3,9-dimethoxy-6-methyl-5H-dibenzo[c,e]azepine-5,7(6H)-dione (541 mg, 1.82 mmol, 1.0 eq.) was suspended in THF (15 mL) and at r.t. BH₃*THF (7.28 mL, 7.28 mmol, 1 M, 4.0 eq.) was added dropwise over the course of 5 min. Upon complete addition, the reaction was heated to reflux and stirred overnight. Following the reaction was quenched with MeOH (200 mL) and stirring at 50° C. was continued for 30 min. Subsequently the volatiles were evaporated and the crude material was purified by MPLC (SiO₂, 40 g, MeOH in EtOAc 0-50%) to obtain 3,9-dimethoxy-6-methyl-6,7-dihydro-5H-dibenzo[c,e]azepine (485 mg, 1.80 mmol, 99%) as an orange-brown solid. ¹H NMR (400 MHz, CDCl₃) δ 7.38 (d, J=8.4 Hz, 2H), 6.97 (dd, J=8.4, 2.7 Hz, 2H), 6.91 (d, J=2.7 Hz, 2H), 3.86 (s, 6H), 3.37 (s, 4H), 2.48 (s, 3H).

Step 4: Synthesis of 6-methyl-6,7-dihydro-5H-dibenzo[c,e]azepine-3,9-diol 3,9-dimethoxy-6-methyl-6,7-dihydro-5H-dibenzo[c,e]azepine (376 mg, 1.40 mmol, 1.0 eq.) was dissolved in DCM (10 mL) and cooled down to 0° C. in an ice-bath and stirring was continued for 5 min. Then BBr₃ (6.28 ml, 1 M in DCM, 6.28 mmol, 4.5 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO₂, 40 g, MeOH in DCM 0-5%) 6-methyl-6,7-dihydro-5H-dibenzo[c,e]

azepine-3,9-diol (190 mg, 0.790 mmol, 56%) as pale orange solid. $^1$H NMR (400 MHz, DMSO) δ 10.92-10.62 (m, 2H), 7.37 (d, J=8.2 Hz, 2H), 7.10-6.93 (m, 4H), 3.16 (s, 4H), 2.83 (d, J=4.6 Hz, 3H).

Synthesis of 2,2'-bis(bromomethyl)-4,4'-dimethoxy-1,1'-biphenyl as a common intermediate Step 1: Synthesis of (4,4'-dimethoxy-[1,1'-biphenyl]-2,2'-diyl)dimethanol

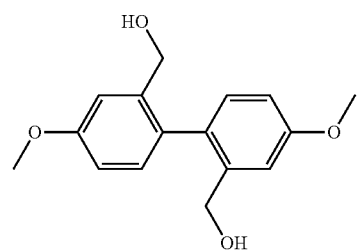

LiAlH$_4$ (251 mg, 6.61 mmol) was added carefully to a solution of 4,4'-dimethoxy-[1,1'-biphenyl]-2,2'-dicarboxylic acid (previously described above) (1.00 g, 3.30 mmol) in THF (8 ml) at 0° c. then refluxed for 4 h (reaction monitored by TLC). After Fieser workup 850 mg of (4,4'-dimethoxy-[1,1'-biphenyl]-2,2'-diyl)dimethanol (810 mg, 2.90 mmol, 89%) as a white solid. $^1$H NMR (400 MHz, CDCl$_3$) δ 7.08-7.03 (m, 4H), 6.87 (dd, J=8.3, 2.8 Hz, 2H), 4.40-4.28 (m, 4H), 3.86 (s, 6H), 2.20 (s, 2H).

Step 2: Synthesis of 2,2'-bis(bromomethyl)-4,4'-dimethoxy-1,1'-biphenyl

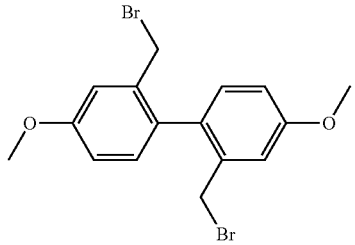

To a solution of (4,4'-dimethoxy-[1,1'-biphenyl]-2,2'-diyl) dimethanol (0.800 g, 2.92 mmol) and CBr$_4$ (4.84 g, 14.6 mmol) in CH$_2$Cl$_2$ (40 mL) cooled to 0° C. under an argon atmosphere was added portion-wise a solution of PPh$_3$ (3.06 g, 11.7 mmol) in CH$_2$Cl$_2$ (20 mL). The reaction was stirred at room temp for 48 hrs, then concentrated and the crude product purified by MPLC on silica gel (EtOAc/hexane: 0% to 10%) to give 2,2'-bis(bromomethyl)-4,4'-dimethoxy-1,1'-biphenyl (0.88 g, 2.20 mmol, 75%) as colorless oil. R$_f$=0.5 (EtOAc/cyclohexane 10%). $^1$H NMR (400 MHz, CDCl$_3$) δ 7.17 (d, J=8.4 Hz, 2H), 7.05 (d, J=2.7 Hz, 2H), 6.91 (dd, J=8.4, 2.7 Hz, 2H), 4.31 (d, J=10.0 Hz, 2H), 4.17 (d, J=10.0 Hz, 2H), 3.87 (s, 6H).

Synthesis of 6-cyclobutyl-6,7-dihydro-5H-dibenzo [c,e]azepine-3,9-diol (69)

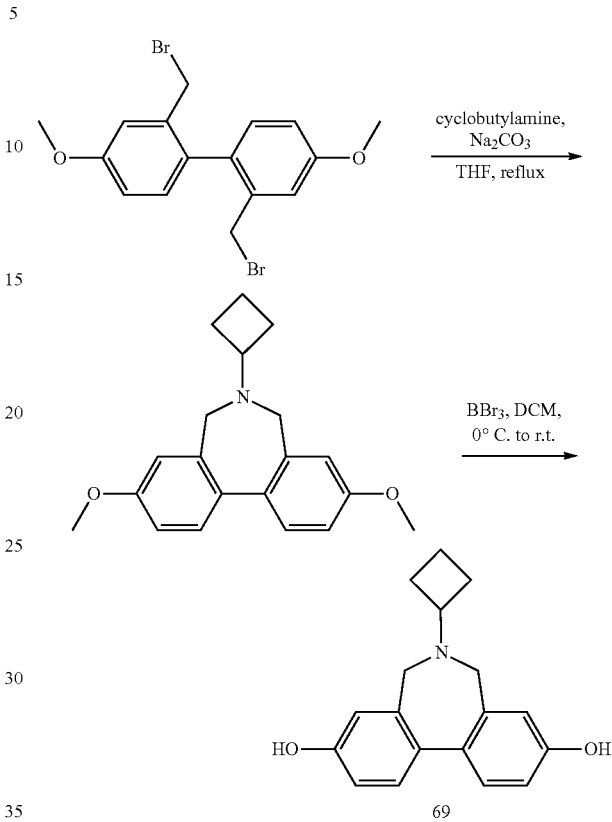

Step 1: Synthesis of 6-cyclobutyl-3,9-dimethoxy-6,7-dihydro-5H-dibenzo[c,e]azepine

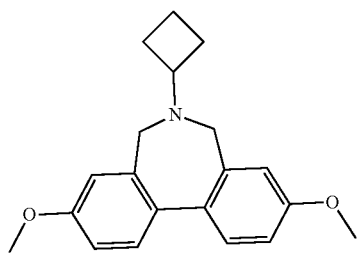

Cyclobutylamine (28 mg, 0.39 mmol) was added to a suspension of 2,2'-bis(bromomethyl)-4,4'-dimethoxy-1,1'-biphenyl (130 mg, 0.325 mmol) and sodium carbonate (138 mg, 130 mmol) in THF 2 ml and the mixture was refluxed for 3 h in THF. The reaction mixture was filtered off and the solvent was removed under vacuum to give 6-cyclobutyl-3,9-dimethoxy-6,7-dihydro-5H-dibenzo[c,e]azepine (100 mg, 0.323 mmol, 99%) as colorless oil. R$_f$=0.3 (EtOAc). $^1$H NMR (400 MHz, CDCl$_3$) δ 7.36 (d, J=8.4 Hz, 2H), 6.95 (dd, J=8.4, 2.7 Hz, 2H), 6.87 (d, J=2.7 Hz, 2H), 3.86 (s, 6H), 3.28 (s, 4H), 3.12 (p, J=8.0 Hz, 1H), 2.21-2.12 (m, 2H), 2.05 (d, J=9.6 Hz, 2H), 1.82-1.65 (m, 2H).

Step 2: Synthesis of 6-cyclobutyl-6,7-dihydro-5H-dibenzo[c,e]azepine-3,9-diol

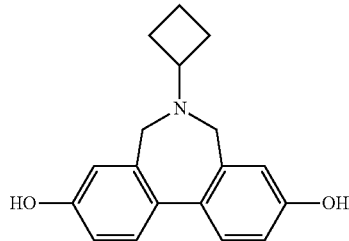

BBr₃ (0.87 ml, 0.87 mmol, 1.0 M in DCM) was added to a solution of 6-cyclobutyl-3,9-dimethoxy-6,7-dihydro-5H-dibenzo[c,e]azepine (90 mg, 0.29 mmol) in dry DCM 3 ml at 0° c. and stirring continued overnight. Methanol 2 ml was added at 0° c. and the mixture was evaporated under vacuum. The crude product purified by flash chromatography on silica gel (Methanol/DCM: 0% to 10%) to give 6-cyclobutyl-6,7-dihydro-5H-dibenzo[c,e]azepine-3,9-diol hydrobromide (35 mg, 0.97 mmol, 33%) as a beige solid. $R_f$=0.3 (MeOH/DCM 8%). MS (ESI+): m/z=282. $^1$H NMR (400 MHz, DMSO) δ 10.72 (s, 1H), 9.85 (s, 2H), 7.37 (d, J=9.0 Hz, 2H), 6.99 (dd, J=5.9, 2.8 Hz, 4H), 3.89 (s, 2H), 3.74 (d, J=8.7 Hz, 1H), 3.51 (s, 2H), 2.37-2.21 (m, 4H), 1.75 (dt, J=28.5, 10.0 Hz, 2H).

Synthesis of 6-isopropyl-6,7-dihydro-5H-dibenzo[c,e]azepine-3,9-diol (70)

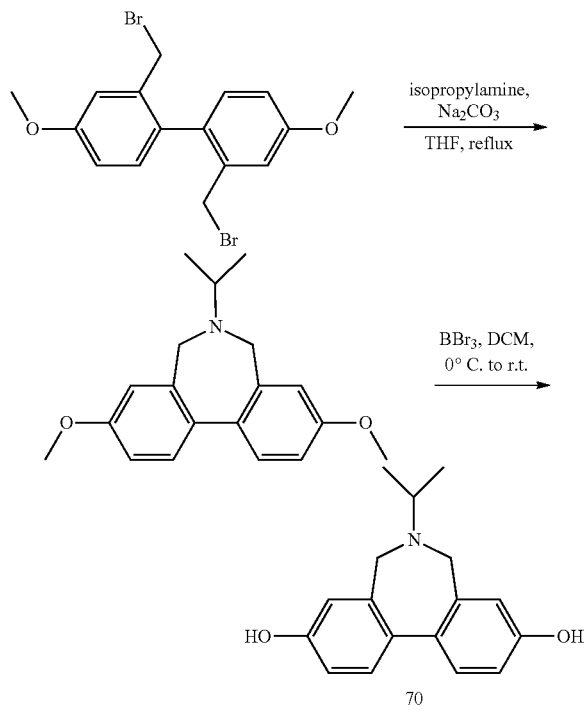

Step 1: Synthesis 6-isopropyl-3,9-dimethoxy-6,7-dihydro-5H-dibenzo[c,e]azepine

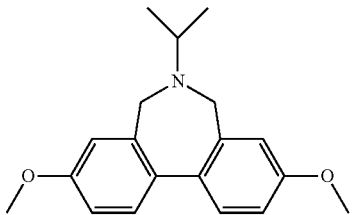

Isopropylamine (27 mg, 0.45 mmol) was added to a suspension of 2,2'-bis(bromomethyl)-4,4'-dimethoxy-1,1'-biphenyl (150 mg, 0.375 mmol) and sodium carbonate (159 mg, 1.50 mmol) in THF (2 ml) and the mixture was refluxed for 3 h in THF. The reaction mixture was filtered off and the solvent was removed under vacuum to 6-isopropyl-3,9-dimethoxy-6,7-dihydro-5H-dibenzo[c,e]azepine (110 mg, 0.323 mmol, 99%) as colourless oil. $^1$H NMR (400 MHz, CDCl₃) δ 7.44-7.33 (m, 2H), 6.99 (d, J=7.3 Hz, 4H), 3.87 (s, 6H), 3.65 (s, 4H), 3.14-3.00 (m, 1H), 1.38 (d, J=6.4 Hz, 6H).

Step 2: Synthesis of 6-isopropyl-6,7-dihydro-5H-dibenzo[c,e]azepine-3,9-diol

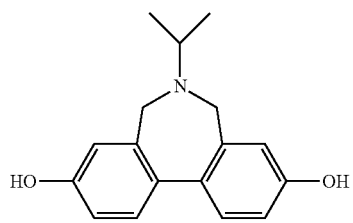

BBr₃ (1.87 ml, 1.87 mmol, 1.0 M in DCM) was added to a solution of 6-isopropyl-3,9-dimethoxy-6,7-dihydro-5H-dibenzo[c,e]azepine (111 mg, 0.370 mmol) in dry DCM 3 ml at 0° C. and stirring continued overnight. Methanol 2 ml was added at 0° C. and the mixture was evaporated under vacuum. The crude product purified by flash chromatography on silica gel (Methanol/DCM: 0% to 10%) to give 6-6-isopropyl-6,7-dihydro-5H-dibenzo[c,e]azepine-3,9-diol (35 mg, 0.97 mmol, 35%) as a beige solid. $R_f$=0.3 (MeOH/DCM 8%). $^1$H NMR (400 MHz, DMSO) δ 10.19 (s, 1H), 9.84 (s, 2H), 7.37 (d, J=8.3 Hz, 2H), 7.05 (d, J=2.6 Hz, 2H), 6.99 (dd, J=8.4, 2.5 Hz, 2H), 3.92 (s, J=4.3 Hz, 4H), 3.63-3.51 (m, 1H), 1.40 (d, J=6.5 Hz, 6H).

C) Imide "A" Group Analogues

Synthesis of 3,9-dihydroxy-5H-dibenzo[c,e]azepine-5,7(6H)-dione (71)

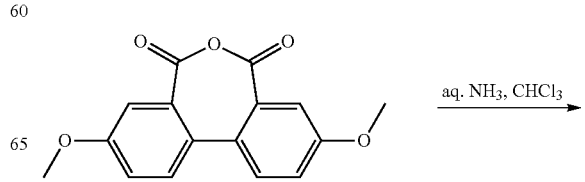

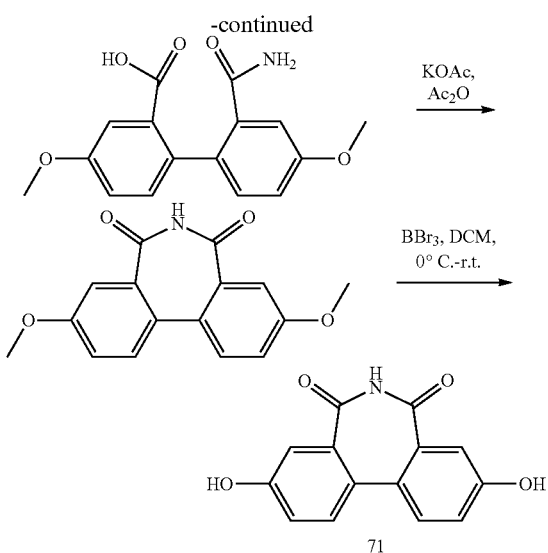

71

Step 1: Synthesis of 2'-carbamoyl-4,4'-dimethoxy-[1,1'-biphenyl]-2-carboxylic acid

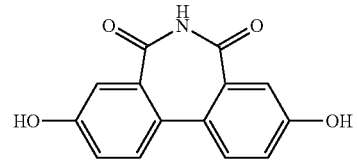

3,9-dimethoxydibenzo[c,e]oxepine-5,7-dione (100 mg, 0.350 mmol, 1.0 eq.) was suspended in 25% aq. NH$_3$ solution (0.70 mL, 0.42 mmol, 1.2 eq.) for 30 min until the complete disappearance of the starting material was confirmed by LCMS (too polar to be monitored by TLC). The reaction mixture was filtered over a glass frit (Por.4) and the filter residue was dried under vacuo to afford pure 2'-carbamoyl-4,4'-dimethoxy-[1,1'-biphenyl]-2-carboxylic acid (106 mg, 0.350 mmol, 99%) as a white solid. LCMS showed clean product after filtration and the product was used without further purification in the next step.

Step 2: Synthesis of 3,9-dimethoxy-5H-dibenzo[c,e]azepine-5,7(6H)-dione

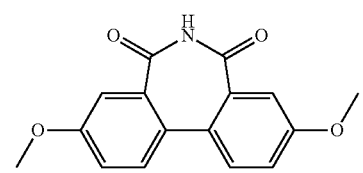

2'-carbamoyl-4,4'-dimethoxy-[1,1'-biphenyl]-2-carboxylic acid (106 mg, 0.350 mmol, 1.0 eq.) was suspended in Ac$_2$O (4 mL) and KOAc (69 mg, 0.70 mmol, 2.0 eq.) was added in one portion. The reaction mixture was stirred at r.t. overnight before being filtered over a small glass frit (Por.4). The precipitate was dried under vacuo to afford 3,9-dimethoxy-5H-dibenzo[c,e]azepine-5,7(6H)-dione (65 mg, 0.23 mmol, 65%) as a white solid. $^1$H NMR (400 MHz, DMSO) δ 11.69 (s, 1H), 7.71 (dd, J=8.7, 1.5 Hz, 2H), 7.40-7.36 (m, 2H), 7.31 (dt, J=8.8, 2.4 Hz, 2H), 3.86 (s, 6H).

Step 3: Synthesis of 3,9-dihydroxy-5H-dibenzo[c,e]azepine-5,7(6H)-dione

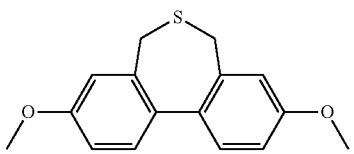

3,9-dimethoxy-5H-dibenzo[c,e]azepine-5,7(6H)-dione (100 mg, 0.350 mmol, 1.0 eq.) was dissolved in DCM (2 mL) and cooled down to 0° C. in an ice-bath and stirring was continued for 5 min. Then BBr$_3$ (1.41 ml, 1 M in DCM, 1.41 mmol, 4.0 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO$_2$, 12 g, MeOH in DCM 0-5%) 3,9-dihydroxy-5H-dibenzo[c,e]azepine-5,7(6H)-dione (56 mg, 0.22 mmol, 62%) as white solid. $^1$H NMR (400 MHz, DMSO) δ 9.66 (s, 2H), 7.13 (d, J=2.6 Hz, 1H), 7.03 (s, 1H), 7.00 (d, J=8.3 Hz, 1H), 6.93 (s, 1H), 6.90 (dd, J=8.3, 2.6 Hz, 1H), 6.87-6.84 (m, 2H), 6.77 (dd, J=8.2, 2.6 Hz, 1H).

D) Thioether and Sulfone "A" Group Analogues

Synthesis 5,7-dihydrodibenzo[c,e]thiepine-3,9-diol (72)

Step 1: Synthesis 3,9-dimethoxy-5,7-dihydrodibenzo[c,e]thiepine

A mixture of 2,2'-bis(bromomethyl)-4,4'-dimethoxy-1,1'-biphenyl (procedure described above) (220 mg, 0.55 mmol) and sodium sulphidehydrate (69 mg, 0.71 mmol) in DMF (3 mL) was heated at 100° C. for 20 min. After cooling, the mixture was poured into water (10 mL), and the precipitate was filtered and washed with water (2×3 mL). The precipitate was taken up in CHCl$_3$ (15 mL), the solution was dried over Na$_2$SO$_4$, and the solvent was evaporated in vacuo to give 3,9-dimethoxy-5,7-dihydrodibenzo[c,e]thiepine (140 mg, 0.510 mmol, 93%) as a yellowish solid.

$^1$H NMR (400 MHz, CDCl$_3$) δ 7.19 (d, J=8.4 Hz, 2H), 6.91 (dd, J=8.3, 2.7 Hz, 2H), 6.87 (d, J=2.6 Hz, 2H), 3.86 (s, 6H), 3.56 (d, J=12.7 Hz, 2H), 3.27 (s, 2H).

Step 2: Synthesis 5,7-dihydrodibenzo[c,e]thiepine-3,9-diol

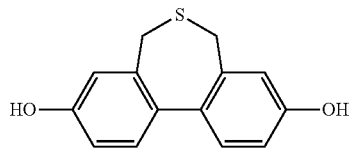
72

A solution of BBr$_3$ (0.59 ml, 0.59 mmol, 1 M in DCM) was added at −78° C. to a solution of 3,9-dimethoxy-5,7-dihydrodibenzo[c,e]thiepine (54 mg, 0.20 mmol) in DCM 2 ml dcm and stirring continued overnight at room temperature. Methanol (5 ml) was added at 0° C. and the solvent was removed in vacuo. The crude was purified by MPLC (SiO$_2$, MeOH/DCM from 0% to 8%) to afford 5,7-dihydrodibenzo[c,e]thiepine-3,9-diol (18 mg, 0.074 mmol, 37%) as a beige solid. R$_f$=0.3 (MeOH/DCM 5%). $^1$H NMR (400 MHz, DMSO) δ 9.46 (s, 2H), 7.09-6.91 (m, 2H), 6.78-6.67 (m, 4H), 3.28 (s, 4H).

Synthesis of 3,9-dihydroxy-5,7-dihydrodibenzo[c,e]thiepine 6,6-dioxide (73)

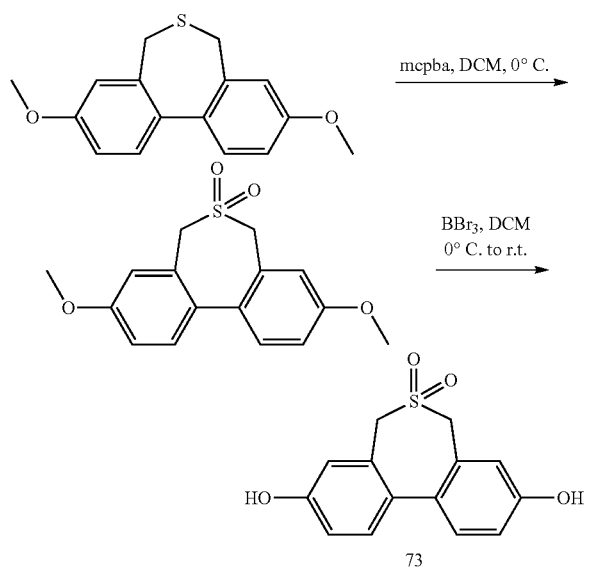

Step 1: Synthesis of 3,9-dimethoxy-5,7-dihydrodibenzo[c,e]thiepine 6,6-dioxide

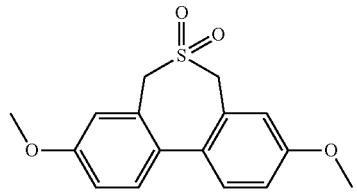

MCPBA (170 mg, 0.690 mmol) was added to 3,9-dimethoxy-5,7-dihydrodibenzo[c,e]thiepine (90 mg, 0.33 mmol) in DCM (2 ml) at 0° c. and the reaction mixture was stirred at room temperature overnight. Na$_2$S$_2$O$_3$ 1 M solution was added and the mixture stirred for 10 minutes, then NaHCO$_3$ saturated solution was added and the mixture was extracted twice with NaHCO$_3$ saturated solution. The organic phase was dried over sodium sulfate, filtered and evaporated under vacuum. The crude was purified by MPLC (SiO$_2$, EtOAc/cyclohexane 0% to 30%) to afford 3,9-dimethoxy-5,7-dihydrodibenzo[c,e]thiepine 6,6-dioxide (90 mg, 0.30 mmol, 89%) as a white solid. $^1$H NMR (400 MHz, CDCl$_3$) δ 7.38 (d, J=8.4 Hz, 2H), 7.03 (dd, J=8.4, 2.6 Hz, 2H), 6.99 (d, J=2.6 Hz, 2H), 4.07-3.93 (q, 4H), 3.88 (s, 6H).

Step 2: Synthesis of 3-9-dihydroxy-5,7-dihydrodibenzo[c,e]thiepine 6,6-dioxide

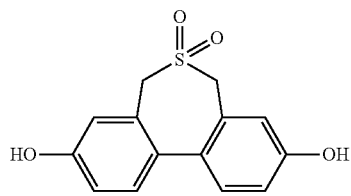
73

A solution of BBr$_3$ (1.0 ml, 1.0 mmol, 1 M in DCM, 3.5 eq.) was added at 0° C. to a solution 3,9-dimethoxy-5,7-dihydrodibenzo[c,e]thiepine 6,6-dioxide (90 mg, 0.30 mmol, 1.0 eq.) in DCM (2 mL) and stirring continued overnight at room temperature. Methanol (5 mL) was added at 0° C. and the solvent was removed in vacuo. The crude was purified by MPLC (EtOAc/Hex from 0% to 70%) to afford 3,9-dihydroxy-5,7-dihydrodibenzo[c,e]thiepine 6,6-dioxide (46 mg, 0.17 mmol, 56%) as a beige solid. R$_f$=0.3 (MeOH/DCM 5%). $^1$H NMR (400 MHz, DMSO) δ 9.76 (s, 2H), 7.26 (d, J=8.1 Hz, 2H). 6.94-6.83 (m, 4H), 4.29 (d, J=13.7 Hz, 2H), 3.73 (d, J=13.7 Hz, 2H)

E) Amides "A" Group Analogues

Synthesis of 3,9-dihydroxy-6,7-dihydro-5H-dibenzo[c,e]azepin-5-one (74)

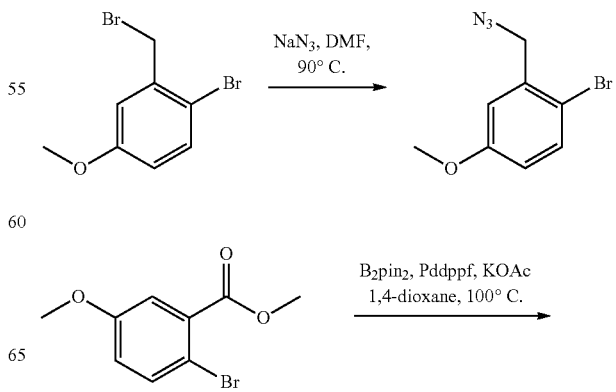

255
-continued

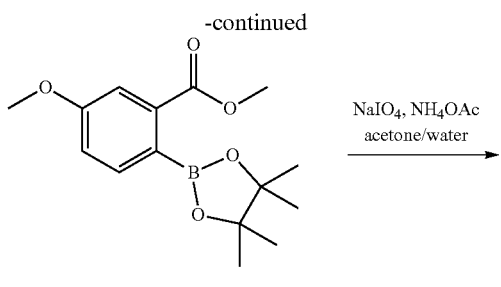

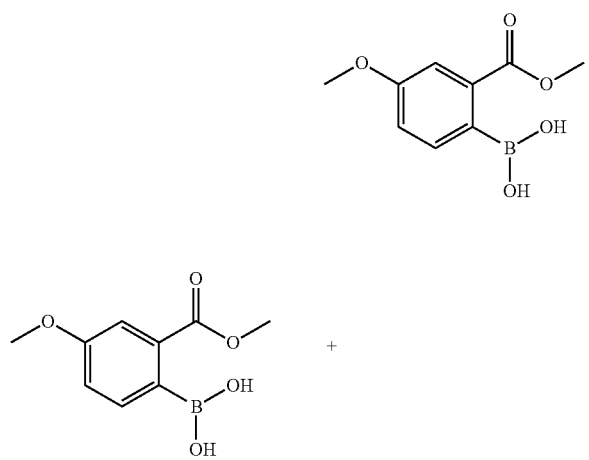

Step 1: Synthesis of 2-(azidomethyl)-1-bromo-4-methoxybenzene

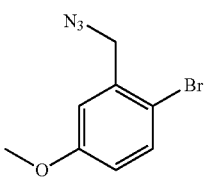

1-bromo-2-(bromomethyl)-4-methoxybenzene (5.00 g, 17.9 mmol, 1.0 eq.) was dissolved in DMF (60 mL) and NaN$_3$ (5.81 g, 89.3 mmol, 5.0 eq.) were added in one portion. Then the reaction mixture was heated to 90° C. and stirring was continued overnight. After overnight stirring the reaction mixture was allowed to cool to r.t., quenched with water (300 mL) and extracted with cyclohexane (3×75 mL). The combined organic layers were dried over anhydrous Na$_2$SO$_4$ and concentrated under vacuo to afford pure 2-(azidomethyl)-1-bromo-4-methoxybenzene (4.32 g, 17.8 mmol, 99%) as a colorless oil. $^1$H NMR (400 MHz, CDCl$_3$) δ 7.47 (d, J=8.8 Hz, 1H), 6.95 (d, J=3.0 Hz, 1H), 6.76 (dd, J=8.8, 3.0 Hz, 1H), 4.45 (s, 2H), 3.81 (s, 3H).

Step 2: Synthesis of 5-methoxy-2-(4,4,5,5-tetramethyl-1,3,2-dioxaborolan-2-yl)benzoate

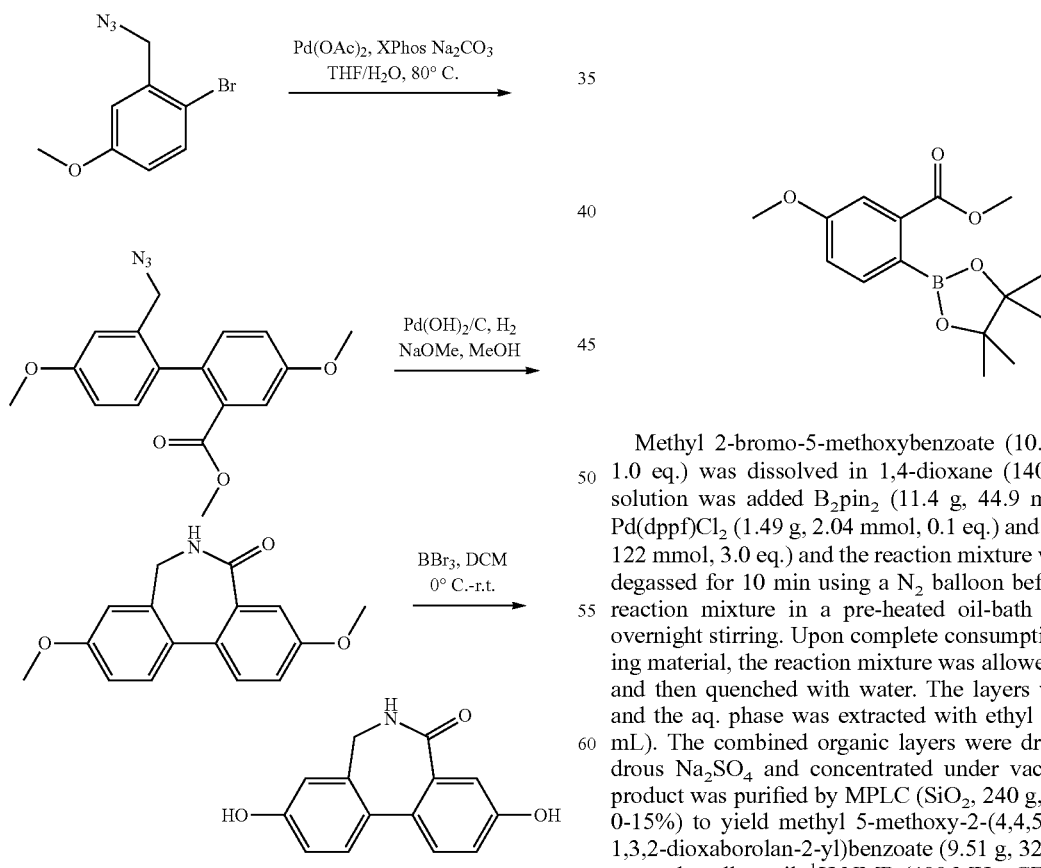

Methyl 2-bromo-5-methoxybenzoate (10.0, 40.8 mmol, 1.0 eq.) was dissolved in 1,4-dioxane (140 mL). To this solution was added B$_2$pin$_2$ (11.4 g, 44.9 mmol, 1.1 eq.), Pd(dppf)Cl$_2$ (1.49 g, 2.04 mmol, 0.1 eq.) and KOAc (12.0 g, 122 mmol, 3.0 eq.) and the reaction mixture was thoroughly degassed for 10 min using a N$_2$ balloon before putting the reaction mixture in a pre-heated oil-bath to 85° C. for overnight stirring. Upon complete consumption of the starting material, the reaction mixture was allowed to cool to r.t. and then quenched with water. The layers were separated and the aq. phase was extracted with ethyl acetate (2×100 mL). The combined organic layers were dried over anhydrous Na$_2$SO$_4$ and concentrated under vacuo. The crude product was purified by MPLC (SiO$_2$, 240 g, EtOAc in Hex 0-15%) to yield methyl 5-methoxy-2-(4,4,5,5-tetramethyl-1,3,2-dioxaborolan-2-yl)benzoate (9.51 g, 32.6 mmol, 78%) as a pale yellow oil. $^1$H NMR (400 MHz, CDCl$_3$) δ 7.27 (d, J=6.1 Hz, 1H), 7.09 (s, 1H), 6.88 (dd, J=8.1, 2.6 Hz, 1H), 3.73 (s, 3H), 3.67 (s, 3H), 1.23 (s, 12H).

Step 3: Synthesis of (4-methoxy-2-(methoxycarbonyl)phenyl)boronic acid

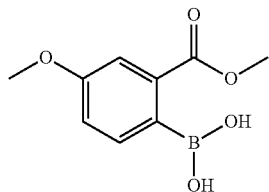

5-methoxy-2-(4,4,5,5-tetramethyl-1,3,2-dioxaborolan-2-yl)benzoate (1.33 g, 4.55 mmol, 1.0 eq.) was dissolved in a mixture of acetone (23 mL) and water (23 mL) and NH$_4$OAc (1.05 g, 13.7 mmol, 3.0 eq.) as well as NaIO4 (2.92, 13.7 mmol, 3.0 eq.) were added in one portion. Upon complete addition the mixture warmed up slightly and stirring was continued overnight. After the disappearance of the starting material (as indicated by TLC) the reaction mixture was filtered and the white precipitate was washed with acetone and the mother liquor concentrated to give pure (4-methoxy-2-(methoxycarbonyl)phenyl)boronic acid (590 mg, 2.81 mmol, 62%) as a white solid. Analytical data matched with the literature.

Step 4: Synthesis of 2'-(azidomethyl)-4,4'-dimethoxy-[1,1'-biphenyl]-2-carboxylate

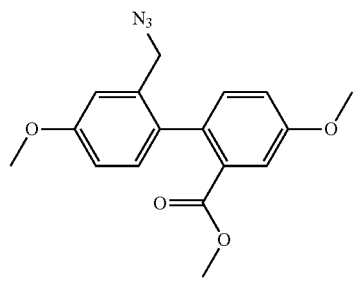

A 20 mL Biotage MW vial was charged with (4-methoxy-2-(methoxycarbonyl)phenyl)boronic acid (563 mg, 2.68 mmol, 1.10 eq.), 2-(azidomethyl)-1-bromo-4-methoxybenzene (590 mg, 2.44 mmol, 1.0 eq.), Pd(OAc)$_2$ (27 mg, 0.12 mmol, 0.05 eq.), XPhos (116 mg, 0.24 mmol, 0.1 eq.) and all reagents were dissolved in THF (15 mL). The reaction mixture was degassed by using a N$_2$ balloon for 10 min and afterwards a solution of Na$_2$CO$_3$ (775 mg, 7.31 mmol, 3.0 eq.) in water (5 mL) was added dropwise at r.t. Upon complete addition the reaction mixture was heated to 80° C. in an oil-bath and stirring was continued overnight. After overnight stirring the reaction mixture was allowed to cool to r.t. and quenched with water, the layers were separated and the aqueous layer was extracted with ethyl acetate (2×10 mL). The combined organic layers were dried over anhydrous Na$_2$SO$_4$ and concentrated under vacuo. The crude product was purified by MPLC (SiO$_2$, 25 g, EtOAc in Hex 0-20%) to give methyl 2'-(azidomethyl)-4,4'-dimethoxy-[1,1'-biphenyl]-2-carboxylate (367 mg, 1.12 mmol, 46%) as a colorless oil. $^1$H NMR (400 MHz, CDCl$_3$) δ 7.47 (d, J=2.7 Hz, 1H), 7.15 (d, J=8.4 Hz, 1H), 7.08 (dd, J=8.4, 2.8 Hz, 1H), 7.04 (d, J=8.4 Hz, 1H), 6.96 (d, J=2.6 Hz, 1H), 6.87 (dd, J=8.4, 2.7 Hz, 1H), 4.09 (d, J=3.1 Hz, 2H), 3.89 (s, 3H), 3.86 (s, 3H), 3.63 (s, 3H).

Step 5: Synthesis of 3,9-dimethoxy-6,7-dihydro-5H-dibenzo[c,e]azepin-5-one

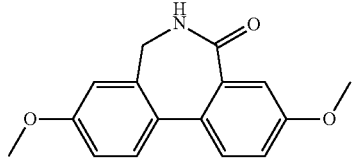

2'-(azidomethyl)-4,4'-dimethoxy-[1,1'-biphenyl]-2-carboxylate (50 mg, 0.15 mmol, 1.0 eq.) was dissolved in MeOH (8 mL) and Pd(OH)$_2$/C (16 mg, 0.02 mmol, 0.15 eq.) as well as NaOMe (33 mg, 0.15 mmol, 1.0 eq.) were added to the solution which was degassed with N$_2$ three times followed by a hydrogen atmosphere exchange for three times. The reaction mixture was stirred overnight at r.t. before being filtered over a pad of celite and purified by MPLC (SiO$_2$, EtOAc in Hex 0-30%) to afford 3,9-dimethoxy-6,7-dihydro-5H-dibenzo[c,e]azepin-5-one (22 mg, 0.08 mmol, 53%) as a white solid. $^1$H NMR (400 MHz, DMSO) δ 8.53 (s, 1H), 7.45 (t, J=8.4 Hz, 2H), 7.28 (d, J=2.8 Hz, 1H), 7.11 (dd, J=8.6, 2.7 Hz, 1H), 6.94 (dd, J=12.2, 3.8 Hz, 2H), 3.84 (dd, J=9.5, 3.6 Hz, 1H), 3.82 (s, 3H), 3.78 (s, 3H), 3.18 (d, J=14.8 Hz, 1H).

Step 6: Synthesis of 3,9-dihydroxy-6,7-dihydro-5H-dibenzo[c,e]azepin-5-one

74

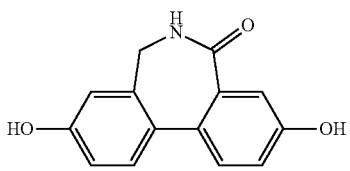

3,9-dimethoxy-6,7-dihydro-5H-dibenzo[c,e]azepin-5-one (64 mg, 0.24 mmol, 1.0 eq.) was dissolved in DCM (2 mL) and cooled down to 0° C. in an ice-bath and stirring was continued for 5 min. Then BBr$_3$ (0.95 ml, 1 M in DCM, 0.95 mmol, 4.0 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO$_2$, 12 g, MeOH in DCM 0-5%) to afford 3,9-dihydroxy-6,7-dihydro-5H-dibenzo[c,e]azepin-5-one (25 mg, 0.10 mmol, 44%) as an orange solid. $^1$H NMR (400 MHz, DMSO) δ 8.39 (t, J=6.1 Hz, 1H), 7.33 (d, J=8.4 Hz, 2H), 7.15 (d, J=2.6 Hz, 1H), 6.97 (dd, J=8.6, 2.6 Hz, 1H), 6.80 (dd, J=8.4, 2.3 Hz, 1H), 6.71 (d, J=2.3 Hz, 1H), 3.80 (ddd, J=35.6, 14.6, 6.1 Hz, 2H).

Synthesis of 3,9-dihydroxy-6-methyl-6,7-dihydro-5H-dibenzo[c,e]azepin-5-one (75)

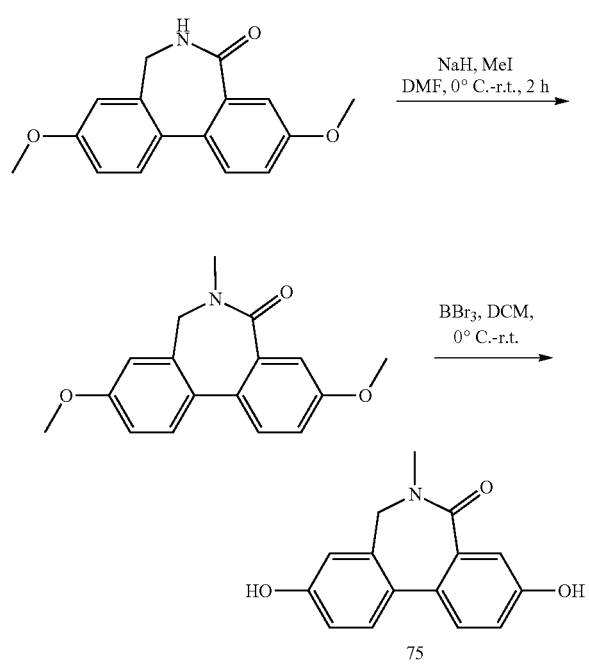

Step 1: Synthesis of 3,9-dimethoxy-6-methyl-6,7-dihydro-5H-dibenzo[c,e]azepin-5-one 3,9-dimethoxy-6,7-dihydro-5H-dibenzo[c,e]azepin-5-one (80 mg, 0.30 mmol, 1.0 eq.) was dissolved in DMF (3.0 mL) and the solution was cooled to 0° C. in an ice-bath and stirring was continued for 10 min before adding 60% NaH in petroleum oil (14 mg, 0.36 mmol, 1.2 eq.) in one portion. The reaction was stirred until the evolution of hydrogen gas completely ceased upon which MeI (0.13 g, 0.89 mmol, 3.0 eq.) was added dropwise. Afterwards the reaction was allowed to warm up to r.t. and stirred for 3 h until the starting material disappeared (as indicated by TLC). The reaction was quenched with ice-water (10 mL) and the aqueous solution was extracted with diethyl ether (3×10 mL) and the organic layers were washed with water and brine, dried over $Na_2SO_4$ and concentrated to afford 3,9-dimethoxy-6-methyl-6,7-dihydro-5H-dibenzo[c,e]azepin-5-one (84 mg, 0.30 mmol, 99%) as a white solid. $^1$H NMR (400 MHz, CDCl$_3$) δ 7.35 (dd, J=16.3, 8.4 Hz, 2H), 7.14 (d, J=2.7 Hz, 1H), 6.96 (dd, J=8.5, 2.7 Hz, 1H), 6.90-6.81 (m, 2H), 4.10-3.75 (m, 2H), 3.10 (s, 3H), 3.00 (s, 3H), 2.90 (s, 3H)

Step 2: Synthesis of 3,9-dihydroxy-6-methyl-6,7-dihydro-5H-dibenzo[c,e]azepin-5-one 3,9-dimethoxy-6-methyl-6,7-dihydro-5H-dibenzo[c,e]azepin-5-one (84 mg, 0.84 mmol, 1.0 eq.) was dissolved in DCM (1 mL) and cooled down to 0° C. in an ice-bath and stirring was continued for 5 min. Then BBr$_3$ (1.20 ml, 1 M in DCM, 1.20 mmol, 4.0 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO$_2$, 12 g, MeOH in DCM 0-5%) to afford 3,9-dihydroxy-6-methyl-6,7-dihydro-5H-dibenzo[c,e]azepin-5-one (40 mg, 0.16 mmol, 52%) as light orange solid. $^1$H NMR (400 MHz, DMSO) δ 9.65 (s, 2H), 7.35 (dd, J=16.3, 8.4 Hz, 2H), 7.14 (d, J=2.7 Hz, 1H), 6.96 (dd, J=8.5, 2.7 Hz, 1H), 6.90-6.81 (m, 2H), 4.20-3.85 (m, 2H), 3.02 (s, 3H).

Synthesis of 3,9-dihydroxy-5,7-dihydro-6H-dibenzo[b,d]azepin-6-one (76)

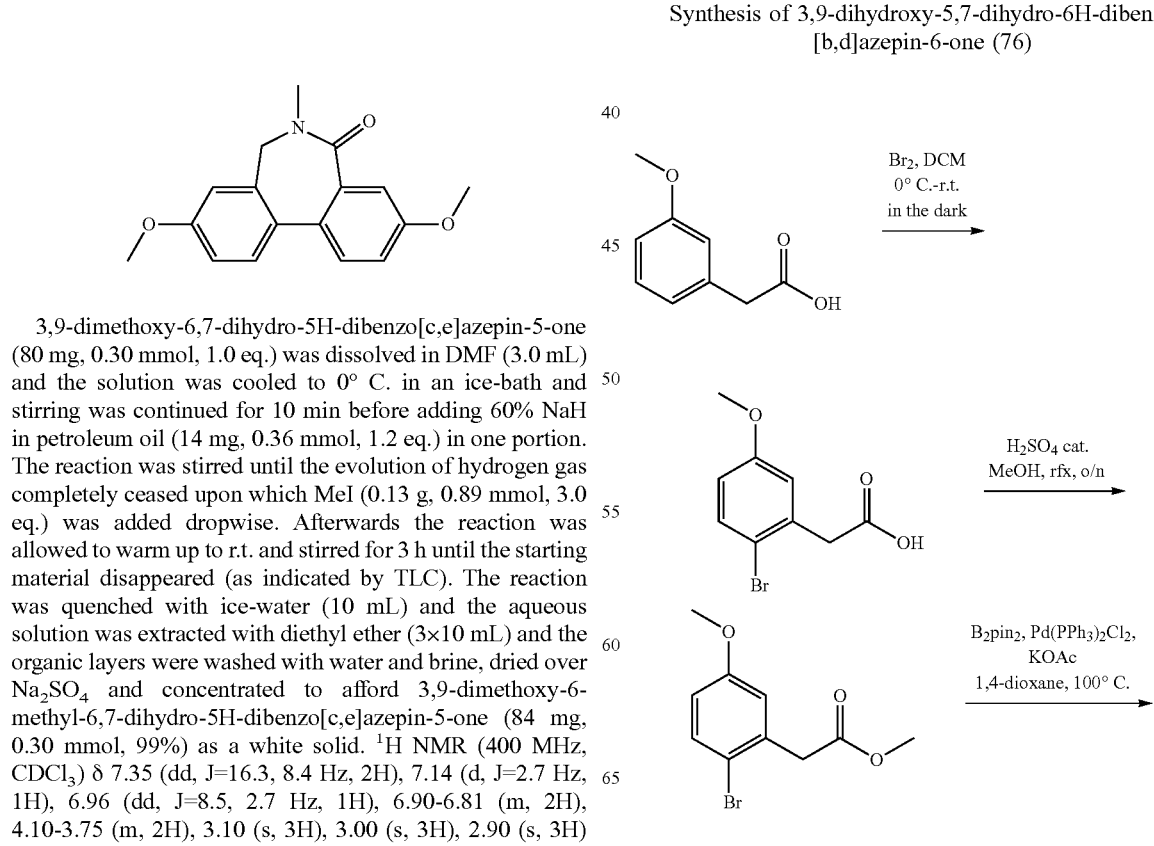

261

-continued

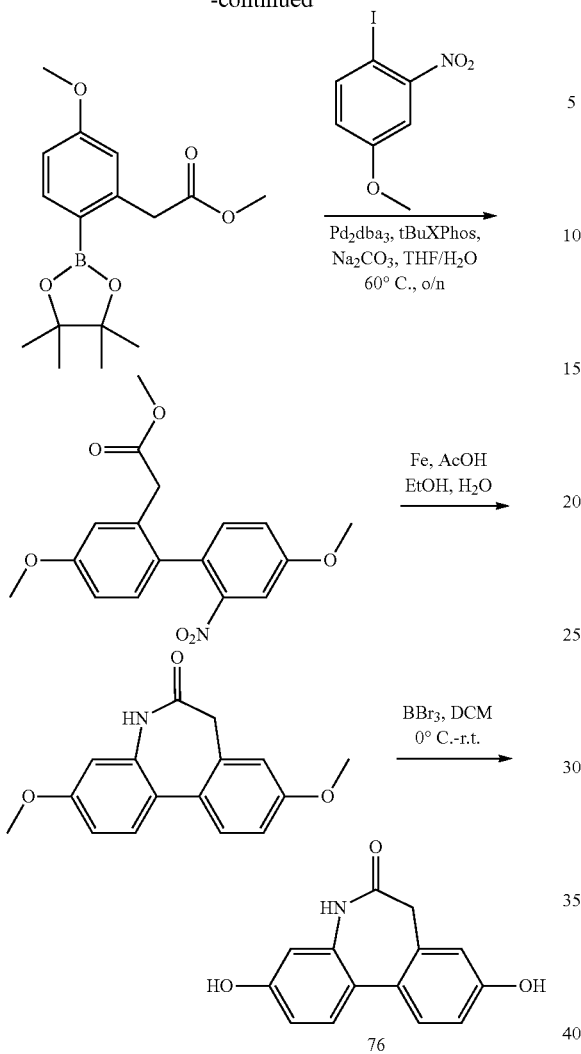

76

Step 1: Synthesis of
2-(2-bromo-5-methoxyphenyl)acetic acid

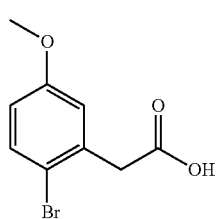

Bromine (1.92 g, 12.0 mmol, 1.0 eq.) was added dropwise to a solution of 2-(3-methoxyphenyl)acetic acid (2.00 g, 12.0 mmol, 1.0 eq.) in DCM (40 mL) at 0° C. Upon complete addition of the bromine, the reaction was allowed to warm to r.t. and stirred overnight while being covered from light using aluminum foil. The dark red solution was discolored with sodium thiosulfate solution (1 M), washed with water (50 mL) and separated. The aqueous layer was extracted into DCM (2×25 mL) and the combined organic layers dried over Na$_2$SO$_4$, filtered and evaporated to dryness

262 to afford 2-(2-bromo-5-methoxyphenyl)acetic acid (2.80 g, 11.0 mmol, 95%) as a pale red solid.

$^1$H NMR (400 MHz, CDCl$_3$) δ 10.07 (s, 1H), 7.45 (d, J=8.8 Hz, 1H), 6.85 (d, J=3.0 Hz, 1H), 6.72 (dd, J=8.8, 3.0 Hz, 1H), 3.79 (s, 2H), 3.78 (s, 3H).

Step 2: Synthesis of
2-(2-bromo-5-methoxyphenyl)acetate

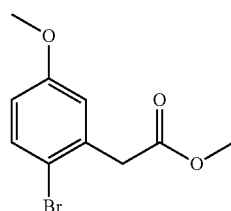

2-(2-bromo-5-methoxyphenyl)acetic acid (6.63 g, 27.1 mmol, 1.0 eq.) was dissolved in MeOH (90 mL) and a catalytic amount of concentrated sulfuric acid (0.2 mL) was added to the mixture which was then refluxed for 4 h before being cooled to r.t., quenched with water and extracted into ethyl acetate (3×100 mL). The organic layers were washed with sat. sodium bicarbonate solution and brine and dried with Na$_2$SO$_4$ and concentrated under vacuo. The crude product was purified by MPLC (SiO$_2$, 240 g, EtOAc in Hex 0-20%) to afford methyl 2-(2-bromo-5-methoxyphenyl)acetate (6.44 g, 24.9 mmol, 92%) as a colorless oil. $^1$H NMR (400 MHz, CDCl$_3$) δ 7.47 (d, J=8.8 Hz, 1H), 6.87 (d, J=3.0 Hz, 1H), 6.74 (dd, J=8.8, 3.0 Hz, 1H), 3.81 (s, 3H), 3.78 (s, 2H), 3.75 (s, 3H).

Step 3: Synthesis of 2-(5-methoxy-2-(4,4,5,5-tetramethyl-1,3,2-dioxaborolan-2-yl)phenyl)acetate

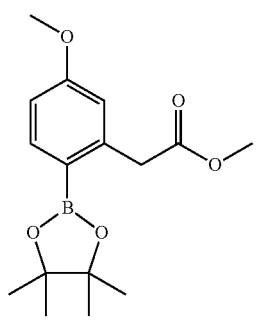

Methyl 2-(2-bromo-5-methoxyphenyl)acetate (2.00 g, 7.72 mmol, 1.0 eq.) was dissolved in 1,4-dioxane (150 mL) and there to was added B$_2$pin$_2$ (3.53 g, 13.9 mmol, 1.8 eq.), Pd(PPh$_3$)$_2$Cl$_2$ (542 mg, 0.770 mmol, 0.1 eq.) and KOAc (3.03 g, 30.9 mmol, 4.0 eq.). The resulting reaction mixture was degassed for 10 min using a N$_2$ balloon before being put into a pre-heated oil-bath at 100° C. overnight. After overnight stirring the mixture was allowed to cool to r.t. and quenched with sat. aq. NH$_4$Cl solution which was extracted into ethyl acetate (3×75 mL). The combined organic layers were dried over anhydrous Na$_2$SO$_4$, concentrated under vacuo and the crude purified by MPLC (SiO$_2$, 120 g, EtOAc in Hex 0-20%) to afford methyl 2-(5-methoxy-2-(4,4,5,5-tetramethyl-1,3,2-dioxaborolan-2-yl)phenyl)acetate (1.32 g, 4.31 mmol, 56%) as a colorless oil. $^1$H NMR (400 MHz, CDCl$_3$) δ 7.78 (d, J=8.3 Hz, 1H), 6.80 (dd, J=8.3, 2.5 Hz, 1H), 6.74 (d, J=2.5 Hz, 1H), 3.96 (s, 2H), 3.81 (s, 3H), 3.66 (s, 3H), 1.30 (s, 12H).

Step 4: Synthesis of 2-(4,4'-dimethoxy-2'-nitro-[1,1'-biphenyl]-2-yl)acetate

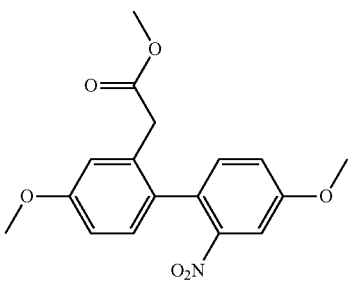

Methyl 2-(5-methoxy-2-(4,4,5,5-tetramethyl-1,3,2-dioxaborolan-2-yl)phenyl)acetate (670 mg, 2.19 mmol, 1.0 eq.) and 1-iodo-4-methoxy-2-nitrobenzene (733 mg, 2.63 mmol, 1.2 eq.) were dissolved in THF (2 mL) and to this solution was added Pd$_2$dba$_3$ (100 mg, 0.110 mmol, 0.05 eq.) as well as tBuXPhos (93 mg, 0.22 mmol, 0.1 eq.). The resulting mixture was degassed for 10 min using a N$_2$ balloon before the dropwise addition of a solution of Na$_2$CO$_3$ (696 mg, 6.56 mmol, 3.0 eq.) in water (4 mL). Following the reaction mixture was heated to 60° C. overnight (until starting material completely disappeared on TLC) before being allowed to cool to r.t., quenched with sat. aq. NH$_4$Cl solution, extracted with ethyl acetate (3×50 mL), dried over anhydrous Na$_2$SO$_4$ and concentrated under vacuo. The resulting crude material was purified by MPLC (SiO$_2$, 40 g, EtOAc in Hex 0-35%) to afford methyl 2-(4,4'-dimethoxy-2'-nitro-[1,1'-biphenyl]-2-yl)acetate (490 mg, 1.48 mmol, 68%) as a green oil. $^1$H NMR (400 MHz, CDCl$_3$) δ 7.48 (d, J=2.7 Hz, 1H), 7.23 (d, J=8.5 Hz, 1H), 7.14 (dd, J=8.5, 2.7 Hz, 1H), 7.03 (d, J=8.4 Hz, 1H), 6.92 (d, J=2.6 Hz, 1H), 6.83 (dd, J=8.4, 2.7 Hz, 1H), 3.91 (s, 3H), 3.84 (s, 3H), 3.59 (s, 3H), 3.48-3.33 (m, 2H).

Step 5: Synthesis of 3,9-dimethoxy-5,7-dihydro-6H-dibenzo[b,d]azepin-6-one

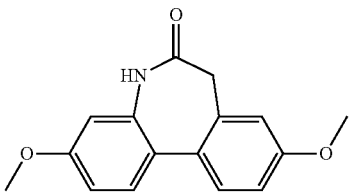

Methyl 2-(4,4'-dimethoxy-T-nitro-[1,1'-biphenyl]-2-yl) acetate (485 mg, 1.46 mmol, 1.0 eq.) was dissolved in H$_2$O (3 mL), AcOH (2 mL) and EtOH (3 mL) and powdered Fe (818 mg, 14.6 mmol, 10.0 eq.) was added to the mixture, which was stirred for 2 h until the TLC showed no more starting material. Then reaction mixture was filtered over a pad of celite and concentrated under reduced pressure (AcOH was removed by azeotropic distillation with cyclohexane) and purified by MPLC (SiO$_2$, 40 g, EtOAc in Hex 0-85%) to afford 3,9-dimethoxy-5,7-dihydro-6H-dibenzo[b,d]azepin-6-one (150 mg, 0.560 mmol, 38%) as a white solid. $^1$H NMR (400 MHz, DMSO) δ 9.93 (s, 1H), 7.50 (d, J=8.7 Hz, 1H), 7.44 (d, J=9.0 Hz, 1H), 7.00-6.94 (m, 2H), 6.85 (dd, J=8.7, 2.6 Hz, 1H), 6.72 (d, J=2.6 Hz, 1H), 3.80 (s, 3H), 3.78 (s, 3H).

Step 6: Synthesis of 3,9-dihydroxy-5,7-dihydro-6H-dibenzo[b,d]azepin-6-one

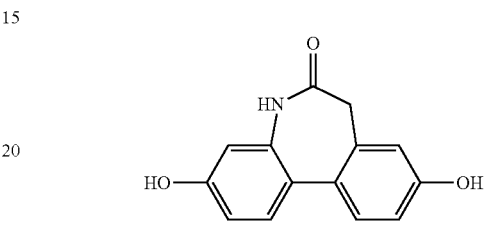

76

3,9-dimethoxy-5,7-dihydro-6H-dibenzo[b,d]azepin-6-one (70 mg, 0.26 mmol, 1.0 eq.) was dissolved in DCM (2 mL) and cooled down to 0° C. in an ice-bath and stirring was continued for 5 min. Then BBr$_3$ (1.30 ml, 1 M in DCM, 1.30 mmol, 5.0 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography (SiO$_2$, 12 g, MeOH in DCM 0-5%) to afford 3,9-dihydroxy-5,7-dihydro-6H-dibenzo[b,d]azepin-6-one (35 mg, 0.15 mmol, 56%) as a light yellow solid. $^1$H NMR (400 MHz, DMSO) δ 9.82 (s, 1H), 9.56 (s, 2H), 7.33 (d, J=8.5 Hz, 1H), 7.27 (d, J=8.4 Hz, 1H), 6.77 (dd, J=8.4, 2.5 Hz, 1H), 6.69 (d, J=2.5 Hz, 1H), 6.63 (dd, J=8.5, 2.5 Hz, 1H), 6.55 (d, J=2.5 Hz, 1H), 3.20 (s, 2H).

Synthesis of 3,9-dihydroxy-5-methyl-5,7-dihydro-6H-dibenzo[b,d]azepin-6-one (77)

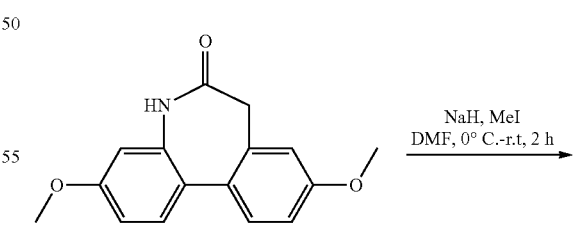

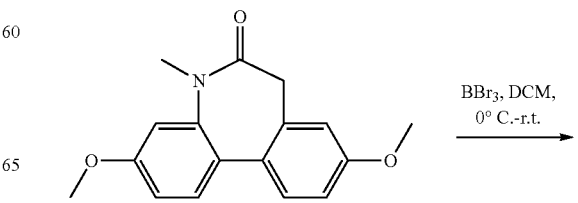

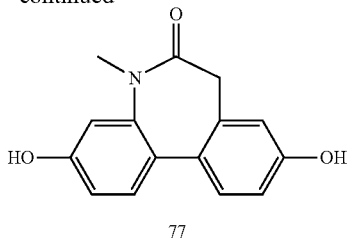

77

Step 1: Synthesis of 3,9-dimethoxy-5-methyl-5,7-dihydro-6H-dibenzo[b,d]azepin-6-one

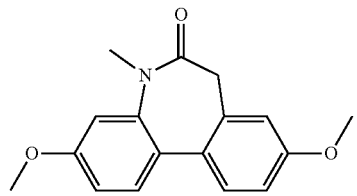

3,9-dimethoxy-5,7-dihydro-6H-dibenzo[b,d]azepin-6-one (85 mg, 0.32 mmol, 1.0 eq.) was dissolved in DMF (3.2 mL) and the solution was cooled to 0° C. in an ice-bath and stirring was continued for 10 min before adding 60% NaH in petroleum oil (14 mg, 0.36 mmol, 1.2 eq.) in one portion. The reaction was stirred until the evolution of hydrogen gas completely ceased upon which MeI (0.060 g, 0.38 mmol, 1.2 eq.) was added dropwise. Afterwards the reaction was allowed to warm up to r.t. and stirred for 3 h until the starting material disappeared (as indicated by TLC). The reaction was quenched with ice-water (10 mL) and the aqueous solution was extracted with diethyl ether (3×10 mL) and the organic layers were washed with water and brine, dried over $Na_2SO_4$ and concentrated to afford 3,9-dimethoxy-5-methyl-5,7-dihydro-6H-dibenzo[b,d]azepin-6-one (60 mg, 0.21 mmol, 67%) as a light yellow solid. $^1$H NMR (400 MHz, $CDCl_3$) δ 7.46 (dd, J=8.4, 5.6 Hz, 2H), 6.98-6.85 (m, 4H), 3.89 (s, 3H), 3.86 (s, 3H), 3.56-3.39 (dd, J=2H), 3.33 (s, 3H).

Step 1: Synthesis of 3,9-dihydroxy-5-methyl-5,7-dihydro-6H-dibenzo[b,d]azepin-6-one

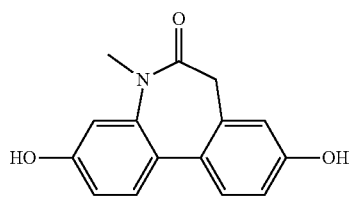

77

3,9-dimethoxy-5,7-dihydro-6H-dibenzo[b,d]azepin-6-one (58 mg, 0.20 mmol, 1.0 eq.) was dissolved in DCM (2 mL) and cooled down to 0° C. in an ice-bath and stirring was continued for 5 min. Then $BBr_3$ (0.82 ml, 1 M in DCM, 0.82 mmol, 4.0 eq.) was added dropwise to the reaction mixture. Upon complete addition the mixture was left in the ice bath and was allowed to warm to r.t. over the course of 2 h. When no more starting material could be observed the reaction mixture was dropwise added into 0° C. cold methanol (10 mL) and stirred for an additional 10 min. Then the mixture was concentrated and loaded on silica to be purified by flash column chromatography ($SiO_2$, 12 g, MeOH in DCM 0-5%) to afford 3,9-dihydroxy-5-methyl-5,7-dihydro-6H-dibenzo[b,d]azepin-6-one (30 mg, 0.12 mmol, 57%) as light orange solid. $^1$H NMR (400 MHz, DMSO) δ 9.74 (s, 1H), 9.57 (s, 1H), 7.31 (dd, J=8.4, 2.3 Hz, 2H), 6.82-6.71 (m, 4H), 3.31-3.20 (m, 2H), 3.15 (s, 3H).

Example 2: Synthesis of Additional Representative Compounds

Reactions were not carried out under an inert atmosphere unless specified, and all solvents and commercial reagents were used as received.

Purification by chromatography refers to purification using the COMBIFLASH® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 μm and nominal 60 Å porosity. Fractions containing the required product (identified by TLC and/or LCMS analysis) were pooled, the organic fraction recovered by evaporation, to give the final product. Where thin layer chromatography (TLC) has been used, it refers to silica-gel TLC plates, typically 3×6 cm silica-gel on aluminium foil plates with a fluorescent indicator (254 nm), (e.g. Fluka 60778). Microwave experiments were carried out using a Biotage Initiator 60™ which uses a single-mode resonator and dynamic field tuning. Temperatures from 40-250° C. can be achieved, and pressures of up to 30 bar can be reached.

NMR spectra were obtained on a Bruker Avance 400 MHz, 5 mm QNP probe H, C, F, P, single Z gradient, two channel instrument running TopSpin 2.1 or on a Bruker Avance III 400 MHz, 5 mm BBFO Plus probe, single Z gradient, two channel instrument running TopSpin 3.0.

Analytical LC-MS Conditions

Method 1: Experiments were performed on a Waters Acquity SQD2 mass spectrometer linked to a Waters Acquity UPLC binary pump/PDA detector. The spectrometer had an electrospray source operating in positive and negative ion mode. Additional detection was achieved using an Acquity UPLC HSS C18 1.7 μm, 100×2.1 mm column maintained at 40° C. and a 0.4 mL/minute flow rate. The initial solvent system was 95% water containing 0.1% formic acid (solvent A) and 5% MeCN containing 0.1% formic acid (solvent B) for the first 0.4 minute followed by a gradient up to 5% solvent A and 95%.

Method 2: Experiments were performed on a Waters Acquity SQD2 mass spectrometer linked to a Waters Acquity UPLC binary pump/PDA detector. The spectrometer had an electrospray source operating in positive and negative ion mode. Additional detection was achieved using an Acquity UPLC BEH Shield RP18 1.7 μm 100×2.1 mm column maintained at 40° C. and a 0.4 mL/minute flow rate. The initial solvent system was 95% water containing 0.03% aqueous ammonia (solvent A) and 5% MeCN containing 0.03% aqueous ammonia (solvent B) for the first 0.4 minute followed by a gradient up to 5% solvent A and 95% solvent B over the next 5.4 min. The final solvent system was held constant for a further 0.8 min.

Method 3: Experiments were performed on a Waters Acquity ZQ mass spectrometer linked to a Waters Acquity UPLC binary pump/PDA detector. The spectrometer had an electrospray source operating in positive and negative ion mode. Additional detection was achieved using an Acquity UPLC BEH C18 1.7 µm, 100×2.1 mm column maintained at 40° C. and a 0.4 mL/minute flow rate. The initial solvent system was 95% water containing 0.1% formic acid (solvent A) and 5% MeCN containing 0.1% formic acid (solvent B) for the first 0.4 minute followed by a gradient up to 5c/c solvent A and 95% solvent B over the next 5.6 min. The final solvent system was held constant for a further 0.8 min.

Method 4: Experiments were performed on a Waters Acquity ZQ mass spectrometer linked to a Waters Acquity UPLC binary pump/PDA detector. The spectrometer had an electrospray source operating in positive and negative ion mode, Additional detection was achieved using an Acquity UPLC BEH C18 1.7 µm, 100×2.1 mm column maintained at 40° C. and a 0.4 mL/minute flow rate. The initial solvent system was 95% water containing 0.03% aqueous ammonia (solvent A) and 5% MeCN containing 0.03% aqueous ammonia (solvent B) for the first 0.4 minute followed by a gradient up to 5% solvent A and 95% solvent B over the next 4 min. The final solvent system was held constant for a further 0.8 min.

Method 5: Experiments were performed on a Waters Acquity ZQ mass spectrometer linked to a Waters Acquity H-class UPLC with DAD detector and QDa. The spectrometer had an electrospray source operating in positive and negative ion mode. Additional detection was achieved using an Acquity UPLC CSH 1.7 µm, 50×2.1 mm column maintained at 40° C. and a 1.0 mL/minute flow rate. The initial solvent system was 97% water containing 0.1% formic acid (solvent A) and 3% MeCN containing 0.1% formic acid (solvent B) for the first 0.4 minute followed by a gradient up to 1% solvent A and 99% solvent B over the next 1.4 min. The final solvent system was held constant for a further 0.5 min.

Method 6: Experiments were performed on a Waters Acquity ZQ mass spectrometer linked to a Waters Acquity H-class UPLC with DAD detector and QDa. The spectrometer had an electrospray source operating in positive and negative ion mode. Additional detection was achieved using an Acquity BEH UPLC 1.7 µm, 50×2.1 mm column maintained at 40° C. and a 0.8 mL/minute flow rate. The initial solvent system was 97% of 7.66 mM ammonia in water (solvent A) and 3% of 7.66 mM ammonia in MeCN containing (solvent B) for the first 0.4 minutes followed by a gradient up to 3% solvent A and 97% solvent B over the next 1.6 min. The final solvent system was held constant for a further 0.5 min.

A) Ester "A" Group Analogues
General Procedure A

4-Chloro-3-hydroxy-6H-benzo[c]chromen-6-one (78)

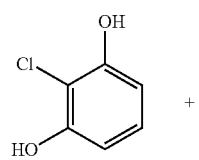

+

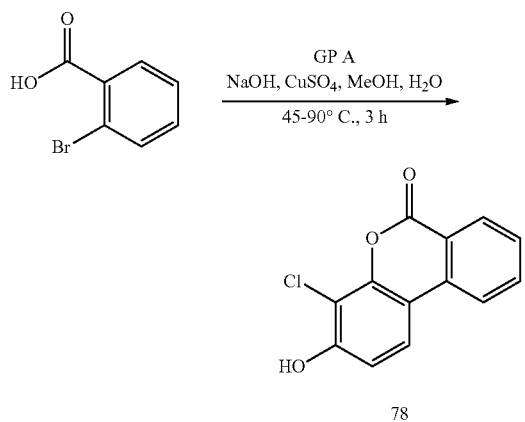

78

To a suspension of 2-bromobenzoic acid (500 mg, 2.49 mmol) in water (8.0 mL) was added 2-chlororesorcinol (719 mg, 4.97 mmol) followed by sodium hydroxide (219 mg, 5.47 mmol). The reaction mixture was heated to 45° C. over 15 min. The mixture was degassed for 10 mins by bubbling nitrogen gas through it before copper sulphate (20 mg, 0.124 mmol) was added. Degassing was repeated for a further 5 mins before the reaction mixture was heated at 90° C. under nitrogen for 2 h. The mixture was cooled to RT and the precipitate was filtered off, washed with water and dried under reduced pressure to afford the title compound as a pink solid (330 mg, 54%). $^1$H NMR (400 MHz, DMSO-$d_6$) δ 11.10 (1H, s), 8.29 (1H, d, J=8.2 Hz), 8.22 (1H, d, J=7.8 Hz), 8.16 (1H, d, J=8.8 Hz), 7.93 (1H, dd, J=7.5, 7.5 Hz), 7.66-7.58 (1H, m), 7.05 (1H, d, J=8.7 Hz); LCMS (Method 2): $R_t$=3.71 min; m/z=247.1, 248.9 [M+H]$^+$ General Procedure B N-(8-Methoxy-6-oxo-6H-benzo[c]chromen-3-yl) methanesulfonamide (79)

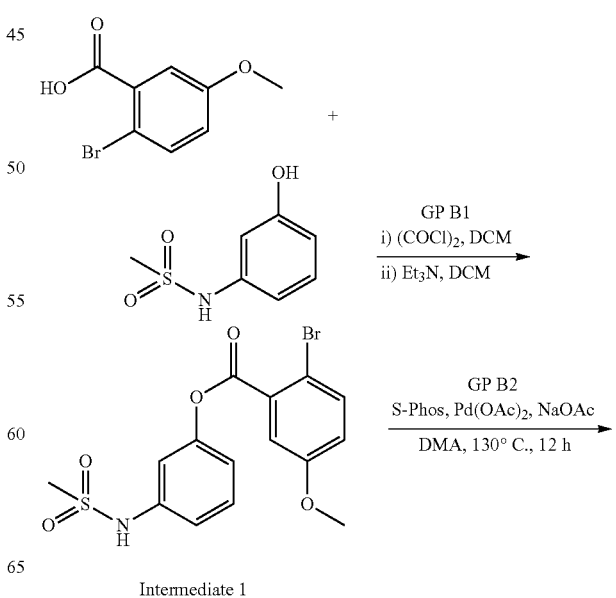

Intermediate 1

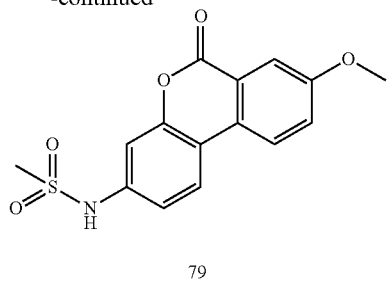

79

GP B1

3-(Methylsulfonamido)phenyl 2-bromo-5-methoxybenzoate (Intermediate 1)

To a suspension of 2-bromo-5-methoxybenzoic acid (642 mg, 2.78 mmol) in DCM (10 mL) was added oxalyl chloride (0.27 mL, 3.06 mmol) dropwise and 1 drop of DMF. The solution was stirred at RT for 1 h and the solvent was removed in vacuo. The resultant mixture was re-dissolved in DCM (5 mL) and a suspension of N-(3-hydroxyphenyl)methanesulfonamide (520 mg, 2.78 mmol) in DCM (5 mL) was added followed by TEA (0.58 mL, 4.17 mmol). The resulting mixture was stirred for 4 h, then diluted with DCM and washed with saturated aq. NH$_4$Cl. The organic extracts were filtered through PTFE and concentrated in vacuo and the crude product was purified by chromatography on silica (ISCO 12 g) using 0-50% EtOAc in cyclohexane as eluant to give the product 3-(methylsulfonamido)phenyl 2-bromo-5-methoxybenzoate as colourless oil (1 g, 90%). LCMS (Method 5): $R_t$ 1.43 min; m/z 398.0/400.0 [M−H]$^-$. $^1$H NMR (400 MHz, CDCl$_3$) δ 7.61 (1H, d, J=8.9 Hz), 7.52 (1H, d, J=3.1 Hz), 7.41 (1H, t, J=8.1 Hz), 7.19-7.08 (3H, m), 6.98 (1H, dd, J=8.9, 3.1 Hz), 6.77 (1H, s), 3.87 (3H, s), 3.07 (6H, s).

GP B2

N-(8-Methoxy-6-oxo-6H-benzo[c]chromen-3-yl)methanesulfonamide (79)

A mixture of 3-(methylsulfonamido)phenyl 2-bromo-5-methoxybenzoate (Intermediate 1) (900 mg, 2.26 mmol), SPhos (92 mg, 0.225 mmol), palladium(II)acetate (50 mg, 0.225 mmol) and sodium acetate (369 mg, 4.5 mmol) in DMA (45 mL) was placed in a sealed tube, degassed and purged with argon (×3). The mixture was heated to 130° C. for 3 h then cooled and diluted with water (400 mL) and extracted into DCM (3×50 mL) and the combined organic extracts were washed with brine and evaporated in vacuo at 80° C. to remove residual DMA. The crude mixture was recrystallised from MeCN to give the product N-(8-methoxy-6-oxo-6H-benzo[c]chromen-3-yl)methanesulfonamide as a cream solid (200 mg, 27%). LCMS (Method 3): $R_t$=3.85 min; m/z=320.0 [M+H]$^+$. $^1$H NMR (400 MHz: DMSO-d$_6$) δ 10.22 (1H, s), 8.30 (1H, d, J=8.6 Hz), 8.25 (1H, d, J=9.2 Hz), 7.65 (1H, d, J=2.8 Hz), 7.54 (1H, dd, J=8.9, 2.8 Hz), 7.22-7.19 (2H, m), 3.92 (3H, s), 3.11 (3H, s).

3-Chloro-8-hydroxy-6H-benzo[c]chromen-6-one (80)

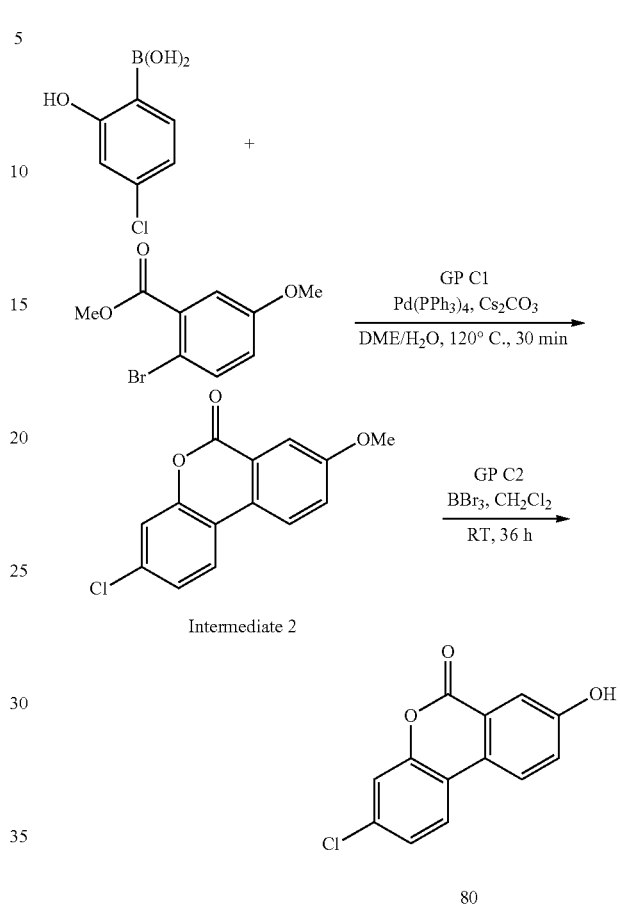

GP C1

3-Chloro-8-methoxy-6H-benzo[c]chromen-6-one (Intermediate 2)

To a solution of 4-chloro-2-hydroxyphenylboronic acid (253 mg, 1.47 mmol) in DME (8.0 mL) and water (2.0 mL) was added methyl 2-bromo-5-methoxybenzoate (300 mg) and cesium carbonate (1.60 g, 4.90 mmol) followed by tetrakis(triphenylphosphine)palladium(0) (141 mg, 0.122 mmol). The reaction mixture was heated at 120° C. in a microwave for 30 mins. The mixture was diluted with EtOAc (100 mL) and washed with water (10 mL) and brine (10 mL). The organic layer was passed through a phase separator and concentrated in vacuo. Purification of the residue by chromatography on silica eluting with 5-15% EtOAc in cyclohexane followed by trituration in MeOH and drying in a vacuum oven afforded the title compound as a white solid (112 mg, 35%). LCMS (Method 1). $R_t$=5.51 min; m/z=261.0, 263.1 [M+H]$^+$. $^1$H NMR (400 MHz: CDCl$_3$) δ 7.99 (1H, d, J=8.8 Hz), 7.91 (1H, d, J=8.3 Hz), 7.81 (1H, d, J=2.8 Hz), 7.44-7.36 (2H, m), 7.31 (1H, dd, J=8.6, 2.0 Hz), 3.95 (3H, s);

GP C2

3-Chloro-8-hydroxy-6H-benzo[c]chromen-6-one (80)

To a solution of 3-chloro-8-methoxy-6H-benzo[c]chromen-6-one (Intermediate 2) (70 mg, 0.268 mmol) in dry DCM (10 mL) under nitrogen was added dropwise a solution of boron tribromide in DCM (1.0 M, 5.4 mL, 5.36 mmol). The reaction mixture was stirred at RT for 3 days. Water (20 mL) was added and the mixture was diluted with DCM (10 mL). The mixture was stirred at RT for 10 mins. The resulting precipitate was filtered off and the aqueous layer was extracted with DCM (2×50 mL). The combined organic layers were passed through a phase separation cartridge and concentrated under reduced pressure. The precipitate was dissolved in MeOH/DCM and concentrated in vacuo. Purification of the combined residues by chromatography on silica eluting with 2-4% MeOH in DCM afforded the title compound as a white solid (28 mg, 42%). LCMS (Method 1): $R_t$=4.55 min; m/z=247.1, 249.0 [M+H]$^+$. $^1$H NMR (400 MHz: DMSO-$d_6$) δ 10.54 (1H, s), 8.35-8.31 (2H, m), 7.63-7.61 (2H, m), 7.51-7.42 (2H, m).

General Procedure D 2-(Dimethylamino)-N-(6-oxo-6H-benzo[c]chromen-3-yl)acetamide (81)

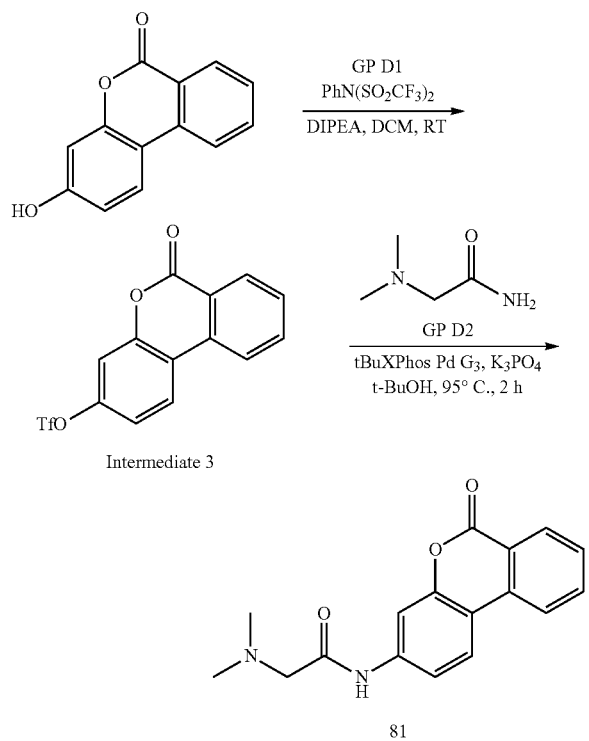

GP D1

6-Oxo-6H-benzo[c]chromen-3-yl trifluoromethanesulfonate (Intermediate 3)

A mixture of 6-hydroxy-6H-benzo[c]chromen-6-one (2.50 g, 11.78 mmol), N-phenyl-bis(trifluoromethanesulfonimide) (5.05 g, 14.1 mmol) and DIPEA (4.1 mL, 23.6 mmol) in DCM (50 mL) was stirred under nitrogen at RT. A catalytic amount of DMAP was added and the mixture stirred for 48 h. The resulting red solution was washed with 1 M HCl (50 mL) and the DCM layer was dried (PTFE frit) and evaporated. The crude residue was recrystallised from DCM/cyclohexane to give the product as a cream solid. The mother liquors were purified by chromatography on silica using 20-100% DCM in cyclohexane as eluant. This afforded additional product 1.22 g (total yield 2.86 g, 71%). LCMS (Method 5): $R_t$=1.60 min (no m/z detected—poor ionization). $^1$H NMR (CDCl$_3$) δ 8.43 (1H, dd, J=1.3, 8.0 Hz), 8.16 (1H, d, J=8.9 Hz), 8.11 (1H, d, J=8.0 Hz), 7.92-7.87 (1H, m), 7.69-7.64 (1H, m), 7.34 (1H, d, J=2.3 Hz), 7.30 (1H, dd, J=2.5, 8.9 Hz).

GP D2

2-(Dimethylamino)-N-(6-oxo-6H-benzo[c]chromen-3-yl)acetamide (81)

A mixture of 6-oxo-6H-benzo[c]chromen-3-yl trifluoromethanesulfonate (Intermediate 3) (344 mg, 1.0 mmol), 2-(dimethylamino)acetamide (153 mg, 1.5 mmol), tBuXPhos-Pd-G3 (24 mg, 0.03 mmol) and potassium phosphate tribasic (318 mg, 1.5 mmol) in a septum-sealed vial was degassed (evacuation and flush with argon 3 cycles). Warm degassed (argon sparged) tert-butanol (8.5 ml) was added via syringe and the mixture was then heated at 95° C. for 2 h. The cooled mixture was diluted with water (15 ml) and the resulting mixture was filtered and dried in vacuo to afford a grey solid. This was taken into DCM (15 mL) and filtered through a 2 g flash Si (II) cartridge which was then further eluted with 2% MeOH in DCM to give the title compound (125 mg, 42%) a white solid. LCMS (Method 3): $R_t$=2.72 min; m/z=296.9 [M+H]$^+$.

$^1$H NMR (400 MHz, DMSO-$d_6$) δ 10.14 (1H, s), 8.37 (1H, d, J=8.1 Hz), 8.29 (1H, d, J=8.8 Hz), 8.23 (1H, dd, J=1.1, 7.9 Hz), 7.96-7.90 (1H, m), 7.88 (1H, d, J=2.1 Hz), 7.68 (1H, dd, J=2.1, 8.7 Hz), 7.66-7.60 (1H, m), 3.13 (2H, s), 2.30 (6H, s).

General Procedure E

Methyl (6-oxo-6H-benzo[c]chromen-3-yl)carbamate (82)

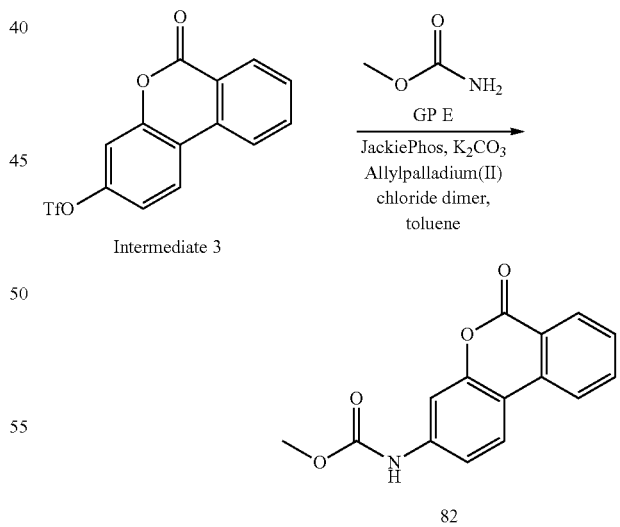

A mixture of 6-oxo-6H-benzo[c]chromen-3-yl trifluoromethanesulfonate (Intermediate 3) (250 mg, 0.73 mmol), methyl carbamate (82 mg, 1.09 mmol), allylpalladium(II) chloride dimer (2.7 mg, 0.007 mmol), JackiePhos (29 mg, 0.036 mmol) and K$_2$CO$_3$ (301 mg, 2.18 mmol) in toluene (6.0 mL) was sparged with argon for 5 min. The reaction vessel was then sealed, and the mixture was heated at 110°

C. for 1 h. The cooled reaction mixture was diluted with DCM (20 ml) and water (20 mL), which gave a suspension in the aqueous phase. The organic phase was separated, and the aqueous phase was washed with DCM (20 mL). The aqueous phase was filtered and the dark solid recovered was taken into 6% MeOH in DCM. This solution was filtered through a 5 g flash Si (II) cartridge which was then further eluted with 6% MeOH in DCM to afford the title compound (129 mg, 65%) as a white solid. LCMS (Method 3): $R_f$=4.05 min; m/z=269.9 [M+H]$^+$. $^1$H NMR (400 MHz, DMSO-d$_6$) δ 10.12 (1H, s), 8.32 (1H, d, J=8.1 Hz), 8.28 (1H, d, J=8.8 Hz), 8.22 (1H, dd, J=1.1, 7.9 Hz), 7.95-7.89 (1H, m), 7.65-7.58 (2H, m), 7.45 (1H, dd, J=2.1, 8.7 Hz), 3.72 (3H, s).

General Procedure F

3-Bromo-8-methoxy-6H-benzo[c]chromen-6-one (84)

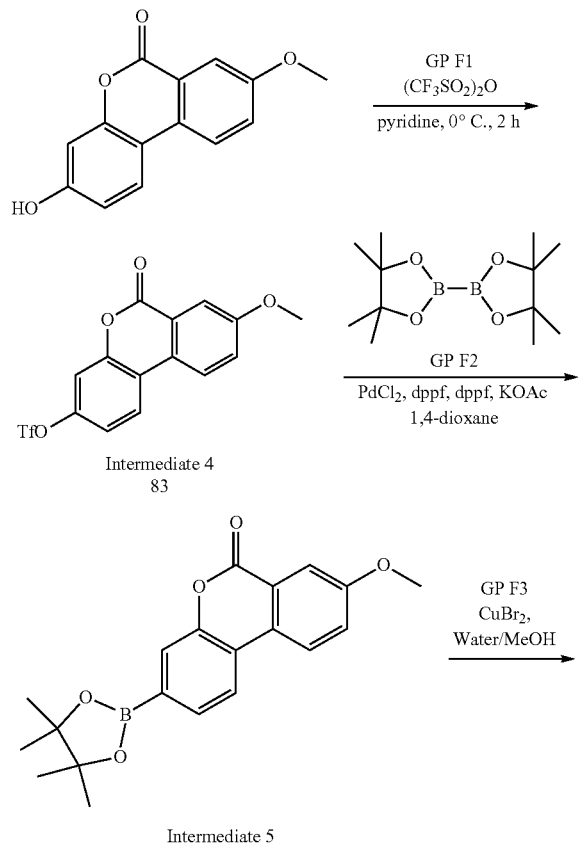

GP F1

8-Methoxy-6-oxo-6H-benzo[c]chromen-3-yl trifluoromethanesulfonate (83) (Intermediate 4

3-Hydroxy-8-methoxy-6H-benzo[c]chromen-6-one (1 g, 4.13 mmol) was dissolved in pyridine (10 mL) and the mixture was cooled in ice-water. Trifluoromethanesulfonic anhydride (1 mL, 6.19 mmol) was added dropwise and the resulting brown mixture was stirred at 0° C. to RT for 2 h. The mixture was concentrated in vacuo and the residue was dissolved in DCM and washed with 1 M HCl, brine, dried (PTFE frit) and concentrated in vacuo. The resultant residue was passed through a silica pad (12 g) and the product was eluted with 50-100% DCM in cyclohexane to give the compound as white crystals (1.2 g, 80%). $^1$H NMR (400 MHz, CDCl$_3$) δ 8.56 (1H, d, J=9.1 Hz), 8.48 (1H, d, J=8.8 Hz), 7.80 (1H, d, J=2.5 Hz), 7.75 (1H, d, J=2.8 Hz), 7.65 (1H, dd, J=2.8, 8.8 Hz), 7.59 (1H, dd, J=2.7, 9.0 Hz), 4.00 (3H, s); LCMS (Method 1): $R_t$=5.64 min; m/z=375.0 [M−H]$^+$.

GP F2

8-Methoxy-3-(4,4,5,5-tetramethyl-1,3,2-dioxaborolan-2-yl)-6H-benzo[c]chromen-6-one (Intermediate 5)

A mixture of 8-methoxy-6-oxo-6H-benzo[c]chromen-3-yl trifluoromethanesulfonate (Intermediate 4) (1.0 g, 2.67 mmol), potassium acetate (393 mg, 4.0 mmol), [1,1-bis(diphenylphosphino)ferrocene] dichloropalladium(II) complex with DCM (65 mg, 0.08 mmol), 1,1-bis(diphenylphosphino)ferrocene (44 mg, 0.08 mmol) and dioxane (20 mL) was sparged with argon. Bis(pinacolato)diboron (746 mg, 2.94 mmol) was added and after a further period of degassing, the mixture was heated at 90° C. under argon for 19 h. The cooled mixture was partitioned between ether (25 mL) and water (25 mL) and the phases were separated, and the aqueous phase extracted with ether (2×25 mL). The combined organic extract was washed with saturated brine, dried (Na$_2$SO$_4$) and concentrated in vacuo. The residue was purified by flash chromatography on a 20 g Si-(II) cartridge eluting with DCM then 10% EtOAc in DCM. The product obtained was triturated with cyclohexane (10 mL) then dried in vacuo to afford the title compound (0.76 g, 81%) as an off white solid. LCMS (Method 5): $R_t$=1.65 min; m/z=353.1 [M+H]$^+$ and $R_t$=1.11 min; m/z=271.1 [M-Pin+H]$^+$.

GP F3

3-Bromo-8-methoxy-6H-benzo[c]chromen-6-one (84)

A suspension of 8-methoxy-3-(4,4,5,5-tetramethyl-1,3,2-dioxaborolan-2-yl)-6H-benzo[c]chromen-6-one (Intermediate 5) (352 mg, 1.0 mmol) in MeOH (10 mL) was treated with a solution of copper(II) bromide (670 mg, 3.0 mmol) in water (10 mL). The resulting mixture was heated at reflux for 16 h then cooled. The cold mixture was extracted with ether (2×25 mL) then DCM (2×25 mL) and the combined organic phase was filtered through a hydrophobic frit then concentrated in vacuo. The residue was purified by flash chromatography on a 5 g Si-(II) cartridge and eluted with [1:1] DCM/cyclohexane then DCM to afford the title compound (240 mg, 78%) as a white solid. $^1$H NMR (400 MHz, CDCl$_3$) δ 8.00 (1H, d, J=8.9 Hz), 7.84 (1H, d, J=8.7 Hz), 7.80 (1H, d, J=3.0 Hz), 7.53 (1H, d, J=1.9 Hz), 7.46-7.39 (2H, m), 3.95 (3H, s); LCMS (Method 5), $R_t$=1.53 min; m/z=304.8, 306.8 [M+H]$^+$.

Procedure G 8-(Difluoromethyl)-3-(methoxymethoxy)-6H-benzo[c]chromen-6-one (85)

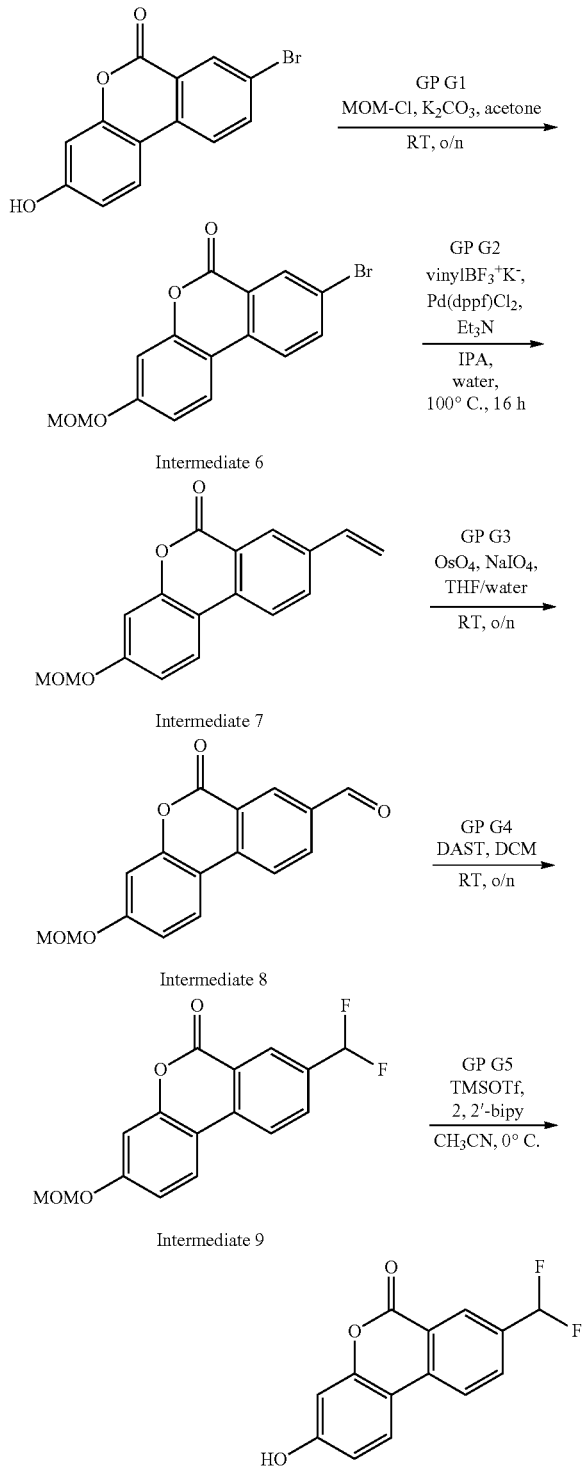

GP G1

8-Bromo-3-(methoxymethoxy)-6H-benzo[c]chromen-6-one (Intermediate 6)

8-Bromo-3-hydroxy-6H-benzo[c]chromen-6-one (1.0 g, 3.44 mmol), $K_2CO_3$ (1.42 g, 10.31 mmol) and chloromethyl methyl ether (0.39 mL, 5.15 mmol) were suspended in acetone (10 mL) and the mixture was stirred for 3 h. An additional aliquot of chloromethyl methyl ether (0.39 mL, 5.15 mmol) was added and the mixture stirred for 2 h. The mixture was concentrated in vacuo and dispersed between DCM and water. The DCM layer was washed with brine, dried (PTFE frit) and evaporated to give the product as a white solid (1 g, 86%). $^1$H NMR (400 MHz, $CDCl_3$) δ 8.50 (1H, s), 7.9-7.88 (3H, m), 7.07-7.02 (2H, m), 5.25-5.24 (2H, m), 3.51 (3H, s).

GP G2

3-(Methoxymethoxy)-8-vinyl-6H-benzo[c]chromen-6-one (Intermediate 7)

A mixture of 8-bromo-3-(methoxymethoxy)-6H-benzo[c]chromen-6-one (Intermediate 6) (1 g, 2.98 mmol), potassium vinyltrifluoroborate (520 mg, 3.88 mmol), TEA (1.2 mL, 8.95 mmol) and [1,1'-bis(diphenylphosphino)ferrocene]dichloropalladium(II) complex with DCM (122 mg, 0.15 mmol) in isopropanol (20 mL) and water (10 mL) was placed in a sealed tube, evacuated and purged with argon (×3). The mixture was heated at 90° C. under argon for 2 h. The cooled mixture was concentrated in vacuo and the residue dispersed between EtOAc and water. The EtOAc layer was washed with brine, dried (PTFE frit) and concentrated in vacuo. The resultant residue was purified by chromatography on silica using 0-50% DCM in cyclohexane as eluant to give the product as a white solid (705 mg, 71%). $^1$H NMR (400 MHz, $CDCl_3$) δ 8.37 (1H, d, J=1.9 Hz), 7.98 (1H, d, J=8.5 Hz), 7.94 (1H, d, J=8.7 Hz), 7.84 (1H, dd, J=2.0, 8.4 Hz), 7.07-7.02 (2H, m), 6.81 (1H, dd, J=10.9, 17.6 Hz), 5.91 (1H, d, J=17.6 Hz), 5.40 (1H, d, J=11.0 Hz), 5.25 (2H, s), 3.51 (3H, s).

GP G3

3-(Methoxymethoxy)-6-oxo-6H-benzo[c]chromene-8-carbaldehyde (Intermediate 8)

To a solution of 3-(methoxymethoxy)-8-vinyl-6H-benzo[c]chromen-6-one (Intermediate 7) (700 mg, 2.48 mmol) in THF (40 mL) was added osmium tetroxide (0.25 mL, 0.025 mmol) followed by a solution of sodium periodate (1.59 g, 7.44 mmol), and the resulting solution was stirred for 18 h, which gave a white suspension. The mixture was concentrated in vacuo and the residue portioned between DCM and water, and the DCM layer was washed with aqueous sodium sulfite, brine then dried (PTFE frit) to give a white solid (700 mg, quant.). $^1$H NMR (400 MHz, $CDCl_3$) δ 10.11 (1H, s), 8.83 (1H, d, J=1.8 Hz), 8.30 (1H, dd, J=1.8, 8.4 Hz), 8.16 (1H, d, J=8.4 Hz), 8.04-8.00 (1H, m), 7.10-7.07 (2H, m), 5.27 (2H, s), 3.52 (3H, s); LCMS (Method 6): $R_t$=1.41 min; m/z=284.2 $[M+1]^+$.

GP G4

8-(Difluoromethyl)-3-(methoxymethoxy)-6H-benzo[c]chromen-6-one (Intermediate 9)

A suspension of 3-(methoxymethoxy)-6-oxo-6H-benzo[c]chromene-8-carbaldehyde (Intermediate 8) (190 mg, 0.67 mmol) in DCM (3 mL) was placed under argon. DAST (0.26 mL, 2.01 mmol) was added dropwise and the resulting mixture was stirred for 18 h at RT. The resulting solution was neutralised with saturated aqueous NaHCO₃ and the DCM layer was washed with brine, dried (PTFE frit) and concentrated in vacuo. The residue was purified by chromatography on silica using 0-70% DCM in cyclohexane as eluant to give the product as a pale-yellow solid (175 mg, 85%). ¹H NMR (400 MHz, CDCl₃, 258114) δ 8.49 (1H, d, J=1.1 Hz), 8.12 (1H, d, J=8.4 Hz), 7.98 (1H, d, J=8.5 Hz), 7.96-7.92 (1H, m), 7.09-7.05 (2H, m), 6.76 (1H, t, J=56.1 Hz), 5.26 (2H, s), 3.51 (3H, s); LCMS (Method 6): $R_t$=1.55 min (no m/z detected—poor ionization).
GP G5

8-(Difluoromethyl)-3-hydroxy-6H-benzo[c]chromen-6-one (85)

A solution of 8-(difluoromethyl)-3-(methoxymethoxy)-6H-benzo[c]chromen-6-one (Intermediate 9) (65 mg, 0.21 mmol) and 2,2'-bipyridyl in MeCN was placed in a sealed tube under argon and cooled in ice-water. Trifluoromethyl trifluoromethane sulfonate (0.08 mL, 0.42 mmol) was added and the solution was stirred for 18 h. The resultant mixture was stirred with water (0.5 mL) for 30 min. then concentrated in vacuo, and the residue was partitioned between EtOAc and water. The EtOAc layer was washed with brine, dried (PTFE frit) and concentrated in vacuo. The crude residue was purified by chromatography on silica using 0-5% MeOH in DCM as eluant to give the product as a pale-yellow solid. The product was further purified by chromatography on silica using 0-50% EtOAc in cyclohexane as eluant to give the title compound as a white solid (25 mg, 45% yield). ¹H NMR (400 MHz, DMSO-d₆) δ 10.50 (1H, s), 8.41 (1H, d, J=8.5 Hz), 8.35 (1H, d, J=1.1 Hz), 8.21 (1H, d, J=8.9 Hz), 8.04 (1H, d, J=8.4 Hz), 7.21 (1H, t, J=55.6 Hz), 6.88 (1H, dd, J=2.4, 8.7 Hz), 6.78 (1H, d, J=2.4 Hz). LCMS (Method 3): $R_t$=4.03 min; m/z=260.9 [M−H]⁻.
Procedure H 3-Amino-8-methoxy-6H-benzo[c]chromen-6-one (86)

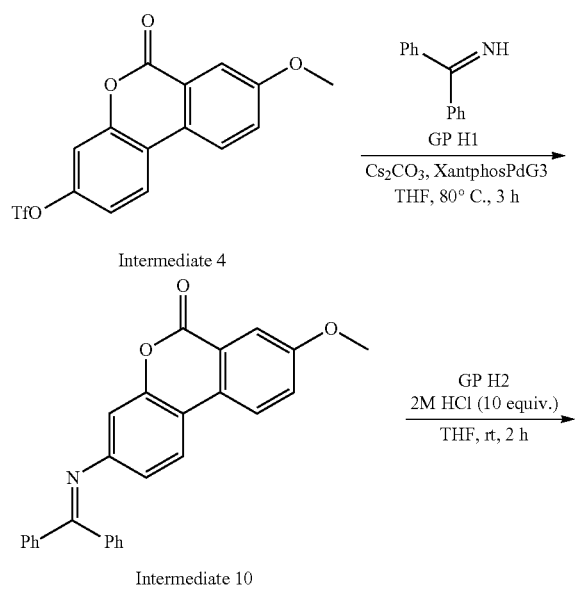

Intermediate 10

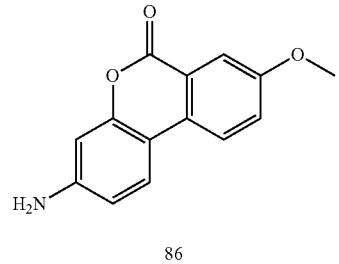

86

GP H1

3-((Diphenylmethylene)amino)-8-methoxy-6H-benzo[c]chromen-6-one (Intermediate 10)

A glass vial was charged with a mixture of 8-methoxy-6-oxo-6H-benzo[c]chromen-3-yl trifluoromethanesulfonate (Intermediate 4) (300 mg, 0.802 mmol), benzophenone imine (0.20 mL, 1.20 mmol), cesium carbonate (392 mg, 1.20 mmol) and XPhos-Pd-G3 (76 mg, 0.080 mmol) in THF (4.0 mL). The reaction mixture was evacuated and purged with nitrogen (×3) and was heated at 80° C. for 2 h. The cooled mixture was partitioned between EtOAc (×2) and water and the combined organic extract was washed with brine, dried (MgSO₄) and concentrated in vacuo. The resultant residue was purified by chromatography on silica using 5-95% EtOAc in cyclohexane as eluant to give the product as a white solid (250 mg, 77%). ¹H NMR (400 MHz, DMSO-d₆) δ 8.23 (1H, d, J=9.0 Hz), 8.05 (1H, d, J=8.5 Hz), 7.61 (1H, d, J=2.8 Hz), 7.72-7.66 (2H, m), 7.53-7.46 (4H, m), 7.36-7.31 (2H, m), 7.33 (1H, ob. s), 7.27-7.21 (2H, m), 6.79 (1H, d, J=2.0 Hz), 6.73 (1H, dd, J=2.0, 8.4 Hz), 3.89 (3H, s). LCMS (Method 5): $R_t$=1.94 min;

m/z=406.3 [M+H]⁺.

GP H1

3-Amino-8-methoxy-6H-benzo[c]chromen-6-one (86)

A solution of 3-((diphenylmethylene)amino)-8-methoxy-6H-benzo[c]chromen-6-one (Intermediate 10) (250 mg, 0.617 mmol) in THF (3.0 mL) was treated with 2 M HCl (3.1 mL) and allowed to stir at RT for 10 mins. A precipitate was collected by filtration, which was then dissolved in MeOH and applied to a MeOH-equilibrated SCX-2 cartridge; after washing with MeOH/DCM the title compound was eluted using 7 M NH₃ in MeOH to give the product as a beige solid (50 mg, 34%). ¹H NMR (400 MHz, DMSO-d₆) δ 8.15 (1H, d, J=8.8 Hz), 7.94 (1H, d, J=8.6 Hz), 7.61 (1H, d, J=2.8 Hz), 7.49 (1H, dd, J=2.8, 8.8 Hz), 6.67 (1H, dd, J=2.3, 8.6 Hz), 6.54 (1H, d, J=2.3 Hz), 5.82 (2H, s), 3.92 (3H, s); LCMS (Method 1): $R_t$=3.91 min; m/z=242.3 [M+H]⁺.

The following examples in Table 1 were prepared using similar methods those described above by utilizing the general procedures (GP) indicated.

TABLE 1

| Ex. | Structure | General procedure | ¹H NMR data (400 MHz, DMSO-d₆) δ | LCMS m/z (M + H) | HPLC R$_t$ (min)/QC Method |
|---|---|---|---|---|---|
| (11) | 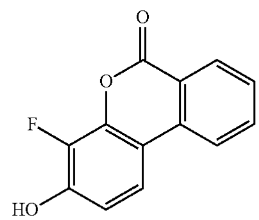 [SMILES: O=c1oc2c(F)c(O)ccc2c2ccccc12] | A | 10.81 (1H, s), 8.34 (1H, d, J = 8.1 Hz), 8.27 (1H, d, J = 7.3 Hz), 8.06-7.94 (2H, m), 7.67 (1H, dd, J = 7.2, 7.2 Hz), 7.05 (1H, dd, J = 8.0, 8.0 Hz) | 231.1 | 3.96/1 |
| (87) | 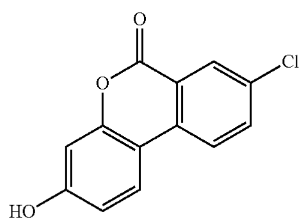 [SMILES: O=c1oc2cc(O)ccc2c2ccc(Cl)cc12] | A | 10.48 (1H, s), 8.36 (1H, d, J = 8.8 Hz), 8.23 (1H, d, J = 8.8 Hz), 8.17 (1H, d, J = 2.3 Hz), 7.98 (1H, dd, J = 2.4 8.7 Hz), 6.91 (1H, dd, J = 2.4, 8.7 Hz), 6.82 (1H, d, J = 2.3 Hz) | 245.1, 247.1 | 4.52/1 |
| (88) | 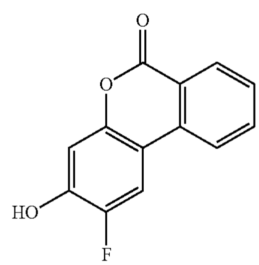 [SMILES: O=c1oc2cc(O)c(F)cc2c2ccccc12] | A | 10.91 (1H, s), 8.39-8.33 (1H, m), 8.29-8.23 (2H, m), 7.95 (1H, dd, J = 7.5, 7.5 Hz), 7.70-7.66 (1H, m), 6.99 (1H, d, J = 3.7 Hz) | 231.1 | 3.07/2 |
| (89) | 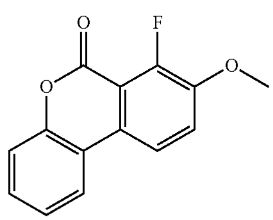 [SMILES: COc1ccc2c(c1F)c(=O)oc1ccccc12] | C | (CDCl₃) 7.98 (1H, dd, J = 1.5, 7.9 Hz), 7.88 (1H, dd, J = 1.7, 9.0 Hz), 7.52-7.42 (2H, m), 7.35-7.28 (3H, m), 4.01 (3H, s) | 245.2 | 4.60/1 |
| (90) | 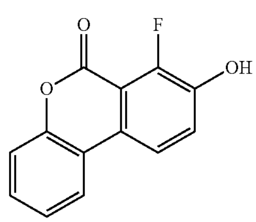 [SMILES: O=c1oc2ccccc2c2ccc(O)c(F)c12] | C | 10.72 (1H, s), 8.26-8.23 (1H, m), 8.13-8.10 (1H, m), 7.58-7.48 (2H, m), 7.40-7.36 (2H, m) | 231.2 | 3.96/1 |
| (91) | 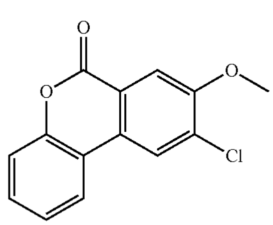 [SMILES: COc1cc2c(=O)oc3ccccc3c2cc1Cl] | C | 8.14 (1H, s), 7.94 (1H, dd, J = 1.5, 8.0 Hz), 7.86 (1H, s), 7.50-7.45 (1H, m), 7.40-7.32 (2H, m), 4.05 (3H, s) | 260.9 | 5.06/3 |

TABLE 1-continued

| Ex. | Structure | General procedure | $^1$H NMR data (400 MHz, DMSO-d$_6$) δ | LCMS m/z (M + H) | HPLC R$_t$ (min)/QC Method |
|---|---|---|---|---|---|
| (92) | 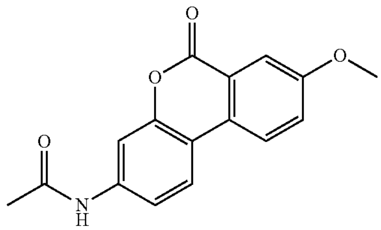 [SMILES: COc1ccc2c(c1)c(=O)oc1cc(NC(C)=O)ccc12] | A/D | 10.29 (1H, s), 8.24 (2H, dd, J = 8.9, 28.4 Hz), 7.78 (1H, d, J = 2.0 Hz), 7.64 (1H, d, J = 2.7 Hz), 7.55-7.46 (2H, m), 3.91 (3H, s), 2.10 (3H, s) | 284.0 | 3.72/3 |
| (93) | 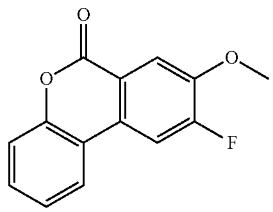 [SMILES: COc1cc2c(=O)oc3ccccc3c2cc1F] | C1 | 8.40 (1H, d, J = 12.5 Hz), 8.30 (1H, dd, J = 1.4, 7.9 Hz), 7.85 (1H, d, J = 8.7 Hz), 7.58-7.53 (1H, m), 7.44-7.38 (2H, m), 4.01 (3H, s) | 244.9 | 4.70/3 |
| (94) | 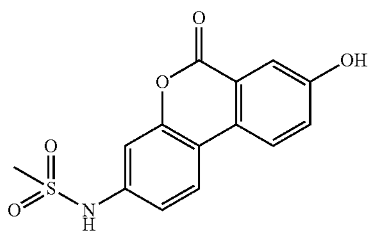 [SMILES: CS(=O)(=O)Nc1ccc2c(c1)oc(=O)c1cc(O)ccc12] | A/D/C2 | 10.38-10.35 (1H, m), 10.15 (1H, s), 8.21-8.17 (2H, m), 7.55 (1H, d, J = 2.6 Hz), 7.36 (1H, dd, J = 2.7, 8.7 Hz), 7.20-7.17 (2H, m), 3.09 (3H, s) | 305.8 | 3.06/3 |
| (95) | 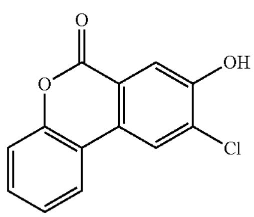 [SMILES: O=c1oc2ccccc2c2cc(Cl)c(O)cc12] | C | 11.30, (1H, br s), 8.52 (1H, s), 8.32 (1H, dd, J = 1.2, 8.0 Hz), 7.76 (1H, s), 7.53-7.47 (1H, m), 7.41-7.34 (2H, m) | 246.9 | 4.31/3 |
| (96) | 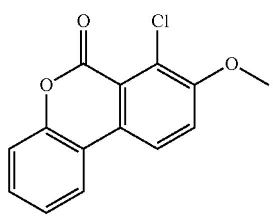 [SMILES: COc1ccc2c(c1Cl)c(=O)oc1ccccc12] | C1 | (CDCl$_3$) 8.08 (1H, d, J = 8.9 Hz), 7.98 (1H, dd J = 1.3, 8.0 Hz), 7.48-7.42 (2H, m), 7.36-7.30 (2H, m), 4.05 (3H, S) | 260.9 | 4.58/3 |
| (97) | 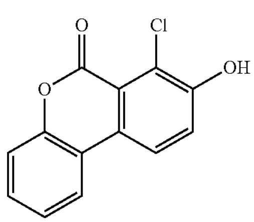 [SMILES: O=c1oc2ccccc2c2ccc(O)c(Cl)c12] | C | 10.98 (1H, s), 8.28 (1H, d J = 8.9 Hz), 8.25-8.21 (1H, m), 7.54 (1H, d J = 8.8 Hz), 7.52-7.46 (1H, m), 7.39-7.33 (2H, m) | 246.9 | 3.94/3 |
| (98) | 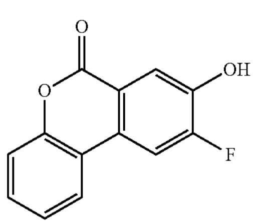 [SMILES: O=c1oc2ccccc2c2cc(F)c(O)cc12] | C | 11.00 (1H, s), 8.32 (1H, d, J = 12.0 Hz), 8.27 (1H, dd, J = 1.3, 8.0 Hz), 7.77 (1H, d, J = 8.9 Hz), 7.54-7.49 (1H, m), 7.41-7.35 (2H, m) | 230.3 | 3.96/3 |

TABLE 1-continued

| Ex. | Structure | General procedure | ¹H NMR data (400 MHz, DMSO-d₆) δ | LCMS m/z (M + H) | HPLC $R_t$ (min)/QC Method |
|---|---|---|---|---|---|
| (99) | 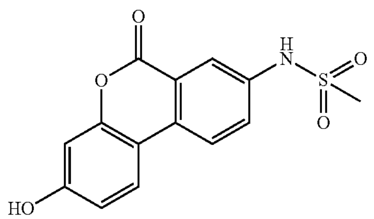 [SMILES: CS(=O)(=O)Nc1ccc2c(c1)c(=O)oc1cc(O)ccc12] | A/D2 | 10.29-10.19 (2H, m), 8.25 (1H, d, J = 8.7 Hz), 8.10 (1H, d, J = 8.9 Hz), 8.00 (1H, d, J = 2.4 Hz), 7.69 (1H, dd, J = 2.4, 8.7 Hz), 6.84 (1H, dd, J = 2.4, 8.7 Hz), 6.76-6.75 (1H, m), 3.07-3.06 (3H, m) | 305.9 | 3.07/3 |
| (100) | 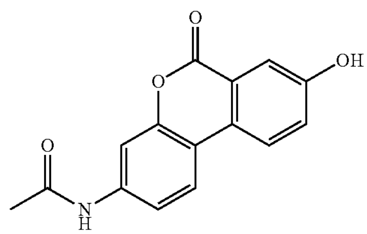 [SMILES: CC(=O)Nc1ccc2c(c1)oc(=O)c1cc(O)ccc12] | A/D/C2 | 10.27 (1H, s), 8.19-8.12 (2H, m), 7.75 (1H, d, J = 2.0 Hz), 7.54 (1H, d, J = 2.6 Hz), 7.46 (1H, dd, J = 2.0, 8.7 Hz), 7.35 (1H, dd, J = 2.7, 8.7 Hz), 2.09 (3H, s) | 269.9 | 2.94/3 |
| (101) | 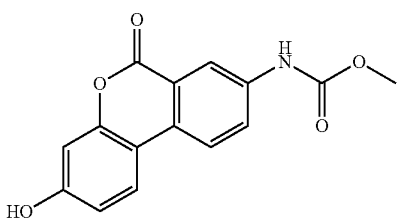 [SMILES: COC(=O)Nc1ccc2c(c1)c(=O)oc1cc(O)ccc12] | A/E | 10.26 (1H, s), 10.07 (1H, s), 8.35 (1H, d, J = 2.3 Hz), 8.20 (1H, d, J = 8.9 Hz), 8.07 (1H, d, J = 8.9 Hz), 7.92 (1H, dd, J = 2.4, 8.8 Hz), 6.83 (1H, dd, J = 2.4, 8.7 Hz), 6.74 (1H, d, J = 2.4 Hz), 3.71 (3H, s) | 285.9 | 3.38/3 |
| (102) | 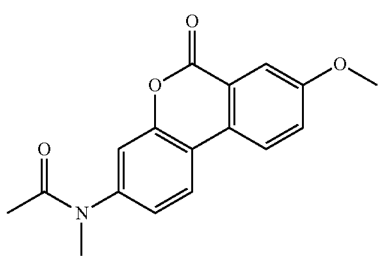 [SMILES: COc1ccc2c(c1)c(=O)oc1cc(N(C)C(C)=O)ccc12] | A/E | 8.41 (1H, d, J = 8.9 Hz), 8.35 (1H, d, J = 8.5 Hz), 7.68 (1H, d, J = 2.8 Hz), 7.57 (1H, dd, J = 2.8, 8.9 Hz), 7.50 (1H, s), 7.38 (1H, dd, J = 2.1, 8.5 Hz), 3.93 (3H, s), 3.24 (3H, s), 1.92 (3H, s) | 297.9 | 3.84/3 |
| (103) | 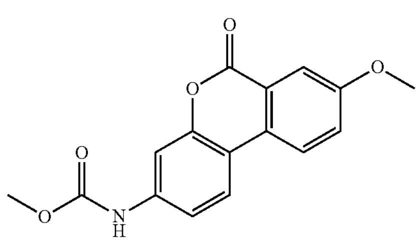 | A/E | 10.06 (1H, s), 8.27 (1H, d, J = 8.9 Hz), 8.20 (1H, d, J = 8.8 Hz), 7.64 (1H, d, J = 2.8 Hz), 7.58 (1H, d, J = 2.0 Hz), 7.53 (1H, dd, J = 2.8, 8.9 Hz), 7.42 (1H, dd, J = 2.1, 8.7 Hz), 3.91 (3H, s), 3.72 (3H, s) | 299.8 | 4.18/3 |
| (104) | 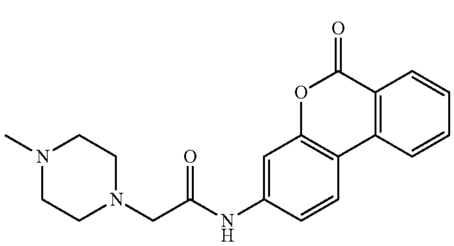 [SMILES: CN1CCN(CC(=O)Nc2ccc3c(c2)oc(=O)c2ccccc23)CC1] | A/D | 10.09 (1H, s), 8.35 (1H, d, J = 8.1 Hz), 8.30 (1H, d, J = 8.8 Hz), 8.23 (1H, dd, J = 1.0, 7.9 Hz), 7.96-7.91 (1H, m), 7.85 (1H, d, J = 2.0 Hz), 7.66-7.60 (2H, m), 3.17 (2H, s), 2.54 (br s, part obscured by solvent), 2.39 (4H, br s), 2.18 (3H, s) | 352.0 | 3.76/4 |

TABLE 1-continued

| Ex. | Structure | General procedure | ¹H NMR data (400 MHz, DMSO-d$_6$) δ | LCMS m/z (M + H) | HPLC R$_t$ (min)/QC Method |
|---|---|---|---|---|---|
| (105) | 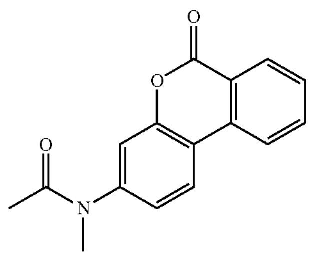 [SMILES: CC(=O)N(C)c1ccc2c(c1)oc(=O)c1ccccc12] | E | 8.46 (1H, d, J = 8.1 Hz), 8.42 (1H, d, J = 8.3 Hz), 8.27 (1H, dd, J = 1.2, 7.9 Hz), 8.01-7.95 (1H, m), 7.74-7.68 (1H, m), 7.52 (1H, d, J = 1.7 Hz), 7.41 (1H, dd, J = 2.2, 8.5 Hz), 3.25 (3H, s), 1.94 (3H, br S) | 268.0 | 3.77/4 |
| (106) | 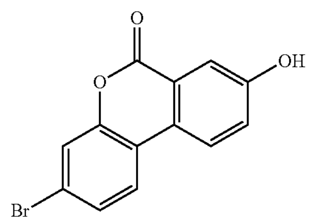 [SMILES: O=c1oc2cc(Br)ccc2c2ccc(O)cc12] | F/C2 | 10.5 (1H, s), 8.29 (1H, d, J = 8.8 Hz), 8.19 (1H, d, J = 8.6 Hz), 7.68 (1H, d, J = 2.0 Hz), 7.57 (1H, d, J = 2.7 Hz), 7.55 (1H, dd, J = 2.0, 8.6 Hz), 7.38 (1H, dd, J = 2.7, 8.8 Hz) | 288.9 | 4.02/4 |
| (107) | 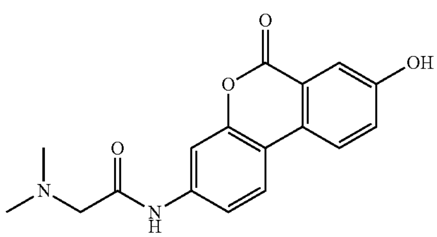 [SMILES: CN(C)CC(=O)Nc1ccc2c(c1)oc(=O)c1cc(O)ccc12] | F/D2 (from bromide Ex 35) | 10.34 (1H, s), 10.06 (1H, s), 8.19 (1H, d, J = 8.9 Hz), 8.15 (1H, d, J = 8.8 Hz), 7.84 (1H, d, J = 1.9 Hz), 7.63 (1H, dd, J = 1.9, 8.6 Hz), 7.55 (1H, d, J = 2.6 Hz), 7.35 (1H, dd, J = 2.6, 8.7 Hz), 4.34 (1H, t, J = 5.0 Hz), 3.48-3.40 (1H, m), 3.12 (2H, s), 2.29 (6H, s), 1.06 (1.8 H, t, J = 7.0 Hz) | 313.0 | 2.99/4 |
| (108) | | F/D2 (from bromide Ex 35) | 10.34 (1H, s), 10.01 (1H, s), 8.20 (1H, d, J = 8.9 Hz), 8.16 (1H, d, J = 8.9 Hz), 7.81 (1H, d, J = 2.1 Hz), 7.59-7.53 (2H, m), 7.35 (1H, dd, J = 2.7, 8.8 Hz), 3.16 (2H, s), 2.53 (br s obscured by solvent), 2.40 (4H, br s), 2.18 (3H, s) | 368.0 | 2.27/3 |
| (108)* | | F/D2 (from bromide Ex 35) | 11.30-10.20 (3H, m), 8.25-8.16 (2H, m), 7.82 (1H, d, J = 1.9 Hz), 7.58-7.53 (2H, m), 7.38, 1H, dd, J = 2.7, 8.8 Hz), 4.15-3.0 (br m, signals obscured by water), 2.80 (3H, s) | 368.0 | 2.80/4 |
| (109) | 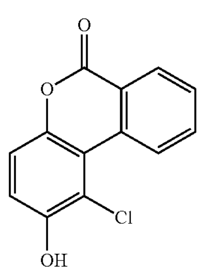 [SMILES: O=c1oc2ccc(O)c(Cl)c2c2ccccc12] | B/C2 | 10.47 (1H, s), 9.39 (1H, d, J = 8.3 Hz), 8.36 (1H, dd, J = 1.4, 7.8 Hz), 8.03-7.97 (1H, m), 7.79-7.74 (1H, m), 7.33 (1H, d, J = 9.0 Hz), 7.23 (1H, d, J = 9.0 Hz) | 246.9 | 4.01/3 |

TABLE 1-continued

| Ex. | Structure | General procedure | ¹H NMR data (400 MHz, DMSO-d$_6$) δ | LCMS m/z (M + H) | HPLC R$_t$ (min)/QC Method |
|---|---|---|---|---|---|
| (110) | 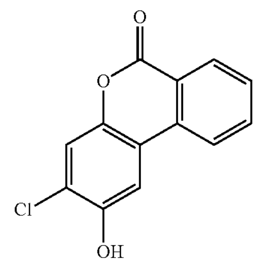 [SMILES: O=c1oc2cc(Cl)c(O)cc2c2ccccc12] | B/C2 | 10.50 (1H, br s), 8.26 (1H, dd, J = 2.2, 7.9 Hz), 8.17 (1H, d, J = 8.0 Hz), 8.00-7.94 (1H, m), 7.75 (1H, s), 7.74-7.68 (1H, m), 7.56 (1H, s) | 246.9 | 3.04/4 |
| (111) | 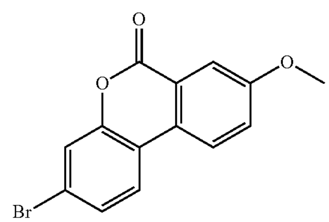 [SMILES: COc1ccc2c(c1)c(=O)oc1cc(Br)ccc12] | F | (CDCl$_3$) 8.00 (1H, d, J = 8.9 Hz), 7.84 (1H, d, J = 8.7 Hz), 7.80 (1H, d, J = 2.8 Hz), 7.53 (1H, d, J = 1.9 Hz), 7.46-7.39 (2H, m), 3.95 (3H, s) | 304.8, 306.8 | 5.30/3 |
| (85) | 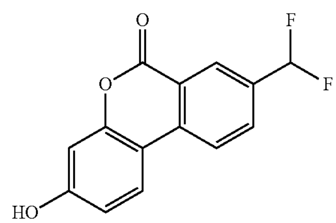 [SMILES: O=c1oc2cc(O)ccc2c2ccc(C(F)F)cc12] | A/G | (CDCl$_3$) 10.50 (1H, s), 8.41 (1H, d, J = 8.7 Hz), 8.35 (1H, d, J = 0.8 Hz), 8.21 (1H, d, J = 8.9 Hz), 8.06-8.02 (1H, m), 7.21 (1H, t, J = 55.5 Hz), 6.88 (1H, dd, J = 2.4, 8.7 Hz), 6.78 (1H, d, J = 2.4 Hz) | 260.9 | 4.03/3 |
| (112) | 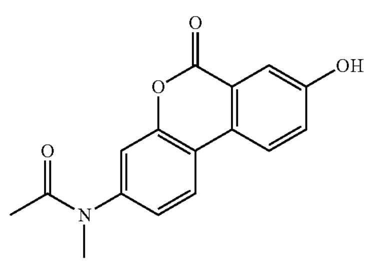 [SMILES: CC(=O)N(C)c1ccc2c(c1)oc(=O)c1cc(O)ccc12] | A/E | 10.46 (s, 1H), 8.32-8.26 (m, 2H), 7.58 (d, J = 2.6 Hz, 1H), 7.46 (s, 1H), 7.41-7.33 (m, 2H), 3.22 (s, 3H), 1.90 (s, 3H). | 283.9 | 3.06/3 |
| (113) | 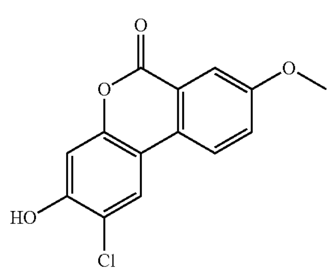 [SMILES: COc1ccc2c(c1)c(=O)oc1cc(O)c(Cl)cc12] | A | 11.05 (1H, br s), 8.35 (1H, s), 8.33 (1H, ob d J = 8.4 Hz), 7.64 (1H, d J = 2.8 Hz), 7.53 (1H, dd J = 2.8, 8.8 Hz), 6.97 (1H, s), 3.94 (3H, s) | 276.9 | 3.00/4 |

*salt was prepared following treatment with 1.1 eq aqueous HCl and lyophilization. NMR spectra were obtained in d$_6$-DMSO unless otherwise stated.

B) Ether and Amide "A" Group Analogues
Procedure 1

2-Chloro-3,8-dihydroxy-6H-benzo[c]chromen-6-one (114) and

2-Chloro-6H-benzo[c]chromene-3,8-diol (115)

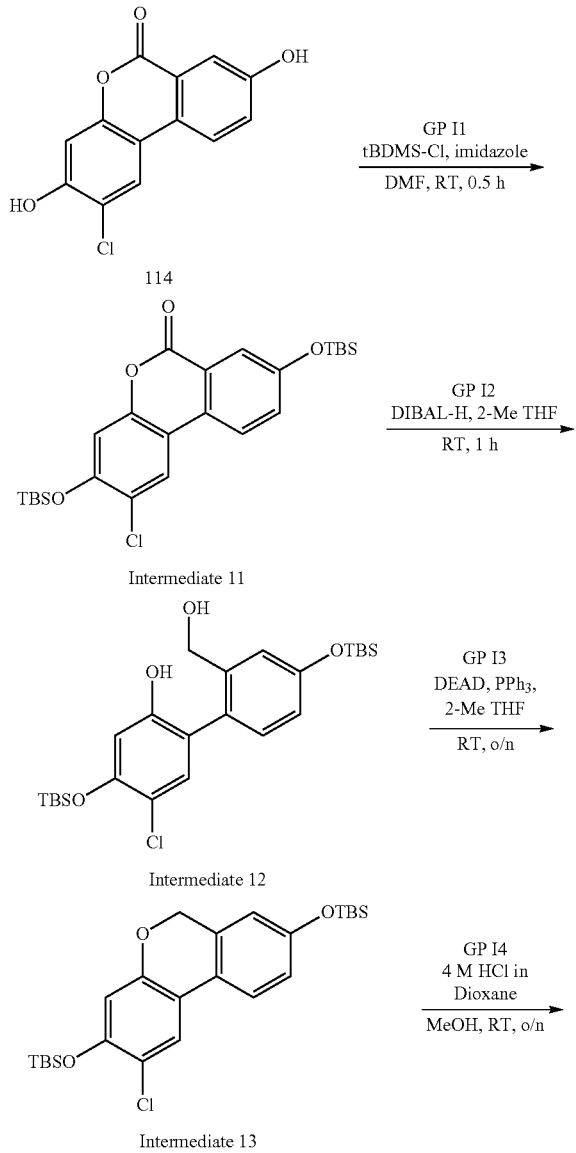

2-Chloro-3,8-dihydroxy-6H-benzo[c]chromen-6-one (114)

2-Chloro-3,8-dihydroxy-6H-benzo[c]chromen-6-one was prepared from 113 using General Procedure C2. $^1$H NMR (400 MHz, DMSO-$d_6$) δ 10.25 (1H, br s), 8.24 (1H, s), 8.19 (1H, d J=8.8 Hz), 7.51 (1H, d J=2.6 Hz), 7.31 (1H, dd J=2.7, 8.7 Hz), 6.91 (1H, s); LCMS (Method 3): $R_t$=3.52 min; m/z=260.9 [M−H]$^-$.

GP I1

3,8-bis((Tert-butyldimethylsilyl)oxy)-2-chloro-6H-benzo[c]chromen-6-one (Intermediate 11)

A suspension of 2-chloro-3,8-dihydroxy-6H-benzo[c]chromen-6-one (114) (2.37 g, 9.04 mmol) in DMF (15 mL) was treated with imidazole (2.46 g, 36.14 mmol) then TBDMSCl and the resulting mixture stirred at RT for 18 h. The reaction was partitioned between EtOAc (×3) and water and the combined organic extract was washed with brine, dried (PTFE frit) and concentrated in vacuo. The resultant residue was purified by chromatography on silica using 0-25% DCM in cyclohexane as eluant to give the product as a white solid (2.0 g, 45%). $^1$H NMR (400 MHz, CDCl$_3$) δ 7.94 (1H, s), 7.85 (1H, d J=8.7 Hz), 7.76 (1H, d J=2.6 Hz), 7.31 (1H, dd J=2.7, 8.7 Hz), 6.89 (1H, s), 1.05 (9H, s), 1.01 (9H, s), 0.28 (6H, s), 0.26 (6H, s).

GP I2

4,4'-bis((Tert-butyldimethylsilyl)oxy)-5-chloro-2'-(hydroxymethyl)-[1,1'-biphenyl]-2-ol (Intermediate 12)

To a solution of 3,8-bis((tert-butyldimethylsilyl)oxy)-2-chloro-6H-benzo[c]chromen-6-one (Intermediate 11) (385 mg, 0.784 mmol) in 2-Me THF (10 mL) was added dropwise, DIBAL-H (1.0 M in THF; 1.60 mL, 1.60 mmol) and the resulting solution was stirred at RT for 1 h. The mixture was cooled in an ice bath then quenched by addition of 15% aqueous NaOH (0.1 mL) followed by water (0.16 mL). After stirring for 30 mins Na$_2$SO$_4$ was added and the resultant mixture stirred for 18 h at RT. The mixture was filtered through Celite® and the pad washed with DCM, and the combined organic layer concentrated in vacuo to give a yellow solid (388 mg, quant.). $^1$H NMR (400 MHz, CDCl$_3$) δ 7.24 (1H, s), 7.04 (1H, d J=8.3 Hz), 6.98 (1H, s), 6.88 (1H, s), 6.79 (1H, d J=7.7 Hz), 6.42 (1H, s), 4.27 (2H, m), 1.23 (1H, m), 1.02 (9H, s), 0.98 (9H, s), 0.20 (6H, s), 0.19 (6H, s).

GP I3

2-Chloro-6H-benzo[c]chromene-3,8-diyl)bis(oxy))bis(tert-butyldimethylsilane) (Intermediate 13)

To a solution of 4,4'-bis((tert-butyldimethylsilyl)oxy)-5-chloro-2'-(hydroxymethyl)-[1,1'-biphenyl]-2-ol (Intermediate 12) (388 mg, 0.783 mmol) and triphenylphosphine (308 mg, 1.17 mmol) in 2-Me THF (5.0 mL) was added dropwise DEAD (0.18 mL), and the mixture was stirred for 30 min at RT. The resulting solution was concentrated in vacuo and purified by chromatography on silica using 0-50% EtOAc in cyclohexane as eluant to give the semi-pure product. LCMS analysis gave desired product plus ~70% of the fully deprotected diol. The crude reaction mixture was taken on to the next stage without purification.

GP I4

2-Chloro-6H-benzo[c]chromene-3,8-diol (115)

A solution of crude ((2-chloro-6H-benzo[c]chromene-3,8-diyl)bis(oxy))bis(tert-butyl dimethyl silane) (Intermediate 13) (0.783 mmol) in MeOH (5.0 mL) was treated with 4 M HCl in dioxane (1.96 mL, 7.83 mmol) and the reaction was allowed to stir at RT for 18 h. The resultant mixture was concentrated in vacuo, and the residue was partitioned between DCM (×2) and water. The combined organic extract was washed with brine, dried (Na$_2$SO$_4$) and concentrated in vacuo and the crude residue was purified by chromatography on silica using 0-50% EtOAc in cyclohexane as eluant to give the title compound as a pale-yellow solid (60 mg, 31% yield). $^1$H NMR (400 MHz, DMSO-d$_6$) δ 10.22 (1H, br s), 9.60 (1H, br s), 7.66 (1H, s), 7.54 (1H, d J=8.3 Hz), 6.74 (1H, d J=7.5 Hz), 6.62 (1H, s), 6.53 (1H, s), 4.99 (2H, s); LCMS (Method 3): R$_t$=3.57 min; m/z=246.9 [M−H]$^−$.

Procedure J

3,8-Dihydroxy-2-methyl-6H-benzo[c]chromen-6-one (116) and

2,6,6-Trimethyl-6H-benzo[c]chromene-3,8-diol (117)

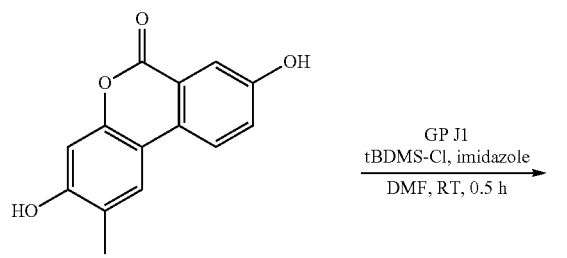

116

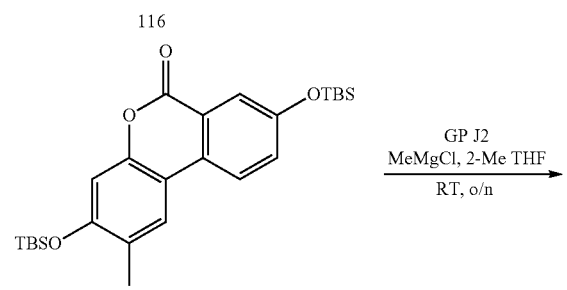

Intermediate 14

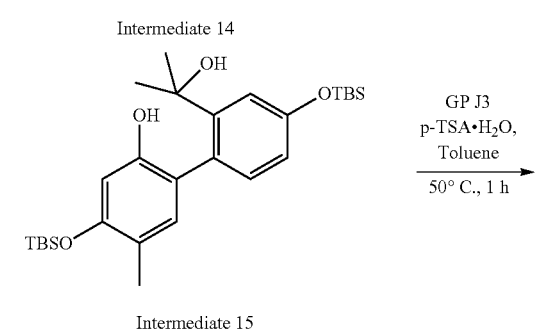

Intermediate 15

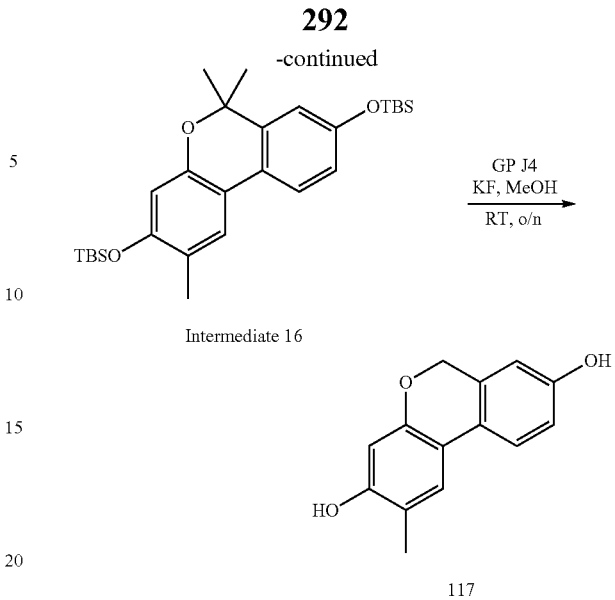

Intermediate 16

117

3,8-Dihydroxy-2-methyl-6H-benzo[c]chromen-6-one (116) 3,8-Dihydroxy-2-methyl-6H-benzo[c]chromen-6-one was prepared using General Procedures A and C2. $^1$H NMR (400 MHz, DMSO-d$_6$) δ 10.15 (2H, br s), 8.11 (1H, d J=8.9 Hz), 7.92 (1H, s), 7.50 (1H, d J=2.7 Hz), 7.31 (1H, dd J=2.7, 8.7 Hz), 6.74 (1H, s), 2.21 (3H, s); LCMS (Method 3): R$_t$=3.45 min; m/z=242.9 [M+1]$^+$.

GP J1

3,8-bis((Tert-butyldimethylsilyl)oxy)-2-methyl-6H-benzo[c]chromen-6-one (Intermediate 14

3,8-bis((tert-butyldimethylsilyl)oxy)-2-methyl-6H-benzo[c]chromen-6-one was prepared from 3,8-dihydroxy-2-methyl-6H-benzo[c]chromen-6-one (120) using General Procedure I1 $^1$H NMR (400 MHz, CDCl$_3$) δ 7.89 (1H, d J=8.7 Hz), 7.76 (1H, d J=2.7 Hz), 7.71 (1H, s), 7.28 (1H, dd J=2.6, 8.8 Hz), 6.78 (1H, s), 2.29 (3H, s), 1.03 (9H, s), 1.01 (9H, s), 0.27 (6H, s), 0.26 (6H, s).

GP J2

4,4'-bis((Tert-butyldimethylsilyl)oxy)-2'-(2-hydroxy-propan-2-yl)-5-methyl-[1,1'-biphenyl]-2-ol (Intermediate 15)

To a solution of 3,8-bis((tert-butyldimethylsilyl)oxy)-2-methyl-6H-benzo[c]chromen-6-one (Intermediate 14) (300 mg, 0.637 mmol) in 2-Me THF (6.0 mL) was added MeMgCl (3.0 M in THF; 0.64 mL, 1.92 mmol) and the resulting solution was stirred at RT for 18 h. The reaction mixture was quenched with saturated aqueous NH$_4$Cl and extracted with EtOAc (×2) prior to drying (Na$_2$SO$_4$) and concentrating in vacuo to give the title compound as a colourless oil (320 mg, quant.). $^1$H NMR (400 MHz, CDCl$_3$) δ 7.10 (1H, d J=2.5 Hz), 6.94 (1H, d J=8.2 Hz), 6.86 (1H, s), 6.75 (1H, dd J=2.5, 8.2 Hz), 6.43 (1H, s), 5.08 (1H, s), 2.13 (3H, s), 2.04 (1H, s), 1.53 (3H, s), 1.42 (3H, s), 1.03 (9H, s), 1.01 (9H, s), 0.26 (3H, s), 0.25 (3H, s), 0.24 (6H, s).

GP J3

((2,6,6-Trimethyl-6H-benzo[c]chromene-3,8-diyl)bis(oxy))bis(tert-butyldimethylsilane) (Intermediate 16)

A solution of 4,4'-bis((tert-butyldimethylsilyl)oxy)-2'-(2-hydroxypropan-2-yl)-5-methyl-[1,1*-biphenyl]-2-ol (Intermediate 15) (320 mg, 0.637 mmol) in toluene (5.0 mL) was treated with PTSA.H₂O and the resulting mixture was heated for 1 h at 50° C. The resulting solution was purified directly by chromatography on silica using DCM as eluant to give the product as a colourless oil (280 mg, 90%). $^1$H NMR (400 MHz, CDCl₃) δ 7.48 (1H, d J=8.4 Hz), 6.38 (1H, s), 6.77 (1H, dd J=2.4, 8.4 Hz), 6.68 (1H, d J=2.4 Hz), 6.39 (1H, s), 2.19 (3H, s), 1.57 (6H, s), 1.02 (9H, s), 0.99 (9H, s), 0.23 (6H, s), 0.21 (6H, s). LCMS (Method 3): R$_t$=3.57 min; m/z=246.9 [M−H]⁻.

GP J4

2,6,6-Trimethyl-6H-benzo[c]chromene-3,8-diol (117)

A suspension of ((2,6,6-trimethyl-6H-benzo[c]chromene-3,8-diyl)bis(oxy))bis(tert-butyl dimethylsilane) (Intermediate 16) (270 mg, 0.557 mmol) in MeOH (5.0 mL) was treated with solid KF (97 mg, 1.67 mmol) and the resulting suspension stirred at RT for 18 h. The resultant mixture was absorbed on to HMN and purified by chromatography on silica using 0-30% EtOAc in cyclohexane as eluant to give semi-pure product as a pale-yellow oil (121 mg). Further purification by trituration from a mixture of DCM and n-pentane gave the title compound as a white solid (91 mg, 64%). $^1$H NMR (400 MHz, DMSO-d₆) δ 9.40 (1H, s), 9.32 (1H, s), 7.47 (1H, d J=8.4 Hz), 7.38 (1H, s), 6.71 (1H, dd J=2.3, 8.4 Hz), 6.66 (1H, d J=2.3 Hz), 6.31 (1H, s), 2.09 (3H, s), 1.50 (6H, s); LCMS (Method 3): R$_t$=3.80 min; m/z=257.1 [M+H]⁺.

Procedure K

1-Fluoro-3,8-dihydroxyphenanthridin-6(5H)-one (118)

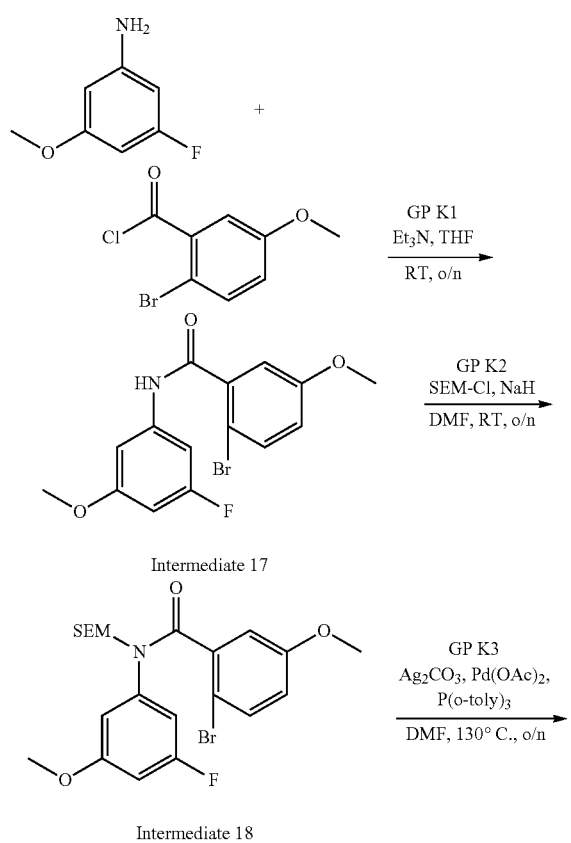

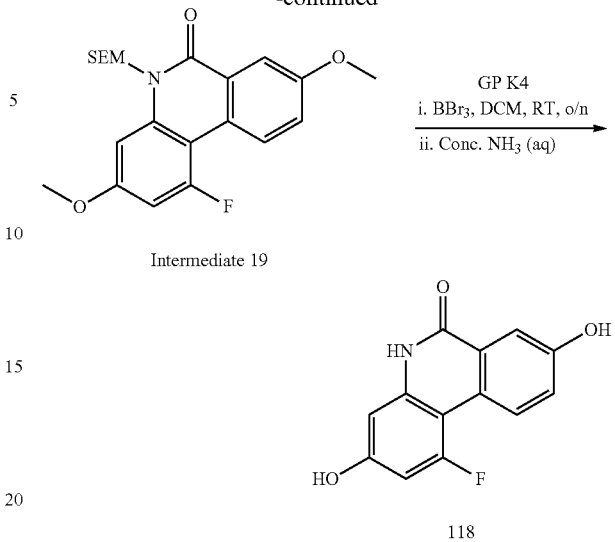

GP K1

2-Bromo-N-(3-fluoro-5-methoxyphenyl)-5-methoxybenzamide (Intermediate 17)

To a solution of 2-bromo-5-methoxybenzoyl chloride (694 mg, 2.78 mmol) in THF (15 mL) was added triethylamine (0.58 mL, 4.17 mmol) followed by 5-methoxyaniline (393 mg, 2.78 mmol). The resulting solution was stirred at RT for 18 h then partitioned between water and DCM (×2) and the combined organic extract was dried and concentrated in vacuo. The residue was purified by chromatography on silica using 0-100% DCM in cyclohexane as eluant to give the title compound as a pale-yellow solid (700 mg, 71% yield). LCMS (Method 6): R$_t$=1.53 min; m/z=354.2/356.2 [M+H]⁺.

GP K2

2-Bromo-N-(3-fluoro-5-methoxyphenyl)-5-methoxy-N-((2-(trimethylsilyl)ethoxy)methyl) benzamide (Intermediate 18)

A solution of 2-bromo-N-(3-fluoro-5-methoxyphenyl)-5-methoxybenzamide (Intermediate 17) (300 mg, 1.09 mmol) in dry DMF (3.0 mL) was treated with NaH (60 wt %; 87 mg, 2.18 mmol) and stirred at RT for 30 mins until gas evolution had ceased. SEM-Cl (0.72 mL, 3.27 mmol) was added to the reaction mixture and stirring was continued for 18 h at RT. The resulting solution was diluted with water (100 mL) then extracted with EtOAc (×3) and the combined organic extract was washed with brine then dried and concentrated in vacuo. The residue was purified by chromatography on silica using 0-30% EtOAc in cyclohexane as eluant to give the title compound as a pale-yellow solid (430 mg, 97% yield). LCMS (Method 6): R$_t$=1.89 min; m/z=482.3/484.3 [M+H]⁺.

GP K3

1-Fluoro-3,8-dimethoxy-5-((2-(trimethylsilyl)ethoxy)methyl)phenanthridin-6(5H)-one (Intermediate 19)

A microwave vial was charged with a solution of 2-bromo-N-(3-fluoro-5-methoxyphenyl)-5-methoxy-N-((2-

(trimethylsilyl)ethoxy)methyl) benzamide (Intermediate 18) (830 mg, 1.71 mmol) in dry DMF (8.0 mL). AgCO$_3$ (945 mg, 3.43 mmol), Pd(OAc)$_2$ (58 mg, 0.257 mmol) and tri(o-tolyl)phosphine (156 mg, 0.514 mmol) was added and the resultant mixture de-gassed under Argon prior to being heated for 18 h at 130° C. The cooled reaction mixture was filtered through Celite® then partitioned between water and EtOAc (×3) and the combined organic extract was washed with brine then dried and concentrated in vacuo. The resultant residue was purified by chromatography on silica using 0-50% EtOAc in cyclohexane as eluant to give the semi-pure product (270 mg). Further purification by trituration from a mixture of DCM and n-pentane gave purer material but an additional purification by chromatography on silica using 0-20% EtOAc in cyclohexane as eluant was required to give pure title compound as a white solid (186 mg, 27%). $^1$H NMR (400 MHz, CDCl$_3$) δ 8.52 (1H, dd J=2.5, 9.1 Hz), 7.98 (1H, d J=3.0 Hz), 7.33 (1H, m), 7.04 (1H, m), 6.66 (1H, dd J=2.5, 14.9 Hz), 5.83 (2H, s), 3.95 (3H, s), 3.90 (3H, s), 3.76 (2H, t J=7.9 Hz), 0.97 (2H, t, J=8.1 Hz), −0.02 (9H, s).
GP K4

1-Fluoro-3,8-dihydroxyphenanthridin-6(5H)-one (118)

A solution of 1-fluoro-3,8-dimethoxy-5-((2-(trimethylsilyl)ethoxy)methyl)phenanthridin-6(5H)-one (Intermediate 19) (86 mg, 0.213 mmol) in DCM (2.0 mL) was treated dropwise with BBr$_3$ and the resulting mixture was stirred for 18 h at RT. The reaction mixture was quenched carefully with water then azeotroped with MeOH (×4) which gave the intermediate hydroxy methyl amide, from partial de-protection of the SEM protecting group, as a yellow solid. LCMS (Method 6): R$_t$=1.09 min; m/z=276.0 [M+1]$^+$.

The intermediate hydroxymethyl amide was treated with concentrated aqueous ammonia (3.0 mL) and the resultant turbid solution stirred for 3 h at RT then azeotroped with MeOH (×4) which gave the crude product as a grey solid. Further purification by reverse-phase chromatography on C18-silica using 3-97% MeCN in water (+0.1% formic acid) gave pure title compound as a grey-white solid following lyophilisation (52 mg, 84%). $^1$H NMR (400 MHz, DMSO-d$_6$) δ 11.60 (1H, br s), 10.05 (2H, br s), 8.28 (1H, d J=9.2 Hz), 7.66 (1H, d J=2.3 Hz), 7.25 (1H, m), 6.64 (1H, s), 6.49 (1H, d J=15.3 Hz); LCMS (Method 3): R$_t$=2.98 min; m/z=246.0 [M+1]$^+$.
Procedure L 6-Methyl-6H-benzo[c]chromene-3,8-diol (119)

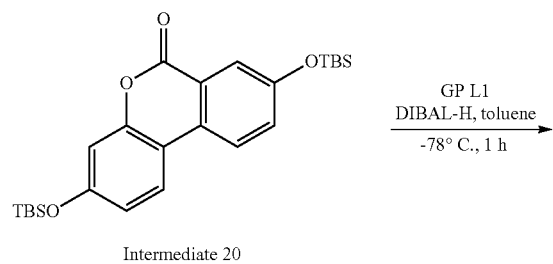

Intermediate 20

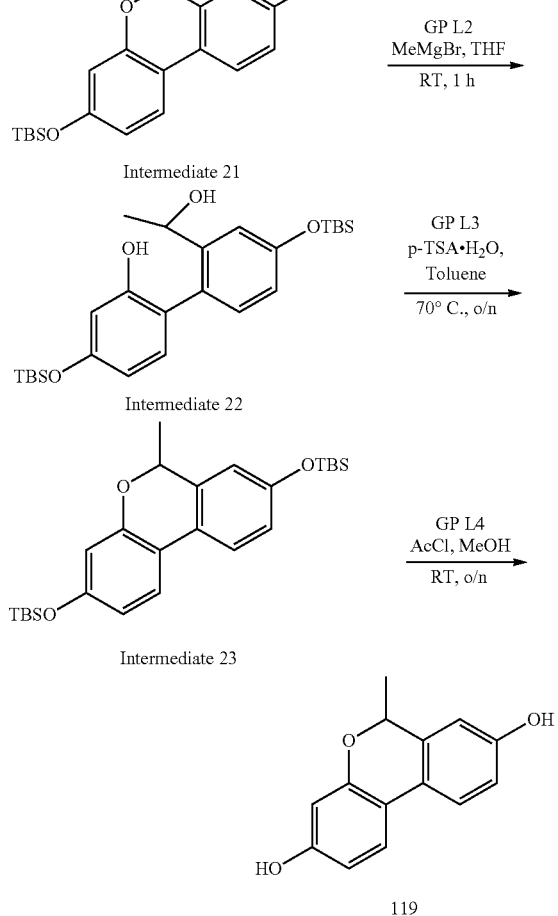

GP L1

3,8-bis((Tert-butyldimethylsilyl)oxy)-6H-benzo[c]chromen-6-one (Intermediate 20)

3,8-bis((Tert-butyldimethylsilyl)oxy)-6H-benzo[c]chromen-6-one was prepared using General Procedure I1. $^1$H NMR (400 MHz, CDCl$_3$) δ 7.89 (d, J=8.8 Hz, 1H), 7.85-7.80 (m, 1H), 7.76 (d, J=2.6 Hz, 1H), 7.29 (dd, J=8.7, 2.7 Hz, 1H), 6.86-6.80 (m, 2H), 1.02 (s, 9H), 0.98 (s, 9H), 0.26 (s, 6H), 0.24 (s, 6H).
GP L2

3,8-bis((Tert-butyldimethylsilyl)oxy)-6H-benzo[c]chromen-6-ol (Intermediate 21)

To a solution of 3,8-bis((tert-butyldimethylsilyl)oxy)-6H-benzo[c]chromen-6-one (Intermediate 20) (912 mg, 2.0 mmol) in toluene (20 mL) under inert atmosphere and at −78° C. was very slowly added DIBAL-H (1 M in toluene, 2.10 mL, 2.10 mmol). Stirring was continued at −78° C. for 1 h. The reaction mixture was quenched by addition of water at −78° C. according to the Fieser work-up followed by the regular Fieser work-up. Filtration through silica and removal of the solvents in vacuo afforded the desired lactol as a white solid, which was used in the next step without further purification (921 mg, quant.). $^1$H NMR (400 MHz, CDCl$_3$)

δ 7.60 (dd, J=8.9, 6.9 Hz, 2H), 6.93 (dd, J=8.5, 2.5 Hz, 1H), 6.83 (d, J=2.6 Hz, 1H), 6.62-6.58 (m, 2H), 6.26 (s, 1H), 1.00 (s, 9H), 0.98 (s, 9H), 0.25-0.18 (m, 12H).
GP L3

4,4'-bis((Tert-butyldimethylsilyl)oxy)-2'-(1-hydroxyethyl)-[1,1'-biphenyl]-2-ol (Intermediate 22)

To a solution of 3,8-bis((tert-butyldimethylsilyl)oxy)-6H-benzo[c]chromen-6-ol (Intermediate 21) (458 mg, 1 mmol) in dry THF (10 mL) under inert atmosphere and at 0° C. was added MeMgBr (3 M in Et$_2$O, 1.0 mL). Stirring was continued at 0° C. for 1 h. The reaction mixture was quenched with water (100 mL) and the mixture extracted with Et$_2$O; the ethereal extracts were dried over Na$_2$SO$_4$, filtered through silica with Et$_2$O washings and then concentrated in vacuo. The crude residue was used in the next step without further purification (475 mg, quant.).
$^1$H NMR (400 MHz, CDCl$_3$) δ 7.15 (d, J=2.6 Hz, 0.4H), 7.12 (d, J=2.6 Hz, 0.6H), 7.07 (s, 0.4H), 7.04 (s, 0.6H), 6.96 (d, J=8.1 Hz, 0.4H), 6.90 (d, J=8.5 Hz, 0.6H), 6.86-6.78 (m, 1H), 6.52-6.43 (m, 2H), 4.79 (q, J=6.4 Hz, 0.4H), 4.73 (q, J=6.5 Hz, 0.6H), 1.36 (d, J=6.4 Hz, 1.2H), 1.30 (d, J=6.4 Hz, 1.8H), 1.01 (s, 7.2H), 1.00 (s, 10.8H), 0.25 (s, 4.8H), 0.24 (s, 7.2H).
GP L4

(((6-Methyl-6H-benzo[c]chromene-3,8-diyl)bis(oxy))bis(tert-butyldimethylsilane) (Intermediate 23)

To a solution of 4,4'-bis((tert-butyldimethylsilyl)oxy)-T-(1-hydroxyethyl)-[1,1'-biphenyl]-2-ol (Intermediate 22) (470 mg, 0.98 mmol) in toluene (10 mL) was added PTSA monohydrate (19.0 mg, 0.19 mmol) and the resulting mixture was heated at 70° C. overnight. The reaction mixture was filtered through silica with DCM washings and concentrated in vacuo. The residue was purified by column chromatography (silica, 0-25% DCM/cyclohexane) to afford the desired ether as a white solid (411 mg, 90%). $^1$H NMR (400 MHz, CDCl$_3$) δ 7.48 (dd, J=8.5, 4.1 Hz, 2H), 6.80 (dd, J=8.4, 2.5 Hz, 1H), 6.61 (dd, J=2.4, 0.8 Hz, 1H), 6.52 (dd, J=8.4, 2.4 Hz, 1H), 6.47 (d, J=2.4 Hz, 1H), 5.17 (q, J=6.5 Hz, 1H), 1.00 (s, 9H), 0.98 (s, 9H) 0.92-0.84 (m, 3H), 0.21 (s, 6H), 0.20 (s, 6H).
GP L5

6-Methyl-6H-benzo[c]chromene-3,8-diol (119)

To a solution of ((6-methyl-6H-benzo[c]chromene-3,8-diyl)bis(oxy))bis(tert-butyldimethylsilane) (Intermediate 23) (411 mg, 0.90 mmol) in dry MeOH (10 mL) at 0° C. was slowly added acetyl chloride (96 mL, 1.35 mmol) and the resulting mixture was stirred overnight. The solvents were removed in vacuo and the residue purified by column chromatography (silica, 0-100% EtOAc/cyclohexane) to provide the title compound as a white solid (202 mg, 98%). $^1$H NMR (400 MHz, DMSO) δ 9.47 (s, 1H), 9.45 (s, 1H), 7.49 (t, J=8.7 Hz, 2H), 6.73 (dd, J=8.4, 2.5 Hz, 1H), 6.60 (d, J=2.4 Hz, 1H), 6.43 (dd, J=8.4, 2.4 Hz, 1H), 6.30 (d, J=2.4 Hz, 1H), 5.14 (q, J=6.5 Hz, 1H), 1.44 (d, J=6.5 Hz, 3H).

The following examples in Table 2 were prepared using similar methods to those described above by utilizing the general procedures (GP) indicated.

TABLE 2

| Ex. | Structure | General procedure | $^1$H NMR data (400 MHz, DMSO-d$_6$) δ | LCMS m/z (M + H) | HPLC R$_t$ (min)/QC Method |
|---|---|---|---|---|---|
| (120) | 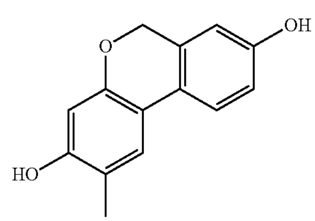 [SMILES: Cc1cc2c(cc1O)OCc1cc(O)ccc1-2] | I | 9.42 (2H, br s), 7.46 (1H, d J = 8.4 Hz), 7.39 (1H, s), 6.72 (1H, m), 6.59 (1H, s), 6.36 (1H, s), 4.91 (2H, s), 2.10 (3H, s) | | 3.46/3 |
| (121) | 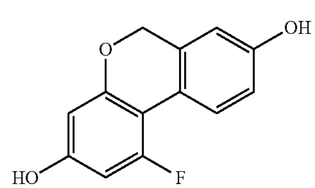 [SMILES: Oc1ccc2c(c1)COc1cc(O)cc(F)c1-2] | I | 9.79 (2H, br s), 7.60 (1H, d J = 8.1 Hz), 6.77 (1H, dd J = 2.5, 8.5 Hz), 6.67 (1H, d J = 2.4 Hz), 6.30 (1H, dd J = 2.3, 13.5 Hz), 6.24 (1H, m), 4.95 (2H, s) | 231.1 [M − H]$^-$ | 3.41/3 |
| (122) | 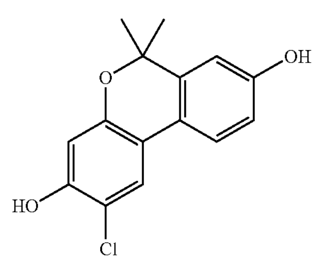 [SMILES: CC1(C)Oc2cc(O)c(Cl)cc2-c2ccc(O)cc21] | J | analytical data in progress | | |

TABLE 2-continued

| Ex. | Structure | General procedure | ¹H NMR data (400 MHz, DMSO-d₆) δ | LCMS m/z (M + H) | HPLC R$_t$ (min)/QC Method |
|---|---|---|---|---|---|
| (123) | 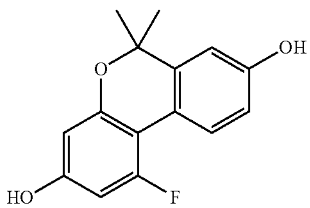 [SMILES: CC1(C)Oc2cc(O)cc(F)c2-c2ccc(O)cc21] | J | 9.76 (2H, v br s), 7.64 (1H, d J = 8.2 Hz), 6.78-6.72 (1H, obs m), 6.74 (1H, s), 6.27 (1H, dd J = 2.3, 13.7 Hz), 6.18 (1H, m), 1.50 (6H, s) | 259.0 [M − H]⁻ | 3.78/3 |
| (124) | 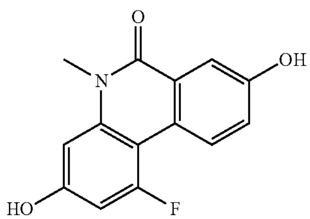 [SMILES: Cn1c(=O)c2cc(O)ccc2c2c(F)cc(O)cc21] | K | 10.18 (2H, br s), 8.32 (1H, d J = 9.2 Hz), 7.73 (1H, d J = 2.4 Hz), 7.25 (1H, m), 6.75 (1H, s), 6.62 (1H, d J = 15.3 Hz), 3.64 (3H, s) | 260.0 | 2.32/4 |
| (125) | 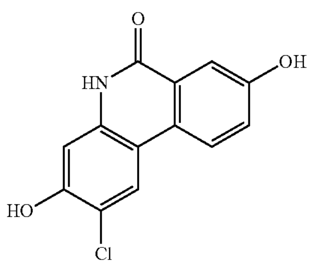 [SMILES: O=c1[nH]c2cc(O)c(Cl)cc2c2ccc(O)cc12] | K | 11.51 (1H, br s), 10.58 (1H, br s), 10.04 (1H, br s), 8.21 (1H, d J = 8.9 Hz), 8.19 (1H, s), 7.58 (1H, d J = 2.7 Hz), 7.21 (1H, d J = 2.7, 8.8 Hz), 6.95 (1H, s) | 259.9 [M − H]⁻ | 3.12/3 |
| (126) | 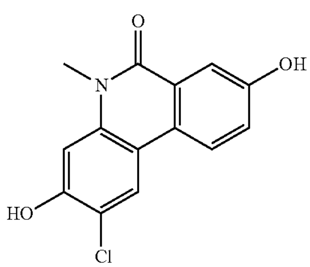 [SMILES: Cn1c(=O)c2cc(O)ccc2c2cc(Cl)c(O)cc21] | K | 10.52 (1H, v br s), 10.07 (1H, br s), 8.30 (1H, s), 8.26 (1H, d J = 8.9 Hz), 7.64 (1H, d J = 2.6 Hz), 7.22 (1H, d J = 2.6, 8.7 Hz), 7.04 (1H, s), 3.62 (3H, s) | 276.0 | 3.34/3 |
| (127) | 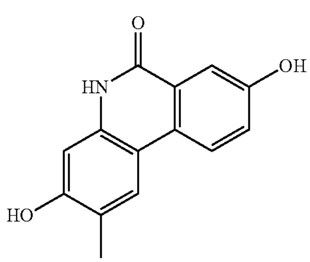 [SMILES: Cc1cc2c(cc1O)[nH]c(=O)c1cc(O)ccc12] | K | 11.34 (1H, s), 9.81-9.76 (2H, br s), 8.15 (1H, d, J = 9.0 Hz), 7.90 (1H, s), 7.57 (1H, d, J = 2.7 Hz), 7.20 (1H, dd, J = 2.7, 8.7 Hz), 6.77 (1H, s), 2.19 (3H, s) | 242.0 | 3.05/3 |
| (128) | 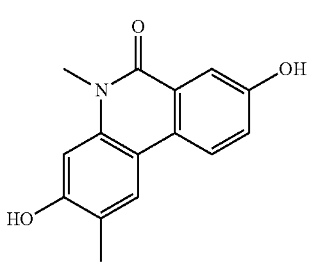 [SMILES: Cc1cc2c3ccc(O)cc3c(=O)n(C)c2cc1O] | K | 9.87 (2H, br s), 8.19 (1H, d J = Hz), 8.03 (1H, s), 7.64 (1H, d J = 2.7 Hz), 7.21 (1H, d J = 2.7, 8.8 Hz), 6.88 (1H, s), 3.62 (3H, s), 2.24 (3H, s) | 256.0 | 3.26/3 |

TABLE 2-continued

| Ex. | Structure | General procedure | ¹H NMR data (400 MHz, DMSO-$d_6$) δ | LCMS m/z (M + H) | HPLC $R_t$ (min)/QC Method |
|---|---|---|---|---|---|
| (129) | 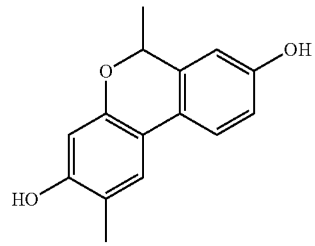 [SMILES: Cc1cc2c(cc1O)OC(C)c1cc(O)ccc1-2] | L | 9.57-9.26 (2H, br s), 9.59 (1H, br s), 7.47 (1H, d J = 8.4 Hz), 7.39 (1H, s), 6.73 (1H, dd J = 2.4, 8.4 Hz), 6.59 (1H, d J = 2.3 Hz), 6.35 (1H, s), 5.09 (1H, q J = 6.5 Hz), 2.10 (3H, s), 1.43 (1H, d J = 6.5 Hz) | 242.0 | 3.63/4 |
| (130) | 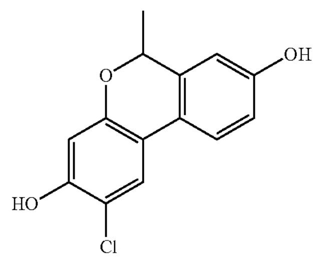 [SMILES: CC1Oc2cc(O)c(Cl)cc2-c2ccc(O)cc21] | L | 10.18 (1H, br s), 9.59 (1H, br s), 7.66 (1H, s), 7.55 (1H, d J = 8.5 Hz), 6.74 (1H, dd J = 2.5, 8.4 Hz), 6.61 (1H, d J = 2.4 Hz), 6.51 (1H, s), 5.18 (1H, q J = 6.5 Hz), 1.43 (1H, d J = 6.5 Hz) | 263.9 | 3.76/3 |
| (131) | 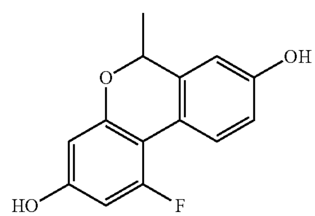 [SMILES: CC1Oc2cc(O)cc(F)c2-c2ccc(O)cc21] | L | 10.31-9.25 (2H, 2 × br s), 7.62 (1H, d J = 8.3 Hz), 6.76 (1H, dd, J = 2.5, 8.5 Hz), 6.66 (1H, d J = 2.5 Hz), 6.28 (1H, dd J = 2.3, 13.6 Hz), 6.23-6.20 (1H, m), 5.18 (1H, q J = 6.5 Hz), 1.45 (1H, d J = 6.5 Hz) | 245.0 [M − H]⁻ | 2.87/4 |

NMR spectra were obtained in DMSO-$d_6$ unless otherwise stated.

Procedure M 10-fluoro-3,9-dihydroxydibenzo[c,e]oxepin-5(7H)-one (132)

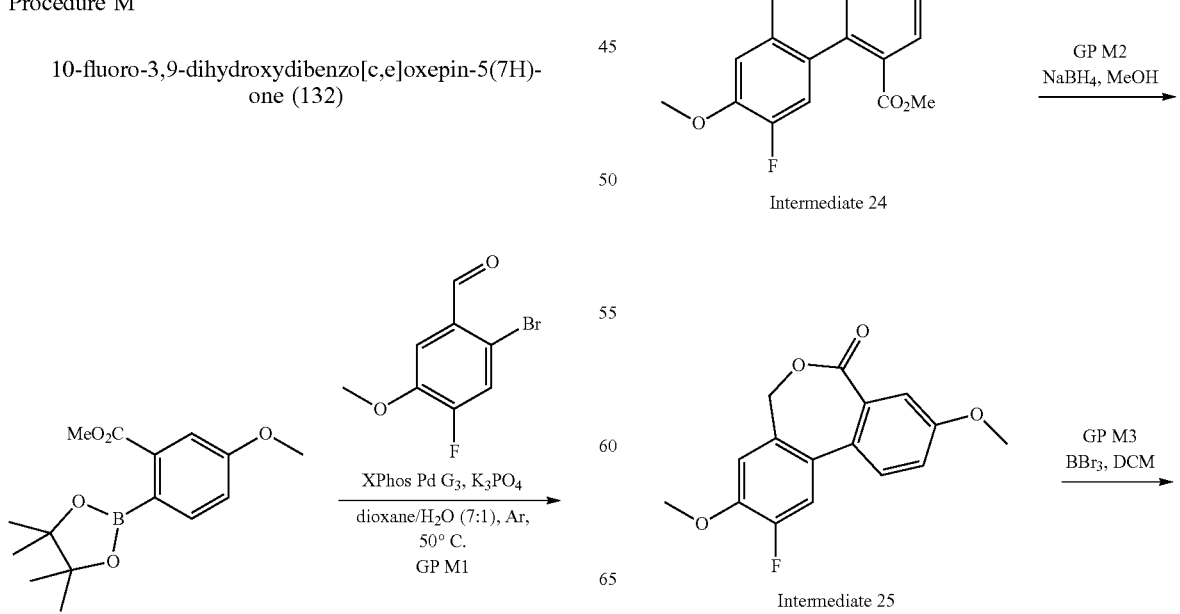

-continued

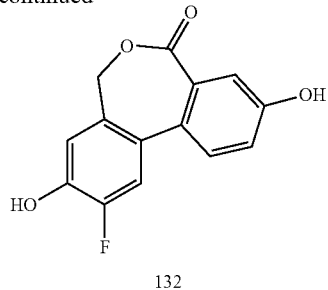

132

GP M1

Methyl 5'-fluoro-2'-formyl-4,4'-dimethoxy-[1,1'-biphenyl]-2-carboxylate (Intermediate 24)

A mixture of 2-bromo-4-fluoro-5-methoxybenzaldehyde (250 mg, 1.07 mmol), methyl 5-methoxy-2-(4,4,5,5-tetramethyl-1,3,2-dioxaborolan-2-yl)benzoate (345 mg, 1.18 mmol), and potassium phosphate (683 mg, 3.22 mmol) in dioxane (4 mL) and water (0.4 mL) was placed in a tube and degassed by purging with argon for 10 min. XPhos-Pd-G3 (45 mg, 0.05 mmol) was then added and the mixture was sealed, degassed and purged with argon. The mixture was heated at 50° C. for 1 h. The resulting cooled mixture was diluted with water then extracted with EtOAc (×3) and the combined organic extract was washed with brine then dried and concentrated in vacuo. The residue was purified by chromatography on silica using 0-25% EtOAc in cyclohexane as eluant to give the title compound as a pale-brown oil (280 mg, 82% yield). $^1$H NMR (400 MHz, CDCl$_3$) δ 9.66 (1H, s), 7.59 (1H, d, J=8.8 Hz), 7.55 (1H, d, J=2.8 Hz), 7.19 (1H, d, J=8.4 Hz), 7.14-7.08 (1H, m), 6.97 (1H, d, J=11.2 Hz), 3.99 (3H, s), 3.91 (3H, s), 3.67 (3H, s).

GP M2

10-Fluoro-3,9-dimethoxydibenzo[c,e]oxepin-5(7H)-one (Intermediate 25)

To a solution of methyl 5'-fluoro-T-formyl-4,4'-dimethoxy-[1,1'-biphenyl]-2-carboxylate (Intermediate 24) (270 mg, 0.85 mmol) in MeOH (4 mL) was added sodium borohydride (32 mg, 0.85 mmol) portionwise. The solution was stirred for 30 min then quenched with water and evaporated. The resulting mixture was diluted with water and EtOAc; this led to a large precipitate at the interface which was isolated by filtration and dissolved in a large volume of ethyl acetate and the combined organic extract was concentrated in vacuo. The solid residue was dissolved in CHCl$_3$/MeOH and evaporated to half volume, whereupon the product crystallised as a white solid; the mother liquors were adsorbed onto HMN and purified by chromatography on silica using 0-5% EtOAc in DCM as eluant to give additional product. The two batches of product were combined to give the title compound as a white solid (150 mg, 61% yield).

$^1$H NMR (400 MHz, CDCl$_3$) δ 7.47 (1H, d, J=2.7 Hz), 7.44 (1H, d, J=8.6 Hz), 7.33 (1H, d, J=11.9 Hz), 7.21 (1H, dd, J=2.7, 8.8 Hz), 7.04 (1H, d, J=8.2 Hz), 5.03-4.89 (2H, m), 3.96 (3H, s), 3.91 (3H, s).

GP M3

10-fluoro-3,9-dihydroxydibenzo[c,e]oxepin-5(7H)-one (132)

10-Fluoro-3,9-dimethoxydibenzo[c,e]oxepin-5(7H)-one (Intermediate 25) (145 mg, 0.5 mmol) was suspended in DCM (10 mL) and boron tribromide (2 mL. 1 M soln in DCM, 2.0 mmol) was added dropwise at RT. The resulting yellow solution was stirred overnight to give a yellow suspension. The mixture was cooled in ice-water and isopropanol (5 mL) was added dropwise to quench the reaction. The solvents were removed in vacuo. The resulting beige powder was dissolved in MeOH and adsorbed onto HMN and purified by chromatography on silica using 0-30% EtOAc in DCM to give the impure product which was re-purified on silica using 0-5% MeOH in DCM as eluant to give the title compound as an off-white solid (25 mg, 19%).

$^1$H NMR (400 MHz, DMSO-d$_6$) δ 10.59-9.60 (2H, m), 7.50 (1H, d, J=4.6 Hz), 7.47 (1H, d, J=8.3 Hz), 7.19 (1H, d, J=2.7 Hz), 7.16 (1H, d, J=8.9 Hz), 7.11 (1H, dd, J=2.7, 8.6 Hz), 5.10-4.74 (2H, m). LCMS (Method 3): R$_t$=2.96 min; m/z=259.0 [M−H]$^-$.

Additional compounds are prepared in accordance with methods adapted from the above procedures.

Example 3: Cell Viability Assay

Cell viability was determined using the CellTiter-Glo® 2.0 Assay. The assay w provides a homogeneous method to determine the number of viable cells in culture by quantitating the amount of ATP present, which indicates the presence of metabolically active cells.

On day 1, C$_2$Cl$_2$ myoblasts (ATCC #CRL-1772) where seeded in white-walled, transparent bottom 96w plates at 8,000 cells/well in regular DMEM medium, added with 10% heat inactivated fetal bovine serum (FBS) and Penicillin-Streptomycin (100 U/mL). On day 2, cells were treated with DMSO at 0.1% (vehicle, n=6 per plate), Torin-2 as a positive control (n=6 per plate) and test compounds in an 8-points concentration-response curve starting from 50 μM with 2-fold dilutions (n=1 per plate and per concentrations). A total of 3 biological replicates per test compound and concentration was obtained using three different 96-well plates with the same treatment schema. On day 3, CellTiter-Glo reagent (2× stock) (Promega) was added, mixed two minutes on orbital shaker and incubated 10 minutes at RT in the dark, before measuring luminescence using PHERAstar reader (0.25 s). The percentage of efficacy (PE) of each test compound concentration corresponds to the inhibition of signal in comparison to vehicle (0.1% DMSO) and was calculated as follows: PE=100−((signal of compound)/(average signal vehicle))×100.

Example 4: Anti-Inflammatory Assay

The anti-inflammatory effect of compounds was determined by measuring the production of IL-6 cytokine upon stimulation with lipopolysaccharide (LPS).

On day 1, RAW264.7 cells (ATCC #TIB-71) were seeded in 96w plates (non-coated) at 20,000 cells/well in regular DMEM medium, added with 10% heat inactivated fetal bovine serum (FBS) and Penicillin-Streptomycin (100 U/mL). On day 2, cells were treated with 0.1% DMSO (vehicle, n=6 per plate), 50 μM Urolitin A (positive control, n=6 per plate), and test compounds in an 8-points concentration-response curve starting from 50 μM with 2-fold dilutions (n=1 per plate and per concentrations). A total of 2 biological replicates per test compound and concentration was obtained using two different 96-well plates with the same treatment schema. Two hours after compound addition, cells were added with LPS at a final concentration of 1,000 ng/mL. On day 3, cell culture supernatants were collected at 24 h post-LPS treatment. Supernatant samples were diluted 10-fold and quantified for IL-6 using U-PLEX® Mouse IL-6 MSD according to supplier's (MesoScale Discoveries; K15069L-2) instructions. The percentage of efficacy (PE) of each test compound concentration corresponds to the inhibition of signal in comparison to vehicle (0.1% DMSO) and was calculated as follows: PE=100−((signal of compound)/(average signal vehicle))×100.

Example 5: Mitophagy Assay

As it was shown previously, treatment of $C_2Cl_2$ myoblasts with UA leads to the induction of mitophagy, characterized by mitochondrial fragmentation and a decrease in mitochondrial content (Ryu et al., Nat Med 2016). The induction of mitophagy was determined using a high-content imaging phenotypic assay, by staining mitochondrial shape and content using TOMM20 immunostaining.

On day 1, $C_2Cl_2$ myoblasts (ATCC #CRL-1772) were seeded in 96w plates at 2,000 cells/well in regular DMEM medium, added with 10% heat inactivated fetal bovine serum (FBS) and Penicillin-Streptomycin (100 U/mL). On day 2, cells were treated with 0.1% DMSO (vehicle, n=6 per well), UA 50 µM (positive control) and test compounds in an 8-points concentration-response curve starting from 50 µM with 2-fold dilutions (n=1 per plate and per concentrations). A total of 3 biological replicates per test compound and concentration was obtained using three different 96-well plates with the same treatment schema. On day 3, after 24 h treatment, cells were fixed using 3.7% formaldehyde, washed with PBS and stored at 4° C. On day 4, cells were first blocked with 3% BSA, 2% FBS, 0.2% Triton-X100 in PBS before immunocytochemistry staining using rabbit anti-Tom20 (CST; 1:300) and donkey anti-rabbit (Cy5), and DAPI-staining for nuclear count. Imaging of DAPI and Cy5 was performed on day 5 on IN Cell 6000 (GE Healthcare). The signal was measuring using high-content imaging analysis of Tom20 area, normalized for number of nuclei (area/nuc) (20×). The percentage of efficacy (PE) of each test compound concentration corresponds to induction normalized to positive control (50 µM UA) and was calculated as follows: PE=100−((average signal control−signal compound)/(average signal control−average signal vehicle))×100.

Example 6: Fatty Acid Oxidation Assays $C_2Cl_2$ myoblasts were cultured in Dulbecco's modified Eagle's medium (DMEM) including glucose 25 mM, 10% fetal calf serum and 1% PenStrep. Differentiation was induced for four days in Dulbecco's modified Eagle's medium (DMEM) including 25 mM glucose, 2% horse serum and 1% PenStrep. Fatty acid oxidation-driven respiration was assessed in $C_2Cl_2$ myotubes using the XF96 Extracellular Flux Analyzer. Once fully differentiated in a 96-well plate, $C_2Cl_2$ myotubes were treated in DMEM-based substrate limited medium, containing 0.5 mM glucose, 1 mM GlutaMAX, 0.5 mM carnitine, for 24 h. Cells were treated with 0.1% DMSO (vehicle, n=6), UA 50 µM (positive control, n=6) and test compounds in an 3-points concentration-response curve starting from 50 µM with 2-fold dilutions (n=4 per plate and per concentrations).

20 min prior to the assay, cells were washed two times with Assay Medium (111 mM NaCl, 4.7 mM KCl, 1.25 mM CaCl2, 2 mM MgSO4, 1.2 mM NaH2PO4, 2.5 mM glucose, 0.5 mM carnitine, and 5 mM HEPES, adjusted to pH 7.4 at 37° C. on the day of the assay). Cells were then incubated for 20 min in a non-$CO_2$ incubator. Just prior to starting the assay, cells were supplemented with XF Palmitate-BSA FAO Substrate (Seahorse Bioscience) at a final concentration of 166 µM palmitate.

Oxygen consumption rate was determined at basal level, and after the addition of FCCP at 1 µM. The percentage of efficacy (PE) of each test compound concentration at basal level corresponds to induction normalized to positive control (50 µM UA) and was calculated as follows: PE=((signal compound−average signal control)/(average signal control−average signal vehicle))×100.

Example 7: Pharmacokinetic Assays

Hepatic Microsomal Stability: Half-Life/Intrinsic Clearance Format

The stability of test compound (1 µM) was measured following incubation at 37° C. with hepatic microsomes (0.5 mg protein/mL for all species) in the presence of the cofactor, NADPH. Incubates were prepared in duplicate, with aliquots removed at 0, 5, 10, 20 and 40 minutes and reactions terminated, and compound extracted by the addition of solvent. The disappearance of parent compound was monitored by LC-MS/MS and the half-life determined over the time-course of incubation. The half-life value was used to calculate the in vitro intrinsic clearance expressed as µL/min/mg protein.

Cryopreserved Hepatocyte Stability: Half-Life/Intrinsic Clearance Format

Cryopreserved hepatocyte stability: half-life/intrinsic clearance format—The stability of test compound (1 µM) was measured following incubation at 37° C. with cryopreserved hepatocytes in suspension at a cell density of 0.5 million cells per mL (0.25 million cells per mL for mouse). Incubates were prepared in duplicate with aliquots removed at seven time points over a period of 120 minutes and reactions terminated and compound extracted by the addition of solvent. The disappearance of parent compound was monitored by LC-MS/MS and half-life determined over the course of the incubation. The half-life value obtained was used to calculate the in vitro intrinsic clearance expressed as µL/min/million cells.

Example 8: Solubility Assay

Using a stock solution of test compound in 100% DMSO, duplicate dilutions were prepared at a nominal concentration of 200 µM in 0.1 M phosphate buffered saline (PBS) at pH 7.4, with a 2% final DMSO content. Test compound calibration standards were prepared at 200 µM and 10 µM in 100% DMSO. The PBS and DMSO dilutions were equilibrated on a shaking platform at room temperature for two hours prior to filtration using a Multiscreen HTS solubility filter plate (Millipore).

Filtrates were analyzed by LC-UV-MS and the concentration of compound in PBS filtrate determined by comparing the UV absorbance peak with that of the two DMSO calibration standards. Mass spectrometry was used to confirm the presence of the expected molecular ion in the UV peak measured. The effective range of the assay is 5-200 µM.

Example 9: Bioavailability of Test Compounds in Plasma after Oral Administration in Mice Protocol No. 1 for In Vivo Sampling Male CD-1 mice were administered with either a single intravenous or a single oral dose of test compound at target dose levels 1 mg/kg and 10 mg/kg respectively.

For intravenous delivery, test compounds were formulated in 20% DMSO, 30% PEG400, 50% water. For oral delivery, test compounds were formulated in a solution of DMSO 15%, 85% (0.5% methylcellulose/0.25% Tween 80 in water). For both formulations, the test compound was first dissolved in DMSO and subsequently diluted with water to achieve the desired dose concentration. Following preparation, the dose vehicles were stirred continuously prior to their administration. Mice had free access to food and water throughout the duration of the study. For the animals dosed intravenously, whole blood was collected at 5 min, 15 min, 1 h, 2 h and 4 h, while animals dosed orally were collected at 30 min, 1 h, 4 h, 6 h.

Protocol No. 2 for In Vivo Sampling

Male CD-1 mice were administered with either a single oral dose of one test compound at a time at target dose level of 10 mg/kg, or with a single intravenous administration of a cassette of up to 5 test compounds at a time at a nominal target dose of 0.5 mg/kg.

For intravenous delivery, test compounds were formulated in 20% DMSO, 30% PEG400, 50% water. For oral delivery, test compounds were formulated in a solution of DMSO 15%, 85% (0.5% methylcellulose/0.25% Tween 80 in water). For both formulations, the test compound was first dissolved in DMSO and subsequently diluted with water to achieve the desired dose concentration. Following preparation, the dose vehicles were stirred continuously prior to their administration. Mice had free access to food and water throughout the duration of the study. For the animals dosed intravenously, whole blood was collected at 5 min, 10 min, 15 min, 30 min, 1 h, 2 h, 4 h and 8 h, while animals dosed orally were collected at 15 min, 4 h and 24 h.

Sample Analysis

Representative aliquots of plasma samples were diluted as appropriate with control matrix to ensure that test compound concentrations were within the range of the calibration curve, then extracted by the precipitation of matrix proteins with a mixture of acetonitrile/water containing an analytical internal standard. Study samples were assayed for test compound against a series of calibration and quality control standards prepared in control matrix matched by species and gender. Representative aliquots of the dose formulations taken at the time of dosing (in triplicate), were serially diluted with DMSO then then spiked into an aliquot of control mouse plasma.

Data Analysis

Pharmacokinetic analysis was performed using mean data, non-compartmental analysis and the nominal dose of test item administered to the mice. Area under the plasma versus time curve up to the last quantifiable concentration, $AUC_{0\text{-}last}$ (h.ng/mL or h.ng/g) or up to infinity $AUC_{0\text{-}\infty}$ (h.ng/mL or h.ng/g) were calculated according to the linear up/log down method. Concentrations below the limit of quantitation were set to zero. Bioavailability was determined by calculating the ratio of AUC after oral administration over the AUC after intravenous administration and expressed in percentage.

Figure 9:
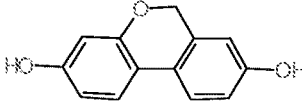
FIG. 9: A table summarizing solubility assay (Kinetic solubility: C (μM): Kinetic solubility measured in water) and in vivo bioavailability measured in mice for exemplary compounds of the invention.
Figure 9:
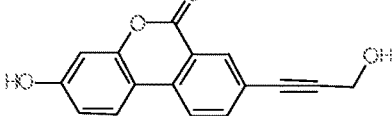
Figure 9:
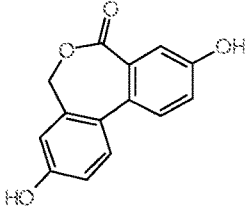
Figure 9:
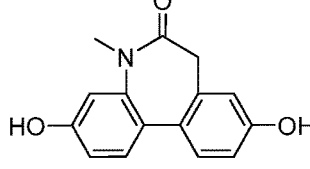
Figure 9:
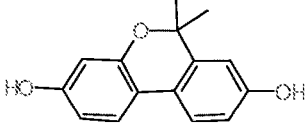
Figure 9:
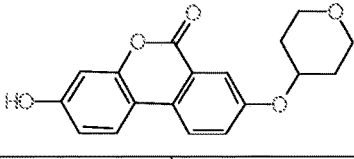
Figure 9:
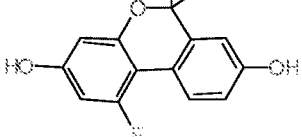

Certain compounds of the present invention displayed unexpectedly improved bioavailability independent of their water solubility. The bioavailability of compounds is limited by their solvation rate. Therefore, it would be expected that a compound with higher water solubility would provide improved solubilization and increased bioavailability. Remarkably, as showing in FIG. 9, the compound recited in row 6 provided an unexpected improved bioavailability despite a low water solubility.

Example 10: Measurement of Muscle and Brain Tissue Penetration in Mice

Protocol for In Vivo Sampling

Male CD-1 mice were administered with a single oral dose of test compound at target dose level of 10 mg/kg. Test compounds were formulated in a solution of DMSO 15%, 85% (0.5% methylcellulose/0.25% Tween 80 in water). The test compound was first dissolved in DMSO and subsequently diluted with water to achieve the desired dose concentration. Following preparation, the dose vehicles were stirred continuously prior to their administration. Mice had free access to food and water throughout the duration of the study.

Brain and muscle tissues were collected at different time points, including 15 min, 2 h, 4 h and 8 h. Brains and skeletal muscle tissue were removed and rinsed with Saline. The samples were blotted dry snap frozen into liquid nitrogen.

Sample Analysis

Representative aliquots of tissue samples were diluted as appropriate with control matrix to ensure that test compound concentrations were within the range of the calibration curve, then extracted by the precipitation of matrix proteins with a mixture of acetonitrile/water containing an analytical internal standard. Study samples were assayed for test compound against a series of calibration and quality control standards prepared in control matrix matched by species and gender. Representative aliquots of the dose formulations taken at the time of dosing (in triplicate), were serially diluted with DMSO then then spiked into an aliquot of control mouse tissue. Concentrations in muscle and brain were corrected for the homogenisation dilution factor and results reported as ng/g of tissue.

Data Analysis

Pharmacokinetic analysis was performed using mean data, non-compartmental analysis and the nominal dose of test item administered to the mice. For each test compound, mean tissue concentrations were calculated per time point and the Cmax (ng/g tissue) (maximal concentration) was determined.

Example 11: Anti-Ferroptotic Assay

Anti-ferroptotic activity of compounds was determined by measuring cellular viability after co-treatment with the ferroptosis inducer 1S,3R-RSL 3 (CAS No.: 1219810-16-8; hereafter RSL3). Cellular viability was measured using the CellTiter-Glo® 2.0 Assay. The assay provides a homogeneous method to determine the number of viable cells in culture by quantitating the amount of ATP present, which indicates the presence of metabolically active cells.

On day 1, $C_2Cl_2$ myoblasts (ATCC #CRL-1772) where seeded in white-walled, transparent bottom 96w plates at 1,500 cells/well in regular DMEM medium, added with 10% heat inactivated fetal bovine serum (FBS) and Penicillin-Streptomycin (100 U/mL). On day 2, cells were treated with DMSO at 0.1% (vehicle, n=8 per plate), RSL3 at 1.25 µM as a positive control (n=8 per plate) and test compounds in a 5-points concentration-response curve starting from 50 µM with 2-fold dilutions (n=4 per plate and per concentrations), in presence or absence of RSL3 1.25 µM. On day 3, CellTiter-Glo reagent (2× stock) (Promega) was added, mixed two minutes on orbital shaker and incubated 10 minutes at RT in the dark, before measuring luminescence using a FLUOstar OPTIMA reader (0.25 s). The percentage of efficacy (PE) of each test compound concentration corresponds to the rescue in cellular viability compared to RSL3 1.25 µM alone and each test compound concentration alone:

$$PE = \left( \frac{\text{signal (compound } [n\ \mu M] + RSL3\ [1.25\ \mu M]) - \text{average signal } (RSL3\ [1.25\ \mu M])}{\text{average signal (compound } [n\ \mu M])} \right) * 100$$

A score of 0% means that the compound does not have any anti-ferroptotic activity. A score of 100% means that the compound rescues completely cellular viability and has the maximal anti-ferroptotic activity possible.

INCORPORATION BY REFERENCE

All of the U.S. patents and U.S. and PCT patent application publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. A compound selected from:

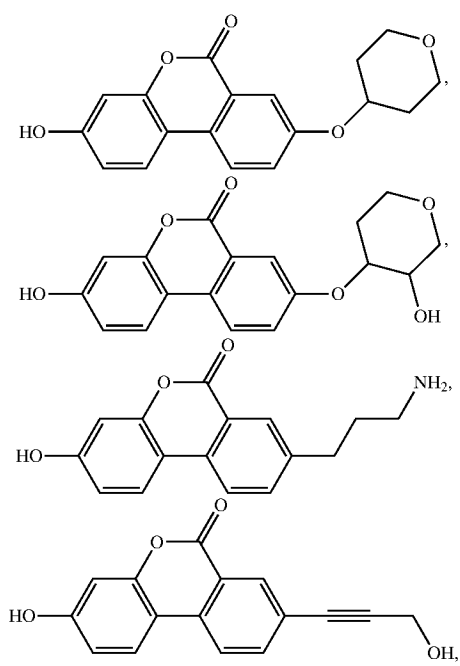

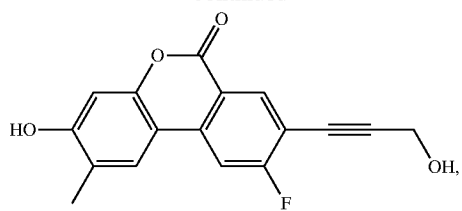

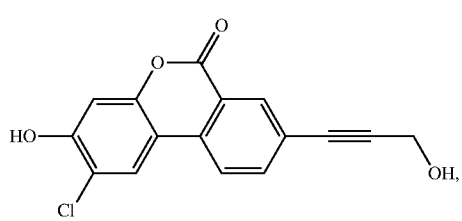

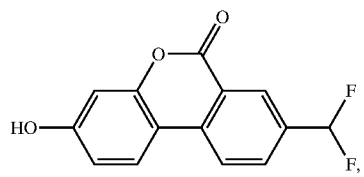

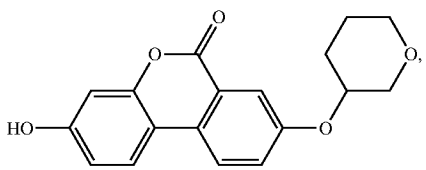

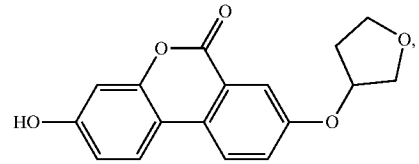

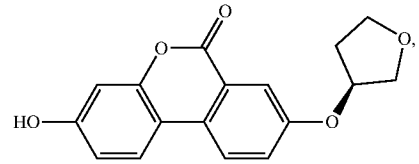

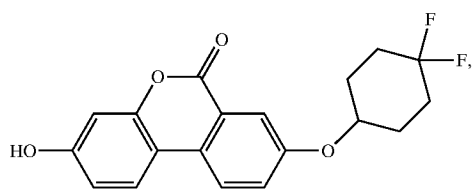

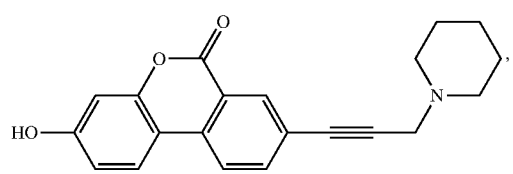

-continued

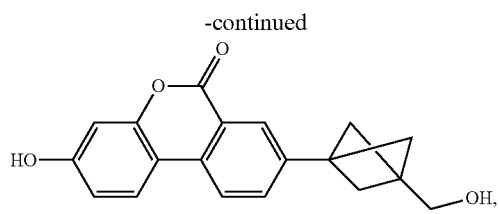

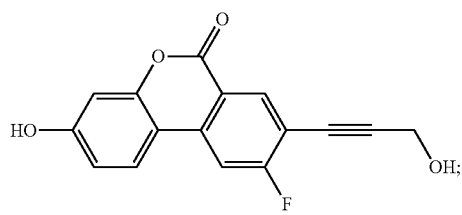

or a pharmaceutically acceptable salt thereof.

2. The compound of claim 1 having the structure:

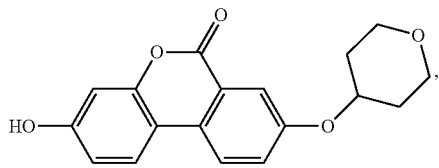 [SMILES: O=c1oc2cc(O)ccc2c2ccc(OC3CCOCC3)cc12]

or a pharmaceutically acceptable salt thereof.

3. The compound of claim 1 having the structure:

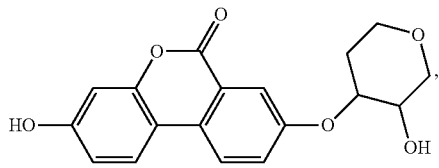 [SMILES: O=c1oc2cc(O)ccc2c2ccc(OC3CCOCC3O)cc12]

or a pharmaceutically acceptable salt thereof.

4. A pharmaceutical composition comprising a compound of claim 1; and a pharmaceutically acceptable carrier.

5. A pharmaceutical composition comprising a compound of claim 2; and a pharmaceutically acceptable carrier.

6. A pharmaceutical composition comprising a compound of claim 3; and a pharmaceutically acceptable carrier.

* * * * *